US012565664B2

(12) United States Patent
Cinnamon et al.

(10) Patent No.: US 12,565,664 B2
(45) Date of Patent: *Mar. 3, 2026

(54) GENOME-EDITED BIRDS

(71) Applicant: The State of Israel, Ministry of Agriculture & Rural Development, Agricultural Research Organization (ARO) (Volcani Center), Rishon Lezion (IL)

(72) Inventors: Yuval Cinnamon, Jerusalem (IL); Enbal Ben-Tal Cohen, Rehovot (IL)

(73) Assignee: The State of Israel, Ministry Of Agriculture & Rural Development, Agricultural Research Organization (ARO) (Volcani Center), Rishon Lezion (IL)

( * ) Notice: Subject to any disclaimer, the term of this patent is extended or adjusted under 35 U.S.C. 154(b) by 968 days.

This patent is subject to a terminal disclaimer.

(21) Appl. No.: 17/435,485

(22) PCT Filed: Mar. 3, 2020

(86) PCT No.: PCT/IL2020/050242
§ 371 (c)(1),
(2) Date: Sep. 1, 2021

(87) PCT Pub. No.: WO2020/178822
PCT Pub. Date: Sep. 10, 2020

(65) Prior Publication Data
US 2022/0136003 A1     May 5, 2022

Related U.S. Application Data

(60) Provisional application No. 62/814,162, filed on Mar. 5, 2019.

(51) Int. Cl.
*C12N 15/85* (2006.01)
*C12N 5/0735* (2010.01)
(Continued)

(52) U.S. Cl.
CPC ........ *C12N 15/8509* (2013.01); *C12N 5/0611* (2013.01); *C12N 9/22* (2013.01);
(Continued)

(58) Field of Classification Search
CPC .... C12N 15/8509; C12N 5/0611; C12N 9/22; C12N 15/113; C12N 2310/20; C12N 2510/00; A01K 2227/30; A01K 67/0275
See application file for complete search history.

(56) References Cited

U.S. PATENT DOCUMENTS

| | | | |
|---|---|---|---|
| 3,791,932 A | 2/1974 | Schuurs et al. | |
| 3,839,153 A | 10/1974 | Schuurs et al. | |
| (Continued) | | | |

FOREIGN PATENT DOCUMENTS

| | | |
|---|---|---|
| CN | 1344796 A | 4/2002 |
| CN | 1433475 A | 7/2003 |
| (Continued) | | |

OTHER PUBLICATIONS

Strauss HM, et al Light-dependent dimerization in the N-terminal sensory module of cyanobacterial phytochrome 1. FEBS Lett. 2005;579:3970-3974 (Year: 2005).*
(Continued)

*Primary Examiner* — Tracy Vivlemore
*Assistant Examiner* — Thomas R. Amick

(57) ABSTRACT

The present disclosure provides exogenous polynucleotide cassettes for generating chimeric bird cells and chimeric birds. The polynucleotide cassettes can be used to produce conditionally-lethal phenotype in male bird embryos. In one
(Continued)

embodiment, the present disclosure provides methods for destroying male chick embryos in-ovo.

30 Claims, 36 Drawing Sheets
(7 of 36 Drawing Sheet(s) Filed in Color)

Specification includes a Sequence Listing.

(51) Int. Cl.
| | |
|---|---|
| *C12N 9/22* | (2006.01) |
| *C12N 15/113* | (2010.01) |

(52) U.S. Cl.
CPC ........ *C12N 15/113* (2013.01); *A01K 2227/30* (2013.01); *C12N 2310/20* (2017.05); *C12N 2510/00* (2013.01)

(56) References Cited

U.S. PATENT DOCUMENTS

| | | | |
|---|---|---|---|
| 3,850,578 A | 11/1974 | McConnell | |
| 3,850,752 A | 11/1974 | Schuurs et al. | |
| 3,853,987 A | 12/1974 | Dreyer | |
| 3,867,517 A | 2/1975 | Ling | |
| 3,879,262 A | 4/1975 | Schuurs et al. | |
| 3,901,654 A | 8/1975 | Gross | |
| 3,935,074 A | 1/1976 | Rubenstein et al. | |
| 3,984,533 A | 10/1976 | Uzgiris | |
| 3,996,345 A | 12/1976 | Ullman et al. | |
| 4,034,074 A | 7/1977 | Miles | |
| 4,098,876 A | 7/1978 | Piasio et al. | |
| 4,666,828 A | 5/1987 | Gusella | |
| 4,683,202 A | 7/1987 | Mullis | |
| 4,801,531 A | 1/1989 | Frossard | |
| 4,879,219 A | 11/1989 | Wands et al. | |
| 5,011,771 A | 4/1991 | Bellet et al. | |
| 5,192,659 A | 3/1993 | Simons | |
| 5,272,057 A | 12/1993 | Smulson et al. | |
| 5,281,521 A | 1/1994 | Trojanowski et al. | |
| 6,774,279 B2 | 8/2004 | Dymecki | |
| 8,021,867 B2 | 9/2011 | Smith et al. | |
| 8,119,381 B2 | 2/2012 | Smith et al. | |
| 8,124,369 B2 | 2/2012 | Smith et al. | |
| 8,129,134 B2 | 3/2012 | Smith et al. | |
| 8,133,697 B2 | 3/2012 | Smith et al. | |
| 8,143,015 B2 | 3/2012 | Smith et al. | |
| 8,143,016 B2 | 3/2012 | Smith et al. | |
| 8,148,098 B2 | 4/2012 | Smith et al. | |
| 8,163,514 B2 | 4/2012 | Smith et al. | |
| 8,304,222 B1 | 11/2012 | Smith et al. | |
| 8,586,526 B2 | 11/2013 | Gregory et al. | |
| 8,771,945 B1 | 7/2014 | Zhang | |
| 2003/0232410 A1 | 12/2003 | Liljedahl et al. | |
| 2004/0053361 A1 | 3/2004 | Vallier | |
| 2005/0026157 A1 | 2/2005 | Baltimore et al. | |
| 2006/0014264 A1 | 1/2006 | Sauer et al. | |
| 2006/0095980 A1 | 5/2006 | Petitte et al. | |
| 2007/0271630 A1 | 11/2007 | Boukharov et al. | |
| 2012/0046263 A1 | 2/2012 | Navara | |
| 2012/0192298 A1 | 7/2012 | Weinstein et al. | |
| 2012/0304323 A1 | 11/2012 | Lauth et al. | |
| 2015/0143552 A1 | 5/2015 | Alphey | |
| 2015/0260704 A1 | 9/2015 | Bruins et al. | |
| 2018/0320164 A1 | 11/2018 | Hay et al. | |
| 2020/0214273 A1 | 7/2020 | Cinnamon | |

FOREIGN PATENT DOCUMENTS

| | | | |
|---|---|---|---|
| CN | 101155509 A | 4/2008 | |
| CN | 101421408 A | 4/2009 | |
| CN | 101868144 A | 10/2010 | |
| CN | 101873795 A | 10/2010 | |
| CN | 102695798 A | 9/2012 | |
| CN | 105524941 A | 4/2016 | |
| CN | 106359073 A | 2/2017 | |
| CN | 108018309 A | 5/2018 | |
| DE | 10248361 A1 | 1/2004 | |
| JP | 2004500865 A | 1/2004 | |
| JP | 2010536346 A | 12/2010 | |
| JP | 2012511915 A | 5/2012 | |
| JP | 2012516689 A | 7/2012 | |
| WO | WO 1997/049450 A1 | 12/1997 | |
| WO | WO 1999/006533 A1 | 2/1999 | |
| WO | 01/39599 A2 | 6/2001 | |
| WO | WO 2009/023800 A1 | 2/2009 | |
| WO | WO 2009/071334 A2 | 6/2009 | |
| WO | 2010/068978 A1 | 6/2010 | |
| WO | WO 2010/088742 A1 | 8/2010 | |
| WO | WO 2011146121 A1 | 11/2011 | |
| WO | WO 2014/018423 A2 | 1/2014 | |
| WO | WO 2014/085593 A1 | 6/2014 | |
| WO | WO 2015/199225 A1 | 12/2015 | |
| WO | WO 2016/076240 A1 | 5/2016 | |
| WO | 2017/094015 A1 | 6/2017 | |
| WO | WO 2018/013759 A1 | 1/2018 | |
| WO | WO 2018/218299 A1 | 12/2018 | |
| WO | WO 2019/058376 A1 | 3/2019 | |
| WO | 2020/178822 A1 | 9/2020 | |

OTHER PUBLICATIONS

Grusch M, et al Spatio-temporally precise activation of engineered receptor tyrosine kinases by light. EMBO J. 2014;33:1713-1726 (Year: 2014).*

Allioli et al. "Use of retroviral vectors to introduce and express the β-galactosidase marker gene in cultured chicken primordial germ cells" Developmental Biology. Sep. 1, 1994;165(1):30-7.

Capecchi MR "Altering the genome by homologous recombination" Science. Jun. 16, 1989;244(4910):1288-92.

Carlson et al. "Efficient TALEN-mediated gene knockout in livestock" Proceedings of the National Academy of Sciences. Oct. 23, 2012;109(43):17382-7.

Certo et al. "Coupling endonucleases with DNA end-processing enzymes to drive gene disruption" Nature methods. Oct. 2012;9(10):973-5.

Chang et al. "Production of germline chimeric chickens by transfer of cultured primordial germ cells" Cell Biol Int. 1997;21:495-9.

Chang et al. "Proliferation of chick primordial germ cells cultured on stroma cells from the germinal ridge" Cell biology international. Feb. 1, 1995;19(2):143-50.

Cho et al. "Targeted genome engineering in human cells with the Cas9 RNA-guided endonuclease" Nature biotechnology. Mar. 2013;31(3):230-2.

Choi et al. "Basic fibroblast growth factor activates MEK/ERK cell signaling pathway and stimulates the proliferation of chicken primordial germ cells" PloS one. Sep. 23, 2010;5(9):e12968.

Cinnamon et al. "Differential effects of N-cadherin-mediated adhesion on the development of myotomal waves" Department of Anatomy and Cell Biology, Hebrew University-Hadassah Medical School. 2006 1101-1112.

Clinton et al. "Sexing chick embryos: a rapid and simple protocol" British poultry science. Mar. 1, 2001;42(1):134-8.

Cong et al. "Multiplex genome engineering using CRISPR/Cas systems" Science. Feb. 15, 2013;339(6121):819-23.

Cooper et al. "Generation of gene edited birds in one generation using sperm transfection assisted gene editing (STAGE)" Transgenic research. Jun. 2017;26(3):331-47.

Dicarlo et al. "Genome engineering in *Saccharomyces cerevisiae* using CRISPR-Cas systems" Nucleic acids research. Apr. 1, 2013;41(7):4336-43.

Eyal-Giladi et al. "From cleavage to primitive streak formation: a complementary normal table and a new look at the first stages of the development of the chick" I. General morphology. Developmental biology. Apr. 1, 1976;49(2):321-37.

GenBank Accession No. ABU63124, Version 1, Jul. 26, 2016.

GenBank Accession No. AAV70486, Version 1, Jun. 23, 2010.

GenBank Accession No. EEF27734, Version 1, Mar. 11, 2015.

(56)                    References Cited

OTHER PUBLICATIONS

GenBank Accession No. CAA00227, Version 1, Jan. 29, 2011.
GenBank Accession No. P07766, Version 2, Feb. 15, 2019.
GenBank Accession No. NP_000560.5, Version 5, Jan. 15, 2016.
GenBank Accession No. NP_000580.1, Version 1, Mar. 4, 2019.
GenBank Accession No. P22301, Version 1, Feb. 15, 2019.
Gene ID No. 396308, updated Apr. 16, 2021.
Gene ID No. 378779, updated May 6, 2021.
Gene ID No. 396165, updated Jun. 28, 2021.
Gene ID No. 396516, updated Aug. 14, 2021.
Gibson et al. "Enzymatic assembly of DNA molecules up to several hundred kilobases" Nature methods. May 2009;6(5):343-5.
Hamburger et al. "A series of normal stages in the development of the chick embryo" Journal of morphology. Jan. 1951;88(1):49-92.
Hussain et al. "CRISPR/Cas system: a game changing genome editing technology, to treat human genetic diseases" Gene. Feb. 15, 2019;685:70-5.
Hwang et al. "Efficient genome editing in zebrafish using a CRISPR-Cas system" Nature biotechnology. Mar. 2013;31(3):227-9.
International Search Report for PCT Application No. PCT/IL2020/050242 dated Jun. 8, 2020.
Jinek et al. "A programmable dual-RNA-guided DNA endonuclease in adaptive bacterial immunity" science. Aug. 17, 2012;337(6096):816-21.
Jinek et al. "RNA-programmed genome editing in human cells" elife. Jan. 29, 2013;2:e00471.
Kaleta et al. "Approaches to determine the sex prior to and after incubation of chicken eggs and of day-old chicks" World's Poultry Science Journal. Sep. 2008;64(3):391-9.
Karagenc et al. "Origin of primordial germ cells in the prestreak chick embryo" Developmental genetics. 1996;19(4):290-301.
Kennedy et al. "Rapid blue-light-mediated induction of protein interactions in living cells" Nature methods. Dec. 2010;7(12):973-5.
Lavoir et al. "Isolation and identification of germ cells from fetal bovine ovaries" Molecular reproduction and development. Apr. 1994;37(4):413-24.
Lee et al. "Site-specific DNA excision via engineered zinc finger nucleases" Trends in biotechnology. Jul. 10, 2010;28(9):445-6.
Li et al. "TAL nucleases (TALNs): hybrid proteins composed of TAL effectors and FokI DNA-cleavage domain" Nucleic acids research. Jan. 1, 2011;39(1):359-72.
Lu et al. "Common developmental requirement for Olig function indicates a motor neuron/oligodendrocyte connection" Cell. Apr. 5, 2002;109(1):75-86.
MacDonald et al. "Characterisation and germline transmission of cultured avian primordial germ cells" PloS one. Nov. 29, 2010;5(11):e15518.
Makarova et al. "An updated evolutionary classification of CRISPR-Cas systems" Nature Reviews Microbiology. Nov. 2015;13(11):722-36.
Mali et al. "Cas9 as a versatile tool for engineering biology" Nature methods. Oct. 2013;10(10):957-63.
Mashiko et al. "Feasibility for a large scale mouse mutagenesis by injecting CRISPR/Cas plasmid into zygotes" Development, growth & differentiation. Jan. 2014;56(1):122-9.
McEwan et al. "Adaptation of standard spreadsheet software for the analysis of DNA sequences" BioTechniques. Jan. 1998;24(1):131-8.
Menke DB "Engineering subtle targeted mutations into the mouse genome" genesis. Sep. 2013;51(9):605-18.
Miller et al. "Human HDAC1 and HDAC2 function in the DNA-damage response to promote DNA nonhomologous end-joining" Nature structural & molecular biology. Sep. 2010;17(9):1144-51.
Motta-Mena et al. "An optogenetic gene expression system with rapid activation and deactivation kinetics" Nature chemical biology. Mar. 2014;10(3):196-202.
Müller et al. "Optogenetics for gene expression in mammalian cells" Biological chemistry. Feb. 1, 2015;396(2):145-52.
Naito et al. "Long-term culture of chicken primordial germ cells isolated from embryonic blood and production of germline chimaeric chickens" Animal reproduction science. Feb. 1, 2015;153:50-61.

Nakamura et al. "Codon usage tabulated from the international DNA sequence databases" Nucleic acids research. Jan. 1, 1996;24(1):214-5.
Nakamura et al. "Increased proportion of donor primordial germ cells in chimeric gonads by sterilisation of recipient embryos using busulfan sustained-release emulsion in chickens" Reproduction, Fertility and Development. Nov. 14, 2008:20(8):900-7.
Nandi et al. "Cryopreservation of specialized chicken lines using cultured primordial germ cells" Poultry science. Aug. 1, 2016;95(8):1905-11.
Ran et al. "Genome engineering using the CRISPR-Cas9 system" Nature protocols. Nov. 2013;8(11):2281-308.
Santiago et al. "Targeted gene knockout in mammalian cells by using engineered zinc-finger nucleases" Proceedings of the National Academy of Sciences. Apr. 15, 2008;105(15):5809-14.
Shmakov et al. "Diversity and evolution of class 2 CRISPR-Cas systems" Nature reviews microbiology. Mar. 2017;15(3):169-82.
Shmakov et al. "Discovery and functional characterization of diverse class 2 CRISPR-Cas systems" Molecular cell. Nov. 5, 2015;60(3):385-97.
Smith et al. "Cell-specific ablation in the testis: what have we learned?" Andrology. Nov. 2015;3(6):1035-49.
Solter et al. "Monoclonal antibody defining a stage-specific mouse embryonic antigen (SSEA-1)" Proceedings of the National Academy of Sciences. Nov. 1, 1978;75(11):5565-9.
Strelchenko N "Bovine pluripotent stem cells" Theriogenology. Jan. 1, 1996;45(1):131-40.
Swift CH "Origin and early history of the primordial germ-cells in the chick" American Journal of Anatomy. Jan. 1914;15(4):483-516.
Taslimi et al. "Optimized second-generation CRY2-CIB dimerizers and photoactivatable Cre recombinase" Nature chemical biology. Jun. 2016;12(6):425-30.
Trefil et al. "Male fertility restored by transplanting primordial germ cells into testes: a new way towards efficient transgenesis in chicken" Scientific reports. Oct. 27, 2017;7(1):1-9.
Urnov et al. "Highly efficient endogenous human gene correction using designed zinc-finger nucleases" Nature. Jun. 2005;435(7042):646-51.
Van De Lavoir et al. "Germline transmission of genetically modified primordial germ cells" Nature. Jun. 2006;441(7094):766-9.
Wang et al. "2A self-cleaving peptide-based multi-gene expression system in the silkworm Bombyx mori" Scientific reports. Nov. 5, 2015;5(1):1-0.
Whyte et al. "FGF, insulin, and SMAD signaling cooperate for avian primordial germ cell self-renewal" Stem cell reports. Dec. 8, 2015;5(6):1171-82.
Yasuda et al. "A method to obtain avian germ-line chimaeras using isolated primordial germ cells" Reproduction. Nov. 1, 1992;96(2):521-8.
Yosef et al. "A genetic system for biasing the sex ratio in mice" EMBO reports. Aug. 2019;20(8):e48269.
Tizard et al. (2014). Precision genome engineering in the chicken: The gap between science and market place. Lecture, August.
Zhang et al. (2017). CRISPR/Cas9 mediated chicken Stra8 gene knockout and inhibition of male germ cell differentiation. PLoS One, 12(2), E0172207.
Cooper et al, Light increases the rate of embryonic development: implications for latitudinal trends in incubation period, Functional Ecology 2011, 25, 769-776.
Leighton et al, Generation of chickens expressing Cre recombinase, Transgenic Res (2016) 25:609-616.
Orban et al, Tissue- and site-specific DNA recombination in transgenic mice, Proc. Natl. Acad. Sci. USA, vol. 89, pp. 6861-6865, Aug. 1992.
Rozenboim et al, The Effect of a Green and Blue Monochromatic Light Combination on Broiler Growth and Development, 2004 Poultry Science 83:842-845.
Seburn et al, Lack of Neuropathy-Related Phenotypes in Hint1 Knockout Mice, J Neuropathol Exp Neurol. Jul. 2014 ; 73(7): 693-701.
Shin et al, Controlling Gene Expression in Mice with Tetracycline: Application in Pigment Cell Research, Pigment Cell Res 13: 326-331. 2000.

(56)            References Cited

OTHER PUBLICATIONS

Watanabe et al, Tet-on inducible system combined with in ovo electroporation dissects multiple roles of genes in somitogenesis of chicken embryos, Elsevier, Developmental Biology 305 (2007) 625-636.

Backstrom N. et al., Gene Conversion Drives the Evolution of HINTW, an Ampliconic Gene on the Female-Specific Avian W Chromosome, Mol. Biol. Evol., 2005, vol. 22, No. 10, p. 1992-1999.

Carlson et al. (2012). Targeting DNA with fingers and TALENs. Molecular Therapy-Nucleic acids, 1, e3.

Cermak et al. Nucleic Acids Research (2011) 39 (12): e82.

Christian et al. (2010). Targeting DNA double-strand breaks with TAL effector nucleases. Genetics, 186(2), 757-761.

Doran et al., Genome editing in poultry—opportunities and impacts, National Institutes Of Bioscience Journal, vol. 1, No. 0, Mar. 15, 2017, XP055500987.

Gandhi Shashank et al.: Optimization of CRISPR/Cas9 genome editing for loss-of-function in the early chick embryo, Developmental Biology, vol. 432, No. 1, Dec. 1, 2017, pp. 86-97, XP055800614.

Hwang et al. (2013). Efficient genome editing in zebrafish using a CRISPR-Cas system. Nature Biotechnology, 31 (3), 227-229.

Jaeyong Han et al: Primordial germ cell-mediated transgenesis and genome editing in birds, Journal Of Animal Science And Biotechnology, Biomed Central Ltd, London, UK, vol. 9, No. 1, Jan. 31, 2018, pp. 1-11, XP021253085.

Julien, O. & Wells, J. A., Caspases and their substrates. Cell Death Differ. (2017). doi: 10.1038/cdd.2017.44.

Kim et al. (1996). Microencapsulation properties of gum arabic and several food proteins: spray-dried orange oil emulsion particles. Journal of Agricultural and Food Chemistry, 44(5), 1314-1320.

Konermann (Nature, 2013, vol. 500, No. 7 463, p. 472-476) (Year: 2013).

Lee et al. (2010). Targeted chromosomal deletions in human cells using zinc finger nucleases. Genome Research, 20 (1), 81-89.

Lee Hong Jo et al: "Targeted gene insertion into Z chromosome of chicken primordial germ cells for avian sexing model development", The Faseb Journal, vol. 33, No. 7, Apr. 5, 2019, pp. 8519-8529, XP055800620.

Li et al. (2011). Modularly assembled designer TAL effector nucleases for targeted gene knockout and gene replacement in eukaryotes. Nucleic Acids Research, 39(14), 6315-6325.

Lorna Taylor et al: Efficient TALEN-mediated gene targeting of chicken primordial germ cells, Development. Mar. 1, 2017; 144(5):, pp. 928-934, XP055592331, DOI: 10.1242/dev.145367.

Macdonald et al., Efficient genetic modification and germ-line transmission of primordial germ cells using piggyBac and Tol2 transposons; Proceedings of the National Academy of Sciences, 109(23), p. 1466-1472. 14.05.2012.

Mahfouz et al. (2011). De nova-engineered transcription activator-like effector.

Mali et al. (2013). RNA-guided human genome engineering via Cas9. Science, 339(6121), 823-826.

McCarthy, J. V & Dixit, V. M. Apoptosis induced by Drosophila reaper and grim in a human system. Attenuation by inhibitor of apoptosis proteins (clAPs). J. Biol. Chem. 273, 24009-15; 1998.

McEwan et al. (1998). The mutational-response index and codon bias in genes from a Frankia nif operon. Theoretical and Applied Genetics, 96(5), 716-718.

McMahon, J. A., et al. (1998). Noggin-mediated antagonism of BMP signaling is requii-ed for growth and patterning of the neural tube and somite. Genes & development, 12(10), 1438-1452.

Miller et al. (2011). A Tale nuclease architecture for efficient genome editing. Nature Biotechnology, 29(2), 143-148.

Nadege Veron et al: CRISPR mediated somatic cell genome engineering in the chicken, Developmental Biology, vol. 407, No. 1, 2015, pp. 68-74, XP055523970, ISSN: 0012-1606, DOI: 10.1016/j.ydbio.2015.08.007.

Nakamura et al. (1996). Emerging understanding of translation termination. Cell, 87(2), 147-150.

Nigel Urwin: Would you prefer to eat genetically modified eggs, or see day-old chicks destroyed? : Nigel Urwin : Opinion, The Guardian, Jan. 16, 2014 (Jan. 16, 2014), XP055387318.

Oishi et al., Targeted mutagenesis in chicken using CRISPR/Cas9 system. Scientific reports, 6, 23980, 06.04.2016.

Reyon et al. (2012). FLASH assembly ofTALENs for high-throughput genome editing. Nature Biotechnology, 30(5), 460.

Sela-Donenfeld, D et al. (1999). Regulation of the onset of neural crest migration by coordinated activity of BMP4 and Nom 1in in the dorsal neural tube. Development, 126(21), 4749-4762.

Wang et al. (1998). Cloning of mammalian Ire1 reveals diversity in the ER stress responses. The EMBO journal, 17 (19), 5708-5717.

Winnier, G., et al. (1995). Bone morpl1ogenetic proteinA is required for mesoderm formation and patterning in the mouse. Genes & development, 9(17), 2105-2116.

Yagi, T., et al. (1990). Homologous recombination at c-fyn locus of mouse embryonic stern cells with use of diphttieria toxin A-fragment gene in negative selection. Proceedings of the National Academy of Sciences, 87(24), 9918-9922.

Yoshioka Hidefumi, Functional analysis of avian sex determination gene and cell fate analysis, KAKEN Project 23570254, Published: 2011-08-04, [retrieved on 2023.03.30], <URL: https://kaken.nii.ac.jp/en/grant/KAKENHI - JET- 23570254 />.

Zhang et al. (2011 ). Efficient construction of sequence-specific TAL effectors for modulating mammalian transcription. Nature Biotechnology, 29(2), 149-153.

\* cited by examiner

No light- inactive Cre
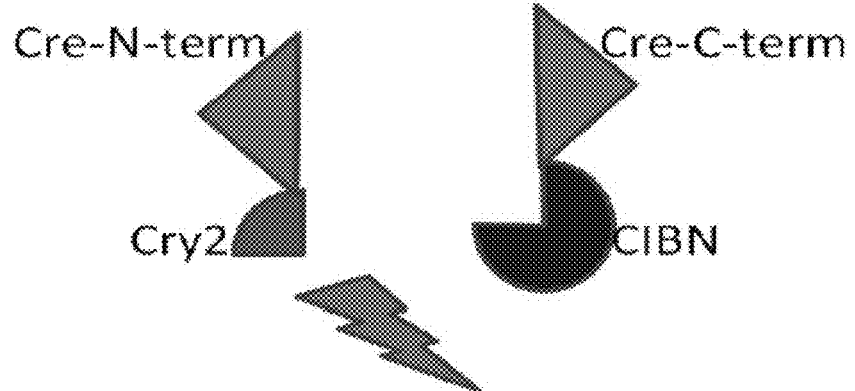
Blue light- active Cre
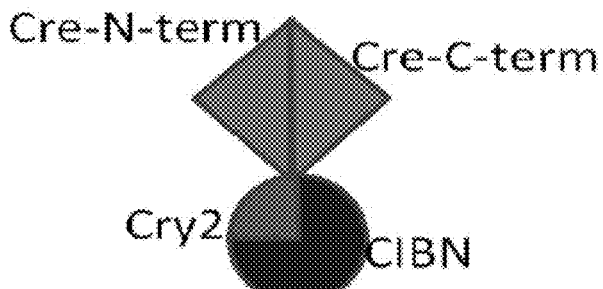
FIG. 2

FIG. 4C
Targeting vectors:
A.
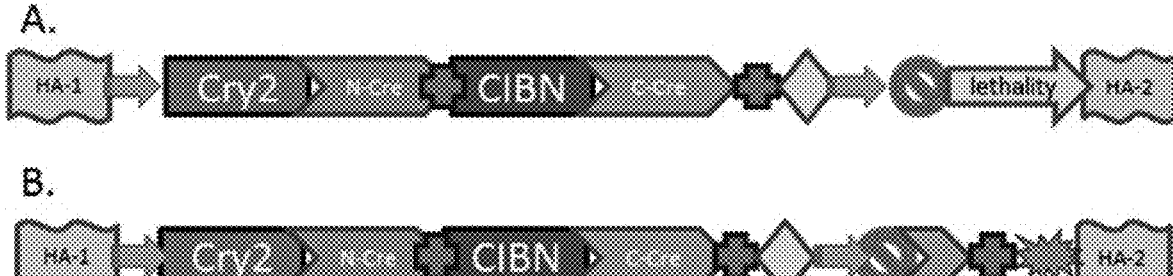
B.
Elements:
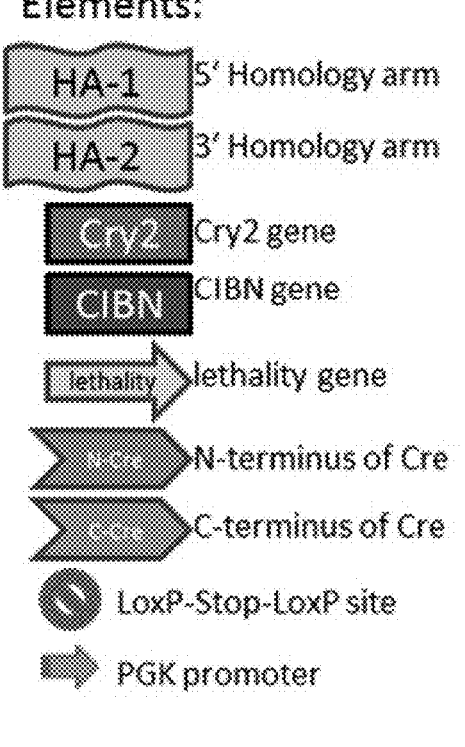
HA-1  5' Homology arm
HA-2  3' Homology arm
Cry2  Cry2 gene
CIBN  CIBN gene
lethality  lethality gene
N-terminus of Cre
C-terminus of Cre
LoxP-Stop-LoxP site
PGK promoter
Internal Ribosome Entry Site
(IRES)
Fluorescent reporter gene
Cas9
sgRNA
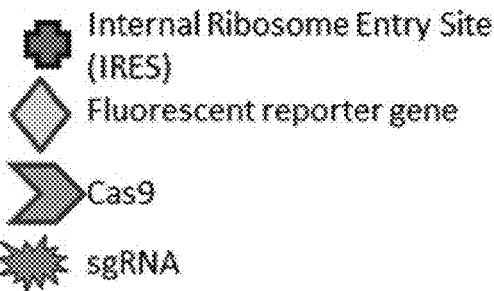

All guides
Scored by inverse likelihood of offtarget binding

| Guide # | Score | Sequnce | PAM | SEQ ID NO: |
|---|---|---|---|---|
| Guide #1 | 92 | GCCAAATAAG GCACGTTATC | TGG | 66 |
| Guide #2 | 87 | AATGTGGAAA CGGCCAAATA | AGG | 67 |
| Guide #3 | 86 | ACCAGATAAC GTGCCTTATT | TGG | 68 |
| Guide #4 | 84 | ACATGACAGC ACGATTTTGT | AGG | 69 |
| Guide #5 | 84 | CTGGTATGAA CCAATCAGAG | TGG | 70 |
| Guide #6 | 81 | TGGTATGAAC CAATCAGAGT | GGG | 71 |
| Guide #7 | 77 | GACCTTGATG CAGAGAAAC | AGG | 72 |
| Guide #8 | 63 | CTCCTGTTTT CTCTGCATCA | AGG | 73 |
| Guide #9 | 54 | GCAGAGAAAA CAGGAGAAGA | AGG | 74 |
| Guide #10 | 52 | AGAAGGATGA GAAAAGAATG | TGG | 75 |
| Guide #11 | 41 | CTGTCATGTC CCACTCTGAT | TGG | 76 |
| Guide #12 | 38 | ATGAGAAAG AATGTGGAAA | CGG | 77 |

FIG. 6B

Off-target analysis of guide #1: GCCAAATAAGGCACGTTATC  PAM - TGG
Quality score:92
On-target locus: chrZ:-44763868

Top 10 genome-wide off-target sites

| SEQ ID NO: | Sequence | PAM | Score | Mismatches | UCSC | Locus |
|---|---|---|---|---|---|---|
| 78 | CCAACAGAAG GCACGTTATC | CAG | 0.9 | 4MMs(1:3:5:7) | | chr2:+3150554 |
| 79 | TCAAAATAAA GTACGTTATC | TAG | 0.7 | 4MMs(1:3:10:12) | | chr3:+47694240 |
| 80 | GGCATATAAA GCACGTTAT | CAG | 0.6 | 4MMs(2:5:10:20) | | chr5:+5997053 |
| 81 | GCATAATAAT GTACGTTATC | TGG | 0.6 | 4MMs(3:4:10:12) | | chr5:-32615473 |
| 82 | ACTAAATCAG GCACGTGATC | TGG | 0.6 | 4MMs(1:3:8:17) | | chr1:-120450563 |
| 83 | GCTAAATTAA GCTCGTTATC | GGG | 0.5 | 4MMs(3:8:10:13) | | chr9:-2097883 |
| 84 | GTCAAATGAG GCATGTTATC | AGG | 0.4 | 3MMs(2:8:14) | | chr1:+41801139 |
| 85 | TTCAAATAAG CCACGTTATT | CAG | 0.4 | 4MMs(1:2:11:20) | | chr1:-85990782 |
| 86 | GTCAAACAAG GCATGTTATC | AGG | 0.3 | 3MMs(2:7:14) | NM_001285201 | chr1:-41801985 |
| 87 | CCCTAATAAA GCACGTTTTC | AGG | 0.3 | 4MMs(1:4:10:18) | | chr1:-46220994 |

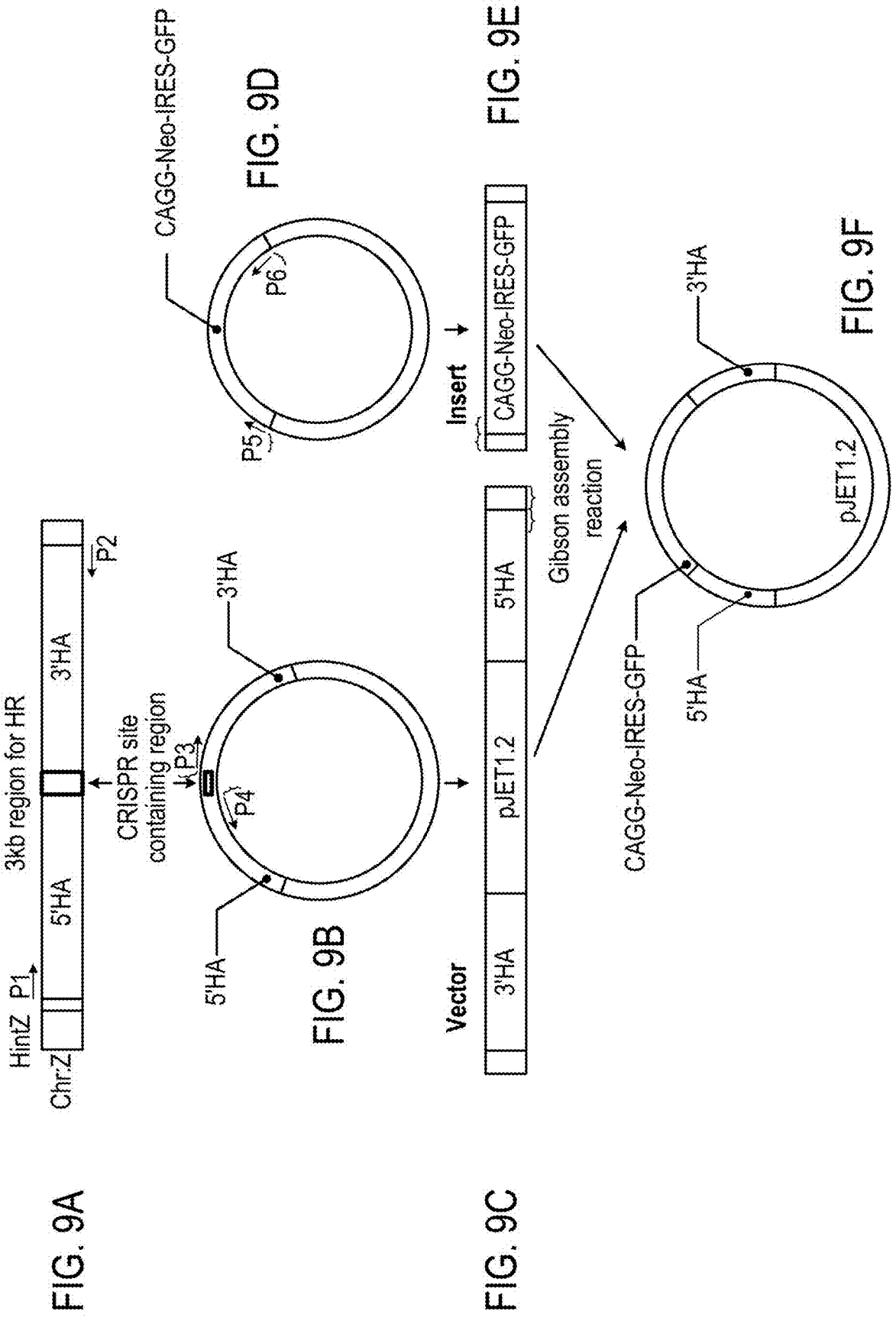

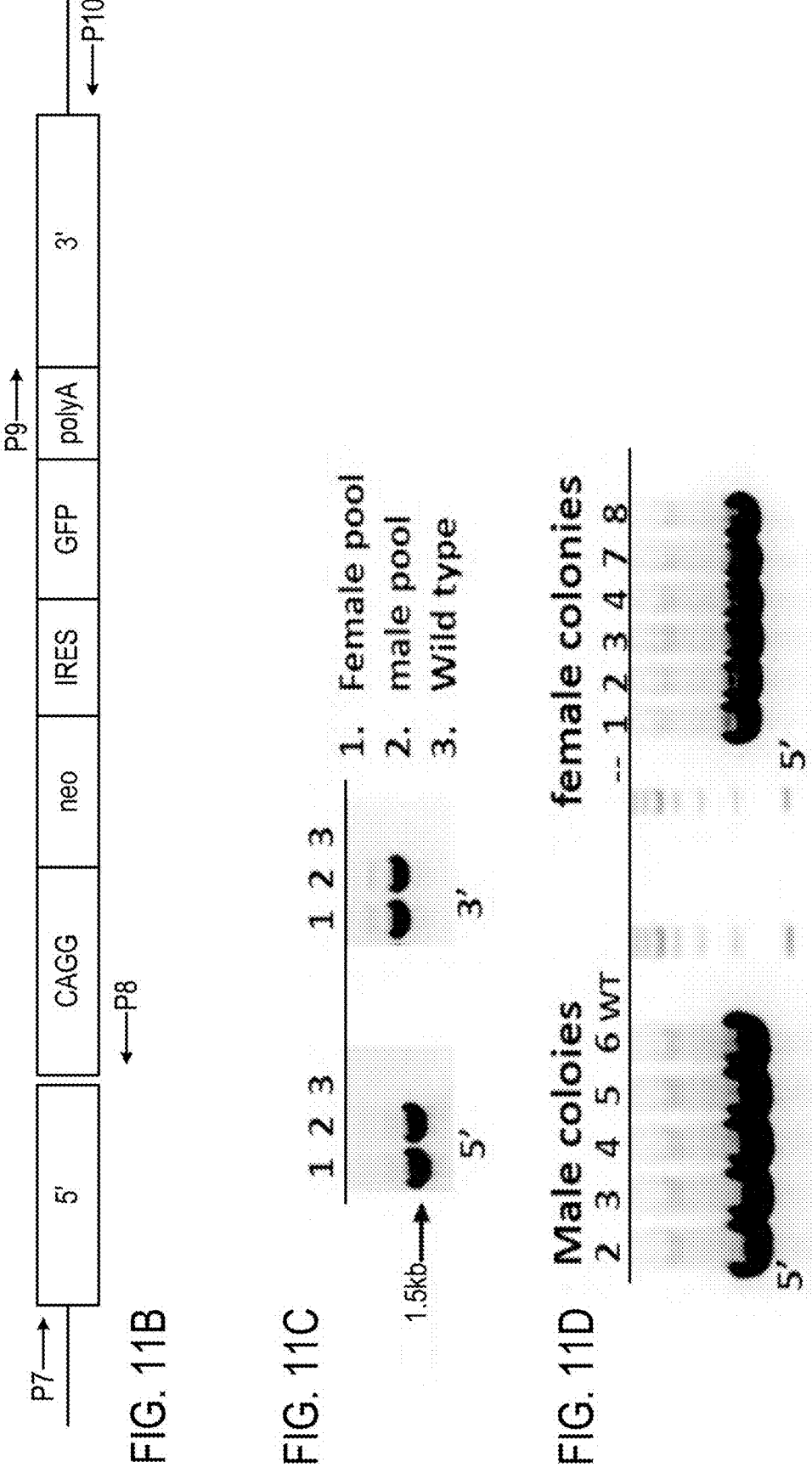

FIG. 12A
FIG. 12B
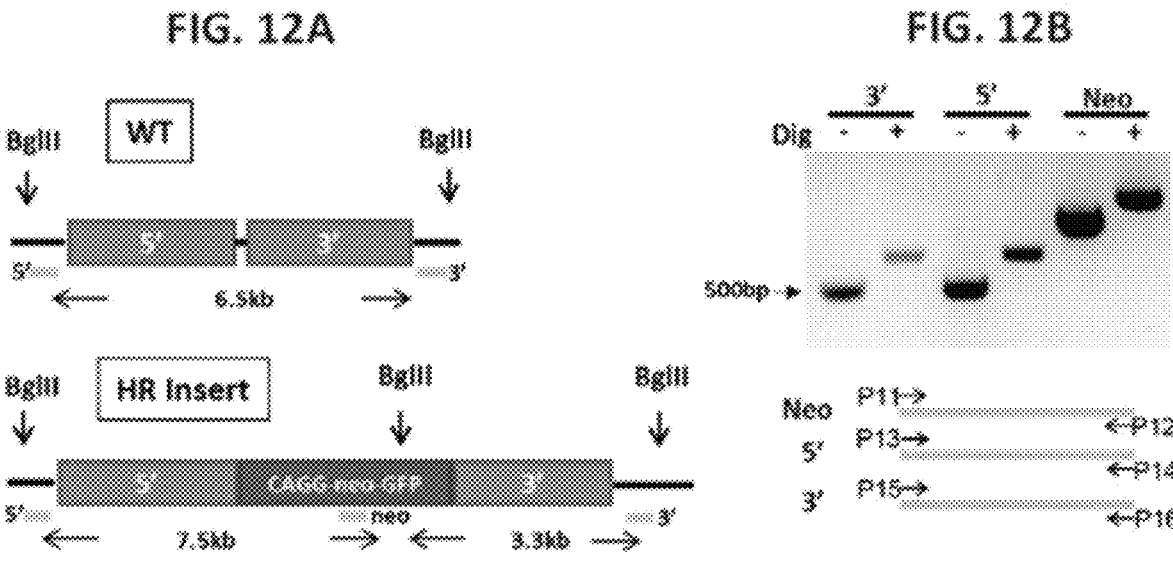
FIG. 12C
FIG. 12D
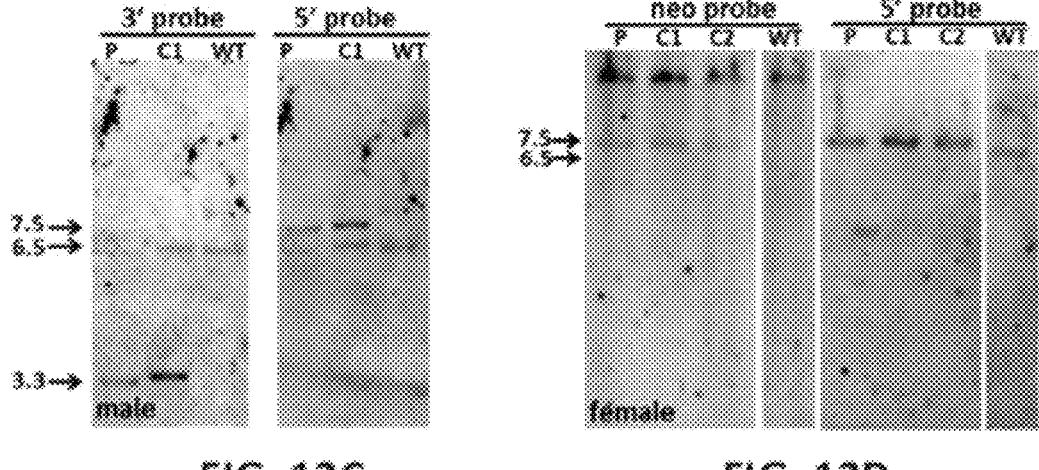

TV4-Cre

TV4-FlpO
Dark

TV4-FlpO
Light

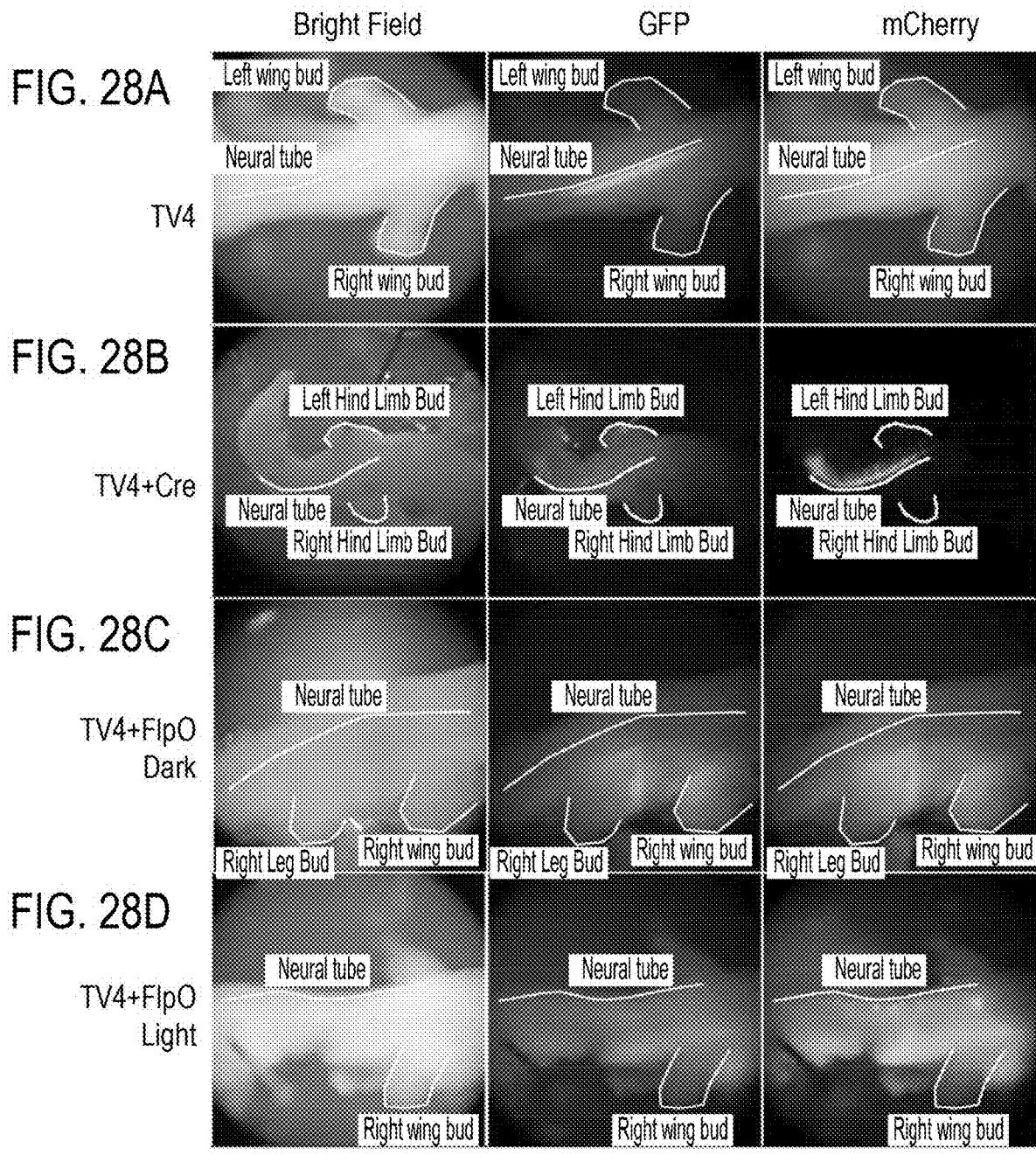

TV1+FlpO
No light
induction

TV1+FlpO
Blue light
induction

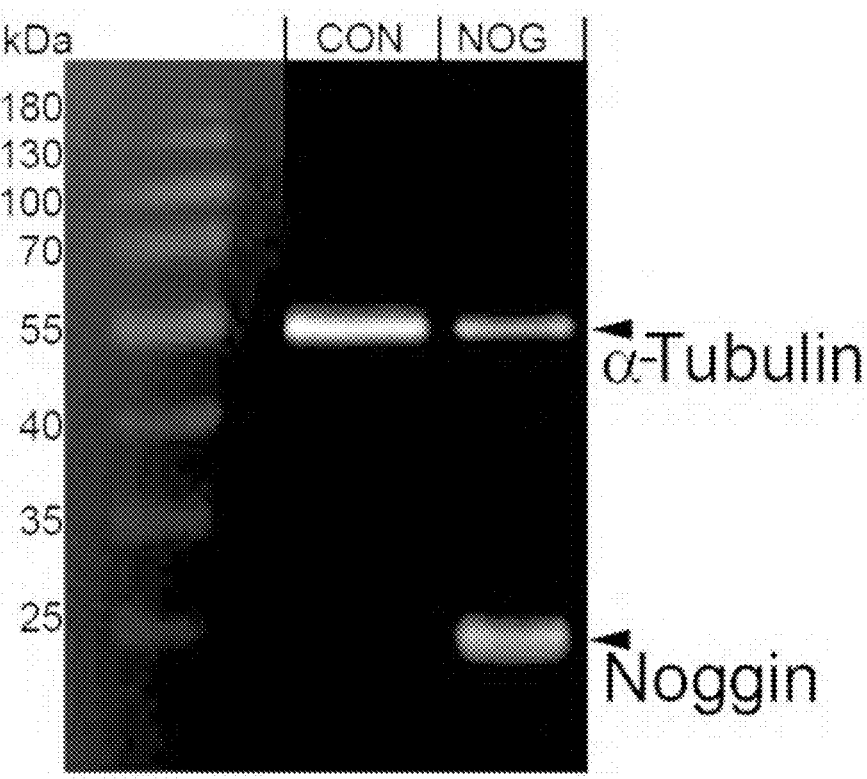
FIG. 30A
FIG. 30B                    FIG. 30C
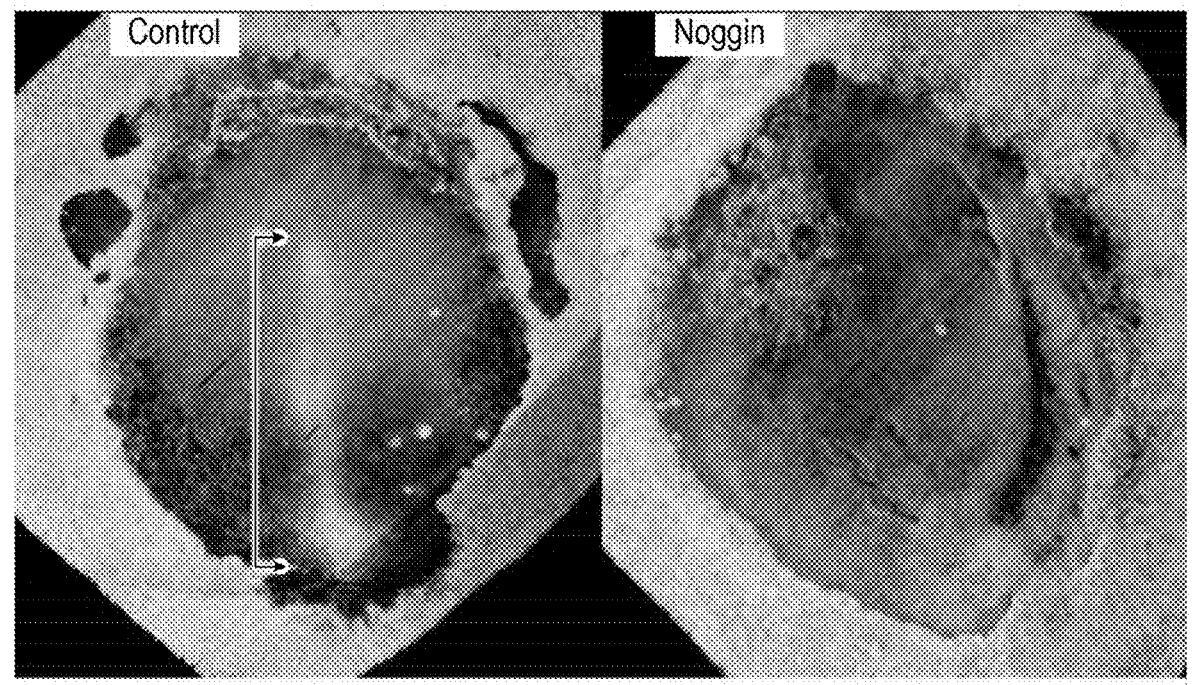

GENOME-EDITED BIRDS

CROSS-REFERENCE TO RELATED APPLICATIONS

This application is a National Phase Application of PCT International Application No. PCT/IL2020/050242, International Filing Date Mar. 3, 2020, claiming the benefit of U.S. Provisional Patent Application No. 62/814,162, filed Mar. 5, 2019, which are hereby incorporated by reference.

SEQUENCE LISTING STATEMENT

The instant application contains a Sequence Listing which has been submitted electronically in ASCII format and is hereby incorporated by reference in its entirety. The ASCII copy, created on Feb. 24, 2020, is named P-585110-PC_ST25.txt and is 355.8 KB in size.

TECHNICAL FIELD

The present disclosure relates to DNA editing agents, and their use in preparing DNA-edited cells and birds. The present disclosure further relates to methods of conferring a conditionally-lethal phenotype to male embryos in eggs of DNA-edited birds.

BACKGROUND

The ZW sex-determination system is a chromosomal system that determines the sex of offspring in birds, some fish and crustaceans, some insects, and some reptiles. The letters Z and W are used to distinguish this system from the XY sex-determination system. In the ZW system, the ovum determines the sex of the offspring. Males are the homogametic sex (ZZ), while females are the heterogametic sex (ZW). The Z chromosome is larger and has more genes, like the X chromosome in the XY system.

Early gender identification and separation are important aspects of all avian commercial applications, in particular in the edible eggs industry. For broilers and turkeys, gender separation allows a better suited management and feeding schemes according to the different needs of the two genders. Essentially all commercial hatcheries use gender separation of flocks. Male chickens, which are of lower commercial value, are culled at the hatchery, whereas female chickens are used for egg production.

Currently, there are three methods available for determining the gender of poultry. The gender of day-old chicks can be determined either by vent/cloaca identification, or by feather-typing methods. Alternatively, male and female chicks can be grown together until secondary gender characteristics become apparent, then the chicks can be separated based on gender. Vent/cloaca typing relies on the appearance of gender-related anatomical structures. Feather typing is based on feather characteristics that differ between male and female chicks, for example down color pattern, and rapid/slow rate of growth of the wing feathers. The third method relies on the appearance of natural secondary gender characteristics, for example in males the combs and wattles become larger than those on females.

The vent/cloaca gender determination of day-old chicks is difficult and expensive. Identifying the gender of a bird requires highly skilled personnel. While easier to perform, feather typing has the disadvantage of being limited to specific genetic crosses of birds. Gender typing by secondary gender characteristics is the easiest method to perform but has the disadvantage of requiring birds of both genders to be grown together for the first weeks after hatching, which because of feed costs and feed conversion considerations can be more expensive to the hatchery than the expense of vent/cloaca typing.

Most importantly, only in the US and Europe, almost a billion of male chicks are destroyed by different methods every year. This is not only an economic problem, but it increasingly becomes an ethical problem.

There is a need in the field of commercial hatcheries for high-throughput methods for preventing the production of male chicks, preferably even at the egg stage, thus avoiding the problems associated with viable male chicks.

SUMMARY OF INVENTION

Provided here is a technology, including compositions and methods, for in-ovo destruction of male embryo chicks. Such compositions and methods are beneficial as they allow a person skilled in the field of bird propagation, such as a farmer, to skew the natural 1:1 ratio between males and female offspring in favor of the more commercially-useful female offspring.

In one embodiment, provided herein is a DNA editing agent comprising a polynucleotide cassette having a formula 5'-LHA (left homology arm)-OIE (optogenetic-inducible element)-LIE (lethality-inducing element)-RHA (right homology arm)-3' or a formula 5'-LHA-LIE-OIE-RHA-3', wherein (i) the LHA comprises a first nucleotide sequence that is substantially homologous to a first corresponding nucleotide sequence on chromosome Z of a bird; (ii) the OIE comprises a first promoter functionally linked to a second nucleotide sequence encoding an inducer-activated site-specific recombinase enzyme; (iii) the LIE comprises a third nucleotide sequence encoding a lethality-promoting protein, which is operatively linked to the activity of the inducer-activated site-specific recombinase enzyme; and (iv) the RHA comprises a fourth nucleotide sequence that is substantially homologous to a second corresponding nucleotide sequence on chromosome Z of a bird.

In certain embodiments, one or both of the LHA and RHA are substantially homologous to a corresponding nucleotide sequence located in an openly transcribed region on chromosome Z of a bird. For example, the openly transcribed region can be located at or downstream to the histidine triad nucleotide binding protein 1-Z (HINT1Z) locus on chromosome Z of a bird.

In certain embodiments, the inducer-activated site-specific recombinase enzyme can be Cre recombinase (Cre) (SEQ ID NO: 113), or Mag (SEQ ID NO: 114 and SEQ ID NO: 65). In certain embodiments, the expression of the inducer-activated site-specific recombinase enzyme is induced by an inducer. In certain embodiments, the inducer is electromagnetic energy. For example, the inducer can be blue light having a wavelength of 450-485 nm.

In certain embodiments, the inducer-activated site-specific recombinase enzyme comprises non-functional peptide fragments of an inducer-activated site-specific recombinase that combine to form an active inducer-activated site-specific recombinase enzyme in the presence of the inducer.

In certain embodiments, the lethality-inducing protein can be a toxin, a pro-apoptotic protein, an inhibitor of the Wingless/Integrated (Wnt) signaling pathway, a bone morphogenetic protein (BMP) antagonist, a fibroblast growth factor (FGF) antagonist, a wild type Caspase 3, a constitutively active Caspase 3, Noggin, or a lethality-inducing fragment of any of the above proteins.

In one embodiment, the DNA editing agent disclosed herein comprises (i) a LHA comprising the sequence of SEQ ID NO:105, (ii) an OIE comprising the sequence of SEQ ID NO:100, which is connected to the sequence of SEQ ID NO:116, which is connected to the sequence of SEQ ID NO:101, which is connected to the sequence of SEQ ID NO:103, which is connected to the sequence of SEQ ID NO:102, which is connected to the sequence of SEQ ID NO:104, which is connected to the sequence of SEQ ID NO:116, or the OIE comprises the sequence of SEQ ID NO:100, which is connected to the sequence of SEQ ID NO:116, which is connected to the sequence of SEQ ID NO:102, which is connected to the sequence of SEQ ID NO:103, which is connected to the sequence of SEQ ID NO:101, which is connected to the sequence of SEQ ID NO:104, which is connected to the sequence of SEQ ID NO:116, or the OIE comprises the sequence of SEQ ID NO:100, which is connected to the sequence of SEQ ID NO:116, which is connected to the sequence of SEQ ID NO:107, which is connected to the sequence of SEQ ID NO:103, which is connected to the sequence of SEQ ID NO:108, which is connected to the sequence of SEQ ID NO:104, which is connected to the sequence of SEQ ID NO:116, or the OIE comprises the sequence of SEQ ID NO:100, which is connected to the sequence of SEQ ID NO:116, which is connected to the sequence of SEQ ID NO:108, which is connected to the sequence of SEQ ID NO:103, which is connected to the sequence of SEQ ID NO:107, which is connected to the sequence of SEQ ID NO:104, which is connected to the sequence of SEQ ID NO:116, (iii) a LIE comprising the sequence of SEQ ID NO:92, or SEQ ID NO:94, or SEQ ID NO:96, or SEQ ID NO:98, and (iv) a RHA comprising the sequence of SEQ ID NO:106.

In certain embodiments, the polynucleotide cassettes disclosed herein can be applied to a bird such as a chicken, a turkey, a duck, a goose, a quail, a pheasant, or an ostrich.

In another embodiment, the present disclosure further provides bird cells that contain the polynucleotide cassettes disclosed herein. In another embodiment, there is provided a chimeric bird comprising bird cells that contain the polynucleotide cassettes disclosed herein.

Further provided, in another aspect, are methods of using the DNA editing agent disclosed herein to generate a chimeric bird. In certain embodiments, the methods comprise the steps of contacting the cells of a bird with the exogenous polynucleotide cassettes disclosed herein, thereby generating genome-edited bird cells, and then transferring these genome-edited bird cells to recipient bird embryos. Further provided, in another aspect, are chimeric birds generated from the above methods.

Further provided, in another aspect, is a method of inducing lethality in a male embryo of a bird, comprising the steps of administering the DNA editing agent disclosed herein to a population of bird cells, thereby generating genome-edited bird cells; transferring these genome-edited bird cells to recipient bird embryos; and exposing the embryos to an inducer that elicits expression of the lethality-promoting protein encoded by the DNA editing agent, thereby inducing lethality in male embryos of the bird.

In another embodiment, the DNA editing agent disclosed herein further comprises a safe-lock element inserted downstream to the promoter in the OIE but upstream of the sequence encoding the inducer-activated site-specific recombinase. The safe-lock element comprises nucleotide sequences (STOP element) that prevent transcription of the inducer-activated site-specific recombinase encoded by the OIE. In one embodiment, the STOP element is flanked by two FRT sites. In one embodiment, each of the DNA editing agents having the sequence of one of SEQ ID NOs:120-127 comprises a safe-lock element. Further provided, in another aspect, is a method of using DNA editing agent that contains a safe-lock element to generate a chimeric bird.

In another embodiment, there is provided a method of using DNA editing agent that contains a safe-lock element to induce lethality in a male embryo of a bird, the method comprises the steps of: administering such DNA editing agent to a population of bird cells, thereby generating genome-edited bird cells; transferring these genome-edited bird cells to recipient bird embryos; and exposing the embryos to an agent that removes the STOP element from the DNA editing agent, thereby eliciting expression of the lethality-promoting protein encoded by the DNA editing agent and inducing lethality in male embryos of the bird.

Unless otherwise defined, all technical and/or scientific terms used herein have the same meaning as commonly understood by one of ordinary skill in the art to which an aspect or an embodiment pertains. Although methods and materials similar or equivalent to those described herein can be used in the practice or testing of embodiments of an aspect, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the office upon request and payment of the necessary fee.

Some embodiments are herein described, by way of example only, with reference to the accompanying drawings. With specific reference now to the drawings in detail, it is stressed that the particulars shown are by way of example and for purposes of illustrative discussion of certain embodiments. In this regard, the description taken with the drawings makes apparent to those skilled in the art how embodiments may be practiced.

Figure 1:
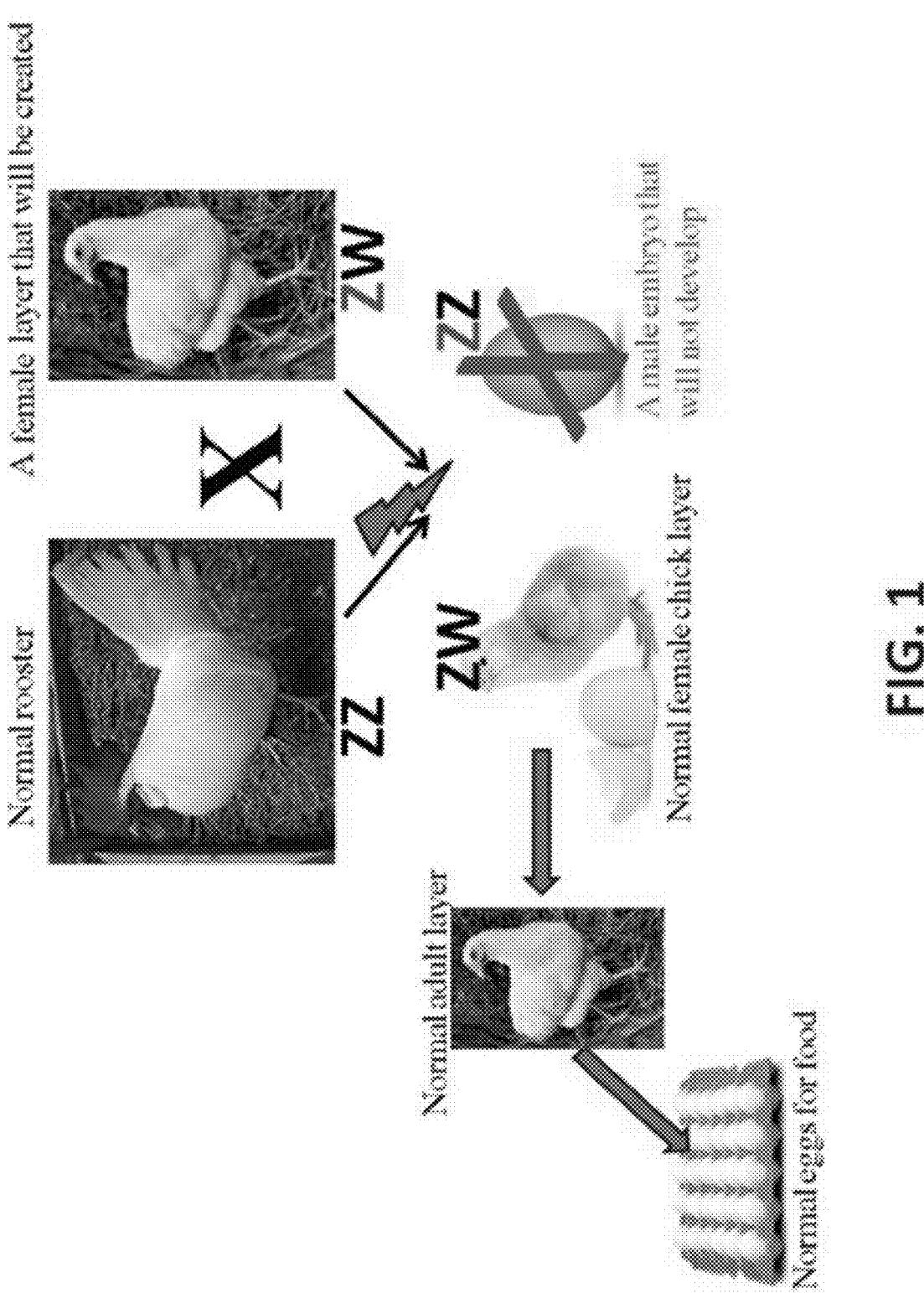

The subject matter regarded provided herein is particularly pointed out and distinctly claimed in the concluding portion of the specification. The embodiments, however, both as to organization and method of operation, together with objects, features, and advantages thereof, may best be understood by reference to the following detailed description when read with the accompanying drawings in which:

FIG. 1 is a cartoon illustrating an embodiment of the generation of an optogenetic inducible chicken line from which only female layer chicks will hatch. By crossing wild-type rooster (ZZ) with genetically modified hen (ZW) all the female fertile eggs will carry wild-type ZW chromosomes. All the male fertile eggs will carry the ZZ chromosomes in which the genetically modified Z is derived from the genetically modified hen's genome. Upon blue light illumination of fertile eggs, the optogenetic system on this genetically modified chromosome will become active and will activate a death mechanism that will result in early male embryonic mortality soon after oviposition. The females which will not be affected by the blue light illumination will hatch, grow to adulthood and will lay unfertile eggs for food.

FIG. 2 illustrates an embodiment of a strategy to control gene expression by means of blue light illumination. Two fusion proteins are created: Cry2 with the non-active N-terminus of Cre (Cry2-CreN-term) and CIBN fused with the non-active C-terminus of Cre (CIBN-Cre-C-term). Without blue light illumination the Cre is inactive. Upon blue light illumination, Cry2 and CIBN form a complex and the two parts of Cre are brought together to form an active Cre enzyme.

Figure 3:
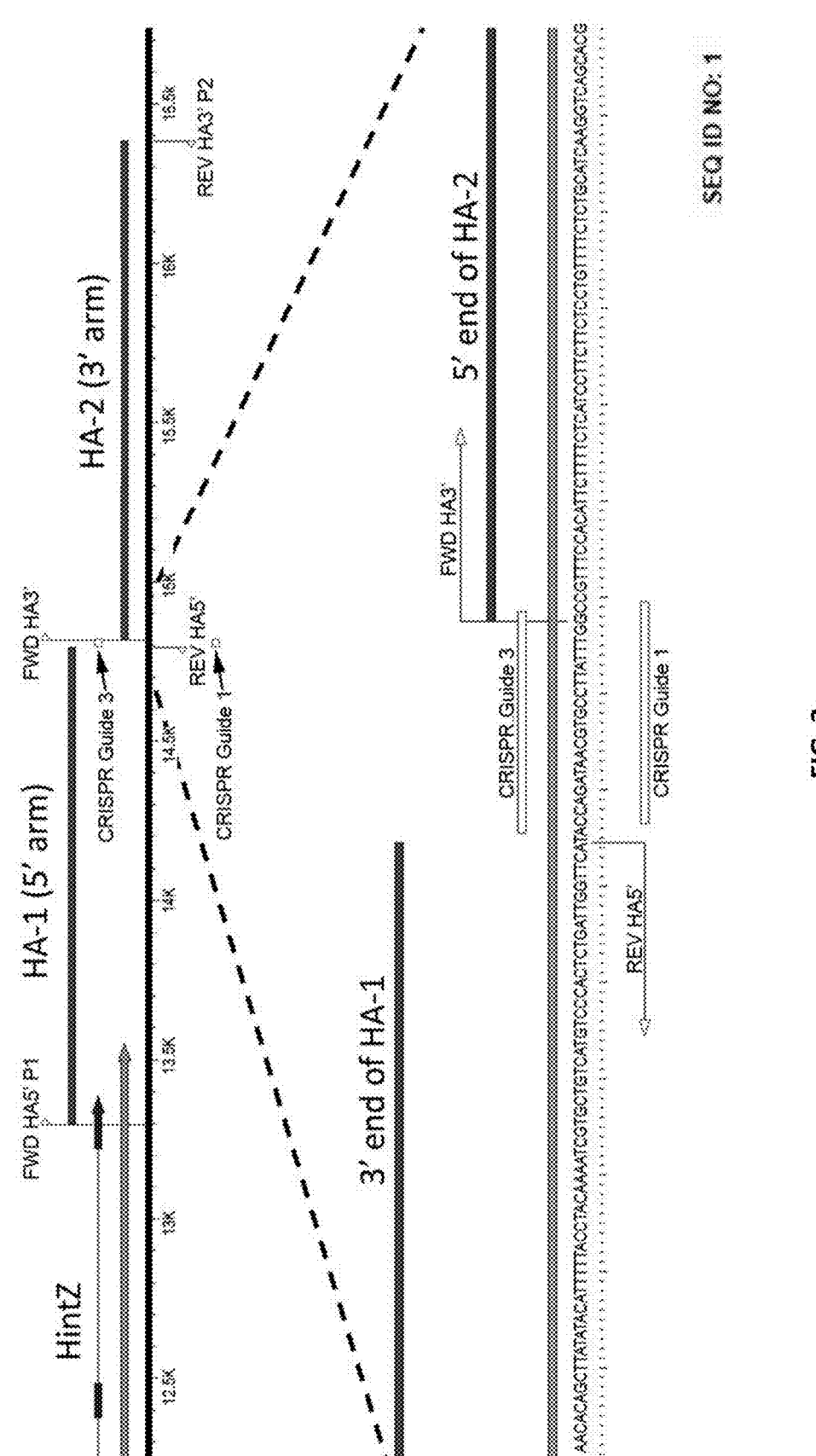

FIG. 3 illustrates an embodiment of the homology arms on chromosome Z. The genomic region downstream to the HINT1Z locus is depicted. The 5' and 3' arms are HA-1 (Left homology arm; LHA) and HA-2 (Right homology arm; RHA), respectively. The primers for amplifying the arms are indicated by hollow arrows (FWD HA5' P1 & REV HA3' P2). In between the homology arms, on both DNA strands, there are sequences for CRISPR-Cas9 (open boxes, CRISPR Guide 1 & 3). Lower part of FIG. 3 shows in high detail the region between the two homology arms. The sequence set forth in SEQ ID NO: 1 is illustrated, including the LHA-CRISPR-RHA fragments.

Figures 4A, 4B:
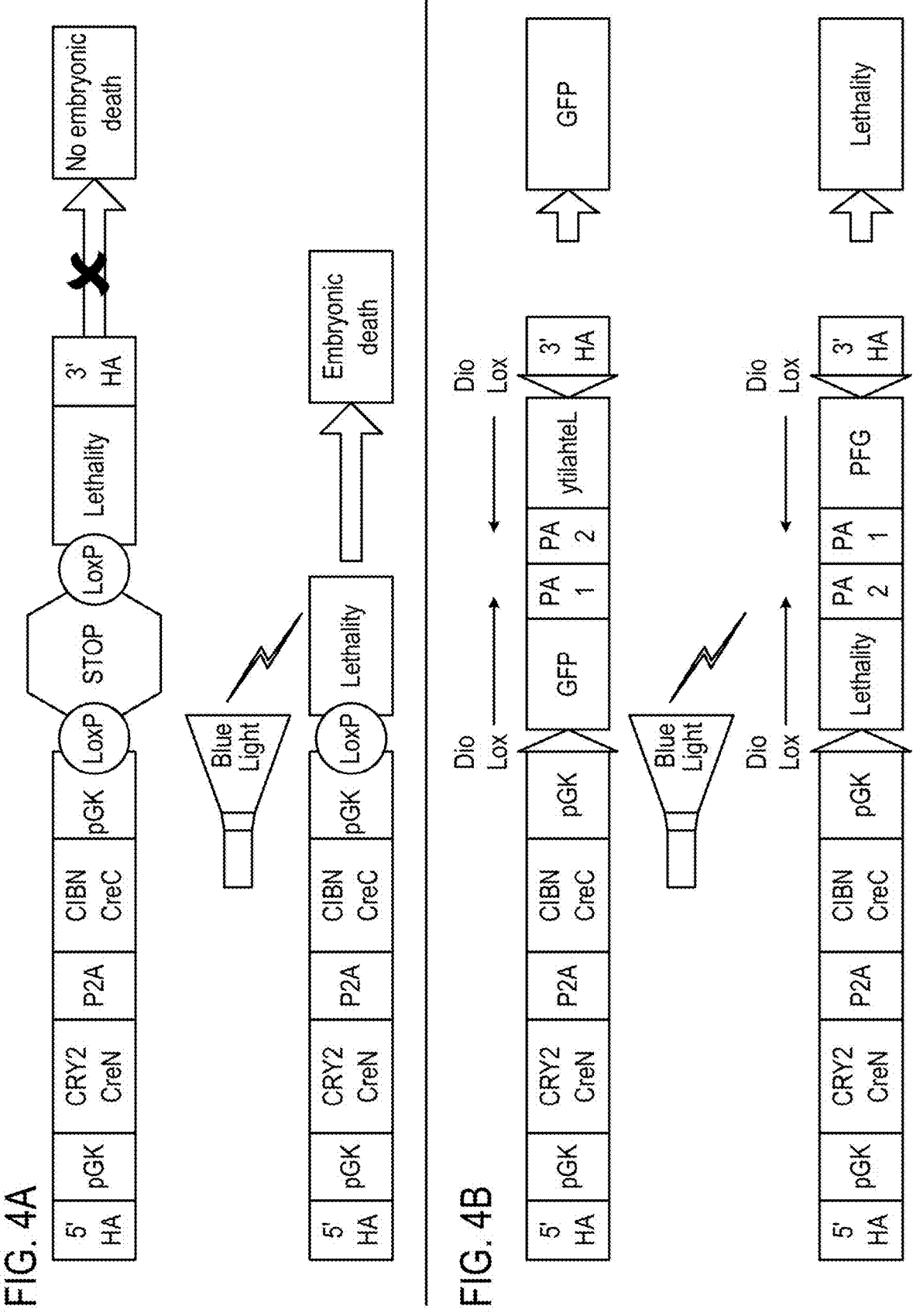

FIGS. 4A-4C illustrate different embodiments of targeting vectors or DNA editing agents. FIG. 4A shows a targeting vector containing 3 main elements. The first, the 5' and 3' homology arms (HA) for homologous recombination (HR), flanking the entire exogenous insertion cassette. The second element is a light-inducible system—in this case the Cry2-CreN and the CIBN-Cre-C. The third element is the lethality gene cassette. In one embodiment of a single targeting vector strategy, the 5' HA is followed by a pGK promoter that drives the expression of the Cry2-CreN and the CIBN-Cre-C genes, which are separated by a self-cleaving peptide P2A. This element is followed by the exogenous lethality gene cassette which contains a pGK promoter followed by a LoxP-STOP-LoxP site (LSL), which is followed by a lethality-inducing gene. This exogenous cassette is followed by the 3' HA. Upon light induction, the Cry2-CreN and the CIBN-Cre-C dimerize to form an active form of Cre. The latter then excises the LSL element, thus allowing expression of the lethality-inducing gene, which leads to embryonic death in all embryos that carry this vector. FIG. 4B shows an alternative approach. Instead of using the LSL element, a Dio-lox flipping strategy is used. In between the Dio-Lox sites a GFP is followed by polyadenylation site #1 (PA1), and a lethality gene is followed by a different polyadenylation site #2 (PA2) in a reverse orientation. In this case, prior to light activation, the pGK promoter drives the expression of the GFP. Upon light activation, the cassette between the Dio-Lox sites flips and the lethality gene is now in the right orientation to be expressed while the GFP is now place in a reverse orientation and it is no longer active. FIG. 4C shows yet another embodiment. Following the activation of Cre, the LSL is removed and the Cas9 and single guide RNA (sgRNA) are expressed. This leads to the introduction of a missense mutation in the coding region of an essential gene (targeted by the sgRNA), thus inducing embryonic lethality.

Figures 5A, 5B, 5C, 5D, 5E, 5F:
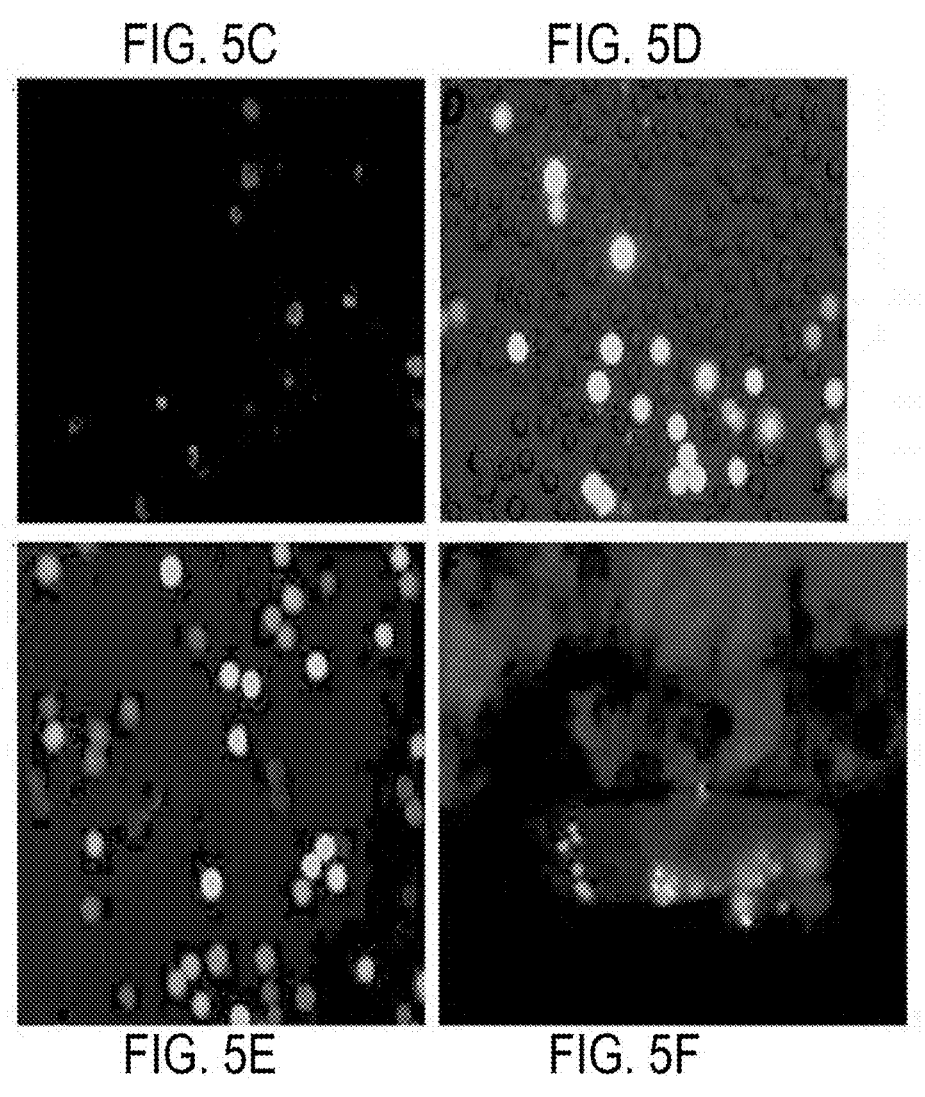

FIGS. 5A-5F: PGCs line derivation and characterization. FIG. 5A, PGCs culture; FIG. 5B, left, mRNA expression of different pluripotent and germ-cells markers as indicated. Right, representative characterization of sex identification of female PGCs (left, two PCR products of Ribosomal S18 and W chromosome) and male PGCs (right, Ribosomal S18 only). FIG. 5C, PGCs staining with anti-SSEA1 antibodies. FIG. 5D, transfection of PGCs with pCAGG-GFP plasmid using Lipofectamine 2000 reagent. FIG. 5E, transfection of PGCs with pCAGG-GFP plasmid using electroporation. FIG. 5F, Gonad (testis) of an embryo, 10 days following transplantation with GFP-expressing cultured PGCs.

Figure 6A:
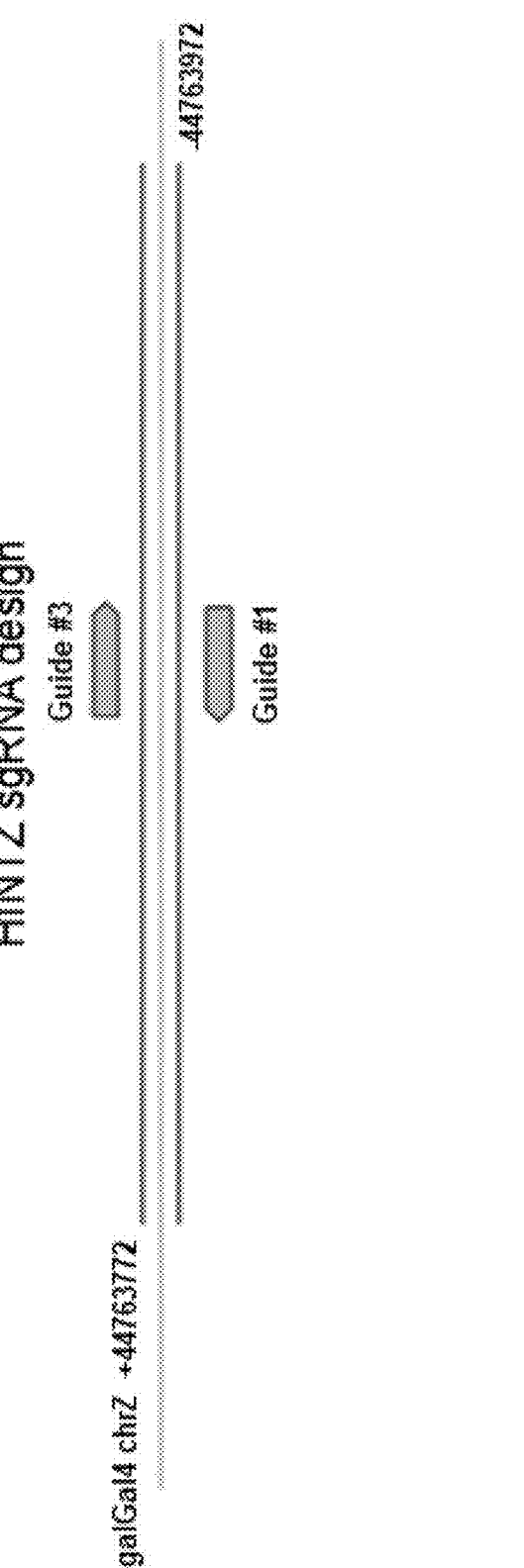

FIGS. 6A-6C. Designing the sgRNA sites for CRISPR-mediated targeting. FIG. 6A shows an example of the genomic area on the Z chromosome for potential CRISPR targeting sites. FIG. 6B shows 12 top sgRNA sequences (Guide #1-#12). Guides #1 and #3, which partially overlap, in opposite orientations, were chosen for further experiments. The 3-nucleotide PAM sequences are not part of the guide sequences, and the PAM sequences are not included in the SEQ ID NOs:66-77. The top 10 results of search for potential off-targets for guide #1 are shown in FIG. 6C. SEQ ID NOs:78-87 do not include the 3-nucleotide PAM sequences.

Figures 7A, 7B, 7C:
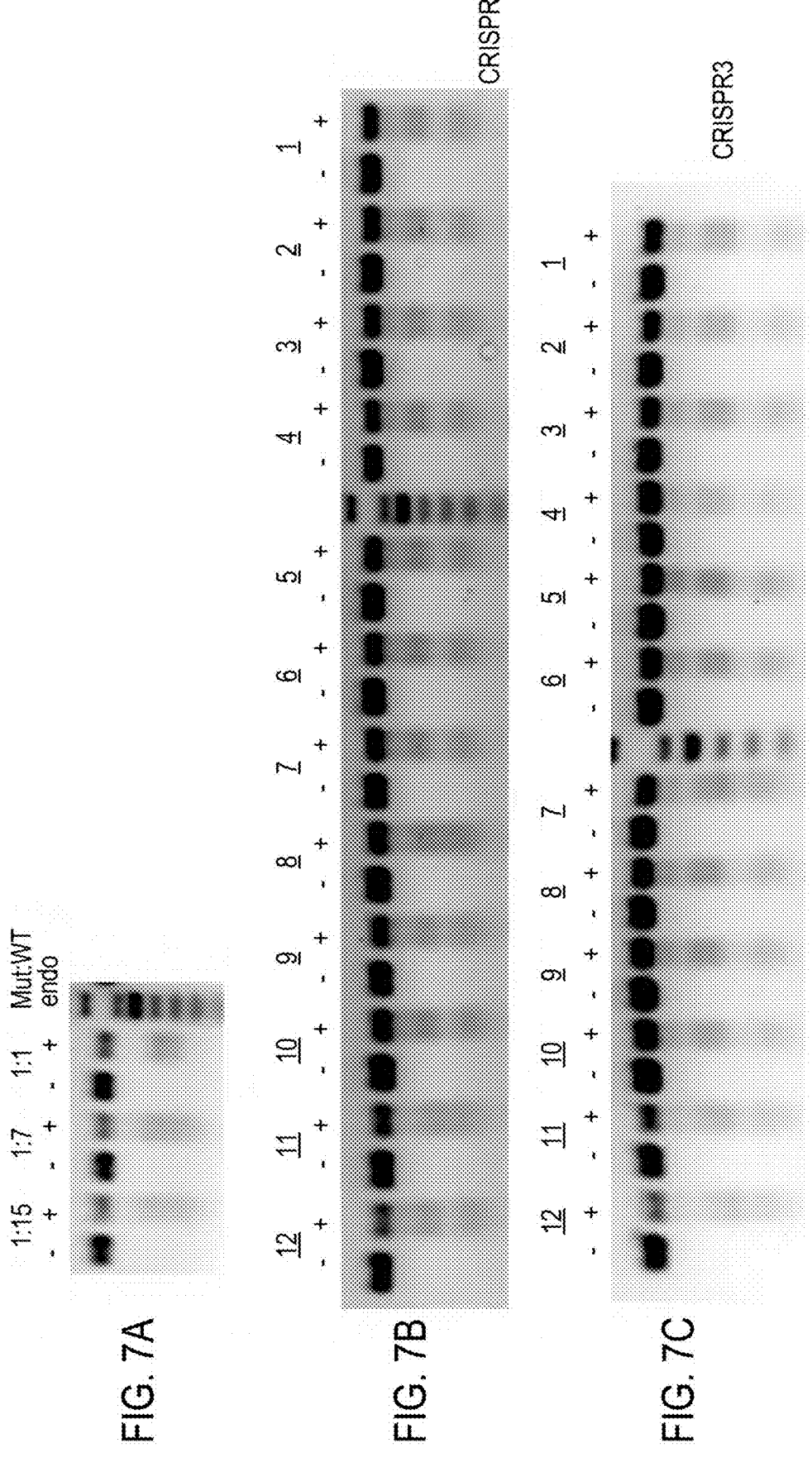

FIGS. 7A-7C. Validating CRISPR activity using endonuclease assay. FIG. 7A. Positive control of the endonuclease assay using annealed WT 320 bp PCR product and a mutated product at the predicted cleavage site of CRISPR1 at the indicated ratios. FIG. 7B. Endonuclease assay on 12 colonies transfected with CRISPR1 plasmid. FIG. 7C. Endonuclease assay on 12 colonies transfected with CRISPR3 plasmid. There is a 12 bp distance between the two predicted cleavage sites of CRISPR1 and CRISPR3.

Figures 8A, 8B, 8C, 8D:
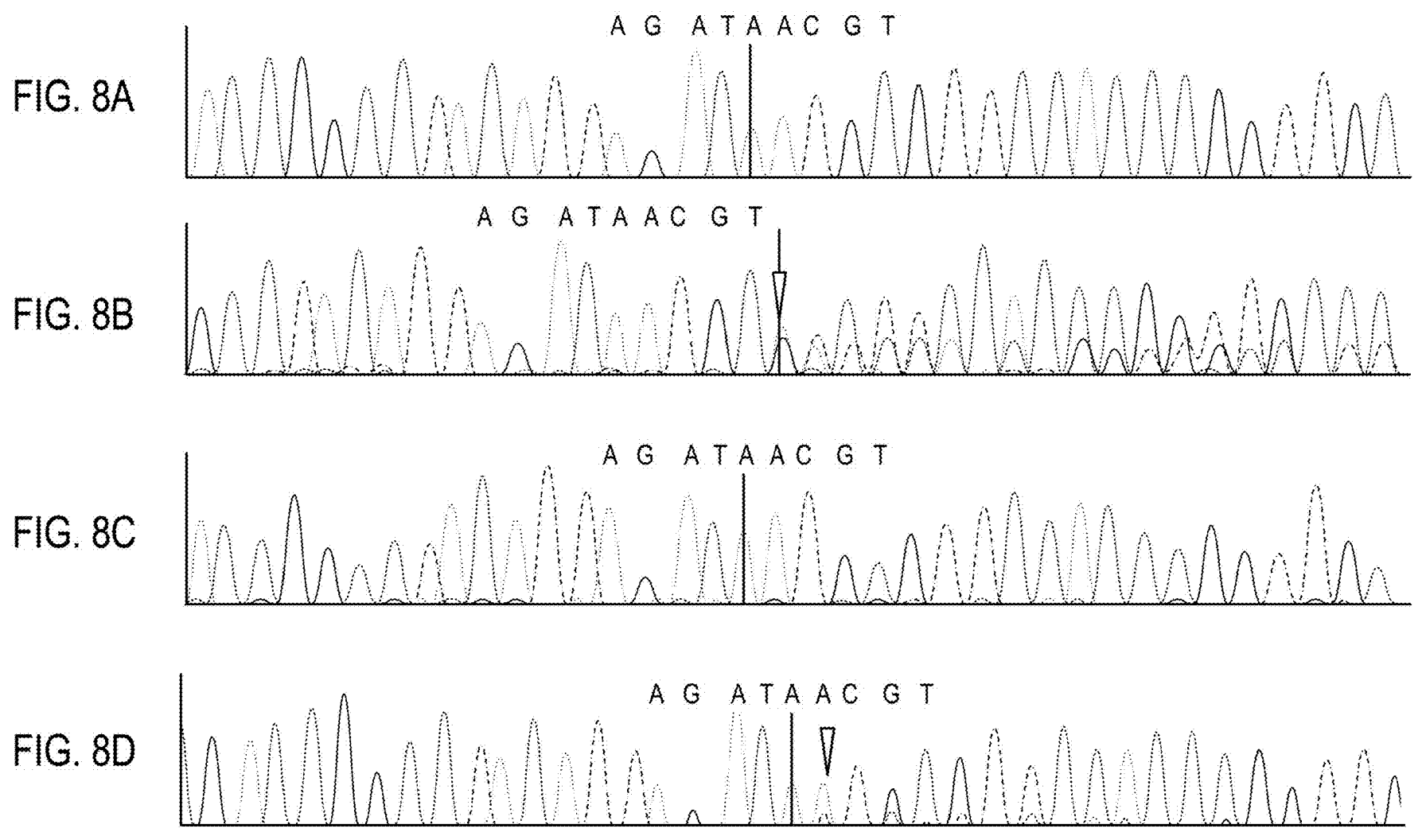

FIGS. 8A-8D. Validating CRISPR activity using DNA Sequencing. FIG. 8A. DNA chromatogram of wild type (WT) genomic region at the predicted cleavage site of CRISPR1, showing a normal sequence as a negative control. FIG. 8B. Sequence of mixture of WT and artificially mutated PCR products showing the appearance of double-peaks (arrowhead) after the predicted cleavage site, as a positive control. FIG. 8C. Sequencing of negative colony showing a normal sequence. FIG. 8D. Sequence of positive colony, showing the appearance of double peaks following the CRISPR1 cleavage site (arrowhead).

FIGS. 9A-9F. Constructing targeting vector for genome integration into the Z chromosome. FIG. 9A—Genomic DNA was used as a template for PCR reaction with primers P1 and P2 which are in the 5'HA and 3'HA regions (demarcated by dashed line), flanking the CRISPR-site-containing region. FIG. 9B—The ~3 kb product, located downstream to the HINT1Z locus was ligated to the shuttle vector pJet1.2. This plasmid was used as a template for PCR with primers P3 and P4. These primers have extension overhang sequences (demarcated by curly brackets) which correspond to the equivalent regions on the pCAGG-Neo-IRES-GFP fragment. FIG. 9C—The linearized product (the vector) containing the two homology arms, excluding the CRISPR-site-containing region, flanked by sequences which bind the ends of the pCAGG-Neo-IRES-GFP cassette during the Gibson reaction. FIG. 9D—The pCAGG-Neo-IRES-GFP plasmid was used as template for PCR reaction with primers P5 and P6. These primers contain extension overhang sequences (demarcated by curly brackets) which correspond to the equivalent regions on the edges of the homology arms. FIG. 9E—The linearized insert cassette flanked by sequences which bind the ends of the homology arms. The vector and the insert were stitched together by the Gibson assembly reaction to create the final targeting vector plasmid as shown in FIG. 9F.

Figures 10A, 10B, 10C, 10D:
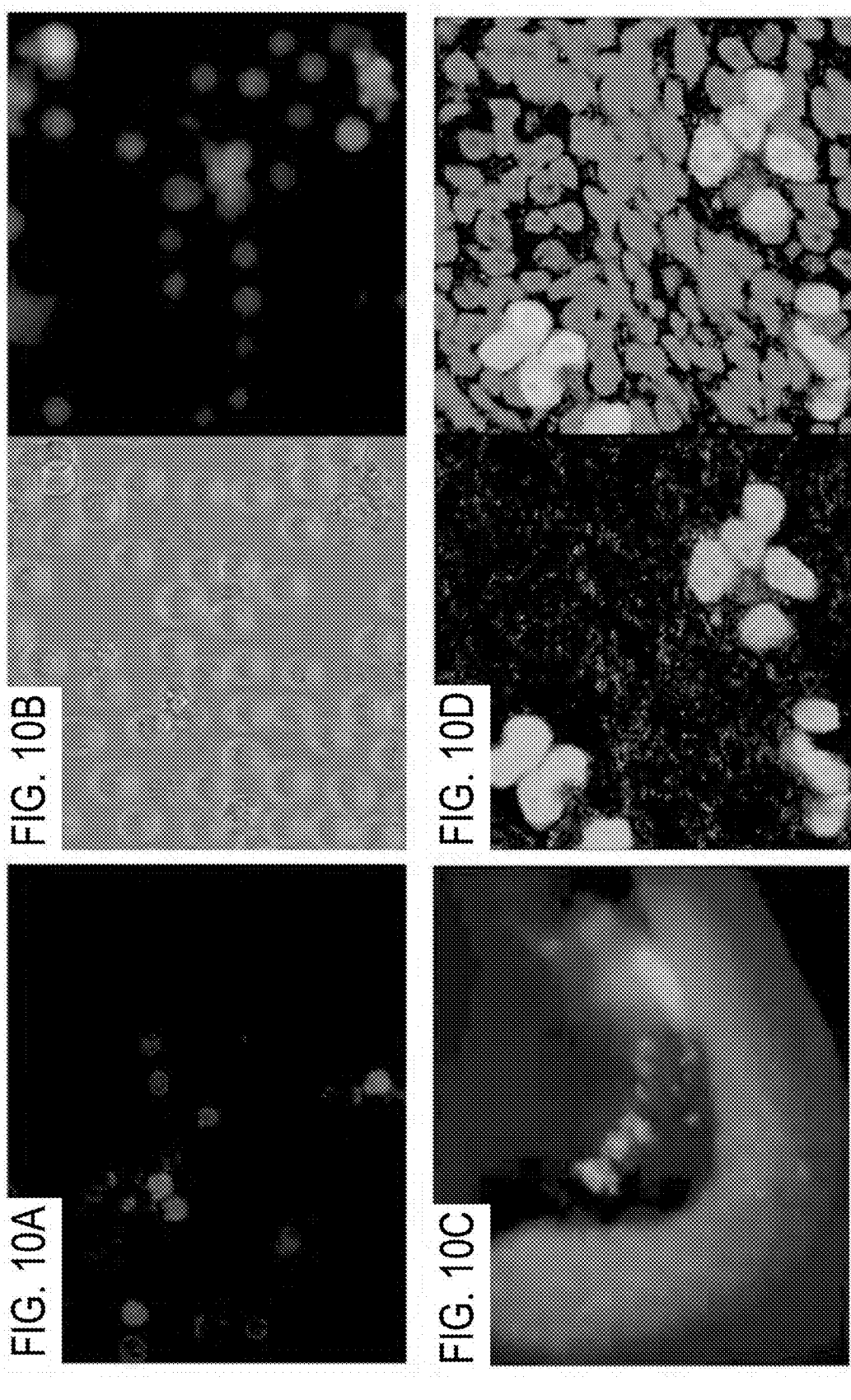

FIGS. 10A-10D. Co-transfection of targeting vector and CRISPR plasmids to PGCs. FIG. 10A. Lipofection-mediated co-transfection to PGCs with CRISPR1 and HR targeting vector plasmids. FIG. 10B. Two weeks after G-418 selection, >99% of the resistant PGCs were positive for GFP. FIG. 10C. Ten days following the injection of targeted PGCs to a host embryo, numerous cells were found to be localized in the gonads (testis). FIG. 10D. The gonads were dissected, immuno-stained with anti-GFP antibody, and scanned using confocal microscope (GFP antibody staining in green and nuclei counterstained with 4', 6 diamidino-2-phenylindole (DAPI) in blue).

Figure 11A:
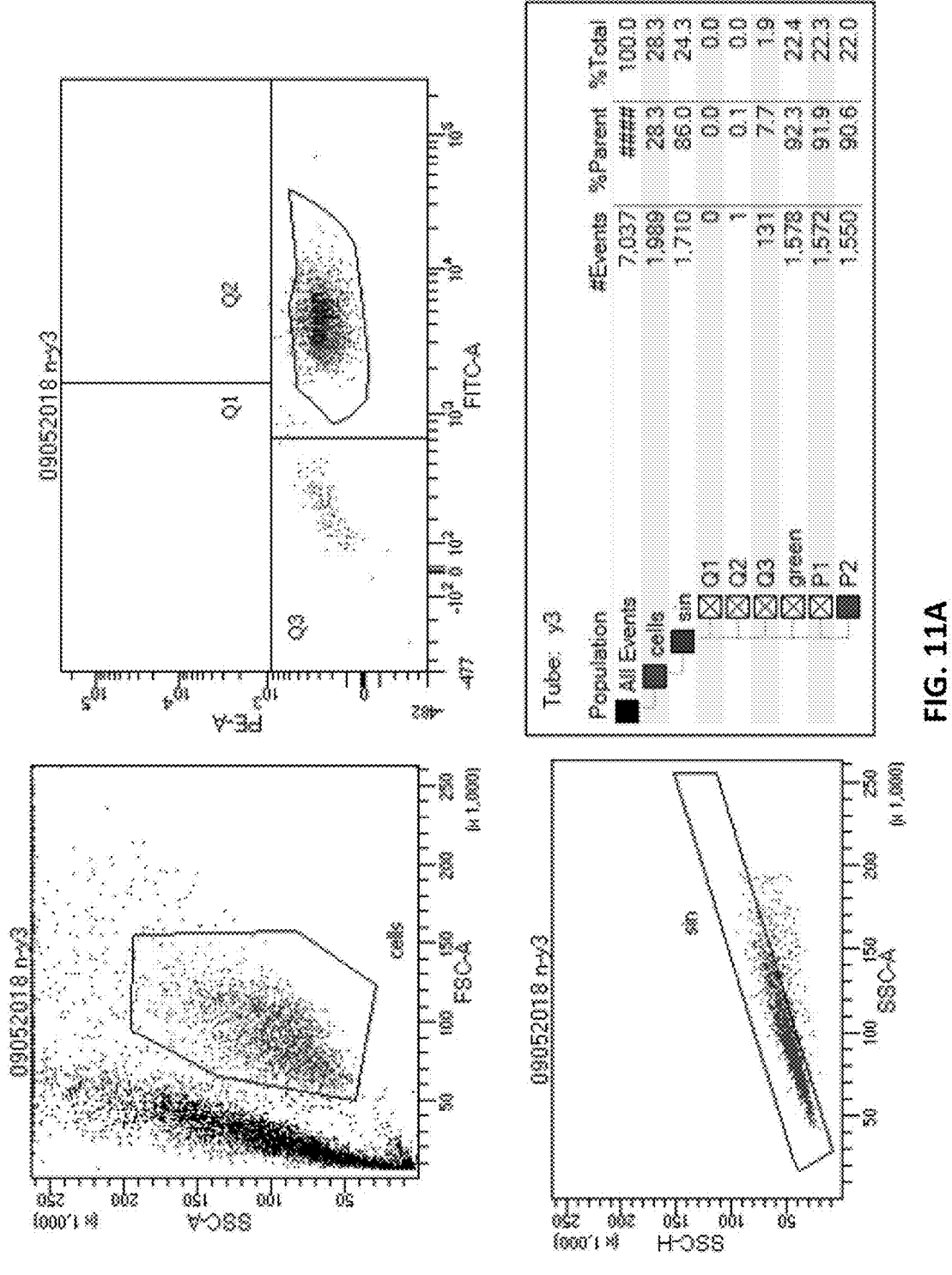

FIGS. 11A-11D. Verification of HR integration in FACS sorted PGCs. FIG. 11A. FACS sorting of G-418 resistant PGCs. FACS gating was designed to sort singular (sin) GFP-positive cells that were sorted as pool or individual cells in 96 well plate. FIG. 11B. For PCR analysis two sets of primers for the 5' integration site (P7 and P8) and the 3' integration site (P9 and P10), were designed. FIG. 11C. Genomic DNA extracted from the pooled cells was used as a template for the PCR and WT DNA served as a negative control. The predicted 1.6 kb and 1.8 kb bands were evident for the correct HR integration in the 5' and 3' regions, respectively. FIG. 11D. Genomic DNA extracted from male and female cell colonies, originated from single cell FACS sorted PGCs, was used as a template for the PCR and WT DNA served as a negative control. The predicted 1.6 kb and 1.8 kb bands were evident for the correct HR integration in the 5' and 3' regions, respectively.

FIGS. 12A-12D. Southern blot analysis of the HR integration. FIG. 12A—schematic representation of the expected BglII cleaved products in Southern blot analysis for the WT allele and the allele which underwent HR integration. The probes used for 5', 3' integration sites and for the neo are marked as short bars. The expected product size, following BglII digestion, for each DNA probe are shown. FIG. 12B—Preparation of the Dig-labeled probes by PCR. Dig-labeled probes (+) or un-labeled (−) were analyzed on an agarose gel. Note that Dig-labeled products are shifted higher than their actual size, confirming the integration of the Dig-labeled nucleotides. The sets of primers used for amplifying the probes are indicated. FIG. 12C—Southern blot analysis with the 5' and 3' probes on DNA extracted from pooled and pure colonies of male-derived PGCs. WT DNA extracted from the original line, prior to the HR, served as a negative control. FIG. 12D—Southern blot analysis with the 5' and the Neo probes on female-derived PGCs. A single 7.5 kb band is evident in both cased, indicating that correct HR occurred and only a single copy of the targeting vector was integrated.

Figure 13:
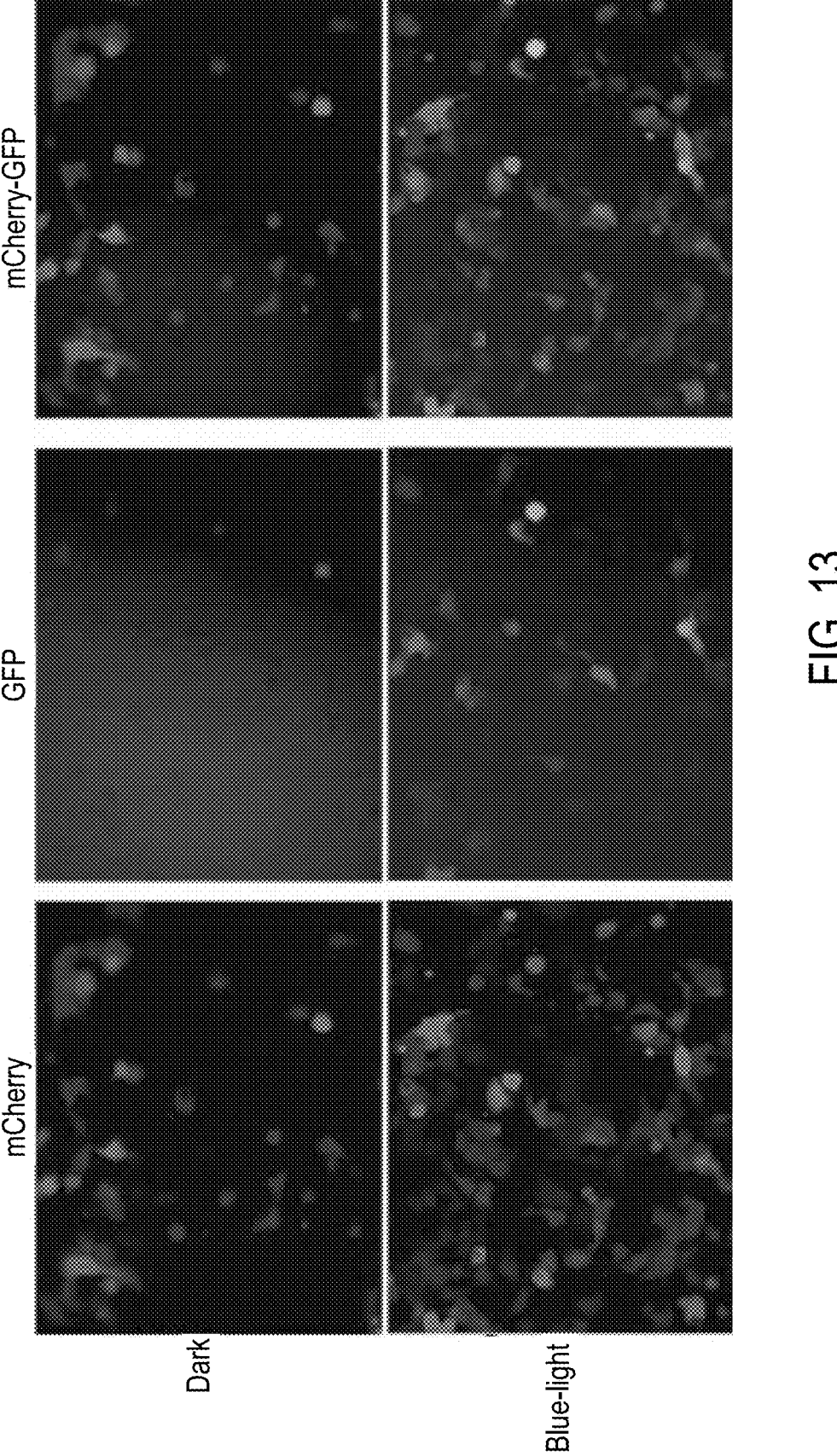

FIG. 13. Validation of the optogenetic system in HEK293 cells, in-vitro. Triple transfection with pmCherry-Cry2-CreN, pmCherry-CIBN-Cre-C and PB-RAGE-GFP plasmids. Twenty-four hours following transfection, cells in experimental group were exposed for 15 seconds of blue light illumination while control cells were kept in dark (upper row). Following illumination (lower row), the cells were further incubated for 24 hours. In these cells, GFP expression was evident confirming the activation of the Cre enzyme upon blue-light illumination.

Figure 14:
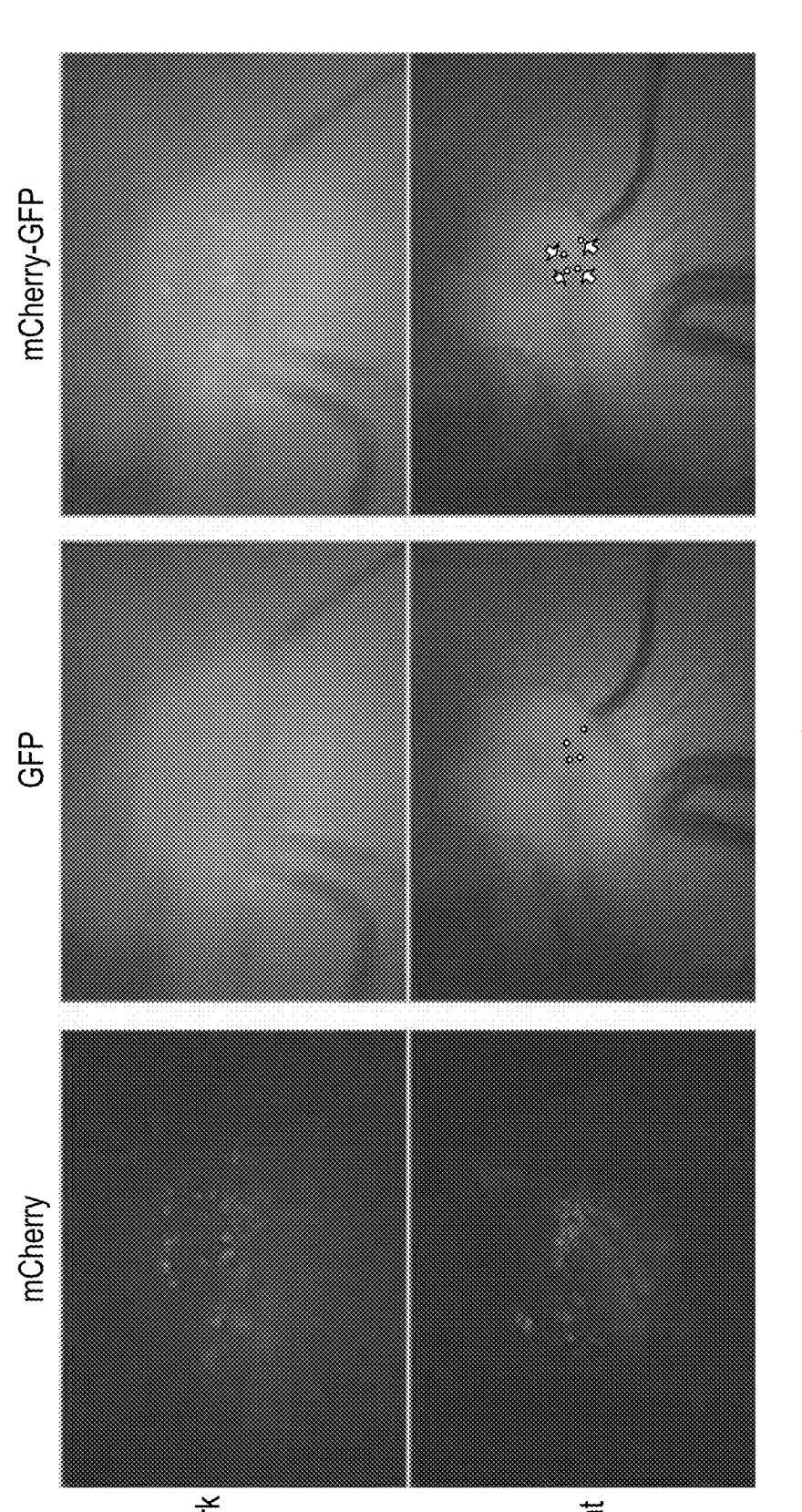

FIG. 14. Validation of the optogenetic system in-ovo in chick embryos, incubated for 54-60 hours prior to electroporation. Triple electroporation to chicken embryos with pmCherry-Cry2-CreN, pmCherry-CIBN-CreC and pB-RAGE-GFP plasmids. Twelve hours following electroporation, experimental group embryos were exposed for 15 seconds of blue light illumination in-ovo while control embryos were kept in dark (upper row). Following illumination (lower row), the embryos from both groups were incubated for additional 12 hours. Following incubation, GFP expressing cells were clearly evident in the illuminated group, thus confirming the activation of the optogenetic system and the Cre enzyme upon blue-light illumination in chicken embryos in-ovo.

Figures 15A, 15B, 15C, 15D, 15E, 15F:
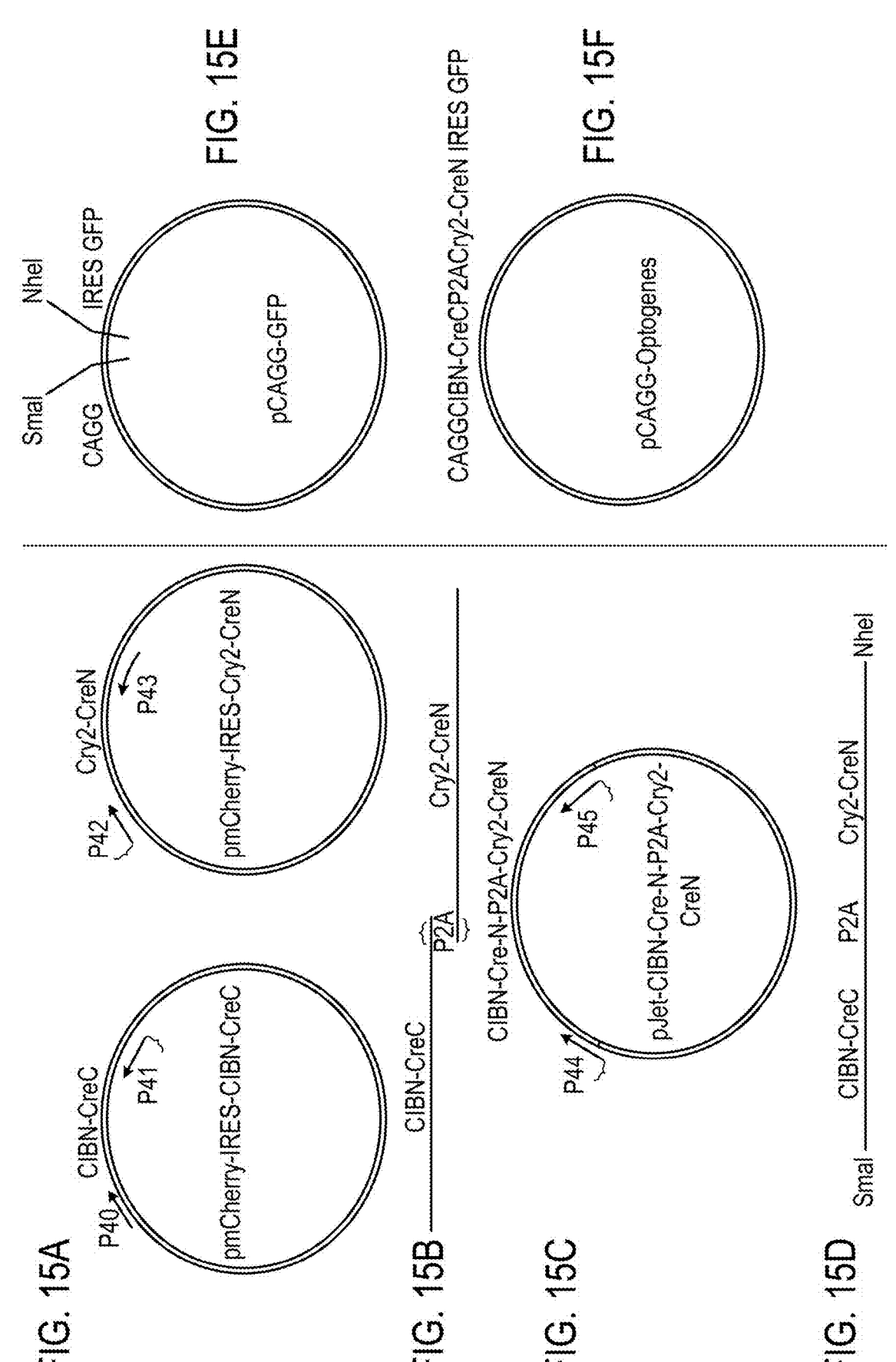

FIGS. 15A-15F. Constructing a single optogene expression vector under the CAGG promoter. FIG. 15A. The optogenes plasmids pmCherry-CIBN-CreC and pmCherry-Cry2-CreN were used as a template to amplify the optogenes fusion proteins using the P40-P41 and P42-P43 primers, respectively. The two products share overlap sequences at the P2A site which was introduced in primers P41 and P42. This allowed for single-cycle overhang extension PCR to unite the two fragments (see FIG. 15B) into one piece, which was ligated to pJet1.2 shuttle vector as shown in FIG. 15C. Using primers P44 and P45, which contain tails with SmaI and NheI restriction sites, respectively, the product in FIG. 15D was generated. This product was digested using the appropriate restriction enzymes and was ligated to pCAGG-IRES-GFP (FIG. 15E) that was digested with the same enzymes to obtain the vector as shown in FIG. 15F.

Figure 16:
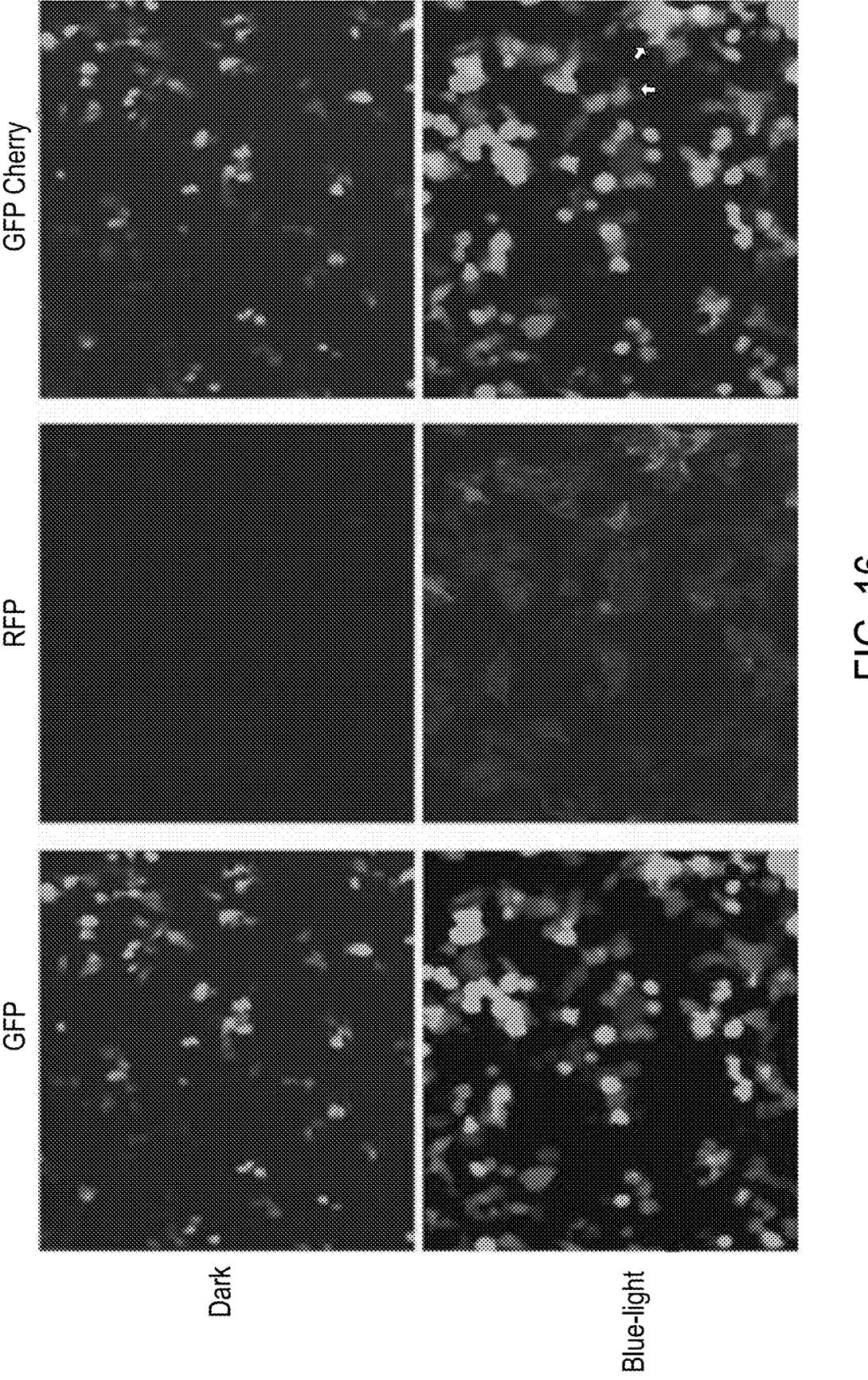

FIG. 16. Validating the activity of the pCAGG-Optogene plasmid in HEK293 cells. Co-transfection with pCAGG-Optogene and pB-RAGE-mCherry plasmids. Twenty-four hours following transfection, while the negative-control group was kept in the dark (upper row), the experimental group cells were exposed for 15 seconds to blue light illumination (lower row). Following illumination (lower row), the cells were further incubated for 24 hours. In these cells, mCherry expression was evident (white arrows) confirming the activation of the Cre enzyme by the pCAGG-Optogene plasmid, upon blue-light illumination.

Figure 17:
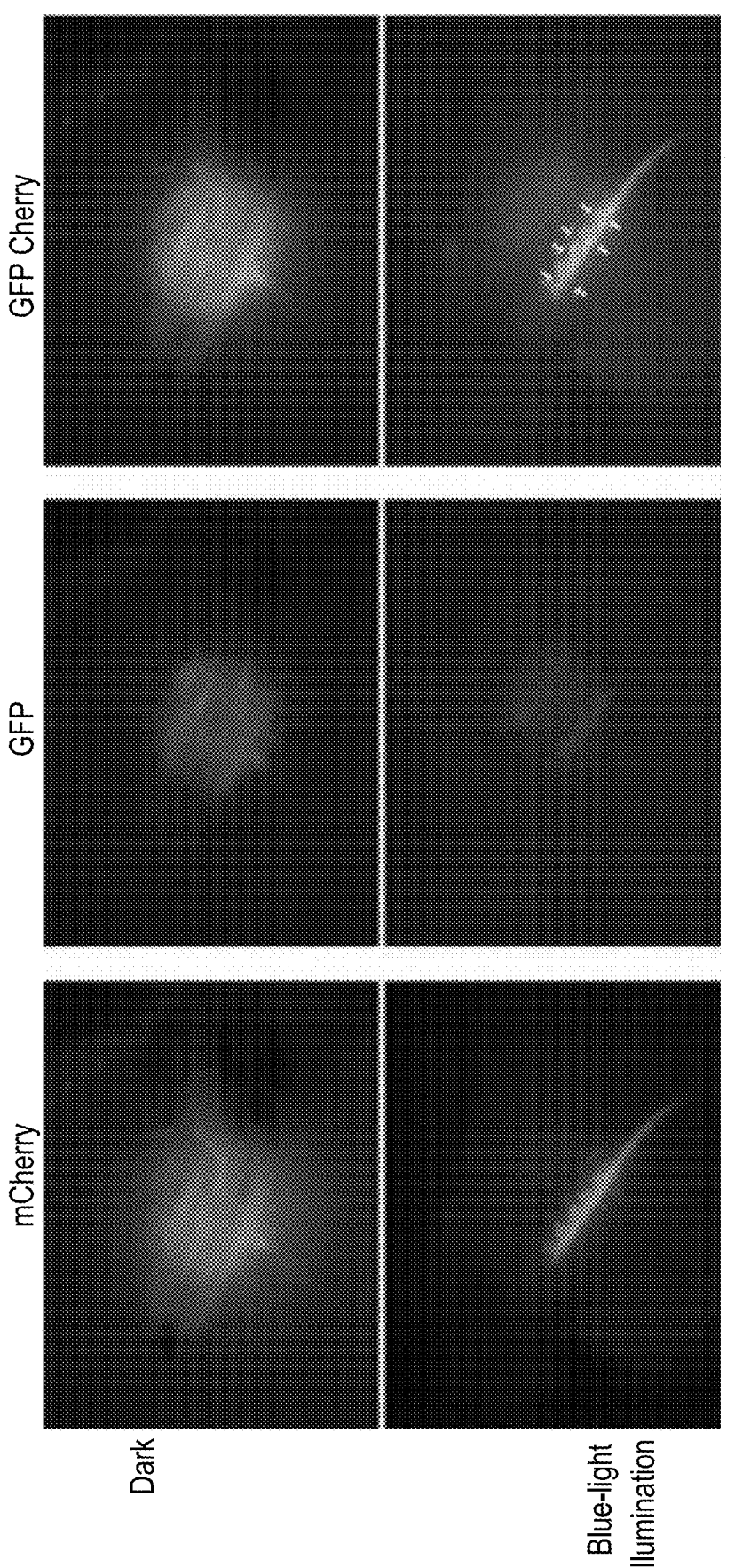

FIG. 17. Verification of the single-vector strategy using the pCAGG-Optogenes plasmid in-ovo. Chicken embryos at stage 14-16H&H were co-electroporated with pCAGG-Optogenes and pB-RAGE-mCherry plasmids. The latter plasmid serves as a reporter gene for the activity of the optogenetic system. Twelve hours following electroporation, the experimental group embryos (lower row) were exposed for 15 sec to blue light illumination in-ovo while control embryos were kept in the dark (upper row). The embryos were further incubated for 12 hours. Following incubation, GFP expressing cells were clearly evident in both groups, indicating successful electroporation, however, only in the illuminated group mCherry-expressing cells were evident, confirming the activation of the optogenetic system and the Cre enzyme upon blue-light illumination in chicken embryos in-ovo.

Figure 18:
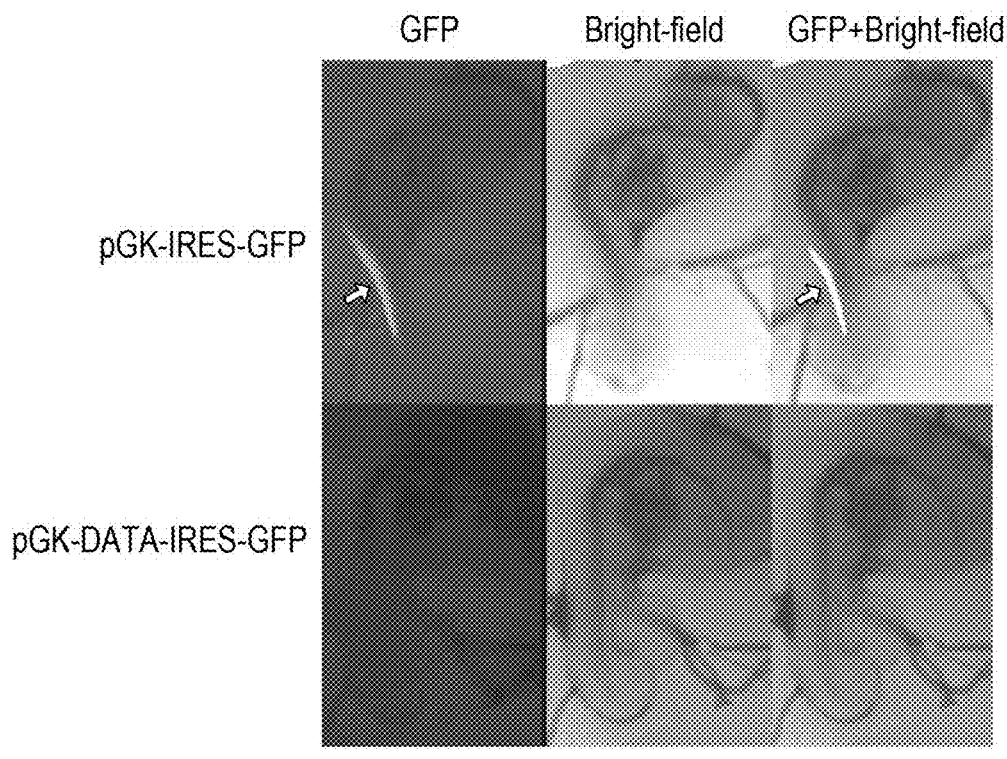

FIG. 18. Expression of DTA under the pGK promoter inhibits protein synthesis in-ovo. Stage 14-16 H&H embryos were electroporated with either the pGK-IRES-GFP (upper row) or pGK-DTA-IRES-GFP (lower row) expression vector. Negative control embryos widely express GFP (upper row, arrow) indicating normal protein synthesis. DTA expressing cells show no GFP expression (lower row), indicating that protein synthesis in these embryos is inhibited. GFP-only, bright-field-only and GFP overlaid on bright-field images are presented.

Figures 19, 19A, 19B:
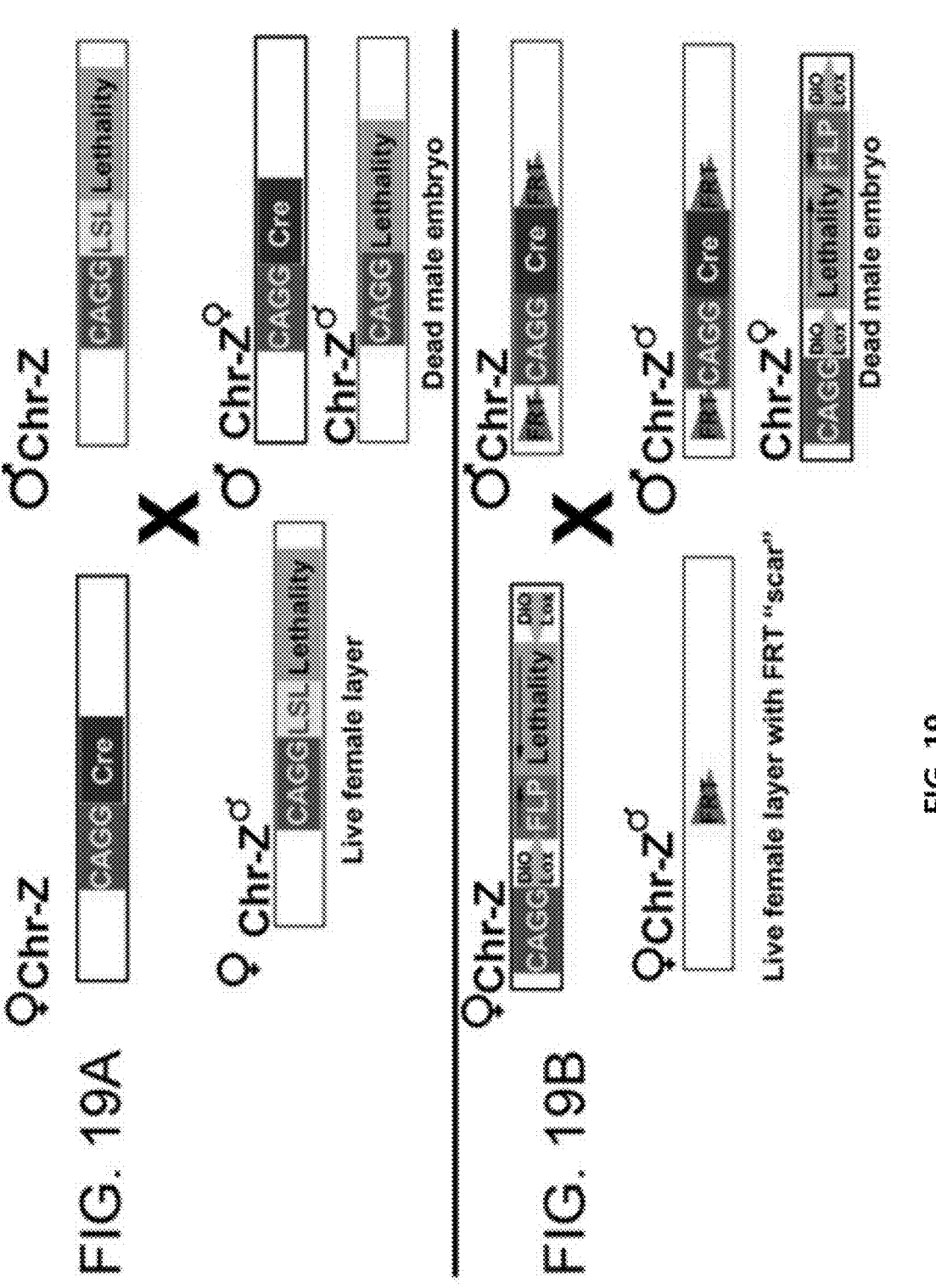

FIGS. 19A-19B. Embodiments of targeting vectors. In these vectors the activating enzyme (Cre for example) is separated from the lethality gene cassette. In FIG. 19A, the activating enzyme is inserted into the genome of the mother hen and the inactive lethality cassette is inserted on the Z chromosome of the rooster, which is homozygote to this allele. In this case the activation of lethality in male embryos is carried out by crossing the two transgenic parents without the need for light induction. The Cre in all males removes the LSL on the maternal derived Z chromosome thereby allowing the lethality gene to be expressed, while the female embryo harbors an inactive lethality cassette, thus it is unaffected. FIG. 19B. Alternatively, the Z chromosome on the mother hen is targeted with Dio-Lox flipping cassette containing the FLP recombinase in the right direction followed by a lethality gene in reverse orientation, driven by the CAGG promoter. The rooster, again homozygote to the Z chromosome which is targeted with CAGG-Cre cassette flanked by FRT sites. Upon crossing the two, male embryos will express the Cre located on the paternal Z chromosome, the Dio-Lox cassette flips and the lethality gene becomes active, thereby leading to embryonic lethality of the male embryo. The zygote of the female embryo from this cross contains maternal contribution of the FLP recombinase enzyme that was produced during oogenesis. This maternal protein, removes the CAGG-Cre cassette from the Z chromosome, leaving the female embryo alive with only a FRT "scar" on the Z chromosome.

Figure 20:
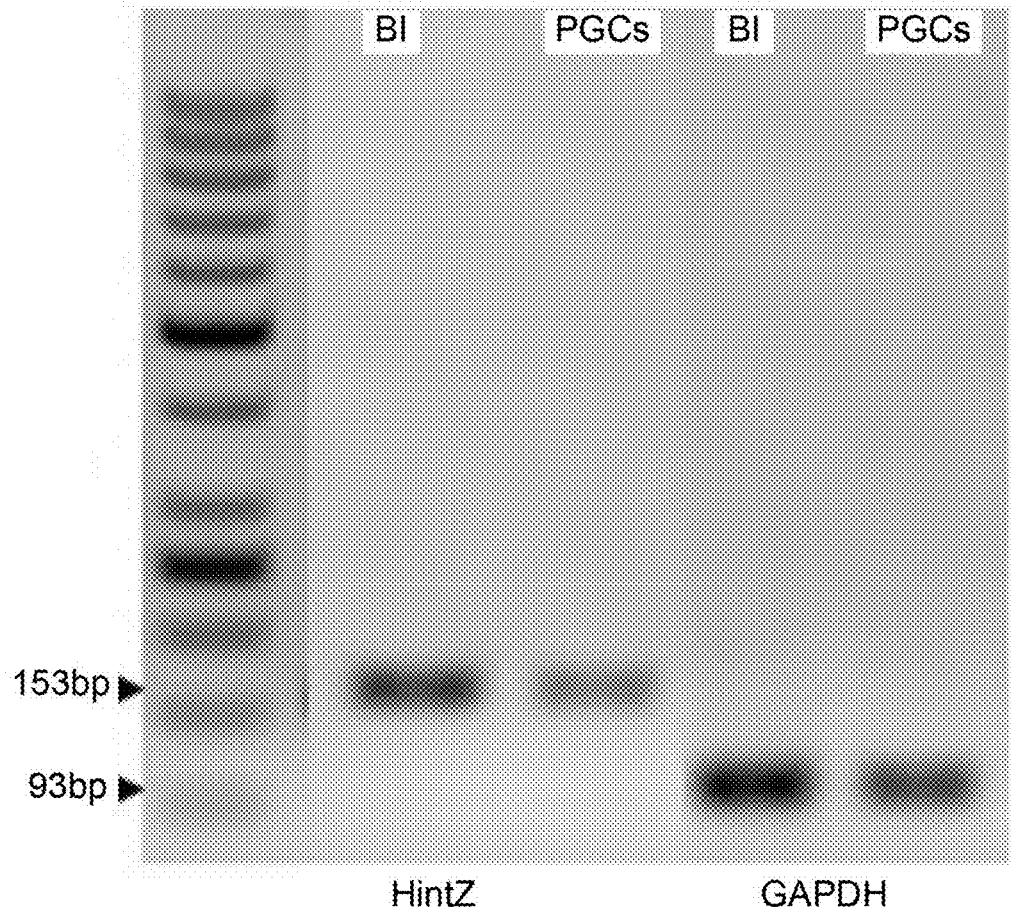

FIG. 20. RT-PCR on cDNA from total RNA extract from whole freshly-laid blastoderms (Bl) and PGCs, with primers for HINT1Z and GAPDH as a positive control (GAPDH primers: Forward—(SEQ ID NO: 90); Reverse—(SEQ ID NO: 91), 93 bp). Bands at the predicted size of 153 bp indicate that in both samples, HINT1Z which is located on the Z chromosome is transcribed.

Figure 21:
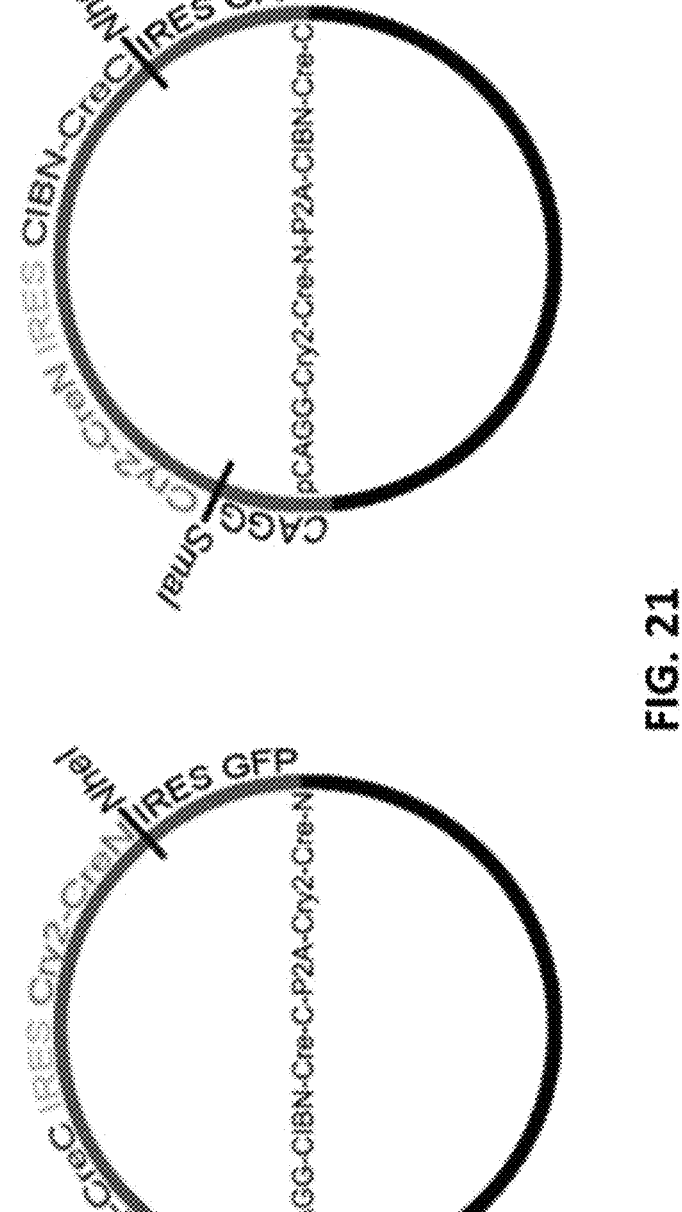

FIG. 21. Schematic diagram of two plasmids containing the modified optogenetic system (pCAGG-CIBN-Cre-C-P2A-Cry2-Cre-N and pCAGG-Cry2-Cre-N-P2A-CIBN-Cre-C).

Figure 22:
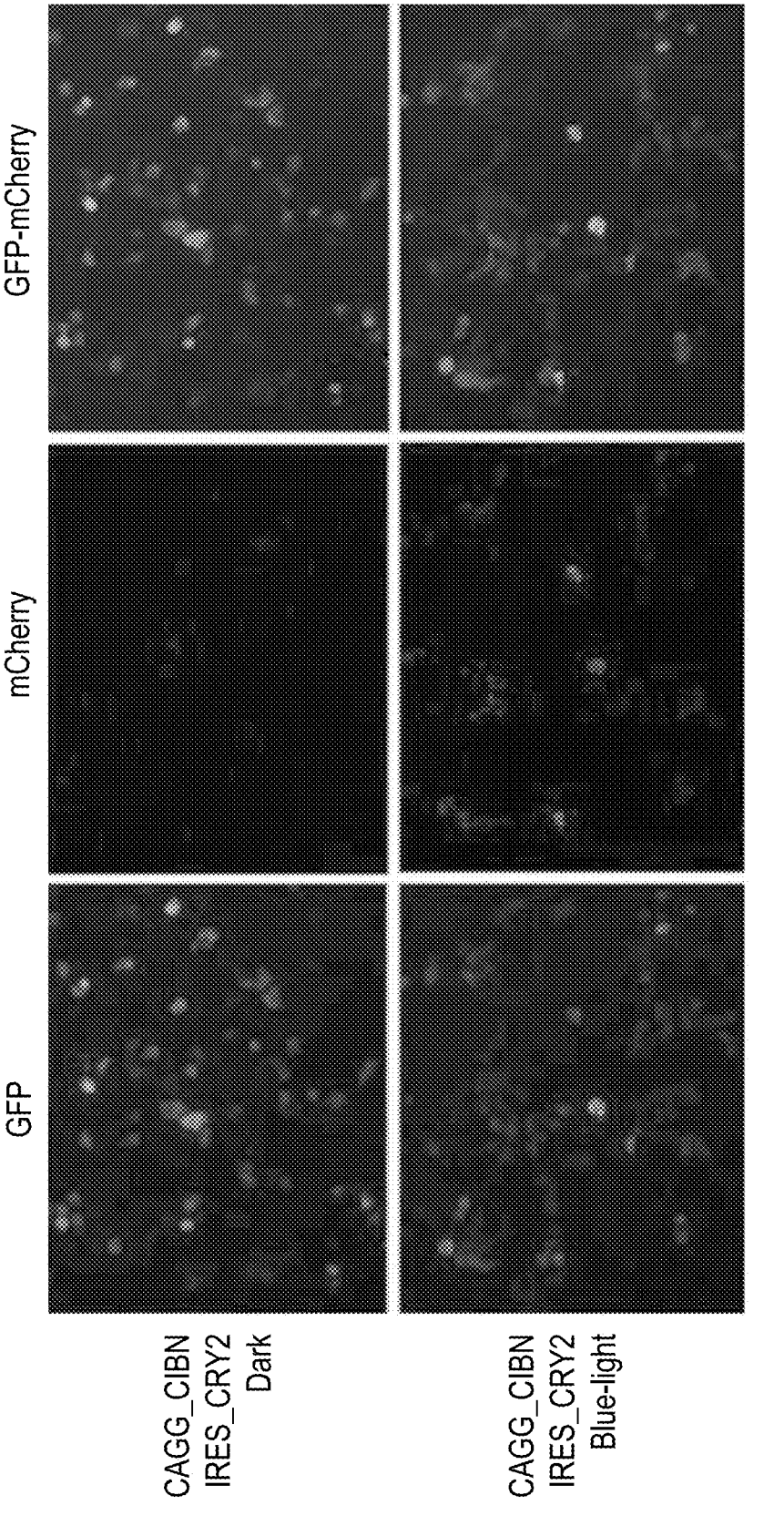

FIG. 22. Validation of the optogenetic system in cultured HEK293 cells. The optogenetic plasmid pCAGG-CIBN-CreC-IRES-Cry2-CreN-IRES-GFP was co-transfected with pB-RAGE-mCherry. Like the PB-RAGE-GFP vector described above, the pB-RAGE-mCherry contains a multiple stop codon sequence flanked by LoxP sites upstream to the mCherry coding region. Upon Cre activation, the stop codons are removed thus allowing the mCherry to be expressed. While in HEK293 cells that were co-transfected and kept in the dark there were no mCherry-positive cells, in the co-transfected HEK293 cells that were exposed to blue-light illumination, many cells were expressing mCherry, confirming that the single-vector strategy of the pCAGG-Optogenes preserves the optogenetic properties of the system.

Figure 23:
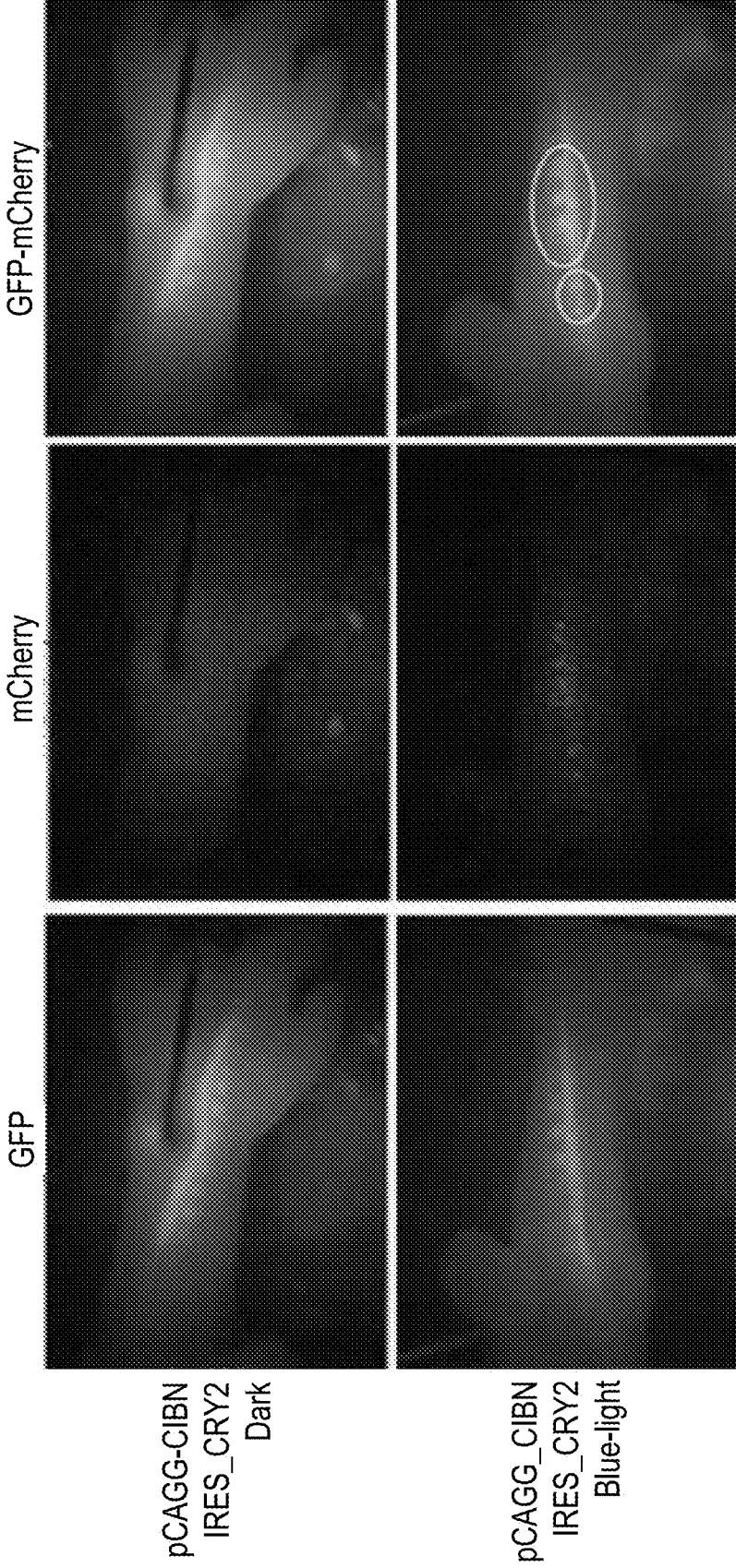

FIG. 23. Validation of optogenetic system by electroporation in chicken embryos. pCAGG-CIBN-IRES-Cry2, which also encodes GFP, was electroporated along with PB-RAGE-mCherry, which gives red fluorescence when in the presence of an active Cre recombinase. When induced with blue light, Cry2-CreN and CIBN-CreC dimerize, thus enabling Cre activity. White circles indicate areas of overlapping fluorescence.

Figure 24A:
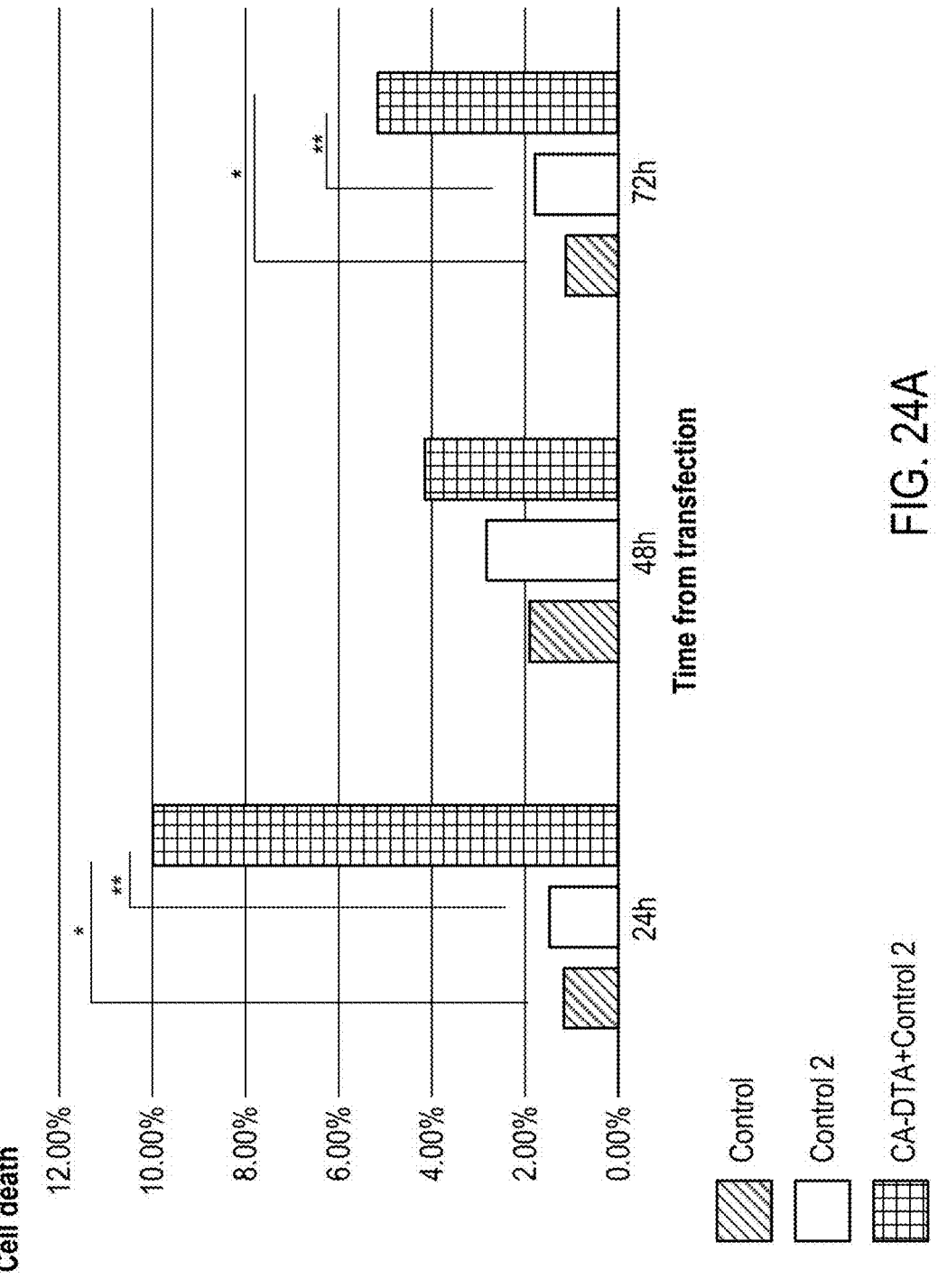
Figure 24B:
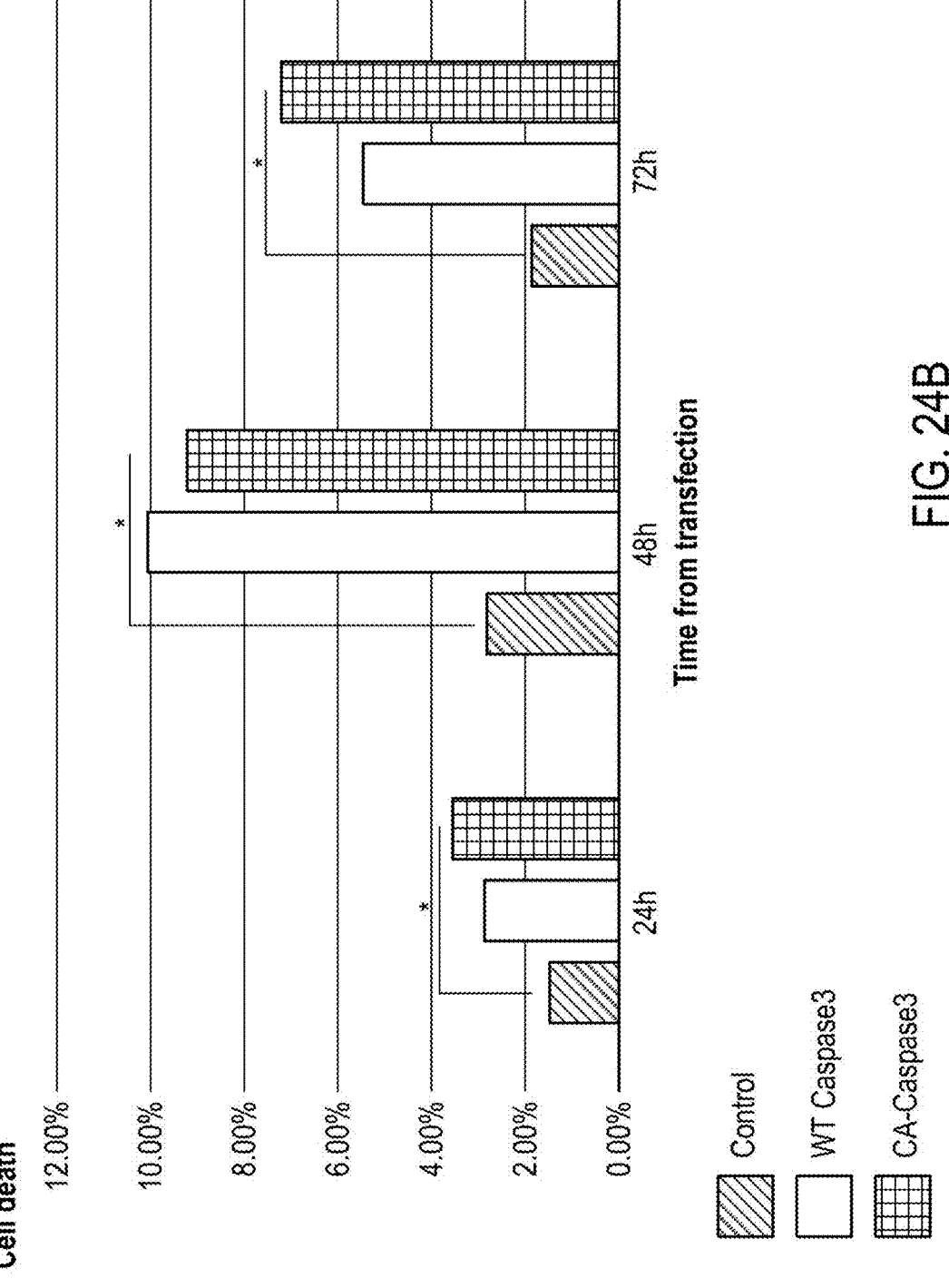

FIGS. 24A-24B. Induction of cell death in PGCs using DTA (FIG. 24A) or Caspase3 (FIG. 24B). FIG. 24A. The effect of DTA on PGC's cell death is presented. PGCs were transfected with control 1 PGK-IRES-GFP, control 2 pCAGG-GFP, or PGK-DTA-IRES-GFP with pCAGG-GFP plasmids and incubated for 24, 48, and 72 h. Cell death was assessed using flow-cytometry for GFP and PI. Results present the ratio between GFP+PI and GFP only cells. FIG. 24B. The effect of Casp's on PGC's cell death is presented. PGCs were transfected with control PGK-IRES-GFP, PGK-WT Caspase3-IRES-GFP or PGK-CA Caspase3-IRES-GFP plasmids and incubated for 24, 48, and 72 h before analysis as illustrated in FIG. 24A.

Figure 25:
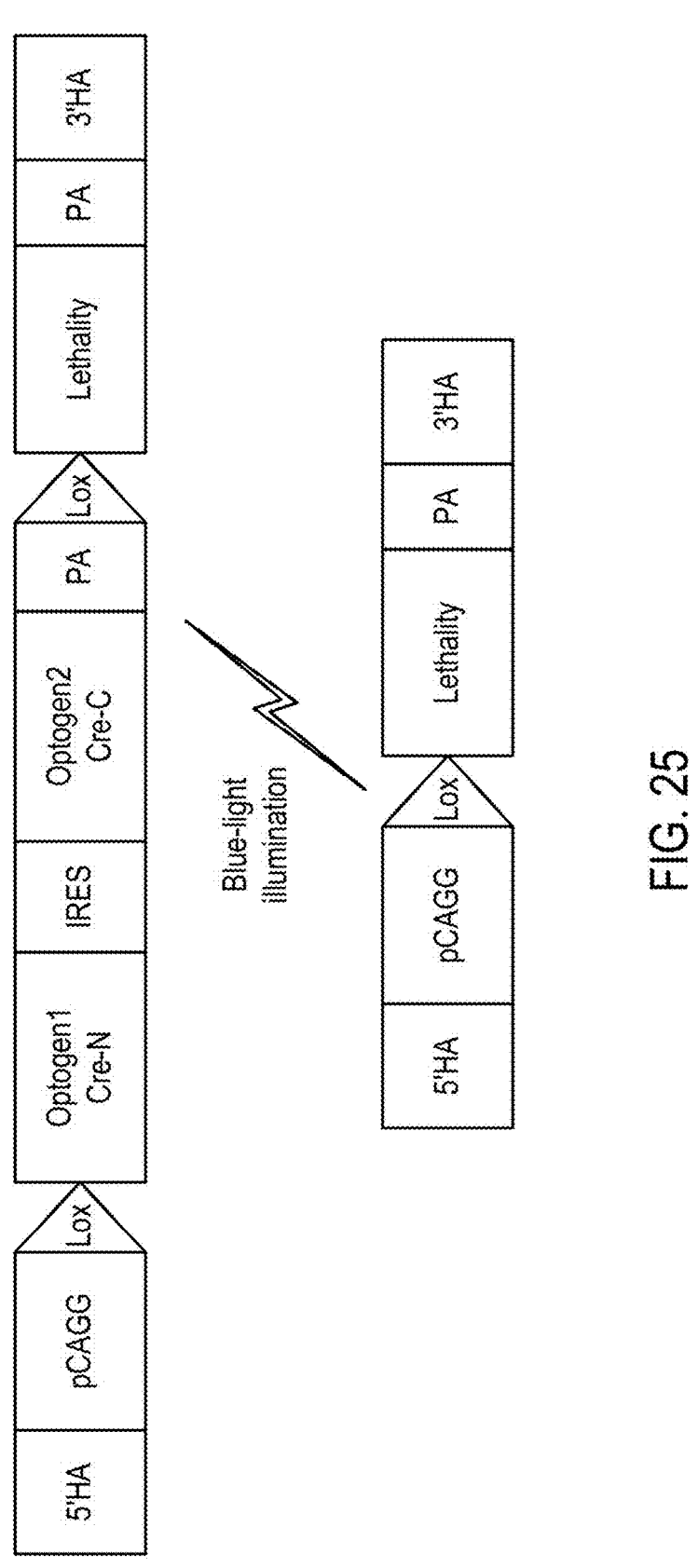

FIG. 25. Schematic illustration of the targeting vector, containing all elements and the activation of the lethality-inducing cassette upon blue-light illumination.

Figures 26A, 26B:
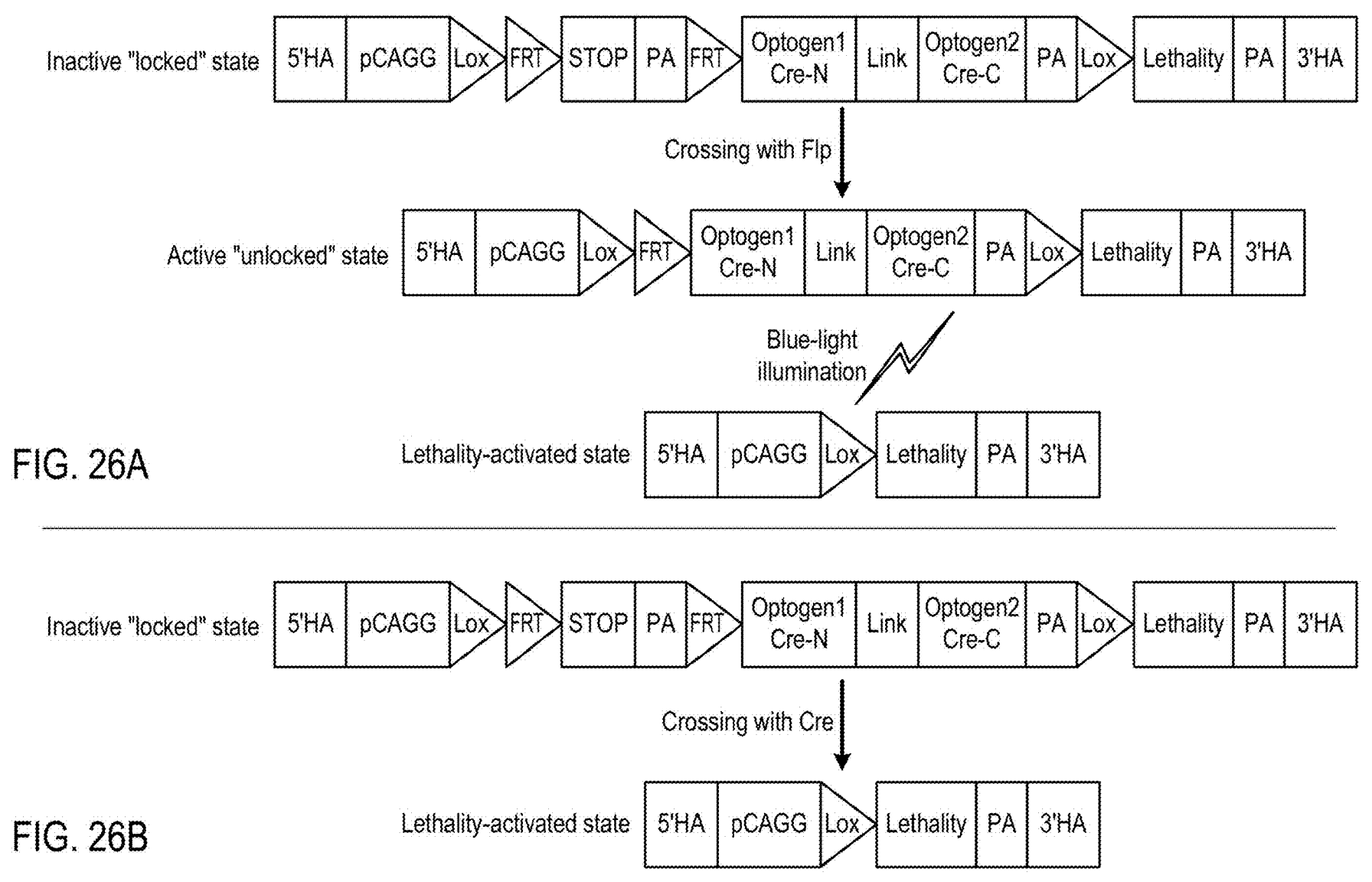

FIGS. 26A-26B. Schematic illustration of the targeting vectors containing a "safe-lock" mechanism as explained in Example 3.

Figures 27A, 27B, 27C, 27D:
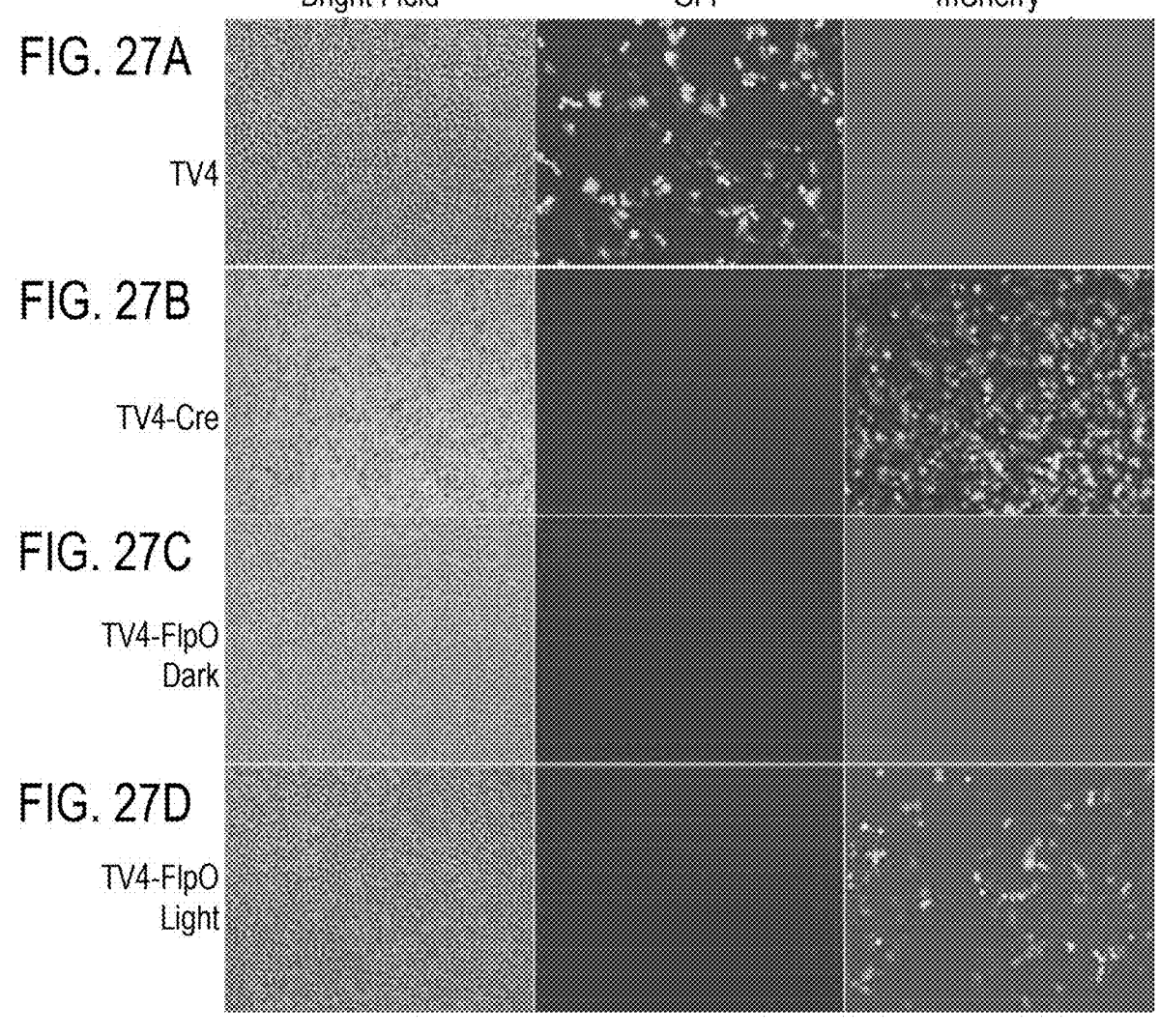

FIGS. 27A-27D. Validation of targeting vectors in cultured HEK293 cells. For in-vitro validation, HEK293 cells were transfected with TV4 alone (FIG. 27A), with pCAGG-Cre (FIG. 27B), or with pCAGG-FlpO plasmids (FIGS. 27C-27D). The cells were kept in dark (FIG. 27C) or was exposed for 15 seconds to blue light 24 hours following transfection (FIG. 27D). Following illumination, the cells were further incubated for 24 hours.

FIGS. 28A-28D. Validation of targeting vectors by electroporation in chicken embryos. Chicken embryos were injected with plasmids to the neural tube and electroporated as described herein. The white lines denote the dorsal mid-line of the neural tube and limb buds for orientation purposes. Four treatment groups were tested: 1. expression of TV4 alone (FIG. 28A), 2. co-electroporation of TV4 and pCAGG-Cre plasmids, as positive control (FIG. 28B), 3. Co-electroporation of TV4 and pCAGG-FlpO plasmids. The cells were kept in the dark (FIG. 28C), and 4. Exposure to blue light for 15 sec after co-electroporation of TV4 and pCAGG-FlpO plasmids, and further incubated for 12 hours (FIG. 28D).

Figures 29A, 29B:
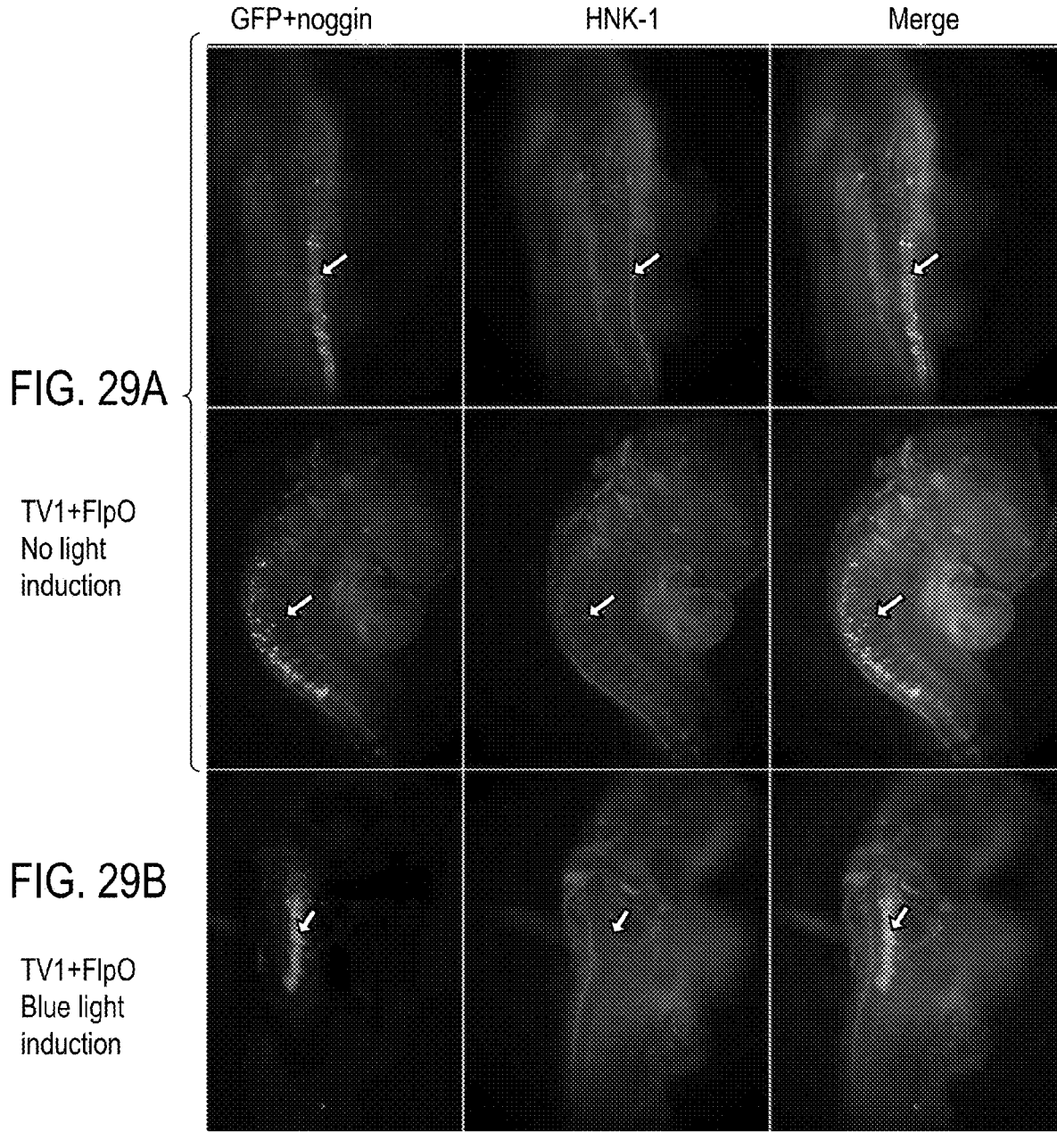

FIGS. 29A-29B. The light-dependent activity of the lethality-inducing gene Noggin. Chick embryos were electroporated in the neural tube with targeting vector TV1, pCAGG-FlpO and pCAGG-IRES-GFP plasmids. Targeting vector TV1 contains the coding sequence of Noggin as a lethality-inducing element. FIG. 29A shows results without light induction; upper row, dorsal view; lower row, right-lateral view. FIG. 29B shows results with blue light induction.

Figure 30D:
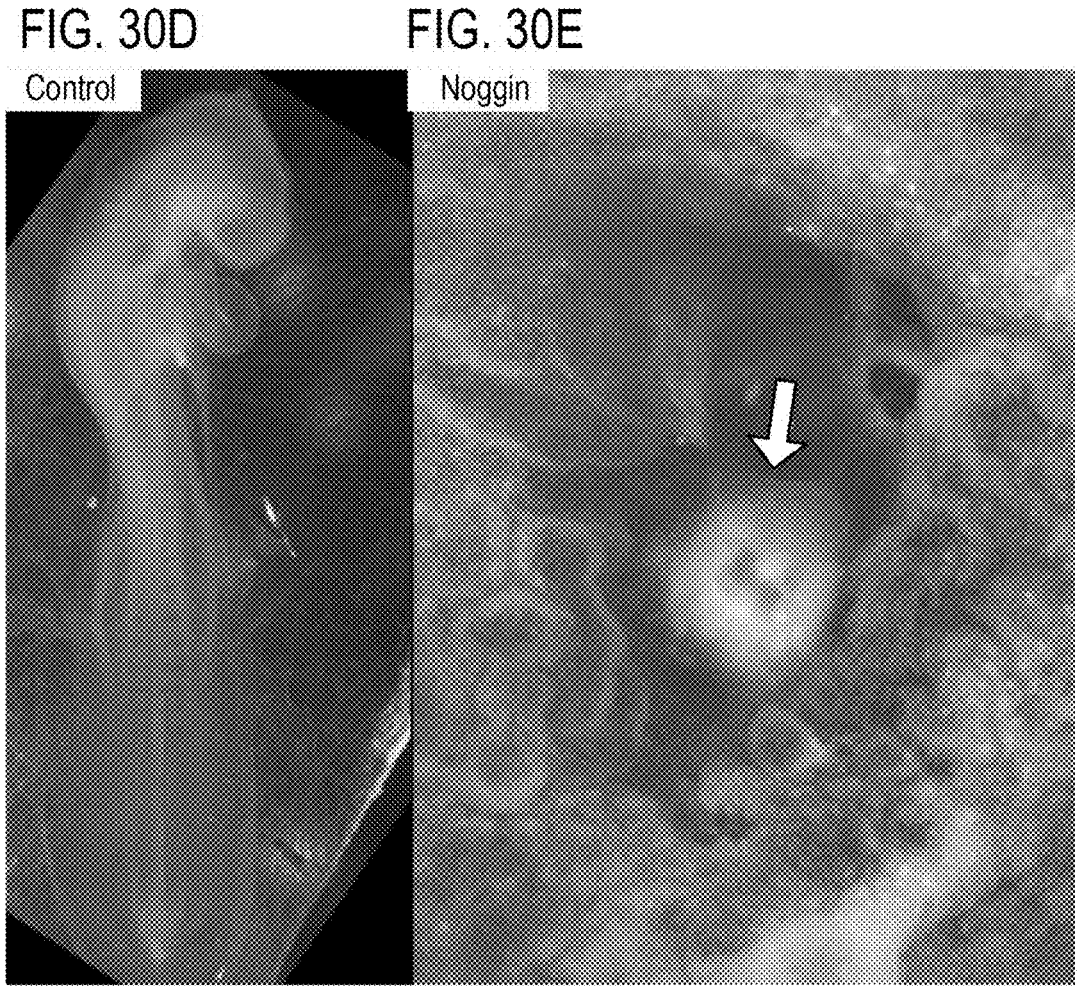
Figure 30E:
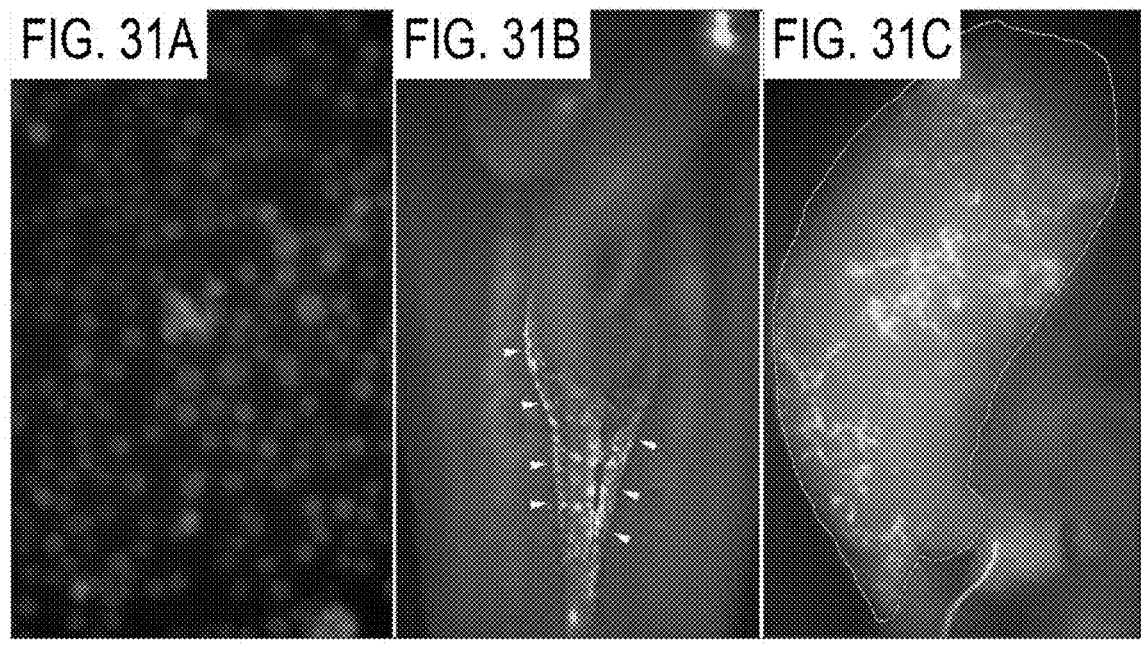

FIGS. 30A-30E. Noggin is able to stop embryonic development at the blastoderm embryonic stage. Blastoderms were treated with exogenous source of Noggin. Plasmids pCAGG-Noggin-IRES-GFP or pCAGG-IRES-GFP (as negative control) were transfected to HEK293 cells. FIG. 30A shows total protein extracted from transfected cells was analyzed by Western blot with anti-Noggin antibody and anti-α-Tubulin-HRP antibody. Conditioned media from control and Noggin expressing cells were injected into freshly-laid fertile eggs that were subsequently incubated for 24 hours (FIG. 30B-C) or 54 hours (FIG. 30D-E).

FIGS. 31A-31C. PGCs that underwent HR on the Z chromosome with TV1 successfully colonize the gonads in chick embryos. FIG. 31A shows pure female PGCs line that underwent HR with TV1, and expressed GFP. FIG. 31B shows a ventral view of an embryo 5 days following PGCs injection. The PGCs colonized the genital ridge which is the anlage of the gonads (FIG. 31B, arrowheads). Female chicks were sacrificed at day 10 post hatch to analyze the ovary. FIG. 31C shows an ovary (delineated by a line) containing numerous GFP positive PGCs.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of the compositions and methods provided herein. However, it will be understood by those skilled in the art that the present disclosure may be practiced without these specific details. In other instances, well-known methods, procedures, and components have not been described in detail so as not to obscure the compositions and methods provided herein.

Before explaining at least one embodiment of the disclosure in detail, it is to be understood that the disclosure is not necessarily limited in its application to the details set forth in the following description or exemplified by the Examples. The disclosure encompasses other embodiments or can be practiced or carried out in various ways.

The terms "comprises", "comprising", "includes", "including", "having" and their conjugates encompass "including but not limited to".

As used herein, the singular form "a", "an" and "the" include plural references unless the context clearly dictates otherwise. For example, the term "a compound" or "at least one compound" may include a plurality of compounds, including mixtures thereof.

In some embodiments, the term "about" refers to a deviance of between 0.0001-5% from the indicated number or range of numbers. In some embodiments, the term "about" refers to a deviance of between 1-10% from the indicated number or range of numbers. In some embodiments, the term "about" refers to a deviance of up to 25% from the indicated number or range of numbers. In some embodiments, the term "about" refers to ±10%.

Throughout this application, various embodiments may be presented in a range format. It should be understood that the description in range format is merely for convenience and brevity and should not be construed as an inflexible limitation on the scope of certain embodiments. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

In one embodiment, the technology, products and methods provided herein generate a chicken breed in which only female layers will hatch while male embryos will cease to develop soon after fertilization. Thus, the need to cull the male chicks is eliminated and 50% of valuable incubation space is saved in hatcheries. Importantly, both the females and the eggs derived from the methods disclose herein are in every aspect identical to the layer-hens and food-eggs currently consumed by the public.

As used herein, the terms "bird" or "avian species" refers to any avian species, including but not limited to chicken, turkey, duck, geese, quail, pheasant, and ostrich. In certain embodiments, the bird is a domestic bird. In certain embodiments, the bird is *Gallus gallus*. In certain embodiments, the bird is domestic *Gallus gallus*. In certain embodiments, the bird is *Gallus gallus domesticus*.

In certain embodiments, the bird is a female. In certain embodiments, the bird is a male. In certain embodiments, the bird is a broiler. In certain embodiments, the bird is a hen.

In certain embodiments, the bird is layer hen. In certain embodiments, the bird is a domestic chicken. In certain embodiments, the bird is *Gallus gallus domesticus* layer hen.

As used herein, the term "egg" refers to an avian egg that contains a viable or a live embryonic bird. In one embodiment, the term "egg" is intended to refer to a fertilized avian egg. In one embodiment, an egg is an egg containing an avian embryo that is capable of undergoing normal embryogenesis.

Genome Editing

Genome editing using engineered endonucleases refers to a genetic method using nucleases to cut and create specific double-stranded breaks at a desired location(s) in the genome (e.g. on the Z chromosome of a bird), which are then repaired by cellular endogenous processes such as, homology directed repair (HDR) and non-homologous end joining (NHEJ). NHEJ directly joins the DNA ends in a double-stranded break, while HDR utilizes a homologous sequence as a template for regenerating the missing DNA sequence at the break point. In order to introduce specific nucleotide modifications to the genomic DNA, a DNA repair template containing the desired sequence must be present during HDR. Genome editing cannot be performed using traditional restriction endonucleases since most restriction enzymes recognize only a few base pairs on the DNA as their target and the probability is very high that the recognized base pair combination will be found in many locations across the genome, resulting in multiple cuts not limited to a desired location. To overcome this challenge and create site-specific single- or double-stranded breaks, several distinct classes of nucleases have been discovered and bioengineered to date. These include the meganucleases, Zinc finger nucleases (ZFNs), transcription-activator like effector nucleases (TALENs) and the CRISPR/Cas system.

Meganucleases—They are commonly grouped into four families: the LAGLIDADG family, the GIY-YIG family, the His-Cys box family and the HNH family. These families are characterized by structural motifs that affect catalytic activity and recognition sequence. For instance, members of the LAGLIDADG family are characterized by having either one or two copies of the conserved LAGLIDADG motif. The four families of meganucleases are widely separated from one another with respect to conserved structural elements and, consequently, DNA recognition sequence specificity and catalytic activity. Meganucleases are found commonly in microbial species and have the unique property of having very long recognition sequences (>14 bp), thus making them naturally very specific for cutting at a desired location. This can be exploited to make site-specific double-stranded breaks in genome editing. One of skilled in the art can use these naturally occurring meganucleases, however the number of such naturally occurring meganucleases is limited. To overcome this challenge, mutagenesis and high throughput screening methods have been used to create meganuclease variants that recognize unique sequences. For example, various meganucleases have been fused to create hybrid enzymes that recognize a new sequence. Alternatively, DNA interacting amino acids of the meganuclease can be altered to design sequence specific meganucleases (e.g. U.S. Pat. No. 8,021,867). Meganucleases can be designed using the methods described in e.g., Certo, M T et al. Nature Methods (2012) 9:073-975; U.S. Pat. Nos. 8,304,222; 8,021,867; 8,119,381; 8,124,369; 8,129,134; 8,133,697; 8,143,015; 8,143,016; 8,148,098; or 8,163,514.

ZFNs and TALENs—Two distinct classes of engineered nucleases, zinc-finger nucleases (ZFNs) and transcription activator-like effector nucleases (TALENs), have both been proven to be effective at producing targeted double-stranded breaks. Basically, ZFNs and TALENs restriction endonuclease technology utilizes a non-specific DNA cutting enzyme which is linked to a specific DNA binding domain (either a series of zinc finger domains or TALE repeats, respectively). Typically, a restriction enzyme whose DNA recognition site and cleaving site are separated from each other is selected. The cleaving portion is separated and then linked to a DNA binding domain, thereby yielding an endonuclease with very high specificity for a desired sequence. An exemplary restriction enzyme with such properties is Fokl. Additionally, Fokl has the advantage of requiring dimerization to have nuclease activity and this means the specificity increases dramatically as each nuclease partner recognizes a unique DNA sequence. To enhance this effect, Fokl nucleases have been engineered that can only function as heterodimers and have increased catalytic activity. The heterodimer functioning nucleases avoid the possibility of unwanted homodimer activity and thus increase specificity of the double-stranded break.

Thus, for example, ZFNs and TALENs can be constructed as nuclease pairs, with each member of the pair designed to bind adjacent sequences at the targeted site. Upon transient expression in cells, the nucleases bind to their target sites and the FokI domains heterodimerize to create a double-stranded break. Repair of these double-stranded breaks through the non-homologous end-joining (NHEJ) pathway most often results in indels which are small deletions or small sequence insertions. Since each repair made by NHEJ is unique, the use of a single nuclease pair can produce an allelic series with a range of different deletions at the target site. The deletions typically range anywhere from a few base pairs to a few hundred base pairs in length, but larger deletions have successfully been generated in cell culture by using two pairs of nucleases simultaneously (see e.g. Carlson et al., 2012, Proc Natl Acad Sci USA.; 109(43):17382-7; Lee et al., 2010, Trends Biotechnol.; 28(9):445-6). In addition, when a fragment of DNA with homology to the targeted region is introduced in conjunction with the nuclease pair, the double-stranded break can be repaired via homology directed repair to generate specific modifications (see e.g. Li et al., 2011, Nucleic Acids Res. 39(1):359-72; Miller et al., 2010, Nat Struct Mol Biol. 17(9):1144-51; Urnov et al., 2005, Nature 435(7042):646-51).

Although the nuclease portions of both ZFNs and TALENs have similar properties, the difference between these engineered nucleases is in their DNA recognition peptide. ZFNs rely on Cys2-His2 zinc fingers and TALENs on TALEs. Both of these DNA recognizing peptide domains have the characteristic that they are naturally found in combinations in their proteins. Cys2-His2 Zinc fingers typically found in repeats that are 3 bp apart and are found in diverse combinations in a variety of nucleic acid interacting proteins. TALEs on the other hand are found in repeats with a one-to-one recognition ratio between the amino acids and the recognized nucleotide pairs. Because both zinc fingers and TALEs happen in repeated patterns, different combinations can be tried to create a wide variety of sequence specificities. Approaches for making site-specific zinc finger endonucleases include, e.g., modular assembly (where Zinc fingers correlated with a triplet sequence are attached in a row to cover the required sequence), OPEN (low-stringency selection of peptide domains vs. triplet nucleotides followed by high-stringency selections of peptide combination vs. the final target in bacterial systems), and bacterial one-hybrid screening of zinc finger libraries, among others.

CRISPR-Cas system—Many bacteria and archaea contain endogenous RNA-based adaptive immune systems that can degrade nucleic acids of invading phages and plasmids. These systems consist of clustered regularly interspaced short palindromic repeat (CRISPR) genes that produce RNA components and CRISPR associated (Cas) genes that encode protein components. The CRISPR RNAs (crRNAs) contain short stretches of homology to specific viruses and plasmids and act as guides to direct Cas nucleases to degrade the complementary nucleic acids of the corresponding pathogen. Studies of the type II CRISPR/Cas system of *Streptococcus pyogenes* have shown that three components form an RNA/protein complex and together are sufficient for sequence-specific nuclease activity: the Cas9 nuclease, a crRNA containing 20 base pairs of homology to the target sequence, and a trans-activating crRNA (tracrRNA) (Jinek et al. Science (2012) 337: 816-821). It was further demonstrated that a synthetic chimeric guide RNA (gRNA) composed of a fusion between crRNA and tracrRNA could direct Cas9 to cleave DNA targets that are complementary to the crRNA in vitro. It was also demonstrated that transient expression of Cas9 in conjunction with synthetic gRNAs can be used to produce targeted double-stranded brakes in a variety of different species (e.g. Cho et al., 2013, Nat Biotechnol. 31(3):230-2; Cong et al., 2013, Science 339 (6121):819-23; DiCarlo et al., 2013, Nucleic Acids Res. 41(7):4336-43; Hwang et al., 2013, Nat Biotechnol. 31(3): 227-9; Jinek et al., 2013, Elife. 2013 Jan. 29; 2:e00471; Mali et al., 2013, Nat Methods. 10(10):957-63).

It is known that the CRIPSR/Cas system for genome editing contains two distinct components: a guide RNA (gRNA) and an endonuclease e.g. Cas9. The gRNA is typically a 20-nucleotide sequence encoding a combination of the target homologous sequence (crRNA) and the endogenous bacterial RNA that links the crRNA to the Cas9 nuclease (tracrRNA) in a single chimeric transcript. The gRNA/Cas9 complex is recruited to the target sequence by base-pairing between the gRNA sequence and the complement genomic DNA. For successful binding of Cas9, the genomic target sequence must also contain the correct Protospacer Adjacent Motif (PAM) sequence immediately following the target sequence. The binding of the gRNA/Cas9 complex localizes the Cas9 to the genomic target sequence so that the Cas9 can cut both strands of the DNA causing a double-strand break. Just as with ZFNs and TALENs, the double-stranded breaks produced by CRISPR/Cas can undergo homologous recombination or NHEJ. In certain embodiments, the CRISPR/Cas system comprises single guide RNA (sgRNA) and a Cas protein. In certain embodiments, the CRISPR/Cas system comprises a complex of single guide RNA (sgRNA) and a Cas protein. In certain embodiments, the Cas of the CRISPR/Cas system comprises a single polypeptide. In certain embodiments, the Cas of the CRISPR/Cas system is an endonuclease. In certain embodiments, the CRISPR/Cas is CRISPR/Cas9.

The Cas9 nuclease has two functional domains: RuvC and HNH, each cutting a different DNA strand. When both domains are active, the Cas9 causes double strand breaks in the genomic DNA. A significant advantage of CRISPR/Cas is that the high efficiency of this system coupled with the ability to easily create synthetic gRNAs enables multiple genes to be targeted simultaneously. Apparent flexibility in the base-pairing interactions between the gRNA sequence and the genomic DNA target sequence allows imperfect matches to the target sequence to be cut by Cas9.

Modified versions of the Cas9 enzyme containing a single inactive catalytic domain, either RuvC- or HNH-, are called 'nickases'. With only one active nuclease domain, the Cas9 nickase cuts only one strand of the target DNA, creating a single-strand break or 'nick'. A single-strand break, or nick, is normally quickly repaired through the HDR pathway, using the intact complementary DNA strand as the template. However, two proximal, opposite strand nicks introduced by a Cas9 nickase are treated as a double-strand break, in what is often referred to as a 'double nick' CRISPR system. A double-nick can be repaired by either NHEJ or HDR depending on the desired effect on the gene target. Thus, if specificity and reduced off-target effects are crucial, using the Cas9 nickase to create a double-nick by designing two gRNAs with target sequences in close proximity and on opposite strands of the genomic DNA would decrease off-target effect as either gRNA alone will result in nicks that will not change the genomic DNA.

Modified versions of the Cas9 enzyme containing two inactive catalytic domains (dead Cas9, or dCas9) have no nuclease activity while still able to bind to DNA based on gRNA specificity. The dCas9 can be utilized as a platform for DNA transcriptional regulators to activate or repress gene expression by fusing the inactive enzyme to known regulatory domains. For example, the binding of dCas9 alone to a target sequence in genomic DNA can interfere with gene transcription. In certain embodiments, the CRISPR/Cas is CRISPR/dCas9.

In order to use the CRISPR system, both gRNA and Cas9 should be expressed in a target cell. The insertion vector can contain both cassettes on a single plasmid or the cassettes are expressed from two separate plasmids. CRISPR plasmids are publicly available such as the px330 plasmid from Addgene. Additionally, mRNA encoding Cas9 and the gRNA can be introduced to the target cells as well as recombinant Cas9 protein in complex with the gRNA (i.e. insert the RNP complex into the cell).

In certain embodiments, the CRISPR/Cas system is a Class 1 CRISPR/Cas system. In certain embodiments, a Class 1 CRISPR/Cas system comprises a multi-subunit crRNA-effector complex. In certain embodiments, the CRISPR/Cas system is a type I CRISPR-Cas system. In certain embodiments, the CRISPR/Cas system is a type III CRISPR/Cas system. In certain embodiments, the CRISPR/Cas system is a type IV CRISPR-Cas system.

In certain embodiments, the CRISPR/Cas system is a Class 2 CRISPR/Cas system. In certain embodiments, a Class 2 CRISPR/Cas system comprises a single subunit crRNA-effector module. In certain embodiments, the CRISPR/Cas system is a type II CRISPR-Cas system. In certain embodiments, the CRISPR/Cas system is a type V CRISPR/Cas system.

In certain embodiments, the Cas in the Class 2 CRISPR/Cas system can be Cas9, Cpf1, C2c1, C2c2 or C2c3. A person of ordinary skill in the art would understand the classification of CRISPR/Cas systems as it is well-known in the art (e.g. Nat Rev Microbiol. 2017 March, 15(3): 169-182; Nat Rev Microbiol. 2015 November, 13(11): 722-736), and that this classification is evolving with time (Mol Cell. 2015 Nov. 5, 60(3): 385-397). In some embodiments, the CRISPR/Cas is any CRISPR associated protein (CAS) endonuclease known in the art.

Genome editing using recombinant adeno-associated viruses (rAAVs) is based on rAAV vectors which enable insertion, deletion or substitution of DNA sequences in the genomes of live mammalian cells. The rAAV genome is a single-stranded deoxyribonucleic acid (ssDNA) molecule, either positive- or negative-sensed, which is about 4.7 kb long. These single-stranded DNA viral vectors have high transduction rates and have a unique property of stimulating endogenous homologous recombination in the absence of double-strand DNA breaks in the genome. One of skill in the art can design a rAAV vector to target a desired genomic locus and perform both gross and/or subtle endogenous gene alterations in a cell. rAAV genome editing has the advantage in that it targets a single allele and does not result in any off-target genomic alterations.

DNA Editing Agent

The technology described herein provides, in certain aspects and embodiments, a DNA-editing agent. The DNA editing agent may be constructed using recombinant DNA technology well known to persons skilled in the art.

In one embodiment, the DNA editing agent disclosed herein may be comprised in a single nucleic acid construct, or comprised in a combination of nucleic acid constructs. In one embodiment, the DNA editing agent comprises at least two key elements as described below:

A first element is a nucleotide sequence cassette which is destined to be stably integrated to a specific location in the genome of a bird. The first element, when integrated into the genome of a bird, changes the genotype of the bird, but also, in certain embodiments and under certain conditions, changes the phenotype of the bird. The altered phenotype of the bird, in comparison to the phenotype of other birds, is the purpose of the technology provided herein. Briefly, and as described in detail by the embodiments provided herein, the altered phenotype is useful in the prevention of the development of viable male chicks out of male embryos. This prevention can save farmers and hatcheries significant economic burdens, as well as preventing the need to sacrifice viable male chicks.

A second element is a first and second nucleotide targeting sequences that flank the first element. The second element is in charge of determining the location in a genome of a bird into which the first element is stably integrated. Random integration of foreign DNA into a genome of any organism would be detrimental if it interferes with genes in charge of basic cell functions. Alternatively, random integration may be immaterial if the foreign DNA integrates to a non-active segment of the DNA. The second element performs the important function of directing integration of the first element into a defined and predetermined region in the bird's DNA. In one embodiment of the present disclosure, the second element directs the incorporation of the first element into openly transcribed regions in chromosome Z of birds, without having any negative effect on basic cell functions.

A person of skill in the art would understand that the term "DNA editing agent" generally refers to any molecule, such as a nucleotide sequence or an enzyme, which promotes a change in a genome of an organism, such as a bird. The change may be an addition to the DNA, e.g. by the agent being integrated to the DNA, a replacement of a sequence of the DNA, e.g. by homological recombination, or a deletion of the DNA.

In one embodiment, the DNA editing agent may be constructed in a viral vector (e.g. using a single vector or multiple vectors). Such vectors are commonly used in gene transfer and gene therapy applications. Different viral vector systems have their own unique advantages and disadvantages. Viral vectors that may be used to integrate the first nucleotide sequence of certain embodiments into the Z chromosome of a bird include, but are not limited to, adenoviral vectors, adeno-associated viral vectors, alphavirus vectors, herpes simplex viral vectors, retroviral vectors, or lentiviral vectors.

A viral construct such as a retroviral construct includes at least one transcriptional promoter/enhancer or locus-defining element(s), or other elements that control gene expression by means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. In certain embodiments, the signal sequence can be a mammalian signal sequence. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, or dendrimers.

In one embodiment, provided herein is a DNA editing agent comprising a polynucleotide cassette having a formula 5'-LHA (left homology arm)-OIE (optogenetic-inducible element)-LIE (lethality-inducing element)-RHA (right homology arm)-3' or a formula 5'-LHA-LIE-OIE-RHA-3', wherein (i) the LHA comprises a first nucleotide sequence that is substantially homologous to a first corresponding nucleotide sequence on chromosome Z of a bird; (ii) the OIE comprises a first promoter functionally linked to a second nucleotide sequence encoding an inducer-activated site-specific recombinase enzyme; (iii) the LIE comprises a third nucleotide sequence encoding a lethality-promoting protein, which is operatively linked to the activity of the inducer-activated site-specific recombinase enzyme; and (iv) the RHA comprises a fourth nucleotide sequence that is substantially homologous to a second corresponding nucleotide sequence on chromosome Z of a bird.

As it would be apparent to those skilled in the art, a formula 5'-LHA-OIE-LIE-RHA-3' or a formula 5'-LHA-LIE-OIE-RHA-3' relate to the respective position of any element (e.g. LHA or OIE or LIE or RHA) in relation to all other elements in the same DNA editing agent molecule. The terminology of 5' and 3' is well accepted and is well-known to a person of ordinary skill in the art.

In certain embodiments, the polynucleotide cassette comprises the formula 5'-LHA-OIE-LIE-RHA-3'. In certain embodiments, the OIE is upstream to the LIE. In certain embodiments, the first promoter in the OIE is functionally linked to the second nucleotide sequence encoding the inducer-activated site-specific recombinase enzyme and is not further functionally linked to the third nucleotide sequence encoding the lethality-promoting protein.

In certain embodiments, the polynucleotide cassette comprises the formula 5'-LHA-LIE-OIE-RHA-3'. In certain embodiments, the LIE is upstream to the OIE. In certain embodiments, the first promoter in the OIE is functionally linked to the second nucleotide sequence encoding the inducer-activated site-specific recombinase enzyme and is not further functionally linked to the third nucleotide sequence encoding the lethality-promoting protein.

In certain embodiments, the DNA editing agent comprises a formula 5'-LHA-OIE-LIE-RHA-3', wherein (i) LHA comprises the sequence set forth in SEQ ID NO: 105, (ii) OIE comprises the sequences set forth in SEQ ID NOs: 101-103, or the sequences set forth in SEQ ID NO: 107, SEQ ID NO: 103, and SEQ ID NO: 108, (iii) LIE comprises the sequence set forth in SEQ ID NO: 92 or comprises the sequence set forth in SEQ ID NO: 94 or the sequence set forth in SEQ ID NO: 96 or the sequence set forth in SEQ ID NO: 98, (iv) RHA comprises the sequence set forth in SEQ ID NO: 106, or (v) any combination of (i), (ii), (iii) and (iv).

In certain embodiments, the OIE comprises the sequence set forth in SEQ ID NO: 101, which is connected to the sequence set forth in SEQ ID NO: 103, which is connected to the sequence set forth in SEQ ID NO: 102. In certain embodiments, the OIE comprises the sequence set forth in SEQ ID NO: 102, which is connected to the sequence set forth in SEQ ID NO: 103, which is connected to the sequence set forth in SEQ ID NO: 101.

In certain embodiments, the OIE comprises the sequence set forth in SEQ ID NO: 107, which is connected to the sequence set forth in SEQ ID NO: 103, which is connected to the sequence set forth in SEQ ID NO: 108. In certain embodiments, the OIE comprises the sequence set forth in SEQ ID NO: 108, which is connected to the sequence set forth in SEQ ID NO: 103, which is connected to the sequence set forth in SEQ ID NO: 107.

In certain embodiments, (i) the LHA comprises the sequence set forth in SEQ ID NO: 105, (ii) the OIE comprises the sequence set forth in SEQ ID NO: 100, which is connected to the sequence set forth in SEQ ID NO: 116, which is connected to the sequence set forth in SEQ ID NO: 101, which is connected to the sequence set forth in SEQ ID NO: 103, which is connected to the sequence set forth in SEQ ID NO: 102, which is connected to the sequence set forth in SEQ ID NO: 104, which is connected to the sequence set forth in SEQ ID NO: 116, or the OIE comprises the sequence of SEQ ID NO:100, which is connected to the sequence of SEQ ID NO:116, which is connected to the sequence of SEQ ID NO:102, which is connected to the sequence of SEQ ID NO:103, which is connected to the sequence of SEQ ID NO:101, which is connected to the sequence of SEQ ID NO:104, which is connected to the sequence of SEQ ID NO:116, or the OIE comprises the sequence set forth in SEQ ID NO: 100, which is connected to the sequence set forth in SEQ ID NO: 116, which is connected to the sequence set forth in SEQ ID NO: 107, which is connected to the sequence set forth in SEQ ID NO: 103, which is connected to the sequence set forth in SEQ ID NO: 108, which is connected to the sequence set forth in SEQ ID NO: 104, which is connected to the sequence set forth in SEQ ID NO: 116, or the OIE comprises the sequence of SEQ ID NO:100, which is connected to the sequence of SEQ ID NO:116, which is connected to the sequence of SEQ ID NO:108, which is connected to the sequence of SEQ ID NO:103, which is connected to the sequence of SEQ ID NO:107, which is connected to the sequence of SEQ ID NO:104, which is connected to the sequence of SEQ ID NO:116, (iii) the LIE comprises the sequence set forth in SEQ ID NO: 92 or comprises the sequence set forth in SEQ ID NO: 94 or the sequence set forth in SEQ ID NO: 96 or the sequence set forth in SEQ ID NO: 98, connected to the sequence set forth in SEQ ID NO: 104, and (iv) RHA comprises the sequence set forth in SEQ ID NO: 106.

In certain embodiments, the DNA editing agent comprises the sequence of one of SEQ ID NOs:120-127.

The DNA editing agent may encode a reporter protein that is readily detectable either by its presence or activity, including, but not limited to, luciferase, fluorescent protein (e.g., green fluorescent protein), chloramphenicol acetyl transferase, beta-galactosidase, secreted placental alkaline phosphatase, beta-lactamase, human growth hormone, and other secreted enzyme reporters. Generally, a reporter gene encodes a polypeptide not otherwise produced by the host cell, which is detectable by analysis of the cell(s), e.g., by the direct fluorometric, radioisotopic or spectrophotometric analysis of the cell(s) and typically without the need to kill the cells for signal analysis. In certain embodiments, a reporter gene encodes an enzyme, which produces a change in fluorometric properties of the host cell, which is detectable by qualitative, quantitative, or semi-quantitative function or transcriptional activation. Exemplary enzymes include esterases, β-lactamase, phosphatases, peroxidases, proteases (tissue plasminogen activator or urokinase) and other enzymes whose function can be detected by appropriate chromogenic or fluorogenic substrates known to those skilled in the art or developed in the future. The reporter gene may report on successful integration of the construct into the Z chromosome.

In certain embodiments, the DNA editing agent may comprise nucleotide sequence that encodes a reporter polypeptide. In certain embodiments, the reporter polypeptide can be a green fluorescence protein (GFP) (SEQ ID NO: 115), or mCherry/RFP (SEQ ID NO: 119).

In certain embodiments, the DNA editing agent further comprises a positive and/or negative selection markers for efficiently selecting transformed cells that underwent a homologous recombination event with the construct. Positive selection provides a means to enrich the population of clones that have taken up foreign DNA. Non-limiting examples of such positive markers include glutamine synthetase, dihydrofolate reductase (DHFR), markers that confer antibiotic resistance, such as neomycin, hygromycin, puromycin, and blasticidin S resistance cassettes. Negative selection markers are necessary to select against random integrations and/or elimination of a marker sequence (e.g. positive marker). Non-limiting examples of such negative markers include the herpes simplex-thymidine kinase (HSV-TK) which converts ganciclovir (GCV) into a cytotoxic nucleoside analog, hypoxanthine phosphoribosyltransferase (HPRT), Diphtheria toxin (DT) and adenine phosphoribosyltransferase (ARPT).

In certain embodiments, the codons encoding the proteins of the DNA editing agent are "optimized" codons, i.e., the codons are those that appear frequently in, e.g., highly expressed genes in the bird species, instead of those codons that are frequently used by, for example, an influenza virus. Such codon usage provides for efficient expression of the protein in avian cells. Codon usage patterns are known in the literature for highly expressed genes of many species (e.g., Nakamura et al., 1996, Nucleic Acids Res. 24(1):214-5; McEwan et al., 1998, Biotechniques. 24(1):131-6, 138).

In certain embodiments, the DNA editing agent may further include self-cleaving peptides such as the 2A, including but not limited to P2A, T2A, E2A (Wang et al., Scientific Report 5, Article 16273 (2015), or internal ribosome entry site (IRES) sequences.

Left and Right Homology Arms

It is generally accepted that the size of the homology arms for HR should be proportionate to the size of the insert between the arms. One of ordinary skill in the art would readily determine and construct a homology arm with suitable length. In one embodiment, the homology arm can be as short as 50 bases. In certain embodiments, (i) the length of the LHA is about 0.5 to about 5 kilobases (kb); (ii) the length of the RHA is about 0.5 to about 5 kb; or (iii) any combination of (i) and (ii). In certain embodiments, (i) the length of the LHA is about 1.5 kb; (ii) the length of the RHA is about 1.5 kb; or (iii) any combination of (i) and (ii). In certain embodiments, the LHR and/or RHA can be as short as 50 bases.

In certain embodiments, the length of the LHA is about 0.5 to about 5 kilobases (kb). In certain embodiments, the length of the LHA is about 0.5 kb. In certain embodiments, the length of the LHA is about 1 kb. In certain embodiments, the length of the LHA is about 1.5 kb. In certain embodiments, the length of the LHA is about 2 kb. In certain embodiments, the length of the LHA is about 2.5 kb. In certain embodiments, the length of the LHA is about 3 kb. In certain embodiments, the length of the LHA is about 3.5 kb. In certain embodiments, the length of the LHA is about 4 kb. In certain embodiments, the length of the LHA is about 4.5 kb. In certain embodiments, the length of the LHA is about 5 kb. In certain embodiments, the LHR can be as short as 50 bases.

In certain embodiments, the length of the RHA is about 0.5 to about 5 kilobases (kb). In certain embodiments, the length of the RHA is about 0.5 kb. In certain embodiments, the length of the RHA is about 1 kb. In certain embodiments, the length of the RHA is about 1.5 kb. In certain embodiments, the length of the RHA is about 2 kb. In certain embodiments, the length of the RHA is about 2.5 kb. In certain embodiments, the length of the RHA is about 3 kb. In certain embodiments, the length of the RHA is about 3.5 kb. In certain embodiments, the length of the RHA is about 4 kb. In certain embodiments, the length of the RHA is about 4.5 kb. In certain embodiments, the length of the RHA is about 5 kb. In certain embodiments, the RHA can be as short as 50 bases.

In certain embodiments, the length of each of the LHA and RHA is about 0.5 kb. In certain embodiments, the length of each of the LHA and RHA is about 1 kb. In certain embodiments, the length of each of the LHA and RHA is about 1.5 kb. In certain embodiments, the length of each of the LHA and RHA is about 2 kb. In certain embodiments, the length of each of the LHA and RHA is about 2.5 kb. In certain embodiments, the length of each of the LHA and RHA is about 3 kb. In certain embodiments, the length of each of the LHA and RHA is about 3.5 kb. In certain embodiments, the length of each of the LHA and RHA is about 4 kb. In certain embodiments, the length of each of the LHA and RHA is about 4.5 kb. In certain embodiments, the length of each of the LHA and RHA is about 5 kb. In certain embodiments, the LHR and RHA can be as short as 50 bases.

In certain embodiments, the length of each of the left and the right homology arms is sufficient to allow specific recombination into chromosomal DNA of a bird. In one embodiment, the LHA and/or the RHA are at least 500 nucleotides long, for example, between 500-3000 nucleotides long. Typically, the required size of the LHA and/or the RHA homology arms relies on the length of the cassettes which are flanked by these arms. Smaller cassettes require shorter arms and vice versa. In one embodiment, the homology arm can be as short as 50 bases.

In certain embodiments, (i) the LHA is substantially homologous to a corresponding first nucleotide sequence located in an openly transcribed region on chromosome Z of a bird; (ii) the RHA is substantially homologous to a corresponding second nucleotide sequence located in an openly transcribed region on chromosome Z of a bird; or (iii) both (i) and (ii).

As it would be apparent to those skilled in the art, a first sequence is "substantially homologous" to a second sequence if the first sequence and the second sequence are similar or identical in sequence, as long as the first sequence and the second sequence can replace one another by homologous recombination. Method to test and identify homologous recombination are well-known in the art.

In certain embodiments, substantially homologous is at least 50% identical. In certain embodiments, substantially homologous is at least 60% identical. In certain embodiments, substantially homologous is at least 70% identical. In certain embodiments, substantially homologous is at least 80% identical. In certain embodiments, substantially homologous is at least 90% identical. In certain embodiments, substantially homologous is at least 95% identical. In certain embodiments, substantially homologous is at least 99% identical.

In certain embodiments, the first nucleotide sequence in the LHA is 50% to 100% identical in sequence to a first corresponding nucleotide sequence on chromosome Z. In certain embodiments, the first nucleotide sequence in the LHA is 80% to 100% identical in sequence to a first corresponding nucleotide sequence on chromosome Z. In certain embodiments, the first nucleotide sequence in the LHA is 85% to 100% identical in sequence to a first corresponding nucleotide sequence on chromosome Z. In certain embodiments, the first nucleotide sequence in the LHA is 90% to 100% identical in sequence to a first corresponding nucleotide sequence on chromosome Z. In certain embodiments, the first nucleotide sequence in the LHA is 95% to 100% identical in sequence to a first corresponding nucleotide sequence on chromosome Z. In certain embodiments, the first nucleotide sequence in the LHA is 99% to 100% identical in sequence to a first corresponding nucleotide sequence on chromosome Z. In certain embodiments, the first nucleotide sequence in the LHA is 100% identical in sequence to a first corresponding nucleotide sequence on chromosome Z.

In certain embodiments, the fourth nucleotide sequence in the RHA is 50% to 100% identical in sequence to a second corresponding nucleotide sequence on chromosome Z. In certain embodiments, the fourth nucleotide sequence in the RHA is 80% to 100% identical in sequence to a second corresponding nucleotide sequence on chromosome Z. In certain embodiments, the fourth nucleotide sequence in the RHA is 85% to 100% identical in sequence to a second corresponding nucleotide sequence on chromosome Z. In certain embodiments, the fourth nucleotide sequence in the RHA is 90% to 100% identical in sequence to a second corresponding nucleotide sequence on chromosome Z. In certain embodiments, the fourth nucleotide sequence in the RHA is 95% to 100% identical in sequence to a second corresponding nucleotide sequence on chromosome Z. In certain embodiments, the fourth nucleotide sequence in the RHA is 99% to 100% identical in sequence to a second corresponding nucleotide sequence on chromosome Z. In certain embodiments, the fourth nucleotide sequence in the RHA is 100% identical in sequence to a second corresponding nucleotide sequence on chromosome Z.

In certain embodiments, the LHA and/or the RHA is homologous or show homology or identity of about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% to at least one nucleotide sequence within a target loci within chromosome Z of a bird that serves as the integration site.

A person of skill in the art would understand that the term "openly transcribed region in a chromosome" generally refers to regions of the chromosome which include genes that are transcribed in a level sufficient to allow other genes to be easily transcribed as well. Non-limiting examples of openly transcribed regions are regions in proximity to house-keeping genes which are highly transcribed during the life of the cell or the organism. Other non-limiting examples of openly transcribed regions are regions in-between loci (e.g. chromatin regulatory elements, non-coding DNA, "junk DNA", etc.). Non-limiting examples of poorly transcribed regions are regions at the ends of each chromosomes, called telomers, which are not transcribed during the life of the cell or the organism. In certain embodiments, the openly transcribed region is located at or downstream to the Hint1Z gene on chromosome Z of a bird.

In one embodiment, the LHA and/or the RHA correspond to a genomic sequence which is present on the Z chromosome in birds. In certain embodiments, the genomic sequence is located at or downstream of a gene which is transcriptionally active (for example, at or downstream to the Hint1Z gene (GeneID: 395424)). Another contemplated target is Isl1 (Gene ID 369383), also on chromosome Z, which is expressed starting from early stages of embryogenesis. FIG. 3 illustrates an embodiment of the homology arms on chromosome Z, downstream to the Hint1Z gene.

The LHA and/or the RHA targeting sequences may be selected such that the LHA and/or the RHA targeting sequence integrates specifically into the Z chromosome and not any other chromosome of the cell, e.g. by spontaneous homologous recombination or by homology directed repair (HDR). Homologous recombination can occur spontaneously. Furthermore, the LHA and/or the RHA targeting sequence may be selected depending on what method is being relied upon to integrate the first targeting sequence into the chromosome. Methods of integrating nucleotide sequences into chromosomes are well known in the art, including targeted homologous recombination, site specific recombinases and genome editing by engineered nucleases (see e.g. Menke D. Genesis (2013) 51:-618; Capecchi, Science (1989) 244:1288-1292; Santiago et al., Proc Natl Acad Sci USA (2008) 105:5809-5814; International Patent Application Nos. WO 2014085593, WO 2009071334 and WO 2011146121; U.S. Pat. Nos. 8,771,945, 8,586,526, 6,774,279 and US Patent Application Publication Nos. 20030232410, 20050026157, 20060014264). PB transposases are also contemplated. Agents for introducing nucleic acid alterations to a gene of interest can be designed by publicly available resources.

In certain embodiments, the first 5' nucleotide of LHA corresponds to chromosome Z, position 44,914,961. In certain embodiments, the first corresponding nucleotide sequence of LHA is located at chromosome Z, position 44,914,961 to position 44,916,456.

In certain embodiments, the first 5' nucleotide of LHA corresponds to Gallus gallus chromosome Z, Assembly GRCg6a, NC_006127.5, position 44,914,961. In certain embodiments, the first corresponding nucleotide sequence of LHA is located at Gallus gallus chromosome Z, Assembly GRCg6a, NC_006127.5, position 44,914,961 to position 44,916,456.

In certain embodiments, the first 5' nucleotide of RHA corresponds to chromosome Z, position 44,916,480. In certain embodiments, the second corresponding nucleotide sequence of RHA is located at chromosome Z, position 44,916,480 to position 44,918,043.

In certain embodiments, the first 5' nucleotide of RHA corresponds to Gallus gallus chromosome Z, Assembly GRCg6a, NC_006127.5, position 44,916,480. In certain embodiments, the second corresponding nucleotide sequence of RHA is located at *Gallus gallus* chromosome Z, Assembly GRCg6a, NC_006127.5, position 44,916,480 to position 44,918,043.

In certain embodiments, (i) the LHA comprises the nucleotide sequence set forth in SEQ ID NO: 105, or a fragment thereof, e.g. at least 50, or at least 500 consecutive nucleotides of the nucleotide sequence set forth in SEQ ID NO: 105; (ii) the RHA comprises the nucleotide sequence set forth in SEQ ID NO: 106, or a fragment thereof, e.g. at least 50, or at least 500 consecutive nucleotides of the nucleotide sequence set forth in SEQ ID NO: 106; or (iii) both (i) and (ii). In certain embodiments, (i) the LHA comprises the nucleotide sequence set forth in SEQ ID NO: 105, or a fragment of at least 1000 consecutive nucleotides of the nucleotide sequence set forth in SEQ ID NO: 105; (ii) the RHA comprises the nucleotide sequence set forth in SEQ ID NO: 106, or a fragment of at least 1000 consecutive nucleotides of the nucleotide sequence set forth in SEQ ID NO: 106; or (iii) both (i) and (ii).

In certain embodiments, the LHA comprises the nucleotide sequence set forth in SEQ ID NO: 105. In certain embodiments, the LHA comprises at least 50, or at least 500 consecutive nucleotides from the nucleotide sequence set forth in SEQ ID NO: 105. In certain embodiments, the LHA comprises at least 1000 consecutive nucleotides from the nucleotide sequence set forth in SEQ ID NO: 105. In certain embodiments, the LHA comprises 500 consecutive nucleotides from the nucleotide sequence set forth in SEQ ID NO: 105. In certain embodiments, the LHA comprises 1000 consecutive nucleotides from the nucleotide sequence set forth in SEQ ID NO: 105.

In certain embodiments, the RHA comprises the nucleotide sequence set forth in SEQ ID NO: 106. In certain embodiments, the RHA comprises at least 50, or at least 500 consecutive nucleotides from the nucleotide sequence set forth in SEQ ID NO: 106. In certain embodiments, the RHA comprises at least 1000 consecutive nucleotides from the nucleotide sequence set forth in SEQ ID NO: 106. In certain embodiments, the RHA comprises 500 consecutive nucleotides from the nucleotide sequence set forth in SEQ ID NO: 106. In certain embodiments, the RHA comprises 1000 consecutive nucleotides from the nucleotide sequence set forth in SEQ ID NO: 106.

In certain embodiments, LHA comprises the nucleotide sequence set forth in SEQ ID NO: 105, or a fragment of at least 50, or at least 500 consecutive nucleotides of the nucleotide sequence set forth in SEQ ID NO: 105; and the RHA comprises the nucleotide sequence set forth in SEQ ID NO: 106, or a fragment of at least 50, or at least 500 consecutive nucleotides of the nucleotide sequence set forth in SEQ ID NO: 106. In certain embodiments, LHA comprises the nucleotide sequence set forth in SEQ ID NO: 105, or a fragment of at least 1000 consecutive nucleotides of the nucleotide sequence set forth in SEQ ID NO: 105; and the RHA comprises the nucleotide sequence set forth in SEQ ID NO: 106, or a fragment of at least 1000 consecutive nucleotides of the nucleotide sequence set forth in SEQ ID NO: 106. In certain embodiments, LHA comprises the nucleotide sequence set forth in SEQ ID NO: 105; and the RHA comprises the nucleotide sequence set forth in SEQ ID NO: 106.

Optogenetic-Inducible Element

Promoters

As it would be apparent to those skilled in the art, a "promoter functionally linked to a nucleotide sequence" encompasses that the promotor is located upstream to and is involved in cis in the transcription of the nucleotide sequence. A non-limiting example of a promoter functionally linked to a nucleotide sequence is the first promoter in the OIE which drives the transcription of the nucleotide sequence in the OIE encoding an inducer-activated site-specific recombinase enzyme.

In certain embodiments, the first promoter is a constitutive promoter in birds. As it would be apparent to those skilled in the art, a "constitutive promoter" encompasses a promoter that allows for continual transcription of its associated nucleotide sequence or gene.

In certain embodiments, the first promoter is an inducible promoter in birds. As it would be apparent to those skilled in the art, an "inducible promoter" encompasses a promoter that allows for non-continual transcription of its associated nucleotide sequence or gene. In certain embodiments, the non-continual transcription is modulated by an inducer. In certain embodiments, the inducer is exogenous to a cell of a bird.

In certain embodiments, the first promoter can be pCAGG (SEQ ID NO: 100), pGK (SEQ ID NO: 109), pCMV (SEQ ID NO: 110), phSyn (SEQ ID NO: 111), or pEFl-a (SEQ ID NO: 112).

Inducer-Activated Site-Specific Recombinase

In certain embodiments, the inducer-activated site-specific recombinase enzyme can be Cre recombinase (Cre) (SEQ ID NO: 113), or Mag (SEQ ID NO: 114 and SEQ ID NO: 65).

According to certain embodiments, the inducer initiates or increases the transcription of the nucleotide sequence encoding the inducer-activated site-specific recombinase enzyme. In other embodiments, the inducer initiates or increases the translation of the mRNA coding for the inducer-activated site-specific recombinase. In yet other embodiments, the inducer initiates or increases the activity of the inducer-activated site-specific recombinase enzyme. According to certain embodiments, the inducer initiates or increases the formation of a functional inducer-activated site-specific recombinase enzyme by complexing non-functional fragments of site-specific recombinase to each other. As it would be apparent to those skilled in the art, a plurality of non-functional fragments (peptides) of an enzyme, where the enzyme is found in nature as a polypeptide, may co-interact to form a functional enzyme, despite each fragment (peptide) not being covalently linked to other fragments (peptides) as illustrated in FIG. 2. In certain embodiments, the inducer-activated site-specific recombinase comprises non-functional peptide fragments of an inducer-activated site-specific recombinase that combine to form an active inducer-activated site-specific recombinase enzyme in the presence of the inducer.

The term "inducible" as used herein may encompass all aspects of a switch irrespective of the molecular mechanism involved. Accordingly, a switch may include, but is not limited to, antibiotic based inducible systems, electromagnetic energy based inducible systems, small molecule based inducible systems, nuclear receptor based inducible systems and hormone based inducible systems. In some embodiments, the switch is a light-inducible system, a tetracycline (Tet)/DOX inducible system, an Abscisic acid (ABA) inducible system, a cumate repressor/operator system, a 40HT/estrogen inducible system, an ecdysone-based inducible systems or a FKBP12/FRAP (FKBP12-rapamycin complex) inducible system. In certain examples, in which the inducer is administered to an unhatched egg, the inducer is able to penetrate the shell of the egg. In certain examples, the inducer is not toxic to a female embryo inside an egg and does not alter the development of a female embryo inside an egg.

As used herein, the term "switch" refers to a single component or a set of components that act in a coordinated manner to affect a change, encompassing all aspects of biological function such as activation, repression, enhancement or termination of that function. In one embodiment, switches relate to inducible and/or repressible systems used in gene regulation. In general, an inducible system may be "off" unless there is the presence of some molecule or energy form (called an inducer) that allows for gene expression. The molecule is said to "induce expression". The manner by which this happens is dependent on the control mechanisms as well as differences in cell type. A repressible system is "off" except in the presence of some molecule or energy form (called a suppressor) that suppresses gene expression. The manner by which this happens is dependent on the control mechanisms as well as differences in cell type.

Exemplary optogenetic switches are illustrated in FIGS. 4A-4C, each of which utilize the light-sensitive dimerizing protein domains cryptochrome 2 (CRY2) and CIB1 from *Arabidopsis thaliana* and a site-specific recombinase as the effector molecule. The CRY2 is fused in frame to one half of a Cre recombinase whereas the CIB1 is fused in frame to the other half of a Cre recombinase—i.e. a split recombinase enzyme. Thus, when the inducer (blue light) is provided, the CRY2 and the CIB1 heterodimerize to produce a functional Cre recombinase which is able to carry out site specific recombination.

In certain embodiments, the expression of the inducer-activated site-specific recombinase enzyme is induced by an inducer. In certain embodiments, the inducer is electromagnetic energy. In certain embodiments, the electromagnetic energy is visible light of a wavelength of 380-740 nm, or a component of visible light. In certain embodiments, the component of visible light is blue light of a wavelength of 450-185 nm.

In one embodiment, the inducer-activated site-specific recombinase is induced using electromagnetic energy. The component of visible light may have a wavelength in the range of 450 nm-700 nm or between 450 nm-500 nm, i.e. blue light. The blue light may be of intensity of at least 0.2 mW/cm2, or of at least 4 mW/cm2. The component of visible light may have a wavelength in the range of 620 nm-700 nm, i.e. red light. Single or multiple applications of visible light, in any order and in any combination are contemplated. The visible light may be delivered as single or multiple continuous applications, or as pulses (pulsatile delivery).

Examples of such optogenetic switches are described in Muller et al., Biol Chem. 2015 February, 396(2):145-52. doi: 10.1515/hsz-2014-0199; Motta Mena et al., Nat Chem Biol. 2014 March, 10(3): 196-202; and WO 2014/018423.

The Cre recombinase derived from the P1 bacteriophage and Flp recombinase derived from the yeast *Saccharomyces cerevisiae* are site-specific DNA recombinases each recognizing a unique 34 base pair DNA sequence (termed "Lox" and "FRT", respectively). Sequences that are flanked by either the Lox sites or the FRT sites can be readily removed via site-specific recombination upon expression of Cre or Flp recombinase, respectively.

In certain embodiments, recombinase recognition sites can be Lox511, Lox5171, Lox2272, m2, Lox71, Lox66, FRT, F1, F2, F3, F4, F5, FRT(LE), FRT(RE), attB, attP, attL, or attR.

For example, the Lox sequence is composed of an asymmetric eight base pair spacer region flanked by 13 base pair inverted repeats. Cre recombines the 34 base pair Lox DNA sequence by binding to the 13 base pair inverted repeats and catalyzes strand cleavage and re-ligation within the spacer region. The staggered DNA cuts made by Cre in the spacer region are separated by 6 base pairs to give an overlapping region that acts as a homology sensor to ensure that only recombination sites having the same overlap region recombine.

In certain embodiments, the site-specific recombinase system is used after homologous recombination for the removal of DNA, e.g. a selection cassette, from a chromosome of a bird. Of note, the Cre and Flp recombinases leave behind a Lox or FRT "scar" of 34 base pairs. The Lox or FRT sites that remain are typically left behind in an intron or 3' UTR of the modified locus, and these sites usually do not significantly interfere with gene function. This system also allows for the generation of conditional altered alleles that can be inactivated or activated in a temporal or tissue-specific manner.

Thus, Cre/Lox and Flp/FRT recombination may involve introduction of a targeting vector with 3' and 5' homology arms containing the mutation of interest, two Lox or FRT sequences and typically a selectable cassette placed between the two Lox or FRT sequences. Positive selection is applied and homologous recombinants that contain targeted mutation are identified. Transient expression of Cre or Flp in conjunction with negative selection results in the excision of the selection cassette and selects for cells where the cassette has been lost. The final targeted allele contains the Lox or FRT scar of exogenous sequences.

In certain embodiments, the inducer is heat, ultrasound, electromagnetic energy or a chemical. In certain embodiments, the inducer is delivered to an egg during the process of egg production inside a bird prior to oviposition.

While unwanted male embryos may be freely exposed to day light (or as an example, to blue light), transgenic cells and organisms may need to be kept under special conditions to prevent unwanted activation of the optogenetic system provided herein. Also, it is known that female birds have higher productivity when reared under green/red light conditions.

In certain embodiments, the methods provided herein are performed under green light. In certain embodiments, the cells and organisms provided herein are kept under green light. In certain embodiments, the green light is of a wavelength of 500-565 nm.

In certain embodiments, the methods provided herein are performed under red light. In certain embodiments, the cells and organisms provided herein are kept under red light. In certain embodiments, the red light is of a wavelength of 625-740 nm.

Several methods of energy activation are contemplated, for example, electric field energy and/or ultrasound which have a similar effect. If necessary, the proteins pairings of the switch may be altered and/or modified for maximal effect by another energy source.

Electric field energy may be administered substantially as described in the art, using one or more electric pulses of from about 1 Volt/cm to about 10 kVolts/cm under in vivo conditions. Instead of or in addition to the pulses, the electric field may be delivered in a continuous manner. The electric pulse may be applied for between 1 and 500 milliseconds, or between 1 and 100 milliseconds. The electric field may be applied continuously or in a pulsed manner for 5 about minutes. As used herein, 'electric field energy' is the electrical energy to which a cell is exposed. In certain embodiments, the electric field has a strength of from about 1 Volt/cm to about 10 kVolts/cm or more under in vivo conditions (see e.g. WO 97/49450).

As used herein, the term "electric field" includes one or more pulses at variable capacitance and voltage and includes exponential and/or square wave and/or modulated wave and/or modulated square wave forms. References to electric fields and electricity should be taken to include reference the presence of an electric potential difference in the environment of a cell. Such an environment may be set up by way of static electricity, alternating current (AC), direct current (DC), etc, as known in the art. The electric field may be uniform, non-uniform or otherwise, and may vary in strength and/or direction in a time dependent manner.

Single or multiple applications of electric field, as well as single or multiple applications of ultrasound are also possible, in any order and in any combination. The ultrasound and/or the electric field may be delivered as single or multiple continuous applications, or as pulses (pulsatile delivery).

Lethality-Inducing Element

As it would be apparent to those skilled in the art, a "first protein operatively linked to the activity of a second protein" encompasses that the second protein controls the operation of the first protein in trans. A non-limiting example of a first protein operatively linked to the activity of a second protein is the lethality-promoting protein encoded in the LIE which becomes active by the activity of the inducer-activated site-specific recombinase enzyme encoded in the OIE. The terminology of "in cis" and "in trans" is well accepted and understood to a person of ordinary skill in the art.

As the inducer-activated site-specific recombinase enzyme activates the lethality-promoting protein in trans, the respective position of the OIE and the LIE in the same molecule, or in different molecules, may be different in different embodiments. In certain embodiments, the OIE and the LIE are in the same molecule. In certain embodiments, the OIE and the LIE are in different molecules.

In certain embodiments, the activating enzyme (e.g. recombinase enzyme, such as Cre) is separated from the lethality gene cassette. In this case, the activating enzyme is inserted into the genome of either the male or female bird and the inactive lethality cassette is inserted on the Z chromosome of the corresponding sex of the bird. In this case, the activation of lethality in male embryos is performed merely by crossing the two transgenic parents. FIGS. 19A-19B are embodiments of targeting vectors in which the activating enzyme (Cre for example) is separated from the lethality gene cassette.

In certain embodiments, the LIE further comprises a second promoter functionally linked to the third nucleotide sequence encoding the lethality-promoting protein. In certain embodiments, the second promoter is a constitutive promoter in birds. In certain embodiments, the second promoter is an inducible promoter in birds. In certain embodiments, the second promoter can be pCAGG (SEQ ID NO: 100), pGK (SEQ ID NO: 109), pCMV (SEQ ID NO: 110), phSyn (SEQ ID NO: 111), or pEFl-a (SEQ ID NO: 112).

Lethality-Promoting Protein

As used herein, the term "lethality-promoting protein" refers to a protein that is lethal to an avian embryo (e.g. male embryo), thus preventing the hatching of a live male bird from the egg.

In certain embodiments, the lethality-inducing protein that can interfere with basic stages of early embryogenesis, such as N-cadherin, and proteins which interfere with essential signaling pathways, such as those mediated by bone morphogenetic proteins (BMPs) or fibroblast growth factors (FGF).

In certain embodiments, the lethality-inducing protein can be a toxin, a pro-apoptotic protein, an inhibitor of the Wingless/Integrated (Wnt) signaling pathway, a bone morphogenetic protein (BMP) antagonist, a fibroblast growth factor (FGF) antagonist, or a lethality-inducing fragment thereof. In certain embodiments, the lethality-inducing protein is a toxin or a lethality-inducing fragment thereof. In certain embodiments, the lethality-inducing protein is a pro-apoptotic protein or a lethality-inducing fragment thereof. In certain embodiments, the lethality-inducing protein is an inhibitor of the Wnt signaling pathway or a lethality-inducing fragment thereof. In certain embodiments, the lethality-inducing protein is a BMP antagonist or a lethality-inducing fragment thereof. In certain embodiments, the lethality-inducing protein is an FGF antagonist or a lethality-inducing fragment thereof. As it would be apparent to those skilled in the art, a "lethality-inducing fragment" of a molecule is any fragment of a molecule that suffices to induce lethality.

In certain embodiments, the lethality-inducing protein can be diphtheria toxin A (DTA) (SEQ ID NO: 93), wild type Caspase 3 (SEQ ID NO: 95), constitutively-active Caspase 3 (SEQ ID NO: 97), or Noggin (SEQ ID NO: 99). In certain embodiments, the lethality-inducing protein can be *Pseudomonas* exotoxin (GenBank Accession No. ABU63124), diphtheria toxin (GenBank Accession No. AAV70486), or ricin toxin (GenBank Accession No. EEF27734). In certain embodiments, the lethality-inducing protein can be interleukin 2 (GenBank Accession No. CAA00227), CD3 (GenBank Accession No. P07766), CD16 (GenBank Accession No. NP_000560.5), interleukin 4 (GenBank Accession No. NP_000580.1) or interleukin 10 (GenBank Accession No. P22301).

In certain embodiments, lethality is mediated by a RNA-guided DNA endonuclease enzyme. In certain embodiments, the DNA editing agent further comprises a nucleotide sequence that encodes for a guide RNA that targets an essential gene of the bird, this nucleotide sequence being operatively linked to the activity of the inducer-activated site-specific recombinase enzyme. In certain embodiments, the essential gene can be bone morphogenetic protein receptor, type IA (BMPR1A, Gene ID: 396308), bone morphogenetic protein 2 (BMP2, Gene ID: 378779), bone morphogenetic protein 4 (BMP4, Gene ID: 396165), or fibroblast growth factor receptor 1 (FGFR1, Gene ID: 396516).

As it would be apparent to those skilled in the art, a "RNA-guided DNA endonuclease enzyme" encompasses a DNA endonuclease enzyme which unwinds DNA and looks for sites complementary to a guide RNA molecule. In certain embodiments, the guide RNA molecule comprises the nucleotide sequence set forth in one of SEQ ID NOs:66-77.

Safe Lock Element

In one embodiment, the DNA editing agent disclosed herein may further comprise a "safe-lock" element which ensures the optogenic-lethality mechanism is inactive until the safe-lock element is removed. This element basically renders the optogenic-lethality system inactive by default. The optogenic-lethality system would become active only when the genome-edited cells are exposed to an agent which could remove the safe-lock element from the DNA editing agent. This "safe-lock" mechanism ensures that throughout the production process, cells which have undergone HR need not be protected from light, since the optogenic system is essentially inactive.

In one embodiment, the safe-lock element is inserted downstream to the promoter in the OIE but upstream of the sequence encoding the inducer-activated site-specific recombinase. The safe-lock element comprises nucleotide sequences (STOP element) that prevent transcription of the inducer-activated site-specific recombinase encoded by the OIE (see FIG. 26A, inactive "locked" state). In one embodiment, the safe-lock element comprises a coding sequence for a protein followed by a polyadenylation site. In other embodiments, any other sequences which will prevent the transcription of downstream coding sequences can also be used as a safe lock element. In one embodiment, the safe-lock element is flanked by two FRT sites. Thus, this safe-lock element can be removed upon the expression of the Flp recombinase. Once the safe-lock element is removed, the optogenes encoded in the OIE could be transcribed and become active in a light-dependent manner (FIG. 26A, active "unlocked" state).

In another embodiment, the safe-lock element and the sequence encoding the inducer-activated site-specific recombinase are flanked by the Lox sequences (FIG. 26B, inactive "locked" state). Upon expressing the Cre recombinase, the safe-lock element as well as the sequence encoding the inducer-activated site-specific recombinase could be removed, thus allowing the expression of the lethality-promoting protein encoded in the LIE (FIG. 26B, lethality-activated state).

Chimeric Chicks

As used herein, the term "chimeric", "chimera" or "chimeric chick" refers to a bird cell that contains the DNA editing agent disclosed herein, or a bird that has cells containing the DNA editing agent disclosed herein. It should also be noted that chimera embryos or chimera adult birds can also be referred as "surrogate"; hence, these terms can be used interchangeably. Representative examples of chimeric bird cells include, but are not limited to, bird primordial germ cells (PGCs) such as gonadal PGCs, blood PGCs, germinal crescent PGCs, or gametes that contain the DNA editing agent disclosed herein. Representative examples of chimeric bird include, but are not limited to, chicken, turkey, duck, geese, quail, pheasant, or ostrich that has cells containing the DNA editing agent disclosed herein.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

In one embodiment, there is provided a bird cell comprising an exogenous polynucleotide cassette as disclosed herein, comprising a formula 5'-OIE-LIE-3' or a formula 5'-LIE-OIE-3', wherein (i) the OIE is optogenetic-inducible element, comprising a first promoter functionally linked to a second nucleotide sequence encoding an inducer-activated site-specific recombinase enzyme; and (ii) the LIE is a lethality-inducing element, comprising a third nucleotide sequence encoding a lethality-promoting protein, operatively linked to the activity of the inducer-activated site-specific recombinase enzyme. The exogenous polynucleotide cassette is stably integrated into the Z chromosome of the cell.

Further provided, in another aspect, is a bird cell population, comprising bird cells that comprise an exogenous polynucleotide cassette as disclosed herein. The polynucleotide cassette comprises a formula 5'-OIE-LIE-3' or a formula 5'-LIE-OIE-3', wherein (i) the OIE is optogenetic-inducible element, comprising a first promoter functionally linked to a second nucleotide sequence encoding an inducer-activated site-specific recombinase enzyme; and (ii) the LIE is a lethality-inducing element, comprising a third nucleotide sequence encoding a lethality-promoting protein, operatively linked to the activity of the inducer-activated site-specific recombinase enzyme. The exogenous polynucleotide cassette is stably integrated into the Z chromosome of the cell.

In certain embodiments, the cells of the bird comprise an exogenous polynucleotide cassette, comprising a formula 5'-LHA-OIE-LIE-RHA-3' or a formula 5'-LHA-LIE-OIE-RHA-3', wherein (i) the LHA is left homology arm, comprising a first nucleotide sequence that is substantially homologous to a first corresponding nucleotide sequence on chromosome Z of a bird; (ii) the OIE is optogenetic-inducible element, comprising a first promoter functionally linked to a second nucleotide sequence encoding an inducer-activated site-specific recombinase enzyme; (iii) the LIE is lethality-inducing element, comprising a third nucleotide sequence encoding a lethality-promoting protein, operatively linked to the activity of the inducer-activated site-specific recombinase enzyme; and (iv) the RHA is right homology arm, comprising a fourth nucleotide sequence, that is substantially homologous to a second corresponding nucleotide sequence on chromosome Z of a bird.

In certain embodiments, the cells of the bird comprising the exogenous polynucleotide cassette comprise bird primordial germ cells (PGCs). In certain embodiments, the bird PGCs can be gonadal PGCs, blood PGCs, or germinal crescent PGCs.

As used herein, the terms "primordial germ cell" and "PGC" refer to a diploid cell that is present in the early embryo and that can differentiate/develop into haploid gametes (i.e. spermatozoa and ova) in an adult bird. PGCs can be obtained from blastoderm as well at early developmental stages.

As is known to those of skill in the art, primordial germ cells can be isolated from different developmental stages and from various sites in a developing avian embryo such as, but not limited to, genital ridge, developing gonad, blood, and germinal crescent (Chang et al., Cell Biol Int 21:495-9, 1997; Chang et al., Cell Biol Int 19:143-9, 1995; Allioli et al., Dev Biol 165:30-7, 1994; Swift, Am J Physiol 15:483-516; PCT International Publication No. WO 99/06533). The genital ridge is a section of a developing embryo that is known to a person of ordinary skill in the art (Strelchenko, Theriogenology 45: 130-141, 1996; Lavoir, J Reprod Dev 37: 413-424, 1994). Typically, PGCs can be stained positively by the periodic acid-Schiff (PAS) technique. In several species, PGCs can be identified using an anti-SSEA antibody (one notable exception being turkeys, the PGCs from which do not display the SSEA antigen). Various techniques for isolation and purification of PGCs are known in the art, including the concentration of PGCs from blood using Ficoll density gradient centrifugation (Yasuda et al., J Reprod Fertil 96:521-528, 1992).

The in-vitro culture of PGCs is possible using a medium containing chicken and bovine serum, conditioned media, feeder cells and growth factors such as FGF2 (van de Lavoir et al. 2006, Nature 441:766-769. doi:10.1038/nature04831; Choi et al. 2010, PLoS ONE 5:e12968. doi:10.1371/journal.pone.0012968; MacDonald et al., 2010. PLoS ONE 5:e15518. doi:10.1371/journal.pone.0015518). It has been shown that a feeder replacement medium containing growth factors to activate the FGF, insulin and TGF-β signaling pathways could be used to propagate PGCs (Whyte et al. 2015, Stem Cell Rep 5:1171-1182. doi:10.1016/j.stemcr.2015.10.008).

Primordial germ cells (PGCs) can be provided and formulated for carrying out the presently disclosed subject matter by any suitable technique, and stored, frozen, cultured, or the like prior to use as desired. For example, primordial germ cells can be collected from donor embryos at an appropriate embryonic stage. Stages of avian development are referred to herein by one of two art-recognized staging systems: the Eyal-Giladi & Kochav system (EG&K; Eyal-Giladi & Kochav, Dev Biol 49:321-327, 1976), which uses Roman numerals to refer the pre-primitive streak stages of development, and the Hamburger & Hamilton staging system (H&H; Hamburger & Hamilton, J Morphol 88:49-92, 1951), which uses Arabic numerals to reference the post-laying stages. Unless otherwise indicated, the stages referred to herein are stages as per the H&H staging system. In certain embodiments, PGCs are derived from blood isolated from stage 14 (H&H) embryos. In certain embodiments, PGCs are derived from blood isolated from stage 15 (H&H) embryos. In certain embodiments, PGCs are derived from blood isolated from stage 16 (H&H) embryos.

In one embodiment, PGCs can be isolated at stage 4, or the germinal crescent stage, through stage 30, with cells being collected from blood, genital ridge, or gonad in the later stages. The primordial germ cells are, in general, twice the size of somatic cells and can easily be distinguished and separated on the basis of size. Male (or homogametic) primordial germ cells (ZZ) can be distinguished from heterogametic primordial germ cells (Zw) by any suitable technique, such as collecting germ cells from a particular donor and typing other cells from that donor, the collected cells being of the same chromosome type as the typed cells.

An alternative to the use of PGCs is the direct transfection of spermatozoa using a DNA editing agent disclosed herein (Cooper et al., 2016 Transgenic Res 26:331-347, doi: 10.1007/s11248-016-0003-0).

In one embodiment, to produce chimeric birds from PGCs edited in-vitro, the exogenous edited cells are injected intravenously into surrogate host embryos at a stage when their endogenous PGCs are migrating to the genital ridge. The "donor" PGCs may be of the same species as the surrogate host embryo or of a different species. The edited "donor" PGCs must remain viable and in one embodiment, out-compete the endogenous PGCs if they are to colonize the forming gonad and transmit the edited chromosome(s) through the germline. To provide donor PGCs with an advantage, the number of endogenous PGCs can be reduced by chemical or genetic ablation (Smith et al., 2015, Andrology 3:1035-1049. doi:10.1111/andr.12107). Exposing the blastoderm of surrogate embryos to emulsified Busulfan has been shown to increase germline transmission of donor PGCs to over 90%, though this rate drops significantly if PGCs have been cultured or cryopreserved (Nakamura et al., 2008, Reprod Fertil Dev 20:900-907. doi:10.1071/RD08138; Naito et al., 2015, Anim Reprod Sci. 153:50-61. doi:10.1016/j.anireprosci.2014.12.003). Other methods of skewing the ratio of edited PGCs to native PGCs are described in US Application No. 2006/0095980.

In certain embodiments, genetically modified PGCs can be transplanted into adult gonads as known in the art (Trefil et al., 2017 Sci Rep, October 27; 7(1):14246 doi: 10.1038/s41598-017-14475-w).

The genetically modified cells (e.g. PGCs) can be formulated for administration to other birds by dissociating the cells (e.g., by mechanical dissociation) and intimately admixing the cells with a pharmaceutically acceptable carrier (e.g., phosphate buffered saline solution). In one embodiment, the primordial germ cells are gonadal primordial germ cells, or blood primordial germ cells ("gonad" or "blood" referring to the tissue of origin of the original embryonic donor). The primordial germ cells administered can be heterogametic (Zw) or homogametic (ZZ). In one embodiment, the PGCs can be administered in physiologically acceptable carrier at a pH of from about 6 to about 8 or 8.5, in a suitable amount to achieve the desired effect (e.g., 100 to 30,000 PGCs per embryo). The PGCs can be administered free of other ingredients or cells, or other cells and ingredients can be administered along with the PGCs.

Administration of the primordial germ cells to the recipient animal in-ovo can be carried out at any suitable time at which the PGCs can still migrate to the developing gonads. In one embodiment, the administration is carried out from about stage IX according to the Eyal-Giladi & Kochav (EG&K) staging system to about stage 30 according to the Hamburger & Hamilton staging system of embryonic development, or in another embodiment, at stage 15. For chickens, the time of administration is thus during days 1, 2, 3, or 4 of embryonic development, for example, day 2 to day 2.5. Administration is typically done by injection into any suitable target site, such as the region defined by the amnion (including the embryo), the yolk sac, etc. In one embodiment, the cells are injected into the embryo itself (including the embryo body wall). In alternative embodiments, intravascular or intracoelomic injection into the embryo can be employed. In other embodiments, the injection is performed into the heart. The methods of the presently disclosed subject matter can be carried out with prior sterilization of the recipient bird in-ovo (e.g. by chemical treatment using Busulfan of by gamma or X-ray irradiation). As used herein, the term "sterilization" refers to render partially or completely incapable of producing gametes derived from endogenous PGCs. When donor gametes are collected from such a recipient, they can be collected as a mixture with gametes of the donor and the recipient. This mixture can be used directly, or the mixture can be further processed to enrich the proportion of donor gametes therein.

The in-ovo administration of the primordial germ cells can be carried out by any suitable technique, either manually or in an automated manner. In one embodiment, in-ovo administration is performed by injection. The mechanism of in-ovo administration is not critical, but the mechanism should not unduly damage the tissues and organs of the embryo or the extraembryonic membranes surrounding it so that the treatment will not unduly decrease hatch rate. A hypodermic syringe fitted with a needle of about 18 to 26 gauge is suitable for the purpose. A sharpened pulled glass pipette with an opening of about 20-50 microns diameter may be used. Depending on the precise stage of development and position of the embryo, a one-inch needle will terminate either in the fluid above the chick or in the chick itself. A pilot hole can be punched or drilled through the shell prior to insertion of the needle to prevent damaging or dulling of the needle. If desired, the egg can be sealed with a substantially bacteria-impermeable sealing material such as wax or the like to prevent subsequent entry of undesirable bacteria. It is envisioned that a high-speed injection system for avian embryos would be suitable for practicing the presently disclosed subject matter. All such devices, as adapted for practicing the methods disclosed herein, comprise an injector containing a formulation of the primordial germ cells as described herein, with the injector positioned to inject an egg carried by the apparatus. In addition, a sealing apparatus operatively connected to the injection apparatus can be provided for sealing the hole in the egg after injection. In another embodiment, a pulled glass micropipette can be used to introduce the PGCs into the appropriate location within the egg, for example directly into the blood stream, either to a vein or an artery or directly into the heart.

Once the eggs have been injected with the modified PGCs, the chimeric embryo is incubated until hatch. In one embodiment, the chick is raised to sexual maturity, wherein the chimeric bird produces gametes derived from the donor PGCs.

In certain embodiments, the cells of the bird comprise bird gametes. The gametes, (either eggs or sperm) from the chimeras (or from material that has been directly genetically manipulated, as described herein above) are then used to raise founder chickens (F1). Molecular biology techniques known in the art (e.g. PCR and/or Southern blot) may be used to confirm germ-line transmission. F1 chickens may be back-crossed to generate homozygous ZZ carrier males and carrier females (F2). Gametes from founder chickens F2 can then be used to expand the breeding colonies. The colonies are typically grown until sexual maturity. Fertile eggs obtained from these flocks may be tested for early embryonic mortality of the males by exposure to an inducer (e.g. blue light) which elicits the lethal phenotype. Following induction (e.g. by blue light illumination), the eggs are incubated (for example for 8 days) and screened (e.g. by light-candling) to detect for early embryonic mortality.

In one embodiment, there is provided a method of generating a chimeric bird, comprising administering to a bird cell population an exogenous polynucleotide cassette having a formula 5'-OIE-LIE-3' or a formula 5'-LIE-OIE-3', wherein (i) the OIE is optogenetic-inducible element, comprising a first promoter functionally linked to a second nucleotide sequence encoding an inducer-activated site-specific recombinase enzyme; and (ii) the LIE is a lethality-inducing element, comprising a third nucleotide sequence encoding a lethality-promoting protein, operatively linked to the activity of the inducer-activated site-specific recombinase enzyme. The exogenous polynucleotide cassette is stably integrated into the Z chromosome of the cells. These genome-edited cells are then injected into a recipient bird embryo.

In another embodiment, there is provided a method of generating a chimeric bird, comprising administering to a bird cell population an exogenous polynucleotide cassette having a formula 5'-LHA-OIE-LIE-RHA-3' or a formula 5'-LHA-LIE-OIE-RHA-3', wherein (i) the LHA is left homology arm, comprising a first nucleotide sequence that is substantially homologous to a first corresponding nucleotide sequence on chromosome Z of a bird; (ii) the OIE is optogenetic-inducible element, comprising a first promoter functionally linked to a second nucleotide sequence encoding an inducer-activated site-specific recombinase enzyme; (iii) the LIE is lethality-inducing element, comprising a third nucleotide sequence encoding a lethality-promoting protein, operatively linked to the activity of the inducer-activated site-specific recombinase enzyme; and (iv) the RHA is right homology arm, comprising a fourth nucleotide sequence, that is substantially homologous to a second corresponding nucleotide sequence on chromosome Z of a bird. The exogenous polynucleotide cassette is stably integrated into the Z chromosome of the cells. These genome-edited cells are then injected into a recipient bird embryo.

In certain embodiments, the method further comprises incubating the chimeric bird embryo, in-ovo, until hatching. In certain embodiments, the method further comprises raising the chimeric bird to sexual maturity, wherein the chimeric bird produces gametes derived from the administered cells.

In certain embodiments, the genome-edited cells are administered by in-ovo injection. In another embodiment, the embryos can be taken out of the egg-shell, injected "ex-ovo" and then placed back in a surrogate egg-shell. In certain embodiments, the administrated cell population is derived from the same avian species as the recipient bird embryo. In certain embodiments, the administrated cell population is derived from a different avian species as the recipient bird embryo.

In another embodiment, the chimeric bird can be generated by injecting the genome-edited PGCs to blastoderm. In general, the genome-edited PGCs can be returned or injected back to where endogenous PGCs are located. In one embodiment, the genome-edited PGCs can be returned back to the blastoderm. Alternatively, the genome-edited PGCs can be returned back to the germinal crescent, blood, embryonic gonads, or even to adult gonads.

In certain embodiments, the genome-edited bird cell population is administered when the recipient embryo is about stage IX according to the Eyal-Giladi & Kochav staging system. In certain embodiments, the bird cell population is administered when the recipient embryo is about stage 30 according to the Hamburger & Hamilton staging system. In certain embodiments, the bird cell population is administered when the recipient embryo is about stage IX according to the Eyal-Giladi & Kochav staging system; and about stage 30 according to the Hamburger & Hamilton staging system. In certain embodiments, the bird cell population is administered when the recipient embryo is after stage 14 according to the Hamburger & Hamilton staging system.

In certain embodiments, the genome-edited bird cell population is administered after irradiation of the embryo. In certain embodiments, the irradiation comprises γ-irradiation or X-ray irradiation. In certain embodiments, the irradiation comprises 600-800 rad of γ irradiation. In certain embodiments, the irradiation comprises 600-800 rad of irradiation. In certain embodiments, the irradiation comprises 400-1000 rad of irradiation. In certain embodiments, the irradiation comprises 200-1200 rad of irradiation.

Further provided, in another aspect, is a chimeric bird obtainable from the methods described above.

Methods of Use

In one embodiment, there is provided a method of generating a cell of a bird, comprising the step of contacting a cell of a bird with an exogenous polynucleotide cassette having a formula 5'-OIE-LIE-3' or a formula 5'-LIE-OIE-3' as described herein. The exogenous polynucleotide cassette is stably integrated into the Z chromosome of the cells. In another embodiment, the method comprises the step of contacting the cell of the bird with an exogenous polynucleotide cassette having a formula 5'-LHA-OIE-LIE-RHA-3' or a formula 5'-LHA-LIE-OIE-RHA-3' as described herein. The exogenous polynucleotide cassette is stably integrated into the Z chromosome of the cells.

In another embodiment, there is provided a method of inducing lethality in a male embryo in a fertilized egg of a bird, comprising the steps of: administering the DNA editing agent disclosed herein to a population of bird cells to generate genome-edited bird cells; transferring these genome-edited bird cells to recipient bird embryos; and exposing the embryos to an inducer that elicits expression of the lethality-promoting protein encoded by the DNA editing agent, thereby inducing lethality of the male embryo in the fertilized egg of the bird. The various elements of the DNA editing agent, such as optogenetic-inducible element, inducer-activated site-specific recombinase, inducer, lethality-promoting protein, etc have been discussed above.

In one embodiment, the DNA editing agent used in the above method of inducing lethality in a male embryo comprises (i) a LHA comprising the sequence of SEQ ID NO:105, (ii) an OIE comprising the sequence of SEQ ID NO:100, which is connected to the sequence of SEQ ID NO:116, which is connected to the sequence of SEQ ID NO:101, which is connected to the sequence of SEQ ID NO:103, which is connected to the sequence of SEQ ID NO:102, which is connected to the sequence of SEQ ID NO:104, which is connected to the sequence of SEQ ID NO:116, or the OIE comprises the sequence of SEQ ID NO:100, which is connected to the sequence of SEQ ID NO:116, which is connected to the sequence of SEQ ID NO:107, which is connected to the sequence of SEQ ID NO:103, which is connected to the sequence of SEQ ID NO:108, which is connected to the sequence of SEQ ID NO:104, which is connected to the sequence of SEQ ID NO:116, (iii) a LIE comprising the sequence of SEQ ID NO:92, or SEQ ID NO:94, or SEQ ID NO:96, or SEQ ID NO:98, and (iv) a RHA comprising the sequence of SEQ ID NO:106.

In another embodiment, there is provided a method of inducing lethality in a male embryo in a fertilized egg of a bird, comprising the steps of: administering to a population of bird cells the DNA editing agent containing a safe-lock element as disclosed herein, thereby generating genome-edited bird cells; transferring these genome-edited bird cells to recipient bird embryos; and exposing the embryos to an agent that removes the STOP element from the STOP element, thereby eliciting expression of the lethality-promoting protein encoded by the DNA editing agent and inducing lethality of the male embryo in the fertilized egg of the bird. The various elements of the DNA editing agent, such as optogenetic-inducible element, inducer-activated site-specific recombinase, inducer, safe-lock element, lethality-promoting protein, etc have been discussed above. In one embodiment, the DNA editing agent used in the above method of inducing lethality in a male embryo comprises the sequence of one of SEQ ID NOs:120-127.

In one embodiment, removal of the STOP element from the DNA editing agent requires the expression of Flp when the STOP element is flanked by two FRT sites (see FIG. 26A, inactive "locked" state). In one embodiment, expression of Flp may be accomplished by contacting the genome-edited bird cells with a nucleotide sequence encoding the Flp protein (e.g. SEQ ID NO:129 or SEQ ID NO:131). Upon expressing the Flp recombinase, the STOP element inserted between the promoter and the sequence encoding the inducer-activated site-specific recombinase in OLE is removed, thus allowing the expression of the inducer-activated site-specific recombinase (FIG. 26A, active "unlocked" state). Upon further exposure to an inducer (e.g. blue light), the inducer-activated site-specific recombinase would be activated, resulting in the removal of OLE and the expression of the lethality-promoting protein encoded in the LIE (FIG. 26A, lethality-activated state).

In another embodiment, removal of the STOP element may be accomplished by contacting the genome-edited bird cells with a nucleotide sequence encoding the Cre protein (e.g. SEQ ID NO:128 or SEQ ID NO:132). In one embodiment, the safe-lock element and the sequence encoding the inducer-activated site-specific recombinase are flanked by the Lox sequences (FIG. 26B, inactive "locked" state). Upon expressing the Cre recombinase, the safe-lock element as well as the sequence encoding the inducer-activated site-specific recombinase are removed, thus allowing the expression of the lethality-promoting protein encoded in the LIE (FIG. 26B, lethality-activated state).

According to the principles of the technology provided herein, the step of lethality induction can be done at any developmental stage, for example soon after oviposition. The sooner death is induced, the earlier the embryo will die. Embryonic mortality is thus achieved thereafter. If a toxin or pro-apoptotic agent is used to induce embryonic death, the embryo dies soon after induction. If LIE is based on a gene that disrupts essential signaling pathway, such as the BMP, for example by expressing the BMP4 antagonist Noggin, cell death will be induced at the developmental time point in which the pathway is active and required. For example, BMP is active during stages comprising blastulation, gastrulation, neurulation, organogenesis. In certain embodiments, lethality is induced during oviposition, and the embryo dies within about 36 hours after exposure to Noggin. As an example, if the optogenetic system is activated soon after oviposition (Stages X-XIII EG&K), the embryo will die at that stage. BMP4 knock-out mice embryos die in-utero from 6.5 days post coitum (dpc) to ~8.5-9 dpc which is equivalent to the first 30-36 hours of incubation in chicken embryo development. In certain embodiments, the lethality is induced during the 21-day period from fertilization to hatching. In certain embodiments, the lethality is induced more than once during the 21 days from fertilization to hatching. In certain embodiments, the lethality is induced in the egg before early blastulation stages known as stages X-XIII EG&K (Eyal-Giladi and Kochav, 1976).

In certain embodiments, the method is performed in-vivo. In certain embodiments, the method is performed ex-vivo. In certain embodiments, the method is performed in-ovo. In certain embodiments, the method is performed in-vitro.

It is appreciated that certain features of certain embodiments, which are, for clarity, described in the context of separate embodiments, may also be provided in combination in a single embodiment. Conversely, various features of certain embodiments, which are, for brevity, described in the context of a single embodiment, may also be provided separately or in any suitable sub-combination or as suitable in any other described embodiment. Certain features described in the context of various embodiments are not to be considered essential features of those embodiments, unless the embodiment is inoperative without those elements.

Various embodiments and aspects as delineated hereinabove and as claimed in the claims section below find experimental support in the following examples.

EXAMPLES

Reference is now made to the following examples, which together with the above descriptions illustrate some embodiments in a non-limiting fashion.

Generally, the nomenclature used herein and the laboratory procedures utilized include molecular, biochemical, microbiological and recombinant DNA techniques. Such techniques are thoroughly explained in the literature. See, for example, "Molecular Cloning: A laboratory Manual"

Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Generating a genome modified chicken line is a multi-step process. The final product is a female layer-hens line which is completely identical, with respect to genome content, to the layer which is used today in the industry (see FIG. 1).

In one embodiment, the workflow comprises 5 main steps: (1) Generating and cultivating chicken Primordial Germ-Cells (PGCs) lines; (2) Genome modification in cultured PGCs; (3) Transplantation of modified PGCs to embryos, and producing chimera chickens that will be screened for germ-line transmission and identifying potential founder carriers; (4) Breeding founder chickens from genetic material obtained from the chimeras; (5) Expanding the founder chickens colonies to founder flocks and re-verifying the germline transmission.

Materials and Methods

PGC Culture Medium: Avian PGC culture medium consists of DMEM (Gibco) calcium free medium diluted with water to 250 mOsmol/L, containing 12.0 mM glucose, 2.0 mM GlutaMax (Gibco), 1.2 mM pyruvate (Gibco), 1×MEM vitamin (Gibco), 1×B-27 supplement (Gibco), 1×NEAA (Gibco), 0.1 mM β-mercaptoethanol (Gibco), 1× nucleosides (Biological industries), 0.2% ovalbumin (Sigma), 0.1 mg/ml sodium heparin (Sigma), CaCl$_2$ 0.15 mM (Sigma), 1×MEM vitamin (Gibco), 1×Pen/Strep (Biological industries), 0.2% chicken serum (Sigma) in avian DMEM. The following growth factors were added before use: human Activin A, 25 ng/mL (Peprotech); human FGF2 4 ng/mL (R&D Biosystems), ovotransferin (5 μg/ml) (Sigma). AkoD-MEM refers to a Diluted medium containing glucose, pyruvate and vitamins.

PGC Line Derivation: PGC lines were derived by placing ~1.0-3.0 μL of blood isolated from stage 14 to 16 (H&H) embryos in 300 μL medium in a 48-well plate. Medium was changed every 2 days. When total cell number reached 1×10$^5$, total volume of medium was changed every 2 days and cells were propagated at 2-4×10$^5$ cells/ml medium. Cells were frozen in PGC culture medium containing 10% DMSO, temperature was gradually decreased to −80° C., stored for 1-3 days and transferred to liquid nitrogen.

Sex Determination and PGC Line Characterization: Each PGC line was characterized for sexing, mRNA expression of PGC markers, and protein expression of the known PGCs marker SSEA14. DNA from the donor embryo was isolated and kept for future reference. For sexing, DNA from 2-4× 10$^5$ PGCs cells was collected, re-suspended in tail buffer (102-T, Viagen) containing 100 μg/ml Proteinase K (Sigma) and incubated at 55° C. for 3 hours. The Proteinase K was inactivated at 85° C. for 45 minutes. PCR for sex determination was performed with primers from W chromosome that target female chromosome (P17, P18) and Ribosomal S18 (P19, P20) as a control. For gene expression analysis, RNA was purified using TRIZOL reagent and 1 μg of RNA was used for cDNA library production by reverse transcription PCR reaction (GoScript Reverse transcriptase, Promega). The cDNA served as a template for PCR by using Dazl, Sox2, cPouV, Nanog, Klf4, cVH primers, P21-P22, P23-P24, P25-P26, P27-P28, P29-P30, P31-P32, respectively.

Immunohistochemistry With Anti SSEA1 Antibody: Cells were collected, fixed with 4% PFA, blocked with 5% normal goat serum in PBS 0.1% triton and stained at 1:100 dilution of anti-SSEA1 antibody (DSHB, Hybridoma bank) in blocking buffer overnight. After washing the cells for 30 min with PBS 0.1% triton secondary antibody was added (Alexa Fluor 488, molecular probes) for 1 hour, cells counterstained with DAPI (Sigma), mounted with mounting medium (Histomount, electron microscopy sciences) and covered.

PGCs Transfection, Selection and FACS Sorting: Plasmid transfection of PGCs was done using lipofection or electroporation. For lipofection, Lipofectamine 2000 was used according to the manufacturer's protocol. 3-5×10$^5$ cells were seeded in 96 well plate in AkoDMEM containing NEAA, pyruvate, vitamins, CaCl$_2$ and growth factors (activinA, hFGF and ovatransferin). 100 ng of plasmid, and 0.25 μl of Lipofectamine 2000 (invitrogen) were diluted separately in 20 μl of OPTI-MEM mix together, incubated for 20 minutes and pipetted on the cells. For electroporation, 3×10$^5$ to 1.5×10$^6$ cells were washed in AkoDMEM and electroporated at 1000V, 12 ms, 3 pulses on Neon electroporator (Invitrogen), and seeded immediately in 96 or 48 well plate, respectively, in antibiotics-free PGCs medium. Medium was changed after 1-3 hours. Selection with 25-100 μg/ml G418 started 72 hours later for 2-4 weeks. Following selection, cells were individually isolated manually or by FACS sorting. For FACS sorting, gentle cells pipetting was done and cells were sorted in PGCs culture medium. Positive GFP cells sorted with FACS Aria II to new 96 wells plate, a single cell per well, or pooled. (FACS analysis performed using a BD FACS Aria II flow cytometer (BD, USA).

Plasmid Preparation

Cloning of CRISPR Plasmids: CRISPR sequences were design using CRISPR design tool, Zhang lab, MIT. px330-GFP plasmid (modified from Addgene plasmid #42230) was cut using BbsI restriction enzyme and served us as the backbone for CRISPR site insertion to form the sgRNA. The oligos for the sgRNA CRISPR sites—CRISPR1, CRISPR3 (oligos P34-P35 and P36-P37, respectively) were denatured at 95° C. for 30 seconds, slowly annealed and ligated to the BbsI cut plasmids, transformed into E. coli, purified and sequence verified as described (Cong L, et al., Science. 2013 Jan. 3. 10.1126/science.1231143 PubMed 23287718).

Cloning of pJet-HAs Plasmid: The genomic region downstream to the HINT1Z locus on the Z chromosome, containing both the 5'HA and 3'HA was amplified from PGCs DNA with P1 and P2 primers, using PCR (Kapa, Roche). PCR product was purified and ligated into pJet1.2 plasmid (Invitrogen) according to manufacturer protocol.

Construction of Targeting Vector: The pCAGG-IRES-Neo-GFP plasmid was used as template for PCR, using P5-P6 primers, to amplify the insert pCAGG-IRES-Neo-GFP. pJet-HAs plasmid was used as template for PCR, using P3-P4 primers, to amplify the vector containing 5'HA and 3'HA. Gibson assembly reaction was done to the purified vector and insert PCR products taking 0.03 pm, 0.06 pm linearized product, respectively. Gibson assembly reaction products were transformed to E. coli for plasmid preparation which was sequence verified.

Construction of the pCAGG-Optogene Vector: To generate the pCAGG-Optogene vector the optogenes plasmids pmCherry-CIBN-CreC and pmCherry-Cry2-CreN11 were used as a template to amplify the optogenes using the P40-P41 and P42-P43 primers, which yielded 1.3 kb and 2.1 kb products respectively. These two products share overlap sequences at the P2A site which was introduced in primers P41 and P42. Single-cycle overhang extension PCR was used to unite to two fragments, to a single 3.5 kb product which was cleaned from an agarose gel. This product was ligated to pJet1.2 shuttle vector that was used as a temple for PCR using primers P44 and P45, which contain tails with SmaI and NheI restriction sites, respectively. This product was digested using the appropriate restriction enzymes and was used as an insert for ligation to ligated to SmaI and NheI digested pCAGG-IRES-GFP plasmid that served as a vector. The ligation products were transformed to E. coli bacteria and the propagated plasmid was sequenced verified.

Construction of pGK-DTA-IRES-GFP Vector: To generate the pGK-DTA-IRES-GFP, the expression vector pSK BS-PGK-DTA was used as a template for PCR with primers P46 and P47 which contain extensions sequences for the XmaI and NheI restriction sites respectively. The 0.65 kb product was digested with the respective enzymes and was used as an insert for ligation to the XmaI-NheI complementary site in the pGK-IRES-GFP plasmid that served as a vector for the ligation. The ligation products were transformed to E coli bacteria and the propagated plasmid was sequenced verified.

In-ovo Electroporation: In-ovo electroporation was conducted essentially as was previously described. Fertile eggs were incubated for 56-60 h at 37.8° C., the eggshell was windowed and plasmid DNA at a concentration of ~2 μg/μl was injected using a sharpened micro-pipette with an opening of 10-15 μm in diameter to the neural tube. Three pulses of 25 V, 30 ms were delivered using ECM 830 square wave electroporation system (BTX). Following electroporation, the eggshell was sealed with parafilm and the embryos were further incubated until analysis.

Endonuclease Assay: PGCs were transfected with CRISPR1 or CRISPR3 plasmids using Lipofectamine 2000 reagent. Forty-eight hours later, individual GFP positive cells were isolated into 96 well plate and grown to form pure colonies. DNA was collected and a 350 bp region flanking the CRISPR sites was PCR amplified with P38-P39 primers. The PCR products undergo denaturation at 95° C. and slowly annealed and incubated with T7 endonuclease for 1 h at 37° C. For calibration purposes and as a positive control, the 350 bp PCR product was sub-cloned to pJet1.2 and the CRISPR site was mutated using site-directed mutagenesis. The mutation that was introduced replaced the WT sequence ATACCAGATAACGTgCCTTATTTGGCCGTT (SEQ ID NO:2) with ATACCAGATAACGTaatCCTTAT-TTGGCCGTT (SEQ ID NO:3). This artificial mutation served as a positive control to both the endonuclease assay (FIG. 7A) and for control sequencing (FIG. 8B).

Southern Blot Assay: Dig-labeling for the 5'HA, 3'HA and Neo gene probes were prepared by PCR amplification (Longamp, NEB) with primers P13-P14, P15-P16 and P11-P12, respectively, using DIG DNA labeling Mix (Roche). Fifteen μg of genomic DNA were digested overnight at 37° C. with BglII restriction enzyme. DNA fragments were separated by electrophoresis on 0.8% (w/v) agarose gel (20 V, 12 h) and transferred onto positively charged nylon membranes (GE Healthcare). Following transfer, humid membranes were cross linked using a UV light set to 254 nm for 3 minutes on each side then rinsed with 2×SSC. Membranes were pre-hybridized for 2 hours at 42° C. using DIG Easy-Hyb hybridization solution (Roche). Probes (50 ng/ml) were denatured by heating to 95° C. for 5 minutes and immediately plunged into ice. Denatured probes were added to 10 ml warm DIG Easy-Hyb solution and hybridized for 12 hours at 42° C. Membranes were washed twice for 10 minutes in 2×SSC, 0.1% SDS at room temperature under agitation and then washed 3 times for 30 minutes in 0.2× SSC, 0.1% SDS at 65° C. under agitation. Further washing and blocking was done with a DIG wash and block buffer set (Roche) and according to their protocol. DIG labeling was detected using Anti-Digoxigenin-AP antibody 1:10000 (Roche) followed by chemiluminescence reaction using CDP-Star reagent (Roche). Images were taken using G:BOX gel imaging system (Syngene).

PGC Injection To Embryos And Whole Mount Staining: Freshly laid eggs were incubated with the pointed end up for 58-62 hours at 37.8° C. with 55% humidity. Following incubation, 4-8 mm window was opened in the egg shell and 3000-8000 PGCs were injected to the blood stream using sharpened micropipette with opening of ~30-40 μm. The window was covered with white egg membrane and further sealed with a Parafilm (Parafilm) or a Leukoplast (BSN medical GmbH) tape. Embryos were incubated until hatching. Some gonads of injected embryos were isolated and taken for whole-mount GFP staining. Gonads were fixed in 4% PFA, washed for 2 h with PBS blocked with 5% normal donkey serum in PBS 1% Triton and stained at 1:20 dilution of mouse anti-SSEA1 antibody or rabbit anti GFP antibody 1:500 (Abcam) in blocking buffer overnight. After washing for 2 h with PBS 1% triton, a secondary donkey anti mouse cy3 antibody 1:500 was added (Jackson Immunoresearch laboratories) or secondary alexa488 anti rabbit antibody 1:500 (Molecular Probes) for 3 hours in blocking buffer. Tissue counterstained with DAPI (Sigma) and mounted in glycerol, and imaged by confocal microscope (Leica, TCS SPE, Wetzlar, Germany).

The sequences for primers P1 to P32 are listed in SEQ ID NOs:4-35, the sequences for primers P34 to P47 are listed in SEQ ID NOs:36-49.

The sequences for the plasmids are listed below:

1. pX330-GFP (SEQ ID NO: 50); 2. CRISPR1 (SEQ ID NO: 51); 3. CRISPR3 (SEQ ID NO: 52); 4. pJet-Has (SEQ ID NO: 53); 5. pCAGG-Neo-IRES-GFP (SEQ ID NO: 54); 6. Targeting Vector (SEQ ID NO: 55); 7. pmCherry-Cry2-CreN (SEQ ID NO: 56); 8. pmCherry-CIBN-CreC (SEQ ID NO: 57); 9. pB-RAGE-GFP (SEQ ID NO: 58); 10. pCAGG-IRES-GFP (SEQ ID NO: 59); 11. pCAGG-Optogenes (SEQ ID NO: 60); 12. pB-RAGE-mCherry (SEQ ID NO: 61); 13. pSK BS-PGK-DTA (SEQ ID NO: 62); 14. pGK-IRES-GFP (SEQ ID NO: 63); 15. pGK-DTA-IRES-GFP (SEQ ID NO: 64).

Results

PGC Lines Derivation and Characterization

During the earliest stages of embryonic development, soon after oviposition and prior to the initiation of gastrulation, PGCs migrate rostrally to the Germinal Crescent region at the anterior part of the extra-embryonic mesoderm layer. It is thought that this migration "protects" the PGCs from undergoing differentiation processes as somatic cells do. It is not until the formation of the Area Opaca Vasculosa, blood and heart-beat, after about 2.5 days of incubation (Stage 14-17 H&H), that the cells return to the embryo through the blood stream and colonize the Genital Ridge which will give rise to the gonads. At these stages, using a micropipette with a ~40-60 μm diameter opening, 1-3 μl of blood was collected from the vasculature system of the embryos and transferred into a well containing PGC culture medium in a 48 well plate. The PGC culture medium allows for fast division of the PGCs (20-24 hours of cell cycle) while retaining their undifferentiated state under feeder free conditions. After 2-3 weeks in culture, blood cells degraded and disappeared. Within another 1-2 more week, the cultured PGCs became confluent (FIG. 5A). These cells can be further grown for gene modification or can be successfully frozen and thawed for latter modifications. Chicken PGCs in culture have been extensively characterized in the literature using morphological features, protein and mRNA expression patterns and finally by their ability of gonad migration when injected back into the vasculature of a stage-matched recipient embryo. These characteristics were examined in the produced PGC cell cultures to show that they keep the well-established PGC features. Morphologically, the PGCs are big, slightly granulated cells about 15-20 μm diameter containing large nuclei. The PGCs are totipotent cells, thus they express pluripotent markers such as the cPouV, SOX2, KLF4 and Nanog and two unique germ cells markers—cVH and DAZL. For each PGC line, DNA was extracted for sex determination using primers for the Ribosomal S18 (P19-P20, 256 bp product size) as a positive control and primers for the W chromosome (P17-P18, 415 bp product size) to identify females (FIG. 5B). Additionally, the PGCs express the membrane SSEA-1 antigen4 (FIG. 5C).

Ten lines of PGCs were established from layers and broilers, both male and female lines. Plasmid transfection was carried out using cationic-lipid transfection reagent Lipofectamine 2000 which interacts with the negatively charged DNA, allowing its penetration into the cell. Transfecting with GFP encoding plasmid (pCAGG-GFP) resulted in about 15-20% transfection efficiency (FIG. 5D). Further, transfection of PGCs using electroporation resulted in higher efficiency of up to 90% (FIG. 5E). To demonstrate that cultured PGCs successfully colonize the gonads, GFP-expressing PGCs were injected into the blood stream of stage 14-16 H&H and the embryos were incubated for 10 days. The embryos were dissected, and GFP-positive cells were identified in the gonads (FIG. 5F).

Designing the CRISPR-Cas9 Targets on the Z Chromosome

In one embodiment, DNA editing into the Z chromosome were done using CRISPR-Cas9 and homologous recombination processes. While CRISPR-Cas9 system will directly cut the DNA at a specific site of the Z chromosome, the endogenous repair system using homology recombination process will allow targeted insertion of the desired DNA into the precise location. For this purpose, constructing a targeting vector plasmid which contains the homology arms corresponding to the insertion site on the Z chromosome is required. The site for DNA insertion at the Z chromosome downstream the coding gene HINT1Z was chosen. The use of the CRISPR system has been shown in many studies to improve direct DNA insertion events. Extensively used for that purpose, the px330 plasmid includes the sgRNA site and the Cas9 enzyme. The sgRNA site contains a unique sequence which directs the Cas9 enzyme to the target site and leads to specific genome targeted DSDB. Using a CRISPR design engine tool, a unique sequence for the sgRNA was identified as shown in FIG. 6A. The top 12 guides, according to their score are depicted in FIG. 6B. The sequences for guides 1 to 12 are listed in SEQ ID NOs:66-77.

Guides #1 and #3 were chosen by conventional similarities of the secondary structure and were used to check possible off-target sites in the chicken genome which scored by the mismatch extent. The top 10 results of search for potential off-targets for guide #1 are shown in FIG. 6C and SEQ ID NOs:78-87. Notably, the top 6 off-targets have 4 mismatches, highlighting the specificity of this guide.

DNA sequence insertion was carried out by cutting a modified px330 plasmid, which contains in-frame GFP fused to the c-terminus of Cas-9. Annealed primers containing the sgRNA sequences were ligated to the BbsI restriction enzyme as previously described. (FIG. 6B). Ligation products were transformed to E. coli, plasmids were purified and sgRNA insertions were verified by sequencing.

Activity Validation of the CRISPR-Cas9 System

By growing PGCs in feeder free culture medium, pure colonies originating from single cells were obtained, thereby allowing characterization of the efficiency of the CRISPR-Cas9 system. To this end PGCs were transfected with either pX330-GFP-CRISPR1 and pX330-GFP CRISPR3 plasmids, and clonal colonies were grown. Total genomic DNA was extracted from colonies originating from single cells expressing GFP. The DNA was analyzed by endonuclease assay and sequenced. For the endonuclease assay, a positive control was designed. This control was a 320 bp PCR product with inserted mutations at the predicted site for CRISPR-Cas9 activity. This product was mixed with similar length WT product in different ratios, 1:15, 1:7, 1:1—mutated:WT respectively, and the annealed mixture was subjected to endonuclease activity (FIG. 7A). Two short bands at the predicted size of 136 bp and 184 bp were clearly visible at the ratios of 1:7 and 1:1, indicating the assay was properly working. Similarly, the same assay was performed on genomic DNA obtained from 12 colonies, transfected with either CRISPR1 and CRISPR3 plasmids (FIGS. 7B, 7C). In 9 out of the 12 colonies, a clear doublet at the predicted size was observed. This indicates that both CRISPR1 and CRISPR3 plasmids, efficiently generate DSDBs at the predicted site.

For sequencing analysis, PCR products that were used for endonuclease assay (FIGS. 7A-7C), were also sequenced (FIGS. 8A-8D). Sequencing of the WT negative control revealed the predicted cleavage site of CRISPR1 (FIG. 8A). Sequencing a mixture of WT and artificially mutated product, as a positive control, revealed the appearance of double peaks on the DNA chromatogram, immediately after the predicted cleavage site (arrowhead, FIG. 8B). Similar sequencing of the same genomic region in the transfected colonies revealed both negative (FIG. 8C) and positive (arrowhead, FIG. 8D) colonies, whereas the latter were >70% of the cases.

Constructing Targeting Vector for Genome Integration

To demonstrate a targeted genomic integration to the Z chromosome, using HR, a targeting vector was designed (FIGS. 9A-9F). The vector contains a pCAGG promoter followed by the neomycin selections gene, internal ribosome entry site (IRES), GFP and the Rabbit beta-globin polyadenylation site. This cassette was flanked by ~1.5 kb homology arms at the 5' and 3' ends respectively. To generate this vector, a ~3 kb DNA fragment, containing both homology arms was amplified using primers P1 and P2, and ligated to a shuttle vector pjet1.2. Full sequencing of this fragment was found to be identical to the chicken genome sequence. This plasmid—pJet-HAs, was used as a template to generate a linearized PCR product containing two separated homology arms excluding a 23 bp sequence between them, which contains the CRISPR sgRNA sites. The amplification was done using the P3 and P4 primers which contain sequences, at their 5' end, which correspond to the edges of the pCAGG-Neo-IRES-GFP cassette. This linear PCR product is referred to as the "vector". The pCAGG-Neo-IRES-GFP plasmid was used as a template to generate a linear PCR product. This fragment was amplified using primers P5 and P6 containing sequences which correspond to the 3' and 5' ends of the 5'HA and 3'HA ends, respectively. This product is referred to as the "insert". The vector and the insert were stitched together using the Gibson assembly reaction to create the final targeting vector.

Homologous Recombination to the Z Chromosome Using the Targeting Vector and CRISPR Plasmids The ability to obtain pure PGCs colonies from a single cell enables the identification of positive colonies that underwent correctly inserted HR, using methods such as PCR and Southern blot. For PGC transfection, lipofection with a 5-10% (FIG. 10A) transfection efficiency or electroporation with >40% efficiency were used. Transfection was carried out with two plasmids, the targeting vector and one of the two CRISPR plasmids described above (CRISPR1 or CRISPR3). Following the transfection, the cells were left to recover for 24 hours, and transferred to G-418 containing media for selection. After two weeks of selection, only G-418 resistant cells survived, of them >99% were GFP positive (FIG. 10B). To verify that the cells retain their ability to colonize the gonads, they were injected into host embryos as was described above in FIG. 1F (FIG. 10C). The gonads were immuno-stained with anti-GFP antibody and the colonization of GFP-positive PGCs cells in the gonads was verified using confocal microscope (FIG. 10D).

The G-418 resistant, GFP-positive cells consist of a potentially heterogeneous population. Thus, in order to verify the HR integration, and to obtain pure homogenous population, single GFP-positive cells were separated using FACS sorting to 96 well plate (FIG. 11A). Pure colonies were raised and genomic DNA was extracted for PCR and Southern blot analysis. In parallel, pooled GFP-positive cells were FACS sorted. For PCR analysis, two sets of primers were designed. The first, forward P7 upstream to the 5'HA and reverse P8 from the CAGG promoter (1.6 kb product size), and the second, forward P9 from the rabbit beta-globin polyadenylation site and reverse P10 downstream to the 3'HA (1.8 kb product length, FIG. 11B). Both in pooled cells (FIG. 11C) and in pure colonies (FIG. 11D), the expected products for the 5' and 3' were detected, indicating that correct HR integration had occur in these cells.

To further verify the correct HR integration as well as to confirm that only a single copy of the targeting vector was integrated into the genome, a Southern blot analysis was conducted. Two PGCs cell lines from male and female donors were analyzed. Notably, the female line has only a single copy of the Z chromosome. Three digoxigenin-labeled (dig-labeled) DNA probes were designed (see FIG. 12A and FIG. 12B). The first two probes, amplified using primers P11-P12 and P13-P14, 500 bp long each, are located upstream and downstream to the 5' and 3' HAs respectively. The third probe, amplified using primers P15-P16, 704 bp long, is designed to detect the Neo gene inside the targeting vector, thus it allows for confirmation that only a single copy of the vector was integrated. The BglII restriction enzyme was used to cleave the genomic DNA for analysis. Two restriction sites, ~6.5 kb apart from each other, are located on the WT chromosome, upstream and downstream to the 5' and 3' probes respectively. Additional BglII site is located in targeting vector, yielding a predicted 7.5 kb and 3.3 kb fragments to identify correct HR integration. The results of the Southern blot analysis on the genomic DNA extracted from the male PGCs line revealed 2 bands at the predicted size, 6.5 kb for the WT allele and 7.5 kb and 3.3 kb for the allele which underwent correct HR integration, for the 5' and 3' sites, respectively. This was confirmed for both the DNA from pooled cells as well as for pure colonies (FIG. 12C). A similar analysis was carried out for the female PGC cell line. In this case a single band at the predicted size of 7.5 kb for the 5' integration site was found. As the female genome contains only a single copy of the Z chromosome, no WT allele (6.5 kb) was detected. Probing the Neo gene, revealed a single band at the predicted size of 7.5 kb, confirming that only a single copy of the targeting vector was integrated into the genome (FIG. 12D).

Validation of the Optogenetic System in HEK293 Cells In-Vitro and in Chicken Embryos In-Ovo.

To verify the activity of the inducible system in-vitro and in chicken embryos in-ovo, three plasmids: pmCherry-Cry2-CreN, pmCherry-CIBN-CreC and the reporter PB-RAGE-GFP were transfected to HEK293 cells (FIG. 13) and to chick embryos (FIG. 14). The first two optogenetic plasmids encode the reporter gene mCherry which confirms successful transfection. The PB-RAGE-GFP expression vector contains a multiple stop codons sequence flanked by LoxP sites upstream to the GFP coding region. Upon Cre activation, the STOP codons are removed thus allowing the GFP to be expressed. While in negative-control HEK293 cells that were triple-transfected and kept in the dark, there were no GFP-positive cells (FIG. 13, upper row). In cells that were exposed to blue-light illumination, 24 hours after transfection, many cells expressed GFP (FIG. 13, lower row), confirming the activation of the optogenetic system in these cells.

To verify the activity of the optogenetic system in-ovo, a triple transfection with pmCherry-Cry2-CreN, pmCherry-CIBN-CreC and PB-RAGE-GFP plasmids by electroporation into chicken embryo neural tubes at stage 16 H&H was performed. Twelve hours following electroporation, experimental group embryos were subjected to 15 seconds of blue-light illumination, while negative control embryos were kept in the dark. The embryos were incubated for an additional 12 hours and checked for GFP expression under fluorescent stereoscope (FIG. 14). While in embryos that were kept in dark (FIG. 14, upper row), only mCherry was expressed, thus confirming successful electroporation, in embryos of the experimental group, GFP positive cells were clearly evident (FIG. 9, lower row), confirming that the light-inducible Cre was activated.

The optogene plasmids pmCherry-Cry2-CreN and pmCherry-CIBN-CreC drive the expression of the genes using the CMV promoter which is unfavorable in chicken cells. To overcome this and to combine the two to a single vector, a plasmid vector which drives the expression of CIBN-CreC and Cry2-CreN, linked by the P2A self-cleaving peptide, followed by IREG-GFP, under the CAGG promoter, was designed, which is highly active in chicken cells. Synthesis of pCAGG-CIBN-CreC-P2A-Cry2-CreN-IRES-GFP was based on a modification of the original optogenes plasmids described in Kennedy et al., 2010 (Nat Methods. 2010 December; 7(12): 973-975). Each of these plasmids encode mCherry followed by IRES sequence with either CIBN-CreC (a truncated form of CIB1 fused to the C-terminal of the Cre enzyme) or CRY2-CreN (Cryptochrome 2 fused to the N-terminal of the Cre enzyme. FIG. 15A). The goal of the following cloning was to join the two fusion optogenes with self-cleaving peptide P2A, under the CAGG promoter, followed by IRES-GFP. To this end, the CIBN-CreC plasmid was used as a template for PCR with P40 and P41 primers and the CRY2-CreN plasmid was used as a template for PCR with P42 and P43 primers (FIG. 15A). Notably primers P41 and P42, which contain the P2A cleavage site, share overlap sequence that allows the two products to be merge by a single-cycle overhang extension PCR (FIG. 15B). This product which contains CIBN-CreC-P2A-CRY2-CreN was ligated to a shuttle vector pJet1.2, and was sequences verified (FIG. 15C). This plasmid served as template for PCR with primers P44 and P45 which added to the product the SmaI and NheI restriction site on the 5' and 3' ends, respectively (FIG. 15D). This product was digested with the restriction enzymes and ligated to the pCAGG-IRES-GFP plasmid which was also cut using the same enzymes (FIG. 15E). This ligation product contains the CAGG promoter, followed by CIBN-CreC, P2A self-cleaving peptide, Cry2-CreN, IRES, GFP and the rabbit beta-globin poly-adenylation site (referred to herein as pCAGG-Optogenes), and was sequenced verified (FIG. 15F).

To verify the activity of the pCAGG-Optogene vector in-vitro, the plasmid, which expresses GFP as a reporter for successful transfection, was co-transfected into HEK293 cells with pB-RAGE-mCherry. Like the PB-RAGE-GFP vector described above (FIG. 13), the pB-RAGE-mCherry contains a multiple stop codon sequence flanked by LoxP sites upstream to the mCherry coding region. Upon Cre activation, the stop codons are removed thus allowing the mCherry to be expressed (FIG. 16). While in HEK293 cells that were co-transfected and kept in the dark there were no mCherry-positive cells (FIG. 16, upper row). In contrast, cells that were exposed to blue-light illumination, many cells were expressing mCherry (FIG. 16, lower row), confirming that the single-vector strategy of the pCAGG-Optogenes, preserves the optogenetic properties of the system.

To verify the activity of the pCAGG-Optogenes vector in living chick embryos in-ovo, the plasmid was co-transfected by electroporation to stage 14-16 H&H chick embryos together with pB-RAGE-mCherry. Twelve hours following electroporation, negative-control group eggs were kept in the dark, while experimental group embryos were exposed to blue-light for 15 seconds (FIG. 17). Both groups were further incubated for 12 h and examined under a fluorescent stereoscope. Following incubation, both groups revealed high level of GFP expression, indicating the successful electroporation. However, only in the light-exposed group (FIG. 17, lower row), mCherry-positive expressing cells were identified, indicating that the optogenetic system, using the single-vector strategy of the pCAGG-Optogenes, was activated in a light-inducible manner Inducing Lethality in Chick Embryos To demonstrate the feasibility of causing mortality using a toxin, the coding region of the DTA12, commonly used as negative selection marker, was cloned into an expression vector containing the pGK promoter followed by an IRES GFP (pGK-IRES-GFP). This plasmid also served as a negative control. The DTA coding region was cloned upstream to the IRES sequence giving rise to the pGK-DTA-IRES-GFP, which upon expression in cells inhibits protein synthesis which leads to cellular death.

To test the effects of DTA expression in chicken embryos, stage 14-16 H&H embryos were electroporated with either pGK-IRES-GFP, as a negative control or with pGK-DTA-IRES-GFP vector. Twelve hours following electroporation, the embryos were analysed for the expression of GFP under a fluorescent microscope (FIG. 18). While in control embryos, GFP was widely expressed in the neural tube (FIG. 18), in DTA expressing embryos, no GFP expression was detected, indicating that protein synthesis was blocked in these cells.

Example 2

The aim of the experiments described herein was to introduce a lethality-inducing cassette into to the Z chromosome of either male or female-derived PGCs. The final goal was to obtain hens harboring a genomic insertion on the Z chromosome. This chromosome will segregate only to the next generation male embryos that upon blue-light induction will activate a lethality-inducing cassette, thus the male embryos will die at early stages of embryogenesis.

The cassette AKA the targeting vector (TV) has 3 elements as described herein. The first element is the "Homology arms". The second element is the "Optogenetic inducible element". The third element is the "lethality-inducing cassette". In one embodiment, two ~1.5 kb homology arms are located on both 5' and 3' ends of the TV. This is designed to direct the homologous recombination (HR) downstream to the HINT1Z locus located on the Z chromosome. This site for HR was chosen since the HINT1Z gene is transcribed in PGCs as well as in whole blastoderms (these are freshly laid chick embryos). All other openly transcribed regions on the Z chromosome are also potentially good candidates for this purpose.

FIG. 20 shows the RT-PCR using FWD primer (SEQ ID NO: 88) and REV primer (SEQ ID NO: 89) on cDNA from PGCs and whole blastoderms. Product predicted size 153 bp.

The second element is the "Optogenetic inducible element". In one embodiment, the optogenetic systems are based on proteins that under certain light wavelengths are excited and change conformation that allows them to be dimerized. It is possible to fuse these proteins with additional proteins so that there will be transcription of a target gene only when the two-optogenetic proteins dimerize. For example, if the first protein is fused with a DNA targeting domain, such as Gal4-BD (Gal4 binding domain), and the second protein is fused with a transcription activator, such as Gal4-AD (Gal4 activation domain), it is possible to activate downstream genes. Similarly, a repression domain could be used to repress gene expression. However, an issue with optogenes is that they have a certain amount of basal dimerization and therefore gene activation that happens regardless of light induction. Finding the right balance between sensitivity to induction and basal dimerization is key to their use. A modified version of the system developed in Kennedy, M. J. et al. (Rapid blue-light mediated induction of protein interactions in living cells. Nat. Methods 7, 973-975, 2010) was used. The original optogene plasmids are pmCherry-Cry2-CreN and pmCherry-CIBN-CreC that drive gene expression using the CMV promoter, which is unfavorable in chicken cells. To overcome this and to combine the two to a single vector, a plasmid vector was designed to use the CAGG promoter, which is highly active in chicken cells, to drive the expression of CIBN-CreC and Cry2-CreN that are linked by the IRES sequence and followed by IREG-GFP. Synthesis of pCAGG-CIBN-CreC-IRES-Cry2-CreN-IRES-GFP was based on a modification of the original optogenes plasmids described in Kennedy et al., 2010 (Nat Methods. 2010, 7(12): 973-975). The goal of cloning was to join the two fusion optogenes with IRES, under the CAGG promoter, followed by IRES-GFP. Construction of similar plasmid in which the order of the optogenes, namely Cry2-CreN followed by CIBN-CreC, was also performed successfully and yielded similar results. FIG. 21 shows a schematic representation of the above described plasmids.

To verify the activity of the pCAGG-Optogene vector in-vitro, the plasmid that expresses GFP as a reporter for successful transfection was co-transfected into HEK293 cells with a reporter plasmid pB-RAGE-mCherry. This plasmid contains Lox-STOP-Lox (LSL, RAGE) element between the pCAGG promoter and the mCherry reporter gene. Thus, when co-transfected with the optogene plasmid, upon blue-light illumination and Cre activation, the LSL is removed and the mCherry is expressed. In the dark when the system is inactive, only the reporter GFP from the optogene plasmid is expressed, as shown in FIG. 22.

To validate the activity of the optogenetic system in living chick embryos in-ovo, the optogenetic plasmid and the reporter pB-RAGE-mCherry plasmid were co-electroporated to the neural tube of 56-60 h incubated chick embryos. The plasmid DNA mixture was injected to the lumen of the neural tube using a sharpened micropipette and electroporation was applied using 2 tungsten electrodes, 3-5 mm apart (Electroporator BTX830). Four pulses of 30V, 45 ms each were delivered with 745 ms interval between each pulse. Following electroporation the eggs were sealed and incubated for 12-18 h. Then, while eggs in control group were kept in dark, eggs in experimental group were exposed to 1 min of blue light illumination through the eggshell. Both groups were placed back in the incubator for another 12-18 hours before analysis.

As shown in FIG. 23, in all experimental group, the reporter GFP was highly and widely expressed in all embryos, indicating a successful electroporation and expression of the plasmids. There was no mCherry expression in eggs that were kept in the dark. In contrast, mCherry was expressed in the neural tube in eggs illuminated by blue-light.

An improved system of the CIBN-Cry2 can be made by modifying the Cry2. This modification includes an insertion of L348F mutation in a truncated Cry2 gene which contains only the first 535 amino acids—Cry2-Δ535-L348F, as published in Nature Chemical Biology volume 12, pages 425-430 (2016).

As an alternative approach to the CIBN-Cry2 optogenetic system, another conceptually similar system can be used to achieve the same goals. This system is based on the MAG-NET system, in which two optogenetic proteins—positively charged P-Mag and negatively charged N-Mag dimerize upon blue light illumination. Each of these proteins is fused to inactive part of the Cre recombinase enzyme and upon dimerization of the two optogenes, an active form of Cre is created (Nature Chemical Biology volume 12, 1059-1064 2016).

The third element is the "lethality-inducing cassette". In one embodiment, the lethality-inducing cassette comprises a gene (e.g. a toxin) which drives early embryonic death by means of cell death or severe intervention in molecular signaling pathway that is required for early stages of embryogenesis (e.g. BMP4). For example, this can be achieved by inducing programmed cell death (apoptosis) with toxins such as the Diphtheria toxin A (DTA), by expressing Caspase genes such as Caspase3 or a mutated constitutively-active mutated form of Caspase 3, or by expressing the inhibitor protein of BMP4—Noggin. The nucleotide sequence for DTA is set forth in SEQ ID NO: 92. The amino acid sequence of DTA is set forth in SEQ ID NO: 93.

In one embodiment, the nucleotide sequence for Chicken Casp3 CDS (WT) is set forth in SEQ ID NO: 94. The amino acid sequence for Chicken Casp3 CDS (WT) is set forth in SEQ ID NO: 95.

In one embodiment, the nucleotide sequence for constitutively-active (mutated) form of Chicken Casp3 is set forth in SEQ ID NO: 96. The amino acid sequence for constitutively-active (mutated) form of Chicken Casp3 protein is set forth in SEQ ID NO: 97.

In one embodiment, the nucleotide sequence for Noggin is set forth in SEQ ID NO: 98. The amino acid sequence for Noggin is set forth in SEQ ID NO: 99.

In certain embodiments, the "lethality-inducing cassette" is based on a gene that disrupts an essential signaling pathway. The sooner death is induced, the earlier the embryo will die. In certain embodiments, the essential signaling pathway involves a bone morphogenetic protein (BMP). In certain embodiments, the BMP is BMP4. In certain embodiments, the lethality-promoting protein is an antagonist of BMP4. In certain embodiments, the BMP4 antagonist is Noggin. In certain embodiments, the expression of the lethality-promoting protein Noggin is induced at a developmental stage in which the BMP pathway is active and required. In certain embodiments, the BMP pathway is active or induced during blastulation, gastrulation, neurulation, or organogenesis. In certain embodiments, the optogenetic system is activated soon after oviposition (Stages X-XIII EG&K). In certain embodiments, the optogenetic system is activated to induce the lethality-promoting protein at Stages X. In certain embodiments, the optogenetic system is activated at Stages XI. In certain embodiments, the optogenetic system is activated at Stages XII. In certain embodiments, the optogenetic system is activated at Stages XIII In certain embodiments, the optogenetic system is activated at any given time during embryonic development starting at fertilization until hatching. In certain embodiments, the lethality is induced during the 21 days period from fertilization to hatching. In certain embodiments, the lethality is induced 1 day after fertilization. In certain embodiments, the lethality is induced 2 days after fertilization. In certain embodiments, the lethality is induced 3 days after fertilization. In certain embodiments, the lethality is induced 4 days after fertilization. In certain embodiments, the lethality is induced 5 days after fertilization. In certain embodiments, the lethality is induced 6 days after fertilization. In certain embodiments, the lethality is induced 7 days after fertilization. In certain embodiments, the lethality is induced 8 days after fertilization. In certain embodiments, the lethality is induced 9 days after fertilization. In certain embodiments, the lethality is induced 10 days after fertilization. In certain embodiments, the lethality is induced 11 days after fertilization. In certain embodiments, the lethality is induced 12 days after fertilization. In certain embodiments, the lethality is induced 13 days after fertilization. In certain embodiments, the lethality is induced 14 days after fertilization. In certain embodiments, the lethality is induced 15 days after fertilization. In certain embodiments, the lethality is induced 16 days after fertilization. In certain embodiments, the lethality is induced 17 days after fertilization. In certain embodiments, the lethality is induced 18 days after fertilization. In certain embodiments, the lethality is induced 19 days after fertilization. In certain embodiments, the lethality is induced 20 days after fertilization. In certain embodiments, the lethality is induced 21 day after fertilization. In certain embodiments, the optogenetic system is activated during chicken embryo development after up to 30 hours of incubation. In certain embodiments, the optogenetic system is activated during chicken embryo development after up to 31 hours of incubation. In certain embodiments, the optogenetic system is activated during chicken embryo development after up to 32 hours of incubation. In certain embodiments, the optogenetic system is activated during chicken embryo development after up to 33 hours of incubation. In certain embodiments, the optogenetic system is activated during chicken embryo development after up to 34 hours of incubation. In certain embodiments, the optogenetic system is activated during chicken embryo development after up to 35 hours of incubation. In certain embodiments, the optogenetic system is activated during chicken embryo development after up to 36 hours of incubation. In certain embodiments, the optogenetic system is activated within the bird. In certain embodiments, the optogenetic system is activated prior to the formation of an eggshell surrounding the embryo. In certain embodiments, the optogenetic system is activated within the bird prior to the formation of an eggshell surrounding the embryo. In certain embodiments, the optogenetic system is activated by directly contacting the embryo with the inducer. In certain embodiments, the inducer is inserted into the egg. In certain embodiments, the eggshell is first at least partly opened, and the inducer is then administered directly to the embryo.

To validate induction of cellular death in chicken cells, the DTA and the two forms of caspase 3 were cloned in an expression vectors with the PGK (Phosphoglycerate Kinase) or CAGG promoters followed by IRES GFP which served to confirm the transfection efficiency. The PGK promoter is weaker and slower than the pCAGG in chicken embryonic cells.

In one embodiment, the vectors created were: PGK-DTA-IRES-GFP, pCAGG-DTA-IRES-GFP, PGK-CASP3-IRES-GFP, pCAGG-CASP3-IRES-GFP, PGK-mCASP3-IRES-GFP, pCAGG-mCASP3-IRES-GFP. The expression vectors without the lethality-inducing genes were used as controls (PGK-IRES-GFP and pCAGG-IRES-GFP).

The expression vectors were transfected to PGCs by electroporation and the cells were incubated for 24, 48 and 72 h before being analyzed using flow cytometry which detected positively expressing cells by the green fluorescence protein (GFP) and dead cells that were identified using Propidium Iodide (PI) staining. The nucleotide sequence encoding the GFP is set forth in SEQ ID NO:115.

The results presented in FIGS. 24A-24B demonstrate the proportion of dead cells out of the total GFP positive cells.

In one embodiment, a targeting vector consolidating the above described three elements into a single active unit which can be integrated to the Z chromosome was constructed. As shown in FIG. 25, the unit is flanked by the 5' and 3' homology arms. The promoter (pCAGG) drives the expression of the two units of the optogenetic system which are separated by an IRES sequence. The optogenetic system is followed by a polyadenylation sequence (PA). The opto-genes cassette is flanked by two LoxP sites. The optogenetic system can be based on the CIBN-Cry2, the MAGNET or any other system as described above. Following the second LoxP site is the lethality-inducing coding sequence which is followed by a second polyadenylation sequence. As this lethality-inducing coding sequence has no promoter, it is inactive until a blue-light illumination is applied which results in the dimerization of the optogenes and activation of the Cre enzyme which removes the optogenes cassette flanked between the LoxP sites. This excision results in placing the lethality coding sequence directly downstream to the pCAGG promoter which drives its expression. This strategy benefits from a shorter design since it contains a single promoter and does not require "STOP" sequence.

In one embodiment, the nucleotide sequence for the pCAGG promotor is set forth in SEQ ID NO:100. The nucleotide sequence for the pGK promotor is set forth in SEQ ID NO:109. The nucleotide sequence for the pCMV promotor is set forth in SEQ ID NO:110. The nucleotide sequence for the phSyn promotor is set forth in SEQ ID NO:111. The nucleotide sequence for the pEF1-a promotor is set forth in SEQ ID NO:112.

In one embodiment, the nucleotide sequence for Optogen 1—NLS-Cry2-Δ535-L348F-CreN (AA 19-104) is set forth in SEQ ID NO:101. The nucleotide sequence for Optogen 2—CIBN(aa1-170)-NLS-Cre-C(aa106-343) is set forth in SEQ ID NO:102. The nucleotide sequence for Cre recombinase is set forth in SEQ ID NO:113. The nucleotide sequence for CreN (AA 19-104) is set forth in SEQ ID NO:117. The nucleotide sequence for CreC (AA 106-343) is set forth in SEQ ID NO:118.

In one embodiment, the nucleotide sequence for the IRES sequence is set forth in SEQ ID NO:103. The nucleotide sequence for the polyadenylation site sequence (Rabbit beta-globin) is set forth in SEQ ID NO:104. The nucleotide sequence for the 5' homology arm (LHA) is set forth in SEQ ID NO:105. The nucleotide sequence for the 3' homology arm (RHA) is set forth in SEQ ID NO:106.

In one embodiment, regarding the MAGNET system, the following sequences are alternative optogens that can be used instead of the Cry2-CIBN system. For example, the nucleotide sequence for the CreN(aa18-59)_N-Mag_NLS is set forth in SEQ ID NO:107. The nucleotide sequence for the NLS_P-Mag_Cre-C(aa60-237) is set forth in SEQ ID NO:108.

In one embodiment, transplantation of modified PGCs to embryos and producing chimera chickens that will be screened for germ-line transmission and potential founder carriers were carried out as follows. Following the generation of the targeting vector, PGC lines, which originated from both female and male embryos, underwent co-electroporation with px330-all-in-one CRISPR-Cas9-GFP encoding plasmid and the targeting vector. The CRISPR plasmid creates a DNA double-strand break at the designed site in chromosome Z, thus facilitating homologous recombination of the targeting vector. The CRISPR plasmid encodes Cas9 fused in-frame with GFP, thus allowing identification of successful transfection. 24-72 hrs following transfection, positive single cells were FACS sorted to single cells in 96-well plate and were grown to form pure PGCs colonies which were screened by PCR and southern blot to identify colonies which underwent proper homologous recombination.

Chimera chickens were generated as follows. The chimera chickens are a mean to transform genetically modified PGCs into functional gametes. To generating chimeras, stage 14-16 H&H embryos were injected to the bloodstream (e.g. to the heart) with >3000 PGCs (normally up to 8000-10000). These cells colonized the embryonic gonads alongside the endogenous PGCs, thus they are referred as chimeras. The efficiency of germline transmission, i.e. the ability to transform genetically modified PGCs to functional PGCs, rely on several factors including the ratio between the endogenous and injected PGCs in the gonad. In order to reduce the amount of endogenous PGCs, freshly-laid fertile eggs are γ irradiated with 600-800 rad. In certain embodiments, the irradiation comprises 600-800 rad of irradiation. In certain embodiments, the irradiation comprises 400-1000 rad of irradiation. In certain embodiments, the irradiation comprises 200-1200 rad of irradiation.

It is thought that PGCs are more susceptible to γ irradiation than somatic cells or that following irradiation the PGCs are less competent to regenerate as somatic cells do. Thus, after irradiation the total amount of endogenous PGCs is reduced. Following irradiation, the eggs were normally incubated until the embryos reach stage 14-16 H&H which is adequate for PGCs injection. As an indication for the efficiency of the irradiation, the incubation time required for the embryos to reach stages 14-16 H&H increases in about 10 h and as much as 70% of the irradiated embryos fail do normally develop and thus are not being used for PGCs injection. Different chicken strains, eggshells type, thick and color may require different irradiation conditions, thus the amount of energy warrants for calibration. Following Injection, the eggs are sealed and incubated until the chimera chicks hatch. The chicks are then reared to sexual maturity and in males, sperm is collected for analysis of germline transmission using semi-quantitative PCR or Real-Time PCR.

Example 3

The present example presents targeting vectors containing an addition element, an element referred herein as the "safe-lock" element. This element basically locks the optogenic-lethality system, so by default, the system is inactive. Only by crossing with "safe-unlocking" strain would the optogenic-lethality system become active. This element benefits the entire system by better protecting the breeds, since in order to be activated there is a need to use additional "unlocking" strain. This also ensures that throughout the production process, cells which have undergone HR need not be protected from light, since the optogenic system is essentially inactive.

The present example discloses eight "All-in-one" targeting vectors, and demonstrates both in-vitro and in-vivo that they work as designed. The data also show that the MAGNET optogenic system is working in chicken embryos and is able to activate the lethality-inducing mechanism. The MAGNET system has been described above. Moreover, the data show that Noggin, as an embryonic lethality-inducing gene, stops embryonic development from oviposition (from the freshly-laid eggs).

The eight targeting vectors disclosed herein cover 8 combinatorial options of 2 optogenic systems (MAGNET and CIBN-Cry2) and 4 lethality-inducing genes (DTA, Noggin, caCASP3, and mCherry, which is used for control and verification process). To clarify, mCherry as such does not induce lethality and was used to confirm the action of the other elements.

As discussed above, the aim of the experiments described herein is to introduce a lethality-inducing cassette into the Z chromosome of either male or female-derived PGCs. The final goal is to obtain hens harboring a genomic insertion on the Z chromosome. This chromosome will segregate only to the next generation male embryos that upon blue-light induction will activate a lethality-inducing cassette, thus the male embryos will die at early stages of embryogenesis. Therefore, due to sex chromosomal segregation, the female laying hen does not acquire modified genetic material, since it gets a WT Z chromosome from the male rooster side and WT W chromosome from the mother hen side (see FIG. 1). In this example, the targeting vectors comprise 4 elements as described below (see examples in FIG. 26).

As shown in FIG. 26, the first element is the "Homology arms". In one embodiment, two ~1.5 kb homology arms are located on both 5' and 3' ends of the vector. This is designed to direct the homologous recombination (HR) downstream to the HINT1Z locus located on the Z chromosome. This site for HR was chosen since the HINT1Z gene is transcribed in PGCs as well as in whole blastoderms (these are freshly laid chick embryos). All other openly transcribed regions on the Z chromosome are also potentially good candidates for this purpose.

The second element is a "safe-lock" mechanism which ensures that the optogenic-lethality mechanism is inactive until the STOP cassette is removed. The STOP cassette is flanked by two FRT sites and it is located between the pCAGG promoter and the optogenes, thereby preventing the expression of the optogenes. Upon crossing with a Flp expressing strain as described below, the STOP element is removed, allowing the optogenes to be transcribed and become active in a light-dependent manner (FIG. 26A, active "unlocked" state). In this example, the "safe-lock" element comprises the coding sequences for GFP followed by a polyadenylation site. Any other sequences which will prevent the transcription of downstream elements can also be used as a "safe lock" element.

The third element is the "Optogenetic inducible element". As discussed above, optogenetic systems are based on proteins which under certain light wavelengths will be excited and change conformation to dimerize with a second specific protein. Examples of optogenetic systems have been discussed above.

In this example, two alternative optogenic systems were tested and used. The first, the MAGNET system, in which two optogenetic proteins—positively charged P-Mag and negatively charged N-Mag dimerize upon blue light illumination. Sequences encoding the site-specific recombinase enzyme Mag are listed in SEQ ID NO:114 and SEQ ID NO:65. Each of these proteins is fused to an inactive part of the Cre recombinase enzyme and upon dimerization of the two optogenes, an active form of Cre is created (see e.g. Nature Chemical Biology volume 12, 1059-1064 2016). In this case, sequences for a self-cleaving peptide P2A ("Link" in FIG. 26) are located between the two optogenes.

The second optogenic system that was used is an improved system of the CIBN(CreC)-Cry2(CreN). In this case a modification includes an insertion of L348F mutation in a truncated Cry2 gene which contains only the first 535 amino acids—Cry2-Δ535-L348F (see Nature Chemical Biology 25 volume 12, pages 425-430 (2016). In one embodiment, the linker between the two optogenes is an IRES sequence ("Link" in FIG. 26).

The fourth element is the "lethality-inducing cassette". In one embodiment, the lethality-inducing cassette comprises a gene which promotes early embryonic death by means of cell death or severe intervention in molecular signaling pathway required for early stages of embryogenesis, such as the BMP4. As discussed above, examples of the lethality-inducing genes include, but not limited to, toxins such as the Diphtheria toxin A (DTA), Caspase genes such as Caspase3 or a mutated constitutively-active mutated form of Caspase 3, or the inhibitor protein of BMP4—Noggin.

The table below lists the features of these eight targeting vectors. In one embodiment, these vectors were cloned into pJet1.2 shuttle vector plasmid.

| Targeting Vector | Optogenic system | Optogenes linker | Lethality gene | SEQ ID NO |
|---|---|---|---|---|
| TV1 | Negative MAGNET-Positive MAGNET | P2A | Noggin | 120 |
| TV2 | Negative MAGNET-Positive MAGNET | P2A | DTA | 121 |
| TV3 | Negative MAGNET-Positive MAGNET | P2A | caCASP3 | 122 |
| TV4 | Negative MAGNET-Positive MAGNET | P2A | mCherry | 123 |
| TV5 | [CIBN-CreC]-[Cry2-Δ535-L348F-CreN] | IRES | Noggin | 124 |
| TV6 | [CIBN-CreC]-[Cry2-Δ535-L348F-CreN] | IRES | DTA | 125 |
| TV7 | [CIBN-CreC]-[Cry2-Δ535-L348F-CreN] | IRES | caCASP3 | 126 |
| TV8 | [CIBN-CreC]-[Cry2-Δ535-L348F-CreN] | IRES | mCherry | 127 |

The activity of the elements in the targeting vectors (TVs) was assessed in-vitro in HEK293 cells (FIG. 27) and in-ovo in chicken embryos (FIGS. 28-29). For in-vitro validation, HEK293 cells were transfected with TV4 alone (FIG. 27A), with pCAGG-Cre (SEQ ID NO:128) (FIG. 27B), or with pCAGG-FlpO (SEQ ID NO:129) plasmids. The latter was done under two treatments, one was kept in dark (FIG. 27C) and the other was exposed for 15 seconds to blue light, 24 hours following transfection. Following illumination, the cells were further incubated for 24 hours (FIG. 27D).

When expressed alone, TV4, like all other TVs, expressed GFP, thus indicating the activity of the "safe-lock" state (FIG. 27A). When co-expressed with pCAGG-Cre plasmid, the "safe-lock" and the optogenes cassettes were removed altogether (FIG. 26B; FIG. 27B), which was indicated by the loss of expression of the GFP and the onset of mCherry expression (as a surrogate for the lethality inducing gene). This result confirms that upon excision of the "safe-lock" and optogenes elements, the lethality-inducing element becomes active. When TV4 was co-expressed with pCAGG-FlpO plasmid, only the "safe lock" element was removed, as indicated by the loss of expression of the GFP (FIG. 26A, FIGS. 27C-D), and the optogenic system became active in a light-dependent manner There was no activation of the optogenic system and no expression of mCherry when the cells were kept in the dark, indicating the lethality cassette was not expressed (FIG. 27C). However, under the same conditions, when the cells are illuminated, the optogenic system became active and was excised (see FIG. 26A) to allow the lethality element to be expressed. This is indicated by the expression of mCherry as shown in FIG. 27D.

To demonstrate the activity of the TV elements in-vivo, chicken embryos were injected with plasmids to the neural tube and electroporated as described above. In FIG. 28, the white lines denote the dorsal mid-line of the neural tube and limb buds for orientation purposes. Four treatment groups were tested: 1. expression of TV4 alone (FIG. 28A), 2. co-electroporation of TV4 and pCAGG-Cre plasmids, as positive control (FIG. 28B), 3. Co-electroporation of TV4 and pCAGG-FlpO plasmids, which were kept in dark (FIG. 28C), and 4. Exposure to blue light for 15 sec, following co-electroporation of TV4 and pCAGG-FlpO plasmids, and further incubation for 12 hours (FIG. 28D).

When electroporated alone, TV4 expressed GFP to indicate the default inactive "safe-lock" state and no mCherry was expressed (FIG. 28A). When co-expressed with pCAGG-Cre plasmid, the "safe-lock" and the optogenes cassettes were removed (FIG. 26B; FIG. 28B), thus there was no GFP expression but mCherry was expressed. This serves as a positive control for activation of the lethality-inducing elements. By co-expressing TV4 with pCAGG-FlpO plasmid, only the FRT-flanked "safe lock" element was removed, thus there was no GFP expression (FIGS. 28C-28D) but the optogenic system was activated in light-dependent manner There was no GFP expression when the cells were kept in the dark, indicating the optogenic system was in its active state, yet mCherry was not expressed, i.e. the lethality cassette was inactive (FIG. 28C). However, when the embryos were illuminated 12 hours following electroporation, the optogenic system became active and was excised to allow the lethality element to be expressed. This is indicated by the expression of mCherry as shown in FIG. 28D.

To demonstrate the activity of the lethality-inducing gene Noggin in a light-dependent manner, TV1, which contains the coding sequence of Noggin as a lethality-inducing element, was co-electroporated with pCAGG-FlpO plasmid to the rostral neural tube (axial level of the mid-brain and hind-brain) of chick embryos that had been incubated for 36 hours. At this stage, neural-crest cells delaminate from the dorsal neural tube in a BMP4-dependent manner. Thus, inhibiting the BMP4 signaling pathway by ectopic expression of Noggin in the dorsal neural tube is predicted to inhibit neural crest cells delamination. In order to visualize neural crest cells, anti-HNK-1 antibodies were used for staining of the neural crest marker HNK-1.

FIG. 29 shows embryos that were electroporated in the neural tube with TV1 (SEQ ID NO:120), pCAGG-FlpO (SEQ ID NO:129) and pCAGG-IRES-GFP (SEQ ID NO:59) plasmids. The latter was added as a positive control to allow monitoring of transfected cells. Twenty four hours after transfection, in embryos that were kept in the dark throughout the experiment (FIG. 29A, upper row, dorsal view, lower row, right-lateral view), neural crest cells delaminated and migrated normally from the dorsal neural tube. The HNK-1 staining revealed bi-lateral symmetry expression pattern in the dorsal tube on both right and left neural folds (the dorsal-most aspect of the neural tube that gives rise to migrating neural crest cells), as well as on migrating neural crest cells (FIG. 29A, arrowhead). However, in embryos that were exposed to light 12 hours after electroporation, neural crest cells failed to delaminate and migrate from the tube, and HNK-1 staining revealed marked reduction in expression on the right neural fold—at the electroporated side

US 12,565,664 B2

55

(FIG. 29B, arrow). Thus, these results indicate that upon removal of the "safe lock" element from TV1, Noggin expression and activity is regulated in a light-dependent manner by the MAGNET optogenic system.

To demonstrate that Noggin is able to stop embryonic development as soon as the egg is laid, at the blastoderm embryonic stage, blastoderms were treated with exogenous source of Noggin, in-ovo (FIG. 30). To this end, pCAGG-Noggin-IRES-GFP (SEQ ID NO:130), or as negative control, pCAGG-IRES-GFP (SEQ ID NO:59) plasmids were transfected to HEK293 cells. To validate the expression of Noggin in transfected cells, total protein extracted from transfected cells was analyzed by Western blot with anti-Noggin antibody (Abcam, ab16054, predicated size ~24 kDa) and anti-α-Tubilin-HRP antibody (Abcam, ab40742, predicted size ~55 kDa) as loading control. FIG. 30A shows that while there was no Noggin expression in the negative control transfected cells (CON), cells transfected with pCAGG-Noggin-IRES-GFP (NOG) produced noggin. Prestained protein ladder was presented in the left lane (Thermo Scientific, PageRuler #26617). Conditioned media from control and Noggin expressing cells were injected into freshly-laid fertile eggs that were subsequently incubated for 24 or 54 hours, as shown in FIG. 30B-C and FIG. 30D-E, respectively. FIG. 30B-C show a High-Resolution Episcopic Microscopy (HREM) 3D reconstructed models of treated embryos. While control-treated embryos (FIG. 30B) continued to develop normally and underwent normal gastrulation, as indicated by the formation of the Primitive Streak (demarcated by arrows), Noggin-treated embryos failed to gastrulate and had no apparent Primitive Streak, indicating that the process of embryogenesis essentially stopped (FIG. 30C). When the embryos were left to further develop for 54 hours of incubation (FIG. 30D-E), control-treated embryos developed normally, underwent normal neurulation process and formed a beating heart (FIG. 30D), whereas Noggin-treated embryos formed a mass of cells with no overt characteristics (FIG. 30E, arrow).

Collectively, the results described above show that the molecular mode-of-action strategy presented in FIG. 26 works as predicted, including the "Safe-lock" elements and MAGNET optogenic system that activates the lethality-inducing element in a light-dependent manner Additionally, inhibiting the BMP signaling pathway by treating blastoderms in freshly-laid eggs with Noggin stopped the progression of embryonic development.

Creating Pure Lines of PGCS Harboring an Integrated Targeting Vector on the Z Chromosome In one embodiment, to generate PGCs with targeted integration to the Z chromosome, the ribonucleoprotein (RNP) system for delivering CRISPR/Cas9 was used. The use of RNP system benefits, among other things, from high efficiency, rapid DNA cleavage and rapid clearing of the RNP complexes from transfected cells. RNP complexes comprise of recombinant Cas9 or High-fidelity Cas9 nucleases and mixture of crRNA:tracrRNA complexes. The tracrRNA are commercially available (IDT), and the crRNA can be custom-made with specific 20 nucleotide sequence corresponding to the desired cleavage site on the targeted genomic DNA. In one embodiment, SEQ ID 66 and SEQ ID 68 disclosed herein were used to synthesize two crRNA oligos (see FIG. 8).

PGCs culture medium and lines derivation has been described above. To electroporate PGCs, 5×10^5 cells were washed in AkoDMEM, then transferred to buffer "R" (Neon buffer, Invitrogen) containing 0.7 μg of the targeting vector plasmid (in this example TV1), 1 μM Alt-R® cas9 electroporation enhancer (IDT), and RNP complexes with final concentration of 1.5 μM recombinant Cas9 or High fidelity Cas9 nucleases (Alt-R® S.p. Cas9 Nuclease or S.p. HiFi Cas9 Nuclease V3, respectively; IDT) and 1.8 μM crRNA:tracrRNA (sgRNA complexes, Custom Alt-R® CRISPR-Cas9 crRNA and Alt-R® tracrRNA; IDT).

The crRNA:tracrRNA complexes were prepared by heating the RNA oligos to 95° C. for 1 minute, and cooling down to room temperature. RNP complexes (Cas9 protein+crRNA:tracrRNA) mixture was prepared by adding recombinant Cas9 or high-fidelity Cas9 nucleases proteins to the crRNA:tracrRNA complexes, and incubating at room temperature for 10-20 min. It is generally believed that high-fidelity Cas9 is supposed to cause less off-targets.

For electroporation, 10 μl of buffer "R", containing the RNP complexes, electroporation enhancer reagent and the targeting vector plasmid, were added to PGCs pellet and the mixture was immediately electroporated with 3 pulses of 1000V, 13 ms duration each, using Neon electroporator (Invitrogen). Subsequently, the cells were immediately seeded in 48-wells plate in PGCs medium containing 1 μM SCR7-pyrazine (SML1546 sigma). Medium was changed after 1-4 hours, and transfected cells were allowed to recover for 7-10 days. SCR7-pyrazine was added for 48 h after electroporation. Transfected cells were individually isolated by FACS sorting. For FACS sorting, gentle cells pipetting was done and cells were sorted in PGCs culture medium. Single GFP positive cells were sorted with FACS Sony sorter (Sony) to a U-shape 96 wells plate. Sorted cells were grown for 2-3 weeks to form pure colonies. From these colonies, total genomic DNA was extracted for analysis, cryopreserved and positive colonies were injected to surrogate host embryos. PCR and Southern blot analysis used to verify correct integration of the targeting vector have been described above (see e.g. FIG. 15-16). Methods of creating surrogate chimera chicks have also been described above.

FIG. 31A shows pure female PGCs line that underwent HR with TV1, and expressed GFP. Cells from this colony were injected to surrogate host embryos that were incubated for 5 day following transplantation. FIG. 31B shows a ventral view of an embryo 5 days following PGCs injection. At this stage, the PGCs colonized the genital ridge which is the anlage of the gonads (FIG. 31B, arrowheads). Other injected embryos were incubated until hatch, and female chicks were sacrificed at day 10 post hatch to analyze the ovary. FIG. 31C shows an ovary (delineated by a line) containing numerous GFP positive PGCs. These results indicate that the PGCs that underwent HR on the Z chromosome with TV1 successfully colonize the gonads.

Creating "Unlocking" Strains Expressing Cre or FlpO.

Transgenic chicken strains expressing the targeting vectors TV1-8 will have the "safe-lock" element in their genome, hence the optogenic-lethality system will be inactive. In order to remove the "safe-lock" element which is flanked by FRT sites (see FIG. 26A), these strains need to be crossed with FlpO-expressing chicken strain. To generate this strain, a targeting vector containing the FlpO enzyme followed by IRES-GFP was created (TV-FlpO-IRES-GFP, SEQ ID NO:131). As a positive control and as a mean to activate the lethality-inducing cassette in a light-independent manner, a Cre-expressing breed can be used. In this case, the "safe-lock" and optogenic elements, which are flanked by LoxP sites, are removed to activate the lethality inducing element (see FIG. 26B). To generate this strain, a targeting vector containing the Cre enzyme followed by P2A-GFP was created (TV-Cre-P2A-GFP, SEQ ID NO:132). These two targeting vectors share the same 5' and 3' homology arms as well as the reporter gene GFP, and are designed to integrate to the Z chromosome as described above for TV1-8.

The above targeting vectors (TV-FlpO-IRES-GFP and TV-Cre-P2A-GFP) have been used to generate PGCs that were injected into surrogate chimera embryos. Methods of transfection of PGCs, FACS analysis, verification of HR integration, embryos injections, etc. have been described above.

In another embodiment, there is an option of using recombinant CRE or FlpO proteins to remove the "safe-lock" element. In one embodiment, sequences encoding the recombinant proteins contain sequences for TAT peptide, which is a cell-penetration peptide, followed by Nuclear Localization Sequence (NLS), which in turn is followed by sequences encoding either the Cre or FlpO enzymes can be applied to the cells or embryos. These recombinant proteins are effective in cultured cells, and they are commercially available. It is believed that these recombinant proteins can be injected into embryos or to adults and potentially activate the system without the need of generating Cre/Flp transgenic chickens and crossing. The accessibility of the chick embryo through an opening on the egg shell allows direct injection to the blood stream or in the vicinity of the embryo. Thus, in one embodiment, the above recombinant proteins can be directly injected into the embryo to remove the "safe-lock" element.

Although certain embodiments have been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

While certain features of aspects or embodiments have been illustrated and described herein, many modifications, substitutions, changes, and equivalents will now occur to those of ordinary skill in the art. It is, therefore, to be understood that the appended claims are intended to cover all such modifications and changes as fall within the true spirit of the aspects or embodiments provided herein.

The invention claimed is:

1. A DNA editing agent, comprising a polynucleotide cassette having a formula 5'-LHA (left homology arm)-OIE (optogenetic-inducible element)-LIE (lethality-inducing element)-RHA (right homology arm)-3' or a formula 5'-LHA-LIE-OIE-RHA-3', wherein (i) the LHA comprises a first nucleotide sequence that is substantially homologous to a first corresponding nucleotide sequence on chromosome Z of a bird;

(ii) the OIE comprises a first promoter functionally linked to a second nucleotide sequence encoding an inducer-activated site-specific recombinase enzyme;

(iii) the LIE comprises a third nucleotide sequence encoding a lethality-promoting protein, which is operatively linked to the activity of the inducer-activated site-specific recombinase enzyme; and (iv) the RHA comprises a fourth nucleotide sequence that is substantially homologous to a second corresponding nucleotide sequence on chromosome Z of a bird;

wherein the first corresponding nucleotide sequence or the second corresponding nucleotide sequence is located in an openly transcribed region on chromosome Z.

2. The DNA editing agent of claim 1, wherein the openly transcribed region is located at or downstream to the histidine triad nucleotide binding protein 1-Z (HINT1Z) locus on chromosome Z of a bird.

3. The DNA editing agent of claim 1, wherein (i) the LHA comprises the nucleotide sequence set forth in SEQ ID NO: 105, or a fragment thereof;

(ii) the RHA comprises the nucleotide sequence set forth in SEQ ID NO: 106, or a fragment thereof; or (iii) both (i) and (ii).

4. The DNA editing agent of claim 1, wherein the first promoter is selected from the group consisting of pCAGG (SEQ ID NO:100), pGK (SEQ ID NO:109), pCMV (SEQ ID NO:110), phSyn (SEQ ID NO:111), and pEF1-a (SEQ ID NO:112).

5. The DNA editing agent of claim 1, wherein the inducer-activated site-specific recombinase enzyme comprises Cre recombinase or Mag recombinase, and wherein expression of the inducer-activated site-specific recombinase enzyme is induced by an inducer.

6. The DNA editing agent of claim 5, wherein the inducer-activated site-specific recombinase enzyme is encoded by a nucleotide sequence comprising the sequence of SEQ ID NO:113, SEQ ID NO: 114, or SEQ ID NO: 65.

7. The DNA editing agent of claim 5, wherein the inducer is electromagnetic energy comprising visible light having a wavelength of 380-740 nm.

8. The DNA editing agent of claim 7, wherein the visible light is blue light having a wavelength of 450-485 nm.

9. The DNA editing agent of claim 5, wherein the inducer-activated site-specific recombinase enzyme comprises non-functional peptide fragments of an inducer-activated site-specific recombinase enzyme that combine to form an active inducer-activated site-specific recombinase enzyme in the presence of the inducer.

10. The DNA editing agent of claim 1, wherein the inducer-activated site-specific recombinase enzyme is an RNA-guided DNA endonuclease enzyme.

11. The DNA editing agent of claim 10, wherein the RNA-guided DNA endonuclease enzyme is a CRISPR associated protein (CAS) endonuclease.

12. The DNA editing agent of claim 10, wherein the polynucleotide cassette further comprises a fifth nucleotide sequence that encodes for a guide RNA that targets an essential gene of the bird, the fifth nucleotide sequence being operatively linked to the activity of the inducer-activated site-specific recombinase enzyme.

13. The DNA editing agent of claim 12, wherein the essential gene is selected from the group consisting of bone morphogenetic protein receptor type IA (BMPR1A), bone morphogenetic protein 2 (BMP2), bone morphogenetic protein 4 (BMP4), and fibroblast growth factor receptor 1 (FGFR1).

14. The DNA editing agent of claim 1, wherein the lethality-promoting protein is selected from the group consisting of a toxin, a pro-apoptotic protein, an inhibitor of the Wnt signaling pathway, a BMP antagonist, a FGF antagonist, a wild type Caspase 3, a constitutively active Caspase 3, Noggin, and a lethality-inducing fragment thereof.

15. The DNA editing agent of claim 14, wherein the lethality-inducing protein has the amino acid sequence of SEQ ID NO:93, SEQ ID NO:95, SEQ ID NO:97, or SEQ ID NO:99.

16. The DNA editing agent of claim 1, wherein (i) the LHA comprises the sequence of SEQ ID NO:105, (ii) the OIE comprises the sequence of SEQ ID NO:100, which is connected to the sequence of SEQ ID NO:116, which is connected to the sequence of SEQ ID NO:101, which is connected to the sequence of SEQ ID NO:103, which is connected to the sequence of SEQ ID NO:102, which is connected to the sequence of SEQ ID NO:104, which is connected to the sequence of SEQ ID NO:116, or the OIE comprises the sequence of SEQ ID NO:100, which is connected to the sequence of SEQ ID NO:116, which is connected to the sequence of SEQ ID NO:107, which is connected to the sequence of SEQ ID NO:103, which is connected to the sequence of SEQ ID NO:108, which is connected to the sequence of SEQ ID NO:104, which is connected to the sequence of SEQ ID NO:116, (iii) the LIE comprises the sequence of SEQ ID NO:92, or SEQ ID NO:94, or SEQ ID NO:96, or SEQ ID NO:98, and (iv) the RHA comprises the sequence of SEQ ID NO:106.

17. The DNA editing agent of claim 1, further comprising a safe-lock element inserted downstream to the promoter in the OIE but upstream of the sequence encoding the inducer-activated site-specific recombinase, said safe-lock element comprises nucleotide sequences (STOP element) that prevent transcription of the inducer-activated site-specific recombinase encoded by the OIE.

18. The DNA editing agent of claim 17, wherein said STOP element is flanked by two FRT sites.

19. The DNA editing agent of claim 17, wherein the editing agent comprises the sequence of one of SEQ ID NOs:120-127.

20. A population of bird cells, wherein the bird cells comprise primordial germ cells (PGCs) or bird gametes comprising the DNA editing agent of claim 1.

21. The population of claim 20, wherein the PGCs are selected from the group consisting of gonadal PGCs, blood PGCs, and germinal crescent PGCs.

22. A chimeric bird, comprising the population of bird cells of claim 20.

23. A method of generating a chimeric bird, comprising the steps of:

administering the DNA editing agent of claim 1 to a population of bird cells, thereby generating genome-edited bird cells; and transferring the genome-edited bird cells to recipient bird embryos, thereby generating a chimeric bird.

24. The method of claim 23, wherein said population of bird cells comprises primordial germ cells (PGCs), said PGCs selected from the group consisting of gonadal PGCs, blood PGCs, and germinal crescent PGCs.

25. A method of inducing lethality in a male embryo of a bird, comprising the steps of:

(a) administering the DNA editing agent of claim 1 to a population of bird cells, thereby generating genome-edited bird cells;

(b) transferring the genome-edited bird cells to recipient bird embryos; and (c) exposing the embryos to an inducer that elicits expression of the lethality-promoting protein encoded by the DNA editing agent, or exposing the embryos to an agent that removes a STOP element from the DNA editing agent, thereby inducing lethality in male embryos of the bird.

26. The method of claim 25, when said method comprises exposing the embryos to an inducer that elicits expression of the lethality-promoting protein encoded by the DNA editing agent, the inducer is blue light having a wavelength of 450-485 nm.

27. The method of claim 25, wherein the DNA editing agent comprises (i) LHA having the sequence of SEQ ID NO:105, (ii) OIE having the sequence of SEQ ID NO:100, which is connected to the sequence of SEQ ID NO:116, which is connected to the sequence of SEQ ID NO:101, which is connected to the sequence of SEQ ID NO:103, which is connected to the sequence of SEQ ID NO:102, which is connected to the sequence of SEQ ID NO:104, which is connected to the sequence of SEQ ID NO:116, or OIE having the sequence of SEQ ID NO:100, which is connected to the sequence of SEQ ID NO:116, which is connected to the sequence of SEQ ID NO:107, which is connected to the sequence of SEQ ID NO:103, which is connected to the sequence of SEQ ID NO:108, which is connected to the sequence of SEQ ID NO:104, which is connected to the sequence of SEQ ID NO:116, (iii) LIE having the sequence of SEQ ID NO:92, or SEQ ID NO:94, or SEQ ID NO:96, or SEQ ID NO:98, and (iv) RHA having the sequence of SEQ ID NO:106.

28. The method of claim 25, wherein when said method comprises exposing the embryos to an agent that removes the STOP element from the DNA editing agent, the DNA editing agent comprises the sequence of one of SEQ ID NOs:120-127.

29. The method of claim 25, wherein when said method comprises exposing the embryos to an agent that removes the STOP element from the DNA editing agent, wherein the agent that removes the STOP element is a nucleotide sequence encoding FlpO protein or Cre protein.

30. The method of claim 25, wherein when said method comprises exposing the embryos to an agent that removes the STOP element from the DNA editing agent, inducing lethality in male embryos further comprises exposing the embryos to blue light having a wavelength of 450-485 nm.

* * * * *

SEQUENCE LISTING

```
<160> NUMBER OF SEQ ID NOS: 132

<210> SEQ ID NO 1
<211> LENGTH: 149
<212> TYPE: DNA
<213> ORGANISM: Artificial Sequence
<220> FEATURE:
<223> OTHER INFORMATION: HA1-CRISPER-HA2

<400> SEQUENCE: 1
aacacagctt atatacattt ttacctacaa aatcgtgctg tcatgtccca ctctgattgg      60
ttcataccag ataacgtgcc ttatttggcc gtttccacat tcttttctca tccttcttct     120
cctgttttct ctgcatcaag gtcagcacg                                        149

<210> SEQ ID NO 2
<211> LENGTH: 30
<212> TYPE: DNA
<213> ORGANISM: Artificial sequence
<220> FEATURE:
<223> OTHER INFORMATION: CRISPER WT Sequence

<400> SEQUENCE: 2
ataccagata acgtgcctta tttggccgtt                                        30

<210> SEQ ID NO 3
<211> LENGTH: 32
<212> TYPE: DNA
<213> ORGANISM: Artificial sequence
<220> FEATURE:
<223> OTHER INFORMATION: CRISPER Mutant Sequence

<400> SEQUENCE: 3
ataccagata acgtaatcct tatttggccg tt                                     32

<210> SEQ ID NO 4
<211> LENGTH: 20
```

```
<212> TYPE: DNA
<213> ORGANISM: Artificial sequence
<220> FEATURE:
<223> OTHER INFORMATION: Primer 1

<400> SEQUENCE: 4
ttttgaatga agggcctgag                                                    20

<210> SEQ ID NO 5
<211> LENGTH: 20
<212> TYPE: DNA
<213> ORGANISM: Artificial Sequence
<220> FEATURE:
<223> OTHER INFORMATION: Primer 2

<400> SEQUENCE: 5
ggttggttca ctgttgtctg                                                    20

<210> SEQ ID NO 6
<211> LENGTH: 45
<212> TYPE: DNA
<213> ORGANISM: Artificial sequence
<220> FEATURE:
<223> OTHER INFORMATION: Primer 3

<400> SEQUENCE: 6
gtccctcttc tcttatggag atcgccgttt ccacattctt ttctc                        45

<210> SEQ ID NO 7
<211> LENGTH: 49
<212> TYPE: DNA
<213> ORGANISM: Artificial sequence
<220> FEATURE:
<223> OTHER INFORMATION: Primer 4

<400> SEQUENCE: 7
ggtggcactt ttcggggaaa tgtgtgaacc aatcagagtg ggacatgac                    49

<210> SEQ ID NO 8
<211> LENGTH: 49
<212> TYPE: DNA
<213> ORGANISM: Artificial sequence
<220> FEATURE:
<223> OTHER INFORMATION: Primer 5

<400> SEQUENCE: 8
gtcatgtccc actctgattg gttcacacat ttccccgaaa agtgccacc                    49

<210> SEQ ID NO 9
<211> LENGTH: 45
<212> TYPE: DNA
<213> ORGANISM: Artificial sequence
<220> FEATURE:
<223> OTHER INFORMATION: Primer 6

<400> SEQUENCE: 9
gagaaaagaa tgtggaaacg gcgatctcca taagagaaga gggac                        45

<210> SEQ ID NO 10
<211> LENGTH: 19
<212> TYPE: DNA
<213> ORGANISM: Artificial sequence
<220> FEATURE:
<223> OTHER INFORMATION: Primer 7

<400> SEQUENCE: 10
```
gaagtgtgct gctaacctg                                                          19

<210> SEQ ID NO 11
<211> LENGTH: 20
<212> TYPE: DNA
<213> ORGANISM: Artificial sequence
<220> FEATURE:
<223> OTHER INFORMATION: Primer 8

<400> SEQUENCE: 11
gctatgaact aatgaccccg                                                        20

<210> SEQ ID NO 12
<211> LENGTH: 21
<212> TYPE: DNA
<213> ORGANISM: Artificial sequence
<220> FEATURE:
<223> OTHER INFORMATION: Primer 9

<400> SEQUENCE: 12
ttttcctcct ctcctgacta c                                                      21

<210> SEQ ID NO 13
<211> LENGTH: 22
<212> TYPE: DNA
<213> ORGANISM: Artificial sequence
<220> FEATURE:
<223> OTHER INFORMATION: Primer 10

<400> SEQUENCE: 13
ggcctggatg ataagagtct tc                                                     22

<210> SEQ ID NO 14
<211> LENGTH: 20
<212> TYPE: DNA
<213> ORGANISM: Artificial sequence
<220> FEATURE:
<223> OTHER INFORMATION: Primer 11

<400> SEQUENCE: 14
gctattcggc tatgactggg                                                        20

<210> SEQ ID NO 15
<211> LENGTH: 20
<212> TYPE: DNA
<213> ORGANISM: Artificial sequence
<220> FEATURE:
<223> OTHER INFORMATION: Primer 12

<400> SEQUENCE: 15
gaaggcgata gaaggcgatg                                                        20

<210> SEQ ID NO 16
<211> LENGTH: 20
<212> TYPE: DNA
<213> ORGANISM: Artificial sequence
<220> FEATURE:
<223> OTHER INFORMATION: Primer 13

<400> SEQUENCE: 16
gtggaacaca gctttttccag                                                       20

<210> SEQ ID NO 17
<211> LENGTH: 20
<212> TYPE: DNA
<213> ORGANISM: Artificial sequence -continued

```
<220> FEATURE:
<223> OTHER INFORMATION: Primer 14

<400> SEQUENCE: 17
gctcttcaac ttgccatttg                                              20

<210> SEQ ID NO 18
<211> LENGTH: 19
<212> TYPE: DNA
<213> ORGANISM: Artificial sequence
<220> FEATURE:
<223> OTHER INFORMATION: Primer 15

<400> SEQUENCE: 18
tcaacagcac gtaagcaac                                               19

<210> SEQ ID NO 19
<211> LENGTH: 20
<212> TYPE: DNA
<213> ORGANISM: Artificial sequence
<220> FEATURE:
<223> OTHER INFORMATION: Primer 16

<400> SEQUENCE: 19
cctgactcca tttttgagcc                                              20

<210> SEQ ID NO 20
<211> LENGTH: 22
<212> TYPE: DNA
<213> ORGANISM: Artificial sequence
<220> FEATURE:
<223> OTHER INFORMATION: Primer 17

<400> SEQUENCE: 20
cccaaatata acacgcttca ct                                           22

<210> SEQ ID NO 21
<211> LENGTH: 23
<212> TYPE: DNA
<213> ORGANISM: Artificial sequence
<220> FEATURE:
<223> OTHER INFORMATION: Primer 18

<400> SEQUENCE: 21
gaaatgaatt attttctggc gac                                          23

<210> SEQ ID NO 22
<211> LENGTH: 20
<212> TYPE: DNA
<213> ORGANISM: Artificial sequence
<220> FEATURE:
<223> OTHER INFORMATION: Primer 19

<400> SEQUENCE: 22
agctctttct cgattccgtg                                              20

<210> SEQ ID NO 23
<211> LENGTH: 20
<212> TYPE: DNA
<213> ORGANISM: Artificial sequence
<220> FEATURE:
<223> OTHER INFORMATION: Primer 20

<400> SEQUENCE: 23
gggtagacac aagctgagcc                                              20
```

<210> SEQ ID NO 24
<211> LENGTH: 20
<212> TYPE: DNA
<213> ORGANISM: Artificial sequence
<220> FEATURE:
<223> OTHER INFORMATION: Primer 21

<400> SEQUENCE: 24
caactatcag gctccaccac                                                                20

<210> SEQ ID NO 25
<211> LENGTH: 20
<212> TYPE: DNA
<213> ORGANISM: Artificial sequence
<220> FEATURE:
<223> OTHER INFORMATION: Primer 22

<400> SEQUENCE: 25
ctcagacggt tttcagggtt                                                                20

<210> SEQ ID NO 26
<211> LENGTH: 20
<212> TYPE: DNA
<213> ORGANISM: Artificial sequence
<220> FEATURE:
<223> OTHER INFORMATION: Primer 23

<400> SEQUENCE: 26
aggctatggg atgatgcaag                                                                20

<210> SEQ ID NO 27
<211> LENGTH: 20
<212> TYPE: DNA
<213> ORGANISM: Artificial sequence
<220> FEATURE:
<223> OTHER INFORMATION: Primer 24

<400> SEQUENCE: 27
gtaggtaggc gatccgttca                                                                20

<210> SEQ ID NO 28
<211> LENGTH: 20
<212> TYPE: DNA
<213> ORGANISM: Artificial sequence
<220> FEATURE:
<223> OTHER INFORMATION: Primer 25

<400> SEQUENCE: 28
cgagaccaac gtgaagggaa                                                                20

<210> SEQ ID NO 29
<211> LENGTH: 20
<212> TYPE: DNA
<213> ORGANISM: Artificial sequence
<220> FEATURE:
<223> OTHER INFORMATION: Primer 26

<400> SEQUENCE: 29
cagacccgga caacgtcttt                                                                20

<210> SEQ ID NO 30
<211> LENGTH: 20
<212> TYPE: DNA
<213> ORGANISM: Artificial sequence
<220> FEATURE:
<223> OTHER INFORMATION: Primer 27

```
<400> SEQUENCE: 30
ctctggggct cacctacaag                                              20

<210> SEQ ID NO 31
<211> LENGTH: 20
<212> TYPE: DNA
<213> ORGANISM: Artificial sequence
<220> FEATURE:
<223> OTHER INFORMATION: Primer 28

<400> SEQUENCE: 31
agccctggtg aaatgtaggg                                              20

<210> SEQ ID NO 32
<211> LENGTH: 20
<212> TYPE: DNA
<213> ORGANISM: Artificial sequence
<220> FEATURE:
<223> OTHER INFORMATION: Primer 29

<400> SEQUENCE: 32
agctctcatc tcaaggcaca                                              20

<210> SEQ ID NO 33
<211> LENGTH: 20
<212> TYPE: DNA
<213> ORGANISM: Artificial sequence
<220> FEATURE:
<223> OTHER INFORMATION: Primer 30

<400> SEQUENCE: 33
ggaaagatcc actgcttcca                                              20

<210> SEQ ID NO 34
<211> LENGTH: 22
<212> TYPE: DNA
<213> ORGANISM: Artificial sequence
<220> FEATURE:
<223> OTHER INFORMATION: Primer 31

<400> SEQUENCE: 34
agcacaggtg gtgaacgaac ca                                           22

<210> SEQ ID NO 35
<211> LENGTH: 23
<212> TYPE: DNA
<213> ORGANISM: Artificial sequence
<220> FEATURE:
<223> OTHER INFORMATION: Primer 32

<400> SEQUENCE: 35
tccaggcctc ttgatgctac cga                                          23

<210> SEQ ID NO 36
<211> LENGTH: 24
<212> TYPE: DNA
<213> ORGANISM: Artificial sequence
<220> FEATURE:
<223> OTHER INFORMATION: Primer 34

<400> SEQUENCE: 36
caccgccaaa taaggcacgt tatc                                         24

<210> SEQ ID NO 37
```

-continued

```
<211> LENGTH: 24
<212> TYPE: DNA
<213> ORGANISM: Artificial sequence
<220> FEATURE:
<223> OTHER INFORMATION: Primer 35

<400> SEQUENCE: 37
aaacgataac gtgccttatt tggc                                          24

<210> SEQ ID NO 38
<211> LENGTH: 25
<212> TYPE: DNA
<213> ORGANISM: Artificial sequence
<220> FEATURE:
<223> OTHER INFORMATION: Primer 36

<400> SEQUENCE: 38
caccgaccag ataacgtgcc ttatt                                         25

<210> SEQ ID NO 39
<211> LENGTH: 24
<212> TYPE: DNA
<213> ORGANISM: Artificial sequence
<220> FEATURE:
<223> OTHER INFORMATION: Primer 37

<400> SEQUENCE: 39
aaacaataag gcacgttatc tggt                                          24

<210> SEQ ID NO 40
<211> LENGTH: 19
<212> TYPE: DNA
<213> ORGANISM: Artificial sequence
<220> FEATURE:
<223> OTHER INFORMATION: Primer 38

<400> SEQUENCE: 40
ttgcagtggt taccgttcg                                                19

<210> SEQ ID NO 41
<211> LENGTH: 20
<212> TYPE: DNA
<213> ORGANISM: Artificial sequence
<220> FEATURE:
<223> OTHER INFORMATION: Primer 39

<400> SEQUENCE: 41
tagtaggcat cttgtggggg                                               20

<210> SEQ ID NO 42
<211> LENGTH: 20
<212> TYPE: DNA
<213> ORGANISM: Artificial sequence
<220> FEATURE:
<223> OTHER INFORMATION: Primer 40

<400> SEQUENCE: 42
atgaatggag ctataggagg                                               20

<210> SEQ ID NO 43
<211> LENGTH: 61
<212> TYPE: DNA
<213> ORGANISM: Artificial sequence
<220> FEATURE:
<223> OTHER INFORMATION: Primer 41

<400> SEQUENCE: 43
```

-continued

```
ccacgtctcc tgcttgcttt aacagagaga agttcgtggc atcgccatct tccagcaggc      60
g                                                                       61

<210> SEQ ID NO 44
<211> LENGTH: 61
<212> TYPE: DNA
<213> ORGANISM: Artificial sequence
<220> FEATURE:
<223> OTHER INFORMATION: Primer 42

<400> SEQUENCE: 44
tgttaaagca agcaggagac gtggaagaaa accccggtcc tatgaagatg gacaaaaaga      60
c                                                                       61

<210> SEQ ID NO 45
<211> LENGTH: 21
<212> TYPE: DNA
<213> ORGANISM: Artificial sequence
<220> FEATURE:
<223> OTHER INFORMATION: Primer 43

<400> SEQUENCE: 45
ttacagcccg gaccgacgat g                                                 21

<210> SEQ ID NO 46
<211> LENGTH: 32
<212> TYPE: DNA
<213> ORGANISM: Artificial sequence
<220> FEATURE:
<223> OTHER INFORMATION: Primer 44

<400> SEQUENCE: 46
atctgacccg ggatgaatgg agctatagga gg                                     32

<210> SEQ ID NO 47
<211> LENGTH: 33
<212> TYPE: DNA
<213> ORGANISM: Artificial sequence
<220> FEATURE:
<223> OTHER INFORMATION: Primer 45

<400> SEQUENCE: 47
gtagctgcta gcttacagcc cggaccgacg atg                                    33

<210> SEQ ID NO 48
<211> LENGTH: 31
<212> TYPE: DNA
<213> ORGANISM: Artificial sequence
<220> FEATURE:
<223> OTHER INFORMATION: Primer 46

<400> SEQUENCE: 48
caggtccccg ggatggatcc tgatgatgtt g                                      31

<210> SEQ ID NO 49
<211> LENGTH: 31
<212> TYPE: DNA
<213> ORGANISM: Artificial sequence
<220> FEATURE:
<223> OTHER INFORMATION: Primer 47

<400> SEQUENCE: 49
gcatgtgcta gcttagagct ttaaatctct g                                      31
```

-continued

<210> SEQ ID NO 50
<211> LENGTH: 9289
<212> TYPE: DNA
<213> ORGANISM: Artificial sequence
<220> FEATURE:
<223> OTHER INFORMATION: pX330-GFP

<400> SEQUENCE: 50

```
gagggcctat ttcccatgat tccttcatat ttgcatatac gatacaaggc tgttagagag      60
ataattggaa ttaatttgac tgtaaacaca aagatattag tacaaaatac gtgacgtaga     120
aagtaataat ttcttgggta gtttgcagtt ttaaaattat gttttaaaat ggactatcat     180
atgcttaccg taacttgaaa gtatttcgat ttcttggctt tatatatctt gtggaaagga     240
cgaaacaccg gtcttcgag aagacctgtt ttagagctag aaatagcaag ttaaaataag     300
gctagtccgt tatcaacttg aaaaagtggc accgagtcgg tgcttttttg ttttagagct     360
agaaatagca agttaaaata aggctagtcc gttttttagcg cgtgcgccaa ttctgcagac     420
aaatggctct agaggtaccc gttacataac ttacggtaaa tggcccgcct ggctgaccgc     480
ccaacgaccc ccgcccattg acgtcaatag taacgccaat agggactttc cattgacgtc     540
aatgggtgga gtatttacgg taaactgccc acttggcagt acatcaagtg tatcatatgc     600
caagtacgcc ccctattgac gtcaatgacg gtaaatggcc cgcctggcat tgtgcccagt     660
acatgacctt atgggacttt cctacttggc agtacatcta cgtattagtc atcgctatta     720
ccatggtcga ggtgagcccc acgttctgct tcactctccc catctccccc ccctccccac     780
ccccaatttt gtatttattt attttttaat tattttgtgc agcgatgggg gcggggggg      840 ggggggggcg cgcgccaggc ggggcggggc ggggcgaggg gcggggcggg gcgaggcgga     900
gaggtgcggc ggcagccaat cagagcggcg cgctccgaaa gtttcctttt atggcgaggc     960
ggcggcggcg gcggccctat aaaaagcgaa gcgcgcggcg ggcgggagtc gctgcgacgc    1020
tgccttcgcc ccgtgccccg ctccgccgcc gcctcgcgcc gcccgccccg gctctgactg    1080
accgcgttac tcccacaggt gagcgggcgg gacggccctt ctcctccggg ctgtaattag    1140
ctgagcaaga ggtaagggtt taagggatgg ttggttggtg gggtattaat gtttaattac    1200
ctggagcacc tgcctgaaat cactttttttt caggttggac cggtgccacc atggactata    1260
aggaccacga cggagactac aaggatcatg atattgatta caaagacgat gacgataaga    1320
tggccccaaa gaagaagcgg aaggtcggta tccacggagt cccagcagcc gacaagaagt    1380
acagcatcgg cctggacatc ggcaccaact ctgtgggctg ggccgtgatc accgacgagt    1440
acaaggtgcc cagcaagaaa ttcaaggtgc tgggcaacac cgaccggcac agcatcaaga    1500
agaacctgat cggagccctg ctgttcgaca gcggcgaaac agccgaggcc acccggctga    1560
agagaaccgc cagaagaaga tacaccagac ggaagaaccg gatctgctat ctgcaagaga    1620
tcttcagcaa cgagatggcc aaggtggacg acagcttctt ccacagactg gaagagtcct    1680
tcctggtgga agaggataag aagcacgagc ggcaccccat cttcggcaac atcgtggacg    1740
aggtggccta ccacgagaag taccccacca tctaccacct gagaaagaaa ctggtggaca    1800
gcaccgacaa ggccgacctg cggctgatct atctggccct ggcccacatg atcaagttcc    1860
ggggccactt cctgatcgag ggcgacctga accccgacaa cagcgacgtg gacaagctgt    1920
tcatccagct ggtgcagacc tacaaccagc tgttcgagga aaaccccatc aacgccagcg    1980
gcgtggacgc caaggccatc ctgtctgcca gactgagcaa gagcagacgg ctggaaaatc    2040
tgatcgccca gctgcccggc gagaagaaga tggcctgtt cggaaacctg attgccctga    2100
```

-continued

```
gcctgggcct gaccccaac ttcaagagca acttcgacct ggccgaggat gccaaactgc    2160
agctgagcaa ggacacctac gacgacgacc tggacaacct gctggcccag atcggcgacc    2220
agtacgccga cctgtttctg gccgccaaga acctgtccga cgccatcctg ctgagcgaca    2280
tcctgagagt gaacaccgag atcaccaagg cccccctgag cgcctctatg atcaagagat    2340
acgacgagca ccaccaggac ctgaccctgc tgaaagctct cgtgcggcag cagctgcctg    2400
agaagtacaa agagattttc ttcgaccaga gcaagaacgg ctacgccggc tacattgacg    2460
gcggagccag ccaggaagag ttctacaagt tcatcaagcc catcctggaa aagatggacg    2520
gcaccgagga actgctcgtg aagctgaaca gagaggacct gctgcggaag cagcggacct    2580
tcgacaacgg cagcatcccc caccagatcc acctgggaga gctgcacgcc attctgcggc    2640
ggcaggaaga tttttaccca ttcctgaagg acaaccggga aaagatcgag aagatcctga    2700
ccttccgcat ccctactac gtgggccctc tggccagggg aaacagcaga ttcgcctgga    2760
tgaccagaaa gagcgaggaa accatcaccc cctggaactt cgaggaagtg gtggacaagg    2820
gcgcttccgc ccagagcttc atcgagcgga tgaccaactt cgataagaac ctgcccaacg    2880
agaaggtgct gcccaagcac agcctgctgt acgagtactt caccgtgtat aacgagctga    2940
ccaaagtgaa atacgtgacc gagggaatga gaaagcccgc cttcctgagc ggcgagcaga    3000
aaaaggccat cgtggacctg ctgttcaaga ccaaccggaa agtgaccgtg aagcagctga    3060
aagaggacta cttcaagaaa atcgagtgct tcgactccgt ggaaatctcc ggcgtggaag    3120
atcggttcaa cgcctccctg ggcacatacc acgatctgct gaaaattatc aaggacaagg    3180
acttcctgga caatgaggaa aacgaggaca ttctggaaga tatcgtgctg accctgacac    3240
tgtttgagga cagagagatg atcgaggaac ggctgaaaac ctatgcccac ctgttcgacg    3300
acaaagtgat gaagcagctg aagcggcgga gatacaccgg ctggggcagg ctgagccgga    3360
agctgatcaa cggcatccgg gacaagcagt ccggcaagac aatcctggat ttcctgaagt    3420
ccgacggctt cgccaacaga aacttcatgc agctgatcca cgacgacagc ctgacctttta    3480 aagaggacat ccagaaagcc caggtgtccg gccagggcga tagcctgcac gagcacattg    3540
ccaatctggc cggcagcccc gccattaaga agggcatcct gcagacagtg aaggtggtgg    3600
acgagctcgt gaaagtgatg ggccggcaca gcccgagaa catcgtgatc gaaatggcca    3660
gagagaacca gaccacccag aagggacaga agaacagccg cgagagaatg aagcggatcg    3720
aagagggcat caaagagctg ggcagccaga tcctgaaaga acaccccgtg gaaaacaccc    3780
agctgcagaa cgagaagctg tacctgtact acctgcagaa tgggcgggat atgtacgtgg    3840
accaggaact ggacatcaac cggctgtccg actacgatgt ggaccatatc gtgcctcaga    3900
gctttctgaa ggacgactcc atcgacaaca aggtgctgac cagaagcgac aagaaccggg    3960
gcaagagcga caacgtgccc tccgaagagg tcgtgaagaa gatgaagaac tactggcggc    4020
agctgctgaa cgccaagctg attacccaga gaaagttcga caatctgacc aaggccgaga    4080
gaggcggcct gagcgaactg gataaggccg gcttcatcaa gagacagctg gtggaaaccc    4140
ggcagatcac aaagcacgtg gcacagatcc tggactcccg gatgaacact aagtacgacg    4200
agaatgacaa gctgatccgg gaagtgaaag tgatcacct gaagtccaag ctggtgtccg    4260
atttccggaa ggattcccag ttttacaaag tgcgcgagat caacaactac caccacgccc    4320
acgacgccta cctgaacgcc gtcgtgggaa ccgccctgat caaaaagtac cctaagctgg    4380
aaagcgagtt cgtgtacggc gactacaagg tgtacgacgt gcggaagatg atcgccaaga    4440
```

-continued

```
gcgagcagga aatcggcaag gctaccgcca agtacttctt ctacagcaac atcatgaact    4500
ttttcaagac cgagattacc ctggccaacg gcgagatccg gaagcggcct ctgatcgaga    4560
caaacggcga aaccggggag atcgtgtggg ataagggccg ggattttgcc accgtgcgga    4620
aagtgctgag catgccccaa gtgaatatcg tgaaaaagac cgaggtgcag acaggcggct    4680
tcagcaaaga gtctatcctg cccaagagga acagcgataa gctgatcgcc agaaagaagg    4740
actgggaccc taagaagtac ggcggcttcg acagccccac cgtggcctat tctgtgctgg    4800
tggtggccaa agtggaaaag ggcaagtcca agaaactgaa gagtgtgaaa gagctgctgg    4860
ggatcaccat catggaaaga agcagcttcg agaagaatcc catcgacttt ctggaagcca    4920
agggctacaa agaagtgaaa aaggacctga tcatcaagct gcctaagtac tccctgttcg    4980
agctggaaaa cggccggaag agaatgctgg cctctgccgg cgaactgcag aagggaaacg    5040
aactggccct gccctccaaa tatgtgaact tcctgtacct ggccagccac tatgagaagc    5100
tgaagggctc ccccgaggat aatgagcaga acagctgtt tgtggaacag cacaagcact    5160
acctggacga gatcatcgag cagatcagcg agttctccaa gagagtgatc ctggccgacg    5220
ctaatctgga caaagtgctg tccgcctaca caagcaccg ggataagccc atcagagagc    5280
aggccgagaa tatcatccac ctgtttaccc tgaccaatct gggagcccct gccgccttca    5340
agtactttga caccaccatc gaccggaaga ggtacaccag caccaaagag gtgctggacg    5400
ccaccctgat ccaccagagc atcaccggcc tgtacgagac acggatcgac ctgtctcagc    5460
tgggaggcga caaaaggccg gcggccacga aaaaggccgg ccaggcaaaa aagaaaaagg    5520
aattcggcag tggagagggc agaggaagtc tgctaacatg cggtgacgtc gaggagaatc    5580
ctggcccagt gagcaagggc gaggagctgt tcaccggggt ggtgcccatc ctggtcgagc    5640
tggacggcga cgtaaacggc cacaagttca gcgtgtccgg cgagggcgag ggcgatgcca    5700
cctacggcaa gctgaccctg aagttcatct gcaccaccgg caagctgccc gtgccctggc    5760
ccaccctcgt gaccaccctg acctacggcg tgcagtgctt cagccgctac cccgaccaca    5820
tgaagcagca cgacttcttc aagtccgcca tgcccgaagg ctacgtccag gagcgcacca    5880
tcttcttcaa ggacgacggc aactacaaga cccgcgccga ggtgaagttc gagggcgaca    5940
ccctggtgaa ccgcatcgag ctgaagggca tcgacttcaa ggaggacggc aacatcctgg    6000
ggcacaagct ggagtacaac tacaacagcc acaacgtcta tatcatggcc gacaagcaga    6060
agaacggcat caaggtgaac ttcaagatcc gccacaacat cgaggacggc agcgtgcagc    6120
tcgccgacca ctaccagcag aacaccccca tcggcgacgg ccccgtgctg ctgcccgaca    6180
accactacct gagcacccag tccgccctga gcaaagaccc caacgagaag cgcgatcaca    6240
tggtcctgct ggagttcgtg accgccgccg ggatcactct cggcatggac gagctgtaca    6300
aggaattcta actagagctc gctgatcagc ctcgactgtg ccttctagtt gccagccatc    6360
tgttgtttgc ccctccccg tgccttcctt gaccctggaa ggtgccactc ccactgtcct    6420
ttcctaataa aatgaggaaa ttgcatcgca ttgtctgagt aggtgtcatt ctattctggg    6480
gggtggggtg gggcaggaca gcaagggga ggattgggaa gagaatagca ggcatgctgg    6540
ggagcggccg caggaacccc tagtgatgga gttggccact ccctctctgc gcgctcgctc    6600
gctcactgag gccgggcgac caaaggtcgc ccgacgcccg gctttgccc gggcggcctc    6660 agtgagcgag cgagcgcgca gctgcctgca ggggcgcctg atgcggtatt ttctccttac    6720
gcatctgtgc ggtatttcac accgcatacg tcaaagcaac catagtacgc gccctgtagc    6780
ggcgcattaa gcgcggcggg tgtggtggtt acgcgcagcg tgaccgctac acttgccagc    6840
```

```
gccctagcgc ccgctccttt cgctttcttc ccttcctttc tcgccacgtt cgccggcttt   6900
ccccgtcaag ctctaaatcg ggggctccct ttagggttcc gatttagtgc tttacggcac   6960
ctcgacccca aaaaacttga tttgggtgat ggttcacgta gtgggccatc gccctgatag   7020 acggttttc gccctttgac gttggagtcc acgttcttta atagtggact cttgttccaa   7080
actggaacaa cactcaaccc tatctcgggc tattcttttg atttataagg gattttgccg   7140
atttcggcct attggttaaa aaatgagctg atttaacaaa aatttaacgc gaattttaac   7200
aaaatattaa cgtttacaat tttatggtgc actctcagta caatctgctc tgatgccgca   7260
tagttaagcc agccccgaca cccgccaaca cccgctgacg cgccctgacg ggcttgtctg   7320
ctcccggcat ccgcttacag acaagctgtg accgtctccg ggagctgcat gtgtcagagg   7380
ttttcaccgt catcaccgaa acgcgcgaga cgaaagggcc tcgtgatacg cctatttta   7440 taggttaatg tcatgataat aatggtttct tagacgtcag gtggcacttt tcggggaaat   7500
gtgcgcggaa cccctatttg tttatttttc taaatacatt caaatatgta tccgctcatg   7560
agacaataac cctgataaat gcttcaataa tattgaaaaa ggaagagtat gagtattcaa   7620
catttccgtg tcgcccttat tccctttttt gcggcatttt gccttcctgt ttttgctcac   7680
ccagaaacgc tggtgaaagt aaaagatgct gaagatcagt tgggtgcacg agtgggttac   7740
atcgaactgg atctcaacag cggtaagatc cttgagagtt ttcgccccga gaacgtttt   7800 ccaatgatga gcacttttaa agttctgcta tgtggcgcgg tattatcccg tattgacgcc   7860
gggcaagagc aactcggtcg ccgcatacac tattctcaga atgacttggt tgagtactca   7920
ccagtcacag aaaagcatct tacggatggc atgacagtaa gagaattatg cagtgctgcc   7980
ataaccatga gtgataacac tgcggccaac ttacttctga caacgatcgg aggaccgaag   8040
gagctaaccg cttttttgca caacatgggg gatcatgtaa ctcgccttga tcgttgggaa   8100
ccggagctga atgaagccat accaaacgac gagcgtgaca ccacgatgcc tgtagcaatg   8160
gcaacaacgt tgcgcaaact attaactggc gaactactta ctctagcttc ccggcaacaa   8220
ttaatagact ggatggaggc ggataaagtt gcaggaccac ttctgcgctc ggcccttccg   8280
gctggctggt ttattgctga taaatctgga gccggtgagc gtggaagccg cggtatcatt   8340
gcagcactgg ggccagatgg taagccctcc cgtatcgtag ttatctacac gacggggagt   8400
caggcaacta tggatgaacg aaatagacag atcgctgaga taggtgcctc actgattaag   8460
cattggtaac tgtcagacca gtttactca tatatacttt agattgattt aaaacttcat   8520
ttttaattta aaaggatcta ggtgaagatc cttttttgata atctcatgac caaaatccct   8580
taacgtgagt tttcgttcca ctgagcgtca gaccccgtag aaaagatcaa aggatcttct   8640
tgagatcctt tttttctgcg cgtaatctgc tgcttgcaaa caaaaaaacc accgctacca   8700
gcggtggttt gtttgccgga tcaagagcta ccaactcttt ttccgaaggt aactggcttc   8760
agcagagcgc agataccaaa tactgtcctt ctagtgtagc cgtagttagg ccaccacttc   8820
aagaactctg tagcaccgcc tacatacctc gctctgctaa tcctgttacc agtggctgct   8880
gccagtggcg ataagtcgtg tcttaccggg ttggactcaa gacgatagtt accggataag   8940
gcgcagcggt cgggctgaac ggggggttcg tgcacacagc ccagcttgga gcgaacgacc   9000
tacaccgaac tgagatacct acagcgtgag ctatgagaaa gcgccacgct tcccgaaggg   9060
agaaaggcgg acaggtatcc ggtaagcggc agggtcggaa caggagagcg cacgagggag   9120
cttccagggg gaaacgcctg gtatctttat agtcctgtcg ggtttcgcca cctctgactt   9180
```

-continued

```
gagcgtcgat ttttgtgatg ctcgtcaggg gggcggagcc tatggaaaaa cgccagcaac    9240
gcggcctttt tacggttcct ggccttttgc tggcctttg ctcacatgt                 9289
```

<210> SEQ ID NO 51
<211> LENGTH: 9291
<212> TYPE: DNA
<213> ORGANISM: Artificial sequence
<220> FEATURE:
<223> OTHER INFORMATION: CRISPR1

<400> SEQUENCE: 51

```
gagggcctat ttcccatgat tccttcatat ttgcatatac gatacaaggc tgttagagag      60
ataattggaa ttaatttgac tgtaaacaca aagatattag tacaaaatac gtgacgtaga     120
aagtaataat ttcttgggta gtttgcagtt ttaaaattat gttttaaaat ggactatcat     180
atgcttaccg taacttgaaa gtatttcgat ttcttggctt tatatatctt gtggaaagga     240
cgaaacaccg ccaaataagg cacgttatcg ttttagagct agaaatagca agttaaaata     300
aggctagtcc gttatcaact tgaaaaagtg gcaccgagtc ggtgcttttt tgttttagag     360
ctagaaatag caagttaaaa taaggctagt ccgtttttag cgcgtgcgcc aattctgcag     420
acaaatggct ctagaggtac ccgttacata acttacggta aatggcccgc ctggctgacc     480
gcccaacgac ccccgcccat tgacgtcaat agtaacgcca atagggactt ccattgacg      540 tcaatgggtg gagtatttac ggtaaactgc ccacttggca gtacatcaag tgtatcatat     600
gccaagtacg ccccctattg acgtcaatga cggtaaatgg cccgcctggc attgtgccca     660
gtacatgacc ttatgggact ttcctacttg gcagtacatc tacgtattag tcatcgctat     720
taccatggtc gaggtgagcc ccacgttctg cttcactctc cccatctccc ccccctcccc     780
acccccaatt ttgtatttat ttattttta attattttgt gcagcgatgg gggcggggggg     840 gggggggggg cgcgcgccag gcggggcggg gcggggcgag gggcggggcg gggcgaggcg     900
gagaggtgcg gcggcagcca atcagagcgg cgcgctccga aagtttcctt ttatggcgag     960
gcggcggcgg cggcggccct ataaaaagcg aagcgcgcgg cgggcgggag tcgctgcgac    1020
gctgccttcg ccccgtgccc cgctccgccg ccgcctcgcg ccgcccgccc cggctctgac    1080
tgaccgcgtt actcccacag gtgagcgggc gggacggccc ttctcctccg ggctgtaatt    1140
agctgagcaa gaggtaaggg tttaagggat ggttggttgg tggggtatta atgtttaatt    1200
acctggagca cctgcctgaa atcactttt ttcaggttgg accggtgcca ccatggacta     1260
taaggaccac gacggagact acaaggatca tgatattgat tacaaagacg atgacgataa    1320
gatggcccca aagaagaagc ggaaggtcgg tatccacgga gtcccagcag ccgacaagaa    1380
gtacagcatc ggcctggaca tcggcaccaa ctctgtgggc tgggccgtga tcaccgacga    1440
gtacaaggtg cccagcaaga aattcaaggt gctgggcaac accgaccggc acagcatcaa    1500
gaagaacctg atcggagccc tgctgttcga cagcggcgaa acagccgagg ccacccggct    1560
gaagagaacc gccagaagaa gatacaccag acggaagaac cggatctgct atctgcaaga    1620
gatcttcagc aacgagatgg ccaaggtgga cgacagcttc ttccacagac tggaagagtc    1680
cttcctggtg gaagaggata gaagcacga gcggcacccc atcttcggca acatcgtgga     1740
cgaggtggcc taccacgaga gtaccccac catctaccac ctgagaaaga aactggtgga     1800
cagcaccgac aaggccgacc tgcggctgat ctatctggcc ctggcccaca tgatcaagtt    1860
ccggggccac ttcctgatcg agggcgacct gaaccccgac aacagcgacg tggacaagct    1920
gttcatccag ctggtgcaga cctacaacca gctgttcgag gaaaacccca tcaacgccag    1980
```

-continued

```
cggcgtggac gccaaggcca tcctgtctgc cagactgagc aagagcagac ggctggaaaa    2040
tctgatcgcc cagctgcccg gcgagaagaa gaatggcctg ttcggaaacc tgattgccct    2100
gagcctgggc ctgaccccca acttcaagag caacttcgac ctggccgagg atgccaaact    2160
gcagctgagc aaggacacct acgacgacga cctggacaac ctgctggccc agatcggcga    2220
ccagtacgcc gacctgtttc tggccgccaa gaacctgtcc gacgccatcc tgctgagcga    2280
catcctgaga gtgaacaccg agatcaccaa ggccccctg agcgcctcta tgatcaagag    2340
atacgacgag caccaccagg acctgaccct gctgaaagct ctcgtgcggc agcagctgcc    2400
tgagaagtac aaagagattt tcttcgacca gagcaagaac ggctacgccg gctacattga    2460
cggcggagcc agccaggaag agttctacaa gttcatcaag cccatcctgg aaaagatgga    2520
cggcaccgag gaactgctcg tgaagctgaa cagagaggac ctgctgcgga agcagcggac    2580
cttcgacaac ggcagcatcc cccaccagat ccacctggga gagctgcacg ccattctgcg    2640
gcggcaggaa gatttttacc cattcctgaa ggacaaccgg gaaaagatcg agaagatcct    2700
gaccttccgc atcccctact acgtgggccc tctggccagg ggaaacagca gattcgcctg    2760
gatgaccaga aagagcgagg aaaccatcac ccctggaac ttcgaggaag tggtggacaa    2820
gggcgcttcc gcccagagct tcatcgagcg gatgaccaac ttcgataaga acctgcccaa    2880
cgagaaggtg ctgcccaagc acagcctgct gtacgagtac ttcaccgtgt ataacgagct    2940
gaccaaagtg aaatacgtga ccgagggaat gagaaagccc gccttcctga gcggcgagca    3000
gaaaaaggcc atcgtggacc tgctgttcaa gaccaaccgg aaagtgaccg tgaagcagct    3060
gaaagaggac tacttcaaga aaatcgagtg cttcgactcc gtggaaatct ccggcgtgga    3120
agatcggttc aacgcctccc tgggcacata ccacgatctg ctgaaaatta tcaaggacaa    3180
ggacttcctg gacaatgagg aaaacgagga cattctggaa gatatcgtgc tgaccctgac    3240
actgtttgag gacagagaga tgatcgagga acggctgaaa acctatgccc acctgttcga    3300
cgacaaagtg atgaagcagc tgaagcggcg gagatacacc ggctggggca ggctgagccg    3360
gaagctgatc aacggcatcc gggacaagca gtccggcaag acaatcctgg atttcctgaa    3420
gtccgacggc ttcgccaaca gaaacttcat gcagctgatc cacgacgaca gcctgacctt    3480
taaagaggac atccagaaag cccaggtgtc cggccagggc gatagcctgc acgagcacat    3540
tgccaatctg gccggcagcc ccgccattaa gaagggcatc ctgcagacag tgaaggtggt    3600
ggacgagctc gtgaaagtga tgggccggca caagcccgag aacatcgtga tcgaaatggc    3660
cagagagaac cagaccaccc agaagggaca gaagaacagc cgcgagagaa tgaagcggat    3720
cgaagagggc atcaaagagc tgggcagcca gatcctgaaa gaacaccccg tggaaaacac    3780
ccagctgcag aacgagaagc tgtacctgta ctacctgcag aatgggcggg atatgtacgt    3840
ggaccaggaa ctggacatca accggctgtc cgactacgat gtggaccata tcgtgcctca    3900
gagctttctg aaggacgact ccatcgacaa caaggtgctg accagaagcg acaagaaccg    3960
gggcaagagc gacaacgtgc cctccgaaga ggtcgtgaag aagatgaaga actactggcg    4020
gcagctgctg aacgccaagc tgattaccca gagaaagttc gacaatctga ccaaggccga    4080
gagaggcggc ctgagcgaac tggataaggc cggcttcatc aagagacagc tggtggaaac    4140
ccggcagatc acaaagcacg tggcacagat cctggactcc cggatgaaca ctaagtacga    4200
cgagaatgac aagctgatcc gggaagtgaa agtgatcacc ctgaagtcca gctggtgtc    4260 cgatttccgg aaggatttcc agttttacaa agtgcgcgag atcaacaact accaccacgc    4320
```

-continued

```
ccacgacgcc tacctgaacg ccgtcgtggg aaccgccctg atcaaaaagt accctaagct    4380
ggaaagcgag ttcgtgtacg gcgactacaa ggtgtacgac gtgcggaaga tgatcgccaa    4440
gagcgagcag gaaatcggca aggctaccgc caagtacttc ttctacagca acatcatgaa    4500 cttttttcaag accgagatta ccctggccaa cggcgagatc cggaagcggc ctctgatcga    4560
gacaaacggc gaaaccgggg agatcgtgtg ggataagggc cgggattttg ccaccgtgcg    4620
gaaagtgctg agcatgcccc aagtgaatat cgtgaaaaag accgaggtgc agacaggcgg    4680
cttcagcaaa gagtctatcc tgcccaagag gaacagcgat aagctgatcg ccagaaagaa    4740
ggactgggac cctaagaagt acggcggctt cgacagcccc accgtggcct attctgtgct    4800
ggtggtggcc aaagtggaaa agggcaagtc caagaaactg aagagtgtga aagagctgct    4860
ggggatcacc atcatggaaa gaagcagctt cgagaagaat cccatcgact ttctggaagc    4920
caagggctac aaagaagtga aaaaggacct gatcatcaag ctgcctaagt actccctgtt    4980
cgagctggaa aacggccgga agagaatgct ggcctctgcc ggcgaactgc agaagggaaa    5040
cgaactggcc ctgccctcca aatatgtgaa cttcctgtac ctggccagcc actatgagaa    5100
gctgaagggc tcccccgagg ataatgagca gaaacagctg tttgtggaac agcacaagca    5160
ctacctggac gagatcatcg agcagatcag cgagttctcc aagagagtga tcctggccga    5220
cgctaatctg gacaaagtgc tgtccgccta caacaagcac cgggataagc ccatcagaga    5280
gcaggccgag aatatcatcc acctgtttac cctgaccaat ctgggagccc ctgccgcctt    5340
caagtacttt gacaccacca tcgaccggaa gaggtacacc agcaccaaag aggtgctgga    5400
cgccaccctg atccaccaga gcatcaccgg cctgtacgag acacggatcg acctgtctca    5460
gctgggaggc gacaaaaggc cggcggccac gaaaaaggcc ggccaggcaa aaaagaaaaa    5520
ggaattcggc agtggagagg gcagaggaag tctgctaaca tgcggtgacg tcgaggagaa    5580
tcctggccca gtgagcaagg gcgaggagct gttcaccggg gtggtgccca tcctggtcga    5640
gctggacggc gacgtaaacg gccacaagtt cagcgtgtcc ggcgagggcg agggcgatgc    5700
cacctacggc aagctgaccc tgaagttcat ctgcaccacc ggcaagctgc ccgtgccctg    5760
gcccaccctc gtgaccaccc tgacctacgg cgtgcagtgc ttcagccgct accccgacca    5820
catgaagcag cacgacttct tcaagtccgc catgcccgaa ggctacgtcc aggagcgcac    5880
catcttcttc aaggacgacg gcaactacaa gacccgcgcc gaggtgaagt tcgagggcga    5940 cacccctggtg aaccgcatcg agctgaaggg catcgacttc aaggaggacg gcaacatcct    6000
ggggcacaag ctggagtaca actacaacag ccacaacgtc tatatcatgg ccgacaagca    6060
gaagaacggc atcaaggtga acttcaagat ccgccacaac atcgaggacg gcagcgtgca    6120
gctcgccgac cactaccagc agaacacccc catcggcgac ggccccgtgc tgctgcccga    6180
caaccactac ctgagcaccc agtccgccct gagcaaagac cccaacgaga gcgcgatca    6240 catggtcctg ctggagttcg tgaccgccgc cgggatcact ctcggcatgg acgagctgta    6300
caaggaattc taactagagc tcgctgatca gcctcgactg tgccttctag ttgccagcca    6360
tctgttgttt gcccctcccc cgtgccttcc ttgaccctgg aaggtgccac tcccactgtc    6420
ctttcctaat aaaatgagga aattgcatcg cattgtctga gtaggtgtca ttctattctg    6480 ggggggtgggg tggggcagga cagcaagggg gaggattggg aagagaatag caggcatgct    6540
ggggagcggc cgcaggaacc cctagtgatg gagttggcca ctccctctct gcgcgctcgc    6600
tcgctcactg aggccgggcg accaaaggtc gcccgacgcc cgggctttgc ccgggcggcc    6660
tcagtgagcg agcgagcgcg cagctgcctg caggggcgcc tgatgcggta ttttctcctt    6720
```

```
acgcatctgt gcggtatttc acaccgcata cgtcaaagca accatagtac gcgccctgta   6780
gcggcgcatt aagcgcggcg ggtgtggtgg ttacgcgcag cgtgaccgct acacttgcca   6840
gcgccctagc gcccgctcct ttcgctttct tcccttcctt tctcgccacg ttcgccggct   6900
ttccccgtca agctctaaat cggggggctcc ctttagggtt ccgatttagt gctttacggc   6960
acctcgaccc caaaaaactt gatttgggtg atggttcacg tagtgggcca tcgccctgat   7020
agacggtttt tcgccctttg acgttggagt ccacgttctt taatagtgga ctcttgttcc   7080
aaactggaac aacactcaac cctatctcgg gctattcttt tgatttataa gggattttgc   7140
cgatttcggc ctattggtta aaaaatgagc tgatttaaca aaaatttaac gcgaatttta   7200
acaaaatatt aacgtttaca attttatggt gcactctcag tacaatctgc tctgatgccg   7260
catagttaag ccagccccga cacccgccaa caccgctga cgcgccctga cgggcttgtc     7320
tgctcccggc atccgcttac agacaagctg tgaccgtctc cgggagctgc atgtgtcaga   7380
ggttttcacc gtcatcaccg aaacgcgcga gacgaaaggg cctcgtgata cgcctatttt   7440
tataggttaa tgtcatgata ataatggttt cttagacgtc aggtggcact tttcggggaa   7500
atgtgcgcgg aacccctatt tgtttatttt tctaaataca ttcaaatatg tatccgctca   7560
tgagacaata accctgataa atgcttcaat aatattgaaa aaggaagagt atgagtattc   7620
aacatttccg tgtcgccctt attccctttt ttgcggcatt ttgccttcct gtttttgctc   7680
acccagaaac gctggtgaaa gtaaaagatg ctgaagatca gttgggtgca cgagtgggtt   7740
acatcgaact ggatctcaac agcggtaaga tccttgagag ttttcgcccc gaagaacgtt   7800
ttccaatgat gagcactttt aaagttctgc tatgtggcgc ggtattatcc cgtattgacg   7860
ccgggcaaga gcaactcggt cgccgcatac actattctca gaatgacttg gttgagtact   7920
caccagtcac agaaaagcat cttacggatg gcatgacagt aagagaatta tgcagtgctg   7980
ccataaccat gagtgataac actgcggcca acttacttct gacaacgatc ggaggaccga   8040
aggagctaac cgcttttttg cacaacatgg gggatcatgt aactcgcctt gatcgttggg   8100
aaccggagct gaatgaagcc ataccaaacg acgagcgtga caccacgatg cctgtagcaa   8160
tggcaacaac gttgcgcaaa ctattaactg gcgaactact tactctagct tcccggcaac   8220
aattaataga ctggatggag gcggataaag ttgcaggacc acttctgcgc tcggcccttc   8280
cggctggctg gtttattgct gataaatctg gagccggtga gcgtggaagc cgcggtatca   8340
ttgcagcact ggggccagat ggtaagccct cccgtatcgt agttatctac acgacgggga   8400
gtcaggcaac tatggatgaa cgaaatagac agatcgctga gataggtgcc tcactgatta   8460
agcattggta actgtcagac caagtttact catatatact ttagattgat ttaaaacttc   8520
atttttaatt taaaaggatc taggtgaaga tcctttttga taatctcatg accaaaatcc   8580
cttaacgtga gttttcgttc cactgagcgt cagaccccgt agaaaagatc aaaggatctt   8640
cttgagatcc tttttttctg cgcgtaatct gctgcttgca acaaaaaaaa ccaccgctac   8700
cagcggtggt ttgtttgccg gatcaagagc taccaactct ttttccgaag gtaactggct   8760
tcagcagagc gcagatacca aatactgtcc ttctagtgta gccgtagtta ggccaccact   8820
tcaagaactc tgtagcaccg cctacatacc tcgctctgct aatcctgtta ccagtggctg   8880
ctgccagtgg cgataagtcg tgtcttaccg ggttggactc aagacgatag ttaccggata   8940
aggcgcagcg tcgggctga acgggggggtt cgtgcacaca gcccagcttg gagcgaacga   9000
cctacaccga actgagatac ctacagcgtg agctatgaga aagcgccacg cttcccgaag   9060
```

```
ggagaaaggc ggacaggtat ccggtaagcg gcagggtcgg aacaggagag cgcacgaggg    9120
agcttccagg gggaaacgcc tggtatcttt atagtcctgt cgggtttcgc cacctctgac    9180
ttgagcgtcg attttttgtga tgctcgtcag gggggcggag cctatggaaa aacgccagca    9240
acgcggcctt tttacggttc ctggcctttt gctggccttt tgctcacatg t             9291
```

```
<210> SEQ ID NO 52
<211> LENGTH: 9292
<212> TYPE: DNA
<213> ORGANISM: Artificial sequence
<220> FEATURE:
<223> OTHER INFORMATION: CRISPR3

<400> SEQUENCE: 52
gagggcctat ttcccatgat tccttcatat ttgcatatac gatacaaggc tgttagagag      60
ataattggaa ttaatttgac tgtaaacaca aagatattag tacaaaatac gtgacgtaga     120
aagtaataat ttcttgggta gtttgcagtt ttaaaattat gttttaaaat ggactatcat     180
atgcttaccg taacttgaaa gtatttcgat ttcttggctt tatatatctt gtggaaagga     240
cgaaacaccg accagataac gtgccttatt gttttagagc tagaaatagc aagttaaaat     300
aaggctagtc cgttatcaac ttgaaaaagt ggcaccgagt cggtgctttt ttgtttttaga    360 gctagaaata gcaagttaaa ataaggctag tccgttttta gcgcgtgcgc caattctgca     420
gacaaatggc tctagaggta cccgttacat aacttacggt aaatggcccg cctggctgac     480
cgcccaacga cccccgccca ttgacgtcaa tagtaacgcc aatagggact tccattgac      540 gtcaatgggt ggagtattta cggtaaactg cccacttggc agtacatcaa gtgtatcata     600
tgccaagtac gccccctatt gacgtcaatg acggtaaatg gcccgcctgg cattgtgccc     660
agtacatgac cttatgggac tttcctactt ggcagtacat ctacgtatta gtcatcgcta     720
ttaccatggt cgaggtgagc cccacgttct gcttcactct ccccatctcc ccccctccc      780 cacccccaat tttgtattta tttatttttt aattattttg tgcagcgatg ggggcggggg     840
gggggggggg gcgcgcgcca ggcggggcgg ggcggggcga ggggcggggc ggggcgaggc     900
ggagaggtgc ggcggcagcc aatcagagcg gcgcgctccg aaagtttcct tttatggcga     960
ggcggcggcg gcggcggccc tataaaaagc gaagcgcgcg gcgggcggga gtcgctgcga    1020
cgctgccttc gccccgtgcc ccgctccgcc gccgcctcgc gccgcccgcc ccggctctga    1080
ctgaccgcgt tactcccaca ggtgagcggg cgggacggcc cttctcctcc gggctgtaat    1140
tagctgagca agaggtaagg gtttaaggga tggttggttg gtggggtatt aatgtttaat    1200
tacctggagc acctgcctga aatcactttt tttcaggttg gaccggtgcc accatggact    1260
ataaggacca cgacggagac tacaaggatc atgatattga ttacaaagac gatgacgata    1320
agatggcccc aaagaagaag cggaaggtcg gtatccacgg agtcccagca gccgacaaga    1380
agtacagcat cggcctggac atcggcacca actctgtggg ctgggccgtg atcaccgacg    1440
agtacaaggt gcccagcaag aaattcaagg tgctgggcaa caccgaccgg cacagcatca    1500
agaagaacct gatcggagcc ctgctgttcg acagcggcga aacagccgag gccacccggc    1560
tgaagagaac cgccagaaga agatacacca cacggaagaa ccggatctgc tatctgcaag    1620
agatcttcag caacgagatg gccaaggtgg acgacagctt cttccacaga ctggaagagt    1680
ccttcctggt ggaagaggat aagaagcacg agcggcaccc catcttcggc aacatcgtgg    1740
acgaggtggc ctaccacgag aagtacccca ccatctacca cctgagaaag aaactggtgg    1800
acagcaccga caaggccgac ctgcggctga tctatctggc cctggcccac atgatcaagt    1860
```

-continued

```
tccggggcca cttcctgatc gagggcgacc tgaaccccga caacagcgac gtggacaagc      1920
tgttcatcca gctggtgcag acctacaacc agctgttcga ggaaaacccc atcaacgcca      1980
gcggcgtgga cgccaaggcc atcctgtctg ccagactgag caagagcaga cggctggaaa      2040
atctgatcgc ccagctgccc ggcgagaaga agaatggcct gttcggaaac ctgattgccc      2100
tgagcctggg cctgaccccc aacttcaaga gcaacttcga cctggccgag gatgccaaac      2160
tgcagctgag caaggacacc tacgacgacg acctggacaa cctgctggcc cagatcggcg      2220
accagtacgc cgacctgttt ctggccgcca agaacctgtc cgacgccatc ctgctgagcg      2280
acatcctgag agtgaacacc gagatcacca aggcccccct gagcgcctct atgatcaaga      2340
gatacgacga gcaccaccag gacctgaccc tgctgaaagc tctcgtgcgg cagcagctgc      2400
ctgagaagta caaagagatt ttcttcgacc agagcaagaa cggctacgcc ggctacattg      2460
acggcggagc cagccaggaa gagttctaca gttcatcaa gcccatcctg gaaaagatgg      2520
acggcaccga ggaactgctc gtgaagctga acagagagga cctgctgcgg aagcagcgga      2580
ccttcgacaa cggcagcatc ccccaccaga tccacctggg agagctgcac gccattctgc      2640
ggcggcagga agattttttac ccattcctga aggacaaccg ggaaaagatc gagaagatcc      2700
tgaccttccg catcccctac tacgtgggcc ctctggccag gggaaacagc agattcgcct      2760
ggatgaccag aaagagcgag gaaaccatca ccccctggaa cttcgaggaa gtggtggaca      2820
agggcgcttc cgcccagagc ttcatcgagc ggatgaccaa cttcgataag aacctgccca      2880
acgagaaggt gctgcccaag cacagcctgc tgtacgagta cttcaccgtg tataacgagc      2940
tgaccaaagt gaaatacgtg accgagggaa tgagaaagcc cgccttcctg agcggcgagc      3000
agaaaaaggc catcgtggac ctgctgttca gaccaaccg gaaagtgacc gtgaagcagc      3060
tgaaagagga ctacttcaag aaaatcgagt gcttcgactc cgtggaaatc tccggcgtgg      3120
aagatcggtt caacgcctcc ctgggcacat accacgatct gctgaaaatt atcaaggaca      3180
aggacttcct ggacaatgag gaaaacgagg acattctgga agatatcgtg ctgacccctga      3240 cactgtttga ggacagagag atgatcgagg aacggctgaa aacctatgcc cacctgttcg      3300
acgacaaagt gatgaagcag ctgaagcggc ggagatacac cggctggggc aggctgagcc      3360
ggaagctgat caacggcatc cgggacaagc agtccggcaa gacaatcctg gatttcctga      3420
agtccgacgg cttcgccaac agaaacttca tgcagctgat ccacgacgac agcctgacct      3480
ttaaagagga catccagaaa gcccaggtgt ccggccaggg cgatagcctg cacgagcaca      3540
ttgccaatct ggccggcagc cccgccatta agaagggcat cctgcagaca gtgaaggtgg      3600
tggacgagct cgtgaaagtg atgggccggc acaagcccga gaacatcgtg atcgaaatgg      3660
ccagagagaa ccagaccacc cagaagggac agaagaacag ccgcgagaga atgaagcgga      3720
tcgaagaggg catcaaagag ctgggcagcc agatcctgaa agaacacccc gtggaaaaca      3780
cccagctgca gaacgagaag ctgtacctgt actacctgca gaatgggcgg gatatgtacg      3840
tggaccagga actggacatc aaccggctgt ccgactacga tgtggaccat atcgtgcctc      3900
agagctttct gaaggacgac tccatcgaca acaaggtgct gaccagaagc gacaagaacc      3960
ggggcaagag cgacaacgtg ccctccgaag aggtcgtgaa gaagatgaag aactactggc      4020
ggcagctgct gaacgccaag ctgattaccc agagaaagtt cgacaatctg accaaggccg      4080
agagaggcgg cctgagcgaa ctggataagg ccggcttcat caagagacag ctggtggaaa      4140
cccggcagat cacaaagcac gtggcacaga tcctggactc ccggatgaac actaagtacg      4200
```

```
acgagaatga caagctgatc cgggaagtga aagtgatcac cctgaagtcc aagctggtgt   4260
ccgatttccg gaaggatttc cagttttaca aagtgcgcga gatcaacaac taccaccacg   4320
cccacgacgc ctacctgaac gccgtcgtgg gaaccgccct gatcaaaaag taccctaagc   4380
tggaaagcga gttcgtgtac ggcgactaca aggtgtacga cgtgcggaag atgatcgcca   4440
agagcgagca ggaaatcggc aaggctaccg ccaagtactt cttctacagc aacatcatga   4500
actttttcaa gaccgagatt accctggcca acggcgagat ccggaagcgg cctctgatcg   4560
agacaaacgg cgaaaccggg gagatcgtgt gggataaggg ccgggatttt gccaccgtgc   4620
ggaaagtgct gagcatgccc caagtgaata tcgtgaaaaa gaccgaggtg cagacaggcg   4680
gcttcagcaa agagtctatc ctgcccaaga ggaacagcga taagctgatc gccagaaaga   4740
aggactggga ccctaagaag tacggcggct tcgacagccc caccgtggcc tattctgtgc   4800
tggtggtggc caaagtggaa aagggcaagt ccaagaaact gaagagtgtg aaagagctgc   4860
tggggatcac catcatggaa agaagcagct cgagaagaa tcccatcgac tttctggaag   4920
ccaagggcta caaagaagtg aaaaaggacc tgatcatcaa gctgcctaag tactccctgt   4980
tcgagctgga aaacggccgg aagagaatgc tggcctctgc cggcgaactg cagaagggaa   5040
acgaactggc cctgccctcc aaatatgtga acttcctgta cctggccagc cactatgaga   5100
agctgaaggg ctcccccgag gataatgagc agaaacagct gtttgtggaa cagcacaagc   5160
actacctgga cgagatcatc gagcagatca gcgagttctc caagagagtg atcctggccg   5220
acgctaatct ggacaaagtg ctgtccgcct acaacaagca ccgggataag cccatcagag   5280
agcaggccga gaatatcatc cacctgttta ccctgaccaa tctgggagcc cctgccgcct   5340
tcaagtactt tgacaccacc atcgaccgga gaggtacac cagcaccaaa gaggtgctgg   5400
acgccaccct gatccaccag agcatcaccg gcctgtacga cacggatc gacctgtctc   5460 agctgggagg cgacaaaagg ccggcggcca cgaaaaaggc cggccaggca aaaaagaaaa   5520
aggaattcgg cagtggagag ggcagaggaa gtctgctaac atgcggtgac gtcgaggaga   5580
atcctggccc agtgagcaag ggcgaggagc tgttcaccgg ggtggtgccc atcctggtcg   5640
agctggacgg cgacgtaaac ggccacaagt tcagcgtgtc cggcgagggc gagggcgatg   5700
ccacctacgg caagctgacc ctgaagttca tctgcaccac cggcaagctg cccgtgccct   5760
ggcccaccct cgtgaccacc ctgacctacg gcgtgcagtg cttcagccgc tacccgacc   5820 acatgaagca gcacgacttc ttcaagtccg ccatgcccga aggctacgtc caggagcgca   5880
ccatcttctt caaggacgac ggcaactaca gacccgcgc cgaggtgaag ttcgagggcg   5940
acaccctggt gaaccgcatc gagctgaagg gcatcgactt caaggaggac ggcaacatcc   6000
tggggcacaa gctggagtac aactacaaca gccacaacgt ctatatcatg gccgacaagc   6060
agaagaacgg catcaaggtg aacttcaaga tccgccacaa catcgaggac ggcagcgtgc   6120
agctcgccga ccactaccag cagaacaccc ccatcggcga cggccccgtg ctgctgcccg   6180
acaaccacta cctgagcacc cagtccgccc tgagcaaaga ccccaacgag aagcgcgatc   6240
acatggtcct gctggagttc gtgaccgccg ccgggatcac tctcggcatg gacgagctgt   6300
acaaggaatt ctaactagag ctcgctgatc agcctcgact gtgccttcta gttgccagcc   6360
atctgttgtt tgcccctccc ccgtgccttc cttgaccctg gaaggtgcca ctcccactgt   6420
cctttcctaa taaaatgagg aaattgcatc gcattgtctg agtaggtgtc attctattct   6480
ggggggtggg gtggggcagg acagcaaggg ggaggattgg gaagagaata gcaggcatgc   6540
tggggagcgg ccgcaggaac ccctagtgat ggagttggcc actccctctc tgcgcgctcg   6600
```

-continued

```
ctcgctcact gaggccgggc gaccaaaggt cgcccgacgc ccgggctttg cccgggcggc     6660
ctcagtgagc gagcgagcgc gcagctgcct gcaggggcgc ctgatgcggt attttctcct     6720
tacgcatctg tgcggtattt cacaccgcat acgtcaaagc aaccatagta cgcgccctgt     6780
agcggcgcat taagcgcggc gggtgtggtg gttacgcgca gcgtgaccgc tacacttgcc     6840
agcgccctag cgcccgctcc tttcgctttc ttcccttcct ttctcgccac gttcgccggc     6900
tttccccgtc aagctctaaa tcggggggctc cctttagggt tccgatttag tgctttacgg     6960
cacctcgacc ccaaaaaact tgatttgggt gatggttcac gtagtgggcc atcgccctga     7020
tagacggttt ttcgcccttt gacgttggag tccacgttct ttaatagtgg actcttgttc     7080
caaactggaa caacactcaa ccctatctcg ggctattctt ttgatttata agggattttg     7140
ccgatttcgg cctattggtt aaaaaatgag ctgatttaac aaaaatttaa cgcgaatttt     7200
aacaaaatat taacgtttac aattttatgg tgcactctca gtacaatctg ctctgatgcc     7260
gcatagttaa gccagccccg acacccgcca cacccgctg acgcgccctg acgggcttgt     7320
ctgctcccgg catccgctta cagacaagct gtgaccgtct ccgggagctg catgtgtcag     7380
aggttttcac cgtcatcacc gaaacgcgcg agacgaaagg gcctcgtgat acgcctattt     7440
ttataggtta atgtcatgat aataatggtt tcttagacgt caggtggcac ttttcgggga     7500
aatgtgcgcg gaacccctat ttgtttattt ttctaaatac attcaaatat gtatccgctc     7560
atgagacaat aaccctgata aatgcttcaa taatattgaa aaaggaagag tatgagtatt     7620
caacatttcc gtgtcgccct tattcccttt tttgcggcat tttgccttcc tgttttttgct     7680 cacccagaaa cgctggtgaa agtaaaagat gctgaagatc agttgggtgc acgagtgggt     7740
tacatcgaac tggatctcaa cagcggtaag atccttgaga gttttcgccc cgaagaacgt     7800
tttccaatga tgagcacttt taaagttctg ctatgtggcg cggtattatc ccgtattgac     7860
gccgggcaag agcaactcgg tcgccgcata cactattctc agaatgactt ggttgagtac     7920
tcaccagtca cagaaaagca tcttacggat ggcatgacag taagagaatt atgcagtgct     7980
gccataacca tgagtgataa cactgcggcc aacttacttc tgacaacgat cggaggaccg     8040
aaggagctaa ccgcttttttt gcacaacatg ggggatcatg taactcgcct tgatcgttgg     8100
gaaccggagc tgaatgaagc cataccaaac gacgagcgtg acaccacgat gcctgtagca     8160
atggcaacaa cgttgcgcaa actattaact ggcgaactac ttactctagc ttcccggcaa     8220
caattaatag actggatgga ggcggataaa gttgcaggac cacttctgcg ctcggccctt     8280
ccggctggct ggtttattgc tgataaatct ggagccggtg agcgtggaag ccgcggtatc     8340
attgcagcac tggggccaga tggtaagccc tcccgtatcg tagttatcta cacgacgggg     8400
agtcaggcaa ctatggatga acgaaataga cagatcgctg agataggtgc ctcactgatt     8460
aagcattggt aactgtcaga ccaagtttac tcatatatac tttagattga tttaaaactt     8520
catttttaat ttaaaaggat ctaggtgaag atcctttttg ataatctcat gaccaaaatc     8580
ccttaacgtg agttttcgtt ccactgagcg tcagacccg tagaaaagat caaaggatct     8640
tcttgagatc ctttttttct gcgcgtaatc tgctgcttgc aaacaaaaaa accaccgcta     8700
ccagcggtgg tttgtttgcc ggatcaagag ctaccaactc tttttccgaa ggtaactggc     8760
ttcagcagag cgcagatacc aaatactgtc cttctagtgt agccgtagtt aggccaccac     8820
ttcaagaact ctgtagcacc gcctacatac ctcgctctgc taatcctgtt accagtggct     8880
gctgccagtg gcgataagtc gtgtcttacc gggttggact caagacgata gttaccggat     8940
```

-continued

```
aaggcgcagc ggtcgggctg aacggggggt tcgtgcacac agcccagctt ggagcgaacg    9000
acctacaccg aactgagata cctacagcgt gagctatgag aaagcgccac gcttcccgaa    9060
gggagaaagg cggacaggta tccggtaagc ggcagggtcg aacaggaga gcgcacgagg     9120 gagcttccag ggggaaacgc ctggtatctt tatagtcctg tcgggtttcg ccacctctga    9180
cttgagcgtc gatttttgtg atgctcgtca gggggcgga gcctatggaa aaacgccagc     9240
aacgcggcct ttttacggtt cctggccttt tgctggcctt ttgctcacat gt            9292
```

<210> SEQ ID NO 53
<211> LENGTH: 6061
<212> TYPE: DNA
<213> ORGANISM: Artificial sequence
<220> FEATURE:
<223> OTHER INFORMATION: pJet-Has

<400> SEQUENCE: 53

```
gcccctgcag ccgaattata ttatttttgc caaataattt ttaacaaaag ctctgaagtc     60
ttcttcattt aaattcttag atgatacttc atctggaaaa ttgtcccaat tagtagcatc    120
acgctgtgag taagttctaa accatttttt tattgttgta ttatctctaa tcttactact    180
cgatgagttt tcggtattat ctctattttt aacttggagc aggttccatt cattgttttt    240
ttcatcatag tgaataaaat caactgcttt aacacttgtg cctgaacacc atatccatcc    300
ggcgtaatac gactcactat agggagagcg gccgccagat cttccggatg gctcgagttt    360
ttcagcaaga tttttgaatg aagggcctga gggtgggcag tctgtctatc atgtacatct    420
ccatattctg ggaggtcgtc agttgggctg gcctcctggc taagattttt gcaccacaag    480
agatgctgca tgtgtacaaa tcactagcaa atagatttgt ttcccatcaa cttagccact    540
gttaatgtaa attgttcttg atatgtgtc tttggagggc aataaatgct ctgaacagca     600
cttgcacaat aaagatacag catgtgggaa tgatctgtct catgtgtctt actgatggta    660
ttggttctgt aagataaaat attgtgtctg ggatgtgttt ggctctacta ttaatggtgc    720
tctattgatt gtgatttgtc atttgaaacc tgaggatgcg actgtatagc agtctttcat    780
gcatttttgg aaaaaaactt aagctttttg aaagctgctg ctacaacttt ttgtattgtt    840
ataaagtttt gtattgtttt tttaattgtg aaattataaa gatgccgtgc agggactgtt    900
tgaagcaaag tgcattgttt tagaaaccta caactctagt tcaagcactc catcagtatc    960
tgcttaatct ttgtcatcct ttgctatgag aaaatattaa gcagtagtct aaaggtacta    1020
tgaaactata acatagctga cattgtattt ataactacgt catgattttg atagaattga    1080
ggacttgaaa atgttaaact attcatgtag ggcctcttaa gatgcttaag ttgtttagta    1140
atgtaagtgt gcatttaatt gagattttat tgggcataat ttgtccatca gtatgacact    1200
ccttgtcagt gttgccttat acttgatgtt gttaccggat ctctgcaagg cagttattct    1260
tgaattaggc tcattgaagt gtctgccagt ataaatatat agcaactgtt ctttgtgtta    1320
aaattgagaa gctaaccagt ttttagtgct tctgactgtt ggaattcttt aagcagatgc    1380
cataagaaaa ttgtatttgt gatcaccact tctccagagt ggttttaaca ccaagggcat    1440
tagagaaaga aaggcaggcg tgtagagaat agtggcacaga caaaagctgt gagttacgtt    1500
atgtttttca gctgaaaagc tgtgtttggt aaaagcatat gaaatcactc aacttggaag    1560
cattctctta gttctctgat agttctgagc agcagaactc ttcacctaag aggttacttc    1620
aactggaaga ctacctagtg cttctgatgg caactatatt taagatgaga ataagaggtg    1680
tttccagtgt ggtagcctca catctgttgc agtggttacc gttcgtcctc ctccgaggga    1740
```

-continued

```
cacagcttgg ccattcactg tggtgacacc aatatgatga tcagcaaatg gtgtttattc      1800
actactaaac acagcttata tacatttta cctacaaat cgtgctgtca tgtcccactc        1860
tgattggttc ataccagata acgtgcctta tttggccgtt tccacattct tttctcatcc      1920
ttcttctcct gttttctctg catcaaggtc agcacgatag cactgtctct ctatgcttag      1980
ggagaggcct gtcctgtaca tcccgtgccc ccacaagatg cctactacaa caacatcttc      2040
tgcatgtcct gcatagcagt gttgggagaa tgtgcactac ttccactctt ctgatttcta      2100
ttttatgtgt ttgctttata ccagtgttgc catttgggaa ttaatacatg gttgatcaaa      2160
tcaattgcat cacagctgta tcctgtatca gaggaacatt atcaaagctt ttgttgctgt      2220
atttggtatc tgacctgcag ataaacatgt tttaggaagg ttttgcaaaa gtagctgtga      2280
aatgagctgg tgttgtgatt taacctgaca ggcagctaaa cagtatacca cagagctatt      2340
cacctacttt ccctcagtgg gaaaagggaa gagaactgag gggggggga ataaataagt        2400 aaataacaaa ataaaactca tggattaaga aaaagacttt gtactggaat ggatgagaag      2460
aataatagta atgataataa tatgtcactc tgaaagtaat gcctcttatt tctgtggaga      2520
ctacaaacat acaaagagca caacattcca tagagcaaat tctcagttac agaatgctat      2580
tttttttttc aacacagtca aaatcattaa ttttttttg cctgcaatgg acaagagctt        2640
tgaagctgtt ctcgtaaaaa tctgtactag cagaagtgac ctgcaatcac tactgctgaa      2700
atgcacaacc caccacatca ttgtgctcac attcactgtt tggtttctgt aaatgtacag      2760
gaattgtctg aaattagata tgattttttt tttctccatg aaggaattca attacacacc      2820
tttgcctcat gcacttcttt gtcattttg tcagactgct tctctcctgc aatttgtctc       2880
atggcaacaa aatataatgg agttctgctg ggaacttccc tactgccata ccactatcat      2940
ctgcctctga catttggac aaatgtaata aaataggagg tattactttc agagcagacc        3000
ttgtatgtat ttacaaaaca agtggtacac aaaaaaaatt gttcatccca ccaaccaatg      3060
cccatcctgt ccctgaatag tagctgtccc ccacagcctt gaccagttta ggtcaacagt      3120
tctgcttctg tcccctccca gctccttgta acccctcagc cccccttgct ggcaggacag      3180
tatgagaagc tgaaaaacta gaatgtccta gttctttgca gtgctgctaa tcaacaacca      3240
aaacagtggt gtgttaccaa tattgttgat atcacagcat cataccatta tgaaggaagt      3300
aacccagcca aaatcaggtc agcttgctaa caagagaact gtgcataagt ttaagatgtg      3360
tgtgttcctc agtaccttaa aaaataagta gtaacgttca aatgagtaga agagtagaac      3420
tgagcttaaa acatctgtca gacaacagtg aaccaaccat cttttctagaa gatctcctac     3480 aatattctca gctgccatgg aaaatcgatg ttcttctttt attctctcaa gattttcagg      3540
ctgtatatta aaacttatat taagaactat gctaaccacc tcatcaggaa ccgttgtagg      3600
tggcgtgggt tttcttggca atcgactctc atgaaaacta cgagctaaat attcaatatg      3660
ttcctcttga ccaactttat tctgcatttt ttttgaacga ggtttagagc aagcttcagg      3720
aaactgagac aggaatttta ttaaaaattt aaattttgaa gaaagttcag ggttaatagc      3780 atccatttt tgctttgcaa gttcctcagc attcttaaca aaagacgtct cttttgacat        3840
gtttaaagtt taaacctcct gtgtgaaatt attatccgct cataattcca cacattatac      3900
gagccggaag cataaagtgt aaagcctggg gtgcctaatg agtgagctaa ctcacattaa      3960
ttgcgttgcg ctcactgcca attgctttcc agtcgggaaa cctgtcgtgc cagctgcatt      4020
aatgaatcgg ccaacgcgcg gggagaggcg gtttgcgtat tgggcgctct tccgcttcct      4080
```

-continued

```
cgctcactga ctcgctgcgc tcggtcgttc ggctgcggcg agcggtatca gctcactcaa   4140
aggcggtaat acggttatcc acagaatcag gggataacgc aggaaagaac atgtgagcaa   4200
aaggccagca aaaggccagg aaccgtaaaa aggccgcgtt gctggcgttt ttccataggc   4260 tccgccccc tgacgagcat cacaaaaatc gacgctcaag tcagaggtgg cgaaacccga    4320
caggactata aagataccag gcgtttcccc ctggaagctc cctcgtgcgc tctcctgttc   4380
cgaccctgcc gcttaccgga tacctgtccg cctttctccc ttcgggaagc gtggcgcttt   4440
ctcatagctc acgctgtagg tatctcagtt cggtgtaggt cgttcgctcc aagctgggct   4500
gtgtgcacga acccccgtt cagcccgacc gctgcgcctt atccggtaac tatcgtcttg    4560
agtccaaccc ggtaagacac gacttatcgc cactggcagc agccactggt aacaggatta   4620
gcagagcgag gtatgtaggc ggtgctacag agttcttgaa gtggtggcct aactacggct   4680
acactagaag gacagtattt ggtatctgcg ctctgctgaa gccagttacc ttcggaaaaa   4740
gagttggtag ctcttgatcc ggcaaacaaa ccaccgctgg tagcggtggt ttttttgttt   4800
gcaagcagca gattacgcgc agaaaaaaag gatctcaaga agatcctttg atcttttcta   4860
cggggtctga cgctcagtgg aacgaaaact cacgttaagg gattttggtc atgagattat   4920
caaaaaggat cttcacctag atccttttaa attaaaaatg aagttttaaa tcaatctaaa   4980
gtatatatga gtaaacttgg tctgacagtt accaatgctt aatcagtgag gcacctatct   5040
cagcgatctg tctatttcgt tcatccatag ttgcctgact ccccgtcgtg tagataacta   5100
cgatacggga gggcttacca tctggcccca gtgctgcaat gataccgcga gacccacgct   5160
caccggctcc agatttatca gcaataaacc agccagccgg aagggccgag cgcagaagtg   5220
gtcctgcaac tttatccgcc tccatccagt ctattaattg ttgccgggaa gctagagtaa   5280
gtagttcgcc agttaatagt ttgcgcaacg ttgttgccat tgctacaggc atcgtggtgt   5340
cacgctcgtc gtttggtatg gcttcattca gctccggttc ccaacgatca aggcgagtta   5400
catgatcccc catgttgtgc aaaaaagcgg ttagctcctt cggtcctccg atcgttgtca   5460
gaagtaagtt ggccgcagtg ttatcactca tggttatggc agcactgcat aattctctta   5520
ctgtcatgcc atccgtaaga tgcttttctg tgactggtga gtactcaacc aagtcattct   5580
gagaatagtg tatgcggcga ccgagttgct cttgcccggc gtcaatacgg gataataccg   5640
cgccacatag cagaacttta aaagtgctca tcattggaaa acgttcttcg gggcgaaaac   5700
tctcaaggat cttaccgctg ttgagatcca gttcgatgta acccactcgt gcacccaact   5760
gatcttcagc atcttttact ttcaccagcg tttctgggtg agcaaaaaca ggaaggcaaa   5820
atgccgcaaa aaagggaata agggcgacac ggaaatgttg aatactcata ctcttccttt   5880
ttcaatatta ttgaagcatt tatcagggtt attgtctcat gagcggatac atatttgaat   5940
gtatttagaa aaataaacaa ataggggttc cgcgcacatt tccccgaaaa gtgccacctg   6000
acgtctaaga aaccattatt atcatgacat taacctataa aaataggcgt atcacgaggc   6060
c                                                                    6061
```

<210> SEQ ID NO 54
<211> LENGTH: 6929
<212> TYPE: DNA
<213> ORGANISM: Artificial sequence
<220> FEATURE:
<223> OTHER INFORMATION: pCAGG-Neo-IRES-GFP

<400> SEQUENCE: 54

```
tcgacattga ttattgacta gttattaata gtaatcaatt acggggtcat tagttcatag     60
```

```
cccatatatg gagttccgcg ttacataact tacggtaaat ggcccgcctg gctgaccgcc      120
caacgacccc cgcccattga cgtcaataat gacgtatgtt cccatagtaa cgccaatagg      180
gactttccat tgacgtcaat gggtggagta tttacggtaa actgcccact tggcagtaca      240
tcaagtgtat catatgccaa gtacgccccc tattgacgtc aatgacggta aatggcccgc      300
ctggcattat gcccagtaca tgaccttatg ggactttcct acttggcagt acatctacgt      360
attagtcatc gctattacca tggtcgaggt gagccccacg ttctgcttca ctctccccat      420 ctccccccc  tccccacccc caattttgta tttatttatt ttttaattat tttgtgcagc      480 gatggggcg  gggggggggg ggggcgcgc gccaggcggg gcgggcggg gcgagggggcg      540 gggcggggcg aggcggagag gtgcggcggc agccaatcag agcggcgcgc tccgaaagtt      600
tccttttatg gcgaggcggc ggcggcgcg gccctataaa aagcgaagcg cgcggcgggc      660
ggggagtcgc tgcgacgctg ccttcgcccc gtgccccgct ccgccgccgc ctcgcgccgc      720 ccgcccggc  tctgactgac cgcgttactc ccacaggtga gcgggcggga cggcccttct      780
cctccgggct gtaattagcg cttggtttaa tgacggcttg tttcttttct gtggctgcgt      840
gaaagccttg aggggctccg ggagggccct ttgtgcgggg ggagcggctc ggggggtgcg      900
tgcgtgtgtg tgtgcgtggg gagcgccgcg tgcggctccg cgctgcccgg cggctgtgag      960
cgctgcgggc gcggcgcggg gctttgtgcg ctccgcagtg tgcgcgaggg gagcgcggcc     1020 ggggcggtg  ccccgcggtg cggggggggc tgcgagggga acaaaggctg cgtgcggggt     1080
gtgtgcgtgg gggggtgagc aggggtgtg  ggcgcgtcgg tcgggctgca accccccctg     1140
cacccccctc cccgagttgc tgagcacggc ccggcttcgg gtgcggggct ccgtacgggg     1200
cgtggcgcgg ggctcgccgt gccgggcggg gggtggcggc aggtgggggt gccgggcggg     1260
gcggggccgc ctcgggccgg ggagggctcg ggggagggggc gcggcggccc ccggagcgcc     1320
ggcggctgtc gaggcgcggc gagccgcagc cattgccttt tatggtaatc gtgcgagagg     1380
gcgcagggac ttcctttgtc ccaaatctgt gcggagccga aatctgggag gcgccgccgc     1440
accccctcta gcgggcgcgg ggcgaagcgg tgcggcgccg gcaggaagga aatgggcggg     1500
gagggccttc gtgcgtcgcc gcgccgccgt ccccttctcc ctctccagcc tcggggctgt     1560
ccgcgggggg acggctgcct tcggggggga cggggcaggg cggggttcgg cttctggcgt     1620
gtgaccggcg gctctagagc ctctgctaac catgttcatg ccttcttctt tttcctacag     1680
ctcctgggca acgtgctggt tattgtgctg tctcatcatt ttggcaaaga attgatggga     1740
tcggccattg aacaagatgg attgcacgca ggttctccgg ccgcttgggt ggagaggcta     1800
ttcggctatg actgggcaca acagacaatc ggctgctctg atgccgccgt gttccggctg     1860
tcagcgcagg ggcgcccggt tctttttgtc aagaccgacc tgtccggtgc cctgaatgaa     1920
ctgcaggacg aggcagcgcg gctatcgtgg ctggccacga cgggcgttcc ttgcgcagct     1980
gtgctcgacg ttgtcactga agcgggaagg gactggctgc tattgggcga agtgccgggg     2040
caggatctcc tgtcatctca ccttgctcct gccgagaaag tatccatcat ggctgatgca     2100
atgcggcggc tgcatacgct tgatccggct acctgcccat cgaccacca  agcgaaacat     2160 cgcatcgagc gagcacgtac tcggatggaa gccggtcttg tcgatcagga tgatctggac     2220
gaagagcatc aggggctcgc gccagccgaa ctgttcgcca ggctcaaggc gcgcatgccc     2280 gacgggcgagg atctcgtcgt gacccatggc gatgcctgct tgccgaatat catggtggaa     2340
aatggccgct tttctggatt catcgactgt ggccggctgg gtgtggcgga ccgctatcag     2400
```

-continued

```
gacatagcgt tggctacccg tgatattgct gaagagcttg gcggcgaatg ggctgaccgc    2460
ttcctcgtgc tttacggtat cgccgctccc gattcgcagc gcatcgcctt ctatcgcctt    2520
cttgacgagt tcttctgatc tagcctccgc ccctctccct cccccccccc taacgttact    2580
ggccgaagcc gcttggaata aggccggtgt gcgtttgtct atatgttatt ttccaccata    2640
ttgccgtctt ttggcaatgt gagggcccgg aaacctggcc ctgtcttctt gacgagcatt    2700
cctaggggtc tttcccctct cgccaaagga atgcaaggtc tgttgaatgt cgtgaaggaa    2760
gcagttcctc tggaagcttc ttgaagacaa acaacgtctg tagcgaccct ttgcaggcag    2820
cggaaccccc cacctggcga caggtgcctc tgcggccaaa agccacgtgt ataagataca    2880
cctgcaaagg cggcacaacc ccagtgccac gttgtgagtt ggatagttgt ggaaagagtc    2940
aaatggctct cctcaagcgt attcaacaag gggctgaagg atgcccagaa ggtaccccat    3000
tgtatgggat ctgatctggg gcctcggtgc acatgcttta catgtgttta gtcgaggtta    3060
aaaaaacgtc taggcccccc gaaccacggg gacgtggttt tcctttgaaa aacacgatga    3120
taatatggcc acaaccatgg tgagcaaggg cgaggagctg ttcaccgggg tggtgcccat    3180
cctggtcgag ctggacggcg acgtaaacgg ccacaagttc agcgtgtccg gcgagggcga    3240
gggcgatgcc acctacggca agctgaccct gaagttcatc tgcaccaccg gcaagctgcc    3300
cgtgccctgg cccaccctcg tgaccaccct gacctacggc gtgcagtgct tcagccgcta    3360
ccccgaccac atgaagcagc acgacttctt caagtccgcc atgcccgaag ctacgtcca     3420 ggagcgcacc atcttcttca aggacgacgg caactacaag acccgcgccg aggtgaagtt    3480
cgagggcgac accctggtga accgcatcga gctgaagggc atcgacttca aggaggacgg    3540
caacatcctg gggcacaagc tggagtacaa ctacaacagc cacaacgtct atatcatggc    3600
cgacaagcag aagaacggca tcaaggtgaa cttcaagatc cgccacaaca tcgaggacgg    3660
cagcgtgcag ctcgccgacc actaccagca gaacaccccc atcggcgacg gccccgtgct    3720
gctgcccgac aaccactacc tgagcaccca gtccgccctg agcaaagacc caacgagaa      3780 gcgcgatcac atggtcctgc tggagttcgt gaccgccgcc gggatcactc tcggcatgga    3840
cgagctgtac aagtaaagcg gccgccaatt cactcctcag gtgcaggctg cctatcagaa    3900
ggtggtggct ggtgtggcca atgccctggc tcacaaatac cactgagatc ttttttcctc    3960
tgccaaaaat tatggggaca tcatgaagcc ccttgagcat ctgacttctg gctaataaag    4020
gaaatttatt ttcattgcaa tagtgtgttg gaattttttg tgtctctcac tcggaaggac    4080
atatgggagg gcaaatcatt taaaacatca gaatgagtat ttggtttaga gtttggcaac    4140
atatgcccat atgctggctg ccatgaacaa aggttggcta taaagaggtc atcagtatat    4200
gaaacagccc cctgctgtcc attccttatt ccatagaaaa gccttgactt gaggttagat    4260 ttttttata ttttgttttg tgttattttt ttctttaaca tccctaaaat tttccttaca    4320
tgttttacta gccagatttt tcctcctctc ctgactactc ccagtcatag ctgtccctct    4380
tctcttatgg agatccctcg acctgcagcc caagcttggc gtaatcatgg tcatagctgt    4440
ttcctgtgtg aaattgttat ccgctcacaa ttccacacaa catacgagcc ggaagcataa    4500
agtgtaaagc ctggggtgcc taatgagtga gctaactcac attaattgcg ttgcgctcac    4560
tgcccgcttt ccagtcggga aacctgtcgt gccagcggat ccgcatctca attagtcagc    4620
aaccatagtc ccgcccctaa ctccgcccat cccgccccta actccgccca gttccgccca    4680
ttctccgccc catggctgac taatttttttt tatttatgca gaggccgagg ccgcctcggc    4740
ctctgagcta ttccagaagt agtgaggagg cttttttgga ggcctaggct tttgcaaaaa    4800
```

```
gctaacttgt ttattgcagc ttataatggt tacaaataaa gcaatagcat cacaaatttc    4860
acaaataaag catttttttc actgcattct agttgtggtt tgtccaaact catcaatgta    4920
tcttatcatg tctggatccg ctgcattaat gaatcggcca acgcgcgggg agaggcggtt    4980
tgcgtattgg gcgctcttcc gcttcctcgc tcactgactc gctgcgctcg tcgttcggc     5040 tgcggcgagc ggtatcagct cactcaaagg cggtaatacg gttatccaca gaatcagggg    5100
ataacgcagg aaagaacatg tgagcaaaag gccagcaaaa ggccaggaac cgtaaaaagg    5160
ccgcgttgct ggcgtttttc cataggctcc gcccccctga cgagcatcac aaaaatcgac    5220
gctcaagtca gaggtggcga aacccgacag gactataaag ataccaggcg tttccccctg    5280
gaagctccct cgtgcgctct cctgttccga ccctgccgct taccggatac ctgtccgcct    5340
ttctcccttc gggaagcgtg cgctttctc atagctcacg ctgtaggtat ctcagttcgg    5400
tgtaggtcgt tcgctccaag ctgggctgtg tgcacgaacc ccccgttcag cccgaccgct    5460
gcgccttatc cggtaactat cgtcttgagt ccaacccggt aagacacgac ttatcgccac    5520
tggcagcagc cactggtaac aggattagca gagcgaggta tgtaggcggt gctacagagt    5580
tcttgaagtg gtggcctaac tacggctaca ctagaagaac agtatttggt atctgcgctc    5640
tgctgaagcc agttaccttc ggaaaaagag ttggtagctc ttgatccggc aaacaaacca    5700
ccgctggtag cggtggtttt tttgtttgca agcagcagat tacgcgcaga aaaaaaggat    5760
ctcaagaaga tcctttgatc ttttctacgg ggtctgacgc tcagtggaac gaaaactcac    5820
gttaagggat tttggtcatg agattatcaa aaaggatctt cacctagatc cttttaaatt    5880
aaaaatgaag ttttaaatca atctaaagta tatatgagta aacttggtct gacagttacc    5940
aatgcttaat cagtgaggca cctatctcag cgatctgtct atttcgttca tccatagttg    6000
cctgactccc cgtcgtgtag ataactacga tacgggaggg cttaccatct ggccccagtg    6060
ctgcaatgat accgcgagac ccacgctcac cggctccaga tttatcagca ataaaccagc    6120
cagccggaag ggccgagcgc agaagtggtc ctgcaacttt atccgcctcc atccagtcta    6180
ttaattgttg ccgggaagct agagtaagta gttcgccagt taatagtttg cgcaacgttg    6240
ttgccattgc tacaggcatc gtggtgtcac gctcgtcgtt tggtatggct tcattcagct    6300
ccggttccca acgatcaagg cgagttacat gatcccccat gttgtgcaaa aaagcggtta    6360
gctccttcgg tcctccgatc gttgtcagaa gtaagttggc cgcagtgtta tcactcatgg    6420
ttatggcagc actgcataat tctcttactg tcatgccatc cgtaagatgc ttttctgtga    6480
ctggtgagta ctcaaccaag tcattctgag aatagtgtat gcggcgaccg agttgctctt    6540
gcccggcgtc aatacgggat aataccgcgc cacatagcag aactttaaaa gtgctcatca    6600
ttggaaaacg ttcttcgggg cgaaaactct caaggatctt accgctgttg agatccagtt    6660
cgatgtaacc cactcgtgca cccaactgat cttcagcatc ttttactttc accagcgttt    6720
ctgggtgagc aaaaacagga aggcaaaatg ccgcaaaaaa gggaataagg cgacacgga     6780 aatgttgaat actcatactc ttcctttttc aatattattg aagcatttat cagggttatt    6840
gtctcatgag cggatacata tttgaatgta tttagaaaaa taaacaaata ggggttccgc    6900
gcacatttcc ccgaaaagtg ccacctggg                                      6929
```

<210> SEQ ID NO 55
<211> LENGTH: 10461
<212> TYPE: DNA
<213> ORGANISM: Artificial sequence
<220> FEATURE:

<223> OTHER INFORMATION: Targeting Vector

<400> SEQUENCE: 55

```
gcccctgcag ccgaattata ttatttttgc caaataattt ttaacaaaag ctctgaagtc     60
ttcttcattt aaattcttag atgatacttc atctggaaaa ttgtcccaat tagtagcatc    120
acgctgtgag taagttctaa accatttttt tattgttgta ttatctctaa tcttactact    180
cgatgagttt tcggtattat ctctattttt aacttggagc aggttccatt cattgttttt    240
ttcatcatag tgaataaaat caactgcttt aacacttgtg cctgaacacc atatccatcc    300
ggcgtaatac gactcactat agggagagcg gccgccagat cttccggatg gctcgagttt    360
ttcagcaaga tttttgaatg aagggcctga gggtgggcag tctgtctatc atgtacatct    420
ccatattctg ggaggtcgtc agttgggctg gcctcctggc taagattttt gcaccacaag    480
agatgctgca tgtgtacaaa tcactagcaa atagatttgt ttcccatcaa cttagccact    540
gttaatgtaa attgttcttg atatgtgtc tttggagggc aataaatgct ctgaacagca    600
cttgcacaat aaagatacag catgtgggaa tgatctgtct catgtgtctt actgatggta    660
ttggttctgt aagataaaat attgtgtctg ggatgtgttt ggctctacta ttaatggtgc    720
tctattgatt gtgatttgtc atttgaaacc tgaggatgcg actgtatagc agtctttcat    780
gcattttggg aaaaaaactt aagctttttg aaagctgctg ctacaacttt ttgtattgtt    840
ataaagtttt gtattgtttt tttaattgtg aaattataaa gatgccgtgc agggactgtt    900
tgaagcaaag tgcattgttt tagaaaccta caactctagt tcaagcactc catcagtatc    960
tgcttaatct ttgtcatcct ttgctatgag aaaatattaa gcagtagtct aaaggtacta   1020
tgaaactata acatagctga cattgtattt ataactacgt catgattttg atagaattga   1080
ggacttgaaa atgttaaact attcatgtag ggcctcttaa gatgcttaag ttgtttagta   1140
atgtaagtgt gcatttaatt gagattttat tgggcataat ttgtccatca gtatgacact   1200
ccttgtcagt gttgccttat acttgatgtt gttaccggat ctctgcaagg cagttattct   1260
tgaattaggc tcattgaagt gtctgccagt ataaatatat agcaactgtt ctttgtgtta   1320
aaattgagaa gctaaccagt ttttagtgct tctgactgtt ggaattcttt aagcagatgc   1380
cataagaaaa ttgtatttgt gatcaccact tctccagagt ggttttaaca ccaagggcat   1440
tagagaaaga aaggcaggcg tgtagagaat agtggacaga caaaagctgt gagttacgtt   1500 atgttttttca gctgaaaagc tgtgtttggt aaaagcatat gaaatcactc aacttggaag   1560
cattctctta gttctctgat agttctgagc agcagaactc ttcacctaag aggttacttc   1620
aactggaaga ctacctagtg cttctgatgg caactatatt taagatgaga ataagaggtg   1680
tttccagtgt ggtagcctca catctgttgc agtggttacc gttcgtcctc ctccgaggga   1740
cacagcttgg ccattcactg tggtgacacc aatatgatga tcagcaaatg gtgtttattc   1800
actactaaac acagcttata tacatttttta cctacaaaat cgtgctgtca tgtcccactc   1860
tgattggttc acacatttcc ccgaaaagtg ccacctgggt cgacattgat tattgactag   1920
ttattaatag taatcaatta cggggtcatt agttcatagc ccatatatgg agttccgcgt   1980
tacataactt acggtaaatg gcccgcctgg ctgaccgccc aacgacccc gcccattgac    2040 gtcaataatg acgtatgttc ccatagtaac gccaataggg actttccatt gacgtcaatg   2100
ggtggagtat ttacggtaaa ctgcccactt ggcagtacat caagtgtatc atatgccaag   2160
tacgccccct attgacgtca atgacggtaa atggcccgcc tggcattatg cccagtacat   2220
gaccttatgg gactttccta cttggcagta catctacgta ttagtcatcg ctattaccat   2280
```

-continued

```
ggtcgaggtg agccccacgt tctgcttcac tctccccatc tcccccccct ccccacccc    2340 aattttgtat ttatttattt tttaattatt ttgtgcagcg atggggggcgg ggggggggggg  2400 ggggcgcgcg ccaggcgggg cggggcgggg cgaggggcgg ggcggggcga ggcggagagg    2460
tgcggcggca gccaatcaga gcggcgcgct ccgaaagttt cctttttatgg cgaggcggcg   2520 gcggcggcgg ccctataaaa agcgaagcgc gcggcgggcg gggagtcgct gcgacgctgc    2580 cttcgcccg tgccccgctc cgccgccgcc tcgcgccgcc cgccccggct ctgactgacc     2640
gcgttactcc cacaggtgag cgggcgggac ggcccttctc ctccgggctg taattagcgc    2700
ttggtttaat gacggcttgt ttcttttctg tggctgcgtg aaagccttga ggggctccgg    2760
gagggccctt tgtgcggggg gagcggctcg ggggtgcgt gcgtgtgtgt gtgcgtgggg     2820
agcgccgcgt gcggctccgc gctgcccggc ggctgtgagc gctgcgggcg cggcgcgggg    2880
ctttgtgcgc tccgcagtgt gcgcgagggg agcgcggccg ggggcggtgc cccgcggtgc    2940 gggggggggct gcgaggggaa caaaggctgc gtgcggggtg tgtgcgtggg ggggtgagca    3000
gggggtgtgg gcgcgtcggt cgggctgcaa ccccccctgc accccctcc ccgagttgct     3060 gagcacggcc cggcttcggg tgcggggctc cgtacgggc gtggcgcggg gctcgccgtg     3120
ccgggcgggg ggtggcggca ggtgggggtg ccgggcgggg cggggccgcc tcgggccggg    3180
gagggctcgg gggagggggcg cggcggcccc cggagcgccg gcggctgtcg aggcgcggcg    3240
agccgcagcc attgcctttt atggtaatcg tgcgagaggg cgcagggact tcctttgtcc    3300
caaatctgtg cggagccgaa atctgggagg cgccgccgca cccctctag cgggcgcggg     3360 gcgaagcggt gcggcgccgg caggaaggaa atgggcgggg agggccttcg tgcgtcgccg    3420
cgccgccgtc cccttctccc tctccagcct cgggctgtc cgcggggggga cggctgcctt    3480 cggggggggac ggggcagggc ggggttcggc ttctggcgtg tgaccggcgg ctctagagcc    3540
tctgctaacc atgttcatgc cttcttcttt ttcctacagc tcctgggcaa cgtgctggtt    3600
attgtgctgt ctcatcattt tggcaaagaa ttgatgggat cggccattga acaagatgga    3660
ttgcacgcag gttctccggc cgcttgggtg gagaggctat tcggctatga ctgggcacaa    3720
cagacaatcg gctgctctga tgccgccgtg ttccggctgt cagcgcaggg gcgcccggtt    3780 cttttttgtca agaccgacct gtccggtgcc ctgaatgaac tgcaggacga ggcagcgcgg    3840
ctatcgtggc tggccacgac gggcgttcct tgcgcagctg tgctcgacgt tgtcactgaa    3900
gcgggaaggg actggctgct attgggcgaa gtgccggggc aggatctcct gtcatctcac    3960
cttgctcctg ccgagaaagt atccatcatg gctgatgcaa tgcggcggct gcatacgctt    4020
gatccggcta cctgcccatt cgaccaccaa gcgaaacatc gcatcgagcg agcacgtact    4080
cggatggaag ccggtcttgt cgatcaggat gatctggacg aagagcatca ggggctcgcg    4140
ccagccgaac tgttcgccag gctcaaggcg cgcatgcccg acggcgagga tctcgtcgtg    4200
acccatggcg atgcctgctt gccgaatatc atggtggaaa atggccgctt ttctggattc    4260
atcgactgtg gccggctggg tgtggcggac cgctatcagg acatagcgtt ggctacccgt    4320
gatattgctg aagagcttgg cggcgaatgg gctgaccgct tcctcgtgct ttacggtatc    4380
gccgctcccg attcgcagcg catcgccttc tatcgccttc ttgacgagtt cttctgatct    4440
agcctccgcc cctctccctc ccccccccct aacgttactg gccgaagccg cttggaataa    4500
ggccggtgtg cgtttgtcta tatgttattt tccaccatat tgccgtcttt ggcaatgtg     4560 agggcccgga aacctggccc tgtcttcttg acgagcattc ctaggggtct ttcccctctc    4620
```

-continued

```
gccaaaggaa tgcaaggtct gttgaatgtc gtgaaggaag cagttcctct ggaagcttct   4680
tgaagacaaa caacgtctgt agcgacccct tgcaggcagc ggaacccccc acctggcgac   4740
aggtgcctct gcggccaaaa gccacgtgta taagatacac ctgcaaaggc ggcacaaccc   4800
cagtgccacg ttgtgagttg atagttgtg gaaagagtca aatggctctc ctcaagcgta   4860
ttcaacaagg ggctgaagga tgcccagaag gtaccccatt gtatgggatc tgatctgggg   4920
cctcggtgca catgctttac atgtgtttag tcgaggttaa aaaaacgtct aggcccccg   4980 aaccacgggg acgtggtttt cctttgaaaa acacgatgat aatatggcca caaccatggt   5040
gagcaagggc gaggagctgt tcaccggggt ggtgcccatc ctggtcgagc tggacggcga   5100
cgtaaacggc cacaagttca gcgtgtccgg cgagggcgag ggcgatgcca cctacggcaa   5160
gctgaccctg aagttcatct gcaccaccgg caagctgccc gtgccctggc ccaccctcgt   5220
gaccaccctg acctacggcg tgcagtgctt cagccgctac cccgaccaca tgaagcagca   5280
cgacttcttc aagtccgcca tgcccgaagg ctacgtccag gagcgcacca tcttcttcaa   5340
ggacgacggc aactacaaga cccgcgccga ggtgaagttc gagggcgaca ccctggtgaa   5400
ccgcatcgag ctgaagggca tcgacttcaa ggaggacggc aacatcctgg ggcacaagct   5460
ggagtacaac tacaacagcc acaacgtcta tatcatggcc gacaagcaga agaacggcat   5520
caaggtgaac ttcaagatcc gccacaacat cgaggacggc agcgtgcagc tcgccgacca   5580
ctaccagcag aacaccccca tcggcgacg ccccgtgctg ctgcccgaca ccactacct   5640 gagcacccag tccgccctga gcaaagaccc caacgagaag cgcgatcaca tggtcctgct   5700
ggagttcgtg accgccgccg ggatcactct cggcatggac gagctgtaca agtaaagcgg   5760
ccgccaattc actcctcagg tgcaggctgc ctatcagaag gtggtggctg gtgtggccaa   5820
tgccctggct cacaaatacc actgagatct ttttccctct gccaaaaatt atggggacat   5880
catgaagccc cttgagcatc tgacttctgg ctaataaagg aaatttattt tcattgcaat   5940
agtgtgttgg aattttttgt gtctctcact cggaaggaca tatgggaggg caaatcattt   6000
aaaacatcag aatgagtatt tggtttagag tttggcaaca tatgcccata tgctggctgc   6060
catgaacaaa ggttggctat aaagaggtca tcagtatatg aaacagcccc ctgctgtcca   6120
ttccttattc catagaaaag ccttgacttg aggttagatt ttttttatat tttgttttgt   6180 gttattttt tctttaacat ccctaaaatt ttccttacat gttttactag ccagattttt   6240
cctcctctcc tgactactcc cagtcatagc tgtccctctt ctcttatgga gatcgccgtt   6300
tccacattct tttctcatcc ttcttctcct gtttttctctg catcaaggtc agcacgatag   6360
cactgtctct ctatgcttag ggagaggcct gtcctgtaca tcccgtgccc ccacaagatg   6420
cctactacaa caacatcttc tgcatgtcct gcatagcagt gttgggagaa tgtgcactac   6480
ttccactctt ctgatttcta ttttatgtgt ttgctttata ccagtgttgc catttgggaa   6540
ttaatacatg gttgatcaaa tcaattgcat cacagctgta tcctgtatca gaggaacatt   6600
atcaaagctt ttgttgctgt atttggtatc tgacctgcag ataaacatgt tttaggaagg   6660
ttttgcaaaa gtagctgtga aatgagctgg tgttgtgatt taacctgaca ggcagctaaa   6720
cagtatacca cagagctatt cacctacttt ccctcagtgg gaaaagggaa gagaactgag   6780 gggggggga ataaataagt aaataacaaa ataaaactca tggattaaga aaaagacttt   6840
gtactggaat ggatgagaag aataatagta atgataataa tatgtcactc tgaaagtaat   6900
gcctcttatt tctgtggaga ctacaaacat acaaagagca caacattcca tagagcaaat   6960
tctcagttac agaatgctat ttttttttttc aacacagtca aaatcattaa ttttttttttg   7020
```

-continued

```
cctgcaatgg acaagagctt tgaagctgtt ctcgtaaaaa tctgtactag cagaagtgac      7080
ctgcaatcac tactgctgaa atgcacaacc caccacatca ttgtgctcac attcactgtt      7140
tggtttctgt aaatgtacag gaattgtctg aaattagata tgattttttt tttctccatg      7200
aaggaattca attacacacc tttgcctcat gcacttcttt gtcatttttg tcagactgct      7260
tctctcctgc aatttgtctc atggcaacaa aatataatgg agttctgctg ggaacttccc      7320
tactgccata ccactatcat ctgcctctga cattttggac aaatgtaata aaataggagg      7380
tattactttc agagcagacc ttgtatgtat ttacaaaaca agtggtacac aaaaaaaatt      7440
gttcatccca ccaaccaatg cccatcctgt ccctgaatag tagctgtccc ccacagcctt      7500
gaccagttta ggtcaacagt tctgcttctg tcccctccca gctccttgta acccctcagc      7560
cccccttgct ggcaggacag tatgagaagc tgaaaaacta gaatgtccta gttctttgca      7620
gtgctgctaa tcaacaacca aaacagtggt gtgttaccaa tattgttgat atcacagcat      7680
cataccatta tgaaggaagt aacccagcca aaatcaggtc agcttgctaa caagagaact      7740
gtgcataagt ttaagatgtg tgtgttcctc agtaccttaa aaaataagta gtaacgttca      7800
aatgagtaga agagtagaac tgagcttaaa acatctgtca gacaacagtg aaccaaccat      7860
ctttctagaa gatctcctac aatattctca gctgccatgg aaaatcgatg ttcttctttt      7920
attctctcaa gattttcagg ctgtatatta aaacttatat taagaactat gctaaccacc      7980
tcatcaggaa ccgttgtagg tggcgtgggt tttcttggca atcgactctc atgaaaacta      8040
cgagctaaat attcaatatg ttcctcttga ccaactttat tctgcatttt ttttgaacga      8100
ggtttagagc aagcttcagg aaactgagac aggaatttta ttaaaaattt aaattttgaa      8160
gaaagttcag ggttaatagc atccattttt tgctttgcaa gttcctcagc attcttaaca      8220
aaagacgtct cttttgacat gtttaaagtt taaacctcct gtgtgaaatt attatccgct      8280
cataattcca cacattatac gagccggaag cataaagtgt aaagcctggg gtgcctaatg      8340
agtgagctaa ctcacattaa ttgcgttgcg ctcactgcca attgctttcc agtcgggaaa      8400
cctgtcgtgc cagctgcatt aatgaatcgg ccaacgcgcg gggagaggcg gtttgcgtat      8460
tgggcgctct tccgcttcct cgctcactga ctcgctgcgc tcggtcgttc ggctgcggcg      8520
agcggtatca gctcactcaa aggcggtaat acggttatcc acagaatcag gggataacgc      8580
aggaaagaac atgtgagcaa aaggccagca aaaggccagg aaccgtaaaa aggccgcgtt      8640
gctggcgttt ttccataggc tccgcccccc tgacgagcat cacaaaaatc gacgctcaag      8700
tcagaggtgg cgaaacccga caggactata aagataccag gcgtttcccc ctggaagctc      8760
cctcgtgcgc tctcctgttc cgaccctgcc gcttaccgga tacctgtccg cctttctccc      8820
ttcgggaagc gtggcgcttt ctcatagctc acgctgtagg tatctcagtt cggtgtaggt      8880
cgttcgctcc aagctgggct gtgtgcacga accccccgtt cagcccgacc gctgcgcctt      8940
atccggtaac tatcgtcttg agtccaaccc ggtaagacac gacttatcgc cactggcagc      9000
agccactggt aacaggatta gcagagcgag gtatgtaggc ggtgctacag agttcttgaa      9060
gtggtggcct aactacggct acactagaag gacagtattt ggtatctgcg ctctgctgaa      9120
gccagttacc ttcggaaaaa gagttggtag ctcttgatcc ggcaaacaaa ccaccgctgg      9180
tagcggtggt ttttttgttt gcaagcagca gattacgcgc agaaaaaaag gatctcaaga      9240
agatcctttg atcttttcta cggggtctga cgctcagtgg aacgaaaact cacgttaagg      9300
gattttggtc atgagattat caaaaaggat cttcacctag atcctttaa attaaaaatg      9360
```

```
aagtttttaaa tcaatctaaa gtatatatga gtaaacttgg tctgacagtt accaatgctt   9420
aatcagtgag gcacctatct cagcgatctg tctatttcgt tcatccatag ttgcctgact   9480
ccccgtcgtg tagataacta cgatacggga gggcttacca tctggcccca gtgctgcaat   9540
gataccgcga gacccacgct caccggctcc agatttatca gcaataaacc agccagccgg   9600
aagggccgag cgcagaagtg gtcctgcaac tttatccgcc tccatccagt ctattaattg   9660
ttgccgggaa gctagagtaa gtagttcgcc agttaatagt ttgcgcaacg ttgttgccat   9720
tgctacaggc atcgtggtgt cacgctcgtc gtttggtatg gcttcattca gctccggttc   9780
ccaacgatca aggcgagtta catgatcccc catgttgtgc aaaaaagcgg ttagctcctt   9840
cggtcctccg atcgttgtca gaagtaagtt ggccgcagtg ttatcactca tggttatggc   9900
agcactgcat aattctctta ctgtcatgcc atccgtaaga tgcttttctg tgactggtga   9960
gtactcaacc aagtcattct gagaatagtg tatgcggcga ccgagttgct cttgcccggc  10020
gtcaatacgg gataataccg cgccacatag cagaacttta aaagtgctca tcattggaaa  10080
acgttcttcg gggcgaaaac tctcaaggat cttaccgctg ttgagatcca gttcgatgta  10140
acccactcgt gcacccaact gatcttcagc atcttttact ttcaccagcg tttctgggtg  10200
agcaaaaaca ggaaggcaaa atgccgcaaa aaagggaata agggcgacac ggaaatgttg  10260
aatactcata ctcttccttt ttcaatatta ttgaagcatt tatcagggtt attgtctcat  10320
gagcggatac atatttgaat gtatttagaa aaataaacaa ataggggttc cgcgcacatt  10380
tccccgaaaa gtgccacctg acgtctaaga aaccattatt atcatgacat taacctataa  10440
aaataggcgt atcacgaggc c                                            10461
```

```
<210> SEQ ID NO 56
<211> LENGTH: 7679
<212> TYPE: DNA
<213> ORGANISM: Artificial sequence
<220> FEATURE:
<223> OTHER INFORMATION: pmCherry-Cry2-CreN

<400> SEQUENCE: 56
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagatcc gctagcgcta    600
ccggtcgcca ccatggtgag caagggcgag gaggataaca tggccatcat caaggagttc    660
atgcgcttca aggtgcacat ggagggctcc gtgaacggcc acgagttcga gatcgagggc    720
gagggcgagg gccgccccta cgagggcacc cagaccgcca agctgaaggt gaccaagggt    780
ggccccctgc ccttcgcctg ggacatcctg tcccctcagt tcatgtacgg ctccaaggcc    840
tacgtgaagc accccgccga catccccgac tacttgaagc tgtccttccc cgagggcttc    900
aagtgggagc gcgtgatgaa cttcgaggac ggcggcgtgg tgaccgtgac ccaggactcc    960
```

```
tccctgcagg acggcgagtt catctacaag gtgaagctgc gcggcaccaa cttcccctcc      1020
gacggccccg taatgcagaa gaagaccatg ggctgggagg cctcctccga gcggatgtac      1080
cccgaggacg gcgccctgaa gggcgagatc aagcagaggc tgaagctgaa ggacggcggc      1140
cactacgacg ctgaggtcaa gaccacctac aaggccaaga agcccgtgca gctgcccggc      1200
gcctacaacg tcaacatcaa gttggacatc acctcccaca acgaggacta caccatcgtg      1260
gaacagtacg aacgcgccga gggccgccac tccaccggcg gcatggacga gctgtacaag      1320
tgtggcggct agtactccgg tattgcggta cccttgtacg cctgttttat actcccttcc      1380
cgtaacttag acgcacaaaa ccaagttcaa tagaagggg tacaaaccag taccaccacg       1440
aacaagcact tctgtttccc cggtgatgtc gtatagactg cttgcgtggt tgaaagcgac      1500
ggatccgtta tccgcttatg tacttcgaga agcccagtac cacctcggaa tcttcgatgc      1560
gttgcgctca gcactcaacc ccagagtgta gcttaggctg atgagtctgg acatccctca      1620
ccggtgacgg tggtccaggc tgcgttggcg gcctacctat ggctaacgcc atgggacgct      1680
agttgtgaac aaggtgtgaa gagcctattg agctacataa gaatcctccg gcccctgaat      1740
gcggctaatc ccaacctcgg agcaggtggt cacaaaccag tgattggcct gtcgtaacgc      1800
gcaagtccgt ggcggaaccg actactttgg gtgtccgtgt ttccttttat tttattgtgg      1860
ctgcttatgg tgacaatcac agattgttat cataaagcga attggatagg atcaagctta      1920
tcgataccgt cgacctcgag ctcgccacca tgaagatgga caaaaagact atagtttggt      1980
ttagaagaga cctaaggatt gaggataatc ctgcattagc agcagctgct cacgaaggat      2040 ctgttttttcc tgtcttcatt tggtgtcctg aagaagaagg acagttttat cctggaagag      2100
cttcaagatg gtggatgaaa caatcacttg ctcacttatc tcaatccttg aaggctcttg      2160
gatctgacct cactttaatc aaaacccaca acacgatttc agcgatcttg gattgtatcc      2220
gcgttaccgg tgctacaaaa gtcgtcttta accacctcta tgatcctgtt tcgttagttc      2280
gggaccatac cgtaaaggag aagctggtgg aacgtgggat ctctgtgcaa agctacaatg      2340
gagatctatt gtatgaaccg tgggagatat actgcgaaaa gggcaaacct tttacgagtt      2400
tcaattctta ctggaagaaa tgcttagata tgtcgattga atccgttatg cttcctcctc      2460
cttggcggtt gatgccaata actgcagcgg ctgaagcgat ttgggcgtgt cgattgaag       2520 aactagggct ggagaatgag gccgagaaac cgagcaatgc gttgttaact agagcttggt      2580
ctccaggatg gagcaatgct gataagttac taaatgagtt catcgagaag cagttgatag      2640
attatgcaaa gaacagcaag aaagttgttg ggaattctac ttcactactt tctccgtatc      2700
tccatttcgg ggaaataagc gtcagacacg ttttccagtg tgcccggatg aaacaaatta      2760
tatgggcaag agataagaac agtgaaggag aagaaagtgc agatcttttt cttaggggaa      2820
tcggtttaag agagtattct cggtatatat gtttcaactt cccgtttact cacgagcaat      2880
cgttgttgag tcatcttcgg tttttccctt gggatgctga tgttgataag ttcaaggcct      2940
ggagacaagg caggaccggt tatccgttgg tggatgccgg aatgagagag ctttgggcta      3000
ccggatggat gcataacaga ataagagtga ttgtttcaag ctttgctgtg aagtttcttc      3060
tccttccatg gaaatggga atgaagtatt tctgggatac acttttggat gctgatttgg      3120
aatgtgacat ccttggctgg cagtatatct ctgggagtat ccccgatggc cacgagcttg      3180
atcgcttgga caatcccgcg ttacaaggcg ccaaatatga cccagaaggt gagtacataa      3240
ggcaatggct tcccgagctt gcgagattgc caactgaatg gatccatcat ccatgggacg      3300
```

-continued

```
ctcctttaac cgtactcaaa gcttctggtg tggaactcgg aacaaactat gcgaaaccca    3360
ttgtagacat cgacacagct cgtgagctac tagctaaagc tatttcaaga acccgtgaag    3420
cacagatcat gatcggagca gcacctgatg agattgtagc agatagcttc gaggccttag    3480
gggctaatac cattaaagaa cctggtcttt gcccatctgt gtcttctaat gaccaacaag    3540
taccttcggc tgttcgttac aacgggtcaa agagagtgaa acctgaggaa gaagaagaga    3600
gagacatgaa gaaatctagg ggattcgatg aaagggagtt gttttcgact gctgaatctt    3660
cttcttcttc gagtgtgttt ttcgtttcgc agtcttgctc gttggcatca gaagggaaga    3720
atctggaagg tattcaagat tcatctgatc agattactac aagtttggga aaaaatggtt    3780
gcaaaggtgg cggtggctct ggaggtggtg ggtccggagg aggcggccgc acgagtgatg    3840
aggttcgcaa gaacctgatg gacatgttca gggatcgcca ggcgttttct gagcatacct    3900
ggaaaatgct tctgtccgtt tgccggtcgt gggcggcatg gtgcaagttg aataaccgga    3960
aatggtttcc cgcagaacct gaagatgttc gcgattatct tctatatctt caggcgcgcg    4020
gtctggcagt aaaaactatc cagcaacatt tgggccagct aaacatgctt catcgtcggt    4080
ccgggctgta acccgggatc caccggatct agataactga tcataatcag ccataccaca    4140
tttgtagagg ttttacttgc tttaaaaaac ctcccacacc tccccctgaa cctgaaacat    4200
aaaatgaatg caattgttgt tgttaacttg tttattgcag cttataatgg ttacaaataa    4260
agcaatagca tcacaaattt cacaaataaa gcattttttt cactgcattc tagttgtggt    4320
ttgtccaaac tcatcaatgt atcttaacgc gtaaattgta agcgttaata ttttgttaaa    4380
attcgcgtta aattttttgtt aaatcagctc attttttaac caataggccg aaatcggcaa    4440
aatcccttat aaatcaaaag aatagaccga gatagggttg agtgttgttc cagtttggaa    4500
caagagtcca ctattaaaga acgtggactc caacgtcaaa gggcgaaaaa ccgtctatca    4560
gggcgatggc ccactacgtg aaccatcacc ctaatcaagt tttttggggt cgaggtgccg    4620
taaagcacta aatcggaacc ctaaagggag cccccgattt agagcttgac ggggaaagcc    4680
ggcgaacgtg gcgagaaagg aagggaagaa agcgaaagga gcgggcgcta gggcgctggc    4740
aagtgtagcg gtcacgctgc gcgtaaccac cacacccgcc gcgcttaatg cgccgctaca    4800
gggcgcgtca ggtggcactt ttcggggaaa tgtgcgcgga acccctattt gtttattttt    4860
ctaaatacat tcaaatatgt atccgctcat gagacaataa ccctgataaa tgcttcaata    4920
atattgaaaa aggaagagtc ctgaggcgga aagaaccagc tgtggaatgt gtgtcagtta    4980
gggtgtggaa agtccccagg ctccccagca ggcagaagta tgcaaagcat gcatctcaat    5040
tagtcagcaa ccaggtgtgg aaagtcccca ggctccccag caggcagaag tatgcaaagc    5100
atgcatctca attagtcagc aaccatagtc ccgcccctaa ctccgcccat cccgccccta    5160
actccgccca gttccgccca ttctccgccc catggctgac taatttttttt tatttatgca    5220 gaggccgagg ccgcctcggc ctctgagcta ttccagaagt agtgaggagg cttttttgga    5280
ggcctaggct tttgcaaaga tcgatcaaga acaggatga ggatcgtttc gcatgattga    5340
acaagatgga ttgcacgcag gttctccggc cgcttgggtg gagaggctat tcggctatga    5400
ctgggcacaa cagacaatcg gctgctctga tgccgccgtg ttccggctgt cagcgcaggg    5460
gcgcccggtt ctttttgtca gaccgacct gtccggtgcc ctgaatgaac tgcaagacga    5520
ggcagcgcgg ctatcgtggc tggccacgac gggcgttcct tgcgcagctg tgctcgacgt    5580
tgtcactgaa gcgggaaggg actggctgct attgggcgaa gtgccggggc aggatctcct    5640
gtcatctcac cttgctcctg ccgagaaagt atccatcatg gctgatgcaa tgcggcggct    5700
```

-continued

```
gcatacgctt gatccggcta cctgcccatt cgaccaccaa gcgaaacatc gcatcgagcg      5760
agcacgtact cggatggaag ccggtcttgt cgatcaggat gatctggacg aagagcatca      5820
ggggctcgcg ccagccgaac tgttcgccag gctcaaggcg agcatgcccg acggcgagga      5880
tctcgtcgtg acccatggcg atgcctgctt gccgaatatc atggtggaaa atggccgctt      5940
ttctggattc atcgactgtg gccggctggg tgtggcggac cgctatcagg acatagcgtt      6000
ggctacccgt gatattgctg aagagcttgg cggcgaatgg gctgaccgct tcctcgtgct      6060
ttacggtatc gccgctcccg attcgcagcg catcgccttc tatcgccttc ttgacgagtt      6120
cttctgagcg ggactctggg gttcgaaatg accgaccaag cgacgcccaa cctgccatca      6180
cgagatttcg attccaccgc cgccttctat gaaaggttgg gcttcggaat cgttttccgg      6240
gacgccggct ggatgatcct ccagcgcggg gatctcatgc tggagttctt cgcccaccct      6300 aggggggaggc taactgaaac acggaaggag acaataccgg aaggaacccg cgctatgacg      6360
gcaataaaaa gacagaataa aacgcacggt gttgggtcgt tgttcataa acgcggggtt      6420 cggtcccagg gctggcactc tgtcgatacc ccaccgagac cccattgggg ccaatacgcc      6480
cgcgtttctt ccttttcccc accccacccc caagttcgg gtgaaggccc agggctcgca      6540
gccaacgtcg gggcggcagg ccctgccata gcctcaggtt actcatatat actttagatt      6600
gatttaaaac ttcattttta atttaaaagg atctaggtga agatcctttt tgataatctc      6660
atgaccaaaa tcccttaacg tgagttttcg ttccactgag cgtcagaccc cgtagaaaag      6720
atcaaaggat cttcttgaga tccttttttt ctgcgcgtaa tctgctgctt gcaaacaaaa      6780
aaaccaccgc taccagcggt ggtttgtttg ccggatcaag agctaccaac tctttttccg      6840
aaggtaactg gcttcagcag agcgcagata ccaaatactg tccttctagt gtagccgtag      6900
ttaggccacc acttcaagaa ctctgtagca ccgcctacat acctcgctct gctaatcctg      6960
ttaccagtgg ctgctgccag tggcgataag tcgtgtctta ccgggttgga ctcaagacga      7020
tagttaccgg ataaggcgca gcggtcgggc tgaacggggg gttcgtgcac acagcccagc      7080
ttggagcgaa cgacctacac cgaactgaga tacctacagc gtgagctatg agaaagcgcc      7140
acgcttcccg aagggagaaa ggcggacagg tatccggtaa gcggcagggt cggaacagga      7200
gagcgcacga gggagcttcc aggggggaaac gcctggtatc tttatagtcc tgtcgggttt      7260
cgccacctct gacttgagcg tcgatttttg tgatgctcgt caggggggcg gagcctatgg      7320
aaaaacgcca gcaacgcggc ctttttacgg ttcctggcct tttgctggcc ttttgctcac      7380
atgttctttc ctgcgttatc ccctgattct gtggataacc gtattaccgc catgcattag      7440
caccgcctac atacctcgct ctgctaatcc tgttaccagt ggctgctgcc agtggcgata      7500
agtcgtgtct taccgggttg gactcaagac gatagttacc ggataaggcg cagcggtcgg      7560
gctgaacggg gggttcgtgc acacagccca gcttggagcg aacgacctac accgaactga      7620
gatacctaca gcgtgagcta tgagaaagcg ccacgcttcc cgaagggaga aaggcggac      7679
```

<210> SEQ ID NO 57
<211> LENGTH: 6655
<212> TYPE: DNA
<213> ORGANISM: Artificial sequence
<220> FEATURE:
<223> OTHER INFORMATION: pmCherry-CIBN-CreC
<220> FEATURE:
<221> NAME/KEY: misc_feature
<222> LOCATION: (1717)..(1717)
<223> OTHER INFORMATION: n is a, c, g, or t

<400> SEQUENCE: 57
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
ggactttcca aaatgtcgta acaactccgc cccattgacg caaatgggcg gtaggcgtgt     540
acggtgggag gtctatataa gcagagctgg tttagtgaac cgtcagatcc gctagcgcta     600
ccggtcgcca ccatggtgag caagggcgag gaggataaca tggccatcat caaggagttc     660
atgcgcttca aggtgcacat ggagggctcc gtgaacggcc acgagttcga gatcgagggc     720
gagggcgagg ccgcccctcta cgagggcacc cagaccgcca agctgaaggt gaccaagggt     780
ggccccctgc ccttcgcctg ggacatcctg tcccctcagt tcatgtacgg ctccaaggcc     840
tacgtgaagc accccgccga catccccgac tacttgaagc tgtccttccc cgagggcttc     900
aagtgggagc gcgtgatgaa cttcgaggac ggcggcgtgg tgaccgtgac ccaggactcc     960
tccctgcagg acggcgagtt catctacaag gtgaagctgc gcggcaccaa cttcccctcc    1020
gacggccccg taatgcagaa gaagaccatg ggctgggagg cctcctccga gcggatgtac    1080
cccgaggacg gcgccctgaa gggcgagatc aagcagaggc tgaagctgaa ggacggcggc    1140
cactacgacg ctgaggtcaa gaccacctac aaggccaaga gcccgtgca gctgcccggc    1200 gcctacaacg tcaacatcaa gttggacatc acctcccaca acgaggacta caccatcgtg    1260
gaacagtacg aacgcgccga gggccgccac tccaccggcg gcatggacga gctgtacaag    1320
tgtggcggct agtactccgg tattgcggta cccttgtacg cctgttttat actcccttcc    1380
cgtaacttag acgcacaaaa ccaagttcaa tagaaggggg tacaaaccag taccaccacg    1440
aacaagcact tctgtttccc cggtgatgtc gtatagactg cttgcgtggt tgaaagcgac    1500
ggatccgtta tccgcttatg tacttcgaga agcccagtac cacctcggaa tcttcgatgc    1560
gttgcgctca gcactcaacc ccagagtgta gcttaggctg atgagtctgg acatccctca    1620
ccggtgacgg tggtccaggc tgcgttggcg gcctacctat ggctaacgcc atgggacgct    1680
agttgtgaac aaggtgtgaa gagcctattg agctacntaa gaatcctccg gcccctgaat    1740
gcggctaatc ccaacctcgg agcaggtggt cacaaaccag tgattggcct gtcgtaacgc    1800
gcaagtccgt ggcggaaccg actactttgg gtgtccgtgt ttccttttat tttattgtgg    1860
ctgcttatgg tgacaatcac agattgttat cataaagcga attggatagg atcaagctta    1920
tcgataccgt cgacctcgag ctcgccacca tgaatggagc tataggaggt gaccttttgc    1980 tcaatttttcc tgacatgtcg gtcctagagc gccaaagggc tcacctcaag tacctcaatc    2040
ccacctttga ttctcctctc gccggcttct ttgccgattc ttcaatgatt accgcggcg    2100 agatggacag ctatctttcg actgccggtt tgaatcttcc gatgatgtac ggtgagacga    2160
cggtggaagg tgattcaaga ctctcaattt cgccggaaac gacgcttggg actggaaatt    2220
tcaagaaacg gaagtttgat acagagacta aggattgtaa tgagaagaag aagaagatga    2280
cgatgaacag agatgaccta gtagaagaag gagaagaaga gaagtcgaaa ataacagagc    2340

-continued

```
aaaacaatgg gagcacaaaa agcatcaaga agatgaaaca caaagccaag aaagaagaga    2400
acaatttctc taatgattca tctaaagtga cgaaggaatt ggagaaaacg gattatattc    2460
atggtggcgg tggctctgga ggtggtgggt ccggaggagg cggccgccga ccaagtgaca    2520
gcaatgctgt ttcactggtt atgcggcgga tccgaaaaga aaacgttgat gccggtgaac    2580
gtgcaaaaca ggctctagcg ttcgaacgca ctgatttcga ccaggttcgt tcactcatgg    2640
aaaatagcga tcgctgccag gatatacgta atctggcatt tctggggatt gcttataaca    2700
ccctgttacg tatagccgaa attgccagga tcagggttaa agatatctca cgtactgacg    2760
gtgggagaat gttaatccat attggcagaa cgaaaacgct ggttagcacc gcaggtgtag    2820
agaaggcact tagcctgggg gtaactaaac tggtcgagcg atggatttcc gtctctggtg    2880
tagctgatga tccgaataac tacctgtttt gccgggtcag aaaaaatggt gttgccgcgc    2940
catctgccac cagccagcta tcaactcgcg ccctggaagg gatttttgaa gcaactcatc    3000
gattgattta cggcgctaag gatgactctg gtcagagata cctggcctgg tctggacaca    3060
gtgcccgtgt cggagccgcg cgagatatgg cccgcgctgg agtttcaata ccggagatca    3120
tgcaagctgg tggctggacc aatgtaaata ttgtcatgaa ctatatccgt aacctggata    3180
gtgaaacagg ggcaatggtg cgcctgctgg aagatggcga ttagcccggg atccaccgga    3240
tctagataac tgatcataat cagccatacc acatttgtag aggttttact tgctttaaaa    3300
aacctcccac acctcccct gaacctgaaa cataaaatga atgcaattgt tgttgttaac    3360
ttgtttattg cagcttataa tggttacaaa taaagcaata gcatcacaaa tttcacaaat    3420
aaagcatttt tttcactgca ttctagttgt ggtttgtcca aactcatcaa tgtatcttaa    3480
cgcgtaaatt gtaagcgtta atattttgtt aaaattcgcg ttaaattttt gttaaatcag    3540 ctcattttt aaccaatagg ccgaaatcgg caaaatccct tataaatcaa aagaatagac    3600
cgagataggg ttgagtgttg ttccagtttg gaacaagagt ccactattaa agaacgtgga    3660
ctccaacgtc aaagggcgaa aaaccgtcta tcagggcgat ggcccactac gtgaaccatc    3720
accctaatca agttttttgg ggtcgaggtg ccgtaaagca ctaaatcgga accctaaagg    3780
gagcccccga tttagagctt gacggggaaa gccggcgaac gtggcgagaa aggaagggaa    3840
gaaagcgaaa ggagcgggcg ctagggcgct ggcaagtgta gcggtcacgc tgcgcgtaac    3900
caccacaccc gccgcgctta atgcgccgct acagggcgcg tcaggtggca cttttcgggg    3960
aaatgtgcgc ggaacccta tttgtttatt tttctaaata cattcaaata tgtatccgct    4020
catgagacaa taaccctgat aaatgcttca ataatattga aaaaggaaga gtcctgaggc    4080
ggaaagaacc agctgtggaa tgtgtgtcag ttagggtgtg gaaagtcccc aggctcccca    4140
gcaggcagaa gtatgcaaag catgcatctc aattagtcag caaccaggtg tggaaagtcc    4200
ccaggctccc cagcaggcag aagtatgcaa agcatgcatc tcaattagtc agcaaccata    4260
gtcccgcccc taactccgcc catcccgccc ctaactccgc ccagttccgc ccattctccg    4320
ccccatggct gactaatttt ttttatttat gcagaggccg aggccgcctc ggcctctgag    4380
ctattccaga agtagtgagg aggcttttt ggaggcctag gcttttgcaa agatcgatca    4440
agagacagga tgaggatcgt ttcgcatgat tgaacaagat ggattgcacg caggttctcc    4500
ggccgcttgg gtggagaggc tattcggcta tgactgggca caacagacaa tcggctgctc    4560
tgatgccgcc gtgttccggc tgtcagcgca ggggcgcccg gttctttttg tcaagaccga    4620
cctgtccggt gccctgaatg aactgcaaga cgaggcagcg cggctatcgt ggctggccac    4680
```

```
gacgggcgtt ccttgcgcag ctgtgctcga cgttgtcact gaagcgggaa gggactggct     4740
gctattgggc gaagtgccgg ggcaggatct cctgtcatct caccttgctc ctgccgagaa     4800
agtatccatc atggctgatg caatgcggcg gctgcatacg cttgatccgg ctacctgccc     4860
attcgaccac caagcgaaac atcgcatcga gcgagcacgt actcggatgg aagccggtct     4920
tgtcgatcag gatgatctgg acgaagagca tcaggggctc gcgccagccg aactgttcgc     4980
caggctcaag gcgagcatgc ccgacggcga ggatctcgtc gtgacccatg gcgatgcctg     5040
cttgccgaat atcatggtgg aaaatggccg cttttctgga ttcatcgact gtggccggct     5100
gggtgtggcg gaccgctatc aggacatagc gttggctacc cgtgatattg ctgaagagct     5160
tggcggcgaa tgggctgacc gcttcctcgt gctttacggt atcgccgctc ccgattcgca     5220
gcgcatcgcc ttctatcgcc ttcttgacga gttcttctga gcgggactct ggggttcgaa     5280
atgaccgacc aagcgacgcc caacctgcca tcacgagatt tcgattccac cgccgccttc     5340
tatgaaaggt tgggcttcgg aatcgttttc cgggacgccg gctggatgat cctccagcgc     5400
ggggatctca tgctggagtt cttcgcccac cctaggggga ggctaactga aacacggaag     5460
gagacaatac cggaaggaac ccgcgctatg acggcaataa aaagacagaa taaaacgcac     5520
ggtgttgggt cgtttgttca taaacgcggg gttcggtccc agggctggca ctctgtcgat     5580
accccaccga gaccccattg gggccaatac gcccgcgttt cttccttttc cccacccccac     5640 cccccaagtt cgggtgaagg cccagggctc gcagccaacg tcggggcggc aggccctgcc     5700
atagcctcag gttactcata tatactttag attgatttaa aacttcattt ttaatttaaa     5760
aggatctagg tgaagatcct ttttgataat ctcatgacca aaatccctta acgtgagttt     5820
tcgttccact gagcgtcaga ccccgtagaa aagatcaaag gatcttcttg agatcctttt     5880
tttctgcgcg taatctgctg cttgcaaaca aaaaaaccac cgctaccagc ggtggtttgt     5940
ttgccggatc aagagctacc aactcttttt ccgaaggtaa ctggcttcag cagagcgcag     6000
ataccaaata ctgtccttct agtgtagccg tagttaggcc accacttcaa gaactctgta     6060
gcaccgccta catacctcgc tctgctaatc ctgttaccag tggctgctgc cagtggcgat     6120
aagtcgtgtc ttaccgggtt ggactcaaga cgatagttac cggataaggc gcagcggtcg     6180
ggctgaacgg ggggttcgtg cacacagccc agcttggagc gaacgaccta caccgaactg     6240
agatacctac agcgtgagct atgagaaagc gccacgcttc ccgaagggag aaaggcggac     6300
aggtatccgg taagcggcag ggtcggaaca ggagagcgca cgagggagct ccagggggga     6360
aacgcctggt atctttatag tcctgtcggg tttcgccacc tctgacttga gcgtcgattt     6420
ttgtgatgct cgtcaggggg gcggagccta tggaaaaacg ccagcaacgc ggcctttttta     6480 cggttcctgg ccttttgctg gccttttgct cacatgttct ttcctgcgtt atccctgat     6540 tctgtggata accgtattac cgccatgcat tagcaccgcc tacatacctc gctctgctaa     6600
tcctgttacc agtggctgct gccagtggcg ataagtcgtg tcttaccggg ttgga         6655
```

<210> SEQ ID NO 58
<211> LENGTH: 8968
<212> TYPE: DNA
<213> ORGANISM: Artificial sequence
<220> FEATURE:
<223> OTHER INFORMATION: pB-RAGE-GFP
<400> SEQUENCE: 58

```
caggtggcac ttttcgggga aatgtgcgcg gaacccctat ttgtttattt ttctaaatac      60
attcaaatat gtatccgctc atgagacaat aaccctgata aatgcttcaa taatattgaa     120
```

-continued

```
aaaggaagag tatgagtatt caacatttcc gtgtcgccct tattcccttt tttgcggcat      180
tttgccttcc tgttttttgct cacccagaaa cgctggtgaa agtaaaagat gctgaagatc     240
agttgggtgc acgagtgggt tacatcgaac tggatctcaa cagcggtaag atccttgaga     300
gttttcgccc cgaagaacgt tttccaatga tgagcacttt taaagttctg ctatgtggcg     360
cggtattatc ccgtattgac gccgggcaag agcaactcgg tcgccgcata cactattctc     420
agaatgactt ggttgagtac tcaccagtca cagaaaagca tcttacggat ggcatgacag     480
taagagaatt atgcagtgct gccataacca tgagtgataa cactgcggcc aacttacttc     540
tgacaacgat cggaggaccg aaggagctaa ccgctttttt gcacaacatg ggggatcatg     600
taactcgcct tgatcgttgg gaaccggagc tgaatgaagc cataccaaac gacgagcgtg     660
acaccacgat gcctgtagca atggcaacaa cgttgcgcaa actattaact ggcgaactac     720
ttactctagc ttcccggcaa caattaatag actggatgga ggcggataaa gttgcaggac     780
cacttctgcg ctcggccctt ccggctggct ggtttattgc tgataaatct ggagccggtg     840
agcgtgggtc tcgcggtatc attgcagcac tggggccaga tggtaagccc tcccgtatcg     900
tagttatcta cacgacgggg agtcaggcaa ctatggatga cgaaataga cagatcgctg     960 agataggtgc ctcactgatt aagcattggt aactgtcaga ccaagtttac tcatatatac    1020
tttagattga tttaaaactt catttttaat ttaaaaggat ctaggtgaag atcctttttg    1080
ataatctcat gaccaaaatc ccttaacgtg agttttcgtt ccactgagcg tcagaccccg    1140
tagaaaagat caaaggatct tcttgagatc ctttttttct gcgcgtaatc tgctgcttgc    1200
aaacaaaaaa accaccgcta ccagcggtgg tttgtttgcc ggatcaagag ctaccaactc    1260
tttttccgaa ggtaactggc ttcagcagag cgcagatacc aaatactgtc cttctagtgt    1320
agccgtagtt aggccaccac ttcaagaact ctgtagcacc gcctacatac ctcgctctgc    1380
taatcctgtt accagtggct gctgccagtg gcgataagtc gtgtcttacc gggttggact    1440
caagacgata gttaccggat aaggcgcagc ggtcgggctg aacggggggt tcgtgcacac    1500
agcccagctt ggagcgaacg acctacaccg aactgagata cctacagcgt gagctatgag    1560
aaagcgccac gcttcccgaa gggagaaagg cggacaggta tccggtaagc ggcagggtcg    1620
gaacaggaga gcgcacgagg gagcttccag ggggaaacgc ctggtatctt tatagtcctg    1680
tcgggtttcg ccacctctga cttgagcgtc gatttttgtg atgctcgtca gggggggcgga    1740 gcctatggaa aaacgccagc aacgcggcct ttttacggtt cctggccttt tgctggcctt    1800
ttgctcacat gttctttcct gcgttatccc ctgattctgt ggataaccgt attaccgcct    1860
ttgagtgagc tgataccgct cgccgcagcc gaacgaccga gcgcagcgag tcagtgagcg    1920
aggaagcgga agagcgccca atacgcaaac cgcctctccc cgcgcgttgg ccgattcatt    1980
aatgcagctg gcacgacagg tttcccgact ggaaagcggg cagtgagcgc aacgcaatta    2040
atgtgagtta gctcactcat taggcacccc aggctttaca ctttatgctt ccggctcgta    2100
tgttgtgtgg aattgtgagc ggataacaat ttcacacagg aaacagctat gaccatgatt    2160
acgccaagct cggaattaac cctcactaaa gggaacaaaa gctggctcgc gcgacttggt    2220
ttgccattct ttagcgcgcg tcgcgtcaca cagcttggcc acaatgtggt ttttgtcaaa    2280
cgaagattct atgacgtgtt taaagtttag gtcgagtaaa gcgcaaatct tttttaaccc    2340
tagaaagata gtctgcgtaa aattgacgca tgcattcttg aaatattgct ctctctttct    2400
aaatagcgcg aatccgtcgc tgtgcattta ggacatctca gtcgccgctt ggagctcccg    2460
```

-continued

```
tgaggcgtgc ttgtcaatgc ggtaagtgtc actgattttg aactataacg accgcgtgag    2520
tcaaaatgac gcatgattat cttttacgtg acttttaaga tttaactcat acgataatta    2580
tattgttatt tcatgttcta cttacgtgat aacttattat atatatattt tcttgttata    2640
gatatcgtga ctaatatata ataaaatggg tagttcttta gacgatgagc atatcctctc    2700
tgctcttctg caaagcgatg acgagcttgt tggctagtta ttaatagtaa tcaattacgg    2760
ggtcattagt tcatagccca tatatggagt tccgcgttac ataacttacg gtaaatggcc    2820
cgcctggctg accgcccaac gacccccgcc cattgacgtc aataatgacg tatgttccca    2880
tagtaacgcc aatagggact ttccattgac gtcaatgggt ggagtattta cggtaaactg    2940
cccacttggc agtacatcaa gtgtatcata tgccaagtac gccccctatt gacgtcaatg    3000
acggtaaatg gcccgcctgg cattatgccc agtacatgac cttatgggac tttcctactt    3060
ggcagtacat ctacgtatta gtcatcgcta ttaccatggt cgaggtgagc cccacgttct    3120
gcttcactct ccccatctcc cccccctccc caccccaat tttgtattta tttattttt    3180 aattattttg tgcagcgatg ggggcgggg gggggggggg gcgcgcgcca ggcggggcgg    3240
ggcggggcga ggggcggggc ggggcgaggc ggagaggtgc ggcggcagcc aatcagagcg    3300
gcgcgctccg aaagtttcct tttatggcga ggcggcggcg gcggcggccc tataaaaagc    3360
gaagcgcgcg gcgggcgggg agtcgctgcg acgctgcctt cgccccgtgc cccgctccgc    3420
cgccgcctcg cgccgcccgc cccggctctg actaccgcg ttactcccac aggtgagcgg    3480
gcgggacggc ccttctcctc cgggctgtaa ttagcgcttg gtttaatgac ggcttgtttc    3540
ttttctgtgg ctgcgtgaaa gccttgaggg gctccgggag ggccctttgt gcgggggggag    3600 cggctcgggg ggtgcgtgcg tgtgtgtgtg cgtggggagc gccgcgtgcg gctccgcgct    3660
gcccggcggc tgtgagcgct gcgggcgcgg cgcggggctt tgtgcgctcc gcagtgtgcg    3720
cgaggggagc gcggccgggg gcggtgcccc gcggtgcggg ggggctgcg aggggaacaa    3780 aggctgcgtg cggggtgtgt gcgtggggggg gtgagcaggg ggtgtgggcg cgtcggtcgg    3840
gctgcaaccc cccctgcacc cccctccccg agttgctgag cacggcccgg cttcgggtgc    3900
ggggctccgt acggggcgtg gcgcggggct cgccgtgccg ggcggggggt ggcggcaggt    3960
gggggtgccg ggcggggcgg ggccgcctcg ggccggggag ggctcggggg aggggcgcgg    4020
cggcccccgg agcgccggcg gctgtcgagg cgcggcgagc cgcagccatt gccttttatg    4080
gtaatcgtgc gagagggcgc agggacttcc tttgtcccaa atctgtgcgg agccgaaatc    4140
tgggaggcgc cgccgcaccc cctctagcgg gcgcggggcg aagcggtgcg gcgccggcag    4200
gaaggaaatg ggcggggagg gccttcgtgc gtcgccgcgc cgccgtcccc ttctccctct    4260
ccagcctcgg ggctgtccgc gggggacgg ctgccttcgg gggggacggg gcagggcggg    4320
gttcggcttc tggcgtgtga ccggcggctc tagagcctct gctaaccatg ttcatgcctt    4380
cttctttttc ctacagctcc tgggcaacgt gctggttatt gtgctgtctc atcattttgg    4440
caaagaattc catcaagctt aggatccgga acccttaata taacttcgta taatgtatgc    4500
tatacgaagt tattaggtcc ctcgacctgc agcccaagct tacttaccat gtcagatcca    4560
gacatgataa gatacattga tgagtttgga caaaccacaa ctagaatgca gtgaaaaaaa    4620
tgctttattt gtgaaatttg tgatgctatt gctttatttg taaccattat aagctgcaat    4680
aaacaagtta acaacaacaa ttgcattcat tttatgtttc aggttcaggg ggaggtgtgg    4740
gaggtttttt aaagcaagta aaacctctac aaatgtggta tggctgatta tgatctctag    4800
tcaaggcact atacatcaaa tattccttat taaccccttt acaaattaaa aagctaaagg    4860
```

-continued

```
tacacaattt ttgagcatag ttattaatag cagacactct atgcctgtgt ggagtaagaa    4920
aaaacagtat gttatgatta taactgttat gcctacttat aaaggttaca gaatattttt    4980
ccataatttt cttgtatagc agtgcagctt tttcctttgt ggtgtaaata gcaaagcaag    5040
caagagttct attactaaac acagcatgac tcaaaaaact tagcaattct gaaggaaagt    5100
ccttggggtc ttctaccttt ctcttctttt ttggaggagt agaatgttga gagtcagcag    5160
tagcctcatc atcactagat ggcatttctt ctgagcaaaa caggttttcc tcattaaagg    5220
cattccacca ctgctcccat tcatcagttc cataggttgg aatctaaaat acacaaacaa    5280
ttagaatcag tagtttaaca cattatacac ttaaaaattt tatatttacc ttagagcttt    5340
aaatctctgt aggtagtttg tccaattatg tcacaccaca gaagtaaggt tccttcacaa    5400
agatccctcg agaaaaaaaa tataaaagag atggaggaac gggaaaaagt tagttgtggt    5460
gataggtggc aagtggtatt ccgtaagaac aacaagaaaa gcatttcata ttatggctga    5520
actgagcgaa caagtgcaaa atttaagcat caacgacaac aacgagaatg gttatgttcc    5580
tcctcactta agaggaaaac caagaagtgc cagaaataac atgagcaact acaataacaa    5640
caacggcggc tacaacggtg gccgtggcgg tggcagcttc tttagcaaca accgtcgtgg    5700
tggttacggc aacggtggtt tcttcggtgg aaacaacggt ggcagcagat ctaacggccg    5760
ttctggtggt agatggatcg atggcaaaca tgtcccagct ccaagaaacg aaaaggccga    5820
gatcgccata tttggtgtcc ccgaggatcc ggaacccta atataacttc gtataatgta    5880
tgctatacga agttattagg tccctcgaag aggttcacta gggctagcat ggtgagcaag    5940
ggcgaggagc tgttcaccgg ggtggtgccc atcctggtcg agctggacgg cgacgtaaac    6000
ggccacaagt tcagcgtgtc cggcgagggc gagggcgatg ccacctacgg caagctgacc    6060
ctgaagttca tctgcaccac cggcaagctg cccgtgccct ggcccaccct cgtgaccacc    6120
ctgacctacg gcgtgcagtg cttcagccgc taccccgacc acatgaagca gcacgacttc    6180
ttcaagtccg ccatgcccga aggctacgtc caggagcgca ccatcttctt caaggacgac    6240
ggcaactaca gaccgcgc cgaggtgaag ttcgagggcg acaccctggt gaaccgcatc    6300
gagctgaagg gcatcgactt caaggaggac ggcaacatcc tggggcacaa gctggagtac    6360
aactacaaca gccacaacgt ctatatcatg gccgacaagc agaagaacgg catcaaggtg    6420
aacttcaaga tccgccacaa catcgaggac ggcagcgtgc agctcgccga ccactaccag    6480
cagaacaccc ccatcggcga cggccccgtg ctgctgcccg acaaccacta cctgagcacc    6540
cagtccgccc tgagcaaaga ccccaacgag aagcgcgatc acatggtcct gctggagttc    6600
gtgaccgccg ccgggatcac tctcggcatg gacgagctgt acaagtaaag cggccgccaa    6660
ttcactcctc aggtgcaggc tgcctatcag aaggtggtgg ctggtgtggc caatgccctg    6720
gctcacaaat accactgaga tctttttccc tctgccaaaa attatgggga catcatgaag    6780 cccttgagc atctgacttc tggctaataa aggaaattta ttttcattgc aatagtgtgt    6840
tggaattttt tgtgtctctc actcggaagg acatatggga gggcaaatca tttaaaacat    6900
cagaatgagt atttggttta gagtttggca acatatgccc atatgctggc tgccatgaac    6960
aaaggttggc tataaagagg tcatcagtat atgaaacagc cccctgctgt ccattcctta    7020
ttccatagaa aagccttgac ttgaggttag attttttttta tattttgttt tgtgttattt    7080
ttttctttaa catccctaaa attttcctta catgttttac tagccagatt tttcctcctc    7140
tcctgactac tcccagtcat agctgtccct cttctcttat ggagatccct cgacctgcag    7200
```

```
cccaagcttg gcgtaatcat ggtcatagct gtttcctgtg tgaaattgtt atccgctcac    7260
aattccacac aacatacgag ccggaagcat aaagtgtaaa gcctggggtg cctaatgagt    7320
gagctaactc acattaattg cgttgcgctc actgcccgct ttccagtcgg gaaacctgtc    7380
gtgccagcgg atccgcatct caattagtca gcaaccatag tcccgcccct aactccgccc    7440
atcccgcccc taactccgcc cagttccgcc cattctccgc cccatggctg actaattttt    7500
tttatttatg cagaggccga ggccgcctcg gcctctgagc tattccagaa gtagtgagga    7560
ggcttttttg gaggcctagg gccgctgatc agcctcgact gtgccttcta gttgccagcc    7620
atctgttgtt tgcccctccc ccgtgccttc cttgaccctg gaaggtgcca ctcccactgt    7680
cctttcctaa taaaatgagg aaattgcatc gcattgtctg agtaggtgtc attctattct    7740
ggggagtggg gtggggcagg acagcaaggg ggaggattgg gaagacaata gcaggcatgc    7800
tggggatgcg gtgggctcta tggcttctga ggcggaaaga accagctggg gcttaattaa    7860
cgagagcata atattgatat gtgccaaagt tgtttctgac tgactaataa gtataatttg    7920
tttctattat gtataggtta agctaattac ttattttata atacaacatg actgttttta    7980
aagtacaaaa taagtttatt tttgtaaaag agagaatgtt taaaagtttt gttactttat    8040
agaagaaatt ttgagttttt gttttttttt aataaataaa taaacataaa taaattgttt    8100
gttgaattta ttattagtat gtaagtgtaa atataataaa acttaatatc tattcaaatt    8160
aataaataaa cctcgatata cagaccgata aaacacatgc gtcaatttta cgcatgatta    8220
tctttaacgt acgtcacaat atgattatct ttctagggtt aaataatagt ttctaatttt    8280
tttattattc agcctgctgt cgtgaatacc gagctccaat tcgccctata gtgagtcgta    8340
ttacaattca ctggccgtcg ttttacaacg tcgtgactgg gaaaaccctg gcgttaccca    8400
acttaatcgc cttgcagcac atcccccttt cgccagctgg cgtaatagcg aagaggcccg    8460
caccgatcgc ccttcccaac agttgcgcag cctgaatggc gaatggcgcg acgcgcctg    8520 tagcggcgca ttaagcgcgg cgggtgtggt ggttacgcgc agcgtgaccg ctacacttgc    8580
cagcgcccta gcgcccgctc ctttcgcttt cttcccttcc tttctcgcca cgttcgccgg    8640
ctttccccgt caagctctaa atcgggggct ccctttaggg ttccgattta gtgctttacg    8700
gcacctcgac cccaaaaaac ttgattaggg tgatggttca cgtagtgggc catcgccctg    8760
atagacggtt tttcgccctt tgacgttgga gtccacgttc tttaatagtg gactcttgtt    8820
ccaaactgga acaacactca accctatctc ggtctattct tttgatttat aagggatttt    8880
gccgatttcg gcctattggt taaaaaatga gctgatttaa caaaaattta cgcgaattt    8940 taacaaaata ttaacgttta caatttcc                                       8968
```

<210> SEQ ID NO 59
<211> LENGTH: 6188
<212> TYPE: DNA
<213> ORGANISM: Artificial sequence
<220> FEATURE:
<223> OTHER INFORMATION: pCAGG-IRES-GFP

<400> SEQUENCE: 59

```
actagttatt aatagtaatc aattacgggg tcattagttc atagcccata tatggagttc      60
cgcgttacat aacttacggt aaatggcccg cctggctgac cgcccaacga ccccgccca      120 ttgacgtcaa taatgacgta tgttcccata gtaacgccaa tagggacttt ccattgacgt      180
caatgggtgg agtatttacg gtaaactgcc cacttggcag tacatcaagt gtatcatatg      240
ccaagtacgc cccctattga cgtcaatgac ggtaaatggc ccgcctggca ttatgcccag      300
```

```
tacatgacct  tatgggactt  tcctacttgg  cagtacatct  acgtattagt  catcgctatt   360
accatggtcg  aggtgagccc  cacgttctgc  ttcactctcc  ccatctcccc  cccctcccca   420
cccccaattt  tgtatttatt  tattttttaa  ttattttgtg  cagcgatggg  ggcggggggg   480
gggggggggc  gcgcgccagg  cggggcgggg  cggggcgagg  ggcggggcgg  ggcgaggcgg   540
agaggtgcgg  cggcagccaa  tcagagcggc  gcgctccgaa  agtttccttt  tatggcgagg   600
cggcggcggc  ggcggcccta  taaaaagcga  agcgcgcggc  gggcggggag  tcgctgcgac   660
gctgccttcg  ccccgtgccc  cgctccgccg  ccgcctcgcg  ccgcccgccc  cggctctgac   720
tgaccgcgtt  actcccacag  gtgagcgggc  gggacggccc  ttctcctccg  ggctgtaatt   780
agcgcttggt  ttaatgacgg  cttgtttctt  ttctgtggct  gcgtgaaagc  cttgaggggc   840
tccgggaggg  ccctttgtgc  ggggggagcg  gctcgggggg  tgcgtgcgtg  tgtgtgtgcg   900
tggggagcgc  cgcgtgcggc  tccgcgctgc  ccggcggctg  tgagcgctgc  gggcgcggcg   960
cggggctttg  tgcgctccgc  agtgtgcgcg  aggggagcgc  ggccggggc   ggtgccccgc  1020 ggtgcggggg  gggctgcgag  gggaacaaag  gctgcgtgcg  gggtgtgtgc  gtgggggggt  1080 gagcagggg   tgtgggcgcg  tcggtcgggc  tgcaacccccc cctgcacccc cctcccccgag 1140 ttgctgagca  cggcccggct  tcgggtgcgg  ggctccgtac  ggggcgtggc  gcggggctcg  1200
ccgtgccggg  cggggggtgg  cggcaggtgg  gggtgccggg  cggggcgggg  ccgcctcggg  1260
ccggggaggg  ctcgggggag  gggcgcggcg  gccccccggag cgccggcggc  tgtcgaggcg  1320
cggcgagccg  cagccattgc  cttttatggt  aatcgtgcga  gagggcgcag  ggacttcctt  1380
tgtcccaaat  ctgtgcggag  ccgaaatctg  ggaggcgccg  ccgcacccccc tctagcgggc  1440 gcggggcgaa  gcggtgcggc  gccggcagga  aggaaatggg  cggggagggc  cttcgtgcgt  1500
cgccgcgccg  ccgtcccctt  ctccctctcc  agcctcgggg  ctgtccgcgg  ggggacggct  1560
gccttcgggg  gggacggggc  agggcggggt  tcggcttctg  gcgtgtgacc  ggcggctcta  1620
gagcctctgc  taaccatgtt  catgccttct  tcttttttcct acagctcctg  ggcaacgtgc  1680
tggttattgt  gctgtctcat  cattttggca  aagaattcag  cacctgcaca  tgggacgtcg  1740
acctgaggta  attataaccc  gggccctata  tatggatcgg  ctagccgatc  cgccctctc   1800 cctccccccc  ccctaacgtt  actggccgaa  gccgcttgga  ataaggccgg  tgtgcgtttg  1860
tctatatgtt  attttccacc  atattgccgt  cttttggcaa  tgtgagggcc  cggaaacctg  1920
gccctgtctt  cttgacgagc  attcctaggg  gtctttcccc  tctcgccaaa  ggaatgcaag  1980
gtctgttgaa  tgtcgtgaag  gaagcagttc  ctctggaagc  ttcttgaaga  caaacaacgt  2040
ctgtagcgac  cctttgcagg  cagcggaacc  ccccacctgg  cgacaggtgc  ctctgcggcc  2100
aaaagccacg  tgtataagat  acacctgcaa  aggcggcaca  accccagtgc  cacgttgtga  2160
gttggatagt  tgtggaaaga  gtcaaatggc  tctcctcaag  cgtattcaac  aaggggctga  2220
aggatgccca  gaaggtaccc  cattgtatgg  gatctgatct  ggggcctcgg  tgcacatgct  2280
ttacatgtgt  ttagtcgagg  ttaaaaaaac  gtctaggccc  cccgaaccac  ggggacgtgg  2340
ttttcctttg  aaaaacacga  tgataatatg  gccacaacca  tggtgagcaa  gggcgaggag  2400
ctgttcaccg  gggtggtgcc  catcctggtc  gagctggacg  gcgacgtaaa  cggccacaag  2460
ttcagcgtgt  ccggcgaggg  cgagggcgat  gccacctacg  gcaagctgac  cctgaagttc  2520
atctgcacca  ccggcaagct  gcccgtgccc  tggcccaccc  tcgtgaccac  cctgacctac  2580
ggcgtgcagt  gcttcagccg  ctaccccgac  cacatgaagc  agcacgactt  cttcaagtcc  2640
```

```
gccatgcccg aaggctacgt ccaggagcgc accatcttct tcaaggacga cggcaactac      2700
aagacccgcg ccgaggtgaa gttcgagggc gacaccctgg tgaaccgcat cgagctgaag      2760
ggcatcgact tcaaggagga cggcaacatc ctggggcaca agctggagta caactacaac      2820
agccacaacg tctatatcat ggccgacaag cagaagaacg gcatcaaggt gaacttcaag      2880
atccgccaca acatcgagga cggcagcgtg cagctcgccg accactacca gcagaacacc      2940
cccatcggcg acggccccgt gctgctgccc gacaaccact acctgagcac ccagtccgcc      3000
ctgagcaaag accccaacga gaagcgcgat cacatggtcc tgctggagtt cgtgaccgcc      3060
gccgggatca ctctcggcat ggacgagctg tacaagtaaa gcggccgcca attcactcct      3120
caggtgcagg ctgcctatca gaaggtggtg gctggtgtgg ccaatgccct ggctcacaaa      3180
taccactgag atcttttttcc ctctgccaaa aattatgggg acatcatgaa gccccttgag      3240
catctgactt ctggctaata aaggaaattt attttcattg caatagtgtg ttggaatttt      3300
ttgtgtctct cactcggaag gacatatggg agggcaaatc atttaaaaca tcagaatgag      3360
tatttggttt agagtttggc aacatatgcc catatgctgg ctgccatgaa caaaggttgg      3420
ctataaagag gtcatcagta tatgaaacag ccccctgctg tccattcctt attccataga      3480
aaagccttga cttgaggtta gattttttttt atattttgtt ttgtgttatt tttttctttta      3540 acatccctaa aattttcctt acatgtttta ctagccagat ttttcctcct ctcctgacta      3600
ctcccagtca tagctgtccc tcttctctta tggagatccc tcgacctgca gcccaagctt      3660
ggcgtaatca tggtcatagc tgtttcctgt gtgaaattgt tatccgctca caattccaca      3720
caacatacga gccggaagca taaagtgtaa agcctggggt gcctaatgag tgagctaact      3780
cacattaatt gcgttgcgct cactgcccgc tttccagtcg ggaaacctgt cgtgccagcg      3840
gatccgcatc tcaattagtc agcaaccata gtcccgcccc taactccgcc catcccgccc      3900
ctaactccgc ccagttccgc ccattctccg ccccatggct gactaattttt ttttatttat      3960 gcagaggccg aggccgcctc ggcctctgag ctattccaga gtagtgagg aggcttttttt      4020 ggaggcctag gcttttgcaa aaagctaact tgtttattgc agcttataat ggttacaaat      4080
aaagcaatag catcacaaat ttcacaaata aagcatttttt ttcactgcat tctagttgtg      4140
gtttgtccaa actcatcaat gtatcttatc atgtctggat ccgctgcatt aatgaatcgg      4200
ccaacgcgcg gggagaggcg gtttgcgtat tgggcgctct tccgcttcct cgctcactga      4260
ctcgctgcgc tcggtcgttc ggctgcggcg agcggtatca gctcactcaa aggcggtaat      4320
acggttatcc acagaatcag gggataacgc aggaaagaac atgtgagcaa aaggccagca      4380
aaaggccagg aaccgtaaaa aggccgcgtt gctggcgttt ttccataggc tccgcccccc      4440
tgacgagcat cacaaaaatc gacgctcaag tcagaggtgg cgaaacccga caggactata      4500
aagataccag gcgtttcccc ctggaagctc cctcgtgcgc tctcctgttc cgaccctgcc      4560
gcttaccgga tacctgtccg cctttctccc ttcgggaagc gtggcgcttt ctcatagctc      4620
acgctgtagg tatctcagtt cggtgtaggt cgttcgctcc aagctgggct gtgtgcacga      4680 acccccccgtt cagcccgacc gctgcgcctt atccggtaac tatcgtcttg agtccaaccc      4740
ggtaagacac gacttatcgc cactggcagc agccactggt aacaggatta gcagagcgag      4800
gtatgtaggc ggtgctacag agttcttgaa gtggtggcct aactacggct acactagaag      4860
aacagtattt ggtatctgcg ctctgctgaa gccagttacc ttcggaaaaa gagttggtag      4920
ctcttgatcc ggcaaacaaa ccaccgctgg tagcggtggt ttttttgttt gcaagcagca      4980
gattacgcgc agaaaaaaag gatctcaaga agatcctttg atctttttcta cggggtctga      5040
```

-continued

```
cgctcagtgg aacgaaaact cacgttaagg gattttggtc atgagattat caaaaaggat    5100
cttcacctag atcctttaa attaaaaatg aagttttaaa tcaatctaaa gtatatatga    5160
gtaaacttgg tctgacagtt accaatgctt aatcagtgag gcacctatct cagcgatctg    5220
tctatttcgt tcatccatag ttgcctgact ccccgtcgtg tagataacta cgatacggga    5280
gggcttacca tctggcccca gtgctgcaat gataccgcga acccacgct caccggctcc     5340 agatttatca gcaataaacc agccagccgg aagggccgag cgcagaagtg gtcctgcaac    5400
tttatccgcc tccatccagt ctattaattg ttgccgggaa gctagagtaa gtagttcgcc    5460
agttaatagt ttgcgcaacg ttgttgccat tgctacaggc atcgtggtgt cacgctcgtc    5520
gtttggtatg gcttcattca gctccggttc ccaacgatca aggcgagtta catgatcccc    5580
catgttgtgc aaaaaagcgg ttagctcctt cggtcctccg atcgttgtca gaagtaagtt    5640
ggccgcagtg ttatcactca tggttatggc agcactgcat aattctctta ctgtcatgcc    5700
atccgtaaga tgcttttctg tgactggtga gtactcaacc aagtcattct gagaatagtg    5760
tatgcggcga ccgagttgct cttgcccggc gtcaatacgg gataataccg cgccacatag    5820
cagaacttta aaagtgctca tcattggaaa acgttcttcg gggcgaaaac tctcaaggat    5880
cttaccgctg ttgagatcca gttcgatgta acccactcgt gcacccaact gatcttcagc    5940
atcttttact ttcaccagcg tttctgggtg agcaaaaaca ggaaggcaaa atgccgcaaa    6000
aaagggaata agggcgacac ggaaatgttg aatactcata ctcttccttt ttcaatatta    6060
ttgaagcatt tatcagggtt attgtctcat gagcggatac atatttgaat gtatttagaa    6120
aaataaacaa ataggggttc cgcgcacatt tccccgaaaa gtgccacctg ggtcgacatt    6180
gattattg                                                            6188
```

<210> SEQ ID NO 60
<211> LENGTH: 9644
<212> TYPE: DNA
<213> ORGANISM: Artificial sequence
<220> FEATURE:
<223> OTHER INFORMATION: pCAGG-Optogenes

<400> SEQUENCE: 60

```
actagttatt aatagtaatc aattacgggg tcattagttc atagcccata tatggagttc      60
cgcgttacat aacttacggt aaatggcccg cctggctgac cgcccaacga cccccgccca     120
ttgacgtcaa taatgacgta tgttcccata gtaacgccaa tagggacttt ccattgacgt     180
caatgggtgg agtatttacg gtaaactgcc cacttggcag tacatcaagt gtatcatatg     240
ccaagtacgc cccctattga cgtcaatgac ggtaaatggc ccgcctggca ttatgcccag     300
tacatgacct tatgggactt tcctacttgg cagtacatct acgtattagt catcgctatt     360
accatggtcg aggtgagccc cacgttctgc ttcactctcc ccatctcccc ccctccccca     420
cccccaattt tgtatttatt tattttttaa ttattttgtg cagcgatggg ggcgggggg     480 ggggggggc gcgcgccagg cggggcgggg cggggcgagg ggcggggcgg ggcgaggcgg     540
agaggtgcgg cggcagccaa tcagagcggc gcgctccgaa agtttccttt tatggcgagg     600
cggcggcggc ggcggcccta taaaaagcga agcgcgcggc gggcggggag tcgctgcgac     660
gctgccttcg ccccgtgccc cgctccgccg ccgcctcgcg ccgcccgccc cggctctgac     720
tgaccgcgtt actcccacag gtgagcgggc gggacggccc ttctcctccg ggctgtaatt     780
agcgcttggt ttaatgacgg cttgtttctt ttctgtggct gcgtgaaagc cttgaggggc     840
```

-continued

```
tccgggaggg ccctttgtgc gggggagcg gctcggggg tgcgtgcgtg tgtgtgtgcg      900
tggggagcgc cgcgtgcggc tccgcgctgc ccggcggctg tgagcgctgc gggcgcggcg      960
cggggctttg tgcgctccgc agtgtgcgcg aggggagcgc ggccgggggc ggtgccccgc     1020
ggtgcggggg gggctgcgag gggaacaaag gctgcgtgcg gggtgtgtgc gtggggggggt     1080 gagcaggggg tgtgggcgcg tcggtcgggc tgcaacccccc cctgcacccc cctccccgag     1140
ttgctgagca cggcccggct tcgggtgcgg ggctccgtac ggggcgtggc gcggggctcg     1200
ccgtgccggg cggggggtgg cggcaggtgg gggtgccggg cggggcgggg ccgcctcggg     1260
ccggggaggg ctcggggggag gggcgcgcg gcccccggag cgccggcggc tgtcgaggcg     1320
cggcgagccg cagccattgc cttttatggt aatcgtgcga gagggcgcag ggacttcctt     1380
tgtcccaaat ctgtgcggag ccgaaatctg ggaggcgccg ccgcaccccc tctagcgggc     1440
gcggggcgaa gcggtgcggc gccggcagga aggaaatggg cggggagggc cttcgtgcgt     1500
cgccgcgccg ccgtcccctt ctccctctcc agcctcgggg ctgtccgcgg ggggacggct     1560
gccttcgggg gggacggggc agggcggggt tcggcttctg gcgtgtgacc ggcggctcta     1620
gagcctctgc taaccatgtt catgccttct tcttttttcct acagctcctg ggcaacgtgc     1680
tggttattgt gctgtctcat cattttggca aagaattcag cacctgcaca tgggacgtcg     1740
acctgaggta attataaccc cccgggatga atggagctat aggaggtgac cttttgctca     1800
attttcctga catgtcggtc ctagagcgcc aaagggctca cctcaagtac ctcaatccca     1860
cctttgattc tcctctcgcc ggcttctttg ccgattcttc aatgattacc ggcggcgaga     1920
tggacagcta tctttcgact gccggtttga atcttccgat gatgtacggt gagacgacgg     1980
tggaaggtga ttcaagactc tcaatttcgc cggaaacgac gcttgggact ggaaatttca     2040
agaaacggaa gtttgataca gagactaagg attgtaatga gaagaagaag aagatgacga     2100
tgaacagaga tgacctagta gaagaaggag aagaagaa gtcgaaaata acagagcaaa     2160
acaatgggag cacaaaaagc atcaagaaga tgaaacacaa agccaagaaa gaagagaaca     2220
atttctctaa tgattcatct aaagtgacga aggaattgga gaaaacggat tatattcatg     2280
gtggcggtgg ctctggaggt ggtgggtccg gaggaggcgg ccgccgacca agtgacagca     2340
atgctgtttc actggttatg cggcggatcc gaaaagaaaa cgttgatgcc ggtgaacgtg     2400
caaaacaggc tctagcgttc gaacgcactg atttcgacca ggttcgttca ctcatggaaa     2460
atagcgatcg ctgccaggat atacgtaatc tggcatttct ggggattgct tataacaccc     2520
tgttacgtat agccgaaatt gccaggatca gggttaaaga tatctcacgt actgacggtg     2580
ggagaatgtt aatccatatt ggcagaacga aaacgctggt tagcaccgca ggtgtagaga     2640
aggcacttag cctgggggta actaaactgg tcgagcgatg gatttccgtc tctggtgtag     2700
ctgatgatcc gaataactac ctgtttttgcc gggtcagaaa aaatggtgtt gccgcgccat     2760
ctgccaccag ccagctatca actcgcgccc tggaagggat ttttgaagca actcatcgat     2820
tgatttacgg cgctaaggat gactctggtc agagatacct ggcctggtct ggacacagtg     2880
cccgtgtcgg agccgcgcga gatatggccc gcgctggagt ttcaataccg gagatcatgc     2940
aagctggtgg ctggaccaat gtaaatattg tcatgaacta tatccgtaac ctggatagtg     3000
aaacaggggc aatggtgcgc ctgctggaag atggcgatgc cacgaacttc tctctgttaa     3060
agcaagcagg agacgtggaa gaaaaccccg gtcctatgaa gatggacaaa aagactatag     3120
tttggtttag aagagaccta aggattgagg ataatcctgc attagcagca gctgctcacg     3180
aaggatctgt ttttcctgtc ttcatttggt gtcctgaaga agaaggacag ttttatcctg     3240
```

-continued

```
gaagagcttc aagatggtgg atgaaacaat cacttgctca cttatctcaa tccttgaagg    3300
ctcttggatc tgacctcact ttaatcaaaa cccacaacac gatttcagcg atcttggatt    3360
gtatccgcgt taccggtgct acaaaagtcg tctttaacca cctctatgat cctgtttcgt    3420
tagttcggga ccataccgta aaggagaagc tggtggaacg tgggatctct gtgcaaagct    3480
acaatggaga tctattgtat gaaccgtggg agatatactg cgaaaagggc aaacctttta    3540
cgagtttcaa ttcttactgg aagaaatgct tagatatgtc gattgaatcc gttatgcttc    3600
ctcctccttg gcggttgatg ccaataactg cagcggctga agcgatttgg gcgtgttcga    3660
ttgaagaact agggctggag aatgaggccg agaaaccgag caatgcgttg ttaactagag    3720
cttggtctcc aggatggagc aatgctgata agttactaaa tgagttcatc gagaagcagt    3780
tgatagatta tgcaaagaac agcaagaaag ttgttgggaa ttctacttca ctactttctc    3840
cgtatctcca tttcggggaa ataagcgtca gacacgtttt ccagtgtgcc cggatgaaac    3900
aaattatatg ggcaagagat aagaacagtg aaggagaaga aagtgcagat cttttttctta    3960 ggggaatcgg tttaagagag tattctcggt atatatgttt caacttcccg tttactcacg    4020
agcaatcgtt gttgagtcat cttcggtttt tcccttggga tgctgatgtt gataagttca    4080
aggcctggag acaaggcagg accggttatc cgttggtgga tgccggaatg agagagcttt    4140
gggctaccgg atggatgcat aacagaataa gagtgattgt ttcaagcttt gctgtgaagt    4200
ttcttctcct tccatggaaa tggggaatga agtatttctg ggatacactt ttggatgctg    4260
atttggaatg tgacatcctt ggctggcagt atatctctgg gagtatcccc gatggccacg    4320
agcttgatcg cttggacaat cccgcgttac aaggcgccaa atatgaccca gaaggtgagt    4380
acataaggca atggcttccc gagcttgcga gattgccaac tgaatggatc catcatccat    4440
gggacgctcc tttaaccgta ctcaaagctt ctggtgtgga actcggaaca aactatgcga    4500
aacccattgt agacatcgac acagctcgtg agctactagc taaagctatt tcaagaaccc    4560
gtgaagcaca gatcatgatc ggagcagcac ctgatgagat tgtagcagat agcttcgagg    4620
ccttaggggc taataccatt aaagaacctg gtctttgccc atctgtgtct tctaatgacc    4680
aacaagtacc ttcggctgtt cgttacaacg ggtcaaagag agtgaaacct gaggaagaag    4740
aagagagaga catgaagaaa tctaggggat tcgatgaaag ggagttgttt tcgactgctg    4800
aatcttcttc ttcttcgagt gtgtttttcg tttcgcagtc ttgctcgttg gcatcagaag    4860
ggaagaatct ggaaggtatt caagattcat ctgatcagat tactacaagt ttgggaaaaa    4920
atggttgcaa aggtggcggt ggctctggag gtggtgggtc cggaggaggc ggccgcacga    4980
gtgatgaggt tcgcaagaac ctgatggaca tgttcaggga tcgccaggcg ttttctgagc    5040
atacctggaa aatgcttctg tccgtttgcc ggtcgtgggc ggcatggtgc aagttgaata    5100
accggaaatg gtttcccgca gaacctgaag atgttcgcga ttatcttcta tatcttcagg    5160
cgcgcggtct ggcagtaaaa actatccagc aacatttggg ccagctaaac atgcttcatc    5220
gtcggtccgg gctgtaagct agcctccgcc cctctccctc cccccccct aacgttactg     5280 gccgaagccg cttggaataa ggccggtgtg cgtttgtcta tatgttattt tccaccatat    5340
tgccgtcttt tggcaatgtg agggcccgga aacctggccc tgtcttcttg acgagcattc    5400 ctagggggtct ttcccctctc gccaaaggaa tgcaaggtct gttgaatgtc gtgaaggaag    5460
cagttcctct ggaagcttct tgaagacaaa caacgtctgt agcgacccct tgcaggcagc    5520
ggaacccccc acctggcgac aggtgcctct gcggccaaaa gccacgtgta taagatacac    5580
```

-continued

```
ctgcaaaggc ggcacaaccc cagtgccacg ttgtgagttg gatagttgtg gaaagagtca    5640
aatggctctc ctcaagcgta ttcaacaagg ggctgaagga tgcccagaag gtaccccatt    5700
gtatgggatc tgatctgggg cctcggtgca catgctttac atgtgtttag tcgaggttaa    5760
aaaaacgtct aggcccccg aaccacgggg acgtggtttt cctttgaaaa acacgatgat    5820
aatatggcca caaccatggt gagcaagggc gaggagctgt tcaccggggt ggtgcccatc    5880
ctggtcgagc tggacggcga cgtaaacggc cacaagttca gcgtgtccgg cgagggcgag    5940
ggcgatgcca cctacggcaa gctgaccctg aagttcatct gcaccaccgg caagctgccc    6000
gtgccctggc ccaccctcgt gaccaccctg acctacggcg tgcagtgctt cagccgctac    6060
cccgaccaca tgaagcagca cgacttcttc aagtccgcca tgcccgaagg ctacgtccag    6120
gagcgcacca tcttcttcaa ggacgacggc aactacaaga cccgcgccga ggtgaagttc    6180
gagggcgaca ccctggtgaa ccgcatcgag ctgaagggca tcgacttcaa ggaggacggc    6240
aacatcctgg ggcacaagct ggagtacaac tacaacagcc acaacgtcta tatcatggcc    6300
gacaagcaga agaacggcat caaggtgaac ttcaagatcc gccacaacat cgaggacggc    6360
agcgtgcagc tcgccgacca ctaccagcag aacacccca tcggcgacgg ccccgtgctg    6420
ctgcccgaca accactacct gagcacccag tccgccctga gcaaagaccc caacgagaag    6480
cgcgatcaca tggtcctgct ggagttcgtg accgccgccg ggatcactct cggcatggac    6540
gagctgtaca agtaaagcgg ccgccaattc actcctcagg tgcaggctgc ctatcagaag    6600
gtggtggctg gtgtggccaa tgccctggct cacaaatacc actgagatct ttttccctct    6660
gccaaaaatt atggggacat catgaagccc cttgagcatc tgacttctgg ctaataaagg    6720
aaatttattt tcattgcaat agtgtgttgg aattttttgt gtctctcact cggaaggaca    6780
tatgggaggc caaatcattt aaaacatcag aatgagtatt tggtttagag tttggcaaca    6840
tatgcccata tgctggctgc catgaacaaa ggttggctat aaagaggtca tcagtatatg    6900
aaacagcccc ctgctgtcca ttccttattc catagaaaag ccttgacttg aggttagatt    6960
ttttttatat tttgttttgt gttatttttt tctttaacat ccctaaaatt ttccttacat    7020
gttttactag ccagattttt cctcctctcc tgactactcc cagtcatagc tgtccctctt    7080
ctcttatgga gatccctcga cctgcagccc aagcttggcg taatcatggt catagctgtt    7140
tcctgtgtga aattgttatc cgctcacaat tccacacaac atacgagccg gaagcataaa    7200
gtgtaaagcc tggggtgcct aatgagtgag ctaactcaca ttaattgcgt tgcgctcact    7260
gcccgctttc cagtcgggaa acctgtcgtg ccagcggatc cgcatctcaa ttagtcagca    7320
accatagtcc cgcccctaac tccgcccatc ccgcccctaa ctccgcccag ttccgcccat    7380
tctccgcccc atggctgact aatttttttt atttatgcag aggccgaggc cgcctcggcc    7440
tctgagctat tccagaagta gtgaggaggc ttttttggag gcctaggctt ttgcaaaaag    7500
ctaacttgtt tattgcagct tataatggtt acaaataaag caatagcatc acaaatttca    7560
caaataaagc atttttttca ctgcattcta gttgtggttt gtccaaactc atcaatgtat    7620
cttatcatgt ctggatccgc tgcattaatg aatcggccaa cgcgcgggga gaggcggttt    7680
gcgtattggg cgctcttccg cttcctcgct cactgactcg ctgcgctcgg tcgttcggct    7740
gcggcgagcg gtatcagctc actcaaaggc ggtaatacgg ttatccacag aatcagggga    7800
taacgcagga aagaacatgt gagcaaaagg ccagcaaaag gccaggaacc gtaaaaaggc    7860
cgcgttgctg gcgtttttcc ataggctccg ccccctgac gagcatcaca aaaatcgacg    7920
ctcaagtcag aggtggcgaa acccgacagg actataaaga taccaggcgt ttcccctgg    7980
```

-continued

```
aagctccctc gtgcgctctc ctgttccgac cctgccgctt accggatacc tgtccgcctt      8040
tctcccttcg ggaagcgtgg cgctttctca tagctcacgc tgtaggtatc tcagttcggt      8100
gtaggtcgtt cgctccaagc tgggctgtgt gcacgaaccc cccgttcagc ccgaccgctg      8160
cgccttatcc ggtaactatc gtcttgagtc caacccggta agacacgact tatcgccact      8220
ggcagcagcc actggtaaca ggattagcag agcgaggtat gtaggcggtg ctacagagtt      8280
cttgaagtgg tggcctaact acggctacac tagaagaaca gtatttggta tctgcgctct      8340
gctgaagcca gttaccttcg gaaaaagagt tggtagctct tgatccggca aacaaaccac      8400
cgctggtagc ggtggttttt ttgtttgcaa gcagcagatt acgcgcagaa aaaaaggatc      8460
tcaagaagat cctttgatct tttctacggg gtctgacgct cagtggaacg aaaactcacg      8520
ttaagggatt ttggtcatga gattatcaaa aaggatcttc acctagatcc ttttaaatta      8580
aaaatgaagt tttaaatcaa tctaaagtat atatgagtaa acttggtctg acagttacca      8640
atgcttaatc agtgaggcac ctatctcagc gatctgtcta tttcgttcat ccatagttgc      8700
ctgactcccc gtcgtgtaga taactacgat acgggagggc ttaccatctg gccccagtgc      8760
tgcaatgata ccgcgagacc cacgctcacc ggctccagat ttatcagcaa taaaccagcc      8820
agccggaagg gccgagcgca gaagtggtcc tgcaacttta tccgcctcca tccagtctat      8880
taattgttgc cgggaagcta gagtaagtag ttcgccagtt aatagtttgc gcaacgttgt      8940
tgccattgct acaggcatcg tggtgtcacg ctcgtcgttt ggtatggctt cattcagctc      9000
cggttcccaa cgatcaaggc gagttacatg atcccccatg ttgtgcaaaa aagcggttag      9060
ctccttcggt cctccgatcg ttgtcagaag taagttggcc gcagtgttat cactcatggt      9120
tatggcagca ctgcataatt ctcttactgt catgccatcc gtaagatgct tttctgtgac      9180
tggtgagtac tcaaccaagt cattctgaga atagtgtatg cggcgaccga gttgctcttg      9240
cccggcgtca atacgggata ataccgcgcc acatagcaga actttaaaag tgctcatcat      9300
tggaaaacgt tcttcggggc gaaaactctc aaggatctta ccgctgttga tccagttc      9360 gatgtaaccc actcgtgcac ccaactgatc ttcagcatct tttactttca ccagcgtttc      9420
tgggtgagca aaaacaggaa ggcaaaatgc cgcaaaaaag ggaataaggg cgacacggaa      9480
atgttgaata ctcatactct tcctttttca atattattga agcatttatc agggttattg      9540
tctcatgagc ggatacatat ttgaatgtat ttagaaaaat aaacaaatag gggttccgcg      9600
cacatttccc cgaaaagtgc cacctgggtc gacattgatt attg                        9644
```

```
<210> SEQ ID NO 61
<211> LENGTH: 9166
<212> TYPE: DNA
<213> ORGANISM: Artificial sequence
<220> FEATURE:
<223> OTHER INFORMATION: pB-RAGE-mCherry

<400> SEQUENCE: 61
caggtggcac ttttcgggga aatgtgcgcg gaacccctat ttgtttattt ttctaaatac        60
attcaaatat gtatccgctc atgagacaat aaccctgata aatgcttcaa taatattgaa       120
aaaggaagag tatgagtatt caacatttcc gtgtcgccct tattcccttt tttgcggcat       180
tttgccttcc tgtttttgct cacccagaaa cgctggtgaa agtaaaagat gctgaagatc       240
agttgggtgc acgagtgggt tacatcgaac tggatctcaa cagcggtaag atccttgaga       300
gttttcgccc cgaagaacgt tttccaatga tgagcacttt taaagttctg ctatgtggcg       360
```

-continued

```
cggtattatc ccgtattgac gccgggcaag agcaactcgg tcgccgcata cactattctc      420
agaatgactt ggttgagtac tcaccagtca cagaaaagca tcttacggat ggcatgacag      480
taagagaatt atgcagtgct gccataacca tgagtgataa cactgcggcc aacttacttc      540
tgacaacgat cggaggaccg aaggagctaa ccgctttttt gcacaacatg ggggatcatg      600
taactcgcct tgatcgttgg gaaccggagc tgaatgaagc cataccaaac gacgagcgtg      660
acaccacgat gcctgtagca atggcaacaa cgttgcgcaa actattaact ggcgaactac      720
ttactctagc ttcccggcaa caattaatag actggatgga ggcggataaa gttgcaggac      780
cacttctgcg ctcggccctt ccggctggct ggtttattgc tgataaatct ggagccggtg      840
agcgtgggtc tcgcggtatc attgcagcac tggggccaga tggtaagccc tcccgtatcg      900
tagttatcta cacgacgggg agtcaggcaa ctatggatga acgaaataga cagatcgctg      960
agataggtgc ctcactgatt aagcattggt aactgtcaga ccaagtttac tcatatatac      1020
tttagattga tttaaaactt cattttttaat ttaaaaggat ctaggtgaag atcctttttg      1080
ataatctcat gaccaaaatc ccttaacgtg agttttcgtt ccactgagcg tcagaccccg      1140
tagaaaagat caaaggatct tcttgagatc ctttttttct gcgcgtaatc tgctgcttgc      1200
aaacaaaaaa accaccgcta ccagcggtgg tttgtttgcc ggatcaagag ctaccaactc      1260
tttttccgaa ggtaactggc ttcagcagag cgcagatacc aaatactgtc cttctagtgt      1320
agccgtagtt aggccaccac ttcaagaact ctgtagcacc gcctacatac ctcgctctgc      1380
taatcctgtt accagtggct gctgccagtg gcgataagtc gtgtcttacc gggttggact      1440
caagacgata gttaccggat aaggcgcagc ggtcgggctg aacggggggt tcgtgcacac      1500
agcccagctt ggagcgaacg acctacaccg aactgagata cctacagcgt gagctatgag      1560
aaagcgccac gcttcccgaa gggagaaagg cggacaggta tccggtaagc ggcagggtcg      1620
gaacaggaga gcgcacgagg gagcttccag ggggaaacgc ctggtatctt tatagtcctg      1680
tcgggtttcg ccacctctga cttgagcgtc gatttttgtg atgctcgtca ggggggcgga      1740
gcctatggaa aaacgccagc aacgcggcct ttttacggtt cctggccttt tgctggcctt      1800
ttgctcacat gttctttcct gcgttatccc ctgattctgt ggataaccgt attaccgcct      1860
ttgagtgagc tgataccgct cgccgcagcc gaacgaccga gcgcagcgag tcagtgagcg      1920
aggaagcgga gagcgcccca atacgcaaac cgcctctccc cgcgcgttgg ccgattcatt      1980
aatgcagctg gcacgacagg tttcccgact ggaaagcggg cagtgagcgc aacgcaatta      2040
atgtgagtta gctcactcat taggcacccc aggctttaca ctttatgctt ccggctcgta      2100
tgttgtgtgg aattgtgagc ggataacaat ttcacacagg aaacagctat gaccatgatt      2160
acgccaagct cggaattaac cctcactaaa gggaacaaaa gctggctcgc gcgacttggt      2220
ttgccattct ttagcgcgcg tcgcgtcaca cagcttggcc acaatgtggt ttttgtcaaa      2280
cgaagattct atgacgtgtt taaagtttag gtcgagtaaa gcgcaaatct tttttaaccc      2340
tagaaagata gtctgcgtaa aattgacgca tgcattcttg aaatattgct ctctctttct      2400
aaatagcgcg aatccgtcgc tgtgcattta ggacatctca gtcgccgctt ggagctcccg      2460
tgaggcgtgc ttgtcaatgc ggtaagtgtc actgattttg aactataacg accgcgtgag      2520
tcaaaatgac gcatgattat cttttacgtg acttttaaga tttaactcat acgataatta      2580
tattgttatt tcatgttcta cttacgtgat aacttattat atatatattt tcttgttata      2640
gatatcgtga ctaatatata ataaaatggg tagttcttta gacgatgagc atatcctctc      2700
tgctcttctg caaagcgatg acgagcttgt tggctagtta ttaatagtaa tcaattacgg      2760
```

-continued

```
ggtcattagt tcatagccca tatatggagt tccgcgttac ataacttacg gtaaatggcc    2820
cgcctggctg accgcccaac gacccccgcc cattgacgtc aataatgacg tatgttccca    2880
tagtaacgcc aatagggact ttccattgac gtcaatgggt ggagtattta cggtaaactg    2940
cccacttggc agtacatcaa gtgtatcata tgccaagtac gccccctatt gacgtcaatg    3000
acggtaaatg gcccgcctgg cattatgccc agtacatgac cttatgggac tttcctactt    3060
ggcagtacat ctacgtatta gtcatcgcta ttaccatggt cgaggtgagc cccacgttct    3120
gcttcactct ccccatctcc cccccctccc caccccaat tttgtattta tttattttt    3180 aattattttg tgcagcgatg gggggcgggg ggggggggg gcgcgcgcca ggcggggcgg    3240
ggcggggcga ggggcggggc ggggcgaggc ggagaggtgc ggcggcagcc aatcagagcg    3300
gcgcgctccg aaagtttcct tttatggcga ggcggcggcg gcggcggccc tataaaaagc    3360
gaagcgcgcg gcgggcgggg agtcgctgcg acgctgcctt cgccccgtgc cccgctccgc    3420
cgccgcctcg cgccgcccgc cccggctctg actgaccgcg ttactcccac aggtgagcgg    3480
gcgggacggc ccttctcctc cgggctgtaa ttagcgcttg gtttaatgac ggcttgtttc    3540
ttttctgtgg ctgcgtgaaa gccttgaggg gctccgggag ggcccttgt gcgggggga    3600 cggctcgggg ggtgcgtgcg tgtgtgtgtg cgtggggagc gccgcgtgcg gctccgcgct    3660
gcccggcggc tgtgagcgct gcgggcgcgg cgcggggctt tgtgcgctcc gcagtgtgcg    3720
cgaggggagc gcggccgggg gcggtgcccc gcggtgcggg ggggctgcg aggggaacaa    3780 aggctgcgtg cggggtgtgt gcgtgggggg gtgagcaggg ggtgtgggcg cgtcggtcgg    3840
gctgcaaccc cccctgcacc ccctccccg agttgctgag cacggcccgg cttcgggtgc    3900
ggggctccgt acggggcgtg gcgcgggct cgccgtgccg ggcgggggt ggcggcaggt    3960 gggggtgccg ggcggggcgg ggccgcctcg ggccggggag ggctcggggg aggggcgcgg    4020 cggccccegg agcgccggcg gctgtcgagg cgcggcgagc cgcagccatt gcctttttatg    4080 gtaatcgtgc gagagggcgc agggacttcc tttgtcccaa atctgtgcgg agccgaaatc    4140
tgggaggcgc cgccgcaccc cctctagcgg gcgcggggcg aagcggtgcg gcgccggcag    4200
gaaggaaatg ggcggggagg gccttcgtgc gtcgccgcgc cgccgtcccc ttctccctct    4260
ccagcctcgg ggctgtccgc ggggggacgg ctgccttcgg gggggacggg gcagggcggg    4320
gttcggcttc tggcgtgtga ccggcggctc tagagcctct gctaaccatg ttcatgcctt    4380
cttctttttc ctacagctcc tgggcaacgt gctggttatt gtgctgtctc atcattttgg    4440
caaagaattc catcaagctt aggatccgga acccttaata taacttcgta taatgtatgc    4500
tatacgaagt tattaggtcc ctcgacctgc agcccaagct tacttaccat gtcagatcca    4560
gacatgataa gatacattga tgagtttgga caaaccacaa ctagaatgca gtgaaaaaaa    4620
tgctttattt gtgaaatttg tgatgctatt gctttatttg taaccattat aagctgcaat    4680
aaacaagtta acaacaacaa ttgcattcat tttatgtttc aggttcaggg ggaggtgtgg    4740
gaggtttttt aaagcaagta aaacctctac aaatgtggta tggctgatta tgatctctag    4800
tcaaggcact atacatcaaa tattccttat taacccctt acaaattaaa aagctaaagg    4860
tacacaattt ttgagcatag ttattaatag cagacactct atgcctgtgt ggagtaagaa    4920
aaaacagtat gttatgatta taactgttat gcctacttat aaaggttaca gaatatttt    4980 ccataatttt cttgtatagc agtgcagctt tttcctttgt ggtgtaaata gcaaagcaag    5040
caagagttct attactaaac acagcatgac tcaaaaaact tagcaattct gaaggaaagt    5100
```

```
ccttggggtc ttctaccttt ctcttctttt ttggaggagt agaatgttga gagtcagcag     5160
tagcctcatc atcactagat ggcatttctt ctgagcaaaa caggttttcc tcattaaagg     5220
cattccacca ctgctcccat tcatcagttc cataggttgg aatctaaaat acacaaacaa     5280
ttagaatcag tagtttaaca cattatacac ttaaaaattt tatatttacc ttagagcttt     5340
aaatctctgt aggtagtttg tccaattatg tcacaccaca gaagtaaggt tccttcacaa     5400
agatccctcg agaaaaaaaa tataaaagag atggaggaac gggaaaaagt tagttgtggt     5460
gataggtggc aagtggtatt ccgtaagaac aacaagaaaa gcatttcata ttatggctga     5520
actgagcgaa caagtgcaaa atttaagcat caacgacaac aacgagaatg gttatgttcc     5580
tcctcactta agaggaaaac caagaagtgc cagaaataac atgagcaact acaataacaa     5640
caacggcggc tacaacggtg gccgtggcgg tggcagcttc tttagcaaca accgtcgtgg     5700
tggttacggc aacggtggtt tcttcggtgg aaacaacggt ggcagcagat ctaacggccg     5760
ttctggtggt agatggatcg atggcaaaca tgtcccagct ccaagaaacg aaaaggccga     5820
gatcgccata tttggtgtcc ccgaggatcc ggaacccta atataacttc gtataatgta     5880
tgctatacga agttattagg tccctcgaag aggttcacta gggctagcag ttataggatc     5940
tccgccacca tgctgtgctg catcagaaga actaaaccgg ttgagaagaa tgaagaggcc     6000
gatcaggagc tgcagtcgac ggtaccgcgg gcccgggatc caccggtagc atccgccacc     6060
atggtgagca agggcgagga ggataacatg gccatcatca aggagttcat gcgcttcaag     6120
gtgcacatgg agggctccgt gaacggccac gagttcgaga tcgagggcga gggcgagggc     6180
cgcccctacg agggcaccca gaccgccaag ctgaaggtga ccaagggtgg cccctgccc     6240 ttcgcctggg acatcctgtc ccctcagttc atgtacggct ccaaggccta cgtgaagcac     6300
cccgccgaca tccccgacta cttgaagctg tccttccccg agggcttcaa gtgggagcgc     6360
gtgatgaact tcgaggacgg cggcgtggtg accgtgaccc aggactcctc cctgcaggac     6420
ggcgagttca tctacaaggt gaagctgcgc ggcaccaact cccctccga cggccccgta     6480 atgcagaaga agaccatggg ctgggaggcc tcctccgagc ggatgtaccc cgaggacggc     6540
gccctgaagg gcgagatcaa gcagaggctg aagctgaagg acggcggcca ctacgacgct     6600
gaggtcaaga ccacctacaa ggccaagaag cccgtgcagc tgcccggcgc ctacaacgtc     6660
aacatcaagt tggacatcac ctcccacaac gaggactaca ccatcgtgga acagtacgaa     6720
cgcgccgagg gccgccactc caccggcggc atggacgagc tgtacaaggg cagtggagag     6780
ggcagaggaa gtctgctaac atgcggtgac gtcgaggaga tcctggccc aactagtgtt     6840 taaacgcggc cgcggcaatt cactcctcag gtgcaggctg cctatcagaa ggtggtggct     6900
ggtgtggcca atgccctggc tcacaaatac cactgagatc tttttccctc tgccaaaaat     6960
tatggggaca tcatgaagcc ccttgagcat ctgacttctg gctaataaag gaaatttatt     7020
ttcattgcaa tagtgtgttg gaattttttg tgtctctcac tcggaaggac atatgggagg     7080
gcaaatcatt taaaacatca gaatgagtat ttggtttaga gtttggcaac atatgcccat     7140
atgctggctg ccatgaacaa aggttggcta taaagaggtc atcagtatat gaaacagccc     7200
cctgctgtcc attccttatt ccatagaaaa gccttgactt gaggttagat ttttttata     7260 ttttgttttg tgttattttt ttctttaaca tccctaaaat tttccttaca tgttttacta     7320
gccagatttt tcctcctctc ctgactactc ccagtcatag ctgtccctct tctcttatgg     7380
agatccctcg acctgcagcc caagcttggc gtaatcatgg tcatagctgt ttcctgtgtg     7440
aaattgttat ccgctcacaa ttccacacaa catacgagcc ggaagcataa agtgtaaagc     7500
```

```
ctggggtgcc taatgagtga gctaactcac attaattgcg ttgcgctcac tgcccgcttt    7560
ccagtcggga aacctgtcgt gccagcggat ccgcatctca attagtcagc aaccatagtc    7620
ccgcccctaa ctccgcccat cccgccccta actccgccca gttccgccca ttctccgccc    7680
catggctgac taattttttt tatttatgca gaggccgagg ccgcctcggc ctctgagcta    7740
ttccagaagt agtgaggagg cttttttgga ggcctagggc cgctgatcag cctcgactgt    7800
gccttctagt tgccagccat ctgttgtttg cccctccccc gtgccttcct tgaccctgga    7860
aggtgccact cccactgtcc tttcctaata aaatgaggaa attgcatcgc attgtctgag    7920
taggtgtcat tctattctgg ggagtggggt ggggcaggac agcaagggggg aggattggga    7980 agacaatagc aggcatgctg gggatgcggt gggctctatg gcttctgagg cggaaagaac    8040
cagctggggc ttaattaacg agagcataat attgatatgt gccaaagttg tttctgactg    8100
actaataagt ataatttgtt tctattatgt ataggttaag ctaattactt attttataat    8160
acaacatgac tgtttttaaa gtacaaaata agtttatttt tgtaaaagag agaatgttta    8220
aaagttttgt tactttatag aagaaatttt gagtttttgt tttttttttaa taaataaata    8280 aacataaata aattgtttgt tgaatttatt attagtatgt aagtgtaaat ataataaaac    8340
ttaatatcta ttcaaattaa taaataaacc tcgatataca gaccgataaa acacatgcgt    8400
caattttacg catgattatc tttaacgtac gtcacaatat gattatcttt ctagggttaa    8460
ataatagttt ctaattttttt tattattcag cctgctgtcg tgaataccga gctccaattc    8520
gccctatagt gagtcgtatt acaattcact ggccgtcgtt ttacaacgtc gtgactggga    8580
aaaccctggc gttacccaac ttaatcgcct tgcagcacat cccccctttcg ccagctggcg    8640 taatagcgaa gaggcccgca ccgatcgccc ttcccaacag ttgcgcagcc tgaatggcga    8700
atggcgcgac gcgccctgta gcggcgcatt aagcgcggcg ggtgtggtgg ttacgcgcag    8760
cgtgaccgct acacttgcca gcgccctagc gcccgctcct ttcgctttct tcccttcctt    8820
tctcgccacg ttcgccggct ttccccgtca gctctaaat cggggggctcc ctttagggtt    8880 ccgatttagt gctttacggc acctcgaccc caaaaaactt gattagggtg atggttcacg    8940
tagtgggcca tcgccctgat agacggtttt tcgccctttg acgttggagt ccacgttctt    9000
taatagtgga ctcttgttcc aaactggaac aacactcaac cctatctcgg tctattcttt    9060
tgatttataa gggattttgc cgatttcggc ctattggtta aaaaatgagc tgatttaaca    9120
aaaatttaac gcgaattttta acaaaatatt aacgtttaca atttcc    9166
```

```
<210> SEQ ID NO 62
<211> LENGTH: 4526
<212> TYPE: DNA
<213> ORGANISM: Artificial sequence
<220> FEATURE:
<223> OTHER INFORMATION: pSK BS-PGK-DTA

<400> SEQUENCE: 62
```

```
gtggcacttt tcggggaaat gtgcgcggaa cccctatttg tttatttttc taaatacatt      60
caaatatgta tccgctcatg agacaataac cctgataaat gcttcaataa tattgaaaaa     120
ggaagagtat gagtattcaa catttccgtg tcgcccttat tcccttttttt gcggcatttt     180 gccttcctgt ttttgctcac ccagaaacgc tggtgaaagt aaaagatgct gaagatcagt     240
tgggtgcacg agtgggttac atcgaactgg atctcaacag cggtaagatc cttgagagtt     300
ttcgccccga agaacgtttt ccaatgatga gcacttttaa agttctgcta tgtggcgcgg     360
```

-continued

```
tattatcccg tattgacgcc gggcaagagc aactcggtcg ccgcatacac tattctcaga    420
atgacttggt tgagtactca ccagtcacag aaaagcatct tacggatggc atgacagtaa    480
gagaattatg cagtgctgcc ataaccatga gtgataacac tgcggccaac ttacttctga    540
caacgatcgg aggaccgaag gagctaaccg cttttttgca caacatgggg gatcatgtaa    600
ctcgccttga tcgttgggaa ccggagctga atgaagccat accaaacgac gagcgtgaca    660
ccacgatgcc tgtagcaatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatctgga gccggtgagc    840
gtgggtctcg cggtatcatt gcagcactgg ggccagatgg taagccctcc cgtatcgtag    900
ttatctacac gacggggagt caggcaacta tggatgaacg aaatagacag atcgctgaga    960
taggtgcctc actgattaag cattggtaac tgtcagacca agtttactca tatatacttt   1020
agattgattt aaaacttcat ttttaattta aaaggatcta ggtgaagatc ctttttgata   1080
atctcatgac caaaatccct taacgtgagt tttcgttcca ctgagcgtca gaccccgtag   1140
aaaagatcaa aggatcttct tgagatcctt tttttctgcg cgtaatctgc tgcttgcaaa   1200
caaaaaaacc accgctacca gcggtggttt gtttgccgga tcaagagcta ccaactcttt   1260
ttccgaaggt aactggcttc agcagagcgc agataccaaa tactgtcctt ctagtgtagc   1320
cgtagttagg ccaccacttc aagaactctg tagcaccgcc tacatacctc gctctgctaa   1380
tcctgttacc agtggctgct gccagtggcg ataagtcgtg tcttaccggg ttggactcaa   1440
gacgatagtt accggataag gcgcagcggt cgggctgaac ggggggttcg tgcacacagc   1500
ccagcttgga gcgaacgacc tacaccgaac tgagatacct acagcgtgag ctatgagaaa   1560
gcgccacgct tcccgaaggg agaaaggcgg acaggtatcc ggtaagcggc agggtcggaa   1620
caggagagcg cacgagggag cttccagggg gaaacgcctg gtatctttat agtcctgtcg   1680
ggtttcgcca cctctgactt gagcgtcgat ttttgtgatg ctcgtcaggg gggcggagcc   1740
tatggaaaaa cgccagcaac gcggcctttt tacggttcct ggccttttgc tggccttttg   1800
ctcacatgtt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcggaaga gcgcccaata cgcaaaccgc ctctccccgc gcgttggccg attcattaat   1980
gcagctggca cgacaggttt cccgactgga aagcgggcag tgagcgcaac gcaattaatg   2040
tgagttagct cactcattag gcaccccagg ctttacactt tatgcttccg gctcgtatgt   2100
tgtgtggaat tgtgagcgga taacaatttc acacaggaaa cagctatgac catgattacg   2160
ccaagcgcgc aattaaccct cactaaaggg aacaaaagct ggagcccac cgcggtggcg   2220 gccgctctag aactagtgga tccccaattc taccgggtag gggaggcgct tttcccaagg   2280
cagtctggag catgcgcttt agcagccccg ctgggcactt ggcgctacac aagtggcctc   2340
tggcctcgca cacattccac atccaccggt aggcgccaac cggctccgtt ctttggtggc   2400
cccttcgcgc caccttctac tcctcccta gtcaggaagt ccccccccgc ccgcagctc    2460 gcgtcgtgca ggacgtgaca aatggaagta gcacgtctca ctagtctcgt gcagatggac   2520
agcaccgctg agcaatggaa gcgggtaggc ctttggggca gcggccaata gcagctttgc   2580
tccttcgctt tctgggctca gaggctggga aggggtgggt ccggggcgg gctcagggggc   2640 gggctcaggg gcggggcggg cgcccgaagg tcctccggag gcccggcatt ctgcacgctt   2700
caaaagcgca cgtctgccgc gctgttctcc tcttcctcat ctccgggcct ttcgacctgc   2760
```

-continued

```
aggtcctcgc catggatcct gatgatgttg ttgattcttc taaatctttt gtgatggaaa      2820
acttttcttc gtaccacggg actaaacctg gttatgtaga ttccattcaa aaaggtatac      2880
aaaagccaaa atctggtaca caaggaaatt atgacgatga ttggaaaggg ttttatagta      2940
ccgacaataa atacgacgct gcgggatact ctgtagataa tgaaaacccg ctctctggaa      3000
aagctggagg cgtggtcaaa gtgacgtatc caggactgac gaaggttctc gcactaaaag      3060
tggataatgc cgaaactatt aagaaagagt taggtttaag tctcactgaa ccgttgatgg      3120
agcaagtcgg aacggaagag tttatcaaaa ggttcggtga tggtgcttcg cgtgtagtgc      3180
tcagccttcc cttcgctgag gggagttcta gcgttgaata tattaataac tgggaacagg      3240
cgaaagcgtt aagcgtagaa cttgagatta attttgaaac ccgtggaaaa cgtggccaag      3300
atgcgatgta tgagtatatg gctcaagcct gtgcaggaaa tcgtgtcagg cgatctcttt      3360
gtgaaggaac cttacttctg tggtgtgaca taattggaca aactacctac agagatttaa      3420
agctctaagg taaatataaa attttttaagt gtataatgtg ttaaactact gattctaatt      3480
gtttgtgtat tttagattcc aacctatgga actgatgaat gggagcagtg gtggaatgca      3540
gatcctagag ctcgctgatc agcctcgact gtgccttcta gttgccagcc atctgttgtt      3600
tgcccctccc ccgtgccttc cttgaccctg gaaggtgcca ctcccactgt cctttcctaa      3660
taaaatgagg aaattgcatc gcattgtctg agtaggtgtc attctattct ggggggtggg      3720
gtggggcagg acagcaaggg ggaggattgg gaagacaata gcaggcatgc tggggatgcg      3780
gtgggctcta tggcttctga ggcggaaaga accagctggg gctcgagata tcaagcttat      3840
cgataccgtc gacctcgagg ggggcccgg tacccaattc gccctatagt gagtcgtatt      3900
acgcgcgctc actggccgtc gttttacaac gtcgtgactg ggaaaaccct ggcgttaccc      3960
aacttaatcg ccttgcagca catccccctt cgccagctg gcgtaatagc gaagaggccc      4020
gcaccgatcg cccttcccaa cagttgcgca gcctgaatgg cgaatggaaa ttgtaagcgt      4080
taatattttg ttaaaattcg cgttaaattt ttgttaaatc agctcatttt ttaaccaata      4140
ggccgaaatc ggcaaaatcc cttataaatc aaaagaatag accgagatag ggttgagtgt      4200
tgttccagtt tggaacaaga gtccactatt aaagaacgtg gactccaacg tcaaagggcg      4260
aaaaaccgtc tatcagggcg atggcccact acgtgaacca tcaccctaat caagtttttt      4320
ggggtcgagg tgccgtaaag cactaaatcg gaaccctaaa gggagcccc gatttagagc      4380 ttgacgggga agccggcga acgtggcgag aaaggaaggg aagaaagcga aaggagcggg      4440
cgctagggcg ctggcaagtg tagcggtcac gctgcgcgta accaccacac ccgccgcgct      4500
taatgcgccg ctacagggcg cgtcag                                          4526
```

<210> SEQ ID NO 63
<211> LENGTH: 4929
<212> TYPE: DNA
<213> ORGANISM: Artificial sequence
<220> FEATURE:
<223> OTHER INFORMATION: pGK-IRES-GFP
<400> SEQUENCE: 63

```
tcgacaccgg gtaggggagg cgcttttccc aaggcagtct ggagcatgcg ctttagcagc        60
cccgctgggc acttggcgct acacaagtgg cctctggcct cgcacacatt ccacatccac       120
cggtaggcgc caaccggctc cgttctttgg tggccccttc gcgccacctt ctactcctcc       180
cctagtcagg aagttccccc ccgccccgca gctcgcgtcg tgcaggacgt gacaaatgga      240
```

-continued

```
agtagcacgt ctcactagtc tcgtgcagat ggacagcacc gctgagcaat ggaagcgggt      300
aggcctttgg ggcagcggcc aatagcagct ttgctccttc gctttctggg ctcagaggct      360
gggaaggggt gggtccgggg gcgggctcag gggcgggctc aggggcgggg cgggcgcccg      420
aaggtcctcc ggaggcccgg cattctgcac gcttcaaaag cgcacgtctg ccgcgctgtt      480
ctcctcttcc tcatctccgg gcctttcgac ctgccccggg ccctatatat ggatcggcta      540
gccgatccgc ccctctccct cccccccccc taacgttact ggccgaagcc gcttggaata      600
aggccggtgt gcgtttgtct atatgttatt ttccaccata ttgccgtctt ttggcaatgt      660
gagggcccgg aaacctggcc ctgtcttctt gacgagcatt cctaggggtc tttcccctct      720
cgccaaagga atgcaaggtc tgttgaatgt cgtgaaggaa gcagttcctc tggaagcttc      780
ttgaagacaa acaacgtctg tagcgaccct ttgcaggcag cggaacccc cacctggcga       840 caggtgcctc tgcggccaaa agccacgtgt ataagataca cctgcaaagg cggcacaacc      900
ccagtgccac gttgtgagtt ggatagttgt ggaaagagtc aaatggctct cctcaagcgt      960
attcaacaag gggctgaagg atgcccagaa ggtaccccat tgtatgggat ctgatctggg     1020
gcctcggtgc acatgcttta catgtgttta gtcgaggtta aaaaaacgtc taggcccccc     1080
gaaccacggg gacgtggttt cctttgaaa aacacgatga taatatggcc acaaccatgg      1140
tgagcaaggg cgaggagctg ttcaccgggg tggtgcccat cctggtcgag ctggacggcg     1200
acgtaaacgg ccacaagttc agcgtgtccg gcgaggcga gggcgatgcc acctacggca      1260
agctgaccct gaagttcatc tgcaccaccg gcaagctgcc cgtgccctgg cccaccctcg     1320
tgaccaccct gacctacggc gtgcagtgct tcagccgcta ccccgaccac atgaagcagc     1380
acgacttctt caagtccgcc atgcccgaag ctacgtcca ggagcgcacc atcttcttca      1440
aggacgacgg caactacaag acccgcgccg aggtgaagtt cgaggcgac accctggtga      1500 accgcatcga gctgaagggc atcgacttca aggaggacgg caacatcctg gggcacaagc     1560
tggagtacaa ctacaacagc cacaacgtct atatcatggc cgacaagcag aagaacggca     1620
tcaaggtgaa cttcaagatc cgccacaaca tcgaggacgg cagcgtgcag ctcgccgacc     1680
actaccagca gaacaccccc atcggcgacg gccccgtgct gctgcccgac aaccactacc     1740
tgagcaccca gtccgccctg agcaaagacc ccaacgagaa gcgcgatcac atggtcctgc     1800
tggagttcgt gaccgccgcc gggatcactc tcggcatgga cgagctgtac aagtaaagcg     1860
gccgccaatt cactcctcag gtgcaggctg cctatcagaa ggtggtggct ggtgtggcca     1920
atgccctggc tcacaaatac cactgagatc ttttttcctc tgccaaaaat tatggggaca     1980
tcatgaagcc ccttgagcat ctgacttctg gctaataaag gaaatttatt ttcattgcaa     2040
tagtgtgttg gaatttttg tgtctctcac tcggaaggac atatgggagg gcaaatcatt      2100
taaaacatca gaatgagtat ttggtttaga gtttggcaac atatgcccat atgctggctg     2160
ccatgaacaa aggttggcta taaagaggtc atcagtatat gaaacagccc cctgctgtcc     2220
attccttatt ccatagaaaa gccttgactt gaggttagat ttttttata ttttgttttg      2280 tgttatttt ttctttaaca tccctaaaat tttccttaca tgttttacta gccagatttt      2340
tcctcctctc ctgactactc ccagtcatag ctgtccctct tctcttatgg agatccctcg     2400
acctgcagcc caagcttggc gtaatcatgg tcatagctgt ttcctgtgtg aaattgttat     2460
ccgctcacaa ttccacacaa catacgagcc ggaagcataa agtgtaaagc ctggggtgcc     2520
taatgagtga gctaactcac attaattgcg ttgcgctcac tgcccgcttt ccagtcggga     2580
aacctgtcgt gccagcggat ccgcatctca attagtcagc aaccatagtc cgcccctaa      2640
```

-continued

```
ctccgcccat cccgcccta actccgccca gttccgccca ttctccgccc catggctgac   2700 taatttttt tatttatgca gaggccgagg ccgcctcggc ctctgagcta ttccagaagt   2760
agtgaggagg cttttttgga ggcctaggct tttgcaaaaa gctaacttgt ttattgcagc   2820
ttataatggt tacaaataaa gcaatagcat cacaaatttc acaaataaag catttttttc   2880
actgcattct agttgtggtt tgtccaaact catcaatgta tcttatcatg tctggatccg   2940
ctgcattaat gaatcggcca acgcgcgggg agaggcggtt tgcgtattgg gcgctcttcc   3000
gcttcctcgc tcactgactc gctgcgctcg gtcgttcggc tgcggcgagc ggtatcagct   3060
cactcaaagg cggtaatacg gttatccaca gaatcagggg ataacgcagg aaagaacatg   3120
tgagcaaaag gccagcaaaa ggccaggaac cgtaaaaagg ccgcgttgct ggcgtttttc   3180
cataggctcc gcccccctga cgagcatcac aaaaatcgac gctcaagtca gaggtggcga   3240
aacccgacag gactataaag ataccaggcg tttcccctg gaagctccct cgtgcgctct   3300
cctgttccga ccctgccgct taccggatac ctgtccgcct ttctcccttc gggaagcgtg   3360
gcgctttctc atagctcacg ctgtaggtat ctcagttcgg tgtaggtcgt tcgctccaag   3420
ctgggctgtg tgcacgaacc ccccgttcag cccgaccgct gcgccttatc cggtaactat   3480
cgtcttgagt ccaacccggt aagacacgac ttatcgccac tggcagcagc cactggtaac   3540
aggattagca gagcgaggta tgtaggcggt gctacagagt tcttgaagtg gtggcctaac   3600
tacggctaca ctagaagaac agtatttggt atctgcgctc tgctgaagcc agttaccttc   3660
ggaaaaagag ttggtagctc ttgatccggc aaacaaacca ccgctggtag cggtggtttt   3720
tttgtttgca agcagcagat tacgcgcaga aaaaaaggat ctcaagaaga tcctttgatc   3780
ttttctacgg ggtctgacgc tcagtggaac gaaaactcac gttaagggat tttggtcatg   3840
agattatcaa aaaggatctt cacctagatc cttttaaatt aaaaatgaag ttttaaatca   3900
atctaaagta tatatgagta aacttggtct gacagttacc aatgcttaat cagtgaggca   3960
cctatctcag cgatctgtct atttcgttca tccatagttg cctgactccc cgtcgtgtag   4020
ataactacga tacgggaggg cttaccatct ggccccagtg ctgcaatgat accgcgagac   4080
ccacgctcac cggctccaga tttatcagca ataaaccagc cagccggaag ggccgagcgc   4140
agaagtggtc ctgcaacttt atccgcctcc atccagtcta ttaattgttg ccgggaagct   4200
agagtaagta gttcgccagt taatagtttg cgcaacgttg ttgccattgc tacaggcatc   4260
gtggtgtcac gctcgtcgtt tggtatggct tcattcagct ccggttccca acgatcaagg   4320
cgagttacat gatcccccat gttgtgcaaa aaagcggtta gctccttcgg tcctccgatc   4380
gttgtcagaa gtaagttggc cgcagtgtta tcactcatgg ttatggcagc actgcataat   4440
tctcttactg tcatgccatc cgtaagatgc ttttctgtga ctggtgagta ctcaaccaag   4500
tcattctgag aatagtgtat gcggcgaccg agttgctctt gcccggcgtc aatacgggat   4560
aataccgcgc cacatagcag aactttaaaa gtgctcatca ttggaaaacg ttcttcgggg   4620
cgaaaactct caaggatctt accgctgttg agatccagtt cgatgtaacc cactcgtgca   4680
cccaactgat cttcagcatc ttttactttc accagcgttt ctgggtgagc aaaaacagga   4740
aggcaaaatg ccgcaaaaaa gggaataagg gcgacacgga aatgttgaat actcatactc   4800
ttcctttttc aatattattg aagcatttat cagggttatt gtctcatgag cggatacata   4860
tttgaatgta tttagaaaaa taaacaaata ggggttccgc gcacatttcc ccgaaaagtg   4920
ccacctggg                                                          4929
```

-continued

```
<210> SEQ ID NO 64
<211> LENGTH: 5568
<212> TYPE: DNA
<213> ORGANISM: Artificial sequence
<220> FEATURE:
<223> OTHER INFORMATION: pGK-DTA-IRES-GFP

<400> SEQUENCE: 64
tcgacaccgg gtaggggagg cgcttttccc aaggcagtct ggagcatgcg ctttagcagc     60
cccgctgggc acttggcgct acacaagtgg cctctggcct cgcacacatt ccacatccac    120
cggtaggcgc caaccggctc cgttctttgg tggcccttc gcgccacctt ctactcctcc     180
cctagtcagg aagttccccc ccgccccgca gctcgcgtcg tgcaggacgt gacaaatgga    240
agtagcacgt ctcactagtc tcgtgcagat ggacagcacc gctgagcaat ggaagcgggt    300
aggcctttgg ggcagcggcc aatagcagct ttgctccttc gctttctggg ctcagaggct    360
gggaaggggt gggtccgggg gcgggctcag gggcgggctc aggggcgggg cgggcgcccg    420
aaggtcctcc ggaggcccgg cattctgcac gcttcaaaag cgcacgtctg ccgcgctgtt    480
ctcctcttcc tcatctccgg gcctttcgac ctgccccggg atggatcctg atgatgttgt    540
tgattcttct aaatctttg tgatggaaaa cttttcttcg taccacggga ctaaacctgg     600
ttatgtagat tccattcaaa aaggtataca aaagccaaaa tctggtacac aaggaaatta    660
tgacgatgat tggaaagggt tttatagtac cgacaataaa tacgacgctg cgggatactc    720
tgtagataat gaaaacccgc tctctggaaa agctggaggc gtggtcaaag tgacgtatcc    780
aggactgacg aaggttctcg cactaaaagt ggataatgcc gaaactatta agaaagagtt    840
aggtttaagt ctcactgaac cgttgatgga gcaagtcgga acggaagagt ttatcaaaag    900
gttcggtgat ggtgcttcgc gtgtagtgct cagccttccc ttcgctgagg ggagttctag    960
cgttgaatat attaataact gggaacaggc gaaagcgtta agcgtagaac ttgagattaa   1020
ttttgaaacc cgtggaaaac gtggccaaga tgcgatgtat gagtatatgg ctcaagcctg   1080
tgcaggaaat cgtgtcaggc gatctctttg tgaaggaacc ttacttctgt ggtgtgacat   1140
aattggacaa actacctaca gagatttaaa gctctaagct agcctccgcc cctctccctc   1200
ccccccccct aacgttactg gccgaagccg cttggaataa ggccggtgtg cgtttgtcta   1260
tatgttattt tccaccatat tgccgtcttt tggcaatgtg agggcccgga aacctggccc   1320
tgtcttcttg acgagcattc ctaggggtct ttcccctctc gccaaaggaa tgcaaggtct   1380
gttgaatgtc gtgaaggaag cagttcctct ggaagcttct tgaagacaaa caacgtctgt   1440
agcgaccctt tgcaggcagc ggaacccccc acctggcgac aggtgcctct gcggccaaaa   1500
gccacgtgta taagatacac ctgcaaaggc ggcacaaccc cagtgccacg ttgtgagttg   1560
gatagttgtg gaaagagtca aatggctctc ctcaagcgta ttcaacaagg gctgaagga    1620 tgcccagaag gtaccccatt gtatgggatc tgatctgggg cctcggtgca catgctttac   1680
atgtgtttag tcgaggttaa aaaaacgtct aggccccccg aaccacgggg acgtggtttt   1740
cctttgaaaa acacgatgat aatatggcca caaccatggt gagcaagggc gaggagctgt   1800
tcaccggggt ggtgcccatc ctggtcgagc tggacggcga cgtaaacggc cacaagttca   1860
gcgtgtccgg cgagggcgag ggcgatgcca cctacggcaa gctgaccctg aagttcatct   1920
gcaccaccgg caagctgccc gtgccctggc ccaccctcgt gaccaccctg acctacggcg   1980
tgcagtgctt cagccgctac cccgaccaca tgaagcagca cgacttcttc aagtccgcca   2040
tgcccgaagg ctacgtccag gagcgcacca tcttcttcaa ggacgacggc aactacaaga   2100
```

-continued

```
cccgcgccga ggtgaagttc gagggcgaca ccctggtgaa ccgcatcgag ctgaagggca    2160
tcgacttcaa ggaggacggc aacatcctgg ggcacaagct ggagtacaac tacaacagcc    2220
acaacgtcta tatcatggcc gacaagcaga agaacggcat caaggtgaac ttcaagatcc    2280
gccacaacat cgaggacggc agcgtgcagc tcgccgacca ctaccagcag aacaccccca    2340
tcggcgacgg ccccgtgctg ctgcccgaca ccactacct gagcacccag tccgccctga    2400
gcaaagaccc caacgagaag cgcgatcaca tggtcctgct ggagttcgtg accgccgccg    2460
ggatcactct cggcatggac gagctgtaca gtaaagcgg ccgccaattc actcctcagg    2520
tgcaggctgc ctatcagaag gtggtggctg gtgtggccaa tgccctggct cacaaatacc    2580
actgagatct tttttccctct gccaaaaatt atggggacat catgaagccc cttgagcatc    2640
tgacttctgg ctaataaagg aaatttattt tcattgcaat agtgtgttgg aatttttttgt    2700 gtctctcact cggaaggaca tatgggaggg caaatcattt aaaacatcag aatgagtatt    2760
tggtttagag tttggcaaca tatgcccata tgctggctgc catgaacaaa ggttggctat    2820
aaagaggtca tcagtatatg aaacagcccc ctgctgtcca ttccttattc catagaaaag    2880
ccttgacttg aggttagatt ttttttatat tttgttttgt gttattttttt tctttaacat    2940 ccctaaaatt ttccttacat gttttactag ccagattttt cctcctctcc tgactactcc    3000
cagtcatagc tgtccctctt ctcttatgga gatccctcga cctgcagccc aagcttggcg    3060
taatcatggt catagctgtt tcctgtgtga aattgttatc cgctcacaat tccacacaac    3120
atacgagccg gaagcataaa gtgtaaagcc tggggtgcct aatgagtgag ctaactcaca    3180
ttaattgcgt tgcgctcact gcccgctttc cagtcgggaa acctgtcgtg ccagcggatc    3240
cgcatctcaa ttagtcagca accatagtcc cgcccctaac tccgcccatc ccgcccctaa    3300
ctccgcccag ttccgcccat tctccgcccc atggctgact aatttttttt atttatgcag    3360
aggccgaggc cgcctcggcc tctgagctat tccagaagta gtgaggaggc ttttttggag    3420
gcctaggctt ttgcaaaaag ctaacttgtt tattgcagct tataatggtt acaaataaag    3480
caatagcatc acaaatttca caaataaagc atttttttca ctgcattcta gttgtggttt    3540
gtccaaactc atcaatgtat cttatcatgt ctggatccgc tgcattaatg aatcggccaa    3600
cgcgcgggga gaggcggttt gcgtattggg cgctcttccg cttcctcgct cactgactcg    3660
ctgcgctcgg tcgttcggct gcggcgagcg gtatcagctc actcaaaggc ggtaatacgg    3720
ttatccacag aatcaggggga taacgcagga aagaacatgt gagcaaaagg ccagcaaaag    3780
gccaggaacc gtaaaaaggc cgcgttgctg gcgtttttcc ataggctccg ccccctgac    3840 gagcatcaca aaaatcgacg ctcaagtcag aggtggcgaa acccgacagg actataaaga    3900
taccaggcgt ttccccctgg aagctccctc gtgcgctctc ctgttccgac cctgccgctt    3960
accggatacc tgtccgcctt tctcccttcg ggaagcgtgg cgctttctca tagctcacgc    4020
tgtaggtatc tcagttcggt gtaggtcgtt cgctccaagc tgggctgtgt gcacgaaccc    4080
cccgttcagc ccgaccgctg cgccttatcc ggtaactatc gtcttgagtc caacccggta    4140
agacacgact tatcgccact ggcagcagcc actggtaaca ggattagcag agcgaggtat    4200
gtaggcggtg ctacagagtt cttgaagtgg tggcctaact acggctacac tagaagaaca    4260
gtatttggta tctgcgctct gctgaagcca gttaccttcg gaaaaagagt tggtagctct    4320
tgatccggca acaaaccac cgctggtagc ggtggttttt ttgtttgcaa gcagcagatt    4380
acgcgcagaa aaaaaggatc tcaagaagat cctttgatct tttctacggg gtctgacgct    4440
```

```
cagtggaacg aaaactcacg ttaagggatt ttggtcatga gattatcaaa aaggatcttc      4500
acctagatcc ttttaaatta aaaatgaagt tttaaatcaa tctaaagtat atatgagtaa      4560
acttggtctg acagttacca atgcttaatc agtgaggcac ctatctcagc gatctgtcta      4620
tttcgttcat ccatagttgc ctgactcccc gtcgtgtaga taactacgat acgggagggc      4680
ttaccatctg gccccagtgc tgcaatgata ccgcgagacc cacgctcacc ggctccagat      4740
ttatcagcaa taaaccagcc agccggaagg gccgagcgca gaagtggtcc tgcaacttta      4800
tccgcctcca tccagtctat taattgttgc cgggaagcta gagtaagtag ttcgccagtt      4860
aatagtttgc gcaacgttgt tgccattgct acaggcatcg tggtgtcacg ctcgtcgttt      4920
ggtatggctt cattcagctc cggttcccaa cgatcaaggc gagttacatg atcccccatg      4980
ttgtgcaaaa aagcggttag ctccttcggt cctccgatcg ttgtcagaag taagttggcc      5040
gcagtgttat cactcatggt tatggcagca ctgcataatt ctcttactgt catgccatcc      5100
gtaagatgct tttctgtgac tggtgagtac tcaaccaagt cattctgaga atagtgtatg      5160
cggcgaccga gttgctcttg cccggcgtca atacgggata ataccgcgcc acatagcaga      5220
actttaaaag tgctcatcat tggaaaacgt tcttcggggc gaaaactctc aaggatctta      5280
ccgctgttga tccagttc gatgtaaccc actcgtgcac ccaactgatc ttcagcatct      5340
tttactttca ccagcgtttc tgggtgagca aaaacaggaa ggcaaaatgc cgcaaaaaag      5400
ggaataaggg cgacacggaa atgttgaata ctcatactct tccttttca atattattga      5460 agcatttatc agggttattg tctcatgagc ggatacatat ttgaatgtat ttagaaaaat      5520
aaacaaatag gggttccgcg cacatttccc cgaaaagtgc cacctggg                   5568
```

```
<210> SEQ ID NO 65
<211> LENGTH: 450
<212> TYPE: DNA
<213> ORGANISM: Artificial sequence
<220> FEATURE:
<223> OTHER INFORMATION: Negative Mag recombinase

<400> SEQUENCE: 65
catactcttt atgcccccgg tggatatgac attatgggat atctggacca gatcggcaac      60
cggccaaacc cgcaggtgga actgggcccc gtggatacat cctgcgcctt gattctttgt     120
gacctgaaac agaaagacac cccgatagtt tacgcgagtg aagccttcct ctacatgaca     180
ggttacagca acgcagaggt gctgggccgg aattgccggt ttctgcaaag ccctgacggc     240
atggtgaagc ccaagagcac ccggaagtac gtggatagta acacaatcaa tactatgcgc     300
aaggcaatcg acaggaatgc cgaggtgcag gttgaagtag tcaattttaa aaagaatgga     360
cagcgatttg ttaatttcct gactatgata cctgttaggg acgaaacagg cgagtatcga     420
tactctatgg gattccagtg cgaaacagaa                                       450
```

```
<210> SEQ ID NO 66
<211> LENGTH: 20
<212> TYPE: DNA
<213> ORGANISM: Artificial sequence
<220> FEATURE:
<223> OTHER INFORMATION: Guide 1

<400> SEQUENCE: 66
gccaaataag gcacgttatc                                                    20
```

```
<210> SEQ ID NO 67
<211> LENGTH: 20
```

```
<212> TYPE: DNA
<213> ORGANISM: Artificial sequence
<220> FEATURE:
<223> OTHER INFORMATION: Guide 2

<400> SEQUENCE: 67
aatgtggaaa cggccaaata                                                          20

<210> SEQ ID NO 68
<211> LENGTH: 20
<212> TYPE: DNA
<213> ORGANISM: Artificial sequence
<220> FEATURE:
<223> OTHER INFORMATION: Guide 3

<400> SEQUENCE: 68
accagataac gtgccttatt                                                          20

<210> SEQ ID NO 69
<211> LENGTH: 20
<212> TYPE: DNA
<213> ORGANISM: Artificial sequence
<220> FEATURE:
<223> OTHER INFORMATION: Guide 4

<400> SEQUENCE: 69
acatgacagc acgatttgt                                                           20

<210> SEQ ID NO 70
<211> LENGTH: 20
<212> TYPE: DNA
<213> ORGANISM: Artificial sequence
<220> FEATURE:
<223> OTHER INFORMATION: Guide 5

<400> SEQUENCE: 70
ctggtatgaa ccaatcagag                                                          20

<210> SEQ ID NO 71
<211> LENGTH: 20
<212> TYPE: DNA
<213> ORGANISM: Artificial sequence
<220> FEATURE:
<223> OTHER INFORMATION: Guide 6

<400> SEQUENCE: 71
tggtatgaac caatcagagt                                                          20

<210> SEQ ID NO 72
<211> LENGTH: 20
<212> TYPE: DNA
<213> ORGANISM: Artificial sequence
<220> FEATURE:
<223> OTHER INFORMATION: Guide 7

<400> SEQUENCE: 72
gaccttgatg cagagaaaac                                                          20

<210> SEQ ID NO 73
<211> LENGTH: 20
<212> TYPE: DNA
<213> ORGANISM: Artificial sequence
<220> FEATURE:
<223> OTHER INFORMATION: Guide 8

<400> SEQUENCE: 73
```

-continued ctcctgtttt ctctgcatca                                                    20

<210> SEQ ID NO 74
<211> LENGTH: 20
<212> TYPE: DNA
<213> ORGANISM: Artificial sequence
<220> FEATURE:
<223> OTHER INFORMATION: Guide 9

<400> SEQUENCE: 74
gcagagaaaa caggagaaga                                                    20

<210> SEQ ID NO 75
<211> LENGTH: 20
<212> TYPE: DNA
<213> ORGANISM: Artificial sequence
<220> FEATURE:
<223> OTHER INFORMATION: Guide 10

<400> SEQUENCE: 75
agaaggatga gaaaagaatg                                                    20

<210> SEQ ID NO 76
<211> LENGTH: 20
<212> TYPE: DNA
<213> ORGANISM: Artificial sequence
<220> FEATURE:
<223> OTHER INFORMATION: Guide 11

<400> SEQUENCE: 76
ctgtcatgtc ccactctgat                                                    20

<210> SEQ ID NO 77
<211> LENGTH: 20
<212> TYPE: DNA
<213> ORGANISM: Artificial sequence
<220> FEATURE:
<223> OTHER INFORMATION: Guide 12

<400> SEQUENCE: 77
atgagaaaag aatgtggaaa                                                    20

<210> SEQ ID NO 78
<211> LENGTH: 23
<212> TYPE: DNA
<213> ORGANISM: Artificial sequence
<220> FEATURE:
<223> OTHER INFORMATION: Guide 1 potential off target

<400> SEQUENCE: 78
ccaacagaag gcacgttatc cag                                                23

<210> SEQ ID NO 79
<211> LENGTH: 23
<212> TYPE: DNA
<213> ORGANISM: Artificial sequence
<220> FEATURE:
<223> OTHER INFORMATION: Guide 1 potential off target

<400> SEQUENCE: 79
tcaaaataaa gtacgttatc tag                                                23

<210> SEQ ID NO 80
<211> LENGTH: 23
<212> TYPE: DNA
<213> ORGANISM: Artificial sequence -continued

```
<220> FEATURE:
<223> OTHER INFORMATION: Guide 1 potential off target

<400> SEQUENCE: 80
ggcatataaa gcacgttata cag                                                    23

<210> SEQ ID NO 81
<211> LENGTH: 23
<212> TYPE: DNA
<213> ORGANISM: Artificial sequence
<220> FEATURE:
<223> OTHER INFORMATION: Guide 1 potential off target

<400> SEQUENCE: 81
gcataataat gtacgttatc tgg                                                    23

<210> SEQ ID NO 82
<211> LENGTH: 23
<212> TYPE: DNA
<213> ORGANISM: Artificial sequence
<220> FEATURE:
<223> OTHER INFORMATION: Guide 1 potential off target

<400> SEQUENCE: 82
actaaatcag gcacgtgatc tgg                                                    23

<210> SEQ ID NO 83
<211> LENGTH: 23
<212> TYPE: DNA
<213> ORGANISM: Artificial sequence
<220> FEATURE:
<223> OTHER INFORMATION: Guide 1 potential off target

<400> SEQUENCE: 83
gctaaattaa gctcgttatc ggg                                                    23

<210> SEQ ID NO 84
<211> LENGTH: 23
<212> TYPE: DNA
<213> ORGANISM: Artificial sequence
<220> FEATURE:
<223> OTHER INFORMATION: Guide 1 potential off target

<400> SEQUENCE: 84
gtcaaatgag gcatgttatc agg                                                    23

<210> SEQ ID NO 85
<211> LENGTH: 23
<212> TYPE: DNA
<213> ORGANISM: Artificial sequence
<220> FEATURE:
<223> OTHER INFORMATION: Guide 1 potential off target

<400> SEQUENCE: 85
ttcaaataag ccacgttatt cag                                                    23

<210> SEQ ID NO 86
<211> LENGTH: 23
<212> TYPE: DNA
<213> ORGANISM: Artificial sequence
<220> FEATURE:
<223> OTHER INFORMATION: Guide 1 potential off target

<400> SEQUENCE: 86
gtcaaacaag gcatgttatc agg                                                    23
```

```
<210> SEQ ID NO 87
<211> LENGTH: 23
<212> TYPE: DNA
<213> ORGANISM: Artificial sequence
<220> FEATURE:
<223> OTHER INFORMATION: Guide 1 potential off target

<400> SEQUENCE: 87
ccctaataaa gcacgttttc agg                                                                       23

<210> SEQ ID NO 88
<211> LENGTH: 22
<212> TYPE: DNA
<213> ORGANISM: Artificial sequence
<220> FEATURE:
<223> OTHER INFORMATION: FWD primer

<400> SEQUENCE: 88
accatcttcg ggaagattat cc                                                                        22

<210> SEQ ID NO 89
<211> LENGTH: 22
<212> TYPE: DNA
<213> ORGANISM: Artificial sequence
<220> FEATURE:
<223> OTHER INFORMATION: REV primer

<400> SEQUENCE: 89
cttctgcttc agataacctg ac                                                                        22

<210> SEQ ID NO 90
<211> LENGTH: 20
<212> TYPE: DNA
<213> ORGANISM: Artificial sequence
<220> FEATURE:
<223> OTHER INFORMATION: GAPDH primers: Forward

<400> SEQUENCE: 90
actgtcaagg ctgagaacgg                                                                           20

<210> SEQ ID NO 91
<211> LENGTH: 20
<212> TYPE: DNA
<213> ORGANISM: Artificial sequence
<220> FEATURE:
<223> OTHER INFORMATION: GAPDH primers: Reverse

<400> SEQUENCE: 91
acctgcatct gcccatttga                                                                           20

<210> SEQ ID NO 92
<211> LENGTH: 657
<212> TYPE: DNA
<213> ORGANISM: Corynebacterium diphtheriae

<400> SEQUENCE: 92
atggatcctg atgatgttgt tgattcttct aaatcttttg tgatggaaaa cttttcttcg          60
taccacggga ctaaacctgg ttatgtagat tccattcaaa aaggtataca aaagccaaaa         120
tctggtacac aaggaaatta tgacgatgat tggaaagggt tttatagtac cgacaataaa         180
tacgacgctg cgggatactc tgtagataat gaaaacccgc tctctggaaa agctggaggc         240
gtggtcaaag tgacgtatcc aggactgacg aaggttctcg cactaaaagt ggataatgcc         300
gaaactatta gaaagagtt aggtttaagt ctcactgaac cgttgatgga gcaagtcgga          360
```

-continued

```
acggaagagt ttatcaaaag gttcggtgat ggtgcttcgc gtgtagtgct cagccttccc      420
ttcgctgagg ggagttctag cgttgaatat attaataact gggaacaggc gaaagcgtta      480
agcgtagaac ttgagattaa tttttgaaacc cgtggaaaac gtggccaaga tgcgatgtat      540
gagtatatgg ctcaagcctg tgcaggaaat cgtgtcaggc gatctctttg tgaaggaacc      600
ttacttctgt ggtgtgacat aattggacaa actacctaca gagatttaaa gctctaa        657
```

```
<210> SEQ ID NO 93
<211> LENGTH: 218
<212> TYPE: PRT
<213> ORGANISM: Corynebacterium diphtheriae

<400> SEQUENCE: 93

Met Asp Pro Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Leu Cys Glu Gly Thr Leu Leu Leu Trp Cys Asp Ile Ile
        195                 200                 205

Gly Gln Thr Thr Tyr Arg Asp Leu Lys Leu
    210                 215
```

```
<210> SEQ ID NO 94
<211> LENGTH: 852
<212> TYPE: DNA
<213> ORGANISM: Gallus gallus domesticus

<400> SEQUENCE: 94
atgatgacag acataaaaga tggaccacgc tcaggggaag atgtatcaga tgcaagatct       60
ttccctggtt ccaaaggaat gaacttacct gctagcaagt ctgtggactc tggaattctg      120
cctgatgaca gttacagaat ggattatcca gagataggag tatgtgttat aataaacaat      180
aagaacttcc accgagatac cggactgtca tctcgttcag gcacggatgc agatgctgca      240
agtgtcagag aagtttttat gaagctggga tataaagtca agcttaacaa tgatctgtca      300
```

```
agcagagata tttttaagct attgaaaaat gtttctgaag aagatcacag caagcgaagc    360
agttttgttt gtgtgttgct aagccatggc gatgaaggac tcttctatgg tacagatggc    420
cctcttgaac tgaaagtact aaccagcctt ttcagaggtg acaagtgcag aagtctagca    480
gggaaaccca aactcttttt cattcaggcc tgtagaggaa cagaattaga ttctggtatt    540
gaagcagaca gtggaccaga tgaaacagtg tgtcaaaaaa tacctgtaga agcagacttc    600
ctgtatgcat attctactgc tccaggctac tactcctgga ggaacgcagc tgaaggctcc    660
tggtttattc agtctctgtg taggatgctg aaggaacacg ccaggaaact tgaactcatg    720
cagattttaa ctcgtgtaaa tcgcagagtg gcagaatatg aatcctgctc cactcgacag    780
gatttcaatg caaagaaaca gattccatgc attgtgtcta tgcttaccaa agaattctac    840
tttccttgct aa                                                        852
```

```
<210> SEQ ID NO 95
<211> LENGTH: 283
<212> TYPE: PRT
<213> ORGANISM: Gallus gallus domesticus

<400> SEQUENCE: 95

Met Met Thr Asp Ile Lys Asp Gly Pro Arg Ser Gly Glu Asp Val Ser
1               5                   10                  15

Asp Ala Arg Ser Phe Pro Gly Ser Lys Gly Met Asn Leu Pro Ala Ser
            20                  25                  30

Lys Ser Val Asp Ser Gly Ile Leu Pro Asp Asp Ser Tyr Arg Met Asp
        35                  40                  45

Tyr Pro Glu Ile Gly Val Cys Val Ile Ile Asn Asn Lys Asn Phe His
    50                  55                  60

Arg Asp Thr Gly Leu Ser Ser Arg Ser Gly Thr Asp Ala Asp Ala Ala
65                  70                  75                  80

Ser Val Arg Glu Val Phe Met Lys Leu Gly Tyr Lys Val Lys Leu Asn
                85                  90                  95

Asn Asp Leu Ser Ser Arg Asp Ile Phe Lys Leu Leu Lys Asn Val Ser
            100                 105                 110

Glu Glu Asp His Ser Lys Arg Ser Ser Phe Val Cys Val Leu Leu Ser
        115                 120                 125

His Gly Asp Glu Gly Leu Phe Tyr Gly Thr Asp Gly Pro Leu Glu Leu
    130                 135                 140

Lys Val Leu Thr Ser Leu Phe Arg Gly Asp Lys Cys Arg Ser Leu Ala
145                 150                 155                 160

Gly Lys Pro Lys Leu Phe Phe Ile Gln Ala Cys Arg Gly Thr Glu Leu
                165                 170                 175

Asp Ser Gly Ile Glu Ala Asp Ser Gly Pro Asp Glu Thr Val Cys Gln
            180                 185                 190

Lys Ile Pro Val Glu Ala Asp Phe Leu Tyr Ala Tyr Ser Thr Ala Pro
        195                 200                 205

Gly Tyr Tyr Ser Trp Arg Asn Ala Ala Glu Gly Ser Trp Phe Ile Gln
    210                 215                 220

Ser Leu Cys Arg Met Leu Lys Glu His Ala Arg Lys Leu Glu Leu Met
225                 230                 235                 240

Gln Ile Leu Thr Arg Val Asn Arg Arg Val Ala Glu Tyr Glu Ser Cys
                245                 250                 255

Ser Thr Arg Gln Asp Phe Asn Ala Lys Lys Gln Ile Pro Cys Ile Val
            260                 265                 270
```

```
Ser Met Leu Thr Lys Glu Phe Tyr Phe Pro Cys
        275                 280
```

<210> SEQ ID NO 96
<211> LENGTH: 852
<212> TYPE: DNA
<213> ORGANISM: Gallus gallus domesticus

<400> SEQUENCE: 96

```
atgatgacag acataaaaga tggaccacgc tcaggggaag atgtatcagc tgcaagatct      60
ttccctggtt ccaaaggaat gaacttacct gctagcaagt ctgtggcctc tggaattctg     120
cctgatgaca gttacagaat ggattatcca gagataggag tatgtgttat aataaacaat     180
aagaacttcc accgagatac cggactgtca tctcgttcag gcacggatgc agatgctgca     240
agtgtcagag aagtttttat gaagctggga tataaagtca agcttaacaa tgatctgtca     300
agcagagata tttttaagct attgaaaaat gtttctgaag aagatcacag caagcgaagc     360
agttttgttt gtgtgttgct aagccatggc gatgaaggac tcttctatgg tacagatggc     420
cctcttgaac tgaaagtact aaccagcctt ttcagaggtg acaagtgcag aagtctagca     480
gggaaaccca aactcttttt cattcaggcc tgtagaggaa cagaattaga ttctggtatt     540
gaagcagcca gtggaccaga tgaaacagtg tgtcaaaaaa tacctgtaga agcagacttc     600
ctgtatgcat attctactgc tccaggctac tactcctgga ggaacgcagc tgaaggctcc     660
tggtttattc agtctctgtg taggatgctg aaggaacacg ccaggaaact tgaactcatg     720
cagattttaa ctcgtgtaaa tcgcagagtg gcagaatatg aatcctgctc cactcgacag     780
gatttcaatg caaagaaaca gattccatgc attgagtcta tgcttaccaa agaattctac     840
tttccttgct aa                                                          852
```

<210> SEQ ID NO 97
<211> LENGTH: 283
<212> TYPE: PRT
<213> ORGANISM: Gallus gallus domesticus

<400> SEQUENCE: 97

```
Met Met Thr Asp Ile Lys Asp Gly Pro Arg Ser Gly Glu Asp Val Ser
1               5                   10                  15

Ala Ala Arg Ser Phe Pro Gly Ser Lys Gly Met Asn Leu Pro Ala Ser
            20                  25                  30

Lys Ser Val Ala Ser Gly Ile Leu Pro Asp Asp Ser Tyr Arg Met Asp
        35                  40                  45

Tyr Pro Glu Ile Gly Val Cys Val Ile Ile Asn Asn Lys Asn Phe His
    50                  55                  60

Arg Asp Thr Gly Leu Ser Ser Arg Ser Gly Thr Asp Ala Asp Ala Ala
65                  70                  75                  80

Ser Val Arg Glu Val Phe Met Lys Leu Gly Tyr Lys Val Lys Leu Asn
                85                  90                  95

Asn Asp Leu Ser Ser Arg Asp Ile Phe Lys Leu Leu Lys Asn Val Ser
            100                 105                 110

Glu Glu Asp His Ser Lys Arg Ser Ser Phe Val Cys Val Leu Leu Ser
        115                 120                 125

His Gly Asp Glu Gly Leu Phe Tyr Gly Thr Asp Gly Pro Leu Glu Leu
    130                 135                 140

Lys Val Leu Thr Ser Leu Phe Arg Gly Asp Lys Cys Arg Ser Leu Ala
145                 150                 155                 160
```

-continued

```
Gly Lys Pro Lys Leu Phe Phe Ile Gln Ala Cys Arg Gly Thr Glu Leu
            165                 170                 175

Asp Ser Gly Ile Glu Ala Ala Ser Gly Pro Asp Glu Thr Val Cys Gln
            180                 185                 190

Lys Ile Pro Val Glu Ala Asp Phe Leu Tyr Ala Tyr Ser Thr Ala Pro
            195                 200                 205

Gly Tyr Tyr Ser Trp Arg Asn Ala Ala Glu Gly Ser Trp Phe Ile Gln
    210                 215                 220

Ser Leu Cys Arg Met Leu Lys Glu His Ala Arg Lys Leu Glu Leu Met
225                 230                 235                 240

Gln Ile Leu Thr Arg Val Asn Arg Arg Val Ala Glu Tyr Glu Ser Cys
                245                 250                 255

Ser Thr Arg Gln Asp Phe Asn Ala Lys Lys Gln Ile Pro Cys Ile Glu
            260                 265                 270

Ser Met Leu Thr Lys Glu Phe Tyr Phe Pro Cys
            275                 280
```

```
<210> SEQ ID NO 98
<211> LENGTH: 672
<212> TYPE: DNA
<213> ORGANISM: Artificial sequence
<220> FEATURE:
<223> OTHER INFORMATION: Noggin Nucleotide

<400> SEQUENCE: 98
atggatcatt cccagtgcct tgtgactata tacgccgcgg cggtgctgct ggggctccgg      60
ctgcagcagg gctcctgcca gcactacctg cacatccgcc cggctcccag cgacaacctg     120
cccctggtgg atctaatcga gcacccggac cctatctttg accccaagga gaaggatctt     180
aacgagacct tgctaaggag cctcatggga ggacacttcg accctaactt tatggctatg     240
tccctgcccg aggaccggct cggggtagac gatctggccg agctggactt gctgctgcgg     300
cagagaccct cgggagcgat gcccggcgaa atcaaggggc tggagttcta cgacgggctg     360
cagccgggca agaagcacag gctgagcaag aagctgcgca ggaagctgca gatgtggctc     420
tggtcccaga ccttctgccc ggtcctatac acgtggaacg atctcggcag ccgcttttgg     480
ccccggtacg tcaaagtggg cagctgctac agtaaaaggt cttgctctgt cccagaaggc     540
atggtctgca aacctgccaa gtccgtgcat ttaacgatcc tgaggtggcg gtgccagcgg     600
cggggcgggc agcggtgcac gtggatcccc atccagtacc ccatcatcgc ggagtgcaag     660
tgctcctgct ag                                                          672
```

```
<210> SEQ ID NO 99
<211> LENGTH: 223
<212> TYPE: PRT
<213> ORGANISM: Artificial sequence
<220> FEATURE:
<223> OTHER INFORMATION: Noggin Aminoacid

<400> SEQUENCE: 99

Met Asp His Ser Gln Cys Leu Val Thr Ile Tyr Ala Ala Ala Val Leu
1               5                   10                  15

Leu Gly Leu Arg Leu Gln Gln Gly Ser Cys Gln His Tyr Leu His Ile
            20                  25                  30

Arg Pro Ala Pro Ser Asp Asn Leu Pro Leu Val Asp Leu Ile Glu His
        35                  40                  45

Pro Asp Pro Ile Phe Asp Pro Lys Glu Lys Asp Leu Asn Glu Thr Leu
    50                  55                  60
```

```
Leu Arg Ser Leu Met Gly Gly His Phe Asp Pro Asn Phe Met Ala Met
65                  70                  75                  80

Ser Leu Pro Glu Asp Arg Leu Gly Val Asp Asp Leu Ala Glu Leu Asp
                85                  90                  95

Leu Leu Leu Arg Gln Arg Pro Ser Gly Ala Met Pro Gly Glu Ile Lys
            100                 105                 110

Gly Leu Glu Phe Tyr Asp Gly Leu Gln Pro Gly Lys Lys His Arg Leu
            115                 120                 125

Ser Lys Lys Leu Arg Arg Lys Leu Gln Met Trp Leu Trp Ser Gln Thr
        130                 135                 140

Phe Cys Pro Val Leu Tyr Thr Trp Asn Asp Leu Gly Ser Arg Phe Trp
145                 150                 155                 160

Pro Arg Tyr Val Lys Val Gly Ser Cys Tyr Ser Lys Arg Ser Cys Ser
                165                 170                 175

Val Pro Glu Gly Met Val Cys Lys Pro Ala Lys Ser Val His Leu Thr
                180                 185                 190

Ile Leu Arg Trp Arg Cys Gln Arg Arg Gly Gly Gln Arg Cys Thr Trp
            195                 200                 205

Ile Pro Ile Gln Tyr Pro Ile Ile Ala Glu Cys Lys Cys Ser Cys
        210                 215                 220
```

```
<210> SEQ ID NO 100
<211> LENGTH: 1686
<212> TYPE: DNA
<213> ORGANISM: Artificial sequence
<220> FEATURE:
<223> OTHER INFORMATION: pCAGG promotor

<400> SEQUENCE: 100
actagttatt aatagtaatc aattacgggg tcattagttc atagcccata tatggagttc      60
cgcgttacat aacttacggt aaatggcccg cctggctgac cgcccaacga cccccgccca     120
ttgacgtcaa taatgacgta tgttcccata gtaacgccaa tagggacttt ccattgacgt     180
caatgggtgg agtatttacg gtaaactgcc cacttggcag tacatcaagt gtatcatatg     240
ccaagtacgc cccctattga cgtcaatgac ggtaaatggc ccgcctggca ttatgcccag     300
tacatgacct tatgggactt tcctacttgg cagtacatct acgtattagt catcgctatt     360
accatggtcg aggtgagccc cacgttctgc ttcactctcc ccatctcccc ccctccccca     420
cccccaattt tgtatttatt tattttttaa ttattttgtg cagcgatggg ggcggggggg     480
gggggggggc gcgcgccagg cggggcgggg cggggcgagg ggcggggcgg ggcgaggcgg     540
agaggtgcgg cggcagccaa tcagagcggc gcgctccgaa agtttccttt tatggcgagg     600
cggcggcggc ggcggcccta taaaaagcga agcgcgcggc gggcggggag tcgctgcgac     660
gctgccttcg ccccgtgccc cgctccgccg ccgcctcgcg ccgcccgccc cggctctgac     720
tgaccgcgtt actcccacag gtgagcgggc gggacggccc ttctcctccg ggctgtaatt     780
agcgcttggt ttaatgacgg cttgtttctt ttctgtggct gcgtgaaagc cttgaggggc     840
tccgggaggg ccctttgtgc gggggagcg gctcggggg tgcgtgcgtg tgtgtgtgcg     900
tggggagcgc gcgtgcggc tccgcgctgc ccggcggctg tgagcgctgc gggcgcggcg     960
cggggctttg tgcgctccgc agtgtgcgcg aggggagcgc ggccggggc ggtgccccgc    1020 ggtgcggggg gggctgcgag gggaacaaag gctgcgtgcg gggtgtgtgc gtggggggt    1080 gagcagggg tgtgggcgcg tcggtcgggc tgcaacccc cctgcacccc cctccccgag    1140
```

-continued

```
ttgctgagca cggcccggct tcgggtgcgg ggctccgtac ggggcgtggc gcggggctcg    1200
ccgtgccggg cggggggtgg cggcaggtgg gggtgccggg cggggcgggg ccgcctcggg    1260
ccggggaggg ctcgggggag gggcgcggcg gcccccggag cgccggcggc tgtcgaggcg    1320
cggcgagccg cagccattgc cttttatggt aatcgtgcga gagggcgcag ggacttcctt    1380
tgtcccaaat ctgtgcggag ccgaaatctg ggaggcgccg ccgcacccec tctagcgggc    1440 gcggggcgaa gcggtgcggc gccggcagga aggaaatggg cggggagggc cttcgtgcgt    1500
cgccgcgccg ccgtcccctt ctccctctcc agcctcgggg ctgtccgcgg ggggacggct    1560
gccttcgggg gggacggggc agggcggggt tcggcttctg gcgtgtgacc ggcggctcta    1620
gagcctctgc taaccatgtt catgccttct tctttttcct acagctcctg ggcaacgtgc    1680
tggtta                                                                1686
```

```
<210> SEQ ID NO 101
<211> LENGTH: 1941
<212> TYPE: DNA
<213> ORGANISM: Artificial Sequence
<220> FEATURE:
<223> OTHER INFORMATION: Optogen 1 - NLS-Cry2-delta535-L348F-Cre-N
      (AA 19-104)

<400> SEQUENCE: 101
```

```
atgcctaaaa agaagcgtaa agtcatgaag atgaagatgg acaaaaagac tatagtttgg     60
tttagaagag acctaaggat tgaggataat cctgcattag cagcagctgc tcacgaagga    120
tctgtttttc ctgtcttcat ttggtgtcct gaagaagaag acagtttta tcctggaaga    180 gcttcaagat ggtggatgaa acaatcactt gctcacttat ctcaatcctt gaaggctctt    240
ggatctgacc tcactttaat caaaacccac aacacgattt cagcgatctt ggattgtatc    300
cgcgttaccg gtgctacaaa agtcgtcttt aaccacctct atgatcctgt ttcgttagtt    360
cgggaccata ccgtaaagga gaagctggtg aacgtgggga tctctgtgca aagctacaat    420
ggagatctat tgtatgaacc gtgggagata tactgcgaaa agggcaaacc ttttacgagt    480
ttcaattctt actggaagaa atgcttagat atgtcgattg aatccgttat gcttcctcct    540
ccttggcggt tgatgccaat aactgcagcg gctgaagcga tttgggcgtg ttcgattgaa    600
gaactagggc tggagaatga ggccgagaaa ccgagcaatg cgttgttaac tagagcttgg    660
tctccaggat ggagcaatgc tgataagtta ctaaatgagt tcatcgagaa gcagttgata    720
gattatgcaa agaacagcaa gaaagttgtt gggaattcta cttcactact ttctccgtat    780
ctccatttcg gggaaataag cgtcagacac gttttccagt gtgcccggat gaaacaaatt    840
atatgggcaa gagataagaa cagtgaagga aagaaagtg cagatctttt tcttagggga    900
atcggtttaa gagagtattc tcggtatata tgtttcaact tcccgtttac tcacgagcaa    960
tcgttgttga gtcatcttcg gttttttccct tgggatgctg atgttgataa gttcaaggcc   1020
tggagacaag gcaggaccgg ttatccgttg gtggatgccg gaatgagaga gttttgggct   1080
accggatgga tgcataacag aataagagtg attgtttcaa gctttgctgt gaagtttctt   1140
ctccttccat ggaaatgggg aatgaagtat ttctgggata cacttttgga tgctgatttg   1200
gaatgtgaca tccttggctg gcagtatatc tctgggagta tccccgatgg ccacgagctt   1260
gatcgcttgg acaatcccgc gttacaaggc gccaaatatg acccagaagg tgagtacata   1320
aggcaatggc ttcccgagct tgcgagattg ccaactgaat ggatccatca tccatgggac   1380
gctcctttaa ccgtactcaa agcttctggt gtggaactcg gaacaaacta tgcgaaaccc   1440
```

-continued

```
attgtagaca tcgacacagc tcgtgagcta ctagctaaag ctatttcaag aacccgtgaa    1500
gcacagatca tgatcggagc agcacctgat gagattgtag cagatagctt cgaggcctta    1560
ggggctaata ccattaaaga acctggtctt tgcccatctg tgtcttctaa tgaccaacaa    1620
gtaccttcgg ctgttggtgg cggtggctct ggaggtggtg ggtccggagg aggcggccgc    1680
acgagtgatg aggttcgcaa gaacctgatg gacatgttca gggatcgcca ggcgttttct    1740
gagcatacct ggaaaatgct tctgtccgtt tgccggtcgt gggcggcatg gtgcaagttg    1800
aataaccgga aatggtttcc cgcagaacct gaagatgttc gcgattatct tctatatctt    1860
caggcgcgcg gtctggcagt aaaaactatc cagcaacatt tgggccagct aaacatgctt    1920
catcgtcggt ccgggctgta a                                              1941
```

<210> SEQ ID NO 102
<211> LENGTH: 1275
<212> TYPE: DNA
<213> ORGANISM: Artificial sequence
<220> FEATURE:
<223> OTHER INFORMATION: Optogen 2 - CIBN(aa1-170)-NLS-Cre-C(aa106-343)

<400> SEQUENCE: 102

```
atgaatggag ctataggagg tgaccttttg ctcaattttc ctgacatgtc ggtcctagag    60
cgccaaaggg ctcacctcaa gtacctcaat cccacctttg attctcctct cgccggcttc    120
tttgccgatt cttcaatgat taccggcggc gagatggaca gctatctttc gactgccggt    180
ttgaatcttc cgatgatgta cggtgagacg acggtggaag gtgattcaag actctcaatt    240
tcgccggaaa cgacgcttgg gactggaaat ttcaagaaac ggaagtttga tacagagact    300
aaggattgta tgagaagaa gaagaagatg acgatgaaca gagatgacct agtagaagaa    360
ggagaagaag agaagtcgaa aataacagag caaaacaatg ggagcacaaa aagcatcaag    420
aagatgaaac acaaagccaa gaaagaagag aacaatttct ctaatgattc atctaaagtg    480
acgaaggaat tggagaaaac ggattatatt catggtggcg gtggctctgg aggtggtggg    540
tccggaggag gcggccgccg accaagtgac agcaatgctg tttcactggt tatgcggcgg    600
atccgaaaag aaaacgttga tgccggtgaa cgtgcaaaac aggctctagc gttcgaacgc    660
actgatttcg accaggttcg ttcactcatg gaaaatagcg atcgctgcca ggatatacgt    720
aatctggcat ttctggggat tgcttataac accctgttac gtatagccga aattgccagg    780
atcagggtta aagatatctc acgtactgac ggtgggagaa tgttaatcca tattggcaga    840
acgaaaacgc tggttagcac cgcaggtgta gagaaggcac ttagcctggg ggtaactaaa    900
ctggtcgagc gatggatttc cgtctctggt gtagctgatg atccgaataa ctacctgttt    960
tgccgggtca gaaaaaatgg tgttgccgcg ccatctgcca ccagccagct atcaactcgc    1020
gccctggaag ggattttga agcaactcat cgattgattt acggcgctaa ggatgactct    1080
ggtcagagat acctggcctg tgtctggacac agtgcccgtg tcggagccgc gcgagatatg    1140
gcccgcgctg agtttcaat accggagatc atgcaagctg tggctggac caatgtaaat    1200 attgtcatga actatatccg taacctggat agtgaaacag gggcaatggt gcgcctgctg    1260
gaagatggcg attag                                                    1275
```

<210> SEQ ID NO 103
<211> LENGTH: 585
<212> TYPE: DNA
<213> ORGANISM: Artificial sequence
<220> FEATURE:
<223> OTHER INFORMATION: IRES sequence

<400> SEQUENCE: 103
gcccctctcc ctcccccccc cctaacgtta ctggccgaag ccgcttggaa taaggccggt        60
gtgcgtttgt ctatatgtta ttttccacca tattgccgtc ttttggcaat gtgagggccc       120
ggaaacctgg ccctgtcttc ttgacgagca ttcctagggg tctttcccct ctcgccaaag       180
gaatgcaagg tctgttgaat gtcgtgaagg aagcagttcc tctggaagct tcttgaagac       240
aaacaacgtc tgtagcgacc ctttgcaggc agcggaaccc cccacctggc gacaggtgcc       300
tctgcggcca aaagccacgt gtataagata cacctgcaaa ggcggcacaa ccccagtgcc       360
acgttgtgag ttggatagtt gtggaaagag tcaaatggct ctcctcaagc gtattcaaca       420
aggggctgaa ggatgcccag aaggtacccc attgtatggg atctgatctg gggcctcggt       480
gcacatgctt tacatgtgtt tagtcgaggt taaaaaaacg tctaggcccc ccgaaccacg       540
gggacgtggt tttcctttga aaaacacgat gataatatgg ccaca                       585

<210> SEQ ID NO 104
<211> LENGTH: 524
<212> TYPE: DNA
<213> ORGANISM: Artificial sequence
<220> FEATURE:
<223> OTHER INFORMATION: polyadenylation site sequence (Rabbit beta-
      globin)

<400> SEQUENCE: 104
actcctcagg tgcaggctgc ctatcagaag gtggtggctg gtgtggccaa tgccctggct        60
cacaaatacc actgagatct ttttccctct gccaaaaatt atggggacat catgaagccc       120
cttgagcatc tgacttctgg ctaataaagg aaatttattt tcattgcaat agtgtgttgg       180 aatttttgt gtctctcact cggaaggaca tatgggaggg caaatcattt aaaacatcag       240
aatgagtatt tggtttagag tttggcaaca tatgcccata tgctggctgc catgaacaaa       300
ggttggctat aaagaggtca tcagtatatg aaacagcccc ctgctgtcca ttccttattc       360
catagaaaag ccttgacttg aggttagatt ttttttatat tttgttttgt gttatttttt       420
tctttaacat ccctaaaatt ttccttacat gttttactag ccagattttt cctcctctcc       480
tgactactcc cagtcatagc tgtccctctt ctcttatgga gatc                       524

<210> SEQ ID NO 105
<211> LENGTH: 1496
<212> TYPE: DNA
<213> ORGANISM: Artificial sequence
<220> FEATURE:
<223> OTHER INFORMATION: 5' homology arm

<400> SEQUENCE: 105
gaatgaaggg cctgagggtg ggcagtctgt ctatcatgta catctccata ttctgggagg        60
tcgtcagttg ggctggcctc ctggctaaga tttttgcacc acaagagatg ctgcatgtgt       120
acaaatcact agcaaataga tttgtttccc atcaacttag ccactgttaa tgtaaattgt       180
tcttggatat gtgtctttgg agggcaataa atgctctgaa cagcacttgc acaataaaga       240
tacagcatgt gggaatgatc tgtctcatgt gtcttactga tggtattggt tctgtaagat       300
aaaatattgt gtctgggatg tgtttggctc tactattaat ggtgctctat tgattgtgat       360
ttgtcatttg aaacctgagg atgcgactgt atagcagtct ttcatgcatt tttggaaaaa       420
aacttaagct ttttgaaagc tgctgctaca actttttgta ttgttataaa gttttgtatt       480
gtttttttaa ttgtgaaatt ataaagatgc cgtgcaggga ctgtttgaag caaagtgcat       540

-continued

```
tgttttagaa acctacaact ctagttcaag cactccatca gtatctgctt aatctttgtc      600
atcctttgct atgagaaaat attaagcagt agtctaaagg tactatgaaa ctataacata      660
gctgacattg tatttataac tacgtcatga ttttgataga attgaggact tgaaaatgtt      720
aaactattca tgtagggcct cttaagatgc ttaagttgtt tagtaatgta agtgtgcatt      780
taattgagat tttattgggc ataatttgtc catcagtatg acactccttg tcagtgttgc      840
cttatacttg atgttgttac cggatctctg caaggcagtt attcttgaat taggctcatt      900
gaagtgtctg ccagtataaa tatatagcaa ctgttctttg tgttaaaatt gagaagctaa      960
ccagttttta gtgcttctga ctgttggaat tctttaagca gatgccataa gaaaattgta     1020
tttgtgatca ccacttctcc agagtggttt taacaccaag ggcattagag aaagaaaggc     1080
aggcgtgtag agaatagtgg acagacaaaa gctgtgagtt acgttatgtt tttcagctga     1140
aaagctgtgt ttggtaaaag catatgaaat cactcaactt ggaagcattc tcttagttct     1200
ctgatagttc tgagcagcag aactcttcac ctaagaggtt acttcaactg gaagactacc     1260
tagtgcttct gatggcaact atatttaaga tgagaataag aggtgtttcc agtgtggtag     1320
cctcacatct gttgcagtgg ttaccgttcg tcctcctccg agggacacag cttggccatt     1380
cactgtggtg acaccaatat gatgatcagc aaatggtgtt tattcactac taaacacagc     1440
ttatatacat ttttacctac aaaatcgtgc tgtcatgtcc cactctgatt ggttca         1496
```

```
<210> SEQ ID NO 106
<211> LENGTH: 1564
<212> TYPE: DNA
<213> ORGANISM: Artificial sequence
<220> FEATURE:
<223> OTHER INFORMATION: 3' homology arm

<400> SEQUENCE: 106
gccgtttcca cattcttttc tcatccttct tctcctgttt tctctgcatc aaggtcagca       60
cgatagcact gtctctctat gcttagggag aggcctgtcc tgtacatccc gtgcccccac      120
aagatgccta ctacaacaac atcttctgca tgtcctgcat agcagtgttg ggagaatgtg      180
cactacttcc actcttctga tttctatttt atgtgtttgc tttataccag tgttgccatt      240
tgggaattaa tacatggttg atcaaatcaa ttgcatcaca gctgtatcct gtatcagagg      300
aacattatca aagcttttgt tgctgtattt ggtatctgac ctgcagataa acatgtttta      360
ggaaggtttt gcaaaagtag ctgtgaaatg agctggtgtt gtgatttaac ctgacaggca      420
gctaaacagt ataccacaga gctattcacc tactttccct cagtgggaaa agggaagaga      480
actgaggggg gggggaataa ataagtaaat aacaaaataa aactcatgga ttaagaaaaa      540
gactttgtac tggaatggat gagaagaata atagtaatga taataatatg tcactctgaa      600
agtaatgcct cttatttctg tggagactac aaacatacaa agagcacaac attccataga      660
gcaaattctc agttacagaa tgctattttt tttttcaaca cagtcaaaat cattaatttt      720
tttttgcctg caatggacaa gagctttgaa gctgttctcg taaaaatctg tactagcaga      780
agtgacctgc aatcactact gctgaaatgc acaacccacc acatcattgt gctcacattc      840
actgtttggt ttctgtaaat gtacaggaat tgtctgaaat tagatatgat ttttttttttc      900 tccatgaagg aattcaatta cacacctttg cctcatgcac ttctttgtca tttttgtcag      960
actgcttctc tcctgcaatt tgtctcatgg caacaaaata taatggagtt ctgctgggaa     1020
cttccctact gccataccac tatcatctgc ctctgacatt ttggacaaat gtaataaaat     1080
```

-continued

```
aggaggtatt actttcagag cagaccttgt atgtatttac aaaacaagtg gtacacaaaa    1140
aaaattgttc atcccaccaa ccaatgccca tcctgtccct gaatagtagc tgtcccccac    1200
agccttgacc agtttaggtc aacagttctg cttctgtccc ctcccagctc cttgtaaccc    1260
ctcagccccc cttgctggca ggacagtatg agaagctgaa aaactagaat gtcctagttc    1320
tttgcagtgc tgctaatcaa caaccaaaac agtggtgtgt taccaatatt gttgatatca    1380
cagcatcata ccattatgaa ggaagtaacc cagccaaaat caggtcagct tgctaacaag    1440
agaactgtgc ataagtttaa gatgtgtgtg ttcctcagta ccttaaaaaa taagtagtaa    1500
cgttcaaatg agtagaagag tagaactgag cttaaaacat ctgtcagaca acagtgaacc    1560
aacc                                                                 1564
```

<210> SEQ ID NO 107
<211> LENGTH: 627
<212> TYPE: DNA
<213> ORGANISM: Artificial sequence
<220> FEATURE:
<223> OTHER INFORMATION: Cre-N(aa18-59)_N-Mag_NLS

<400> SEQUENCE: 107

```
atggccacct ctgatgaagt caggaagaac ctgatggaca tgttcaggga caggcaggcc      60
ttctctgaac acacctggaa gatgctcctg tctgtgtgca gatcctgggc tgcctggtgc     120
aagctgaacg gtacccatac tctttatgcc cccggtggat atgacattat gggatatctg     180
gaccagatcg gcaaccggcc aaacccgcag gtggaactgg ccccgtggga tacatcctgc     240
gccttgattc tttgtgacct gaaacagaaa gacacccccga tagtttacgc gagtgaagcc     300
ttcctctaca tgacaggtta cagcaacgca gaggtgctgg ccggaattg ccggtttctg      360 caaagccctg acggcatggt gaagcccaag agcacccgga gtacgtggga tagtaacaca     420
atcaatacta tgcgcaaggc aatcgacagg aatgccgagg tgcaggttga agtagtcaat     480
tttaaaaaga atggacagcg atttgttaat ttcctgacta tgatacctgt tagggacgaa     540
acaggcgagt atcgatactc tatgggattc cagtgcgaaa cagaaggcgg aagcggtggc     600
gtgcccaaga agaagaggaa agtctag                                          627
```

<210> SEQ ID NO 108
<211> LENGTH: 1344
<212> TYPE: DNA
<213> ORGANISM: Artificial sequence
<220> FEATURE:
<223> OTHER INFORMATION: NLS_P-Mag_Cre-C(aa60-237)

<400> SEQUENCE: 108

```
atggtgccca agaagaagag gaaagtcggc ggacatactc tttatgcccc cggtggatat      60
gacattatgg gatatctgag gcagatcagg aaccggccaa acccgcaggt ggaactgggc     120
cccgtggata tcctgcgcgc cttgattctt tgtgacctga acagaaaga caccccgata      180 gtttacgcga gtgaagcctt cctctacatg acaggttaca gcaacgcaga ggtgctgggc     240
cggaattgcc ggtttctgca aagccctgac ggcatggtga gcccaagag cacccggaag     300 tacgtggata gtaacacaat caatactatg cgcaaggcaa tcgacaggaa tgccgaggtg     360
caggttgaag tagtcaattt aaaaagaat ggacagcgat ttgttaattt cctgactatg     420
atacctgtta gggacgaaac aggcgagtat cgatactcta tgggattcca gtgcgaaaca     480
gaaggtacca acaggaaatg gttccctgct gaacctgagg atgtgaggga ctacctcctg     540
tacctgcaag ccagaggcct ggctgtgaag accatccaac agcacctggg ccagctcaac     600
```

-continued

```
atgctgcaca ggagatctgg cctgcctcgc ccttctgact ccaatgctgt gtccctggtg      660
atgaggagaa tcagaaagga gaatgtggat gctggggaga gagccaagca ggccctggcc      720
tttgaacgca ctgactttga ccaagtcaga tccctgatgg agaactctga cagatgccag      780
gacatcagga acctggcctt cctgggcatt gcctacaaca ccctgctgcg cattgccgaa      840
attgccagaa tcagagtgaa ggacatctcc cgcaccgatg gtgggagaat gctgatccac      900
attggcagga ccaagaccct ggtgtccaca gctggtgtgg agaaggccct gtccctgggg      960
gttaccaagc tggtggagag atggatctct gtgtctggtg tggctgatga ccccaacaac     1020
tacctgttct gccgggtcag aaagaatggt gtggctgccc cttctgccac ctcccaactg     1080
tccacccggg ccctggaagg gatctttgag gccacccacc gcctgatcta tggtgccaag     1140
gatgactctg ggcagagata cctggcctgg tctggccact ctgccagagt gggtgctgcc     1200
agggacatgg ccagggctgg tgtgtccatc cctgaaatca tgcaggctgg tggctggacc     1260
aatgtgaaca ttgtgatgaa ctacatcaga aacctggact ctgagactgg ggccatggtg     1320
aggctgctcg aagatgggga ctag                                            1344
```

<210> SEQ ID NO 109
<211> LENGTH: 509
<212> TYPE: DNA
<213> ORGANISM: Artificial sequence
<220> FEATURE:
<223> OTHER INFORMATION: pGK promotor

<400> SEQUENCE: 109

```
accgggtagg ggaggcgctt ttcccaaggc agtctggagc atgcgcttta gcagccccgc       60
tgggcacttg gcgctacaca agtggcctct ggcctcgcac acattccaca tccaccggta      120
ggcgccaacc ggctccgttc tttggtggcc ccttcgcgcc accttctact cctcccctag      180
tcaggaagtt ccccccccgcc ccgcagctcg cgtcgtgcag gacgtgacaa atggaagtag      240
cacgtctcac tagtctcgtg cagatggaca gcaccgctga gcaatggaag cgggtaggcc      300
tttggggcag cggccaatag cagctttgct ccttcgcttt ctgggctcag aggctgggaa      360
ggggtgggtc cggggcggg ctcagggggcg ggctcagggg cggggcgggc gcccgaaggt      420
cctccggagg cccggcattc tgcacgcttc aaaagcgcac gtctgccgcg ctgttctcct      480
cttcctcatc tccgggcctt tcgacctgc                                        509
```

<210> SEQ ID NO 110
<211> LENGTH: 508
<212> TYPE: DNA
<213> ORGANISM: Artificial sequence
<220> FEATURE:
<223> OTHER INFORMATION: pCMV promotor

<400> SEQUENCE: 110

```
cgttacataa cttacggtaa atggcccgcc tggctgaccg cccaacgacc cccgcccatt       60
gacgtcaata atgacgtatg ttcccatagt aacgccaata gggactttcc attgacgtca      120
atgggtggag tatttacggt aaactgccca cttggcagta catcaagtgt atcatatgcc      180
aagtacgccc cctattgacg tcaatgacgg taaatggccc gcctggcatt atgcccagta      240
catgacctta tgggactttc ctacttggca gtacatctac gtattagtca tcgctattac      300
catggtgatg cggttttggc agtacatcaa tgggcgtgga tagcggtttg actcacgggg      360
atttccaagt ctccaccccca ttgacgtcaa tgggagtttg ttttggcacc aaaatcaacg      420
```

-continued

```
ggactttcca aaatgtcgta acaactccgc cccattgacg caaatgggcg gtaggcgtgt      480
acggtgggag gtctatataa gcagagct                                        508

<210> SEQ ID NO 111
<211> LENGTH: 448
<212> TYPE: DNA
<213> ORGANISM: Artificial sequence
<220> FEATURE:
<223> OTHER INFORMATION: phSyn promotor

<400> SEQUENCE: 111
agtgcaagtg ggttttagga ccaggatgag gcggggtggg ggtgcctacc tgacgaccga       60
ccccgaccca ctggacaagc acccaacccc cattccccaa attgcgcatc ccctatcaga      120 gaggggggagg ggaaacagga tgcggcgagg cgcgtgcgca ctgccagctt cagcaccgcg     180
gacagtgcct tcgcccccgc ctggcggcgc gcgccaccgc cgcctcagca ctgaaggcgc      240
gctgacgtca ctcgccggtc ccccgcaaac tccccttccc ggccaccttg gtcgcgtccg      300
cgccgccgcc ggcccagccg gaccgcacca cgcgaggcgc gagatagggg ggcacgggcg      360
cgaccatctg cgctgcggcg ccggcgactc agcgctgcct cagtctgcgg tgggcagcgg      420
aggagtcgtg tcgtgcctga gagcgcag                                        448

<210> SEQ ID NO 112
<211> LENGTH: 1189
<212> TYPE: DNA
<213> ORGANISM: Artificial sequence
<220> FEATURE:
<223> OTHER INFORMATION: pEF1-a promotor

<400> SEQUENCE: 112
cgtgaggctc cggtgcccgt cagtgggcag agcgcacatc gcccacagtc cccgagaagt       60
tggggggagg ggtcggcaat tgaaccggtg cctagagaag gtggcgcggg gtaaactggg      120
aaagtgatgt cgtgtactgg ctccgccttt ttcccgaggg tggggggagaa ccgtatataa     180 gtgcagtagt cgccgtgaac gttctttttc gcaacgggtt tgccgccaga acacaggtaa      240
gtgccgtgtg tggttcccgc gggcctggcc tctttacggg ttatggccct tgcgtgcctt      300
gaattacttc cacgcccctg gctgcagtac gtgattcttg atcccgagct tcgggttgga      360
agtgggtggg agagttcgag gccttgcgct taaggagccc cttcgcctcg tgcttgagtt      420
gaggcctggc ctgggcgctg gggccgccgc gtgcgaatct ggtggcacct tcgcgcctgt      480
ctcgctgctt tcgataagtc tctagccatt taaaattttt gatgacctgc tgcgacgctt      540
tttttctggc aagatagtct tgtaaatgcg ggccaagatc tgcacactgg tatttcggtt      600
tttggggccg cgggcggcga cggggcccgt gcgtcccagc gcacatgttc ggcgaggcgg      660
ggcctgcgag cgcggccacc gagaatcgga cgggggtagt ctcaagctgg ccggcctgct      720
ctggtgcctg gcctcgcgcc gccgtgtatc gccccgccct gggcggcaag gctggcccgg      780
tcggcaccag ttgcgtgagc ggaaagatgg ccgcttcccg gccctgctgc agggagctca      840
aaatggagga cgcggcgctc gggagagcgg gcgggtgagt cacccacaca aaggaaaagg      900
gcctttccgt cctcagccgt cgcttcatgt gactccacgg agtaccgggc gccgtccagg      960
cacctcgatt agttctcgag cttttggagt acgtcgtctt taggttgggg ggaggggttt     1020
tatgcgatgg agtttcccca cactgagtgg gtgagactg aagttaggcc agcttggcac      1080
ttgatgtaat tctccttgga atttgccctt tttgagtttg gatcttggtt cattctcaag     1140
cctcagacag tggttcaaag ttttttttctt ccatttcagg tgtcgtgag              1189
```

<210> SEQ ID NO 113
<211> LENGTH: 1056
<212> TYPE: DNA
<213> ORGANISM: Artificial sequence
<220> FEATURE:
<223> OTHER INFORMATION: Cre recombinase

<400> SEQUENCE: 113
atggcaccca agaagaagag gaaggtgtcc aatttactga ccgtacacca aaatttgcct        60
gcattaccgg tcgatgcaac gagtgatgag gttcgcaaga acctgatgga catgttcagg       120
gatcgccagc cgttttctga gcatacctgg aaaatgcttc tgtccgtttg ccggtcgtgg       180
gcggcatggt gcaagttgaa taaccggaaa tggtttcccg cagaacctga agatgttcgc       240
gattatcttc tatatcttca ggcgcgcggt ctggcagtaa aaactatcca gcaacatttg       300
ggccagctaa acatgcttca tcgtcggtcc gggctgccac gaccaagtga cagcaatgct       360
gtttcactgg ttatgcggcg gatccgaaaa gaaaacgttg atgccggtga acgtgcaaaa       420
caggctctag cgttcgaacg cactgatttc gaccaggttc gttcactcat ggaaaatagc       480
gatcgctgcc aggatatacg taatctggca tttctgggga ttgcttataa caccctgtta       540
cgtatagccg aaattgccag gatcagggtt aaagatatct cacgtactga cggtgggaga       600
atgttaatcc atattggcag aacgaaaacg ctggttagca ccgcaggtgt agagaaggca       660
cttagcctgg gggtaactaa actggtcgag cgatggattt ccgtctctgg tgtagctgat       720
gatccgaata actacctgtt ttgccgggtc agaaaaaatg gtgttgccgc gccatctgcc       780
accagccagc tatcaactcg cgccctggaa gggatttttg aagcaactca tcgattgatt       840
tacggcgcta aggatgactc tggtcagaga tacctggcct ggtctggaca cagtgcccgt       900
gtcggagccg cgcgagatat ggcccgcgct ggagtttcaa taccggagat catgcaagct       960
ggtggctgga ccaatgtaaa tattgtcatg aactatatcc gtaacctgga tagtgaaaca      1020
ggggcaatgg tgcgcctgct ggaagatggc gattag                                1056

<210> SEQ ID NO 114
<211> LENGTH: 450
<212> TYPE: DNA
<213> ORGANISM: Artificial sequence
<220> FEATURE:
<223> OTHER INFORMATION: Positive Mag recombinase

<400> SEQUENCE: 114
catactcttt atgcccccgg tggatatgac attatgggat atctgaggca gatcaggaac        60
cggccaaacc cgcaggtgga actgggcccc gtggatacat cctgcgcctt gattctttgt       120
gacctgaaac agaaagacac cccgatagtt tacgcgagtg aagccttcct ctacatgaca       180
ggttacagca acgcagaggt gctgggccgg aattgccggt ttctgcaaag ccctgacggc       240
atggtgaagc ccaagagcac ccggaagtac gtggatagta acacaatcaa tactatgcgc       300
aaggcaatcg acaggaatgc cgaggtgcag gttgaagtag tcaattttaa aaagaatgga       360
cagcgatttg ttaatttcct gactatgata cctgttaggg acgaaacagg cgagtatcga       420
tactctatgg gattccagtg cgaaacagaa                                        450

<210> SEQ ID NO 115
<211> LENGTH: 720
<212> TYPE: DNA
<213> ORGANISM: Artificial sequence
<220> FEATURE:

```
<223> OTHER INFORMATION: green fluorescence protein (GFP)

<400> SEQUENCE: 115
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720

<210> SEQ ID NO 116
<211> LENGTH: 34
<212> TYPE: DNA
<213> ORGANISM: Artificial sequence
<220> FEATURE:
<223> OTHER INFORMATION: Lox site

<400> SEQUENCE: 116
ataacttcgt ataatgtatg ctatacgaag ttat                                   34

<210> SEQ ID NO 117
<211> LENGTH: 258
<212> TYPE: DNA
<213> ORGANISM: Artificial sequence
<220> FEATURE:
<223> OTHER INFORMATION: CreN (AA 19-104)

<400> SEQUENCE: 117
acgagtgatg aggttcgcaa gaacctgatg gacatgttca gggatcgcca ggcgttttct      60
gagcatacct ggaaaatgct tctgtccgtt tgccggtcgt gggcggcatg gtgcaagttg     120
aataaccgga aatggtttcc cgcagaacct gaagatgttc gcgattatct tctatatctt     180
caggcgcgcg gtctggcagt aaaaactatc cagcaacatt tgggccagct aaacatgctt     240
catcgtcggt ccgggctg                                                    258

<210> SEQ ID NO 118
<211> LENGTH: 717
<212> TYPE: DNA
<213> ORGANISM: Artificial sequence
<220> FEATURE:
<223> OTHER INFORMATION: CreC (AA 106-343)

<400> SEQUENCE: 118
cgaccaagtg acagcaatgc tgtttcactg gttatgcggc ggatccgaaa agaaaacgtt      60
gatgccggtg aacgtgcaaa acaggctcta gcgttcgaac gcactgattt cgaccaggtt     120
cgttcactca tggaaaatag cgatcgctgc caggatatac gtaatctggc atttctgggg     180
attgcttata caccctgtt acgtatagcc gaaattgcca ggatcagggt aaagatatc      240 tcacgtactg acggtgggag aatgttaatc catattggca gaacgaaaac gctggttagc     300
```

```
accgcaggtg tagagaaggc acttagcctg ggggtaacta aactggtcga gcgatggatt      360
tccgtctctg gtgtagctga tgatccgaat aactacctgt tttgccgggt cagaaaaaat      420
ggtgttgccg cgccatctgc caccagccag ctatcaactc gcgccctgga agggattttt      480
gaagcaactc atcgattgat ttacggcgct aaggatgact ctggtcagag atacctggcc      540
tggtctggac acagtgcccg tgtcggagcc gcgcgagata tggcccgcgc tggagtttca      600
ataccggaga tcatgcaagc tggtggctgg accaatgtaa atattgtcat gaactatatc      660
cgtaacctgg atagtgaaac aggggcaatg gtgcgcctgc tggaagatgg cgattag        717
```

```
<210> SEQ ID NO 119
<211> LENGTH: 711
<212> TYPE: DNA
<213> ORGANISM: Artificial sequence
<220> FEATURE:
<223> OTHER INFORMATION: mCherry/RFP

<400> SEQUENCE: 119
atggtgagca agggcgagga ggataacatg gccatcatca aggagttcat gcgcttcaag       60
gtgcacatgg agggctccgt gaacggccac gagttcgaga tcgagggcga gggcgagggc      120
cgcccctacg agggcaccca gaccgccaag ctgaaggtga ccaagggtgg ccccctgccc      180
ttcgcctggg acatcctgtc ccctcagttc atgtacggct ccaaggccta cgtgaagcac      240
cccgccgaca tccccgacta cttgaagctg tccttccccg agggcttcaa gtgggagcgc      300
gtgatgaact tcgaggacgg cggcgtggtg accgtgaccc aggactcctc cctgcaggac      360
ggcgagttca tctacaaggt gaagctgcgc ggcaccaact cccctccga cggccccgta      420 atgcagaaga agaccatggg ctgggaggcc tcctccgagc ggatgtaccc cgaggacggc      480
gccctgaagg gcgagatcaa gcagaggctg aagctgaagg acggcggcca ctacgacgct      540
gaggtcaaga ccacctacaa ggccaagaag cccgtgcagc tgcccggcgc ctacaacgtc      600
aacatcaagt tggacatcac ctcccacaac gaggactaca ccatcgtgga acagtacgaa      660
cgcgccgagg ccgccactc caccggcggc atggacgagc tgtacaagta a               711
```

```
<210> SEQ ID NO 120
<211> LENGTH: 9811
<212> TYPE: DNA
<213> ORGANISM: Artificial Sequence
<220> FEATURE:
<223> OTHER INFORMATION: Targeting Vector TV1

<400> SEQUENCE: 120
gaatgaaggg cctgagggtg ggcagtctgt ctatcatgta catctccata ttctgggagg       60
tcgtcagttg ggctggcctc ctggctaaga tttttgcacc acaagagatg ctgcatgtgt      120
acaaatcact agcaaataga tttgtttccc atcaacttag ccactgttaa tgtaaattgt      180
tcttggatat gtgtctttgg agggcaataa atgctctgaa cagcacttgc acaataaaga      240
tacagcatgt gggaatgatc tgtctcatgt gtcttactga tggtattggt tctgtaagat      300
aaaatattgt gtctgggatg tgtttggctc tactattaat ggtgctctat tgattgtgat      360
ttgtcatttg aaacctgagg atgcgactgt atagcagtct ttcatgcatt tttggaaaaa      420
aacttaagct ttttgaaagc tgctgctaca acttttttgta ttgttataaa gttttgtatt      480
gtttttttaa ttgtgaaatt ataaagatgc gtgcaggga ctgtttgaag caaagtgcat      540 tgtttttagaa acctacaact ctagttcaag cactccatca gtatctgctt aatctttgtc      600
```

-continued

```
atcctttgct atgagaaaat attaagcagt agtctaaagg tactatgaaa ctataacata      660
gctgacattg tatttataac tacgtcatga ttttgataga attgaggact tgaaaatgtt      720
aaactattca tgtagggcct cttaagatgc ttaagttgtt tagtaatgta agtgtgcatt      780
taattgagat tttattgggc ataatttgtc catcagtatg acactccttg tcagtgttgc      840
cttatacttg atgttgttac cggatctctg caaggcagtt attcttgaat taggctcatt      900
gaagtgtctg ccagtataaa tatatagcaa ctgttctttg tgttaaaatt gagaagctaa      960
ccagttttta gtgcttctga ctgttggaat tctttaagca gatgccataa gaaaattgta     1020
tttgtgatca ccacttctcc agagtggttt taacaccaag ggcattagag aaagaaaggc     1080
aggcgtgtag agaatagtgg acagacaaaa gctgtgagtt acgttatgtt tttcagctga     1140
aaagctgtgt ttggtaaaag catatgaaat cactcaactt ggaagcattc tcttagttct     1200
ctgatagttc tgagcagcag aactcttcac ctaagaggtt acttcaactg gaagactacc     1260
tagtgcttct gatggcaact atatttaaga tgagaataag aggtgtttcc agtgtggtag     1320
cctcacatct gttgcagtgg ttaccgttcg tcctcctccg agggacacag cttggccatt     1380
cactgtggtg acaccaatat gatgatcagc aaatggtgtt tattcactac taaacacagc     1440
ttatatacat ttttacctac aaaatcgtgc tgtcatgtcc cactctgatt ggttcacaca     1500
tttccccgaa aagtgccacc tgggtcgaca ttgattattg actagttatt aatagtaatc     1560
aattacgggg tcattagttc atagcccata tatggagttc cgcgttacat aacttacggt     1620
aaatggcccg cctggctgac cgcccaacga cccccgccca ttgacgtcaa taatgacgta     1680
tgttcccata gtaacgccaa tagggacttt ccattgacgt caatgggtgg agtatttacg     1740
gtaaactgcc cacttggcag tacatcaagt gtatcatatg ccaagtacgc cccctattga     1800
cgtcaatgac ggtaaatggc ccgcctggca ttatgcccag tacatgacct tatgggactt     1860
tcctacttgg cagtacatct acgtattagt catcgctatt accatggtcg aggtgagccc     1920
cacgttctgt ttcactctcc ccatctcccc cccctcccca cccccaattt tgtatttatt     1980
tattttttaa ttattttgtg cagcgatggg ggcggggggg gggggggggc gcgcgccagg     2040
cggggcgggg cggggcgagg ggcggggcgg ggcgaggcgg agaggtgcgg cggcagccaa     2100
tcagagcggc gcgctccgaa agtttccttt tatggcgagg cggcggcggc ggcggcccta     2160
taaaaagcga agcgcgcggc gggcggggag tcgctgcgac gctgccttcg ccccgtgccc     2220
cgctccgccg ccgcctcgcg ccgcccgccc cggctctgac tgaccgcgtt actcccacag     2280
gtgagcgggc gggacggccc ttctcctccg ggctgtaatt agcgcttggt ttaatgacgg     2340
cttgtttctt ttctgtggct gcgtgaaagc cttgaggggc tccgggaggg ccctttgtgc     2400 gggggggagcg gctcgggggg tgcgtgcgtg tgtgtgtgcg tggggagcgc cgcgtgcggc     2460
tccgcgctgc ccggcggctg tgagcgctgc gggcgcggcg cggggctttg tgcgctccgc     2520
agtgtgcgcg aggggagcgc ggccgggggc ggtgccccgc ggtgcggggg gggctgcgag     2580
gggaacaaag gctgcgtgcg gggtgtgtgc gtgggggggt gagcagggg tgtgggcgcg     2640 tcggtcgggc tgcaacccc cctgcacccc cctccccgag ttgctgagca cggcccggct     2700
tcgggtgcgg ggctccgtac ggggcgtggc gcggggctcg ccgtgccggg cggggggtgg     2760
cggcaggtgg gggtgccggg cggggcgggg ccgcctcggg ccggggaggg ctcgggggag     2820
gggcgcggcg gccccggag cgccggcggc tgtcgaggcg cggcgagccg cagccattgc     2880
cttttatggt aatcgtgcga gagggcgcag ggacttcctt tgtcccaaat ctgtgcggag     2940
ccgaaatctg ggaggcgccg ccgcacccc tctagcgggc gcggggcgaa gcggtgcggc     3000
```

-continued

```
gccggcagga aggaaatggg cggggagggc cttcgtgcgt cgccgcgccg ccgtcccctt   3060
ctccctctcc agcctcgggg ctgtccgcgg ggggacggct gccttcgggg gggacggggc   3120
agggcggggt tcggcttctg gcgtgtgacc ggcggctcta gagcctctgc taaccatgtt   3180
catgccttct tcttttttcct acagctcctg ggcaacgtgc tggttaataa cttcgtataa   3240
tgtatgctat acgaagttat accggtgaag ttcctattcc gaagttccta ttctctagaa   3300
agtataggaa cttcgccacc atggtgagca agggcgagga gctgttcacc ggggtggtgc   3360
ccatcctggt cgagctggac ggcgacgtaa acggccacaa gttcagcgtg tccggcgagg   3420
gcgagggcga tgccacctac ggcaagctga ccctgaagtt catctgcacc accggcaagc   3480
tgcccgtgcc ctggcccacc ctcgtgacca ccctgaccta cggcgtgcag tgcttcagcc   3540
gctaccccga ccacatgaag cagcacgact tcttcaagtc cgccatgccc gaaggctacg   3600
tccaggagcg caccatcttc ttcaaggacg acggcaacta caagacccgc gccgaggtga   3660
agttcgaggg cgacaccctg gtgaaccgca tcgagctgaa gggcatcgac ttcaaggagg   3720
acggcaacat cctggggcac aagctggagt acaactacaa cagccacaac gtctatatca   3780
tggccgacaa gcagaagaac ggcatcaagg tgaacttcaa gatccgccac aacatcgagg   3840
acggcagcgt gcagctcgcc gaccactacc agcagaacac ccccatcggc gacggccccg   3900
tgctgctgcc cgacaaccac tacctgagca cccagtccgc cctgagcaaa gaccccaacg   3960
agaagcgcga tcacatggtc ctgctggagt tcgtgaccgc cgccgggatc actctcggca   4020
tggacgagct gtacaagggc agcggcgcca ccaacttcag cctgctgaag caggccggcg   4080
acgtggagga gaaccccggc cccgctagct aaagcggccg ccaattccta gagctcgctg   4140
atcagcctcg actgtgcctt ctagttgcca gccatctgtt gtttgcccct cccccgtgcc   4200
ttccttgacc ctggaaggtg ccactcccac tgtcctttcc taataaaatg aggaaattgc   4260
atcgcattgt ctgagtaggt gtcattctat tctggggggt ggggtggggc aggacagcaa   4320 ggggggaggat tgggaagaca atagcaggca tgctggggag aagttcctat tccgaagttc   4380
ctattctcta gaaagtatag gaacttcgct agcaccggtg ccaccatggc cacctctgat   4440
gaagtcagga agaacctgat ggacatgttc agggacaggc aggccttctc tgaacacacc   4500
tggaagatgc tcctgtctgt gtgcagatcc tgggctgcct ggtgcaagct gaacggtacc   4560
catactcttt atgcccccgg tggatatgac attatgggat atctggacca gatcggcaac   4620
cggccaaacc cgcaggtgga actgggcccc gtggatacat cctgcgcctt gattctttgt   4680
gacctgaaac agaaagacac cccgatagtt tacgcgagtg aagccttcct ctacatgaca   4740
ggttacagca acgcagaggt gctgggccgg aattgccggt ttctgcaaag ccctgacggc   4800
atggtgaagc ccaagagcac ccggaagtac gtggatagta acacaatcaa tactatgcgc   4860
aaggcaatcg acaggaatgc cgaggtgcag gttgaagtag tcaattttaa aaagaatgga   4920
cagcgatttg ttaatttcct gactatgata cctgttaggg acgaaacagg cgagtatcga   4980
tactctatgg gattccagtg cgaaacagaa ggcggaagcg gtggcgtgcc caagaagaag   5040
aggaaagtct tcgaaggcag cggcgccacc aacttcagcc tgctgaagca ggccggcgac   5100
gtggaggaga accccggccc cttcgaagtg cccaagaaga gaggaaagt cggcggacat   5160 actctttatg cccccggtgg atatgacatt atgggatatc tgaggcagat caggaaccgg   5220
ccaaacccgc aggtggaact gggccccgtg gatacatcct gcgccttgat tctttgtgac   5280
ctgaaacaga aagacacccc gatagtttac gcgagtgaag ccttcctcta catgacaggt   5340
```

-continued

```
tacagcaacg cagaggtgct gggccggaat tgccggtttc tgcaaagccc tgacggcatg      5400
gtgaagccca agagcacccg gaagtacgtg gatagtaaca caatcaatac tatgcgcaag      5460
gcaatcgaca ggaatgccga ggtgcaggtt gaagtagtca attttaaaaa gaatggacag      5520
cgatttgtta atttcctgac tatgatacct gttaggacg  aaacaggcga gtatcgatac      5580
tctatgggat tccagtgcga aacagaaggt accaacagga aatggttccc tgctgaacct      5640
gaggatgtga gggactacct cctgtacctg caagccagag gcctggctgt gaagaccatc      5700
caacagcacc tgggccagct caacatgctg cacaggagat ctggcctgcc tcgcccttct      5760
gactccaatg ctgtgtccct ggtgatgagg agaatcagaa aggagaatgt ggatgctggg      5820
gagagagcca agcaggccct ggcctttgaa cgcactgact ttgaccaagt cagatccctg      5880
atggagaact ctgacagatg ccaggacatc aggaacctgg ccttcctggg cattgcctac      5940
aacaccctgc tgcgcattgc cgaaattgcc agaatcagag tgaaggacat ctcccgcacc      6000
gatggtggga gaatgctgat ccacattggc aggaccaaga ccctggtgtc cacagctggt      6060
gtggagaagg ccctgtccct gggggttacc aagctggtgg agagatggat ctctgtgtct      6120
ggtgtggctg atgaccccaa caactacctg ttctgccggg tcagaaagaa tggtgtggct      6180
gccccttctg ccacctccca actgtccacc cgggccctgg aagggatctt tgaggccacc      6240
caccgcctga tctatggtgc caaggatgac tctgggcaga gatacctggc ctggtctggc      6300
cactctgcca gagtgggtgc tgccagggac atggccaggc tggtgtgtc  catccctgaa      6360 atcatgcagg ctggtggctg gaccaatgtg aacattgtga tgaactacat cagaaacctg      6420
gactctgaga ctgggggccat ggtgaggctg ctcgaagatg gggactaatt aattaactcc      6480
tcaggtgcag gctgcctatc agaaggtggt ggctggtgtg gccaatgccc tggctcacaa      6540
ataccactga gatcttttc  cctctgccaa aaattatggg gacatcatga agccccttga      6600
gcatctgact tctggctaat aaaggaaatt tattttcatt gcaatagtgt gttggaattt      6660
tttgtgtctc tcactcggaa ggacatatgg gagggcaaat catttaaaac atcagaatga      6720
gtatttggtt tagagtttgg caacatatgc ccatatgctg gctgccatga acaaaggttg      6780
gctataaaga ggtcatcagt atatgaaaca gccccctgct gtccattcct tattccatag      6840
aaaagccttg acttgaggtt agatttttt  tatattttgt tttgtgttat ttttttcttt      6900
aacatcccta aaattttcct tacatgtttt actagccaga ttttccctcc tctcctgact      6960
actcccagtc atagctgtcc ctcttctctt atggagatca taacttcgta taatgtatgc      7020
tatacgaagt tatacgcgtg ccaccatgga tcattcccag tgccttgtga ctatatacgc      7080
cgcggcggtg ctgctggggc tccggctgca gcagggctcc tgccagcact acctgcacat      7140
ccgcccggct cccagcgaca acctgcccct ggtggatcta atcgagcacc cggaccctat      7200
ctttgacccc aaggagaagg atcttaacga gaccttgcta aggagcctca tgggaggaca      7260
cttcgaccct aacttatgg  ctatgtccct gcccgaggac cggctcgggg tagacgatct      7320
ggccgagctg gacttgctgc tgcggcagag accctcggga gcgatgcccg cgaaatcaa      7380 ggggctggag ttctacgacg ggctgcagcc gggcaagaag cacaggctga gcaagaagct      7440
gcgcaggaag ctgcagatgt ggctctggtc ccagaccttc tgcccggtcc tatacacgtg      7500
gaacgatctc ggcagccgct tttggccccg gtacgtcaaa gtgggcagct gctacagtaa      7560
aaggtcttgc tctgtcccag aaggcatggt ctgcaaacct gccaagtccg tgcatttaac      7620
gatcctgagg tggcggtgcc agcggcgggg cgggcagcgg tgcacgtgga tccccatcca      7680
gtaccccatc atcgcggagt gcaagtgctc ctgctagacg cgtactcctc aggtgcaggc      7740
```

```
tgcctatcag aaggtggtgg ctggtgtggc caatgccctg gctcacaaat accactgaga     7800 tcttttttccc tctgccaaaa attatgggga catcatgaag ccccttgagc atctgacttc     7860
tggctaataa aggaaattta ttttcattgc aatagtgtgt tggaattttt tgtgtctctc     7920
actcggaagg acatatggga gggcaaatca tttaaaacat cagaatgagt atttggttta     7980
gagtttggca acatatgccc atatgctggc tgccatgaac aaaggttggc tataaagagg     8040
tcatcagtat atgaaacagc cccctgctgt ccattcctta ttccatagaa aagccttgac     8100
ttgaggttag attttttta tattttgttt tgtgttattt ttttctttaa catccctaaa     8160
attttcctta catgttttac tagccagatt tttcctcctc tcctgactac tcccagtcat     8220
agctgtccct cttctcttat ggagatcgcc gtttccacat tcttttctca tccttcttct     8280
cctgttttct ctgcatcaag gtcagcacga tagcactgtc tctctatgct tagggagagg     8340
cctgtcctgt acatcccgtg cccccacaag atgcctacta caacaacatc ttctgcatgt     8400
cctgcatagc agtgttggga gaatgtgcac tacttccact cttctgattt ctattttatg     8460
tgtttgcttt ataccagtgt tgccatttgg gaattaatac atggttgatc aaatcaattg     8520
catcacagct gtatcctgta tcagaggaac attatcaaag cttttgttgc tgtatttggt     8580
atctgacctg cagataaaca tgttttagga aggtttttgca aaagtagctg tgaaatgagc     8640
tggtgttgtg atttaacctg acaggcagct aaacagtata ccacagagct attcacctac     8700
tttccctcag tgggaaaagg gaagagaact gaggggggggg ggaataaata agtaaataac     8760
aaaataaaac tcatggatta agaaaaagac tttgtactgg aatggatgag aagaataata     8820
gtaatgataa taatatgtca ctctgaaagt aatgcctctt atttctgtgg agactacaaa     8880
catacaaaga gcacaacatt ccatagagca aattctcagt tacagaatgc tattttttt     8940 ttcaacacag tcaaaatcat taattttttt ttgcctgcaa tggacaagag ctttgaagct     9000
gttctcgtaa aaatctgtac tagcagaagt gacctgcaat cactactgct gaaatgcaca     9060
acccaccaca tcattgtgct cacattcact gtttggtttc tgtaaatgta caggaattgt     9120
ctgaaattag atatgatttt tttttttctcc atgaaggaat tcaattacac acctttgcct     9180
catgcacttc tttgtcattt ttgtcagact gcttctctcc tgcaatttgt ctcatggcaa     9240
caaaatataa tggagttctg ctgggaactt ccctactgcc ataccactat catctgcctc     9300
tgacattttg gacaaatgta ataaaatagg aggtattact ttcagagcag accttgtatg     9360
tatttacaaa acaagtggta cacaaaaaaa attgttcatc ccaccaacca atgcccatcc     9420
tgtccctgaa tagtagctgt cccccacagc cttgaccagt ttaggtcaac agttctgctt     9480
ctgtcccctc ccagctcctt gtaacccctc agcccccctt gctggcagga cagtatgaga     9540
agctgaaaaa ctagaatgtc ctagttcttt gcagtgctgc taatcaacaa ccaaaacagt     9600
ggtgtgttac caatattgtt gatatcacag catcatacca ttatgaagga agtaacccag     9660
ccaaaatcag gtcagcttgc taacaagaga actgtgcata agtttaagat gtgtgtgttc     9720
ctcagtacct taaaaaataa gtagtaacgt tcaaatgagt agaagagtag aactgagctt     9780
aaaacatctg tcagacaaca gtgaaccaac c                                     9811
```

<210> SEQ ID NO 121
<211> LENGTH: 9796
<212> TYPE: DNA
<213> ORGANISM: Artificial Sequence
<220> FEATURE:
<223> OTHER INFORMATION: Targeting Vector TV2

```
<400> SEQUENCE: 121
gaatgaaggg cctgagggtg ggcagtctgt ctatcatgta catctccata ttctgggagg      60
tcgtcagttg ggctggcctc ctggctaaga ttttttgcacc acaagagatg ctgcatgtgt     120
acaaatcact agcaaataga tttgtttccc atcaacttag ccactgttaa tgtaaattgt      180
tcttggatat gtgtctttgg agggcaataa atgctctgaa cagcacttgc acaataaaga      240
tacagcatgt gggaatgatc tgtctcatgt gtcttactga tggtattggt tctgtaagat      300
aaaatattgt gtctgggatg tgtttggctc tactattaat ggtgctctat tgattgtgat      360
ttgtcatttg aaacctgagg atgcgactgt atagcagtct ttcatgcatt tttggaaaaa      420
aacttaagct ttttgaaagc tgctgctaca acttttttgta ttgttataaa gttttgtatt     480 gttttttttaa ttgtgaaatt ataaagatgc cgtgcaggga ctgtttgaag caaagtgcat     540
tgttttagaa acctacaact ctagttcaag cactccatca gtatctgctt aatctttgtc      600
atcctttgct atgagaaaat attaagcagt agtctaaagg tactatgaaa ctataacata      660
gctgacattg tatttataac tacgtcatga ttttgataga attgaggact tgaaaatgtt      720
aaactattca tgtagggcct cttaagatgc ttaagttgtt tagtaatgta agtgtgcatt      780
taattgagat tttattgggc ataatttgtc catcagtatg acactccttg tcagtgttgc      840
cttatacttg atgttgttac cggatctctg caaggcagtt attcttgaat taggctcatt      900
gaagtgtctg ccagtataaa tatatagcaa ctgttctttg tgttaaaatt gagaagctaa      960
ccagttttta gtgcttctga ctgttggaat tctttaagca gatgccataa gaaaattgta     1020
tttgtgatca ccacttctcc agagtggttt taacaccaag ggcattagag aaagaaaggc     1080
aggcgtgtag agaatagtgg acagacaaaa gctgtgagtt acgttatgtt tttcagctga     1140
aaagctgtgt ttggtaaaag catatgaaat cactcaactt ggaagcattc tcttagttct     1200
ctgatagttc tgagcagcag aactcttcac ctaagaggtt acttcaactg gaagactacc     1260
tagtgcttct gatggcaact atatttaaga tgagaataag aggtgtttcc agtgtggtag     1320
cctcacatct gttgcagtgg ttaccgttcg tcctcctccg agggacacag cttggccatt     1380
cactgtggtg acaccaatat gatgatcagc aaatggtgtt tattcactac taaacacagc     1440
ttatatacat ttttacctac aaaatcgtgc tgtcatgtcc cactctgatt ggttcacaca     1500
tttccccgaa aagtgccacc tgggtcgaca ttgattattg actagttatt aatagtaatc     1560
aattacgggg tcattagttc atagcccata tatggagttc cgcgttacat aacttacggt     1620
aaatggcccg cctggctgac cgcccaacga cccccgccca ttgacgtcaa taatgacgta     1680
tgttcccata gtaacgccaa tagggacttt ccattgacgt caatgggtgg agtatttacg     1740
gtaaactgcc cacttggcag tacatcaagt gtatcatatg ccaagtacgc cccctattga     1800
cgtcaatgac ggtaaatggc ccgcctggca ttatgcccag tacatgacct tatgggactt     1860
tcctacttgg cagtacatct acgtattagt catcgctatt accatggtcg aggtgagccc     1920
cacgttctgc ttcactctcc ccatctcccc ccctcccca cccccaattt tgtatttatt      1980
tattttttaa ttattttgtg cagcgatggg ggcgggggg ggggggggc gcgcgccagg      2040 cggggcgggg cggggcgagg ggcgggggcgg ggcgaggcgg agaggtgcgg cggcagccaa    2100
tcagagcggc gcgctccgaa agtttccttt tatggcgagg cggcggcggc ggcggcccta     2160
taaaaagcga agcgcgcggc gggcggggag tcgctgcgac gctgccttcg ccccgtgccc     2220
cgctccgccg ccgcctcgcg ccgcccgccc cggctctgac tgaccgcgtt actcccacag     2280
gtgagcgggc gggacggccc ttctcctccg ggctgtaatt agcgcttggt ttaatgacgg     2340
```

-continued

```
cttgtttctt ttctgtggct gcgtgaaagc cttgaggggc tccgggaggg ccctttgtgc      2400 gggggagcg gctcgggggg tgcgtgcgtg tgtgtgtgcg tggggagcgc cgcgtgcggc       2460
tccgcgctgc ccggcggctg tgagcgctgc gggcgcggcg cggggctttg tgcgctccgc      2520
agtgtgcgcg aggggagcgc ggccgggggc ggtgccccgc ggtgcggggg gggctgcgag     2580
gggaacaaag gctgcgtgcg gggtgtgtgc gtgggggggt gagcaggggg tgtgggcgcg      2640
tcggtcgggc tgcaacccc cctgcacccc cctccccgag ttgctgagca cggcccggct       2700
tcgggtgcgg ggctccgtac ggggcgtggc gcggggctcg ccgtgccggg cgggggtgg      2760 cggcaggtgg gggtgccggg cggggcgggg ccgcctcggg ccggggaggg ctcggggag      2820 gggcgcggcg gcccccggag cgccggcggc tgtcgaggcg cggcgagccg cagccattgc     2880
cttttatggt aatcgtgcga gagggcgcag ggacttcctt tgtcccaaat ctgtgcggag      2940
ccgaaatctg ggaggcgccg ccgcaccccc tctagcgggc gcggggcgaa gcggtgcggc     3000
gccggcagga aggaaatggg cggggagggc cttcgtgcgt cgccgcgccg ccgtcccctt      3060
ctccctctcc agcctcgggg ctgtccgcgg ggggacggct gccttcgggg gggacggggc     3120
agggcggggt tcggcttctg gcgtgtgacc ggcggctcta gagcctctgc taaccatgtt     3180
catgccttct tctttttcct acagctcctg ggcaacgtgc tggttaataa cttcgtataa     3240
tgtatgctat acgaagttat accggtgaag ttcctattcc gaagtcccta ttctctagaa      3300
agtataggaa cttcgccacc atggtgagca agggcgagga gctgttcacc ggggtggtgc      3360
ccatcctggt cgagctggac ggcgacgtaa acggccacaa gttcagcgtg tccggcgagg     3420
gcgagggcga tgccacctac ggcaagctga ccctgaagtt catctgcacc accggcaagc     3480
tgcccgtgcc ctggcccacc ctcgtgacca ccctgaccta cggcgtgcag tgcttcagcc     3540
gctaccccga ccacatgaag cagcacgact tcttcaagtc cgccatgccc gaaggctacg     3600
tccaggagcg caccatcttc ttcaaggacg acggcaacta caagacccgc gccgaggtga     3660
agttcgaggg cgacaccctg gtgaaccgca tcgagctgaa gggcatcgac ttcaaggagg     3720
acggcaacat cctggggcac aagctggagt acaactacaa cagccacaac gtctatatca     3780
tggccgacaa gcagaagaac ggcatcaagg tgaacttcaa gatccgccac aacatcgagg     3840
acggcagcgt gcagctcgcc gaccactacc agcagaacac ccccatcggc gacggccccg     3900
tgctgctgcc cgacaaccac tacctgagca cccagtccgc cctgagcaaa gaccccaacg     3960
agaagcgcga tcacatggtc ctgctggagt tcgtgaccgc cgccgggatc actctcggca     4020
tggacgagct gtacaagggc agcggcgcca ccaacttcag cctgctgaag caggccggcg     4080
acgtggagga gaaccccggc cccgctagct aaagcggccg ccaattccta gagctcgctg     4140
atcagcctcg actgtgcctt ctagttgcca gccatctgtt gtttgcccct cccccgtgcc      4200
ttccttgacc ctggaaggtg ccactcccac tgtcctttcc taataaaatg aggaaattgc      4260
atcgcattgt ctgagtaggt gtcattctat tctggggggt ggggtggggc aggacagcaa      4320
gggggaggat tgggaagaca atagcaggca tgctggggag aagttcctat tccgaagttc      4380
ctattctcta gaaagtatag gaacttcgct agcaccggtg ccaccatggc cacctctgat      4440
gaagtcagga agaacctgat ggacatgttc agggacaggc aggccttctc tgaacacacc      4500
tggaagatgc tcctgtctgt gtgcagatcc tgggctgcct ggtgcaagct gaacggtacc     4560
catactcttt atgcccccgg tggatatgac attatgggat atctggacca gatcggcaac      4620
cggccaaacc cgcaggtgga actgggcccc gtggatacat cctgcgcctt gattctttgt     4680
```

-continued

```
gacctgaaac agaaagacac cccgatagtt tacgcgagtg aagccttcct ctacatgaca      4740
ggttacagca acgcagaggt gctgggccgg aattgccggt ttctgcaaag ccctgacggc      4800
atggtgaagc ccaagagcac ccggaagtac gtggatagta acacaatcaa tactatgcgc      4860
aaggcaatcg acaggaatgc cgaggtgcag gttgaagtag tcaattttaa aaagaatgga      4920
cagcgatttg ttaatttcct gactatgata cctgttaggg acgaaacagg cgagtatcga      4980
tactctatgg gattccagtg cgaaacagaa ggcggaagcg gtggcgtgcc caagaagaag      5040
aggaaagtct tcgaaggcag cggcgccacc aacttcagcc tgctgaagca ggccggcgac      5100
gtggaggaga accccggccc cttcgaagtg cccaagaaga gaggaaagt cggcggacat      5160 actctttatg cccccggtgg atatgacatt atgggatatc tgaggcagat caggaaccgg      5220
ccaaacccgc aggtggaact gggccccgtg gatacatcct gcgccttgat tctttgtgac      5280
ctgaaacaga aagacacccc gatagtttac gcgagtgaag ccttcctcta catgacaggt      5340
tacagcaacg cagaggtgct gggccggaat tgccggtttc tgcaaagccc tgacggcatg      5400
gtgaagccca agagcacccg gaagtacgtg gatagtaaca caatcaatac tatgcgcaag      5460
gcaatcgaca ggaatgccga ggtgcaggtt gaagtagtca attttaaaaa gaatggacag      5520
cgatttgtta atttcctgac tatgatacct gttagggacg aaacaggcga gtatcgatac      5580
tctatgggat ccagtgcgaa acagaaggt accaacagga aatggttccc tgctgaacct      5640
gaggatgtga gggactacct cctgtacctg caagccagg gcctggctgt gaagaccatc      5700
caacagcacc tgggccagct caacatgctg cacaggagat ctggcctgcc tcgcccttct      5760
gactccaatg ctgtgtccct ggtgatgagg agaatcagaa aggagaatgt ggatgctggg      5820
gagagagcca gcaggccct ggcctttgaa cgcactgact ttgaccaagt cagatccctg      5880
atggagaact ctgacagatg ccaggacatc aggaacctgg ccttcctggg cattgcctac      5940
aacaccctgc tgcgcattgc cgaaattgcc agaatcagag tgaaggacat ctcccgcacc      6000
gatggtggga aatgctgat ccacattggc aggaccaaga ccctggtgtc cacagctggt      6060
gtggagaagg ccctgtccct gggggttacc aagctggtgg agagatggat ctctgtgtct      6120
ggtgtggctg atgaccccaa caactacctg ttctgccggg tcagaaagaa tggtgtggct      6180
gccccttctg ccacctccca actgtccacc cgggccctgg aagggatctt tgaggccacc      6240
caccgcctga tctatggtgc caaggatgac tctgggcaga gataccctggc ctggtctggc      6300 cactctgcca gagtgggtgc tgccagggac atggccaggg ctggtgtgtc catccctgaa      6360
atcatgcagg ctggtggctg gaccaatgtg aacattgtga tgaactacat cagaaacctg      6420
gactctgaga ctggggccat ggtgaggctg ctcgaagatg gggactaatt aattaactcc      6480
tcaggtgcag gctgcctatc agaaggtggt ggctggtgtg gccaatgccc tggctcacaa      6540
ataccactga gatctttttc cctctgccaa aaattatggg gacatcatga agcccttga      6600 gcatctgact tctggctaat aaaggaaatt tattttcatt gcaatagtgt gttggaattt      6660
tttgtgtctc tcactcggaa ggacatatgg gaggcaaat catttaaaac atcagaatga      6720
gtatttggtt tagagtttgg caacatatgc ccatatgctg gctgccatga acaaaggttg      6780
gctataaaga ggtcatcagt atatgaaaca gccccctgct gtccattcct tattccatag      6840
aaaagccttg acttgaggtt agatttttt tatattttgt tttgtgttat ttttttcttt      6900 aacatccta aaattttcct tacatgtttt actagccaga tttttcctcc tctcctgact      6960
actcccagtc atagctgtcc ctcttctctt atggagatca taacttcgta taatgtatgc      7020
tatacgaagt tatacgcgtg ccaccatgga tcctgatgat gttgttgatt cttctaaatc      7080
```

```
ttttgtgatg gaaaactttt cttcgtacca cgggactaaa cctggttatg tagattccat   7140
tcaaaaaggt atacaaaagc caaaatctgg tacacaagga aattatgacg atgattggaa   7200 agggtttat agtaccgaca ataaatacga cgctgcggga tactctgtag ataatgaaaa    7260
cccgctctct ggaaaagctg gaggcgtggt caaagtgacg tatccaggac tgacgaaggt   7320
tctcgcacta aaagtggata atgccgaaac tattaagaaa gagttaggtt taagtctcac   7380
tgaaccgttg atggagcaag tcggaacgga agagtttatc aaaaggttcg gtgatggtgc   7440
ttcgcgtgta gtgctcagcc ttcccttcgc tgaggggagt tctagcgttg aatatattaa   7500
taactgggaa caggcgaaag cgttaagcgt agaacttgag attaattttg aaacccgtgg   7560
aaaacgtggc caagatgcga tgtatgagta tatggctcaa gcctgtgcag gaaatcgtgt   7620
caggcgatct ctttgtgaag gaaccttact tctgtggtgt gacataattg gacaaactac    7680
ctacagagat ttaaagctct aaacgcgtac tcctcaggtg caggctgcct atcagaaggt   7740
ggtggctggt gtggccaatg ccctggctca caaataccac tgagatcttt ttccctctgc   7800
caaaaattat ggggacatca tgaagcccct tgagcatctg acttctggct aataaaggaa   7860
atttattttc attgcaatag tgtgttggaa ttttttgtgt ctctcactcg gaaggacata   7920
tgggagggca aatcatttaa aacatcagaa tgagtatttg gtttagagtt tggcaacata   7980
tgcccatatg ctggctgcca tgaacaaagg ttggctataa agaggtcatc agtatatgaa   8040 acagcccct gctgtccatt ccttattcca tagaaaagcc ttgacttgag gttagatttt    8100
ttttatattt tgttttgtgt tatttttttc tttaacatcc ctaaaatttt ccttacatgt   8160
tttactagcc agatttttcc tcctctcctg actactccca gtcatagctg tccctcttct   8220
cttatggaga tcgccgtttc cacattcttt tctcatcctt cttctcctgt tttctctgca   8280
tcaaggtcag cacgatagca ctgtctctct atgcttaggg agaggcctgt cctgtacatc   8340
ccgtgccccc acaagatgcc tactacaaca acatcttctg catgtcctgc atagcagtgt   8400
tgggagaatg tgcactactt ccactcttct gatttctatt ttatgtgttt gctttatacc   8460
agtgttgcca tttgggaatt aatacatggt tgatcaaatc aattgcatca cagctgtatc   8520
ctgtatcaga ggaacattat caaagctttt gttgctgtat ttggtatctg acctgcagat   8580
aaacatgttt taggaaggtt ttgcaaaagt agctgtgaaa tgagctggtg ttgtgattta   8640
acctgacagg cagctaaaca gtataccaca gagctattca cctactttcc ctcagtggga   8700
aaagggaaga gaactgaggg gggggggaat aaataagtaa ataacaaaat aaaactcatg   8760
gattaagaaa aagactttgt actggaatgg atgagaagaa taatagtaat gataataata   8820
tgtcactctg aaagtaatgc ctcttatttc tgtggagact acaaacatac aaagagcaca   8880
acattccata gagcaaattc tcagttacag aatgctattt ttttttttcaa cacagtcaaa   8940 atcattaatt ttttttttgcc tgcaatggac aagagctttg aagctgttct cgtaaaaatc   9000
tgtactagca gaagtgacct gcaatcacta ctgctgaaat gcacaaccca ccacatcatt   9060
gtgctcacat tcactgtttg gtttctgtaa atgtacagga attgtctgaa attagatatg   9120 atttttttt tctccatgaa ggaattcaat tacacacctt tgcctcatgc acttctttgt   9180 cattttgtc agactgcttc tctcctgcaa tttgtctcat ggcaacaaaa tataatggag   9240
ttctgctggg aacttcccta ctgccatacc actatcatct gcctctgaca ttttggacaa   9300
atgtaataaa ataggaggta ttactttcag agcagacctt gtatgtattt acaaaacaag   9360
tggtacacaa aaaaaattgt tcatcccacc aaccaatgcc catcctgtcc ctgaatagta   9420
```

-continued

```
gctgtccccc acagccttga ccagtttagg tcaacagttc tgcttctgtc ccctcccagc     9480
tccttgtaac ccctcagccc cccttgctgg caggacagta tgagaagctg aaaaactaga     9540
atgtcctagt tctttgcagt gctgctaatc aacaaccaaa acagtggtgt gttaccaata     9600
ttgttgatat cacagcatca taccattatg aaggaagtaa cccagccaaa atcaggtcag     9660
cttgctaaca agagaactgt gcataagttt aagatgtgtg tgttcctcag taccttaaaa     9720
aataagtagt aacgttcaaa tgagtagaag agtagaactg agcttaaaac atctgtcaga     9780
caacagtgaa ccaacc                                                     9796
```

```
<210> SEQ ID NO 122
<211> LENGTH: 9991
<212> TYPE: DNA
<213> ORGANISM: Artificial Sequence
<220> FEATURE:
<223> OTHER INFORMATION: Targeting Vector TV3

<400> SEQUENCE: 122
```

```
gaatgaaggg cctgagggtg ggcagtctgt ctatcatgta catctccata ttctgggagg       60
tcgtcagttg ggctggcctc ctggctaaga tttttgcacc acaagagatg ctgcatgtgt      120
acaaatcact agcaaataga tttgtttccc atcaacttag ccactgttaa tgtaaattgt      180
tcttggatat gtgtctttgg agggcaataa atgctctgaa cagcacttgc acaataaaga      240
tacagcatgt gggaatgatc tgtctcatgt gtcttactga tggtattggt tctgtaagat      300
aaaatattgt gtctgggatg tgtttggctc tactattaat ggtgctctat tgattgtgat      360
ttgtcatttg aaacctgagg atgcgactgt atagcagtct ttcatgcatt tttggaaaaa      420
aacttaagct ttttgaaagc tgctgctaca acttttttgta ttgttataaa gttttgtatt      480
gtttttttaa ttgtgaaatt ataaagatgc cgtgcaggga ctgtttgaag caaagtgcat      540 tgtttttagaa acctacaact ctagttcaag cactccatca gtatctgctt aatctttgtc      600
atcctttgct atgagaaaat attaagcagt agtctaaagg tactatgaaa ctataacata      660
gctgacattg tatttataac tacgtcatga ttttgataga attgaggact tgaaaatgtt      720
aaactattca tgtagggcct cttaagatgc ttaagttgtt tagtaatgta agtgtgcatt      780
taattgagat tttattgggc ataatttgtc catcagtatg acactccttg tcagtgttgc      840
cttatacttg atgttgttac cggatctctg caaggcagtt attcttgaat taggctcatt      900
gaagtgtctg ccagtataaa tatatagcaa ctgttctttg tgttaaaatt gagaagctaa      960
ccagttttta gtgcttctga ctgttggaat tctttaagca gatgccataa gaaaattgta     1020
tttgtgatca ccacttctcc agagtggttt taacaccaag ggcattagag aaagaaaggc     1080
aggcgtgtag agaatagtgg acagacaaaa gctgtgagtt acgttatgtt tttcagctga     1140
aaagctgtgt ttggtaaaag catatgaaat cactcaactt ggaagcattc tcttagttct     1200
ctgatagttc tgagcagcag aactcttcac ctaagaggtt acttcaactg gaagactacc     1260
tagtgcttct gatggcaact atatttaaga tgagaataag aggtgtttcc agtgtggtag     1320
cctcacatct gttgcagtgg ttaccgttcg tcctcctccg agggacacag cttggccatt     1380
cactgtggtg acaccaatat gatgatcagc aaatggtgtt tattcactac taaacacagc     1440
ttatatacat ttttacctac aaaatcgtgc tgtcatgtcc cactctgatt ggttcacaca     1500
tttccccgaa aagtgccacc tgggtcgaca ttgattattg actagttatt aatagtaatc     1560
aattacgggg tcattagttc atagcccata tatggagttc cgcgttacat aacttacggt     1620
aaatggcccg cctggctgac cgcccaacga cccccgccca ttgacgtcaa taatgacgta     1680
```

```
tgttcccata gtaacgccaa tagggacttt ccattgacgt caatgggtgg agtatttacg      1740
gtaaactgcc cacttggcag tacatcaagt gtatcatatg ccaagtacgc cccctattga      1800
cgtcaatgac ggtaaatggc ccgcctggca ttatgcccag tacatgacct tatgggactt      1860
tcctacttgg cagtacatct acgtattagt catcgctatt accatggtcg aggtgagccc      1920
cacgttctgc ttcactctcc ccatctcccc cccctcccca cccccaattt tgtatttatt      1980
tattttttaa ttattttgtg cagcgatggg ggcgggggg ggggggggc gcgcgccagg        2040 cggggcgggg cggggcgagg ggcggggcgg ggcgaggcgg agaggtgcgg cggcagccaa      2100
tcagagcggc gcgctccgaa agtttccttt tatggcgagg cggcggcggc ggcggcccta      2160
taaaaagcga agcgcgcggc gggcggggag tcgctgcgac gctgccttcg ccccgtgccc      2220
cgctccgccg ccgcctcgcg ccgcccgccc cggctctgac tgaccgcgtt actcccacag      2280
gtgagcgggc gggacggccc ttctcctccg ggctgtaatt agcgcttggt ttaatgacgg      2340
cttgtttctt ttctgtggct gcgtgaaagc cttgaggggc tccgggaggg ccctttgtgc      2400
ggggggagcg gctcggggg tgcgtgcgtg tgtgtgtgcg tggggagcgc cgcgtgcggc       2460
tccgcgctgc ccgcggctg tgagcgctgc gggcgcggcg cggggctttg tgcgctccgc       2520
agtgtgcgcg aggggagcgc ggccgggggc ggtgccccgc ggtgcggggg gggctgcgag      2580
gggaacaaag gctgcgtgcg gggtgtgtgc gtggggggt gagcaggggg tgtgggcgcg       2640
tcggtcgggc tgcaacccc cctgcacccc cctccccgag ttgctgagca cggcccggct       2700
tcgggtgcgg ggctccgtac ggggcgtggc gcggggctcg ccgtgccggg cggggggtgg      2760
cggcaggtgg gggtgccggg cggggcgggg ccgcctcggg ccggggaggg ctcgggggag      2820
gggcgcggcg gccccggag cgccggcggc tgtcgaggcg cggcgagccg cagccattgc       2880
cttttatggt aatcgtgcga gagggcgcag ggacttcctt tgtcccaaat ctgtgcggag      2940
ccgaaatctg ggaggcgccg ccgcaccccc tctagcgggc gcggggcgaa gcggtgcggc      3000
gccggcagga aggaaatggg cggggagggc cttcgtgcgt cgccgcgccg ccgtcccctt      3060
ctccctctcc agcctcgggg ctgtccgcgg gggacggct gccttcgggg gggacggggc       3120
agggcggggt tcggcttctg gcgtgtgacc ggcggctcta gagcctctgc taaccatgtt      3180
catgccttct tctttttcct acagctcctg ggcaacgtgc tggttaataa cttcgtataa      3240
tgtatgctat acgaagttat accggtgaag ttcctattcc gaagttccta ttctctagaa      3300
agtataggaa cttcgccacc atggtgagca agggcgagga gctgttcacc ggggtggtgc      3360
ccatcctggt cgagctggac ggcgacgtaa acggccacaa gttcagcgtg tccggcgagg      3420
gcgagggcga tgccacctac ggcaagctga ccctgaagtt catctgcacc accggcaagc      3480
tgcccgtgcc ctggcccacc ctcgtgacca ccctgaccta cggcgtgcag tgcttcagcc      3540
gctaccccga ccacatgaag cagcacgact tcttcaagtc cgccatgccc gaaggctacg      3600
tccaggagcg caccatcttc ttcaaggacg acggcaacta caagacccgc gccgaggtga      3660
agttcgaggg cgacaccctg gtgaaccgca tcgagctgaa gggcatcgac ttcaaggagg      3720
acggcaacat cctggggcac aagctggagt acaactacaa cagccacaac gtctatatca      3780
tggccgacaa gcagaagaac ggcatcaagg tgaacttcaa gatccgccac aacatcgagg      3840
acggcagcgt gcagctcgcc gaccactacc agcagaacac ccccatcggc gacggccccg      3900
tgctgctgcc cgacaaccac tacctgagca cccagtccgc cctgagcaaa gaccccaacg      3960
agaagcgcga tcacatggtc ctgctggagt tcgtgaccgc cgccgggatc actctcggca      4020
```

-continued

```
tggacgagct gtacaagggc agcggcgcca ccaacttcag cctgctgaag caggccggcg   4080
acgtggagga gaaccccggc cccgctagct aaagcggccg ccaattccta gagctcgctg   4140
atcagcctcg actgtgcctt ctagttgcca gccatctgtt gtttgcccct ccccgtgcc    4200 ttccttgacc ctggaaggtg ccactcccac tgtcctttcc taataaaatg aggaaattgc   4260
atcgcattgt ctgagtaggt gtcattctat tctggggggt ggggtggggc aggacagcaa   4320
gggggaggat tgggaagaca atagcaggca tgctggggag aagttcctat tccgaagttc   4380
ctattctcta gaaagtatag gaacttcgct agcaccggtg ccaccatggc cacctctgat   4440
gaagtcagga agaacctgat ggacatgttc agggacaggc aggccttctc tgaacacacc   4500
tggaagatgc tcctgtctgt gtgcagatcc tgggctgcct ggtgcaagct gaacggtacc   4560
catactcttt atgccccgg tggatatgac attatgggat atctggacca gatcggcaac   4620
cggccaaacc cgcaggtgga actgggcccc gtggatacat cctgcgcctt gattctttgt   4680
gacctgaaac agaaagacac cccgatagtt tacgcgagtg aagccttcct ctacatgaca   4740
ggttacagca acgcagaggt gctgggccgg aattgccggt ttctgcaaag ccctgacggc   4800
atggtgaagc ccaagagcac ccggaagtac gtggatagta acacaatcaa tactatcgc   4860 aaggcaatcg acaggaatgc cgaggtgcag gttgaagtag tcaattttaa aaagaatgga   4920
cagcgatttg ttaatttcct gactatgata cctgttaggg acgaaacagg cgagtatcga   4980
tactctatgg gattccagtg cgaaacagaa ggcggaagcg gtggcgtgcc caagaagaag   5040
aggaaagtct tcgaaggcag cggcgccacc aacttcagcc tgctgaagca ggccggcgac   5100
gtggaggaga accccggccc cttcgaagtg cccaagaaga gaggaaagt cggcggacat   5160 actctttatg cccccggtgg atatgacatt atgggatatc tgaggcagat caggaaccgg   5220
ccaaacccgc agtggaact gggccccgtg atacatcct gcgccttgat tctttgtgac   5280
ctgaaacaga aagacacccc gatagtttac gcgagtgaag ccttcctcta catgacaggt   5340
tacagcaacg cagaggtgct gggccggaat tgccggtttc tgcaaagccc tgacggcatg   5400
gtgaagccca gagcacccg gaagtacgtg gatagtaaca caatcaatac tatgcgcaag   5460
gcaatcgaca ggaatgccga ggtgcaggtt gaagtagtca ttttaaaaa gaatggacag   5520 cgatttgtta atttcctgac tatgatacct gttagggacg aaacaggcga gtatcgatac   5580
tctatgggat tccagtgcga aacagaaggt accaacagga aatggttccc tgctgaacct   5640
gaggatgtga gggactacct cctgtacctg caagccagag cctggctgt gaagaccatc   5700 caacagcacc tgggccagct caacatgctg cacaggagat ctggcctgcc tcgcccttct   5760
gactccaatg ctgtgtccct ggtgatgagg agaatcagaa aggagaatgt ggatgctggg   5820
gagagagcca agcaggccct ggcctttgaa cgcactgact ttgaccaagt cagatccctg   5880
atggagaact ctgacagatg ccaggacatc aggaacctgg ccttcctggg cattgcctac   5940
aacaccctgc tgcgcattgc cgaaattgcc agaatcagag tgaaggacat ctcccgcacc   6000
gatggtggga gaatgctgat ccacattggc aggaccaaga ccctggtgtc cacagctggt   6060
gtggagaagg ccctgtccct gggggttacc aagctggtgg agagatggat ctctgtgtct   6120 ggtgtggct atgacccca caactacctg ttctgccggg tcagaaagaa tggtgtggct   6180
gcccctcctg ccacctccca actgtccacc cgggccctgg aagggatctt tgaggccacc   6240
caccgcctga tctatggtgc caaggatgac tctgggcaga gatacctggc ctggtctggc   6300
cactctgcca gagtgggtgc tgccaggac atggccaggc tggtgtgtc catccctgaa   6360 atcatgcagg ctggtggctg gaccaatgtg aacattgtga tgaactacat cagaaacctg   6420
```

-continued

```
gactctgaga ctggggccat ggtgaggctg ctcgaagatg gggactaatt aattaactcc   6480
tcaggtgcag gctgcctatc agaaggtggt ggctggtgtg gccaatgccc tggctcacaa   6540
ataccactga gatctttttc cctctgccaa aaattatggg gacatcatga agccccttga   6600
gcatctgact tctggctaat aaaggaaatt tattttcatt gcaatagtgt gttggaattt   6660
tttgtgtctc tcactcggaa ggacatatgg gagggcaaat catttaaaac atcagaatga   6720
gtatttggtt tagagtttgg caacatatgc ccatatgctg gctgccatga acaaaggttg   6780
gctataaaga ggtcatcagt atatgaaaca gcccctgct gtccattcct tattccatag   6840
aaaagccttg acttgaggtt agattttttt tatattttgt tttgtgttat ttttttcttt   6900 aacatccta aaattttcct tacatgtttt actagccaga ttttcctcc tctcctgact   6960 actcccagtc atagctgtcc ctcttctctt atggagatca taacttcgta taatgtatgc   7020
tatacgaagt tatacgcgtg ccaccatgat gacagacata aaagatggac cacgctcagg   7080
ggaagatgta tcagctgcaa gatctttccc tggttccaaa ggaatgaact tacctgctag   7140
caagtctgtg gcctctggaa ttctgcctga tgacagttac agaatggatt atccagagat   7200
aggagtatgt gttataataa acaataagaa cttccaccga gataccggac tgtcatctcg   7260
ttcaggcacg gatgcagatg ctgcaagtgt cagagaagtt tttatgaagc tgggatataa   7320
agtcaagctt aacaatgatc tgtcaagcag agatattttt aagctattga aaaatgtttc   7380
tgaagaagat cacagcaagc gaagcagttt tgtttgtgtg ttgctaagcc atggcgatga   7440
aggactcttc tatggtacag atggccctct tgaactgaaa gtactaacca gccttttcag   7500
aggtgacaag tgcagaagtc tagcagggaa acccaaactc tttttcattc aggcctgtag   7560
aggaacagaa ttagattctg gtattgaagc agccagtgga ccagatgaaa cagtgtgtca   7620 aaaaataacct gtagaagcag acttcctgta tgcatattct actgctccag gctactactc   7680
ctggaggaac gcagctgaag gctcctggtt tattcagtct ctgtgtagga tgctgaagga   7740
acacgccagg aaacttgaac tcatgcagat tttaactcgt gtaaatcgca gagtggcaga   7800
atatgaatcc tgctccactc gacaggattt caatgcaaag aaacagattc catgcattga   7860
gtctatgctt accaaagaat tctactttcc ttgctaaacg cgtactcctc aggtgcaggc   7920
tgcctatcag aaggtggtgg ctggtgtggc caatgccctg gctcacaaat accactgaga   7980
tctttttccc tctgccaaaa attatgggga catcatgaag cccttgagc atctgacttc   8040 tggctaataa aggaaattta ttttcattgc aatagtgtgt tggattttt tgtgtctctc   8100 actcggaagg acatatggga gggcaaatca tttaaaacat cagaatgagt atttggttta   8160
gagtttggca acatatgccc atatgctggc tgccatgaac aaaggttggc tataaagagg   8220
tcatcagtat atgaaacagc ccctgctgt ccattcctta ttccatagaa aagccttgac   8280
ttgaggttag attttttta tattttgttt tgtgttattt ttttctttaa catccctaaa   8340
attttcctta catgttttac tagccagatt tttcctcctc tcctgactac tcccagtcat   8400
agctgtccct cttctcttat ggagatcgcc gtttccacat tcttttctca tccttcttct   8460
cctgttttct ctgcatcaag gtcagcacga tagcactgtc tctctatgct tagggagagg   8520
cctgtcctgt acatcccgtg cccccacaag atgcctacta caacaacatc ttctgcatgt   8580
cctgcatagc agtgttggga gaatgtgcac tacttccact cttctgattt ctattttatg   8640
tgtttgcttt ataccagtgt tgccatttgg gaattaatac atggttgatc aaatcaattg   8700
catcacagct gtatcctgta tcagaggaac attatcaaag cttttgttgc tgtatttggt   8760
```

```
atctgacctg cagataaaca tgttttagga aggttttgca aaagtagctg tgaaatgagc      8820
tggtgttgtg atttaacctg acaggcagct aaacagtata ccacagagct attcacctac      8880
tttccctcag tgggaaaagg gaagagaact gagggggggg ggaataaata agtaaataac      8940
aaaataaaac tcatggatta agaaaaagac tttgtactgg aatggatgag aagaataata      9000
gtaatgataa taatatgtca ctctgaaagt aatgcctctt atttctgtgg agactacaaa      9060
catacaaaga gcacaacatt ccatagagca aattctcagt tacagaatgc tatttttttt      9120
ttcaacacag tcaaaatcat taattttttt ttgcctgcaa tggacaagag ctttgaagct      9180
gttctcgtaa aaatctgtac tagcagaagt gacctgcaat cactactgct gaaatgcaca      9240
acccaccaca tcattgtgct cacattcact gtttggtttc tgtaaatgta caggaattgt      9300
ctgaaattag atatgatttt tttttctcc atgaaggaat tcaattacac acctttgcct      9360
catgcacttc tttgtcattt ttgtcagact gcttctctcc tgcaatttgt ctcatggcaa      9420
caaaatataa tggagttctg ctgggaactt ccctactgcc ataccactat catctgcctc      9480
tgacattttg gacaaatgta ataaaatagg aggtattact ttcagagcag accttgtatg      9540
tatttacaaa acaagtggta cacaaaaaaa attgttcatc ccaccaacca atgcccatcc      9600
tgtccctgaa tagtagctgt cccccacagc cttgaccagt ttaggtcaac agttctgctt      9660
ctgtcccctc ccagctcctt gtaacccctc agccccctt gctggcagga cagtatgaga      9720
agctgaaaaa ctagaatgtc ctagttcttt gcagtgctgc taatcaacaa ccaaaacagt      9780
ggtgtgttac caatattgtt gatatcacag catcatacca ttatgaagga agtaacccag      9840
ccaaaatcag gtcagcttgc taacaagaga actgtgcata agtttaagat gtgtgtgttc      9900
ctcagtacct taaaaaataa gtagtaacgt tcaaatgagt agaagagtag aactgagctt      9960
aaaacatctg tcagacaaca gtgaaccaac c                                       9991
```

```
<210> SEQ ID NO 123
<211> LENGTH: 9859
<212> TYPE: DNA
<213> ORGANISM: Artificial Sequence
<220> FEATURE:
<223> OTHER INFORMATION: Targeting Vector TV4

<400> SEQUENCE: 123
gaatgaaggg cctgagggtg ggcagtctgt ctatcatgta catctccata ttctgggagg       60
tcgtcagttg ggctggcctc ctggctaaga tttttgcacc acaagagatg ctgcatgtgt      120
acaaatcact agcaaataga tttgtttccc atcaacttag ccactgttaa tgtaaattgt      180
tcttggatat gtgtctttgg agggcaataa atgctctgaa cagcacttgc acaataaaga      240
tacagcatgt gggaatgatc tgtctcatgt gtcttactga tggtattggt tctgtaagat      300
aaaatattgt gtctgggatg tgtttggctc tactattaat ggtgctctat tgattgtgat      360
ttgtcatttg aaacctgagg atgcgactgt atagcagtct ttcatgcatt tttgaaaaaa      420
aacttaagct ttttgaaagc tgctgctaca acttttttgta ttgttataaa gttttgtatt      480
gtttttttaa ttgtgaaatt ataaagatgc cgtgcaggga ctgtttgaag caaagtgcat      540
tgttttagaa acctacaact ctagttcaag cactccatca gtatctgctt aatctttgtc      600
atcctttgct atgagaaaat attaagcagt agtctaaagg tactatgaaa ctataacata      660
gctgacattg tatttataac tacgtcatga ttttgataga attgaggact tgaaaatgtt      720
aaactattca tgtagggcct cttaagatgc ttaagttgtt tagtaatgta agtgtgcatt      780
taattgagat tttattgggc ataatttgtc catcagtatg acactccttg tcagtgttgc      840
```

```
cttatacttg atgttgttac cggatctctg caaggcagtt attcttgaat taggctcatt      900
gaagtgtctg ccagtataaa tatatagcaa ctgttctttg tgttaaaatt gagaagctaa      960
ccagttttta gtgcttctga ctgttggaat tctttaagca gatgccataa gaaaattgta     1020
tttgtgatca ccacttctcc agagtggttt taacaccaag ggcattagag aaagaaaggc     1080
aggcgtgtag agaatagtgg acagacaaaa gctgtgagtt acgttatgtt tttcagctga     1140
aaagctgtgt ttggtaaaag catatgaaat cactcaactt ggaagcattc tcttagttct     1200
ctgatagttc tgagcagcag aactcttcac ctaagaggtt acttcaactg gaagactacc     1260
tagtgcttct gatggcaact atatttaaga tgagaataag aggtgtttcc agtgtggtag     1320
cctcacatct gttgcagtgg ttaccgttcg tcctcctccg agggacacag cttggccatt     1380
cactgtggtg acaccaatat gatgatcagc aaatggtgtt tattcactac taaacacagc     1440
ttatatacat ttttacctac aaaatcgtgc tgtcatgtcc cactctgatt ggttcacaca     1500
tttccccgaa aagtgccacc tgggtcgaca ttgattattg actagttatt aatagtaatc     1560
aattacgggg tcattagttc atagcccata tatggagttc cgcgttacat aacttacggt     1620
aaatggcccg cctggctgac cgcccaacga ccccgccca ttgacgtcaa taatgacgta     1680
tgttcccata gtaacgccaa tagggacttt ccattgacgt caatgggtgg agtatttacg     1740
gtaaactgcc cacttggcag tacatcaagt gtatcatatg ccaagtacgc cccctattga     1800
cgtcaatgac ggtaaatggc ccgcctggca ttatgcccag tacatgacct tatgggactt     1860
tcctacttgg cagtacatct acgtattagt catcgctatt accatggtcg aggtgagccc     1920
cacgttctgc ttcactctcc ccatctcccc ccctcccca cccccaattt tgtatttatt     1980
tattttttaa ttattttgtg cagcgatggg ggcgggggg ggggggggc gcgcgccagg     2040 cggggcgggg cggggcgagg ggcggggcgg ggcgaggcgg agaggtgcgg cggcagccaa     2100
tcagagcggc gcgctccgaa agtttccttt tatggcgagg cggcggcggc ggcggcccta     2160
taaaaagcga agcgcgcggc gggcggggag tcgctgcgac gctgccttcg ccccgtgccc     2220
cgctccgccg ccgcctcgcg ccgcccgccc cggctctgac tgaccgcgtt actcccacag     2280
gtgagcgggc gggacggccc ttctcctccg ggctgtaatt agcgcttggt ttaatgacgg     2340
cttgtttctt ttctgtggct gcgtgaaagc cttgaggggc tccgggaggg ccctttgtgc     2400
ggggggagcg gctcgggggg tgcgtgcgtg tgtgtgtgcg tggggagcgc cgcgtgcggc     2460
tccgcgctgc ccggcggctg tgagcgctgc gggcgcggcg cggggctttg tgcgctccgc     2520
agtgtgcgcg aggggagcgc ggccgggggc ggtgccccgc ggtgcggggg gggctgcgag     2580
gggaacaaag gctgcgtgcg gggtgtgtgc gtgggggggt gagcagggg tgtgggcgcg     2640 tcggtcgggc tgcaacccc cctgcacccc cctccccgag ttgctgagca cggcccggct     2700
tcgggtgcgg ggctccgtac ggggcgtggc gcggggctcg ccgtgccggg cggggggtgg     2760
cggcaggtgg gggtgccggg cggggcgggg ccgcctcggg ccggggaggg ctcggggag     2820 gggcgcggcg gcccccggag cgccggcggc tgtcgaggcg cggcgagccg cagccattgc     2880
cttttatggt aatcgtgcga gagggcgcag ggacttcctt tgtcccaaat ctgtgcggag     2940
ccgaaatctg ggaggcgccg ccgcaccccc tctagcgggc gcggggcgaa gcggtgcggc     3000
gccggcagga aggaaatggg cggggagggc cttcgtgcgt cgccgcgccg ccgtcccctt     3060
ctccctctcc agcctcgggg ctgtccgcg ggggacggct gccttcgggg gggacgggc     3120 agggcggggt tcggcttctg gcgtgtgacc ggcggctcta gagcctctgc taaccatgtt     3180
```

-continued

```
catgccttct tctttttcct acagctcctg ggcaacgtgc tggttaataa cttcgtataa      3240
tgtatgctat acgaagttat accggtgaag ttcctattcc gaagttccta ttctctagaa      3300
agtataggaa cttcgccacc atggtgagca agggcgagga gctgttcacc ggggtggtgc      3360
ccatcctggt cgagctggac ggcgacgtaa acggccacaa gttcagcgtg tccggcgagg      3420
gcgagggcga tgccacctac ggcaagctga ccctgaagtt catctgcacc accggcaagc      3480
tgcccgtgcc ctggcccacc ctcgtgacca ccctgaccta cggcgtgcag tgcttcagcc      3540
gctaccccga ccacatgaag cagcacgact tcttcaagtc cgccatgccc gaaggctacg      3600
tccaggagcg caccatcttc ttcaaggacg acggcaacta caagacccgc gccgaggtga      3660
agttcgaggg cgacaccctg gtgaaccgca tcgagctgaa gggcatcgac ttcaaggagg      3720
acggcaacat cctggggcac aagctggagt acaactacaa cagccacaac gtctatatca      3780
tggccgacaa gcagaagaac ggcatcaagg tgaacttcaa gatccgccac aacatcgagg      3840
acggcagcgt gcagctcgcc gaccactacc agcagaacac ccccatcggc gacggccccg      3900
tgctgctgcc cgacaaccac tacctgagca cccagtccgc cctgagcaaa gaccccaacg      3960
agaagcgcga tcacatggtc ctgctggagt tcgtgaccgc cgccgggatc actctcggca      4020
tggacgagct gtacaagggc agcggcgcca ccaacttcag cctgctgaag caggccggcg      4080
acgtggagga gaaccccggc cccgctagct aaagcggccg ccaattccta gagctcgctg      4140
atcagcctcg actgtgcctt ctagttgcca gccatctgtt gtttgcccct cccccgtgcc      4200
ttccttgacc ctggaaggtg ccactcccac tgtcctttcc taataaaatg aggaaattgc      4260
atcgcattgt ctgagtaggt gtcattctat tctggggggt ggggtggggc aggacagcaa      4320
gggggaggat tgggaagaca atagcaggca tgctggggag aagttcctat tccgaagttc      4380
ctattctcta gaaagtatag gaacttcgct agcaccggtg ccaccatggc cacctctgat      4440
gaagtcagga agaacctgat ggacatgttc agggacaggc aggccttctc tgaacacacc      4500
tggaagatgc tcctgtctgt gtgcagatcc tgggctgcct ggtgcaagct gaacggtacc      4560
catactcttt atgcccccgg tggatatgac attatgggat atctggacca gatcggcaac      4620
cggccaaacc cgcaggtgga actgggcccc gtggatacat cctgcgcctt gattctttgt      4680
gacctgaaac agaaagacac cccgatagtt tacgcgagtg aagccttcct ctacatgaca      4740
ggttacagca acgcagaggt gctgggccgg aattgccggt ttctgcaaag ccctgacggc      4800
atggtgaagc ccaagagcac ccggaagtac gtggatagta acacaatcaa tactatgcgc      4860
aaggcaatcg acaggaatgc cgaggtgcag gttgaagtag tcaattttaa aaagaatgga      4920
cagcgatttg ttaatttcct gactatgata cctgttaggg acgaaacagg cgagtatcga      4980
tactctatgg gattccagtg cgaaacagaa ggcggaagcg gtggcgtgcc caagaagaag      5040
aggaaagtct tcgaaggcag cggcgccacc aacttcagcc tgctgaagca ggccggcgac      5100
gtggaggaga accccggccc cttcgaagtg cccaagaaga gaggaaagt cggcggacat      5160 actctttatg cccccggtgg atatgacatt atgggatatc tgaggcagat caggaaccgg      5220
ccaaacccgc aggtggaact gggccccgtg gatacatcct gcgccttgat tctttgtgac      5280
ctgaaacaga aagacacccc gatagtttac gcgagtgaag ccttcctcta catgacaggt      5340
tacagcaacg cagaggtgct gggccggaat tgccggtttc tgcaaagccc tgacggcatg      5400
gtgaagccca gagcacccg gaagtacgtg atagtaaca caatcaatac tatgcgcaag      5460
gcaatcgaca ggaatgccga ggtgcaggtt gaagtagtca attttaaaaa gaatggacag      5520
cgatttgtta atttcctgac tatgatacct gttagggacg aaacaggcga gtatcgatac      5580
```

-continued

```
tctatgggat tccagtgcga aacagaaggt accaacagga aatggttccc tgctgaacct    5640
gaggatgtga gggactacct cctgtacctg caagccagag gcctggctgt gaagaccatc    5700
caacagcacc tgggccagct caacatgctg cacaggagat ctggcctgcc tcgcccttct    5760
gactccaatg ctgtgtccct ggtgatgagg agaatcagaa aggagaatgt ggatgctggg    5820
gagagagcca agcaggccct ggcctttgaa cgcactgact ttgaccaagt cagatccctg    5880
atggagaact ctgacagatg ccaggacatc aggaacctgg ccttcctggg cattgcctac    5940
aacaccctgc tgcgcattgc cgaaattgcc agaatcagag tgaaggacat ctcccgcacc    6000
gatggtggga gaatgctgat ccacattggc aggaccaaga ccctggtgtc cacagctggt    6060
gtggagaagg ccctgtccct gggggttacc aagctggtgg agagatggat ctctgtgtct    6120
ggtgtggctg atgaccccaa caactacctg ttctgccggg tcagaaagaa tggtgtggct    6180
gccccttctg ccacctccca actgtccacc cgggccctgg aagggatctt tgaggccacc    6240
caccgcctga tctatggtgc caaggatgac tctgggcaga gatacctggc ctggtctggc    6300
cactctgcca gagtgggtgc tgccagggac atggccaggg ctggtgtgtc catccctgaa    6360
atcatgcagg ctggtggctg gaccaatgtg aacattgtga tgaactacat cagaaacctg    6420
gactctgaga ctggggccat ggtgaggctg ctcgaagatg gggactaatt aattaactcc    6480
tcaggtgcag gctgcctatc agaaggtggt ggctggtgtg gccaatgccc tggctcacaa    6540
ataccactga gatctttttc cctctgccaa aaattatggg gacatcatga agccccttga    6600
gcatctgact tctggctaat aaaggaaatt tattttcatt gcaatagtgt gttggaattt    6660
tttgtgtctc tcactcggaa ggacatatgg gagggcaaat catttaaaac atcagaatga    6720
gtatttggtt tagagtttgg caacatatgc ccatatgctg gctgccatga acaaaggttg    6780
gctataaaga ggtcatcagt atatgaaaca gccccctgct gtccattcct tattccatag    6840
aaaagccttg acttgaggtt agattttttt tatattttgt tttgtgttat ttttttcttt    6900
aacatcccta aaattttcct tacatgtttt actagccaga ttttttcctcc tctcctgact    6960 actcccagtc atagctgtcc ctcttctctt atggagatca taacttcgta taatgtatgc    7020
tatacgaagt tatacgcgtg ccaccatggt gagcaagggc gaggaggata acatggccat    7080
catcaaggag ttcatgcgct tcaaggtgca catggagggc tccgtgaacg gccacgagtt    7140
cgagatcgag ggcgagggcg agggccgccc ctacgagggc acccgaccg ccaagctgaa    7200 ggtgaccaag ggtggccccc tgcccttcgc ctgggacatc ctgtcccctc agttcatgta    7260
cggctccaag gcctacgtga agcaccccgc cgacatcccc gactacttga agctgtcctt    7320
ccccgagggc ttcaagtggg agcgcgtgat gaacttcgag gacggcggcg tggtgaccgt    7380
gacccaggac tcctccctgc aggacggcga gttcatctac aaggtgaagc tgcgcggcac    7440
caacttcccc tccgacggcc ccgtaatgca gaagaagacc atgggctggg aggcctcctc    7500
cgagcggatg taccccgagg acggcgccct gaagggcgag atcaagcaga ggctgaagct    7560
gaaggacggc ggccactacg acgctgaggt caagaccacc tacaaggcca agaagcccgt    7620
gcagctgccc ggcgcctaca cgtcaacat caagttggac atcacctccc acaacgagga    7680
ctacaccatc gtggaacagt acgaacgcgc cgagggccgc cactccaccg gcggcatgga    7740
cgagctgtac aagtgtggcg gctagacgcg tactcctcag gtgcaggctg cctatcagaa    7800
ggtggtggct ggtgtggcca atgccctggc tcacaaatac cactgagatc ttttttccctc    7860 tgccaaaaat tatggggaca tcatgaagcc ccttgagcat ctgacttctg gctaataaag    7920
```

-continued

```
gaaatttatt ttcattgcaa tagtgtgttg gaatttttg tgtctctcac tcggaaggac      7980
atatgggagg gcaaatcatt taaaacatca gaatgagtat ttggtttaga gtttggcaac      8040
atatgcccat atgctggctg ccatgaacaa aggttggcta taaagaggtc atcagtatat      8100
gaaacagccc cctgctgtcc attccttatt ccatagaaaa gccttgactt gaggttagat      8160 ttttttata ttttgtttg tgttattttt ttctttaaca tccctaaaat tttccttaca      8220
tgttttacta gccagatttt tcctcctctc ctgactactc ccagtcatag ctgtccctct      8280
tctcttatgg agatcgccgt ttccacattc ttttctcatc cttcttctcc tgttttctct      8340
gcatcaaggt cagcacgata gcactgtctc tctatgctta gggagaggcc tgtcctgtac      8400
atcccgtgcc cccacaagat gcctactaca acaacatctt ctgcatgtcc tgcatagcag      8460
tgttgggaga atgtgcacta cttccactct tctgatttct attttatgtg tttgctttat      8520
accagtgttg ccatttggga attaatacat ggttgatcaa atcaattgca tcacagctgt      8580
atcctgtatc agaggaacat tatcaaagct tttgttgctg tatttggtat ctgacctgca      8640
gataaacatg ttttaggaag gttttgcaaa agtagctgtg aaatgagctg gtgttgtgat      8700
ttaacctgac aggcagctaa acagtatacc acagagctat tcacctactt tccctcagtg      8760
ggaaaaggga agagaactga gggggggggg aataaataag taaataacaa aataaaactc      8820
atggattaag aaaaagactt tgtactggaa tggatgagaa gaataatagt aatgataata      8880
atatgtcact ctgaaagtaa tgcctcttat ttctgtggag actacaaaca tacaaagagc      8940
acaacattcc atagagcaaa ttctcagtta cagaatgcta tttttttttt caacacagtc      9000
aaaatcatta atttttttt gcctgcaatg gacaagagct ttgaagctgt tctcgtaaaa      9060
atctgtacta gcagaagtga cctgcaatca ctactgctga aatgcacaac ccaccacatc      9120
attgtgctca cattcactgt ttggtttctg taaatgtaca ggaattgtct gaaattagat      9180
atgatttttt ttttctccat gaaggaattc aattacacac ctttgcctca tgcacttctt      9240
tgtcattttt gtcagactgc ttctctcctg caatttgtct catggcaaca aaatataatg      9300
gagttctgct gggaacttcc ctactgccat accactatca tctgcctctg acattttgga      9360
caaatgtaat aaaataggag gtattacttt cagagcagac cttgtatgta tttacaaaac      9420
aagtggtaca caaaaaaaat tgttcatccc accaaccaat gcccatcctg tccctgaata      9480
gtagctgtcc cccacagcct tgaccagttt aggtcaacag ttctgcttct gtcccctccc      9540
agctccttgt aacccctcag ccccccttgc tggcaggaca gtatgagaag ctgaaaaact      9600
agaatgtcct agttctttgc agtgctgcta atcaacaacc aaaacagtgg tgtgttacca      9660
atattgttga tatcacagca tcataccatt atgaaggaag taacccagcc aaaatcaggt      9720
cagcttgcta acaagagaac tgtgcataag tttaagatgt gtgtgttcct cagtacctta      9780
aaaaataagt agtaacgttc aaatgagtag aagagtagaa ctgagcttaa aacatctgtc      9840
agacaacagt gaaccaacc                                                    9859
```

```
<210> SEQ ID NO 124
<211> LENGTH: 11581
<212> TYPE: DNA
<213> ORGANISM: Artificial Sequence
<220> FEATURE:
<223> OTHER INFORMATION: Targeting Vector TV5

<400> SEQUENCE: 124
gaatgaaggg cctgagggtg ggcagtctgt ctatcatgta catctccata ttctgggagg        60
tcgtcagttg ggctggcctc ctggctaaga tttttgcacc acaagagatg ctgcatgtgt       120
```

-continued

```
acaaatcact  agcaaataga  tttgtttccc  atcaacttag  ccactgttaa  tgtaaattgt   180
tcttggatat  gtgtctttgg  agggcaataa  atgctctgaa  cagcacttgc  acaataaaga   240
tacagcatgt  gggaatgatc  tgtctcatgt  gtcttactga  tggtattggt  tctgtaagat   300
aaaatattgt  gtctgggatg  tgtttggctc  tactattaat  ggtgctctat  tgattgtgat   360
ttgtcatttg  aaacctgagg  atgcgactgt  atagcagtct  ttcatgcatt  tttggaaaaa   420
aacttaagct  ttttgaaagc  tgctgctaca  actttttgta  ttgttataaa  gttttgtatt   480
gtttttttaa  ttgtgaaatt  ataaagatgc  cgtgcaggga  ctgtttgaag  caaagtgcat   540
tgttttagaa  acctacaact  ctagttcaag  cactccatca  gtatctgctt  aatctttgtc   600
atcctttgct  atgagaaaat  attaagcagt  agtctaaagg  tactatgaaa  ctataacata   660
gctgacattg  tatttataac  tacgtcatga  ttttgataga  attgaggact  tgaaaatgtt   720
aaactattca  tgtagggcct  cttaagatgc  ttaagttgtt  tagtaatgta  agtgtgcatt   780
taattgagat  tttattgggc  ataatttgtc  catcagtatg  acactccttg  tcagtgttgc   840
cttatacttg  atgttgttac  cggatctctg  caaggcagtt  attcttgaat  taggctcatt   900
gaagtgtctg  ccagtataaa  tatatagcaa  ctgttctttg  tgttaaaatt  gagaagctaa   960
ccagttttta  gtgcttctga  ctgttggaat  tctttaagca  gatgccataa  gaaaattgta  1020
tttgtgatca  ccacttctcc  agagtggttt  taacaccaag  ggcattagag  aaagaaaggc  1080
aggcgtgtag  agaatagtgg  acagacaaaa  gctgtgagtt  acgttatgtt  tttcagctga  1140
aaagctgtgt  ttggtaaaag  catatgaaat  cactcaactt  ggaagcattc  tcttagttct  1200
ctgatagttc  tgagcagcag  aactcttcac  ctaagaggtt  acttcaactg  gaagactacc  1260
tagtgcttct  gatggcaact  atatttaaga  tgagaataag  aggtgtttcc  agtgtggtag  1320
cctcacatct  gttgcagtgg  ttaccgttcg  tcctcctccg  agggacacag  cttggccatt  1380
cactgtggtg  acaccaatat  gatgatcagc  aaatggtgtt  tattcactac  taaacacagc  1440
ttatatacat  ttttacctac  aaaatcgtgc  tgtcatgtcc  cactctgatt  ggttcacaca  1500
tttccccgaa  aagtgccacc  tgggtcgaca  ttgattattg  actagttatt  aatagtaatc  1560
aattacgggg  tcattagttc  atagcccata  tatggagttc  cgcgttacat  aacttacggt  1620
aaatggcccg  cctggctgac  cgcccaacga  cccccgccca  ttgacgtcaa  taatgacgta  1680
tgttcccata  gtaacgccaa  tagggacttt  ccattgacgt  caatgggtgg  agtatttacg  1740
gtaaactgcc  cacttggcag  tacatcaagt  gtatcatatg  ccaagtacgc  ccctattga  1800 cgtcaatgac  ggtaaatggc  ccgcctggca  ttatgcccag  tacatgacct  tatgggactt  1860
tcctacttgg  cagtacatct  acgtattagt  catcgctatt  accatggtcg  aggtgagccc  1920
cacgttctgc  ttcactctcc  ccatctcccc  cccctcccca  ccccaattt  tgtatttatt  1980 tattttttaa  ttattttgtg  cagcgatggg  ggcggggggg  ggggggggc  gcgcgccagg  2040 cggggcgggg  cggggcgagg  ggcggggcgg  ggcgaggcgg  agaggtgcgg  cggcagccaa  2100
tcagagcggc  gcgctccgaa  agtttccttt  tatggcgagg  cggcggcggc  ggcggcccta  2160
taaaaagcga  agcgcgcggc  gggcggggag  tcgctgcgac  gctgccttcg  ccccgtgccc  2220
cgctccgccg  ccgcctcgcg  ccgcccgccc  cggctctgac  tgaccgcgtt  actcccacag  2280
gtgagcgggc  gggacggccc  ttctcctccg  ggctgtaatt  agcgcttggt  ttaatgacgg  2340
cttgtttctt  ttctgtggct  gcgtgaaagc  cttgaggggc  tccgggaggg  cccttttgtgc  2400 ggggggagcg  gctcgggggg  tgcgtgcgtg  tgtgtgtgcg  tggggagcgc  cgcgtgcggc  2460
```

```
tccgcgctgc ccggcggctg tgagcgctgc gggcgcggcg cggggctttg tgcgctccgc     2520
agtgtgcgcg aggggagcgc ggccgggggc ggtgccccgc ggtgcggggg gggctgcgag     2580
gggaacaaag gctgcgtgcg gggtgtgtgc gtgggggggt gagcagggggg tgtgggcgcg     2640 tcggtcgggc tgcaacccccc cctgcaccccc cctccccgag ttgctgagca cggcccggct     2700
tcgggtgcgg ggctccgtac ggggcgtggc gcggggctcg ccgtgccggg cgggggggtgg     2760 cggcaggtgg gggtgccggg cggggcgggg ccgcctcggg ccggggaggg ctcggggggag     2820 gggcgcggcg gcccccggag cgccggcggc tgtcgaggcg cggcgagccg cagccattgc     2880
cttttatggt aatcgtgcga gagggcgcag ggacttcctt tgtcccaaat ctgtgcggag     2940
ccgaaatctg ggaggcgccg ccgcaccccc tctagcgggc gcggggcgaa gcggtgcggc     3000
gccggcagga aggaaatggg cggggagggc cttcgtgcgt cgccgcgccg ccgtcccctt     3060
ctccctctcc agcctcgggg ctgtccgcgg ggggacggct gccttcgggg gggacggggc     3120
agggcggggt tcggcttctg gcgtgtgacc ggcggctcta gagcctctgc taaccatgtt     3180
catgccttct tctttttcct acagctcctg ggcaacgtgc tggttaataa cttcgtataa     3240
tgtatgctat acgaagttat accggtgaag ttcctattcc gaagttccta ttctctagaa     3300
agtataggaa cttcgccacc atggtgagca aggggcgagga gctgttcacc ggggtggtgc     3360
ccatcctggt cgagctggac ggcgacgtaa acggccacaa gttcagcgtg tccggcgagg     3420
gcgagggcga tgccacctac ggcaagctga ccctgaagtt catctgcacc accggcaagc     3480
tgcccgtgcc ctggcccacc ctcgtgacca ccctgaccta cggcgtgcag tgcttcagcc     3540
gctaccccga ccacatgaag cagcacgact tcttcaagtc cgccatgccc gaaggctacg     3600
tccaggagcg caccatcttc ttcaaggacg acggcaacta caagacccgc gccgaggtga     3660
agttcgaggg cgacacccctg gtgaaccgca tcgagctgaa gggcatcgac ttcaaggagg     3720
acggcaacat cctggggcac aagctggagt acaactacaa cagccacaac gtctatatca     3780
tggccgacaa gcagaagaac ggcatcaagg tgaacttcaa gatccgccac aacatcgagg     3840
acggcagcgt gcagctcgcc gaccactacc agcagaacac ccccatcggc gacggccccg     3900
tgctgctgcc cgacaaccac tacctgagca cccagtccgc cctgagcaaa gacccccaacg     3960 agaagcgcga tcacatggtc ctgctggagt tcgtgaccgc cgccgggatc actctcggca     4020
tggacgagct gtacaaggggc agcggcgcca ccaacttcag cctgctgaag caggccggcg     4080
acgtggagga gaacccccggc cccgctagct aaagcggccg ccaattccta gagctcgctg     4140
atcagcctcg actgtgcctt ctagttgcca gccatctgtt gtttgccccct cccccgtgcc     4200 ttccttgacc ctggaaggtg ccactcccac tgtcctttcc taataaaatg aggaaattgc     4260
atcgcattgt ctgagtaggt gtcattctat tctgggggggt ggggtggggc aggacagcaa     4320 ggggggaggat tgggaagaca atagcaggca tgctggggag aagttcctat tccgaagttc     4380
ctattctcta gaaagtatag gaacttcgct agcaccggtg ccaccatgaa tggagctata     4440
ggaggtgacc ttttgctcaa ttttcctgac atgtcggtcc tagagcgcca aagggctcac     4500
ctcaagtacc tcaatcccac ctttgattct cctctcgccg gcttctttgc cgattcttca     4560
atgattaccg gcggcgagat ggacagctat cttttcgactg ccggtttgaa tcttccgatg     4620
atgtacggtg agacgacggt ggaaggtgat tcaagactct caatttcgcc ggaaacgacg     4680
cttgggactg gaaatttcaa gaaacggaag tttgatacag agactaagga ttgtaatgag     4740
aagaagaaga agatgacgat gaacagagat gacctagtag aagaaggaga agaagagaag     4800
tcgaaaataa cagagcaaaa caatgggagc acaaaaagca tcaagaagat gaaacacaaa     4860
```

-continued

```
gccaagaaag aagagaacaa tttctctaat gattcatcta aagtgacgaa ggaattggag    4920
aaaacggatt atattcatgg tggcggtggc tctggaggtg gtgggtccgg aggaggcggc    4980
cgccgaccaa gtgacagcaa tgctgtttca ctggttatgc ggcggatccg aaaagaaaac    5040
gttgatgccg gtgaacgtgc aaaacaggct ctagcgttcg aacgcactga tttcgaccag    5100
gttcgttcac tcatggaaaa tagcgatcgc tgccaggata tacgtaatct ggcatttctg    5160
gggattgctt ataacaccct gttacgtata gccgaaattg ccaggatcag ggttaaagat    5220
atctcacgta ctgacggtgg gagaatgtta atccatattg gcagaacgaa aacgctggtt    5280
agcaccgcag gtgtagagaa ggcacttagc ctgggggtaa ctaaactggt cgagcgatgg    5340
atttccgtct ctggtgtagc tgatgatccg aataactacc tgttttgccg ggtcagaaaa    5400
aatggtgttg ccgcgccatc tgccaccagc cagctatcaa ctcgcgccct ggaagggatt    5460
tttgaagcaa ctcatcgatt gatttacggc gctaaggatg actctggtca gagatacctg    5520
gcctggtctg gacacagtgc ccgtgtcgga gccgcgcgag atatggcccg cgctggagtt    5580
tcaataccgg agatcatgca agctggtggc tggaccaatg taaatattgt catgaactat    5640
atccgtaacc tggatagtga aacaggggca atggtgcgcc tgctggaaga tggcgattag    5700
cccgggtagg cccctctccc tccccccccc ctaacgttac tggccgaagc cgcttggaat    5760
aaggccggtg tgcgtttgtc tatatgttat tttccaccat attgccgtct tttggcaatg    5820
tgagggcccg gaaacctggc cctgtcttct tgacgagcat cctaggggt ctttcccctc     5880 tcgccaaagg aatgcaaggt ctgttgaatg tcgtgaagga agcagttcct ctggaagctt    5940
cttgaagaca acaacgtct gtagcgaccc tttgcaggca gcggaacccc ccacctggcg      6000
acaggtgcct ctgcggccaa aagccacgtg tataagatac acctgcaaag gcggcacaac    6060
cccagtgcca cgttgtgagt tggatagttg tggaaagagt caaatggctc tcctcaagcg    6120
tattcaacaa ggggctgaag gatgcccaga aggtacccca ttgtatggga tctgatctgg    6180
ggcctcggtg cacatgcttt acatgtgttt agtcgaggtt aaaaaaacgt ctaggccccc    6240
cgaaccacgg ggacgtggtt ttcctttgaa aaacacgatg ataatatggc cacaaccatg    6300
cctaaaaaga agcgtaaagt catgaagatg aagatggaca aaaagactat agtttggttt    6360
agaagagacc taaggattga ggataatcct gcattagcag cagctgctca cgaaggatct    6420 gttttttcctg tcttcatttg gtgtcctgaa gaagaaggac agttttatcc tggaagagct    6480
tcaagatggt ggatgaaaca atcacttgct cacttatctc aatccttgaa ggctcttgga    6540
tctgacctca ctttaatcaa aacccacaac acgatttcag cgatcttgga ttgtatccgc    6600
gttaccggtg ctacaaaagt cgtctttaac cacctctatg atcctgtttc gttagttcgg    6660
gaccataccg taaaggagaa gctggtggaa cgtgggatct ctgtgcaaag ctacaatgga    6720
gatctattgt atgaaccgtg ggagatatac tgcgaaaagg gcaaaccttt tacgagtttc    6780
aattcttact ggaagaaatg cttagatatg tcgattgaat ccgttatgct tcctcctcct    6840
tggcggttga tgccaataac tgcagcggct gaagcgattt gggcgtgttc gattgaagaa    6900
ctagggctgg agaatgaggc cgagaaaccg agcaatgcgt tgttaactag agcttggtct    6960
ccaggatgga gcaatgctga taagttacta aatgagttca tcgagaagca gttgatagat    7020
tatgcaaaga acagcaagaa agttgttggg aattctactt cactactttc tccgtatctc    7080
catttcgggg aaataagcgt cagacacgtt ttccagtgtg cccggatgaa acaaattata    7140
tgggcaagag ataagaacag tgaaggagaa gaaagtgcag atctttttct taggggaatc    7200
```

-continued

```
ggtttaagag agtattctcg gtatatatgt ttcaacttcc cgtttactca cgagcaatcg      7260
ttgttgagtc atcttcggtt tttcccttgg gatgctgatg ttgataagtt caaggcctgg      7320
agacaaggca ggaccggtta tccgttggtg gatgccggaa tgagagagtt ttgggctacc      7380
ggatggatgc ataacagaat aagagtgatt gtttcaagct ttgctgtgaa gtttcttctc      7440
cttccatgga aatggggaat gaagtatttc tgggatacac ttttggatgc tgatttggaa      7500
tgtgacatcc ttggctggca gtatatctct gggagtatcc ccgatggcca cgagcttgat      7560
cgcttggaca atcccgcgtt acaaggcgcc aaatatgacc cagaaggtga gtacataagg      7620
caatggcttc ccgagcttgc gagattgcca actgaatgga tccatcatcc atgggacgct      7680
cctttaaccg tactcaaagc ttctggtgtg gaactcggaa caaactatgc gaaacccatt      7740
gtagacatcg acacagctcg tgagctacta gctaaagcta tttcaagaac ccgtgaagca      7800
cagatcatga tcggagcagc acctgatgag attgtagcag atagcttcga ggccttaggg      7860
gctaatacca ttaaagaacc tggtctttgc ccatctgtgt cttctaatga ccaacaagta      7920
ccttcggctg ttggtggcgg tggctctgga ggtggtgggt ccgaggagg cggccgcacg      7980 agtgatgagg ttcgcaagaa cctgatggac atgttcaggg atcgccaggc gttttctgag      8040
catacctgga aaatgcttct gtccgtttgc cggtcgtggg cggcatggtg caagttgaat      8100
aaccggaaat ggtttcccgc agaacctgaa gatgttcgcg attatcttct atatcttcag      8160
gcgcgcggtc tggcagtaaa aactatccag caacatttgg gccagctaaa catgcttcat      8220
cgtcggtccg ggctgtaatt aattaactcc tcaggtgcag gctgcctatc agaaggtggt      8280
ggctggtgtg gccaatgccc tggctcacaa ataccactga gatctttttc cctctgccaa      8340
aaattatggg gacatcatga agcccctga gcatctgact tctggctaat aaaggaaatt      8400
tattttcatt gcaatagtgt gttggaattt tttgtgtctc tcactcggaa ggacatatgg      8460
gagggcaaat catttaaaac atcagaatga gtatttggtt tagagtttgg caacatatgc      8520
ccatatgctg gctgccatga acaaaggttg gctataaaga ggtcatcagt atatgaaaca      8580
gccccctgct gtccattcct tattccatag aaaagccttg acttgaggtt agatttttt      8640 tatattttgt tttgtgttat ttttttcttt aacatcccta aaattttcct tacatgtttt      8700
actagccaga ttttttcctcc tctcctgact actcccagtc atagctgtcc ctcttctctt      8760
atggagatca taacttcgta taatgtatgc tatacgaagt tatacgcgtg ccaccatgga      8820
tcattcccag tgccttgtga ctatatacgc cgcggcggtg ctgctggggc tccggctgca      8880
gcagggctcc tgccagcact acctgcacat ccgcccggct cccagcgaca acctgcccct      8940
ggtggatcta atcgagcacc cggaccctat ctttgacccc aaggagaagg atcttaacga      9000
gaccttgcta aggagcctca tgggaggaca cttcgaccct aactttatgg ctatgtccct      9060
gcccgaggac cggctcgggg tagacgatct ggccgagctg gacttgctgc tgcggcagag      9120
accctcggga gcgatgcccg cgaaatcaa ggggctggag ttctacgacg gctgcagcc      9180 gggcaagaag cacaggctga gcaagaagct gcgcaggaag ctgcagatgt ggctctggtc      9240
ccagaccttc tgcccggtcc tatacacgtg gaacgatctc ggcagccgct tttggccccg      9300
gtacgtcaaa gtgggcagct gctacagtaa aaggtcttgc tctgtcccag aaggcatggt      9360
ctgcaaacct gccaagtccg tgcatttaac gatcctgagg tggcggtgcc agcggcgggg      9420
cgggcagcgg tgcacgtgga tccccatcca gtaccccatc atcgcggagt gcaagtgctc      9480
ctgctagacg cgtactcctc aggtgcaggc tgcctatcag aaggtggtgg ctggtgtggc      9540
caatgccctg gctcacaaat accactgaga tcttttttcc tctgccaaaa attatgggga      9600
```

```
catcatgaag cccctttgagc atctgacttc tggctaataa aggaaattta ttttcattgc    9660
aatagtgtgt tggaattttt tgtgtctctc actcggaagg acatatggga gggcaaatca    9720
tttaaaacat cagaatgagt atttggttta gagtttggca acatatgccc atatgctggc    9780
tgccatgaac aaaggttggc tataaagagg tcatcagtat atgaaacagc ccctgctgt    9840 ccattcctta ttccatagaa aagccttgac ttgaggttag attttttta tattttgttt    9900 tgtgttattt ttttctttaa catccctaaa attttcctta catgtttac tagccagatt    9960 tttcctcctc tcctgactac tcccagtcat agctgtccct cttctcttat ggagatcgcc    10020
gtttccacat tcttttctca tccttcttct cctgttttct ctgcatcaag gtcagcacga    10080
tagcactgtc tctctatgct tagggagagg cctgtcctgt acatcccgtg cccccacaag    10140
atgcctacta caacaacatc ttctgcatgt cctgcatagc agtgttggga gaatgtgcac    10200
tacttccact cttctgattt ctattttatg tgtttgcttt ataccagtgt tgccatttgg    10260
gaattaatac atggttgatc aaatcaattg catcacagct gtatcctgta tcagaggaac    10320
attatcaaag cttttgttgc tgtatttggt atctgacctg cagataaaca tgttttagga    10380
aggttttgca aaagtagctg tgaaatgagc tggtgttgtg atttaacctg acaggcagct    10440
aaacagtata ccacagagct attcacctac tttccctcag tgggaaaagg gaagagaact    10500 gaggggggg ggaataaata agtaaataac aaaataaaac tcatggatta agaaaaagac    10560
tttgtactgg aatggatgag aagaataata gtaatgataa taatatgtca ctctgaaagt    10620
aatgcctctt atttctgtgg agactacaaa catacaaaga gcacaacatt ccatagagca    10680
aattctcagt tacagaatgc tatttttttt ttcaacacag tcaaaatcat taattttttt    10740
ttgcctgcaa tggacaagag ctttgaagct gttctcgtaa aaatctgtac tagcagaagt    10800
gacctgcaat cactactgct gaaatgcaca acccaccaca tcattgtgct cacattcact    10860
gtttggtttc tgtaaatgta caggaattgt ctgaaattag atatgatttt ttttttctcc    10920
atgaaggaat tcaattacac acctttgcct catgcacttc tttgtcattt ttgtcagact    10980
gcttctctcc tgcaatttgt ctcatggcaa caaaatataa tggagttctg ctgggaactt    11040
ccctactgcc ataccactat catctgcctc tgacattttg gacaaatgta ataaaatagg    11100
aggtattact ttcagagcag accttgtatg tatttacaaa acaagtggta cacaaaaaaa    11160
attgttcatc ccaccaacca atgcccatcc tgtccctgaa tagtagctgt cccccacagc    11220
cttgaccagt ttaggtcaac agttctgctt ctgtcccctc ccagctcctt gtaacccctc    11280 agccccctt gctggcagga cagtatgaga agctgaaaaa ctagaatgtc ctagttcttt    11340
gcagtgctgc taatcaacaa ccaaaacagt ggtgtgttac caatattgtt gatatcacag    11400
catcatacca ttatgaagga agtaacccag ccaaaatcag gtcagcttgc taacaagaga    11460
actgtgcata agtttaagat gtgtgtgttc ctcagtacct taaaaaataa gtagtaacgt    11520
tcaaatgagt agaagagtag aactgagctt aaaacatctg tcagacaaca gtgaaccaac    11580
c                                                                     11581
```

<210> SEQ ID NO 125
<211> LENGTH: 11566
<212> TYPE: DNA
<213> ORGANISM: Artificial Sequence
<220> FEATURE:
<223> OTHER INFORMATION: Targeting Vector TV6

<400> SEQUENCE: 125

-continued

```
gaatgaaggg cctgagggtg ggcagtctgt ctatcatgta catctccata ttctgggagg      60
tcgtcagttg ggctggcctc ctggctaaga tttttgcacc acaagagatg ctgcatgtgt     120
acaaatcact agcaaataga tttgtttccc atcaacttag ccactgttaa tgtaaattgt     180
tcttggatat gtgtctttgg agggcaataa atgctctgaa cagcacttgc acaataaaga     240
tacagcatgt gggaatgatc tgtctcatgt gtcttactga tggtattggt tctgtaagat     300
aaaatattgt gtctgggatg tgtttggctc tactattaat ggtgctctat tgattgtgat     360
ttgtcatttg aaacctgagg atgcgactgt atagcagtct ttcatgcatt tttggaaaaa     420
aacttaagct ttttgaaagc tgctgctaca actttttgta ttgttataaa gttttgtatt     480 gttttttttaa ttgtgaaatt ataaagatgc cgtgcaggga ctgtttgaag caaagtgcat     540
tgttttagaa acctacaact ctagttcaag cactccatca gtatctgctt aatctttgtc     600
atcctttgct atgagaaaat attaagcagt agtctaaagg tactatgaaa ctataacata     660
gctgacattg tatttataac tacgtcatga ttttgataga attgaggact tgaaaatgtt     720
aaactattca tgtagggcct cttaagatgc ttaagttgtt tagtaatgta agtgtgcatt     780
taattgagat tttattgggc ataatttgtc catcagtatg acactccttg tcagtgttgc     840
cttatacttg atgttgttac cggatctctg caaggcagtt attcttgaat taggctcatt     900
gaagtgtctg ccagtataaa tatatagcaa ctgttctttg tgttaaaatt gagaagctaa     960 ccagtttttta gtgcttctga ctgttggaat tctttaagca gatgccataa gaaaattgta    1020
tttgtgatca ccacttctcc agagtggttt taacaccaag ggcattagag aaagaaaggc    1080
aggcgtgtag agaatagtgg acagacaaaa gctgtgagtt acgttatgtt tttcagctga    1140
aaagctgtgt ttggtaaaag catatgaaat cactcaactt ggaagcattc tcttagttct    1200
ctgatagttc tgagcagcag aactcttcac ctaagaggtt acttcaactg gaagactacc    1260
tagtgcttct gatggcaact atatttaaga tgagaataag aggtgtttcc agtgtggtag    1320
cctcacatct gttgcagtgg ttaccgttcg tcctcctccg agggacacag cttggccatt    1380
cactgtggtg acaccaatat gatgatcagc aaatggtgtt tattcactac taaacacagc    1440
ttatatacat ttttacctac aaaatcgtgc tgtcatgtcc cactctgatt ggttcacaca    1500
tttccccgaa aagtgccacc tgggtcgaca ttgattattg actagttatt aatagtaatc    1560
aattacgggg tcattagttc atagcccata tatggagttc cgcgttacat aacttacggt    1620
aaatggcccg cctggctgac cgcccaacga cccccgccca ttgacgtcaa taatgacgta    1680
tgttcccata gtaacgccaa tagggacttt ccattgacgt caatgggtgg agtatttacg    1740
gtaaactgcc cacttggcag tacatcaagt gtatcatatg ccaagtacgc cccctattga    1800
cgtcaatgac ggtaaatggc ccgcctggca ttatgcccag tacatgacct tatgggactt    1860
tcctacttgg cagtacatct acgtattagt catcgctatt accatggtcg aggtgagccc    1920
cacgttctgc ttcactctcc ccatctcccc cccctcccca cccccaattt tgtatttatt    1980
tattttttaa ttattttgtg cagcgatggg ggcggggggg ggggggggc gcgcgccagg    2040 cggggcgggg cggggcgagg ggcggggcgg ggcgaggcgg agaggtgcgg cggcagccaa    2100
tcagagcggc gcgctccgaa agtttccttt tatggcgagg cggcggcggc ggcggccta    2160 taaaaagcga agcgcgcggc gggcggggag tcgctgcgac gctgccttcg ccccgtgccc    2220
cgctccgccg ccgcctcgcg ccgcccgccc cggctctgac tgaccgcgtt actcccacag    2280
gtgagcgggc gggacggccc ttctcctccg ggctgtaatt agcgcttggt ttaatgacgg    2340
cttgtttctt ttctgtggct gcgtgaaagc cttgaggggc tccgggaggg ccctttgtgc    2400
```

-continued

```
gggggagcg gctcggggg tgcgtgcgtg tgtgtgtgcg tggggagcgc cgcgtgcggc      2460
tccgcgctgc ccggcggctg tgagcgctgc gggcgcggcg cggggctttg tgcgctccgc      2520
agtgtgcgcg aggggagcgc ggccggggc ggtgccccgc ggtgcggggg gggctgcgag      2580
gggaacaaag gctgcgtgcg gggtgtgtgc gtgggggggt gagcaggggg tgtgggcgcg      2640
tcggtcgggc tgcaacccc cctgcacccc cctccccgag ttgctgagca cggcccggct      2700
tcgggtgcgg ggctccgtac ggggcgtggc gcggggctcg ccgtgccggg cggggggtgg      2760
cggcaggtgg gggtgccggg cggggcgggg ccgcctcggg ccggggaggg ctcgggggag      2820
gggcgcggcg gccccggag cgccggcggc tgtcgaggcg cggcgagccg cagccattgc      2880
cttttatggt aatcgtgcga gagggcgcag ggacttcctt tgtcccaaat ctgtgcggag      2940
ccgaaatctg ggaggcgccg ccgcaccccc tctagcgggc gcggggcgaa gcggtgcggc      3000
gccggcagga aggaaatggg cggggagggc cttcgtgcgt cgccgcgccg ccgtcccctt      3060
ctccctctcc agcctcgggg ctgtccgcgg ggggacggct gccttcgggg gggacggggc      3120
agggcggggt tcggcttctg gcgtgtgacc ggcggctcta gagcctctgc taaccatgtt      3180
catgccttct tctttttcct acagctcctg ggcaacgtgc tggttaataa cttcgtataa      3240
tgtatgctat acgaagttat accggtgaag ttcctattcc gaagttccta ttctctagaa      3300
agtataggaa cttcgccacc atggtgagca agggcgagga gctgttcacc ggggtggtgc      3360
ccatcctggt cgagctggac ggcgacgtaa acggccacaa gttcagcgtg tccggcgagg      3420
gcgagggcga tgccacctac ggcaagctga ccctgaagtt catctgcacc accggcaagc      3480
tgcccgtgcc ctggcccacc ctcgtgacca ccctgaccta cggcgtgcag tgcttcagcc      3540
gctaccccga ccacatgaag cagcacgact tcttcaagtc cgccatgccc gaaggctacg      3600
tccaggagcg caccatcttc ttcaaggacg acggcaacta caagacccgc gccgaggtga      3660
agttcgaggg cgacaccctg gtgaaccgca tcgagctgaa gggcatcgac ttcaaggagg      3720
acggcaacat cctggggcac aagctggagt acaactacaa cagccacaac gtctatatca      3780
tggccgacaa gcagaagaac ggcatcaagg tgaacttcaa gatccgccac aacatcgagg      3840
acggcagcgt gcagctcgcc gaccactacc agcagaacac ccccatcggc gacggccccg      3900
tgctgctgcc cgacaaccac tacctgagca cccagtccgc cctgagcaaa gaccccaacg      3960
agaagcgcga tcacatggtc ctgctggagt tcgtgaccgc cgccgggatc actctcggca      4020
tggacgagct gtacaagggc agcggcgcca ccaacttcag cctgctgaag caggccggcg      4080
acgtggagga gaaccccggc cccgctagct aaagcggccg ccaattccta gagctcgctg      4140
atcagcctcg actgtgcctt ctagttgcca gccatctgtt gtttgcccct ccccgtgcc       4200 ttccttgacc ctggaaggtg ccactcccac tgtcctttcc taataaaatg aggaaattgc      4260
atcgcattgt ctgagtaggt gtcattctat tctggggggt ggggtggggc aggacagcaa      4320
gggggaggat tgggaagaca atagcaggca tgctggggag aagttcctat tccgaagttc      4380
ctattctcta gaaagtatag gaacttcgct agcaccggtg ccaccatgaa tggagctata      4440
ggaggtgacc ttttgctcaa ttttcctgac atgtcggtcc tagagcgcca aagggctcac      4500
ctcaagtacc tcaatcccac ctttgattct cctctcgccg gcttctttgc cgattcttca      4560
atgattaccg gcggcgagat ggacagctat ctttcgactg ccggtttgaa tcttccgatg      4620
atgtacggtg agacgacggt ggaaggtgat tcaagactct caatttcgcc ggaaacgacg      4680
cttgggactg gaaatttcaa gaaacggaag tttgatacag agactaagga ttgtaatgag      4740
```

-continued

```
aagaagaaga agatgacgat gaacagagat gacctagtag aagaaggaga agaagagaag    4800
tcgaaaataa cagagcaaaa caatgggagc acaaaaagca tcaagaagat gaaacacaaa    4860
gccaagaaag aagagaacaa tttctctaat gattcatcta aagtgacgaa ggaattggag    4920
aaaacggatt atattcatgg tggcggtggc tctggaggtg gtgggtccgg aggaggcggc    4980
cgccgaccaa gtgacagcaa tgctgtttca ctggttatgc ggcggatccg aaaagaaaac    5040
gttgatgccg gtgaacgtgc aaaacaggct ctagcgttcg aacgcactga tttcgaccag    5100
gttcgttcac tcatggaaaa tagcgatcgc tgccaggata tacgtaatct ggcatttctg    5160
gggattgctt ataacaccct gttacgtata gccgaaattg ccaggatcag ggttaaagat    5220
atctcacgta ctgacggtgg gagaatgtta atccatattg gcagaacgaa aacgctggtt    5280
agcaccgcag gtgtagagaa ggcacttagc ctggggggtaa ctaaactggt cgagcgatgg    5340
atttccgtct ctggtgtagc tgatgatccg aataactacc tgtttttgccg ggtcagaaaa    5400 aatggtgttg ccgcgccatc tgccaccagc cagctatcaa ctcgcgccct ggaagggatt    5460
tttgaagcaa ctcatcgatt gatttacggc gctaaggatg actctggtca gagatacctg    5520
gcctggtctg gacacagtgc ccgtgtcgga gccgcgcgag atatggcccg cgctggagtt    5580
tcaataccgg agatcatgca agctggtggc tggaccaatg taaatattgt catgaactat    5640
atccgtaacc tggatagtga aacaggggca atggtgcgcc tgctggaaga tggcgattag    5700
cccgggtagg cccctctccc tccccccccc ctaacgttac tggccgaagc cgcttggaat    5760
aaggccggtg tgcgtttgtc tatatgttat tttccaccat attgccgtct tttggcaatg    5820
tgagggcccg gaaacctggc cctgtcttct tgacgagcat tcctaggggt ctttcccctc    5880
tcgccaaagg aatgcaaggt ctgttgaatg tcgtgaagga agcagttcct ctggaagctt    5940
cttgaagaca aacaacgtct gtagcgaccc tttgcaggca gcggaacccc ccacctggcg    6000
acaggtgcct ctgcggccaa aagccacgtg tataagatac acctgcaaag gcggcacaac    6060
cccagtgcca cgttgtgagt tggatagttg tggaaagagt caaatggctc tcctcaagcg    6120
tattcaacaa ggggctgaag gatgcccaga aggtacccca ttgtatggga tctgatctgg    6180
ggcctcggtg cacatgcttt acatgtgttt agtcgaggtt aaaaaaacgt ctaggccccc    6240
cgaaccacgg ggacgtggtt ttcctttgaa aaacacgatg ataatatggc cacaaccatg    6300
cctaaaaaga agcgtaaagt catgaagatg aagatggaca aaaagactat agtttggttt    6360
agaagagacc taaggattga ggataatcct gcattagcag cagctgctca cgaaggatct    6420 gttttttcctg tcttcatttg gtgtcctgaa gaagaaggac agtttttatcc tggaagagct    6480 tcaagatggt ggatgaaaca atcacttgct cacttatctc aatccttgaa ggctcttgga    6540
tctgacctca ctttaatcaa aacccacaac acgatttcag cgatcttgga ttgtatccgc    6600
gttaccggtg ctacaaaagt cgtctttaac cacctctatg atcctgtttc gttagttcgg    6660
gaccataccg taaaggagaa gctggtggaa cgtgggatct ctgtgcaaag ctacaatgga    6720
gatctattgt atgaaccgtg ggagatatac tgcgaaaagg gcaaacctttt tacgagtttc    6780 aattcttact ggaagaaatg cttagatatg tcgattgaat ccgttatgct tcctcctcct    6840
tggcggttga tgccaataac tgcagcggct gaagcgattt gggcgtgttc gattgaagaa    6900
ctagggctgg agaatgaggc cgagaaaccg agcaatgcgt tgttaactag agcttggtct    6960
ccaggatgga gcaatgctga taagttacta aatgagttca tcgagaagca gttgatagat    7020
tatgcaaaga acagcaagaa agttgttggg aattctactt cactactttc tccgtatctc    7080
catttcgggg aaataagcgt cagacacgtt ttccagtgtg cccggatgaa acaaattata    7140
```

-continued

```
tgggcaagag ataagaacag tgaaggagaa gaaagtgcag atcttttct taggggaatc      7200 ggtttaagag agtattctcg gtatatatgt ttcaacttcc cgtttactca cgagcaatcg      7260
ttgttgagtc atcttcggtt tttcccttgg gatgctgatg ttgataagtt caaggcctgg      7320
agacaaggca ggaccggtta tccgttggtg gatgccggaa tgagagagtt ttgggctacc      7380
ggatggatgc ataacagaat aagagtgatt gtttcaagct ttgctgtgaa gtttcttctc      7440
cttccatgga aatggggaat gaagtatttc tgggatacac ttttggatgc tgatttggaa      7500
tgtgacatcc ttggctggca gtatatctct gggagtatcc ccgatggcca cgagcttgat      7560
cgcttggaca atcccgcgtt acaaggcgcc aaatatgacc cagaaggtga gtacataagg      7620
caatggcttc ccgagcttgc gagattgcca actgaatgga tccatcatcc atgggacgct      7680
cctttaaccg tactcaaagc ttctggtgtg gaactcggaa caaactatgc gaaacccatt      7740
gtagacatcg acacagctcg tgagctacta gctaaagcta tttcaagaac ccgtgaagca      7800
cagatcatga tcggagcagc acctgatgag attgtagcag atagcttcga ggccttaggg      7860
gctaatacca ttaaagaacc tggtctttgc ccatctgtgt cttctaatga ccaacaagta      7920
ccttcggctg ttggtggcgg tggctctgga ggtggtgggg ccggaggagg cggccgcacg      7980
agtgatgagg ttcgcaagaa cctgatggac atgttcaggg atcgccaggc gttttctgag      8040
catacctgga aaatgcttct gtccgtttgc cggtcgtggg cggcatggtg caagttgaat      8100
aaccggaaat ggtttcccgc agaacctgaa gatgttcgcg attatcttct atatcttcag      8160
gcgcgcggtc tggcagtaaa aactatccag caacatttgg gccagctaaa catgcttcat      8220
cgtcggtccg ggctgtaatt aattaactcc tcaggtgcag gctgcctatc agaaggtggt      8280
ggctggtgtg gccaatgccc tggctcacaa ataccactga gatcttttc cctctgccaa      8340 aaattatggg gacatcatga agccccttga gcatctgact tctggctaat aaaggaaatt      8400
tattttcatt gcaatagtgt gttggaattt tttgtgtctc tcactcggaa ggacatatgg      8460
gagggcaaat catttaaaac atcagaatga gtatttggtt tagagtttgg caacatatgc      8520
ccatatgctg gctgccatga acaaaggttg gctataaaga ggtcatcagt atatgaaaca      8580
gccccctgct gtccattcct tattccatag aaaagccttg acttgaggtt agattttttt      8640
tatattttgt tttgtgttat ttttttcttt aacatcccta aaattttcct tacatgtttt      8700
actagccaga ttttttcctcc tctcctgact actcccagtc atagctgtcc ctcttctctt      8760
atggagatca taacttcgta taatgtatgc tatacgaagt tatacgcgtg ccaccatgga      8820
tcctgatgat gttgttgatt cttctaaatc ttttgtgatg gaaaactttt cttcgtacca      8880
cgggactaaa cctggttatg tagattccat tcaaaaaggt atacaaaagc caaatctgg       8940 tacacaagga aattatgacg atgattggaa agggttttat agtaccgaca ataaatacga      9000
cgctgcggga tactctgtag ataatgaaaa cccgctctct ggaaaagctg gaggcgtggt      9060
caaagtgacg tatccaggac tgacgaaggt tctcgcacta aaagtggata atgccgaaac      9120
tattaagaaa gagttaggtt taagtctcac tgaaccgttg atggagcaag tcggaacgga      9180
agagtttatc aaaaggttcg gtgatggtgc ttcgcgtgta gtgctcagcc ttcccttcgc      9240
tgaggggagt tctagcgttg aatatattaa taactgggaa caggcgaaag cgttaagcgt      9300
agaacttgag attaattttg aaacccgtgg aaaacgtggc caagatgcga tgtatgagta      9360
tatggctcaa gcctgtgcag gaaatcgtgt caggcgatct ctttgtgaag gaaccttact      9420
tctgtggtgt gacataattg gacaaactac ctacagagat ttaaagctct aaacgcgtac      9480
```

```
tcctcaggtg caggctgcct atcagaaggt ggtggctggt gtggccaatg ccctggctca      9540
caaataccac tgagatcttt ttccctctgc caaaaattat ggggacatca tgaagcccct      9600
tgagcatctg acttctggct aataaaggaa atttattttc attgcaatag tgtgttggaa      9660
ttttttgtgt ctctcactcg gaaggacata tgggagggca aatcatttaa aacatcagaa      9720
tgagtatttg gtttagagtt tggcaacata tgcccatatg ctggctgcca tgaacaaagg      9780
ttggctataa agaggtcatc agtatatgaa acagccccct gctgtccatt ccttattcca      9840
tagaaaagcc ttgacttgag gttagatttt ttttatattt tgttttgtgt tatttttttc      9900
tttaacatcc ctaaaatttt ccttacatgt tttactagcc agattttcc tcctctcctg       9960 actactccca gtcatagctg tccctcttct cttatggaga tcgccgtttc cacattcttt     10020
tctcatcctt cttctcctgt tttctctgca tcaaggtcag cacgatagca ctgtctctct     10080
atgcttaggg agaggcctgt cctgtacatc ccgtgccccc acaagatgcc tactacaaca     10140
acatcttctg catgtcctgc atagcagtgt tgggagaatg tgcactactt ccactcttct     10200
gatttctatt ttatgtgttt gctttatacc agtgttgcca tttgggaatt aatacatggt     10260
tgatcaaatc aattgcatca cagctgtatc ctgtatcaga ggaacattat caaagctttt     10320
gttgctgtat ttggtatctg acctgcagat aaacatgttt taggaaggtt ttgcaaaagt     10380
agctgtgaaa tgagctggtg ttgtgattta acctgacagg cagctaaaca gtataccaca     10440
gagctattca cctactttcc ctcagtggga aaagggaaga gaactgaggg gggggggaat     10500
aaataagtaa ataacaaaat aaaactcatg gattaagaaa aagactttgt actggaatgg     10560
atgagaagaa taatagtaat gataataata tgtcactctg aaagtaatgc ctcttatttc     10620
tgtggagact acaaacatac aaagagcaca acattccata gagcaaattc tcagttacag     10680
aatgctattt tttttttcaa cacagtcaaa atcattaatt ttttttttgcc tgcaatggac     10740 aagagctttg aagctgttct cgtaaaaatc tgtactagca gaagtgacct gcaatcacta     10800
ctgctgaaat gcacaaccca ccacatcatt gtgctcacat tcactgtttg gtttctgtaa     10860
atgtacagga attgtctgaa attagatatg attttttttt tctccatgaa ggaattcaat     10920
tacacacctt tgcctcatgc acttctttgt catttttgtc agactgcttc tctcctgcaa     10980
tttgtctcat ggcaacaaaa tataatggag ttctgctggg aacttccta ctgccatacc      11040 actatcatct gcctctgaca ttttggacaa atgtaataaa ataggaggta ttactttcag     11100
agcagacctt gtatgtattt acaaaacaag tggtacacaa aaaaaattgt tcatcccacc     11160
aaccaatgcc catcctgtcc ctgaatagta gctgtccccc acagccttga ccagtttagg     11220
tcaacagttc tgcttctgtc ccctcccagc tccttgtaac ccctcagccc cccttgctgg     11280
caggacagta tgagaagctg aaaaactaga atgtcctagt tctttgcagt gctgctaatc     11340
aacaaccaaa acagtggtgt gttaccaata ttgttgatat cacagcatca taccattatg     11400
aaggaagtaa cccagccaaa atcaggtcag cttgctaaca agagaactgt gcataagttt     11460
aagatgtgtg tgttcctcag taccttaaaa aataagtagt aacgttcaaa tgagtagaag     11520
agtagaactg agcttaaaac atctgtcaga caacagtgaa ccaacc                     11566
```

```
<210> SEQ ID NO 126
<211> LENGTH: 11761
<212> TYPE: DNA
<213> ORGANISM: Artificial Sequence
<220> FEATURE:
<223> OTHER INFORMATION: Targeting Vector TV7

<400> SEQUENCE: 126
```

```
gaatgaaggg cctgagggtg ggcagtctgt ctatcatgta catctccata ttctgggagg     60
tcgtcagttg ggctggcctc ctggctaaga tttttgcacc acaagagatg ctgcatgtgt    120
acaaatcact agcaaataga tttgtttccc atcaacttag ccactgttaa tgtaaattgt    180
tcttggatat gtgtctttgg agggcaataa atgctctgaa cagcacttgc acaataaaga    240
tacagcatgt gggaatgatc tgtctcatgt gtcttactga tggtattggt tctgtaagat    300
aaaatattgt gtctgggatg tgtttggctc tactattaat ggtgctctat tgattgtgat    360
ttgtcatttg aaacctgagg atgcgactgt atagcagtct ttcatgcatt tttggaaaaa    420
aacttaagct ttttgaaagc tgctgctaca acttttgta ttgttataaa gttttgtatt    480
gtttttttaa ttgtgaaatt ataaagatgc cgtgcaggga ctgtttgaag caaagtgcat    540
tgttttagaa acctacaact ctagttcaag cactccatca gtatctgctt aatctttgtc    600
atcctttgct atgagaaaat attaagcagt agtctaaagg tactatgaaa ctataacata    660
gctgacattg tatttataac tacgtcatga ttttgataga attgaggact tgaaaatgtt    720
aaactattca tgtagggcct cttaagatgc ttaagttgtt tagtaatgta agtgtgcatt    780
taattgagat tttattgggc ataatttgtc catcagtatg acactccttg tcagtgttgc    840
cttatacttg atgttgttac cggatctctg caaggcagtt attcttgaat taggctcatt    900
gaagtgtctg ccagtataaa tatatagcaa ctgttctttg tgttaaaatt gagaagctaa    960
ccagttttta gtgcttctga ctgttggaat tctttaagca gatgccataa gaaaattgta   1020
tttgtgatca ccacttctcc agagtggttt taacaccaag ggcattagag aaagaaaggc   1080
aggcgtgtag agaatagtgg acagacaaaa gctgtgagtt acgttatgtt tttcagctga   1140
aaagctgtgt ttggtaaaag catatgaaat cactcaactt ggaagcattc tcttagttct   1200
ctgatagttc tgagcagcag aactcttcac ctaagaggtt acttcaactg gaagactacc   1260
tagtgcttct gatggcaact atatttaaga tgagaataag aggtgtttcc agtgtggtag   1320
cctcacatct gttgcagtgg ttaccgttcg tcctcctccg agggacacag cttggccatt   1380
cactgtggtg acaccaatat gatgatcagc aaatggtgtt tattcactac taaacacagc   1440
ttatatacat ttttacctac aaaatcgtgc tgtcatgtcc cactctgatt ggttcacaca   1500
tttccccgaa aagtgccacc tgggtcgaca ttgattattg actagttatt aatagtaatc   1560
aattacgggg tcattagttc atagcccata tatggagttc cgcgttacat aacttacggt   1620
aaatggcccg cctggctgac cgcccaacga cccccgccca ttgacgtcaa taatgacgta   1680
tgttcccata gtaacgccaa tagggacttt ccattgacgt caatgggtgg agtatttacg   1740
gtaaactgcc cacttggcag tacatcaagt gtatcatatg ccaagtacgc cccctattga   1800
cgtcaatgac ggtaaatggc ccgcctggca ttatgcccag tacatgacct tatgggactt   1860
tcctacttgg cagtacatct acgtattagt catcgctatt accatggtcg aggtgagccc   1920
cacgttctgc ttcactctcc ccatctcccc ccctcccca cccccaattt tgtatttatt   1980
tattttttaa ttattttgtg cagcgatggg ggcggggggg ggggggggc gcgcgccagg   2040 cggggcgggg cggggcgagg ggcggggcgg ggcgaggcgg agaggtgcgg cggcagccaa   2100
tcagagcggc gcgctccgaa agtttccttt tatggcgagg cggcggcggc ggcggcccta   2160
taaaaagcga agcgcgcggc gggcggggag tcgctgcgac gctgccttcg ccccgtgccc   2220
cgctccgccg ccgcctcgcg ccgcccgccc cggctctgac tgaccgcgtt actcccacag   2280
gtgagcgggc gggacggccc ttctcctccg ggctgtaatt agcgcttggt ttaatgacgg   2340
```

-continued

```
cttgtttctt ttctgtggct gcgtgaaagc cttgaggggc tccgggaggg ccctttgtgc     2400
ggggggagcg gctcgggggg tgcgtgcgtg tgtgtgtgcg tggggagcgc cgcgtgcggc     2460
tccgcgctgc ccggcggctg tgagcgctgc gggcgcggcg cggggctttg tgcgctccgc     2520
agtgtgcgcg aggggagcgc ggccgggggc ggtgccccgc ggtgcggggg gggctgcgag     2580
gggaacaaag gctgcgtgcg gggtgtgtgc gtgggggggt gagcagggg tgtgggcgcg      2640 tcggtcgggc tgcaacccc cctgcacccc cctccccgag ttgctgagca cggcccggct     2700
tcgggtgcgg ggctccgtac ggggcgtggc gcggggctcg ccgtgccggg cggggggtgg     2760
cggcaggtgg gggtgccggg cggggcgggg ccgcctcggg ccggggaggg ctcgggggag     2820
gggcgcggcg gcccccggag cgccggcggc tgtcgaggcg cggcgagccg cagccattgc     2880
cttttatggt aatcgtgcga gagggcgcag ggacttcctt tgtcccaaat ctgtgcggag     2940
ccgaaatctg ggaggcgccg ccgcaccccc tctagcgggc gcggggcgaa gcggtgcggc     3000
gccggcagga aggaaatggg cggggagggc cttcgtgcgt cgccgcgccg ccgtcccctt     3060
ctccctctcc agcctcgggg ctgtccgcgg ggggacggct gccttcgggg gggacggggc     3120
agggcggggt tcggcttctg gcgtgtgacc ggcggctcta gagcctctgc taaccatgtt     3180
catgccttct tcttttttcct acagctcctg ggcaacgtgc tggttaataa cttcgtataa     3240
tgtatgctat acgaagttat accggtgaag ttcctattcc gaagttccta ttctctagaa     3300
agtataggaa cttcgccacc atggtgagca agggcgagga gctgttcacc ggggtggtgc     3360
ccatcctggt cgagctggac ggcgacgtaa acggccacaa gttcagcgtg tccggcgagg     3420
gcgagggcga tgccacctac ggcaagctga ccctgaagtt catctgcacc accggcaagc     3480
tgcccgtgcc ctggcccacc ctcgtgacca ccctgaccta cggcgtgcag tgcttcagcc     3540
gctaccccga ccacatgaag cagcacgact tcttcaagtc cgccatgccc gaaggctacg     3600
tccaggagcg caccatcttc ttcaaggacg acggcaacta caagacccgc gccgaggtga     3660
agttcgaggg cgacaccctg gtgaaccgca tcgagctgaa gggcatcgac ttcaaggagg     3720
acggcaacat cctggggcac aagctggagt acaactacaa cagccacaac gtctatatca     3780
tggccgacaa gcagaagaac ggcatcaagg tgaacttcaa gatccgccac aacatcgagg     3840
acggcagcgt gcagctcgcc gaccactacc agcagaacac ccccatcggc gacggccccg     3900
tgctgctgcc cgacaaccac tacctgagca cccagtccgc cctgagcaaa gacccccaacg     3960 agaagcgcga tcacatggtc ctgctggagt tcgtgaccgc cgccgggatc actctcggca     4020
tggacgagct gtacaagggc agcggcgcca ccaacttcag cctgctgaag caggccggcg     4080
acgtggagga gaaccccggc cccgctagct aaagcggccg ccaattccta gagctcgctg     4140
atcagcctcg actgtgcctt ctagttgcca gccatctgtt gtttgcccct ccccgtgcc     4200 ttccttgacc ctggaaggtg ccactcccac tgtcctttcc taataaaatg aggaaattgc     4260
atcgcattgt ctgagtaggt gtcattctat tctggggggt ggggtggggc aggacagcaa     4320
gggggaggat tgggaagaca atagcaggca tgctggggag aagttcctat tccgaagttc     4380
ctattctcta gaaagtatag gaacttcgct agcaccggtg ccaccatgaa tggagctata     4440
ggaggtgacc ttttgctcaa tttttcctgac atgtcggtcc tagagcgcca aagggctcac     4500
ctcaagtacc tcaatcccac ctttgattct cctctcgccg gcttctttgc cgattcttca     4560
atgattaccg gcggcgagat ggacagctat cttcgactg ccggtttgaa tcttccgatg     4620
atgtacggtg agacgacggt ggaaggtgat tcaagactct caatttcgcc ggaaacgacg     4680
cttgggactg gaaatttcaa gaaacggaag tttgatacag agactaagga ttgtaatgag     4740
```

-continued

```
aagaagaaga agatgacgat gaacagagat gacctagtag aagaaggaga agaagagaag    4800
tcgaaaataa cagagcaaaa caatgggagc acaaaaagca tcaagaagat gaaacacaaa    4860
gccaagaaag aagagaacaa tttctctaat gattcatcta aagtgacgaa ggaattggag    4920
aaaacggatt atattcatgg tggcggtggc tctggaggtg gtgggtccgg aggaggcggc    4980
cgccgaccaa gtgacagcaa tgctgtttca ctggttatgc ggcggatccg aaaagaaaac    5040
gttgatgccg gtgaacgtgc aaaacaggct ctagcgttcg aacgcactga tttcgaccag    5100
gttcgttcac tcatggaaaa tagcgatcgc tgccaggata tacgtaatct ggcatttctg    5160
gggattgctt ataacaccct gttacgtata gccgaaattg ccaggatcag ggttaaagat    5220
atctcacgta ctgacggtgg gagaatgtta atccatattg gcagaacgaa aacgctggtt    5280
agcaccgcag gtgtagagaa ggcacttagc ctgggggtaa ctaaactggt cgagcgatgg    5340
atttccgtct ctggtgtagc tgatgatccg aataactacc tgttttgccg ggtcagaaaa    5400
aatggtgttg ccgcgccatc tgccaccagc cagctatcaa ctcgcgccct ggaagggatt    5460
tttgaagcaa ctcatcgatt gatttacggc gctaaggatg actctggtca gagatacctg    5520
gcctggtctg gacacagtgc ccgtgtcgga gccgcgcgag atatggcccg cgctggagtt    5580
tcaataccgg agatcatgca agctggtggc tggaccaatg taaatattgt catgaactat    5640
atccgtaacc tggatagtga aacaggggca atggtgcgcc tgctggaaga tggcgattag    5700
cccgggtagg cccctctccc tcccccccc ctaacgttac tggccgaagc cgcttggaat    5760
aaggccggtg tgcgtttgtc tatatgttat tttccaccat attgccgtct tttggcaatg    5820
tgagggcccg gaaacctggc cctgtcttct tgacgagcat tcctaggggt ctttcccctc    5880
tcgccaaagg aatgcaaggt ctgttgaatg tcgtgaagga agcagttcct ctggaagctt    5940
cttgaagaca aacaacgtct gtagcgaccc tttgcaggca gcggaacccc ccacctggcg    6000
acaggtgcct ctgcggccaa aagccacgtg tataagatac acctgcaaag gcggcacaac    6060
cccagtgcca cgttgtgagt tggatagttg tggaaagagt caaatggctc tcctcaagcg    6120
tattcaacaa ggggctgaag gatgcccaga aggtacccca ttgtatggga tctgatctgg    6180
ggcctcggtg cacatgcttt acatgtgttt agtcgaggtt aaaaaaacgt ctaggccccc    6240
cgaaccacgg ggacgtggtt ttcctttgaa aaacacgatg ataatatggc cacaaccatg    6300
cctaaaaaga agcgtaaagt catgaagatg aagatggaca aaaagactat agtttggttt    6360
agaagagacc taaggattga ggataatcct gcattagcag cagctgctca cgaaggatct    6420 gttttttcctg tcttcatttg gtgtcctgaa gaagaaggac agtttatcc tggaagagct    6480 tcaagatggt ggatgaaaca atcacttgct cacttatctc aatccttgaa ggctcttgga    6540
tctgacctca ctttaatcaa aacccacaac acgatttcag cgatcttgga ttgtatccgc    6600
gttaccggtg ctacaaaagt cgtctttaac cacctctatg atcctgtttc gttagttcgg    6660
gaccataccg taaaggagaa gctggtggaa cgtgggatct ctgtgcaaag ctacaatgga    6720
gatctattgt atgaaccgtg ggagatatac tgcgaaaagg gcaaaccttt tacgagtttc    6780
aattcttact ggaagaaatg cttagatatg tcgattgaat ccgttatgct tcctcctcct    6840
tggcggttga tgccaataac tgcagcggct gaagcgattg gggcgtgttc gattgaagaa    6900
ctagggctgg agaatgaggc cgagaaaccg agcaatgcgt tgttaactag agcttggtct    6960
ccaggatggc gcaatgctga taagttacta aatgagttca tcgagaagca gttgatagat    7020
tatgcaaaga acagcaagaa agttgttggg aattctactt cactactttc tccgtatctc    7080
```

-continued

```
catttcgggg aaataagcgt cagacacgtt ttccagtgtg cccggatgaa acaaattata      7140
tgggcaagag ataagaacag tgaaggagaa gaaagtgcag atctttttct taggggaatc      7200
ggtttaagag agtattctcg gtatatatgt ttcaacttcc cgtttactca cgagcaatcg      7260
ttgttgagtc atcttcggtt tttcccttgg gatgctgatg ttgataagtt caaggcctgg      7320
agacaaggca ggaccggtta tccgttggtg gatgccggaa tgagagagtt ttgggctacc      7380
ggatggatgc ataacagaat aagagtgatt gtttcaagct ttgctgtgaa gtttcttctc      7440
cttccatgga aatggggaat gaagtatttc tgggatacac ttttggatgc tgatttggaa      7500
tgtgacatcc ttggctggca gtatatctct gggagtatcc ccgatggcca cgagcttgat      7560
cgcttggaca atcccgcgtt acaaggcgcc aaatatgacc cagaaggtga gtacataagg      7620
caatggcttc ccgagcttgc gagattgcca actgaatgga tccatcatcc atgggacgct      7680
cctttaaccg tactcaaagc ttctggtgtg gaactcggaa caaactatgc gaaacccatt      7740
gtagacatcg acacagctcg tgagctacta gctaaagcta tttcaagaac ccgtgaagca      7800
cagatcatga tcggagcagc acctgatgag attgtagcag atagcttcga ggccttaggg      7860
gctaatacca ttaaagaacc tggtctttgc ccatctgtgt cttctaatga ccaacaagta      7920
ccttcggctg ttggtggcgg tggctctgga ggtggtgggt ccggaggagg cggccgcacg      7980
agtgatgagg ttcgcaagaa cctgatggac atgttcaggg atcgccaggc gttttctgag      8040
catacctgga aaatgcttct gtccgtttgc cggtcgtggg cggcatggtg caagttgaat      8100
aaccggaaat ggtttcccgc agaacctgaa gatgttcgcg attatcttct atatcttcag      8160
gcgcgcggtc tggcagtaaa aactatccag caacatttgg gccagctaaa catgcttcat      8220
cgtcggtccg ggctgtaatt aattaactcc tcaggtgcag gctgcctatc agaaggtggt      8280
ggctggtgtg gccaatgccc tggctcacaa ataccactga gatctttttc cctctgccaa      8340
aaattatggg gacatcatga agccccttga gcatctgact tctggctaat aaaggaaatt      8400
tattttcatt gcaatagtgt gttggaattt tttgtgtctc tcactcggaa ggacatatgg      8460
gagggcaaat catttaaaac atcagaatga gtatttggtt tagagtttgg caacatatgc      8520
ccatatgctg gctgccatga acaaaggttg gctataaaga ggtcatcagt atatgaaaca      8580 gcccctgct gtccattcct tattccatag aaaagccttg acttgaggtt agattttttt      8640
tatattttgt tttgtgttat tttttttcttt aacatcccta aaattttcct tacatgtttt      8700
actagccaga ttttttcctcc tctcctgact actcccagtc atagctgtcc ctcttctctt      8760
atggagatca taacttcgta taatgtatgc tatacgaagt tatacgcgtg ccaccatgat      8820
gacagacata aaagatggac cacgctcagg ggaagatgta tcagctgcaa gatctttccc      8880
tggttccaaa ggaatgaact tacctgctag caagtctgtg gcctctggaa ttctgcctga      8940
tgacagttac agaatggatt atccagagat aggagtatgt gttataataa acaataagaa      9000
cttccaccga gataccggac tgtcatctcg ttcaggcacg gatgcagatg ctgcaagtgt      9060
cagagaagtt tttatgaagc tgggatataa agtcaagctt aacaatgatc tgtcaagcag      9120
agatattttt aagctattga aaaatgtttc tgaagaagat cacagcaagc gaagcagttt      9180
tgtttgtgtg ttgctaagcc atggcgatga aggactcttc tatggtacag atggccctct      9240
tgaactgaaa gtactaacca gccttttcag aggtgacaag tgcagaagtc tagcagggaa      9300
acccaaactc tttttcattc aggcctgtag aggaacagaa ttagattctg gtattgaagc      9360
agccagtgga ccagatgaaa cagtgtgtca aaaaatacct gtagaagcag acttcctgta      9420
tgcatattct actgctccag gctactactc ctggaggaac gcagctgaag gctcctggtt      9480
```

-continued

```
tattcagtct ctgtgtagga tgctgaagga acacgccagg aaacttgaac tcatgcagat    9540
tttaactcgt gtaaatcgca gagtggcaga atatgaatcc tgctccactc gacaggattt    9600
caatgcaaag aaacagattc catgcattga gtctatgctt accaaagaat tctactttcc    9660
ttgctaaacg cgtactcctc aggtgcaggc tgcctatcag aaggtggtgg ctggtgtggc    9720
caatgccctg gctcacaaat accactgaga tcttttttccc tctgccaaaa attatgggga    9780
catcatgaag cccctgagc atctgacttc tggctaataa aggaaattta ttttcattgc     9840
aatagtgtgt tggaattttt tgtgtctctc actcggaagg acatatggga gggcaaatca    9900
tttaaaacat cagaatgagt atttggttta gagtttggca acatatgccc atatgctggc    9960
tgccatgaac aaaggttggc tataaagagg tcatcagtat atgaaacagc cccctgctgt    10020
ccattcctta ttccatagaa aagccttgac ttgaggttag attttttttta tattttgttt    10080 tgtgttattt ttttctttaa catccctaaa attttccttta catgttttac tagccagatt    10140
tttcctcctc tcctgactac tcccagtcat agctgtccct cttctcttat ggagatcgcc    10200
gtttccacat tcttttctca tccttcttct cctgttttct ctgcatcaag gtcagcacga    10260
tagcactgtc tctctatgct tagggagagg cctgtcctgt acatcccgtg cccccacaag    10320
atgcctacta caacaacatc ttctgcatgt cctgcatagc agtgttggga gaatgtgcac    10380
tacttccact cttctgattt ctattttatg tgtttgcttt ataccagtgt tgccatttgg    10440
gaattaatac atggttgatc aaatcaattg catcacagct gtatcctgta tcagaggaac    10500
attatcaaag ctttttgttgc tgtatttggt atctgacctg cagataaaca tgtttttagga    10560 aggttttgca aaagtagctg tgaaatgagc tggtgttgtg atttaacctg acaggcagct    10620
aaacagtata ccacagagct attcacctac tttccctcag tgggaaaagg gaagagaact    10680
gagggggggg ggaataaata agtaaataac aaaataaaac tcatggatta agaaaaagac    10740
tttgtactgg aatggatgag aagaataata gtaatgataa taatatgtca ctctgaaagt    10800
aatgcctctt atttctgtgg agactacaaa catacaaaga gcacaacatt ccatagagca    10860
aattctcagt tacagaatgc tattttttttt ttcaacacag tcaaaatcat taattttttt    10920
ttgcctgcaa tggacaagag ctttgaagct gttctcgtaa aaatctgtac tagcagaagt    10980
gacctgcaat cactactgct gaaatgcaca acccaccaca tcattgtgct cacattcact    11040
gtttggtttc tgtaaatgta caggaattgt ctgaaattag atatgatttt tttttttctcc    11100 atgaaggaat tcaattacac acctttgcct catgcacttc tttgtcattt ttgtcagact    11160
gcttctctcc tgcaatttgt ctcatggcaa caaaatataa tggagttctg ctgggaactt    11220
ccctactgcc ataccactat catctgcctc tgacattttg dacaaatgta ataaaatagg    11280
aggtattact ttcagagcag accttgtatg tatttacaaa acaagtggta cacaaaaaaa    11340
attgttcatc ccaccaacca atgcccatcc tgtccctgaa tagtagctgt cccccacagc    11400
cttgaccagt ttaggtcaac agttctgctt ctgtcccctc ccagctcctt gtaaccctc     11460 agcccccctt gctggcagga cagtatgaga agctgaaaaa ctagaatgtc ctagttcttt    11520
gcagtgctgc taatcaacaa ccaaaacagt ggtgtgttac caatattgtt gatatcacag    11580
catcatacca ttatgaagga agtaacccag ccaaaatcag gtcagcttgc taacaagaga    11640
actgtgcata agtttaagat gtgtgtgttc ctcagtacct taaaaaataa gtagtaacgt    11700
tcaaatgagt agaagagtag aactgagctt aaaacatctg tcagacaaca gtgaaccaac    11760
c                                                                    11761
```

<210> SEQ ID NO 127
<211> LENGTH: 11629
<212> TYPE: DNA
<213> ORGANISM: Artificial Sequence
<220> FEATURE:
<223> OTHER INFORMATION: Targeting Vector TV8

<400> SEQUENCE: 127

```
gaatgaaggg cctgagggtg ggcagtctgt ctatcatgta catctccata ttctgggagg      60
tcgtcagttg ggctggcctc ctggctaaga tttttgcacc acaagagatg ctgcatgtgt     120
acaaatcact agcaaataga tttgtttccc atcaacttag ccactgttaa tgtaaattgt     180
tcttggatat gtgtctttgg agggcaataa atgctctgaa cagcacttgc acaataaaga     240
tacagcatgt gggaatgatc tgtctcatgt gtcttactga tggtattggt tctgtaagat     300
aaaatattgt gtctgggatg tgtttggctc tactattaat ggtgctctat tgattgtgat     360
ttgtcatttg aaacctgagg atgcgactgt atagcagtct ttcatgcatt tttggaaaaa     420
aacttaagct ttttgaaagc tgctgctaca acttttttgta ttgttataaa gttttgtatt    480 gttttttttaa ttgtgaaatt ataaagatgc cgtgcaggga ctgtttgaag caaagtgcat    540
tgttttagaa acctacaact ctagttcaag cactccatca gtatctgctt aatctttgtc     600
atcctttgct atgagaaaat attaagcagt agtctaaagg tactatgaaa ctataacata     660
gctgacattg tatttataac tacgtcatga ttttgataga attgaggact tgaaaatgtt     720
aaactattca tgtagggcct cttaagatgc ttaagttgtt tagtaatgta agtgtgcatt     780
taattgagat tttattgggc ataatttgtc catcagtatg acactccttg tcagtgttgc     840
cttatacttg atgttgttac cggatctctg caaggcagtt attcttgaat taggctcatt     900
gaagtgtctg ccagtataaa tatatagcaa ctgttctttg tgttaaaatt gagaagctaa     960
ccagttttta gtgcttctga ctgttggaat tctttaagca gatgccataa gaaaattgta    1020
tttgtgatca ccacttctcc agagtggttt taacaccaag ggcattagag aaagaaaggc    1080
aggcgtgtag agaatagtgg acagacaaaa gctgtgagtt acgttatgtt tttcagctga    1140
aaagctgtgt ttggtaaaag catatgaaat cactcaactt ggaagcattc tcttagttct    1200
ctgatagttc tgagcagcag aactcttcac ctaagaggtt acttcaactg gaagactacc    1260
tagtgcttct gatggcaact atatttaaga tgagaataag aggtgtttcc agtgtggtag    1320
cctcacatct gttgcagtgg ttaccgttcg tcctcctccg agggacacag cttggccatt    1380
cactgtggtg acaccaatat gatgatcagc aaatggtgtt tattcactac taaacacagc    1440
ttatatacat ttttacctac aaaatcgtgc tgtcatgtcc cactctgatt ggttcacaca    1500
tttccccgaa aagtgccacc tgggtcgaca ttgattattg actagttatt aatagtaatc    1560
aattacgggg tcattagttc atagcccata tatggagttc cgcgttacat aacttacggt    1620
aaatggcccg cctggctgac cgcccaacga ccccgcccca ttgacgtcaa taatgacgta    1680
tgttcccata gtaacgccaa tagggacttt ccattgacgt caatgggtgg agtatttacg    1740
gtaaactgcc cacttggcag tacatcaagt gtatcatatg ccaagtacgc ccctattga     1800 cgtcaatgac ggtaaatggc ccgcctggca ttatgcccag tacatgacct tatgggactt    1860
tcctacttgg cagtacatct acgtattagt catcgctatt accatggtcg aggtgagccc    1920
cacgttctgc ttcactctcc ccatctcccc cccctcccca cccccaattt tgtatttatt    1980
tattttttaa ttattttgtg cagcgatggg ggcgggggg ggggggggc gcgcgccagg     2040 cggggcgggg cggggcgagg ggcggggcgg ggcgaggcgg agaggtgcgg cggcagccaa    2100
```

-continued

```
tcagagcggc gcgctccgaa agtttccttt tatggcgagg cggcggcggc ggcggcccta   2160
taaaaagcga agcgcgcggc gggcggggag tcgctgcgac gctgccttcg ccccgtgccc   2220
cgctccgccg ccgcctcgcg ccgcccgccc cggctctgac tgaccgcgtt actcccacag   2280
gtgagcgggc gggacggccc ttctcctccg ggctgtaatt agcgcttggt ttaatgacgg   2340
cttgtttctt ttctgtggct gcgtgaaagc cttgaggggc tccgggaggg ccctttgtgc   2400
ggggggagcg gctcggggg tgcgtgcgtg tgtgtgtgcg tggggagcgc cgcgtgcggc   2460
tccgcgctgc ccggcggctg tgagcgctgc gggcgcggcg cggggctttg tgcgctccgc   2520
agtgtgcgcg aggggagcgc ggccgggggc ggtgccccgc ggtgcggggg gggctgcgag   2580
gggaacaaag gctgcgtgcg gggtgtgtgc gtggggggt gagcaggggg tgtgggcgcg   2640
tcggtcgggc tgcaacccccc cctgcacccc cctccccgag ttgctgagca cggcccggct   2700
tcgggtgcgg ggctccgtac ggggcgtggc gcggggctcg ccgtgccggg cgggggggtgg   2760 cggcaggtgg gggtgccggg cggggcgggg ccgcctcggg ccggggaggg ctcgggggag   2820
gggcgcggcg gcccccggag cgccggcggc tgtcgaggcg cggcgagccg cagccattgc   2880
cttttatggt aatcgtgcga gagggcgcag ggacttcctt tgtcccaaat ctgtgcggag   2940
ccgaaatctg ggaggcgccg ccgcaccccc tctagcgggc gcggggcgaa gcggtgcggc   3000
gccggcagga aggaaatggg cggggagggc cttcgtgcgt cgccgcgccg ccgtcccctt   3060
ctccctctcc agcctcgggg ctgtccgcgg ggggacggct gccttcgggg gggacggggc   3120
agggcggggt tcggcttctg gcgtgtgacc ggcggctcta gagcctctgc taaccatgtt   3180
catgccttct tcttttttcct acagctcctg ggcaacgtgc tggttaataa cttcgtataa   3240
tgtatgctat acgaagttat accggtgaag ttcctattcc gaagttccta ttctctagaa   3300
agtataggaa cttcgccacc atggtgagca agggcgagga gctgttcacc ggggtggtgc   3360
ccatcctggt cgagctggac ggcgacgtaa acggccacaa gttcagcgtg tccggcgagg   3420
gcgagggcga tgccacctac ggcaagctga ccctgaagtt catctgcacc accggcaagc   3480
tgcccgtgcc ctggcccacc ctcgtgacca ccctgaccta cggcgtgcag tgcttcagcc   3540
gctaccccga ccacatgaag cagcacgact tcttcaagtc cgccatgccc gaaggctacg   3600
tccaggagcg caccatcttc ttcaaggacg acggcaacta caagacccgc gccgaggtga   3660
agttcgaggg cgacaccctg gtgaaccgca tcgagctgaa gggcatcgac ttcaaggagg   3720
acggcaacat cctggggcac aagctggagt acaactacaa cagccacaac gtctatatca   3780
tggccgacaa gcagaagaac ggcatcaagg tgaacttcaa gatccgccac aacatcgagg   3840
acggcagcgt gcagctcgcc gaccactacc agcagaacac ccccatcggc gacggccccg   3900
tgctgctgcc cgacaaccac tacctgagca cccagtccgc cctgagcaaa gaccccaacg   3960
agaagcgcga tcacatggtc ctgctggagt tcgtgaccgc cgccgggatc actctcggca   4020
tggacgagct gtacaagggc agcggcgcca ccaacttcag cctgctgaag caggccggcg   4080
acgtggagga gaaccccggc cccgctagct aaagcggccg ccaattccta gagctcgctg   4140
atcagcctcg actgtgcctt ctagttgcca gccatctgtt gtttgcccct ccccccgtgcc   4200 ttccttgacc ctggaaggtg ccactcccac tgtcctttcc taataaaatg aggaaattgc   4260
atcgcattgt ctgagtaggt gtcattctat tctggggggt ggggtggggc aggacagcaa   4320
ggggagggat tgggaagaca atagcaggca tgctggggag aagttcctat tccgaagttc   4380
ctattctcta gaaagtatag gaacttcgct agcaccggtg ccaccatgaa tggagctata   4440
```

-continued

```
ggaggtgacc ttttgctcaa ttttcctgac atgtcggtcc tagagcgcca aagggctcac    4500
ctcaagtacc tcaatcccac ctttgattct cctctcgccg gcttctttgc cgattcttca    4560
atgattaccg gcggcgagat ggacagctat cttcgactg  ccggtttgaa tcttccgatg    4620
atgtacggtg agacgacggt ggaaggtgat tcaagactct caatttcgcc ggaaacgacg    4680
cttgggactg gaaatttcaa gaaacggaag tttgatacag agactaagga ttgtaatgag    4740
aagaagaaga agatgacgat gaacagagat gacctagtag aagaaggaga agaagagaag    4800
tcgaaaataa cagagcaaaa caatgggagc acaaaaagca tcaagaagat gaaacacaaa    4860
gccaagaaag aagagaacaa tttctctaat gattcatcta aagtgacgaa ggaattggag    4920
aaaacggatt atattcatgg tggcggtggc tctggaggtg gtgggtccgg aggaggcggc    4980
cgccgaccaa gtgacagcaa tgctgtttca ctggttatgc ggcggatccg aaaagaaaac    5040
gttgatgccg gtgaacgtgc aaaacaggct ctagcgttcg aacgcactga tttcgaccag    5100
gttcgttcac tcatggaaaa tagcgatcgc tgccaggata tacgtaatct ggcatttctg    5160
gggattgctt ataacaccct gttacgtata gccgaaattg ccaggatcag ggttaaagat    5220
atctcacgta ctgacggtgg gagaatgtta atccatattg gcagaacgaa aacgctggtt    5280
agcaccgcag gtgtagagaa ggcacttagc ctgggggtaa ctaaactggt cgagcgatgg    5340
atttccgtct ctggtgtagc tgatgatccg aataactacc tgttttgccg ggtcagaaaa    5400
aatggtgttg ccgcgccatc tgccaccagc cagctatcaa ctcgcgccct ggaagggatt    5460
tttgaagcaa ctcatcgatt gatttacggc gctaaggatg actctggtca gagatacctg    5520
gcctggtctg gacacagtgc ccgtgtcgga gccgcgcgag atatggcccg cgctggagtt    5580
tcaataccgg agatcatgca agctggtggc tggaccaatg taaatattgt catgaactat    5640
atccgtaacc tggatagtga aacaggggca atggtgcgcc tgctggaaga tggcgattag    5700
cccgggtagg cccctctccc tccccccccc ctaacgttac tggccgaagc cgcttggaat    5760
aaggccggtg tgcgtttgtc tatatgttat tttccaccat attgccgtct tttggcaatg    5820
tgagggcccg gaaacctggc cctgtcttct tgacgagcat cctaggggt  cttteccctc    5880 tcgccaaagg aatgcaaggt ctgttgaatg tcgtgaagga agcagttcct ctggaagctt    5940
cttgaagaca aacaacgtct gtagcgaccc tttgcaggca gcggaacccc ccacctggcg    6000
acaggtgcct ctgcggccaa aagccacgtg tataagatac acctgcaaag gcggcacaac    6060
cccagtgcca cgttgtgagt tggatagttg tggaaagagt caaatggctc tcctcaagcg    6120
tattcaacaa ggggctgaag gatgcccaga aggtacccca ttgtatggga tctgatctgg    6180
ggcctcggtg cacatgcttt acatgtgttt agtcgaggtt aaaaaaacgt ctaggccccc    6240
cgaaccacgg ggacgtggtt ttcctttgaa aaacacgatg ataatatggc cacaaccatg    6300
cctaaaaaga agcgtaaagt catgaagatg aagatggaca aaaagactat agtttggttt    6360
agaagagacc taaggattga ggataatcct gcattagcag cagctgctca cgaaggatct    6420 gttttttcctg tcttcatttg gtgtcctgaa gaagaaggac agtttttatcc tggaagagct    6480 tcaagatggt ggatgaaaca atcacttgct cacttatctc aatccttgaa ggctcttgga    6540
tctgacctca ctttaatcaa aacccacaac acgatttcag cgatcttgga ttgtatccgc    6600
gttaccggtg ctacaaaagt cgtctttaac cacctctatg atcctgtttc gttagttcgg    6660
gaccataccg taaaggagaa gctggtggaa cgtgggatct ctgtgcaaag ctacaatgga    6720
gatctattgt atgaaccgtg ggagatatac tgcgaaaagg gcaaaccttt tacgagtttc    6780
aattcttact ggaagaaatg cttagatatg tcgattgaat ccgttatgct tcctcctcct    6840
```

-continued

```
tggcggttga tgccaataac tgcagcggct gaagcgattt gggcgtgttc gattgaagaa    6900
ctagggctgg agaatgaggc cgagaaaccg agcaatgcgt tgttaactag agcttggtct    6960
ccaggatgga gcaatgctga taagttacta aatgagttca tcgagaagca gttgatagat    7020
tatgcaaaga acagcaagaa agttgttggg aattctactt cactactttc tccgtatctc    7080
catttcgggg aaataagcgt cagacacgtt ttccagtgtg cccggatgaa acaaattata    7140
tgggcaagag ataagaacag tgaaggagaa gaaagtgcag atcttttct taggggaatc     7200 ggtttaagag agtattctcg gtatatatgt ttcaacttcc cgtttactca cgagcaatcg    7260
ttgttgagtc atcttcggtt tttccttgg gatgctgatg ttgataagtt caaggcctgg      7320
agacaaggca ggaccggtta tccgttggtg gatgccggaa tgagagagtt ttgggctacc    7380
ggatggatgc ataacagaat aagagtgatt gtttcaagct ttgctgtgaa gtttcttctc    7440
cttccatgga aatggggaat gaagtatttc tgggatacac ttttggatgc tgatttggaa    7500
tgtgacatcc ttggctggca gtatatctct gggagtatcc ccgatggcca cgagcttgat    7560
cgcttggaca atcccgcgtt acaaggcgcc aaatatgacc cagaaggtga gtacataagg    7620
caatggcttc ccgagcttgc gagattgcca actgaatgga tccatcatcc atgggacgct    7680
cctttaaccg tactcaaagc ttctggtgtg gaactcggaa caaactatgc gaaacccatt    7740
gtagacatcg acacagctcg tgagctacta gctaaagcta tttcaagaac ccgtgaagca    7800
cagatcatga tcggagcagc acctgatgag attgtagcag atagcttcga ggccttaggg    7860
gctaatacca ttaaagaacc tggtctttgc ccatctgtgt cttctaatga ccaacaagta    7920
ccttcggctg ttggtggcgg tggctctgga ggtggtgggt ccggaggagg cggccgcacg    7980
agtgatgagg ttcgcaagaa cctgatggac atgttcaggg atcgccaggc gttttctgag    8040
catacctgga aaatgcttct gtccgtttgc cggtcgtggg cggcatggtg caagttgaat    8100
aaccggaaat ggtttcccgc agaacctgaa gatgttcgcg attatcttct atatcttcag    8160
gcgcgcggtc tggcagtaaa aactatccag caacatttgg gccagctaaa catgcttcat    8220
cgtcggtccg ggctgtaatt aattaactcc tcaggtgcag gctgcctatc agaaggtggt    8280
ggctggtgtg gccaatgccc tggctcacaa ataccactga gatctttttc cctctgccaa    8340
aaattatggg gacatcatga agccccttga gcatctgact tctggctaat aaaggaaatt    8400
tattttcatt gcaatagtgt gttggaattt tttgtgtctc tcactcggaa ggacatatgg    8460
gagggcaaat catttaaaac atcagaatga gtatttggtt tagagtttgg caacatatgc    8520
ccatatgctg gctgccatga acaaaggttg gctataaaga ggtcatcagt atatgaaaca    8580
gccccctgct gtccattcct tattccatag aaaagccttg acttgaggtt agattttttt    8640
tatattttgt tttgtgttat ttttttcttt aacatcccta aattttcct tacatgtttt    8700 actagccaga ttttttcctcc tctcctgact actcccagtc atagctgtcc ctcttctctt    8760
atggagatca taacttcgta taatgtatgc tatacgaagt tatacgcgtg ccaccatggt    8820
gagcaagggc gaggaggata acatggccat catcaaggag ttcatgcgct tcaaggtgca    8880
catggagggc tccgtgaacg gccacgagtt cgagatcgag ggcgagggcg agggccgccc    8940
ctacgagggc acccagaccg ccaagctgaa ggtgaccaag gtggccccc tgcccttcgc     9000 ctgggacatc ctgtcccctc agttcatgta cggctccaag gcctacgtga agcacccagc    9060
cgacatcccc gactacttga agctgtcctt ccccgagggc ttcaagtggg agcgcgtgat    9120
gaacttcgag gacggcggcg tggtgaccgt gacccaggac tcctccctgc aggacggcga    9180
```

-continued

```
gttcatctac aaggtgaagc tgcgcggcac caacttcccc tccgacggcc ccgtaatgca      9240
gaagaagacc atgggctggg aggcctcctc cgagcggatg tacccgagg  acggcgccct      9300 gaagggcgag atcaagcaga ggctgaagct gaaggacggc ggccactacg acgctgaggt      9360
caagaccacc tacaaggcca agaagcccgt gcagctgccc ggcgcctaca acgtcaacat      9420
caagttggac atcacctccc acaacgagga ctacaccatc gtggaacagt acgaacgcgc      9480
cgagggccgc cactccaccg gcggcatgga cgagctgtac aagtgtggcg gctagacgcg      9540
tactcctcag gtgcaggctg cctatcagaa ggtggtggct ggtgtggcca atgccctggc      9600
tcacaaatac cactgagatc tttttccctc tgccaaaaat tatggggaca tcatgaagcc      9660
ccttgagcat ctgacttctg gctaataaag gaaatttatt ttcattgcaa tagtgtgttg      9720 gaatttttg  tgtctctcac tcggaaggac atatgggagg gcaaatcatt taaaacatca      9780
gaatgagtat ttggtttaga gtttggcaac atatgcccat atgctggctg ccatgaacaa      9840
aggttggcta taaagaggtc atcagtatat gaaacagccc cctgctgtcc attccttatt      9900
ccatagaaaa gccttgactt gaggttagat ttttttatta ttttgttttg tgttattttt      9960
ttctttaaca tccctaaaat tttccttaca tgttttacta gccagatttt tcctcctctc      10020
ctgactactc ccagtcatag ctgtccctct tctcttatgg agatcgccgt ttccacattc      10080
ttttctcatc cttcttctcc tgttttctct gcatcaaggt cagcacgata gcactgtctc      10140
tctatgctta gggagaggcc tgtcctgtac atcccgtgcc cccacaagat gcctactaca      10200
acaacatctt ctgcatgtcc tgcatagcag tgttgggaga atgtgcacta cttccactct      10260
tctgatttct attttatgtg tttgctttat accagtgttg ccatttggga attaatacat      10320
ggttgatcaa atcaattgca tcacagctgt atcctgtatc agaggaacat tatcaaagct      10380
tttgttgctg tatttggtat ctgacctgca gataaacatg ttttaggaag gttttgcaaa      10440
agtagctgtg aaatgagctg gtgttgtgat ttaacctgac aggcagctaa acagtatacc      10500
acagagctat tcacctactt tccctcagtg ggaaaaggga agagaactga ggggggggg       10560 aataaataag taaataacaa aataaaactc atggattaag aaaaagactt tgtactggaa      10620
tggatgagaa gaataatagt aatgataata atatgtcact ctgaaagtaa tgcctcttat      10680
ttctgtggag actacaaaca tacaaagagc acaacattcc atagagcaaa ttctcagtta      10740
cagaatgcta tttttttttt caacacagtc aaaatcatta attttttttt gcctgcaatg      10800
gacaagagct ttgaagctgt tctcgtaaaa atctgtacta gcagaagtga cctgcaatca      10860
ctactgctga aatgcacaac ccaccacatc attgtgctca cattcactgt ttggtttctg      10920
taaatgtaca ggaattgtct gaaattagat atgatttttt ttttctccat gaaggaattc      10980
aattacacac ctttgcctca tgcacttctt tgtcattttt gtcagactgc ttctctcctg      11040
caatttgtct catggcaaca aaatataatg gagttctgct gggaacttcc ctactgccat      11100
accactatca tctgcctctg acattttgga caaatgtaat aaaataggag gtattacttt      11160
cagagcagac cttgtatgta tttacaaaac aagtggtaca caaaaaaaat tgttcatccc      11220
accaaccaat gcccatcctg tccctgaata gtagctgtcc cccacagcct tgaccagttt      11280
aggtcaacag ttctgcttct gtcccctccc agctccttgt aacccctcag cccccttgc       11340 tggcaggaca gtatgagaag ctgaaaaact agaatgtcct agttctttgc agtgctgcta      11400
atcaacaacc aaaacagtgg tgtgttacca atattgttga tatcacagca tcataccatt      11460
atgaaggaag taacccagcc aaaatcaggt cagcttgcta acaagagaac tgtgcataag      11520
tttaagatgt gtgtgttcct cagtacctta aaaaataagt agtaacgttc aaatgagtag      11580
```

```
aagagtagaa ctgagcttaa aacatctgtc agacaacagt gaaccaacc           11629

<210> SEQ ID NO 128
<211> LENGTH: 5894
<212> TYPE: DNA
<213> ORGANISM: Artificial Sequence
<220> FEATURE:
<223> OTHER INFORMATION: Plasmid pCAGG-Cre

<400> SEQUENCE: 128
actagttatt aatagtaatc aattacgggg tcattagttc atagcccata tatggagttc      60
cgcgttacat aacttacggt aaatggcccg cctggctgac cgcccaacga cccccgccca     120
ttgacgtcaa taatgacgta tgttcccata gtaacgccaa tagggacttt ccattgacgt     180
caatgggtgg agtatttacg gtaaactgcc cacttggcag tacatcaagt gtatcatatg     240
ccaagtacgc cccctattga cgtcaatgac ggtaaatggc ccgcctggca ttatgcccag     300
tacatgacct tatgggactt tcctacttgg cagtacatct acgtattagt catcgctatt     360
accatggtcg aggtgagccc cacgttctgc ttcactctcc ccatctcccc ccctcccca      420 ccccaattt tgtatttatt tattttttaa ttattttgtg cagcgatggg ggcggggggg      480
gggggggggc gcgcgccagg cggggcgggg cggggcgagg ggcggggcgg ggcgaggcgg     540
agaggtgcgg cggcagccaa tcagagcggc gcgctccgaa agtttccttt tatggcgagg     600
cggcggcggc ggcggcccta taaaaagcga agcgcgcggc gggcggggag tcgctgcgac     660
gctgccttcg ccccgtgccc cgctccgccg ccgcctcgcg ccgcccgccc cggctctgac     720
tgaccgcgtt actcccacag gtgagcgggc gggacggccc ttctcctccg ggctgtaatt     780
agcgcttggt ttaatgacgg cttgtttctt ttctgtggct gcgtgaaagc cttgaggggc     840
tccgggaggg cccttttgtgc gggggagcg gctcggggggg tgcgtgcgtg tgtgtgtgcg     900
tggggagcgc cgcgtgcggc tccgcgctgc ccggcggctg tgagcgctgc gggcgcggcg     960
cggggctttg tgcgctccgc agtgtgcgcg aggggagcgc ggccgggggc ggtgccccgc    1020
ggtgcggggg gggctgcgag gggaacaaag gctgcgtgcg gggtgtgtgc gtgggggggt    1080
gagcaggggg tgtgggcgcg tcggtcgggc tgcaaccccc cctgcacccc cctccccgag    1140
ttgctgagca cggcccggct tcgggtgcgg ggctccgtac ggggcgtggc gcggggctcg    1200
ccgtgccggg cgggggtgg cggcaggtgg gggtgccggg cggggcgggg ccgcctcggg    1260
ccggggaggg ctcgggggag gggcgcggcg gccccccggag cgccggcggc tgtcgaggcg    1320
cggcgagccg cagccattgc cttttatggt aatcgtgcga gagggcgcag ggacttcctt    1380
tgtcccaaat ctgtgcggag ccgaaatctg ggaggcgccg ccgcaccccc tctagcgggc    1440
gcggggcgaa gcggtgcggc gccggcagga aggaaatggg cggggagggc cttcgtgcgt    1500
cgccgcgccg ccgtcccctt ctccctctcc agcctcgggg ctgtccgcgg gggacggct    1560 gccttcgggg gggacggggc agggcggggt tcggcttctg gcgtgtgacc ggcggctcta    1620
gagcctctgc taaccatgtt catgccttct tctttttcct acagctcctg ggcaacgtgc    1680
tggttattgt gctgtctcat cattttggca aagaattcgg cttgatcgaa gcttgcccac    1740
catggcaccc aagaagaaga ggaaggtgtc caatttactg accgtacacc aaaatttgcc    1800
tgcattaccg gtcgatgcaa cgagtgatga ggttcgcaag aacctgatgg acatgttcag    1860
ggatcgccag gcgtttttctg agcatacctg gaaaatgctt ctgtccgttt gccggtcgtg    1920
ggcggcatgg tgcaagttga ataaccggaa atggtttccc gcagaacctg aagatgttcg    1980
```

```
cgattatctt ctatatcttc aggcgcgcgg tctggcagta aaaactatcc agcaacattt   2040
gggccagcta aacatgcttc atcgtcggtc cgggctgcca cgaccaagtg acagcaatgc   2100
tgtttcactg gttgtgcggc ggatccgaaa agaaaacgtt gatgccggtg aacgtgcaaa   2160
acaggctcta gcgttcgaac gcactgattt cgaccaggtt cgttcactca tggaaaatag   2220
cgatcgctgc caggatatac gtaatctggc atttctgggg attgcttata acaccctgtt   2280
acgtatagcc gaaattgcca ggatcagggt taaagatatc tcacgtactg acggtgggag   2340
aatgttaatc catattggca gaacgaaaac gctggttagc accgcaggtg tagagaaggc   2400
acttagcctg ggggtaacta aactggtcga gcgatggatt tccgtctctg gtgtagctga   2460
tgatccgaat aactacctgt tttgccgggt cagaaaaaat ggtgttgccg cgccatctgc   2520
caccagccag ctatcaactc gcgccctgga agggattttt gaagcaactc atcgattgat   2580
ttacggcgct aaggatgact ctggtcagag atacctggcc tggtctggac acagtgcccg   2640
tgtcggagcc gcgcgagata tggcccgcgc tggagtttca ataccggaga tcatgcaagc   2700
tggtggctgg accaatgtaa atattgtcat gaactatatc cgtaacctgg atagtgaaac   2760
aggggcaatg gtgcgcctgc tgcaagatgg cgattagaag ctttcgatca agccgaattc   2820
actcctcagg tgcaggctgc ctatcagaag gtggtggctg gtgtggccaa tgccctggct   2880
cacaaatacc actgagatct ttttccctct gccaaaaatt atggggacat catgaagccc   2940
cttgagcatc tgacttctgg ctaataaagg aaatttattt tcattgcaat agtgtgttgg   3000
aattttttgt gtctctcact cggaaggaca tatgggaggg caaatcattt aaaacatcag   3060
aatgagtatt tggtttagag tttggcaaca tatgcccata tgctggctgc catgaacaaa   3120
ggttggctat aaagaggtca tcagtatatg aaacagcccc ctgctgtcca ttccttattc   3180
catagaaaag ccttgacttg aggttagatt ttttttatat tttgttttgt gttatttttt   3240
tctttaacat ccctaaaatt ttccttacat gttttactag ccagattttt cctcctctcc   3300
tgactactcc cagtcatagc tgtccctctt ctcttatgga gatccctcga cctgcagccc   3360
aagcttggcg taatcatggt catagctgtt tcctgtgtga aattgttatc cgctcacaat   3420
tccacacaac atacgagccg gaagcataaa gtgtaaagcc tggggtgcct aatgagtgag   3480
ctaactcaca ttaattgcgt tgcgctcact gcccgctttc cagtcgggaa acctgtcgtg   3540
ccagcggatc cgcatctcaa ttagtcagca accatagtcc cgcccctaac tccgcccatc   3600
ccgcccctaa ctccgcccag ttccgcccat tctccgcccc atggctgact aattttttttt   3660 atttatgcag aggccgaggc cgcctcggcc tctgagctat tccagaagta gtgaggaggc   3720 tttttttggag gcctaggctt ttgcaaaaag ctaacttgtt tattgcagct tataatggtt   3780
acaaataaag caatagcatc acaaatttca caaataaagc atttttttca ctgcattcta   3840
gttgtggttt gtccaaactc atcaatgtat cttatcatgt ctggatccgc tgcattaatg   3900
aatcggccaa cgcgcgggga gaggcggttt gcgtattggg cgctcttccg cttcctcgct   3960
cactgactcg ctgcgctcgg tcgttcggct gcggcgagcg gtatcagctc actcaaaggc   4020
ggtaatacgg ttatccacag aatcagggga taacgcagga agaacatgt gagcaaaagg   4080 ccagcaaaag gccaggaacc gtaaaaaggc cgcgttgctg gcgtttttcc ataggctccg   4140
cccccctgac gagcatcaca aaaatcgacg ctcaagtcag aggtggcgaa acccgacagg   4200
actataaaga taccaggcgt ttcccccctgg aagctccctc gtgcgctctc ctgttccgac   4260
cctgccgctt accggatacc tgtccgcctt tctcccttcg ggaagcgtgg cgctttctca   4320
tagctcacgc tgtaggtatc tcagttcggt gtaggtcgtt cgctccaagc tgggctgtgt   4380
```

-continued

```
gcacgaaccc cccgttcagc ccgaccgctg cgccttatcc ggtaactatc gtcttgagtc     4440
caacccggta agacacgact tatcgccact ggcagcagcc actggtaaca ggattagcag     4500
agcgaggtat gtaggcggtg ctacagagtt cttgaagtgg tggcctaact acggctacac     4560
tagaagaaca gtatttggta tctgcgctct gctgaagcca gttaccttcg gaaaaagagt     4620
tggtagctct tgatccggca aacaaaccac cgctggtagc ggtggttttt ttgtttgcaa     4680
gcagcagatt acgcgcagaa aaaaggatc tcaagaagat cctttgatct tttctacggg     4740
gtctgacgct cagtggaacg aaaactcacg ttaagggatt ttggtcatga gattatcaaa     4800
aaggatcttc acctagatcc ttttaaatta aaaatgaagt tttaaatcaa tctaaagtat     4860
atatgagtaa acttggtctg acagttacca atgcttaatc agtgaggcac ctatctcagc     4920
gatctgtcta tttcgttcat ccatagttgc ctgactcccc gtcgtgtaga taactacgat     4980
acgggagggc ttaccatctg gccccagtgc tgcaatgata ccgcgagacc cacgctcacc     5040
ggctccagat ttatcagcaa taaaccagcc agccggaagg gccgagcgca gaagtggtcc     5100
tgcaacttta tccgcctcca tccagtctat taattgttgc cgggaagcta gagtaagtag     5160
ttcgccagtt aatagtttgc gcaacgttgt tgccattgct acaggcatcg tggtgtcacg     5220
ctcgtcgttt ggtatggctt cattcagctc cggttcccaa cgatcaaggc gagttacatg     5280
atcccccatg ttgtgcaaaa aagcggttag ctccttcggt cctccgatcg ttgtcagaag     5340
taagttggcc gcagtgttat cactcatggt tatggcagca ctgcataatt ctcttactgt     5400
catgccatcc gtaagatgct tttctgtgac tggtgagtac tcaaccaagt cattctgaga     5460
atagtgtatg cggcgaccga gttgctcttg cccggcgtca atacgggata ataccgcgcc     5520
acatagcaga actttaaaag tgctcatcat tggaaaacgt tcttcggggc gaaaactctc     5580
aaggatctta ccgctgttga tccagttc gatgtaaccc actcgtgcac ccaactgatc     5640
ttcagcatct tttactttca ccagcgtttc tgggtgagca aaaacaggaa ggcaaaatgc     5700
cgcaaaaaag ggaataaggg cgacacggaa atgttgaata ctcatactct tcctttttca     5760
atattattga agcatttatc agggttattg tctcatgagc ggatacatat ttgaatgtat     5820
ttagaaaaat aaacaaatag gggttccgcg cacatttccc cgaaaagtgc cacctgggtc     5880
gacattgatt attg                                                       5894
```

<210> SEQ ID NO 129
<211> LENGTH: 6086
<212> TYPE: DNA
<213> ORGANISM: Artificial Sequence
<220> FEATURE:
<223> OTHER INFORMATION: Plasmid pCAGG-FlpO

<400> SEQUENCE: 129

```
actagttatt aatagtaatc aattacgggg tcattagttc atagcccata tatggagttc      60
cgcgttacat aacttacggt aaatggcccg cctggctgac cgcccaacga cccccgccca     120
ttgacgtcaa taatgacgta tgttcccata gtaacgccaa tagggacttt ccattgacgt     180
caatgggtgg agtatttacg gtaaactgcc cacttggcag tacatcaagt gtatcatatg     240
ccaagtacgc cccctattga cgtcaatgac ggtaaatggc ccgcctggca ttatgcccag     300
tacatgacct tatgggactt tcctacttgg cagtacatct acgtattagt catcgctatt     360
accatggtcg aggtgagccc cacgttctgc ttcactctcc ccatctcccc ccctccccca     420
cccccaattt tgtatttatt tattttttaa ttattttgtg cagcgatggg ggcgggggggg     480
```

-continued

```
gggggggggc gcgcgccagg cggggcgggg cggggcgagg ggcggggcgg ggcgaggcgg    540
agaggtgcgg cggcagccaa tcagagcggc gcgctccgaa agtttccttt tatggcgagg    600
cggcggcggc ggcggccctc taaaaagcga agcgcgcggc gggcggggag tcgctgcgac    660
gctgccttcg ccccgtgccc cgctccgccg ccgcctcgcg ccgccgccc cggctctgac     720 tgaccgcgtt actcccacag gtgagcgggc gggacggccc ttctcctccg ggctgtaatt    780
agcgcttggt ttaatgacgg cttgtttctt ttctgtggct gcgtgaaagc cttgaggggc    840
tccgggaggg ccctttgtgc ggggggagcg gctcgggggg tgcgtgcgtg tgtgtgtgcg    900
tggggagcgc cgcgtgcggc tccgcgctgc ccggcggctg tgagcgctgc gggcgcggcg    960
cggggctttg tgcgctccgc agtgtgcgcg aggggagcgc ggccggggc ggtgccccgc    1020 ggtgcggggg gggctgcgag gggaacaaag gctgcgtgcg gggtgtgtgc gtgggggggt    1080
gagcaggggg tgtgggcgcg tcggtcgggc tgcaacccc cctgcacccc cctccccgag     1140
ttgctgagca cggcccggct tcgggtgcgg ggctccgtac ggggcgtggc gcggggctcg    1200
ccgtgccggg cggggggtgg cggcaggtgg gggtgccggg cggggcgggg ccgcctcggg    1260
ccggggaggg ctcgggggag gggcgcggcg gcccccggag cgccggcggc tgtcgaggcg    1320
cggcgagccg cagccattgc cttttatggt aatcgtgcga gagggcgcag ggacttcctt    1380
tgtcccaaat ctgtgcggag ccgaaatctg ggaggcgccg ccgcacccc tctagcgggc     1440 gcggggcgaa gcggtgcggc gccggcagga aggaaatggg cggggagggc cttcgtgcgt    1500
cgccgcgccg ccgtcccctt ctccctctcc agcctcgggg ctgtccgcgg ggggacggct    1560
gccttcgggg gggacggggc agggcggggt tcggcttctg gcgtgtgacc ggcggctcta    1620
gagcctctgc taaccatgtt catgccttct tcttttcct acagctcctg ggcaacgtgc     1680
tggttattgt gctgtctcat cattttggca aagaattggc ggccgccacc atgagccagt    1740
tcgacatcct gtgcaagacc cccccaagg tgctggtgcg gcagttcgtg gagagattcg      1800
agaggcccag cggcgagaag atcgccagct gtgccgccga gctgacctac ctgtgctgga    1860
tgatcaccca caacggcacc gccatcaaga gggccacctt catgagctac aacaccatca    1920
tcagcaacag cctgagcttc gacatcgtga acaagagcct gcagttcaag tacaagaccc    1980
agaaggccac catcctggag gccagcctga agaagctgat ccccgcctgg gagttcacca    2040
tcatccctta caacggccag aagcaccaga gcgacatcac cgacatcgtg tccagcctgc    2100
agctgcagtt cgagagcagc gaggaggccg acaagggcaa cagccacagc aagaagatgc    2160
tgaaggccct gctgtccgag ggcgagagca tctgggagat caccgagaag atcctgaaca    2220
gcttcgagta caccagcagg ttcaccaaga ccaagacct gtaccagttc ctgttcctgg      2280
ccacattcat caactgcggc aggttcagcg acatcaagaa cgtggacccc aagagcttca    2340
agctggtgca gaacaagtac ctgggcgtga tcattcagtg cctggtgacc gagaccaaga    2400
caagcgtgtc caggcacatc tactttttca gcgccagagg caggatcgac cccctggtgt    2460
acctggacga gttcctgagg aacagcgagc ccgtgctgaa gagagtgaac aggaccggca    2520
acagcagcag caacaagcag gagtaccagc tgctgaagga caacctggtg cgcagctaca    2580
acaaggccct gaagaagaac gcccctacc ccatcttcgc tatcaagaac ggccctaaga     2640
gccacatcgg caggcacctg atgaccagct ttctgagcat gaagggcctg accgagctga    2700
caaacgtggt gggcaactgg agcgacaaga gggcctccgc cgtggccagg accacctaca    2760
cccaccagat caccgccatc cccgaccact acttcgccct ggtgtccagg tactacgcct    2820
acgaccccat cagcaaggag atgatcgccc tgaaggacga gaccaacccc atcgaggagt    2880
```

-continued

```
ggcagcacat cgagcagctg aagggcagcg ccgagggcag catcagatac cccgcctgga   2940
acggcatcat cagccaggag gtgctggact acctgagcag ctacatcaac aggcggatct   3000
gatgaggaat tcactcctca ggtgcaggct gcctatcaga aggtggtggc tggtgtggcc   3060
aatgccctgg ctcacaaata ccactgagat cttttttccct ctgccaaaaa ttatggggac   3120
atcatgaagc cccttgagca tctgacttct ggctaataaa ggaaatttat tttcattgca   3180
atagtgtgtt ggaattttttt gtgtctctca ctcggaagga catatgggag ggcaaatcat   3240
ttaaaacatc agaatgagta tttggtttag agtttggcaa catatgccca tatgctggct   3300
gccatgaaca aaggttggct ataaagaggt catcagtata tgaaacagcc ccctgctgtc   3360
cattccttat tccatagaaa agccttgact tgaggttaga ttttttttat attttgtttt   3420
gtgttatttt tttctttaac atccctaaaa ttttccttac atgttttact agccagattt   3480
ttcctcctct cctgactact cccagtcata gctgtccctc ttctcttatg gagatccctc   3540
gacctgcagc ccaagcttgg cgtaatcatg gtcatagctg tttcctgtgt gaaattgtta   3600
tccgctcaca attccacaca acatacgagc cggaagcata aagtgtaaag cctggggtgc   3660
ctaatgagtg agctaactca cattaattgc gttgcgctca ctgcccgctt tccagtcggg   3720
aaacctgtcg tgccagcgga tccgcatctc aattagtcag caaccatagt cccgccccta   3780
actccgccca tcccgcccct aactccgccc agttccgccc attctccgcc ccatggctga   3840 ctaattttttt ttatttatgc agaggccgag gccgcctcgg cctctgagct attccagaag   3900
tagtgaggag gcttttttgg aggcctaggc ttttgcaaaa agctaacttg tttattgcag   3960
cttataatgg ttacaaataa agcaatagca tcacaaattt cacaaataaa gcatttttttt   4020 cactgcattc tagttgtggt ttgtccaaac tcatcaatgt atcttatcat gtctggatcc   4080
gctgcattaa tgaatcggcc aacgcgcggg gagaggcggt ttgcgtattg ggcgctcttc   4140
cgcttcctcg ctcactgact cgctgcgctc ggtcgttcgg ctgcggcgag cggtatcagc   4200
tcactcaaag gcggtaatac ggttatccac agaatcaggg gataacgcag gaaagaacat   4260
gtgagcaaaa ggccagcaaa aggccaggaa ccgtaaaaag gccgcgttgc tggcgtttttt   4320 ccataggctc cgcccccctg acgagcatca caaaaatcga cgctcaagtc agaggtggcg   4380
aaacccgaca ggactataaa gataccaggc gtttccccct ggaagctccc tcgtgcgctc   4440
tcctgttccg accctgccgc ttaccggata cctgtccgcc tttctccctt cgggaagcgt   4500
ggcgctttct catagctcac gctgtaggta tctcagttcg gtgtaggtcg ttcgctccaa   4560
gctgggctgt gtgcacgaac cccccgttca gcccgaccgc tgcgccttat ccggtaacta   4620
tcgtcttgag tccaacccgg taagacacga cttatcgcca ctggcagcag ccactggtaa   4680
caggattagc agagcgaggt atgtaggcgg tgctacagag ttcttgaagt ggtggcctaa   4740
ctacggctac actagaagaa cagtatttgg tatctgcgct ctgctgaagc cagttacctt   4800
cggaaaaaga gttggtagct cttgatccgg caaacaaacc accgctggta gcggtggttt   4860
ttttgtttgc aagcagcaga ttacgcgcag aaaaaaagga tctcaagaag atcctttgat   4920
cttttctacg gggtctgacg ctcagtggaa cgaaaactca cgttaaggga ttttggtcat   4980
gagattatca aaaaggatct tcacctagat ccttttaaat taaaaatgaa gttttaaatc   5040
aatctaaagt atatatgagt aaacttggtc tgacagttac caatgcttaa tcagtgaggc   5100
acctatctca gcgatctgtc tatttcgttc atccatagtt gcctgactcc ccgtcgtgta   5160
gataactacg atacgggagg gcttaccatc tggccccagt gctgcaatga taccgcgaga   5220
```

-continued

```
cccacgctca ccggctccag atttatcagc aataaaccag ccagccggaa gggccgagcg      5280
cagaagtggt cctgcaactt tatccgcctc catccagtct attaattgtt gccgggaagc      5340
tagagtaagt agttcgccag ttaatagttt gcgcaacgtt gttgccattg ctacaggcat      5400
cgtggtgtca cgctcgtcgt ttggtatggc ttcattcagc tccggttccc aacgatcaag      5460
gcgagttaca tgatccccca tgttgtgcaa aaaagcggtt agctccttcg gtcctccgat      5520
cgttgtcaga agtaagttgg ccgcagtgtt atcactcatg gttatggcag cactgcataa      5580
ttctcttact gtcatgccat ccgtaagatg cttttctgtg actggtgagt actcaaccaa      5640
gtcattctga aatagtgta tgcggcgacc gagttgctct tgcccggcgt caatacggga      5700
taataccgcg ccacatagca gaactttaaa agtgctcatc attggaaaac gttcttcggg      5760
gcgaaaactc tcaaggatct taccgctgtt gagatccagt tcgatgtaac ccactcgtgc      5820
acccaactga tcttcagcat cttttacttt caccagcgtt tctgggtgag caaaaacagg      5880
aaggcaaaat gccgcaaaaa agggaataag ggcgacacgg aaatgttgaa tactcatact      5940
cttccttttt caatattatt gaagcattta tcagggttat tgtctcatga gcggatacat      6000
atttgaatgt atttagaaaa ataaacaaat aggggttccg cgcacatttc cccgaaaagt      6060
gccacctggg tcgacattga ttattg                                          6086
```

<210> SEQ ID NO 130
<211> LENGTH: 6842
<212> TYPE: DNA
<213> ORGANISM: Artificial Sequence
<220> FEATURE:
<223> OTHER INFORMATION: Plasmid pCAGG-Noggin-IRES-GFP

<400> SEQUENCE: 130

```
actagttatt aatagtaatc aattacgggg tcattagttc atagcccata tatggagttc        60
cgcgttacat aacttacggt aaatggcccg cctggctgac cgcccaacga cccccgccca       120
ttgacgtcaa taatgacgta tgttcccata gtaacgccaa tagggacttt ccattgacgt       180
caatgggtgg agtatttacg gtaaactgcc cacttggcag tacatcaagt gtatcatatg       240
ccaagtacgc cccctattga cgtcaatgac ggtaaatggc ccgcctggca ttatgcccag       300
tacatgacct tatgggactt tcctacttgg cagtacatct acgtattagt catcgctatt       360
accatggtcg aggtgagccc cacgttctgc ttcactctcc ccatctcccc ccctccccca       420
cccccaattt tgtatttatt tattttttaa ttattttgtg cagcgatggg ggcggggggg       480 ggggggggc gcgcgccagg cggggcgggg cggggcgagg ggcggggcgg ggcgaggcgg       540
agaggtgcgg cggcagccaa tcagagcggc gcgctccgaa agtttccttt tatggcgagg       600
cggcggcggc ggcggcccta taaaaagcga agcgcgcggc gggcggggag tcgctgcgac       660
gctgccttcg ccccgtgccc cgctccgccg ccgcctcgcg ccgcccgccc cggctctgac       720
tgaccgcgtt actcccacag gtgagcgggc gggacggccc ttctcctccg gctgtaatt       780 agcgcttggt ttaatgacgg cttgtttctt ttctgtggct gcgtgaaagc cttgagggggc       840 tccgggaggg ccctttgtgc ggggggagcg gctcggggggg tgcgtgcgtg tgtgtgtgcg       900
tggggagcgc cgcgtgcggc tccgcgctgc ccggcggctg tgagcgctgc gggcgcggcg       960
cggggctttg tgcgctccgc agtgtgcgcg aggggagcgc ggccggggggc ggtgccccgc      1020 ggtgcggggg gggctgcgag gggaacaaag gctgcgtgcg gggtgtgtgc gtggggggggt      1080 gagcaggggg tgtgggcgcg tcggtcgggc tgcaacccc cctgcacccc cctccccgag       1140
ttgctgagca cggcccggct tcgggtgcgg ggctccgtac ggggcgtggc gcggggctcg      1200
```

-continued

```
ccgtgccggg cggggggtgg cggcaggtgg gggtgccggg cggggcgggg ccgcctcggg      1260
ccggggaggg ctcggggggag gggcgcggcg gcccccggag cgccggcggc tgtcgaggcg      1320
cggcgagccg cagccattgc cttttatggt aatcgtgcga gagggcgcag ggacttcctt      1380
tgtcccaaat ctgtgcggag ccgaaatctg ggaggcgccg ccgcacccc tctagcgggc       1440 gcggggcgaa gcggtgcggc gccggcagga aggaaatggg cggggagggc cttcgtgcgt      1500
cgccgcgccg ccgtcccctt ctccctctcc agcctcgggg ctgtccgcgg ggggacggct      1560
gccttcgggg gggacggggc agggcggggt tcggcttctg gcgtgtgacc ggcggctcta      1620
gagcctctgc taaccatgtt catgccttct tcttttttcct acagctcctg ggcaacgtgc      1680
tggttattgt gctgtctcat cattttggca aagaattcag cacctgcaca tgggacgtcg      1740
acctgaggta attataaccc gggatggatc attcccagtg ccttgtgact atatacgccg      1800
cggcggtgct gctggggctc cggctgcagc agggctcctg ccagcactac ctgcacatcc      1860
gcccggctcc cagcgacaac ctgcccctgg tggatctaat cgagcacccg gaccctatct      1920
ttgaccccaa ggagaaggat cttaacgaga ccttgctaag gagcctcatg ggaggacact      1980
tcgaccctaa ctttatggct atgtccctgc ccgaggaccg gctcggggta gacgatctgg      2040
ccgagctgga cttgctgctg cggcagagac cctcgggagc gatgcccggc gaaatcaagg      2100
ggctggagtt ctacgacggg ctgcagccgg gcaagaagca caggctgagc aagaagctgc      2160
gcaggaagct gcagatgtgg ctctggtccc agaccttctg cccggtccta tacacgtgga      2220
acgatctcgg cagccgcttt tggccccggt acgtcaaagt gggcagctgc tacagtaaaa      2280
ggtcttgctc tgtcccagaa ggcatggtct gcaaacctgc caagtccgtg catttaacga      2340
tcctgaggtg gcggtgccag cggcgggggcg ggcagcggtg cacgtggatc cccatccagt      2400 acccccatcat cgcggagtgc aagtgctcct gctaggctag cctccgcccc tctccctccc      2460
ccccccctaa cgttactggc cgaagccgct tggaataagg ccggtgtgcg tttgtctata      2520
tgttattttc caccatattg ccgtcttttg gcaatgtgag ggcccggaaa cctggccctg      2580
tcttcttgac gagcattcct aggggtcttt ccctctcgc caaaggaatg caaggtctgt       2640
tgaatgtcgt gaaggaagca gttcctctgg aagcttcttg aagacaaaca acgtctgtag      2700
cgaccctttg caggcagcgg aacccccac ctggcgacag gtgcctctgc ggccaaaagc       2760
cacgtgtata agatacacct gcaaaggcgg cacaacccca gtgccacgtt gtgagttgga      2820
tagttgtgga aagagtcaaa tggctctcct caagcgtatt caacaagggg ctgaaggatg      2880
cccagaaggt accccattgt atgggatctg atctgggggcc tcggtgcaca tgctttacat      2940
gtgtttagtc gaggttaaaa aaacgtctag gccccccgaa ccacggggac gtggttttcc      3000
tttgaaaaac acgatgataa tatggccaca accatggtga gcaagggcga ggagctgttc      3060
accggggtgg tgcccatcct ggtcgagctg gacggcgacg taaacggcca caagttcagc      3120
gtgtccggcg agggcgaggg cgatgccacc tacggcaagc tgaccctgaa gttcatctgc      3180
accaccggca agctgcccgt gccctggccc accctcgtga ccaccctgac ctacggcgtg      3240
cagtgcttca gccgctaccc cgaccacatg aagcagcacg acttcttcaa gtccgccatg      3300
cccgaaggct acgtccagga gcgcaccatc ttcttcaagg acgacggcaa ctacaagacc      3360
cgcgccgagg tgaagttcga gggcgacacc ctggtgaacc gcatcgagct gaagggcatc      3420
gacttcaagg aggacggcaa catcctgggg cacaagctgg agtacaacta caacagccac      3480
aacgtctata tcatggccga caagcagaag aacggcatca aggtgaactt caagatccgc      3540
```

-continued

```
cacaacatcg aggacggcag cgtgcagctc gccgaccact accagcagaa cacccccatc    3600
ggcgacggcc ccgtgctgct gcccgacaac cactacctga gcacccagtc cgccctgagc    3660
aaagacccca acgagaagcg cgatcacatg gtcctgctgg agttcgtgac cgccgccggg    3720
atcactctcg gcatggacga gctgtacaag taaagcggcc gccaattcac tcctcaggtg    3780
caggctgcct atcagaaggt ggtggctggt gtggccaatg ccctggctca caaataccac    3840
tgagatcttt ttccctctgc caaaaattat ggggacatca tgaagcccct tgagcatctg    3900
acttctggct aataaaggaa atttattttc attgcaatag tgtgttggaa ttttttgtgt    3960
ctctcactcg gaaggacata tgggagggca aatcatttaa aacatcagaa tgagtatttg    4020
gtttagagtt tggcaacata tgcccatatg ctggctgcca tgaacaaagg ttggctataa    4080
agaggtcatc agtatatgaa acagcccct gctgtccatt ccttattcca tagaaaagcc    4140
ttgacttgag gttagatttt ttttatattt tgttttgtgt tatttttttc tttaacatcc    4200 ctaaatttt ccttacatgt tttactagcc agatttttcc tcctctcctg actactccca    4260
gtcatagctg tccctcttct cttatggaga tccctcgacc tgcagcccaa gcttggcgta    4320
atcatggtca tagctgtttc ctgtgtgaaa ttgttatccg ctcacaattc cacacaacat    4380
acgagccgga agcataaagt gtaaagcctg gggtgcctaa tgagtgagct aactcacatt    4440
aattgcgttg cgctcactgc ccgctttcca gtcgggaaac ctgtcgtgcc agcggatccg    4500
catctcaatt agtcagcaac catagtcccg cccctaactc cgcccatccc gcccctaact    4560
ccgcccagtt ccgcccattc tccgccccat ggctgactaa ttttttttat ttatgcagag    4620
gccgaggccg cctcggcctc tgagctattc cagaagtagt gaggaggctt ttttggaggc    4680
ctaggctttt gcaaaaagct aacttgttta ttgcagctta taatggttac aaataaagca    4740
atagcatcac aaatttcaca aataaagcat tttttcact gcattctagt tgtggtttgt    4800
ccaaactcat caatgtatct tatcatgtct ggatccgctg cattaatgaa tcggccaacg    4860
cgcggggaga ggcggtttgc gtattgggcg ctcttccgct tcctcgctca ctgactcgct    4920
gcgctcggtc gttcggctgc ggcgagcggt atcagctcac tcaaaggcgg taatacggtt    4980
atccacagaa tcaggggata acgcaggaaa gaacatgtga gcaaaaggcc agcaaaaggc    5040
caggaaccgt aaaaaggccg cgttgctggc gtttttccat aggctccgcc ccctgacga    5100 gcatcacaaa aatcgacgct caagtcagag gtggcgaaac ccgacaggac tataaagata    5160
ccaggcgttt cccctggaa gctccctcgt gcgctctcct gttccgaccc tgccgcttac    5220
cggatacctg tccgcctttc tcccttcggg aagcgtggcg ctttctcata gctcacgctg    5280
taggtatctc agttcggtgt aggtcgttcg ctccaagctg ggctgtgtgc acgaaccccc    5340
cgttcagccc gaccgctgcg ccttatccgg taactatcgt cttgagtcca acccggtaag    5400
acacgactta tcgccactgg cagcagccac tggtaacagg attagcagag cgaggtatgt    5460
aggcggtgct acagagttct tgaagtggtg gcctaactac ggctacacta gaagaacagt    5520
atttggtatc tgcgctctgc tgaagccagt taccttcgga aaaagagttg gtagctcttg    5580
atccggcaaa caaaccaccg ctggtagcgg tggttttttt gtttgcaagc agcagattac    5640
gcgcagaaaa aaaggatctc aagaagatcc tttgatcttt tctacggggt ctgacgctca    5700
gtggaacgaa aactcacgtt aagggatttt ggtcatgaga ttatcaaaaa ggatcttcac    5760
ctagatcctt ttaaattaaa aatgaagttt taaatcaatc taaagtatat atgagtaaac    5820
ttggtctgac agttaccaat gcttaatcag tgaggcacct atctcagcga tctgtctatt    5880
tcgttcatcc atagttgcct gactccccgt cgtgtagata actacgatac gggagggctt    5940
```

```
accatctggc cccagtgctg caatgatacc gcgagaccca cgctcaccgg ctccagattt      6000
atcagcaata aaccagccag ccggaagggc cgagcgcaga agtggtcctg caactttatc      6060
cgcctccatc cagtctatta attgttgccg ggaagctaga gtaagtagtt cgccagttaa      6120
tagtttgcgc aacgttgttg ccattgctac aggcatcgtg gtgtcacgct cgtcgtttgg      6180
tatggcttca ttcagctccg gttcccaacg atcaaggcga gttacatgat cccccatgtt      6240
gtgcaaaaaa gcggttagct ccttcggtcc tccgatcgtt gtcagaagta agttggccgc      6300
agtgttatca ctcatggtta tggcagcact gcataattct cttactgtca tgccatccgt      6360
aagatgcttt tctgtgactg gtgagtactc aaccaagtca ttctgagaat agtgtatgcg      6420
gcgaccgagt tgctcttgcc cggcgtcaat acgggataat accgcgccac atagcagaac      6480
tttaaaagtg ctcatcattg gaaaacgttc ttcggggcga aaactctcaa ggatcttacc      6540
gctgttgaga tccagttcga tgtaacccac tcgtgcaccc aactgatctt cagcatcttt      6600
tactttcacc agcgtttctg ggtgagcaaa aacaggaagg caaaatgccg caaaaaaggg      6660
aataagggcg acacggaaat gttgaatact catactcttc cttttcaat attattgaag      6720 catttatcag ggttattgtc tcatgagcgg atacatattt gaatgtattt agaaaaataa      6780
acaaataggg gttccgcgca catttccccg aaaagtgcca cctgggtcga cattgattat      6840
tg                                                                     6842
```

```
<210> SEQ ID NO 131
<211> LENGTH: 7999
<212> TYPE: DNA
<213> ORGANISM: Artificial Sequence
<220> FEATURE:
<223> OTHER INFORMATION: TV-FlpO-IRES-GFP

<400> SEQUENCE: 131
```

```
gaatgaaggg cctgagggtg ggcagtctgt ctatcatgta catctccata ttctgggagg       60
tcgtcagttg ggctggcctc ctggctaaga tttttgcacc acaagagatg ctgcatgtgt      120
acaaatcact agcaaataga tttgtttccc atcaacttag ccactgttaa tgtaaattgt      180
tcttggatat gtgtctttgg agggcaataa atgtctgaa cagcacttgc acaataaaga      240
tacagcatgt gggaatgatc tgtctcatgt gtcttactga tggtattggt tctgtaagat      300
aaaatattgt gtctgggatg tgtttggctc tactattaat ggtgctctat tgattgtgat      360
ttgtcatttg aaacctgagg atgcgactgt atagcagtct ttcatgcatt tttggaaaaa      420
aacttaagct ttttgaaagc tgctgctaca acttttttgta ttgttataaa gttttgtatt      480
gtttttttaa ttgtgaaatt ataaagatgc cgtgcaggga ctgtttgaag caaagtgcat      540
tgttttagaa acctacaact ctagttcaag cactccatca gtatctgctt aatctttgtc      600
atcctttgct atgagaaaat attaagcagt agtctaaagg tactatgaaa ctataacata      660
gctgacattg tatttataac tacgtcatga ttttgataga attgaggact tgaaaatgtt      720
aaactattca tgtagggcct cttaagatgc ttaagttgtt tagtaatgta agtgtgcatt      780
taattgagat tttattgggc ataatttgtc catcagtatg acactccttg tcagtgttgc      840
cttatacttg atgttgttac cggatctctg caaggcagtt attcttgaat taggctcatt      900
gaagtgtctg ccagtataaa tatatagcaa ctgttctttg tgttaaaatt gagaagctaa      960
ccagttttta gtgcttctga ctgttggaat tctttaagca gatgccataa gaaaattgta     1020
tttgtgatca ccacttctcc agagtggttt taacaccaag ggcattagag aaagaaaggc     1080
```

-continued

```
aggcgtgtag agaatagtgg acagacaaaa gctgtgagtt acgttatgtt tttcagctga    1140
aaagctgtgt ttggtaaaag catatgaaat cactcaactt ggaagcattc tcttagttct    1200
ctgatagttc tgagcagcag aactcttcac ctaagaggtt acttcaactg gaagactacc    1260
tagtgcttct gatggcaact atatttaaga tgagaataag aggtgtttcc agtgtggtag    1320
cctcacatct gttgcagtgg ttaccgttcg tcctcctccg agggacacag cttggccatt    1380
cactgtggtg acaccaatat gatgatcagc aaatggtgtt tattcactac taaacacagc    1440
ttatatacat ttttacctac aaaatcgtgc tgtcatgtcc cactctgatt ggttcactag    1500
ttattaatag taatcaatta cggggtcatt agttcatagc ccatatatgg agttccgcgt    1560
tacataactt acggtaaatg gcccgcctgg ctgaccgccc aacgacccc gcccattgac      1620 gtcaataatg acgtatgttc ccatagtaac gccaataggg actttccatt gacgtcaatg    1680
ggtggagtat ttacggtaaa ctgcccactt ggcagtacat caagtgtatc atatgccaag    1740 tacgcccct attgacgtca atgacggtaa atggcccgcc tggcattatg cccagtacat      1800
gaccttatgg gactttccta cttggcagta catctacgta ttagtcatcg ctattaccat    1860
ggtcgaggtg agccccacgt tctgcttcac tctccccatc tccccccct ccccacccc       1920 aattttgtat ttatttattt tttaattatt ttgtgcagcg atggggcgg ggggggggg       1980 ggggcgcgcg ccaggcgggg cggggcgggg cgaggcgcgg ggcggggcga ggcggagagg    2040
tgcggcggca gccaatcaga gcggcgcgct ccgaaagttt cctttttatgg cgaggcggcg    2100 gcggcggcgg ccctataaaa agcgaagcgc gcggcggcg gggagtcgct gcgacgctgc      2160
cttcgccccg tgccccgctc cgccgccgcc tcgcgccgcc cgccccggct ctgactgacc    2220
gcgttactcc cacaggtgag cgggcgggac ggcccttctc ctccgggctg taattagcgc    2280
ttggtttaat gacggcttgt ttcttttctg tggctgcgtg aaagccttga ggggctccgg    2340
gagggccctt tgtgcggggg gagcggctcg ggggtgcgt gcgtgtgtgt gtgcgtgggg      2400
agcgccgcgt gcggctccgc gctgcccggc ggctgtgagc gctgcgggcg cggcgcgggg    2460
ctttgtgcgc tccgcagtgt gcgcgagggg agcgcggccg ggggcggtgc cccgcggtgc    2520
ggggggggct gcgaggggaa caaaggctgc gtgcggggtg tgtgcgtggg ggggtgagca    2580
gggggtgtgg gcgcgtcggt cgggctgcaa cccccctgc accccctcc ccgagttgct      2640 gagcacggcc cggcttcggg tgcggggctc cgtacggggc gtggcgcggg gctcgccgtg    2700
ccgggcgggg ggtggcggca ggtgggggtg ccgggcgggg cggggccgcc tcgggccggg    2760
gagggctcgg gggaggggcg cggcggcccc cggagcgccg gcggctgtcg aggcgcggcg    2820
agccgcagcc attgcctttt atggtaatcg tgcgagaggg cgcagggact tcctttgtcc    2880
caaatctgtg cggagccgaa atctgggagg cgccgccgca ccccctctag cgggcgcggg    2940
gcgaagcggt gcggcgccgg caggaaggaa atgggcgggg agggccttcg tgcgtcgccg    3000
cgccgccgtc cccttctccc tctccagcct cggggctgtc cgcggggggga cggctgcctt    3060 cgggggggac ggggcagggc ggggttcggc ttctggcgtg tgaccggcgg ctctagagcc    3120
tctgctaacc atgttcatgc cttcttcttt ttcctacagc tcctgggcaa cgtgctggtt    3180
attgtgctgt ctcatcattt tggcaaagaa ttcagcacct gcacatggga cgtcgacctg    3240
aggtaattat aacccgggc caccatggct cctaagaaga agaggaaggt gatgagccag        3300
ttcgacatcc tgtgcaagac cccccccaag gtgctggtgc ggcagttcgt ggagagattc    3360
gagaggccca gcgcgagaa gatcgccagc tgtgccgccg agctgaccta cctgtgctgg    3420
atgatcaccc acaacggcac cgccatcaag agggccacct tcatgagcta caacaccatc    3480
```

-continued

```
atcagcaaca gcctgagctt cgacatcgtg aacaagagcc tgcagttcaa gtacaagacc      3540
cagaaggcca ccatcctgga ggccagcctg aagaagctga tccccgcctg ggagttcacc      3600
atcatccctt acaacggcca gaagcaccag agcgacatca ccgacatcgt gtccagcctg      3660
cagctgcagt tcgagagcag cgaggaggcc gacaagggca cagccacag caagaagatg       3720 ctgaaggccc tgctgtccga gggcgagagc atctgggaga tcaccgagaa gatcctgaac      3780
agcttcgagt acaccagcag gttcaccaag accaagaccc tgtaccagtt cctgttcctg      3840
gccacattca tcaactgcgg caggttcagc gacatcaaga acgtggaccc caagagcttc      3900
aagctggtgc agaacaagta cctgggcgtg atcattcagt gcctggtgac cgagaccaag      3960
acaagcgtgt ccaggcacat ctactttttc agcgccagag gcaggatcga cccctggtg       4020 tacctggacg agttcctgag gaacagcgag cccgtgctga agagagtgaa caggaccggc      4080
aacagcagca gcaacaagca ggagtaccag ctgctgaagg acaacctggt gcgcagctac      4140
aacaaggccc tgaagaagaa cgccccctac cccatcttcg ctatcaagaa cggccctaag      4200
agccacatcg gcaggcacct gatgaccagc tttctgagca tgaagggcct gaccgagctg      4260
acaaacgtgg tgggcaactg gagcgacaag agggcctccg ccgtggccag gaccacctac      4320
acccaccaga tcaccgccat ccccgaccac tacttcgccc tggtgtccag gtactacgcc      4380
tacgacccca tcagcaagga gatgatcgcc ctgaaggacg agaccaaccc catcgaggag      4440
tggcagcaca tcgagcagct gaagggcagc gccgagggca gcatcagata ccccgcctgg      4500
aacggcatca tcagccagga ggtgctggac tacctgagca gctacatcaa caggcggatc      4560
tgagctagcc gatccgcccc tctccctccc ccccccctaa cgttactggc cgaagccgct      4620
tggaataagg ccggtgtgcg tttgtctata tgttatttc caccatattg ccgtcttttg       4680
gcaatgtgag ggcccggaaa cctggccctg tcttcttgac gagcattcct aggggtcttt      4740
cccctctcgc caaaggaatg caaggtctgt tgaatgtcgt gaaggaagca gttcctctgg      4800
aagcttcttg aagacaaaca cgtctgtag cgaccctttg caggcagcgg aaccccccac       4860
ctggcgacag gtgcctctgc ggccaaaagc cacgtgtata agatacacct gcaaaggcgg      4920 cacaaccca gtgccacgtt gtgagttgga tagttgtgga aagagtcaaa tggctctcct       4980
caagcgtatt caacaagggg ctgaaggatg cccagaaggt accccattgt atgggatctg      5040
atctggggcc tcggtgcaca tgctttacat gtgtttagtc gaggttaaaa aaacgtctag      5100 gcccccgaa ccacggggac gtggttttcc tttgaaaaac acgatgataa tatggccaca       5160
accatggtga gcaaggcgaa ggagctgttc accggggtgg tgcccatcct ggtcgagctg      5220
gacggcgacg taaacggcca caagttcagc gtgtccggcg agggcgaggg cgatgccacc      5280
tacggcaagc tgaccctgaa gttcatctgc accaccggca agctgcccgt gccctggccc      5340
accctcgtga ccaccctgac ctacggcgtg cagtgcttca gccgctaccc cgaccacatg      5400
aagcagcacg acttcttcaa gtccgccatg cccgaaggct acgtccagga gcgcaccatc      5460
ttcttcaagg acgacggcaa ctacaagacc cgcgccgagg tgaagttcga gggcgacacc      5520
ctggtgaacc gcatcgagct gaagggcatc gacttcaagg aggacggcaa catcctgggg      5580
cacaagctgg agtacaacta caacagccac aacgtctata tcatggccga caagcagaag      5640
aacggcatca aggtgaactt caagatccgc cacaacatcg aggacggcag cgtgcagctc      5700
gccgaccact accagcagaa cacccccatc ggcgacggcc ccgtgctgct gcccgacaac      5760
cactacctga gcacccagtc cgccctgagc aaagacccca acgagaagcg cgatcacatg      5820
```

-continued

```
gtcctgctgg agttcgtgac cgccgccggg atcactctcg gcatggacga gctgtacaag    5880
taaagcggcc gccaattcac tcctcaggtg caggctgcct atcagaaggt ggtggctggt    5940
gtggccaatg ccctggctca caaataccac tgagatcttt ttccctctgc caaaaattat    6000
ggggacatca tgaagcccct tgagcatctg acttctggct aataaaggaa atttattttc    6060
attgcaatag tgtgttggaa ttttttgtgt ctctcactcg gaaggacata tgggagggca    6120
aatcatttaa aacatcagaa tgagtatttg gtttagagtt tggcaacata tgcccatatg    6180
ctggctgcca tgaacaaagg ttggctataa agaggtcatc agtatatgaa acagcccct    6240 gctgtccatt ccttattcca tagaaaagcc ttgacttgag gttagatttt ttttatattt    6300
tgttttgtgt tattttttc tttaacatcc ctaaaatttt ccttacatgt tttactagcc    6360 agattttcc tcctctcctg actactccca gtcatagctg tccctcttct cttatggaga    6420
tccctcgacc tgcatgccgt ttccacattc ttttctcatc cttcttctcc tgttttctct    6480
gcatcaaggt cagcacgata gcactgtctc tctatgctta gggagaggcc tgtcctgtac    6540
atcccgtgcc cccacaagat gcctactaca acaacatctt ctgcatgtcc tgcatagcag    6600
tgttgggaga atgtgcacta cttccactct tctgatttct attttatgtg tttgctttat    6660
accagtgttg ccatttggga attaatacat ggttgatcaa atcaattgca tcacagctgt    6720
atcctgtatc agaggaacat tatcaaagct tttgttgctg tatttggtat ctgacctgca    6780
gataaacatg ttttaggaag gttttgcaaa agtagctgtg aaatgagctg gtgttgtgat    6840
ttaacctgac aggcagctaa acagtatacc acagagctat tcacctactt tccctcagtg    6900
ggaaaaggga agagaactga gggggggggg aataaataag taaataacaa aataaaactc    6960
atggattaag aaaaagactt tgtactggaa tggatgagaa gaataatagt aatgataata    7020
atatgtcact ctgaaagtaa tgcctcttat ttctgtggag actacaaaca tacaaagagc    7080
acaacattcc atagagcaaa ttctcagtta cagaatgcta ttttttttt caacacagtc    7140 aaaatcatta atttttttt gcctgcaatg gacaagagct ttgaagctgt tctcgtaaaa    7200
atctgtacta gcagaagtga cctgcaatca ctactgctga aatgcacaac ccaccacatc    7260
attgtgctca cattcactgt ttggtttctg taaatgtaca ggaattgtct gaaattagat    7320
atgatttttt ttttctccat gaaggaattc aattacacac ctttgcctca tgcacttctt    7380
tgtcattttt gtcagactgc ttctctcctg caatttgtct catggcaaca aaatataatg    7440
gagttctgct gggaacttcc ctactgccat accactatca tctgcctctg acattttgga    7500
caaatgtaat aaaataggag gtattacttt cagagcagac cttgtatgta tttacaaaac    7560
aagtggtaca caaaaaaaat tgttcatccc accaaccaat gcccatcctg tccctgaata    7620
gtagctgtcc cccacagcct tgaccagttt aggtcaacag ttctgcttct gtccctccc    7680 agctccttgt aacccctcag ccccccttgc tggcaggaca gtatgagaag ctgaaaaact    7740
agaatgtcct agttctttgc agtgctgcta atcaacaacc aaaacagtgg tgtgttacca    7800
atattgttga tatcacagca tcataccatt atgaaggaag taacccagcc aaaatcaggt    7860
cagcttgcta acaagagaac tgtgcataag tttaagatgt gtgtgttcct cagtacctta    7920
aaaaataagt agtaacgttc aaatgagtag aagagtagaa ctgagcttaa aacatctgtc    7980
agacaacagt gaaccaacc                                                 7999
```

```
<210> SEQ ID NO 132
<211> LENGTH: 7263
<212> TYPE: DNA
<213> ORGANISM: Artificial Sequence
```

-continued

```
<220> FEATURE:
<223> OTHER INFORMATION: TV-Cre-P2A-GFP

<400> SEQUENCE: 132
gaatgaaggg cctgagggtg ggcagtctgt ctatcatgta catctccata ttctgggagg      60
tcgtcagttg ggctggcctc ctggctaaga tttttgcacc acaagagatg ctgcatgtgt     120
acaaatcact agcaaataga tttgtttccc atcaacttag ccactgttaa tgtaaattgt     180
tcttggatat gtgtctttgg agggcaataa atgctctgaa cagcacttgc acaataaaga     240
tacagcatgt gggaatgatc tgtctcatgt gtcttactga tggtattggt tctgtaagat     300
aaaatattgt gtctgggatg tgtttggctc tactattaat ggtgctctat tgattgtgat     360
ttgtcatttg aaacctgagg atgcgactgt atagcagtct ttcatgcatt tttggaaaaa     420
aacttaagct ttttgaaagc tgctgctaca acttttttgta ttgttataaa gttttgtatt     480 gttttttttaa ttgtgaaatt ataaagatgc cgtgcaggga ctgtttgaag caaagtgcat     540
tgttttagaa acctacaact ctagttcaag cactccatca gtatctgctt aatctttgtc     600
atcctttgct atgagaaaat attaagcagt agtctaaagg tactatgaaa ctataacata     660
gctgacattg tatttataac tacgtcatga ttttgataga attgaggact tgaaaatgtt     720
aaactattca tgtagggcct cttaagatgc ttaagttgtt tagtaatgta agtgtgcatt     780
taattgagat tttattgggc ataatttgtc catcagtatg acactccttg tcagtgttgc     840
cttatacttg atgttgttac cggatctctg caaggcagtt attcttgaat taggctcatt     900
gaagtgtctg ccagtataaa tatatagcaa ctgttctttg tgttaaaatt gagaagctaa     960
ccagttttta gtgcttctga ctgttggaat tctttaagca gatgccataa gaaaattgta    1020
tttgtgatca ccacttctcc agagtggttt taacaccaag ggcattagag aaagaaaggc    1080
aggcgtgtag agaatagtgg acagacaaaa gctgtgagtt acgttatgtt tttcagctga    1140
aaagctgtgt ttggtaaaag catatgaaat cactcaactt ggaagcattc tcttagttct    1200
ctgatagttc tgagcagcag aactcttcac ctaagaggtt acttcaactg gaagactacc    1260
tagtgcttct gatggcaact atatttaaga tgagaataag aggtgtttcc agtgtggtag    1320
cctcacatct gttgcagtgg ttaccgttcg tcctcctccg agggacacag cttggccatt    1380
cactgtggtg acaccaatat gatgatcagc aaatggtgtt tattcactac taaacacagc    1440
ttatatacat ttttacctac aaaatcgtgc tgtcatgtcc cactctgatt ggttcattaa    1500
ttaagaagtt cctattccga agttcctatt ctctagaaag tataggaact tcgtcgacat    1560
tgattattga ctagttatta atagtaatca attacggggt cattagttca tagcccatat    1620
atggagttcc gcgttacata acttacggta atggcccgc ctggctgacc gcccaacgac     1680
ccccgcccat tgacgtcaat aatgacgtat gttcccatag taacgccaat agggactttc    1740
cattgacgtc aatgggtgga gtatttacgg taaactgccc acttggcagt acatcaagtg    1800
tatcatatgc caagtacgcc ccctattgac gtcaatgacg gtaaatggcc cgcctggcat    1860
tatgcccagt acatgacctt atgggacttt cctacttggc agtacatcta cgtattagtc    1920
atcgctatta ccatggtcga ggtgagcccc acgttctgct tcactctccc catctccccc    1980
ccctccccac ccccaatttt gtatttattt attttttaat tattttgtgc agcgatgggg    2040 gcggggggg gggggggcg cgcgccaggc ggggcggggc ggggcgaggg gcggggcggg     2100
gcgaggcgga gaggtgcggc ggcagccaat cagagcggcg cgctccgaaa gtttcctttt    2160
atggcgaggc ggcggcggcg gcggccctat aaaaagcgaa gcgcgcggcg ggcggggagt    2220
```

-continued

```
cgctgcgacg ctgccttcgc cccgtgcccc gctccgccgc cgcctcgcgc cgcccgcccc   2280
ggctctgact gaccgcgtta ctcccacagg tgagcgggcg ggacggccct tctcctccgg   2340
gctgtaatta gcgcttggtt taatgacggc ttgtttcttt tctgtggctg cgtgaaagcc   2400
ttgaggggct ccgggagggc cctttgtgcg ggggagcggg ctcggggggt gcgtgcgtgt   2460
gtgtgtgcgt ggggagcgcc gcgtgcggct ccgcgctgcc cggcggctgt gagcgctgcg   2520
ggcgcggcgc ggggctttgt gcgctccgca gtgtgcgcga ggggagcgcg gccggggggcg   2580 gtgccccgcg gtgcggggggg ggctgcgagg ggaacaaagg ctgcgtgcgg ggtgtgtgcg   2640
tgggggggtg agcagggggt gtgggcgcgt cggtcgggct gcaacccccc ctgcacccccc   2700 ctccccgagt tgctgagcac ggcccggctt cgggtgcggg gctccgtacg gggcgtggcg   2760
cggggctcgc cgtgccgggc ggggggtggc ggcaggtggg ggtgccgggc ggggcggggc   2820
cgcctcgggc cggggagggc tcggggagg ggcgcggcgg ccccccggagc gccggcggct   2880 gtcgaggcgc ggcgagccgc agccattgcc ttttatggta atcgtgcgag agggcgcagg   2940
gacttccttt gtcccaaatc tgtgcggagc cgaaatctgg gaggcgccgc cgcaccccct   3000
ctagcgggcg cggggcgaag cggtgcggcg ccggcaggaa ggaaatgggc ggggagggcc   3060
ttcgtgcgtc gccgcgccgc cgtccccttc tccctctcca gcctcggggc tgtccgcggg   3120
gggacggctg ccttcggggg ggacggggca gggcggggtt cggcttctgg cgtgtgaccg   3180
gcggctctag agcctctgct aaccatgttc atgccttctt cttttttccta cagctcctgg   3240 gcaacgtgct ggttaggtac catggcaccc aagaagaaga ggaaggtgtc caatttactg   3300
accgtacacc aaaatttgcc tgcattaccg gtcgatgcaa cgagtgatga ggttcgcaag   3360
aacctgatgg acatgttcag ggatcgccag gcgttttctg agcatacctg gaaaatgctt   3420
ctgtccgttt gccggtcgtg ggcggcatgg tgcaagttga ataaccggaa atggtttccc   3480
gcagaacctg aagatgttcg cgattatctt ctatatcttc aggcgcgcgg tctggcagta   3540
aaaactatcc agcaacattt gggccagcta aacatgcttc atcgtcggtc cgggctgcca   3600
cgaccaagtg acagcaatgc tgtttcactg gttgtgcggc ggatccgaaa agaaaacgtt   3660
gatgccggtg aacgtgcaaa acaggctcta gcgttcgaac gcactgattt cgaccaggtt   3720
cgttcactca tggaaaatag cgatcgctgc caggatatac gtaatctggc atttctgggg   3780
attgcttata acaccctgtt acgtatagcc gaaattgcca ggatcagggt aaagatatc   3840 tcacgtactg acggtgggag aatgttaatc catattggca gaacgaaaac gctggttagc   3900 accgcaggt tagagaaggc acttagcctg ggggtaacta aactggtcga gcgatggatt   3960
tccgtctctg gtgtagctga tgatccgaat aactacctgt tttgccgggt cagaaaaaat   4020
ggtgttgccg cgccatctgc caccagccag ctatcaactc gcgccctgga agggattttt   4080
gaagcaactc atcgattgat ttacggcgct aaggatgact ctggtcagag ataccctggcc   4140 tggtctggac acagtgcccg tgtcggagcc gcgcgagata tggcccgcgc tggagtttca   4200
ataccggaga tcatgcaagc tggtggctgg accaatgtaa atattgtcat gaactatatc   4260
cgtaacctgg atagtgaaac aggggcaatg gtgcgcctgc tgcaagatgg cgatcccggg   4320
ggaagcggag ctactaactt cagcctgctg aagcaggctg cgacgtgga ggagaaccct   4380 ggacctatgg tgagcaaggg cgaggagctg ttcaccgggg tggtgcccat cctggtcgag   4440
ctggacggcg acgtaaacgg ccacaagttc agcgtgtccg gcgagggcga gggcgatgcc   4500
acctacggca agctgaccct gaagttcatc tgcaccaccg gcaagctgcc cgtgccctgg   4560 cccacccctcg tgaccacccct gacctacggc gtgcagtgct tcagccgcta ccccgaccac   4620
```

-continued

```
atgaagcagc acgacttctt caagtccgcc atgcccgaag gctacgtcca ggagcgcacc   4680
atcttcttca aggacgacgg caactacaag acccgcgccg aggtgaagtt cgagggcgac   4740
accctggtga accgcatcga gctgaagggc atcgacttca aggaggacgg caacatcctg   4800
gggcacaagc tggagtacaa ctacaacagc cacaacgtct atatcatggc cgacaagcag   4860
aagaacggca tcaaggtgaa cttcaagatc cgccacaaca tcgaggacgg cagcgtgcag   4920
ctcgccgacc actaccagca gaacaccccc atcggcgacg gccccgtgct gctgcccgac   4980
aaccactacc tgagcaccca gtccgccctg agcaaagacc ccaacgagaa gcgcgatcac   5040
atggtcctgc tggagttcgt gaccgccgcc gggatcactc tcggcatgga cgagctgtac   5100
aagtaaagcg gccgccaatt cactcctcag gtgcaggctg cctatcagaa ggtggtggct   5160
ggtgtggcca atgccctggc tcacaaatac cactgagatc ttttttccctc tgccaaaaat   5220 tatggggaca tcatgaagcc ccttgagcat ctgacttctg gctaataaag gaaatttatt   5280
ttcattgcaa tagtgtgttg gaattttttg tgtctctcac tcggaaggac atatgggagg   5340
gcaaatcatt taaaacatca gaatgagtat ttggtttaga gtttggcaac atatgcccat   5400
atgctggctg ccatgaacaa aggttggcta taaagaggtc atcagtatat gaaacagccc   5460
cctgctgtcc attccttatt ccatagaaaa gccttgactt gaggttagat tttttttata   5520
ttttgttttg tgttattttt ttctttaaca tccctaaaat tttccttaca tgttttacta   5580
gccagatttt tcctcctctc ctgactactc ccagtcatag ctgtccctct tctcttatgg   5640
agatcgaagt tcctattccg aagttcctat tctctagaaa gtataggaac ttcgctagcg   5700
ccgtttccac attcttttct catccttctt ctcctgtttt ctctgcatca aggtcagcac   5760
gatagcactg tctctctatg cttagggaga ggcctgtcct gtacatcccg tgcccccaca   5820
agatgcctac tacaacaaca tcttctgcat gtcctgcata gcagtgttgg gagaatgtgc   5880
actacttcca ctcttctgat ttctatttta tgtgtttgct ttataccagt gttgccattt   5940
gggaattaat acatggttga tcaaatcaat tgcatcacag ctgtatcctg tatcagagga   6000
acattatcaa agcttttgtt gctgtatttg gtatctgacc tgcagataaa catgtttttag   6060 gaaggttttg caaaagtagc tgtgaaatga gctggtgttg tgatttaacc tgacaggcag   6120
ctaaacagta taccacagag ctattcacct actttccctc agtgggaaaa gggaagagaa   6180 ctgaggggggg ggggaataaa taagtaaata acaaaataaa actcatggat taagaaaaag   6240
actttgtact ggaatggatg agaagaataa tagtaatgat aataatatgt cactctgaaa   6300
gtaatgcctc ttatttctgt ggagactaca aacatacaaa gagcacaaca ttccatagag   6360
caaattctca gttacagaat gctattttt ttttcaacac agtcaaaatc attaattttt   6420
ttttgcctgc aatggacaag agctttgaag ctgttctcgt aaaaatctgt actagcagaa   6480
gtgacctgca atcactactg ctgaaatgca caacccacca catcattgtg ctcacattca   6540
ctgtttggtt tctgtaaatg tacaggaatt gtctgaaatt agatatgatt ttttttttct   6600
ccatgaagga attcaattac acaccttttgc ctcatgcact tctttgtcat ttttgtcaga   6660
ctgcttctct cctgcaattt gtctcatggc aacaaaatat aatggagttc tgctgggaac   6720
ttccctactg ccataccact atcatctgcc tctgacattt tggacaaatg taataaaata   6780
ggaggtatta ctttcagagc agaccttgta tgtatttaca aaacaagtgg tacacaaaaa   6840
aaattgttca tccaccaac caatgcccat cctgtccctg aatagtagct gtcccccaca   6900
gccttgacca gtttaggtca acagttctgc ttctgtcccc tcccagctcc ttgtaacccc   6960
```

-continued

```
tcagcccccc ttgctggcag gacagtatga gaagctgaaa aactagaatg tcctagttct    7020
ttgcagtgct gctaatcaac aaccaaaaca gtggtgtgtt accaatattg ttgatatcac    7080
agcatcatac cattatgaag gaagtaaccc agccaaaatc aggtcagctt gctaacaaga    7140
gaactgtgca taagtttaag atgtgtgtgt tcctcagtac cttaaaaaat aagtagtaac    7200
gttcaaatga gtagaagagt agaactgagc ttaaaacatc tgtcagacaa cagtgaacca    7260
acc                                                                  7263
```